US011944681B2

(12) United States Patent
Haynes et al.

(10) Patent No.: US 11,944,681 B2
(45) **Date of Patent: *Apr. 2, 2024**

(54) HIV-1 NEUTRALIZING ANTIBODIES AND USES THEREOF

(71) Applicants: Duke University, Durham, NC (US); University of Maryland, College Park, MD (US)

(72) Inventors: Barton F. Haynes, Durham, NC (US); Hua-Xin Liao, Durham, NC (US); M. Anthony Moody, Durham, NC (US); LaTonya Williams, Durham, NC (US); Kevin J. Wiehe, Durham, NC (US); Gilad Adi Ofek, College Park, MD (US)

(73) Assignees: Duke University, Durham, NC (US); University of Maryland, College Park, MD (US)

( * ) Notice: Subject to any disclaimer, the term of this patent is extended or adjusted under 35 U.S.C. 154(b) by 269 days.

This patent is subject to a terminal disclaimer.

(21) Appl. No.: 17/357,725

(22) Filed: Jun. 24, 2021

(65) Prior Publication Data

US 2022/0096632 A1 Mar. 31, 2022

Related U.S. Application Data

(63) Continuation of application No. 15/559,314, filed as application No. PCT/US2016/023488 on Mar. 21, 2016, now Pat. No. 11,071,783.

(60) Provisional application No. 62/261,233, filed on Nov. 30, 2015, provisional application No. 62/260,100, filed on Nov. 25, 2015, provisional application No. 62/222,057, filed on Sep. 22, 2015, provisional application No. 62/191,095, filed on Jul. 10, 2015, provisional application No. 62/191,054, filed on Jul. 10, 2015, provisional application No. 62/135,309, filed on Mar. 19, 2015.

(51) Int. Cl.

| | |
|---|---|
| ***A61K 39/42*** | (2006.01) |
| ***A61K 31/18*** | (2006.01) |
| ***A61K 39/44*** | (2006.01) |
| ***A61P 31/18*** | (2006.01) |
| ***C07K 16/10*** | (2006.01) |
| *A61K 39/00* | (2006.01) |

(52) U.S. Cl.

CPC .............. *A61K 39/42* (2013.01); *A61K 39/44* (2013.01); *A61P 31/18* (2018.01); *C07K 16/1045* (2013.01); *A61K 2039/507* (2013.01); *C07K 2299/00* (2013.01); *C07K 2317/24* (2013.01); *C07K 2317/54* (2013.01); *C07K 2317/55* (2013.01); *C07K 2317/56* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 7,458,704 | B2 | 12/2008 | Naoi | |
| 8,784,821 | B1 | 7/2014 | Kufer et al. | |
| 8,795,667 | B2 | 8/2014 | Johnson et al. | |
| 10,450,368 | B2 | 10/2019 | Haynes et al. | |
| 11,071,783 | B2 * | 7/2021 | Haynes .................. | A61K 39/44 |
| 2005/0037000 | A1 | 2/2005 | Stavenhagen et al. | |
| 2005/0064514 | A1 | 3/2005 | Stavenhagen et al. | |
| 2009/0060910 | A1 | 3/2009 | Johnson et al. | |
| 2010/0093979 | A1 | 4/2010 | Lazar | |
| 2010/0174053 | A1 | 7/2010 | Johnson et al. | |
| 2011/0081347 | A1 | 4/2011 | Gorlatov | |
| 2013/0295121 | A1 | 11/2013 | Johnson et al. | |
| 2014/0088295 | A1 | 3/2014 | Smith et al. | |
| 2014/0099318 | A1 | 4/2014 | Huang et al. | |
| 2014/0170149 | A1 | 6/2014 | Neijssen et al. | |
| 2014/0205607 | A1 | 7/2014 | Mascola et al. | |
| 2014/0206846 | A1 | 7/2014 | Beckmann | |
| 2014/0328836 | A1 | 11/2014 | Johnson et al. | |
| 2014/0348785 | A1 | 11/2014 | Connors et al. | |
| 2015/0152183 | A1 | 6/2015 | Chamberlain et al. | |

FOREIGN PATENT DOCUMENTS

| | | | |
|---|---|---|---|
| EP | 2158221 | A2 | 3/2010 |
| EP | 2376109 | A1 | 10/2011 |
| EP | 2714079 | B1 | 9/2016 |
| EP | 2601216 | B1 | 1/2018 |
| WO | WO-2004/063351 | A2 | 7/2004 |
| WO | WO-2005/111079 | A2 | 11/2005 |
| WO | WO-2010/080538 | A1 | 7/2010 |
| WO | WO-2011/034582 | A2 | 3/2011 |
| WO | WO-2011/038290 | A2 | 3/2011 |
| WO | WO-2011/046623 | A2 | 4/2011 |
| WO | WO-2012/018687 | A1 | 2/2012 |
| WO | WO-2012/162068 | A2 | 11/2012 |
| WO | WO-2013/070776 | A1 | 5/2013 |

(Continued)

OTHER PUBLICATIONS

Adams, P. D., et al., "Phenix: A Comprehensive Python-Based System for Macromolecular Structure Solution," Acta Crystallographica, Section D, Biological Crystallography, vol. 66, pp. 213-221, 9 pages (2010).

Adams, P.D., et al., "PHENIX: Building New Software for Automated Crystallographic Structure Determination," Acta Crystallographica, Section D, Biological Crystallography, vol. 58, pp. 1948-1954, 7 pages (2002).

Alam, S. M., et al., "Differential Reactivity of Germ Line Allelic Variants of a Broadly Neutralizing HIV-1 Antibody to a gp41 Fusion Intermediate Bonformation," Journal of Virology, vol. 85, No. 22, pp 11725-11731 (Nov. 2011).

(Continued)

*Primary Examiner* — Stacy B Chen

(74) *Attorney, Agent, or Firm* — Baker Donelson

(57) ABSTRACT

The invention is directed to HIV-1 neutralizing antibodies and methods for their uses.

28 Claims, 235 Drawing Sheets

Specification includes a Sequence Listing.

(56) References Cited

FOREIGN PATENT DOCUMENTS

| | | | |
|---|---|---|---|
| WO | WO-2014/159940 | A1 | 10/2014 |
| WO | WO-2015/021089 | A1 | 2/2015 |
| WO | WO-2015/026892 | A1 | 2/2015 |
| WO | WO-2015/026894 | A2 | 2/2015 |
| WO | WO-2016/149698 | A2 | 9/2016 |
| WO | WO-2016/149710 | A2 | 9/2016 |
| WO | WO-2017/011413 | A1 | 1/2017 |
| WO | WO-2017/011414 | A1 | 1/2017 |

OTHER PUBLICATIONS

Alam, S. M., et al., “Role of HIV Membrane in Neutralization by Two Broadly Neutralizing Antibodies,” Proceedings of the National Academy of Sciences of the United States of America, vol. 106, pp. 20234-20239 (Dec. 1, 2009).
Alam, S. M., et al., “The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes,” Journal of Immunology, vol. 178, pp. 4424-4435 (2007). Alamyar, E., et al., “IMGT® Tools for the Nucleotide Analysis of Immunoglobulin (IG) and T Cell Receptor (TR) V-(D)-J Repertoires, Polymorphisms, and IG Mutations: IMGT/V-QUEST and IMGT/HighV-QUEST for NGS,” Immunogenetics, Methods in Molecular Biology, vol. 882, pp. 569-604 (Abstract only—2 pages) (Apr. 26, 2012).
Altschul, S. F., et al., “Basic Local Alignment Search Tool,” Journal of Molecular Biology, vol. 215, pp. 403-410 (May 15, 1990).
Altschul, S.F., et al., “Issues in searching molecular sequence databases ,” Nature Genetics, vol. 6, pp. 119-129 (Feb. 1994).
Amanna, I. J., et al., “Duration of humoral immunity to common viral and vaccine antigens,” The New England Journal of Medicine, vol. 357, pp. 1903-1915 (2007).
Atwell, J., et al., “Stable Heterodimers From Remodeling the Domain Interface of a Homodimer Using a Phage Display Library,” Journal of Molecular Biology, vol. 270, pp. 26-35 (Apr. 25, 1997).
Barouch, D. H., et al., “Therapeutic Efficacy of Potent Neutralizing HIV-1 Specific Monoclonal Antibodies in SHIV-Infected Rhesus Monkeys,” Nature, vol. 503, pp. 224-228, Author Manuscript—24 total pages (Nov. 14, 2013).
Bird, R. E., et al., “Single-Chain Antigen-Binding Proteins,” Science, vol. 242, pp. 423-426 (Oct. 21, 1988).
Bolotin, D. A., et al., “MiXCR: Software for Comprehensive Adaptive Immunity Profiling,” Nature Methods, vol. 12, No. 5, pp. 380-381 (May 2015).
Bonsignori, M., et al., “Analysis of a Clonal Lineage of HIV-1 Envelope V2/V3 Conformational Epitope-Specific Broadly Neutralizing Antibodies and Their Inferred Unmutated Common Ancestors,” Journal of Virology, vol. 85, pp. 9998-10009 (Jul. 18, 2011).
Bonsignori, M., et al., “HIV-1 Envelope Induces Memory B Cell Responses that Correlate with Plasma Antibody Levels After Envelope gp 120 Protein Vaccination or HIV-1 Infection,” Journal of Immunology, vol. 183, pp. 2708-2717 Author Manuscript—24 total pages (Aug. 15, 2009).
Bonsignori, M., et al., “Two Distinct Broadly Neutralizing Antibody Specificities of Different Clonal Lineages in a Single HIV-1-Infected Donor: Implications for Vaccine Design,” Journal of Virology, vol. 86, pp. 4688-4692 (Apr. 2012).
Boutz, D.R., et al., “Proteomic Identification of Monoclonal Antibodies from Serum,” Analytical Chemistry, vol. 86, pp. 4758-4766 (2014).
Byrne, H., et al., “A Tale of Two Specificities: Bispecific Antibodies for Therapeutic and Diagnostic Applications,” Trends in Biotechnology, vol. 31, No. 11, pp. 621-632 (Nov. 2013).
Chen, J., et al., “Mechanism of HIV-I neutralization by antibodies targeting a membrane-proximal region of gp4l,” Journal of Virology, vol. 88, pp. 1249-1258 (2014).
Chen, K. S., et al., “Monoclonal Antibody Therapy for Malignant Glioma,” Giloma, Advances in Experimental Medicine and Biology, vol. 746, pp. 121-141, 39 total pages (2012).
Chen, Y., et al., “Development of Polyether Urethane Intravaginal Rings for the Sustained Delivery of Hydroxychloroquine,” Drug Design, Development and Therapy, vol. 8, pp. 1801-1815 (2014).
Cheung, W. C., et al., “A Proteomics Approach for the Identification and Cloning of Monoclonal Antibodies from Serum,” Nature Biotechnology, vol. 30, No. 5, pp. 447-452, 8 total pages including “Online Methods” (May 2012).
Chuang, G. Y., et al., “Residue-Level Prediction of HIV-1 Antibody Epitopes Based on Neutralization of Diverse Viral Strains,” Journal of Virology, vol. 87, pp. 10047-10058 (2013).
Chuang, G., et al., “Eliminating Antibody Polyreactivity Through Addition of N-Linked Glycosylation,” Protein Science, vol. 24, pp. 1019-1030 (May 12, 2015).
Corpet, F., “Multiple Sequence Alignment with Hierarchical Clustering,” Nucleic Acids Research, vol. 16, No. 22, pp. 10881-10890 (Nov. 25, 1988).
Costa, A. R., et al., “Guidelines to Cell Engineering for Monoclonal Antibody Production,” European Journal of Pharmaceutics and Biopharmaceutics, vol. 74, No. 2, pp. 127-138 (Feb. 2010).
DeKosky, B. J., et al., “High-Throughput Sequencing of the Paired Human Immunoglobulin Heavy and Light Chain Repertoire,” Nature Biotechnology, vol. 31, No. 2, pp. 166-169, Author Manuscript—13 total pages (Feb. 2013).
DeKosky, B. J., et al., “In-Depth Determination and Analysis of the Human Paired Heavy- and Light-Chain Antibody Repertoire,” Nature Medicine, vol. 21, No. 2, pp. 86-91, 8 total pages (Jan. 1, 2015).
Emsley, P., et al., “Coot: Model-Building Tools for Molecular Graphics,” Acta Crystallographica Section D, Biology Crystallography, vol. 60, pp. 2126-2132 (2004).
Fahrner, R. L., et al., “Industrial Purification of Pharmaceutical Antibodies: Development, Operation, and Validation of Chromatography Processes,” Biotechnology & Genetic Engineering Reviews, vol. 18, pp. 301-327 (2001).
Felstein, Joseph, PHYLIP (Phylogeny Inference Package) version 3.695, Distributed by the author, Department of Genome Sciences, University of Washington, Seattle, 74 total pages (Apr. 2013).
Frey, G., et al., “Distinct Conformational States of HIV-1 gp41 are Recognized by Neutralizing and Non-Neutralizing Antibodies,” Nature Structural & Molecular Biology, vol. 17, pp. 1486-1491, Author Manuscript—22 total pages (2010).
Gao, F., et al., “Cooperation of B cell lineages in induction of HIV-1-broadly neutralizing antibodies,” Cell, vol. 158, No. 3, pp. 481-491, Author Manuscript—15 total pags (Jul. 31, 2014).
Garber, K., “Bispecific Antibodies Rise Again,” Nature Reviews—Drug Discovery, vol. 13, pp. 799-801 (Nov. 2014).
Georgiev, I. S., et al., “Delineating Antibody Recognition in Polyclonal Sera from Patterns of HIV-1 Isolate Neutralization,” Science, vol. 340, pp. 751-756 (May 10, 2013).
Gray E. S., et al., “Antibody Specificities Associated with Neutralization Breadth in Plasma from Human Immunodeficiency Virus Type 1 subtype C-Infected Blood Donors,” Journal of Virology, vol. 83, pp. 8925-8937 (2009).
Gray, E. S., et al., “Broad Neutralization of Human Immunodeficiency Virus Type 1 Mediated by Plasma Antibodies against the gp41 Membrane Proximal External Region,” Journal of Virology, vol. 83, No. 21, pp. 11265-11274 (Aug. 19, 2009).
Gray, E. S., et al., “Insensitivity of Paediatric HIV-1 subtype C Viruses to Broadly Neutralising Monoclonal Antibodies Raised Against Subtype B,” Public Library of Science Medicine, vol. 3, pp. 1023-1031 (2006).
Haynes, B. F., et al., “Immune-Correlates Analysis of an HIV-1 Vaccine Efficacy Trial,” The New England Journal of Medicine, vol. 366, pp. 1275-1286 (2012).
Haynes, B. F., et al., “Cardiolipin Polyspecific Autoreactivity in Two Broadly Neutralizing HIV-1 Antibodies,” Science, vol. 308, pp. 1906-1908 (Jun. 25, 2005).
Higgins, D. G., et al., “CLUSTAL: A Package for Performing Multiple Sequence Alignment on a Microcomputer,” Gene, vol. 73, No. 1, pp. 237-244, Abstract Only—1 page (Dec. 15, 1988).
Higgins, D. G., et al., “Fast and Sensitive Multiple Sequence Alignments on a Microcomputer,” CABIOS, vol. 5, No. 2, pp. 151-153, Abstract only—1 page (Apr. 5, 1989).

(56) References Cited

OTHER PUBLICATIONS

Hladik, F., et al., "Mucosal Effects of Tenofovir 1% Gel," Elife, vol. 4, 21 pages (2015).
Holliger, P., et al., "Specific Killing of Lymphoma Cells by Cytotoxic T-Cells Mediated by a Bispecific Diabody," Protein Engineering, vol. 9, pp. 299-305 (1996).
Huang, J., et al., "Broad and Potent Neutralization of HIV-1 by a gp41-Specific Human Antibody," Nature, vol. 491, No. 7424, pp. 406-412, Author Manuscript—22 pages (Nov. 15, 2012).
Huston, J. S., et al., "Protein Engineering of Antibody Binding Sites: Recovery of Specific Activity in an Anti-Digoxin Single-Chain Fv Analogue Produced in *Escherichia Coli*," Proceedings of the National Academy of Sciences of the United States of America, vol. 85, pp. 5879-5883 (Aug. 1988).
Kardava, L., et al., "Abnormal B Cell Memory Subsets Dominate HIV-Specific Responses in Infected Individuals," The Journal of Clinical Investigation, vol. 124, No. 7, pp. 3252-3262 (Jul. 2014).
Kepler, T. B., "Reconstructing a B-cell clonal lineage. I. Statistical inference of unobserved ancestors," F1000Research, vol. 2, No. 103 (Apr. 3, 2013).
Kepler, T. B., et al., "Reconstructing a B-Cell Clonal Lineage. II. Mutation, Selection, and Affinity Maturation," Frontiers in Immunology, vol. 5, No. 170, pp. 1-10 (Apr. 22, 2014).
Kim, J. Y., et al., "CHO Cells in Biotechnology for Production of Recombinant Proteins: Current State and Further Potential," Applied Microbiology and Biotechnology, vol. 93, No. 3, pp. 917-930 (Feb. 2012).
Kipriyanov, S. M., et al., "Bispecific Tandem Diabody for Tumor Therapy with Improved Antigen Binding and Pharmacokinetics," Journal of Molecular Biology, vol. 293, No. 1 pp. 41-66 (Oct. 15, 1999).
Ko, S.-Y., et al., "Enhanced Neonatal Fc Receptor Function Improves Protection Against Primate SHIV Infection," Nature, vol. 514, No. 7524, pp. 642-645, Author Manuscript—22 total pages (Oct. 30, 2014).
Kostelny, et al., "Formation of a bispecific antibody by the use of leucine zippers," J. Immunol, vol. 148, pp. 1547-1553 (1992).
Krissinel, E., et al., "Inference of Macromolecular Assemblies from Crystalline State," Journal of Molecular Biology, vol. 372, No. 3, pp. 774-797 (May 13, 2007).
Kuo, T., et al., "Neonatal Fe Receptor and IgG-based Therapeutics," mAbs, vol. 3, No. 5, pp. 422-430, 10 total pages (2011).
Lavinder, J. J., et al., "Identification and Characterization of the Constituent Human Serum Antibodies Elicited by Vaccination," Proceedings of the National Academy of Sciences of the United States of America, vol. 111, No. 6, pp. 2259-2264 (Feb. 11, 2014).
Lavinder, J. J., et al., "Next-Generation Sequencing and Protein Mass Spectrometry for the Comprehensive Analysis of Human Cellular and Serum Antibody Repertoires," Current Opinion in Chemical Biology, vol. 24, pp. 112-120 (Feb. 2015).
Levesque, M. C., et al., "Polyclonal B Cell Differentiation and Loss of Gastrointestinal Tract Germinal Centers in the Earliest Stages of HIV-1 Infection," Public Library of Science Medicine, vol. 6, No. 7, pp. 1-19 (Jul. 2009).
Li, M., et al., "Human immunodeficiency virus type 1 env clones from acute and early subtype B infections for standardized assessments of vaccine-elicited neutralizing antibodies," Journal of virology, vol. 79, No. 16, pp. 10108-10125 (Aug. 2005).
Liao, H.-X., et al., "Co-Evolution of a Broadly Neutralizing HIV-1 Antibody and Founder Virus," Nature, vol. 496, No. 7446, pp. 469-476—25 total pages (Apr. 25, 2013).
Liao, H.-X., et al., "High-throughput isolation of immunoglobulin genes from single human B cells and expression as monoclonal antibodies," Journal of Virological Methods, vol. 158, Nos. 1-2, pp. 171-179, Author Manuscript—22 total pages (Jun. 2009).
Liu, M., et al., "Polyreactivity and Autoreactivity Among HIV-1 Antibodies," Journal of Virology, vol. 89, No. 1, pp. 784-798 (Jan. 2015).
Magoc, T., et al., "FLASH: fast length adjustment of short reads to improve genome assemblies," Bioinformatics, vol. 27, No. 21, pp. 2957-2963 (2011).
Malcolm, R.K., et al., "Beyond HIV microbicides: multipurpose prevention technology products," Royal College of Obstetricians and Gynaecologists, vol. 121, Suppl. 5, pp. 62-69 (2014).
Mascola, et al., "HIV-1 Neutralizing Antibodies: Understanding Nature's Pathways," Immunological Reviews, vol. 254, No. 1, pp. 225-244, Author Manuscript—29 total pages (Jun. 16, 2013).
McCafferty, J., et al., "Phage Antibodies: Filamentous Phage Displaying Antibody Variable Domains," Nature, vol. 348, pp. 552-554 (Dec. 6, 1990).
McDaniel, J. R., et al., "Ultra-High-Throughput Sequencing of the Immune Receptor Repertoire from Millions of Lymphocytes," Nature Protocols, vol. 11, pp. 429-442, 14 total pages (Feb. 4, 2016).
Moir, S. et al., "Evidence for HIV-Associated B Cell Exhaustion in a Dysfunctional Memory B Cell Compartment in HIV-infected Viremic Individuals," The Journal of Experimental Medicine, vol. 205, No. 8, pp. 1797-1805 (Aug. 4, 2008).
Moldt, B., et al., "A Nonfucosylated Variant of the Anti-HIV-1 Monoclonal Antibody b12 Has Enhanced FcγRIIIa-Mediated Antiviral Activity In Vitro but Does Not Improve Protection Against Mucosal SHIV Challenge in Macaques," Journal of Virology, vol. 86, No. 11, pp. 6189-6196, (Jun. 2012).
Montefiori, D. C., "Evaluating Neutralizing Antibodies Against HIV, SIV, and SHIV in Luciferase Reporter Gene Assays," Current Protocols in Immunology, vol. 64, No. 1, Chapter 12, Unit 11, pp. 12.11.1-12.11.17, Abstract Only—1 total page (2005).
Montefiori, D. C., "Measuring HIV Neutralization in a Luciferase Reporter Gene Assay," HIV Protocols: Methods In Molecular Biology, vol. 485, pp. 395-405 (2009).
Moody, M. A., et al., "HIV-1 gpl20 Vaccine Induces Affinity Maturation in Both New and Persistent Antibody Clonal Lineages," Journal of Virology, vol. 86, No. 14, pp. 7496-7507, 13 total pages (2012).
Moore, P., et al., "Application of Dual Affinity Retargeting Molecules to Achieve Optimal Redirected T-cell Killing of B-cell Lymphoma," Blood Journal, vol. 117, No. 17, pp. 4542-4551 (2011).
Morris, L., et al., "Isolation of a Human Anti-HIV gp41 Membrane Proximal Region Neutralizing Antibody by Antigen-Specific Single B Cell Sorting," PLoS ONE, vol. 6, No. 9, pp. 1-10 (Sep. 30, 2011).
Nagorsen, D., et al., "Immunomodulatory Therapy of Cancer with T Cell-Engaging BiTE Antibody Blinatumomab," Experimental Cell Research, vol. 317, No. 9, pp. 1255-1260 (May 16, 2011).
Needleman, S. B., et al., "A General Method Applicable to the Search for Similarities in the Amino Acid Sequence of Two Proteins," Journal of Molecular Biology, vol. 48, No. 3, pp. 443-453 (Mar. 28, 1970).
Otwinowski, Z., et al., "Processing of X-ray diffraction data collected in oscillation mode," Methods in Enzymology, vol. 276, pp. 307-326 (1997).
Pearson, W. R., et al., "Improved Tools for Biological Sequence Comparison," Proceedings of the National Academy of Sciences of the United States of America, vol. 85, No. 8, pp. 2444-2448 (Apr. 1988).
Purtha, W. E., et al., "Memory B Cells, but Not Long-Lived Plasma Cells, Possess Antigen Specificities for Viral Escape Mutants," The Journal of Experimental Medicine, vol. 208, No. 13, pp. 2599-2606 (Dec. 19, 2011).
Ridgway, J. B. B., et al., "'Knobs-Into-Holes' Engineering of Antibody CH3 Domains for Heavy Chain Heterodimerization," Protein Engineering, vol. 9, No. 7, pp. 617-621 (1996).
Robbie, G. J., et al., "A Novel Investigational Fe-Modified Humanized Monoclonal Antibody, Motavizumab-YTE, Has an Extended Half-Life in Healthy Adults," Antimicrobial Agents and Chemotherapy, vol. 57, No. 12, pp. 6147-6153 (Dec. 2013).
Romain, G., et al., "Antibody Fc Engineering Improves Frequency and Promotes Kinetic Boosting of Serial Killing Mediated by NK Cells," Blood Journal, vol. 124, No. 22, pp. 3241-3249, (Nov. 20, 2014).
Rouet, R., et al., "Bispecific Antibodies with Native Chain Structure," Nature Biotechnology, vol. 32, No. 2, 136-137 (Feb. 2014).

(56) References Cited

OTHER PUBLICATIONS

Rudicell, R. S., et al., "Enhanced Potency of a Broadly Neutralizing HIV-I Antibody In Vitro Improves Protection against Lentiviral Infection In Vivo," Journal of Virology, vol. 88, No. 21, pp. 12669-12682 (Nov. 2014).
Sarzotti-Kelsoe, M., et al., "Optimization and Validation of the TZM-bl Assay for Standardized Assessments of Neutralizing Antibodies Against HIV-1," Journal of Immunoligical Methods, vol. 409, pp. 131-146, Author Manuscript—37 total pages (Jul. 2014).
Scheid, J. F., et al., "Broad Diversity of Neutralizing Antibodies Isolated from Memory B Cells in HIV-infected Individuals," Nature, vol. 458, No. 7238, pp. 636-640 (Apr. 2, 2009).
Seaman, M. S., et al., "Tiered categorization of a diverse panel of HIV-1 Env pseudoviruses for assessment of neutralizing antibodies," Journal of Virology, vol. 84, No. 3, pp. 1439-1452 (Feb. 2010).
Seimetz, D., et al., "Development and approval of the trifunctional antibody catumaxomab (anti-EpCAM × anti-CD3) as a targeted cancer immunotherapy," Cancer Treatment Reviews, vol. 36, No. 6, pp. 458-467 (Oct. 2010).
Shen, X., et al., "Prolonged Exposure of the HIV-1 gp41 Membrane Proximal Region with L669S Substitution," Proceedings of the National Academy of Sciences USA, vol. 107, No. 13, pp. 5972-5977 (Mar. 30, 2010).
Shields, R. L., et al., "High Resolution Mapping of the Binding Site on Human IgG1 for FcγRI, FcγRII, FcγRIII, and FcRn and Design of IgG1 Variants with Improved Binding to the FcγR," Journal of Biological Chemistry, vol. 276, No. 9, pp. 6591-6604 (Mar. 2, 2001).
Shingai, M., et al., "Antibody Mediated Immunotherapy of Macaques Chronically Infected with SHIV Suppresses Viremia," Nature, vol. 503, No. 7475, pp. 277-280, Author Manuscript—21 pages (Nov. 14, 2013).
Simek, M. D., et al., "Human Immunodeficiency Virus Type 1 Elite Neutralizers: Individuals with Broad and Potent Neutralizing Activity Identified by Using a High-Throughput Neutralization Assay together with an Analytical Selection Algorithm," Journal of Virology, vol. 83, No. 14, pp. 7337-7348 (Jul. 2009).
Smith, T. F., et al., "Comparison of Biosequences," Advances in Applied Mathematics, vol. 2, No. 4, pp. 482-489, (Dec. 1981).
Songsivilai, S., "Bispecific Antibody: A Tool for Diagnosis and Treatment of Disease," Clinical and Experimental Immunology, vol. 79, No. 3, pp. 315-321 (Mar. 1990).
Stone, A., "Multipurpose Prevention Technologies for Reproductive and Sexual Health," Reproductive Health Matters, vol. 22, No. 44, pp. 213-217 (2014).
Sun, Z.-Y. J., et al., "HIV-1 Broadly Neutralizing Antibody Extracts Its Epitope from a Kinked gp41 Ectodomain Region on the Viral Membrane," Immunity, vol. 28, No. 1, pp. 52-63 (Jan. 18, 2008).
Tiller, T., et al., "Efficient Generation of Monoclonal Antibodies from Single Human B Cells by Single Cell RT-PCR and Expression Vector Cloning," Journal of Immunological Methods, vol. 329, No. 1-2, pp. 112-124, Author Manuscript—19 total pages (Jan. 1, 2008).
Tomaras, G. D., et al., "Polyclonal B Cell Responses to Conserved Neutralization Epitopes in a Subset of HIV-1-Infected Individuals," Journal of Virology, vol. 85, No. 21, pp. 11502-11519 (Nov. 2011).
U.S. Appl. No. 62/056,568, filed Sep. 28, 2014 entitled "CH0848 DH270 Ab" (47 total pages).
U.S. Appl. No. 62/170,558, filed Jun. 3, 2015 entitled "Neutralizing Antibodies to HIV-1 Env and Their Use" (135 total pages).
Walker, L. M., et al., "A Limited Number of Antibody Specificities Mediate Broad and Potent Serum Neutralization in Selected HIV-1 Infected Individuals," Public Library of Science Pathogens, vol. 6, No. 8, pp. 1-14 (Aug. 2010).
Walker, L. M., et al., "Broad Neutralization Coverage of HIV by Multiple Highly Potent Antibodies," Nature, vol. 477, No. 7365, pp. 466-470, Author Manuscript—14 total pages (Sep. 22, 2011).
Walker, L. M., et al., "Broad and potent neutralizing antibodies from an African donor reveal a new HIV-1 vaccine target," Science, vol. 326, pp. 285-289 (Oct. 19, 2009).
Wine, Y., et al., "Molecular Deconvolution of the Monoclonal Antibodies that Comprise the Polyclonal Serum Response," Proceedings of the National Academy of Sciences of the United States of America, vol. 110, No. 8, pp. 2993-2998 (Feb. 19, 2013).
Wine, Y., et al., "Serology in the 21st century: the molecular-level analysis of the serum antibody repertoire," Current Opinion in Immunology, vol. 35, pp. 89-97, Author Manuscript 17 pages (Aug. 2015).
Winn, M. D., et al., "Overview of the CCP4 suite and current developments. Acta crystallographica," Acta Crystallographica Section D, Biological Crystallography, vol. 67, pp. 235-242 (2011).
Wrammert, J., et al., "Broadly Cross-Reactive Antibodies Dominate the Human B Cell Response Against 2009 Pandemic RINI Influenza Virus Infection," The Journal of Experimental Medicine, vol. 208, No. 1, pp. 181-193 (Jan. 17, 2011).
Wu, C., et al., "Generation and Characterization of a Dual Variable Domain Immunoglobulin (DVD-Ig™) Molecule," Antibody Engineering, vol. 2, Springer Berlin Heidelberg, pp. 239-250, 23 total pages (2010).
Xie, Z., et al., "A New Format of Bispecific Antibody: Highly Efficient Heterodimerization, Expression and Tumor Cell Lysis," Journal of Immunological Methods, vol. 296, Nos. 1-2 pp. 95-101 (Jan. 2005).
Yang, G., et al., "Identification of Autoantigens Recognized by the 2F5 and 4E10 Broadly Neutralizing HIV-1 Antibodies," The Journal of Experimental Medicine, vol. 210, No. 2, pp. 241-256 (2013).
Yang, L., et al., "Passive Immunization against HIV/AIDS by Antibody Gene Transfer," Viruses, vol. 6, pp. 428-447 (2014).
Zalevsky, et al., "Enhanced Antibody Half-Life Improves in vivo Activity," Nature Biotechnology, vol. 28, No. 2, pp. 157-159, Author Manuscript—6 total pages (Feb. 2010).
Zwick, M. B., et al., "Broadly Neutralizing Antibodies Targeted to the Membrane-Proximal External Region of Human Immunodeficiency Virus Type 1 Glycoprotein gp41," Journal of virology, vol. 75, No. 22, pp. 10892-10905 (Nov. 2001).
Nelson, J.D., et al., "An Affinity-Enhanced Neutralizing Antibody against the Membrane-Proximal External Region of Human Immunodeficiency Virus Type 1 gp41 Recognizes an Epitope between Those of 2F5 and 4E10," Journal of Virology, vol. 81, No. 8, pp. 4033-4043 (Apr. 2007).
Hulsik, D.L., et al., "A gp41 MPER-specific Llama VHH Requires a Hydrophobic CDR3 for Neutralization but not for Antigen Recognition," PLOS Pathog., vol. 9, Issue 3, e1003202, pp. 1-16 (Mar. 2013).
Kong, R., et al., "Improving Neutralization Potency and Breadth by Combining Broadly Reactive HIV-1 Antibodies Targeting Major Neutralization Epitopes," Journal of Virology, vol. 89, No. 5, pp. 2659-2671 (Mar. 2015).
International Search Report and Written Opinion dated Sep. 26, 2016 in PCT/US2016/023488 (13 total pages).
Alam, S.M., "Human Immunodeficiency Virus Type 1 gp41 Antibodies That Mask Membrane Proximal Region Epitopes: Antibody Binding Kinetics, Induction, and Potential for Regulation in Acute Infection," Journal of Virology, vol. 82, No. 1, pp. 115-225 (Jan. 2008).
McGuire, A.T., et al., "Diverse Recombinant HIV-1 Envs Fail to Activate B Cells Expressing the Germline B Cell Receptors of the Broadly Neutralizing Anti-HIV-1 Antibodies PG9 and 447-52D," Journal of Virology, vol. 88, No. 5, pp. 2645-2657 (Mar. 2014).
GenBank Accession No. AAY33460.1, last downloaded from <https://www.ncbi.nlm.nih.gov/> on Aug. 31, 2016 (2 total pages).
Kramer, R..A, et al., "The human antibody repertoire specific for rabies virus glycoprotein as selected from immune libraries," Eur. J. Immunol., vol. 35, pp. 2131-2145 (2005).
Williams, L., et al., "The Memory B Cell and Serum Antibody Repertoire Share Clonal Lineage Members of HIV-1 gp41 Broadly Neutralizing Antibodies," abstract presented at Keystone 2016 Meeting (1 total page).

(56) References Cited

OTHER PUBLICATIONS

Sievers, S.A., et al., "Antibody Engineering for Increased Potency, Breadth and Half-life," Curr. Opin. HIV AIDS, vol. 10, No. 3, pp. 151-159 (May 2015).
Brunel, F.M., et al., "Structure-Function Analysis of the Epitope for 4E10, a Broadly Neutralizing Human Immunodeficiency Virus Type 1 Antibody," vol. 80, No. 4, pp. 1680-1687 (Feb. 2006).

* cited by examiner

MPR.03-biotin: KKK-NEQELLELDKWASLWNWFDITNWLWYIR

MPR.03: NEQELLELDKWASLWNWFDITNWLWYIR

| PT ID | Antibody ID | VH ID | VH | DH | JH | Mutation | HCDR3 | VK/L ID | VK/VL | JK/L | Mutation | LCDR3 |
|---|---|---|---|---|---|---|---|---|---|---|---|---|
| 704-01-021-0 | DH511 | H510056 | 3~15 | 3~3 | 6 | 15.7% | 24 | K510037 | VK1~39 | 2 | 17.2% | 11 |
| 704-01-021-0 | DH512 | H510049 | 3~15 | 3~3 | 6 | 20.1% | 23 | K510032 | VK1~39 | 2 | 14.7% | 11 |
| 704-01-021-0 | DH513 | H570022 | 3~15 | 3~3 | 6 | 15.3% | 24 | K570010 | VK1~39 | 2 | 16.3% | 11 |
| 704-01-021-0 | DH514 | H570029 | 3~15 | 3~3 | 6 | 20.5% | 23 | K570016 | VK1~39 | 2 | 14.6% | 11 |
| 704-01-021-0 | DH515 | H510052 | 3~15 | 3~3 | 6 | 21.8% | 23 | K510035 | VK1~39 | 2 | 18.3% | 11 |
| 704-01-021-0 | DH516 | H510048 | 3~15 | 3~3 | 6 | 16.0% | 24 | K510031 | VK1~39 | 2 | 19.0% | 11 |
| 704-01-021-0 | DH517 | H510053 | 4~34 | 2~2 | 6 | 22.8% | 24 | L510018 | VL3-19 | 2 | 14.3% | 12 |
| 707-01-053-6 | DH518 | H570010 | 4~39 | 3~3 | 4 | 16.2% | 20 | K570004 | VK1~39 | 2 | 15.4% | 9 |
| 704-01-124-4 | DH536* | H510127 | 1~69 | 3~3 | 2 | 8.3% | 18 | L510050 | VL2~14 | 2 | 5.6% | 10 |
| 707-01-058-5 | DH537* | H008587 | 1~69 | 1~1 | 5 | 9.0% | 17 | K006517 | VK1~39 | 2 | 6.9% | 9 |

Figure 4

| PT ID | Antibody ID | Old Antibody ID | Netralization Titer (TCID50), ug/ml | | | | |
|---|---|---|---|---|---|---|---|
| | | | BG1168 | CH505 | DU172 | MN | MuLV |
| 704-01-021-0 | **DH511** | Ab510056 | <0.023 | 18.573 | 1.238 | <0.023 | >50 |
| 704-01-021-0 | **DH512** | Ab510049 | 0.22 | 8.537 | 3.43 | <0.023 | >50 |
| 704-01-021-0 | **DH513** | Ab570022 | 0.651 | 24.19 | 3.212 | <0.023 | >50 |
| 704-01-021-0 | **DH514** | Ab570029 | 0.809 | 28.229 | 3.815 | <0.023 | >50 |
| 704-01-021-0 | **DH515** | Ab510052 | 0.712 | 40.39 | 6.122 | 0.041 | >50 |
| 704-01-021-0 | **DH516** | Ab510048 | 0.608 | 45 | 6.538 | <0.023 | >50 |
| 704-01-021-0 | **DH517** | Ab510053 | 2.518 | >50 | 16.53 | 0.791 | >50 |
| 707-01-053-6 | **DH518** | Ab570010 | <0.023 | >50 | 5.174 | <0.023 | >50 |
| 703-01-124-4 | **DH536** | Ab510127 | >50 | >50 | >50 | 9.606 | >50 |
| 707-01-058-5 | **DH537** | Ab008587 | >50 | >50 | >50 | 0.246 | >50 |
| | | | <0.1 | >0.1-1.0 | >1.0-10 | >10-25 | >25-50 |

Figure 5

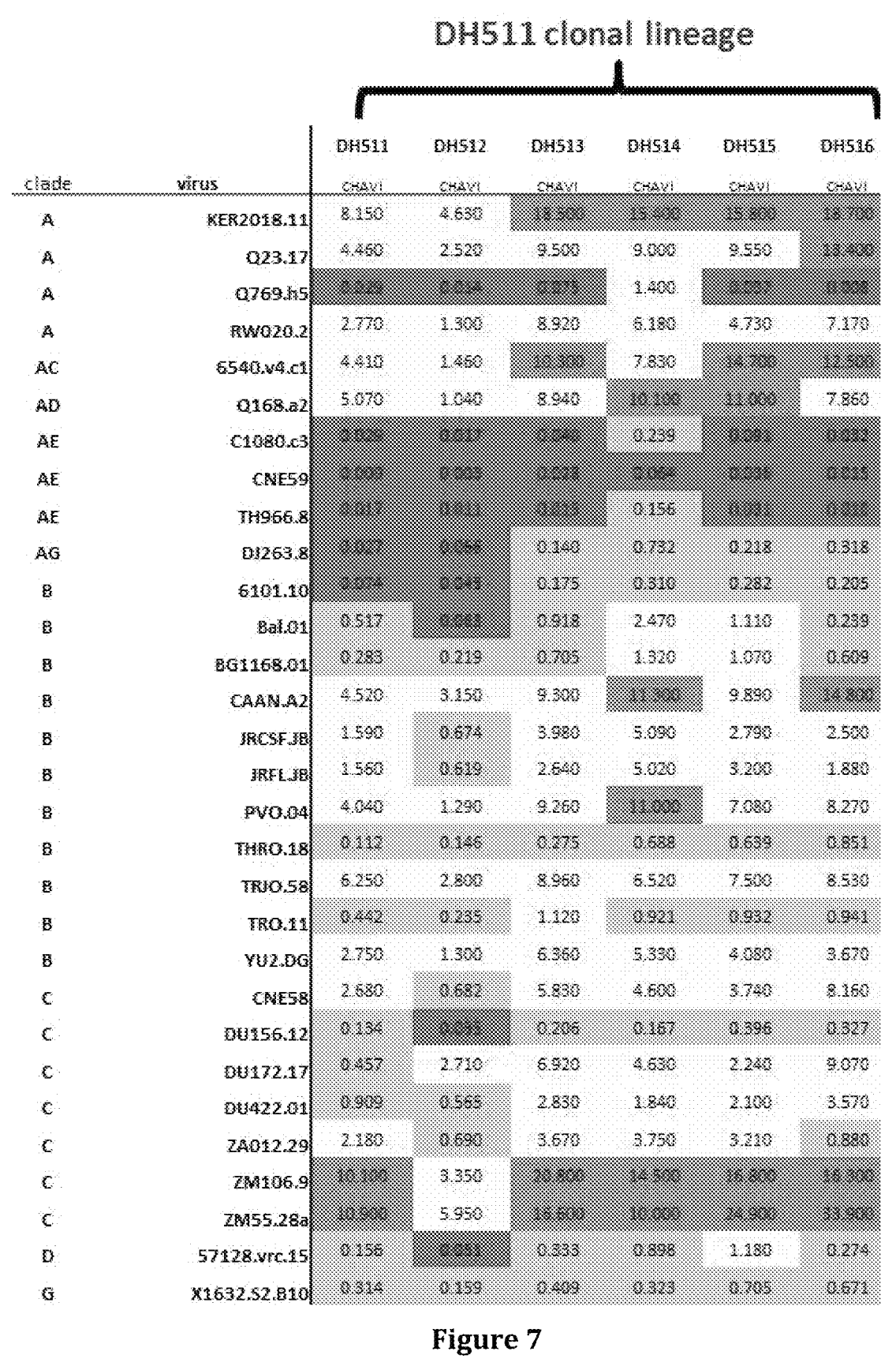

DH511 clonal lineage

| clade | virus | DH511 CHAVI | DH512 CHAVI | DH513 CHAVI | DH514 CHAVI | DH515 CHAVI | DH516 CHAVI |
|---|---|---|---|---|---|---|---|
| A | KER2018.11 | 8.150 | 4.630 | [illegible] | [illegible] | [illegible] | [illegible] |
| A | Q23.17 | 4.460 | 2.520 | 9.500 | 9.000 | 9.550 | [illegible] |
| A | Q769.h5 | [illegible] | [illegible] | [illegible] | 1.400 | [illegible] | [illegible] |
| A | RW020.2 | 2.770 | 1.300 | 8.920 | 6.180 | 4.730 | 7.170 |
| AC | 6540.v4.c1 | 4.410 | 1.460 | [illegible] | 7.830 | [illegible] | [illegible] |
| AD | Q168.a2 | 5.070 | 1.040 | 8.940 | [illegible] | [illegible] | 7.860 |
| AE | C1080.c3 | [illegible] | [illegible] | [illegible] | 0.239 | [illegible] | [illegible] |
| AE | CNE59 | [illegible] | [illegible] | [illegible] | [illegible] | [illegible] | [illegible] |
| AE | TH966.8 | [illegible] | [illegible] | [illegible] | 0.156 | [illegible] | [illegible] |
| AG | DJ263.8 | [illegible] | [illegible] | 0.140 | 0.732 | 0.218 | 0.318 |
| B | 6101.10 | [illegible] | [illegible] | 0.175 | 0.310 | 0.282 | 0.205 |
| B | Bal.01 | 0.517 | [illegible] | 0.918 | 2.470 | 1.110 | 0.239 |
| B | BG1168.01 | 0.283 | 0.219 | 0.705 | 1.320 | 1.070 | 0.609 |
| B | CAAN.A2 | 4.520 | 3.150 | 9.300 | [illegible] | 9.890 | [illegible] |
| B | JRCSF.JB | 1.590 | 0.674 | 3.980 | 5.090 | 2.790 | 2.500 |
| B | JRFL.JB | 1.560 | 0.619 | 2.640 | 5.020 | 3.200 | 1.880 |
| B | PVO.04 | 4.040 | 1.290 | 9.260 | [illegible] | 7.080 | 8.270 |
| B | THRO.18 | 0.112 | 0.146 | 0.275 | 0.688 | 0.639 | 0.851 |
| B | TRJO.58 | 6.250 | 2.800 | 8.960 | 6.520 | 7.500 | 8.530 |
| B | TRO.11 | 0.442 | 0.235 | 1.120 | 0.921 | 0.932 | 0.941 |
| B | YU2.DG | 2.750 | 1.300 | 6.360 | 5.330 | 4.080 | 3.670 |
| C | CNE58 | 2.680 | 0.682 | 5.830 | 4.600 | 3.740 | 8.160 |
| C | DU156.12 | 0.134 | [illegible] | 0.206 | 0.167 | 0.396 | 0.327 |
| C | DU172.17 | 0.457 | 2.710 | 6.920 | 4.630 | 2.240 | 9.070 |
| C | DU422.01 | 0.909 | 0.565 | 2.830 | 1.840 | 2.100 | 3.570 |
| C | ZA012.29 | 2.180 | 0.690 | 3.670 | 3.750 | 3.210 | 0.880 |
| C | ZM106.9 | 10.100 | 3.350 | [illegible] | 14.500 | 16.800 | [illegible] |
| C | ZM55.28a | [illegible] | 5.950 | [illegible] | [illegible] | [illegible] | [illegible] |
| D | 57128.vrc.15 | 0.156 | [illegible] | 0.333 | 0.898 | 1.180 | 0.274 |
| G | X1632.S2.B10 | 0.314 | 0.159 | 0.409 | 0.323 | 0.705 | 0.671 |

Figure 7

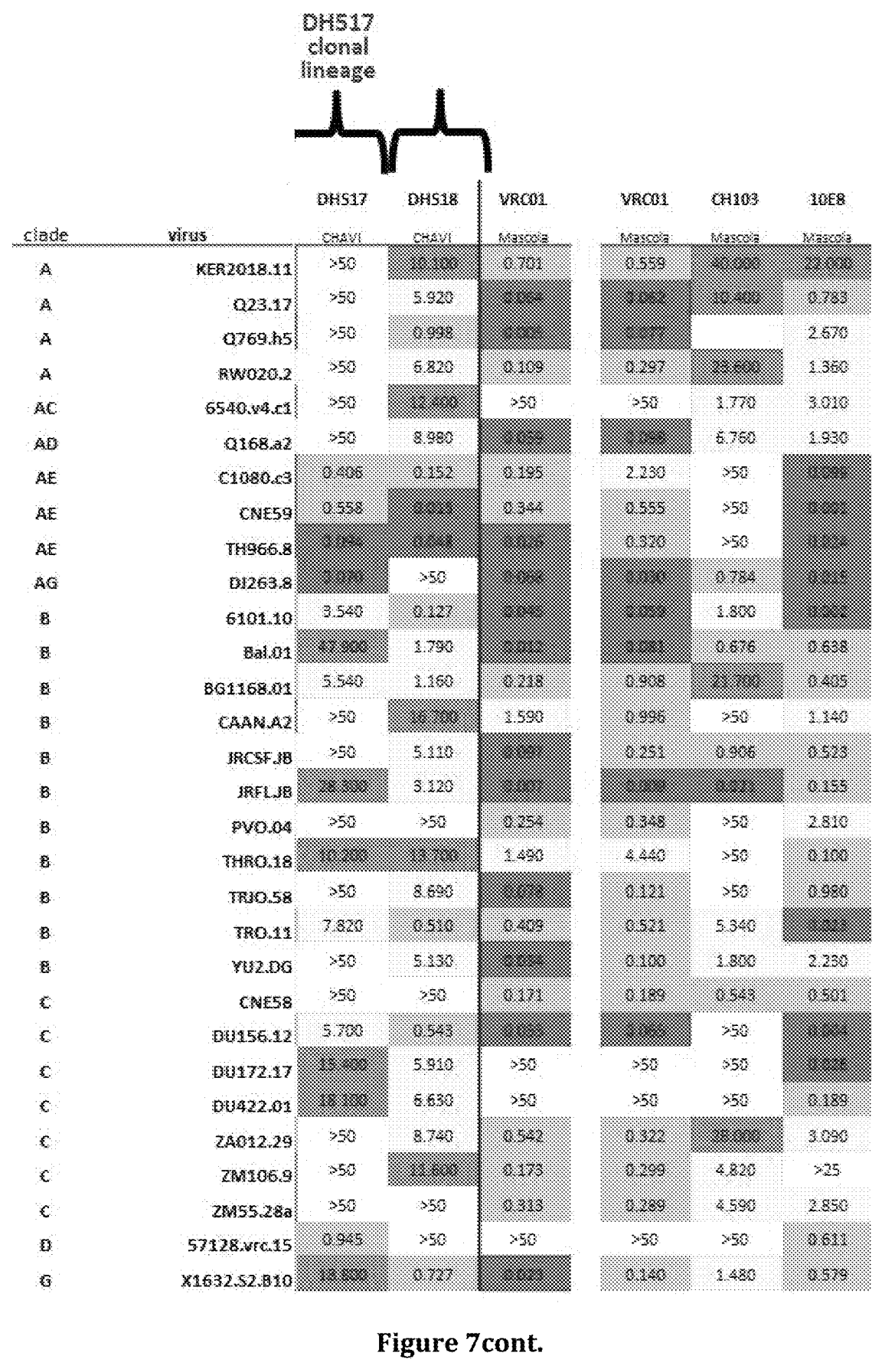

DH517 clonal lineage

| clade | virus | DH517 | DH518 | VRC01 | VRC01 | CH103 | 10E8 |
|---|---|---|---|---|---|---|---|
| | | CHAVI | CHAVI | Mascola | Mascola | Mascola | Mascola |
| A | KER2018.11 | >50 | 10.100 | 0.701 | 0.559 | 40.000 | 22.000 |
| A | Q23.17 | >50 | 5.920 | [illegible] | [illegible] | 10.400 | 0.783 |
| A | Q769.h5 | >50 | 0.998 | [illegible] | [illegible] | | 2.670 |
| A | RW020.2 | >50 | 6.820 | 0.109 | 0.297 | 23.600 | 1.360 |
| AC | 6540.v4.c1 | >50 | 12.400 | >50 | >50 | 1.770 | 3.010 |
| AD | Q168.a2 | >50 | 8.980 | [illegible] | [illegible] | 6.760 | 1.930 |
| AE | C1080.c3 | 0.406 | 0.152 | 0.195 | 2.230 | >50 | [illegible] |
| AE | CNE59 | 0.558 | [illegible] | 0.344 | 0.555 | >50 | [illegible] |
| AE | TH966.8 | [illegible] | [illegible] | [illegible] | 0.320 | >50 | [illegible] |
| AG | DJ263.8 | [illegible] | >50 | [illegible] | [illegible] | 0.784 | [illegible] |
| B | 6101.10 | 3.540 | 0.127 | [illegible] | [illegible] | 1.800 | [illegible] |
| B | Bal.01 | 47.900 | 1.790 | [illegible] | [illegible] | 0.676 | 0.638 |
| B | BG1168.01 | 5.540 | 1.160 | 0.218 | 0.908 | 21.700 | 0.405 |
| B | CAAN.A2 | >50 | 16.700 | 1.590 | 0.996 | >50 | 1.140 |
| B | JRCSF.JB | >50 | 5.110 | [illegible] | 0.251 | 0.906 | 0.523 |
| B | JRFL.JB | 28.300 | 3.120 | [illegible] | [illegible] | [illegible] | 0.155 |
| B | PVO.04 | >50 | >50 | 0.254 | 0.348 | >50 | 2.810 |
| B | THRO.18 | 10.200 | 13.700 | 1.490 | 4.440 | >50 | 0.100 |
| B | TRJO.58 | >50 | 8.690 | [illegible] | 0.121 | >50 | 0.980 |
| B | TRO.11 | 7.820 | 0.510 | 0.409 | 0.521 | 5.340 | [illegible] |
| B | YU2.DG | >50 | 5.130 | [illegible] | 0.100 | 1.800 | 2.230 |
| C | CNE58 | >50 | >50 | 0.171 | 0.189 | 0.543 | 0.501 |
| C | DU156.12 | 5.700 | 0.543 | [illegible] | [illegible] | >50 | [illegible] |
| C | DU172.17 | 15.400 | 5.910 | >50 | >50 | >50 | [illegible] |
| C | DU422.01 | 18.100 | 6.630 | >50 | >50 | >50 | 0.189 |
| C | ZA012.29 | >50 | 8.740 | 0.542 | 0.322 | 35.000 | 3.090 |
| C | ZM106.9 | >50 | 11.600 | 0.173 | 0.299 | 4.820 | >25 |
| C | ZM55.28a | >50 | >50 | 0.313 | 0.289 | 4.590 | 2.850 |
| D | 57128.vrc.15 | 0.949 | >50 | >50 | >50 | >50 | 0.611 |
| G | X1632.S2.B10 | 18.800 | 0.727 | [illegible] | 0.140 | 1.480 | 0.579 |

Figure 7cont.

| Antibody | IC50 | IC80 | IC50 <50ug/ml | IC80 <5ug/ml |
|---|---|---|---|---|
| 10E8 | 0.58 | 2.46 | 97% | 65% |
| DH512 | 0.65 | 5.12 | 100% | 50% |
| DH517 | 5.70 | 20.30 | 50% | 3% |
| DH518 | 5.13 | 14.00 | 83% | 20% |
| VRC01 | 0.27 | 0.73 | 87% | 81% |
| CH01+ CH31 | 3.73 | NA | 93% | NA |

Figure 8

| Antibody | IC50 | IC80 | IC50 <50ug/ml | IC80 <5ug/ml | Antibody Specificity |
|---|---|---|---|---|---|
| **PGT121** | **0.06** | **0.27** | **63%** | **48%** | **V3-glycan** |
| **PGT128** | **0.07** | **NA** | **63%** | **NA** | **V3-glycan** |
| *DH270IA1* | *0.07* | *0.22* | *63%* | *61%* | *V3-glycan* |
| *DH429* | *0.06* | *0.22* | *63%* | *60%* | *V3-glycan* |
| **VRC01** | **0.27** | **0.73** | **87%** | **81%** | **VH1-2 CD4bs** |
| *CH31* | *0.10* | *0.42* | *83%* | *80%* | *VH1-2 CD4bs (VRC01-like)* |
| *CH01* | *3.79* | *NA* | *46%* | *NA* | *V1V2-glycan* |
| *CH01+ CH31* | *3.73* | *NA* | *93%* | *NA* | *V1V2-glycan + VH1-2 CD4bs* |
| *CH103* | *4.54* | *NA* | *55%* | *NA* | *HCDR3 binder CD4 bs* |
| *CH98* | *4.20* | *NA* | *63%* | *NA* | *HCDR3 binder CD4 bs* |
| *DH493* | *5.98* | *NA* | *83%* | *NA* | *VH1-46 CD4bs (ANC131-like)* |
| *DH540* | *0.10* | *NA* | *90%* | *NA* | *N276-dependent CD4bs Ab (HJ16-like)* |

Figure 9

| Antibody | IC50 | IC80 | IC50 <50ug/ml | IC80 <5ug/ml | Antibody Specificity |
|---|---|---|---|---|---|
| DH429 | 0.06 | 0.22 | 63% | 60% | V3-glycan |
| DH512 | 0.65 | 5.12 | 100% | 50% | MPER (10E8-like) |
| CH31 | 0.10 | 0.42 | 83% | 80% | VH1-2 CD4bs (VRC01-like) |
| CH01 | 3.79 | NA | 46% | NA | V1V2-glycan |
| CH01+ CH31 | 3.73 | NA | 93% | NA | V1V2-glycan + VH1-2 CD4bs |
| DH493 | 5.98 | NA | 83% | NA | VH1-46 CD4bs (ANC131-like) |
| DH540 | 0.10 | NA | 90% | NA | N276-dependent CD4bs Ab (HJ16-like) |

Figure 10

| | 656–683 | Clone 511 |
|---|---|---|
| MPER656-biotin | KKKNEQELLELDKWASLWNWFNITNWLWYIK---biotin | − |
| MPER656.1-biotin | KKKNEQDLLALDKWASLWNWFDISNWLWYIK---KKK-biotin | + |
| MPER656.2-biotin | KKKNEKDLLALDSWKNLWNWFSITKWLWYIK---KKK-biotin | (−) |
| MPER656.3-biotin | KKKNEQELLALDKWNNLWSWFDITNWLWYIR---KKK-biotin | + |
| CAP206_0moB5_MPER656-biotin | KKKNEKDLLALDSWKNLWNWFDITKWLWYIK---KKK-biotin | + |
| MPER656.3dYIK-biotin | KKKNEQELLALDKWNNLWSWFDITNWLWYIR---KKK-biotin | + |
| MPER656.3YIKd664_6A-biotin | KKKNEQELLALAKANNLWSWFDITNWLWYIRYIKKKK-biotin | + |
| MPER656.3dYIK664_6A-biotin | KKKNEQELLALAKANNLWSWFDITNWLWYIR---KKK-biotin | + |
| MPER656.2dYIK683R-biotin | KKKNEKDLLALDSWKNLWNWFSITKWLWYIR---KKK-biotin | (−) |
| MPER656.3YIKd664A-biotin | KKKNEQELLALAKWNNLWSWFDITNWLWYIRYIKKKK-biotin | + |
| CAP206_0moB5_MPER656d683R-biotin | KKKNEKDLLALDSWKNLWNWFDITKWLWYIR---KKK-biotin | + |
| MPR.03-biotin | KKKNEQELLELDKWASLWNWFDITNWLWYIR---KKK-biotin | + |

Residues shown in light blue indicate positions that differ from MPER656-biotin.

GAGGTTCAGCTGGTGGAGTCTGGGGGAGGCTTGGTGAAGCCGGGGGGGTCTCTTAGA
CTCCCCGGTGCAGCCTCTGGTTTCACTTTCACCAACACGTGGATGAGTTGGGTCCGT
CAGGCGCCAGGGAAGGGACTGGAGTGGGTCGGTCGGATTAGCCGGAACAAAGATGGC
GCGAAAACAGAGTACGCCGCACCCGTGAGAGGCAGATTCACCATCTCAAGAGATGAC
TCCAGAGACACATTGTATCTGCAGATGACCAGCCTGAAAATAGAGGATTCAGGCCGG
TATTTTTGCACCGCAGATCTTGGGGAGCCCGTGGTGTCACGATCCATTTTTGAGTGG
GGGTCTTATTATTATTATATGGACCTCTGGGGCAAGGGGACCACGGTCACCGTCTCT
TCA

>DH511VK

GACATCCAGTTGACCCAGTCTCCATCTCCCCTGTCTGCGTCTGTGGGAGACACAGTC
ACTATCACTTGTCGGGCCAGCCAGAAGATTAGCGACTATTTGAACTGGTACCAACAG
AAGCCGGGGAGAGCCCCCAAAATACTCATTTACGCTGCGTCCAAGTTGGGGAGTGGC
GTCCCATCAAGGTTCAGTGGCAGTGGATATGGCAGAGATTTCACTCTCACCATCACC
GGTCTGCAGCCTGAAGATTTTGCAACCTATTATTGTCAGGAGGCTTACAGTTCTACT
CCCACGTTAACTTTTGGCCAGGGGACCAGGCTGGATCTCAAAC

>DH512VH

CAGGTGCAGCTGGTACAGTCTGGGGGAGGTCTGGTGAAGCCGGGGGGGTCCCTCACA
CTCTCCTGTTCAGCCTCTGGATTCTTTTTCGATAATTCATGGATGGGGTGGGTCCGT
CAGGCGCCAGGGAAGGGACTGGAGTGGGTTGGCCGCATTAGAAGGCTCAAAGACGGT
GCGACAGGAGAATATGGTGCAGCCGTGAAGGACAGATTCACCATTTCAAGAGATGAC
AGTAGAAATATGCTGTACCTGCACATGAGGACCCTGAAAACCGAGGACTCAGGCACT
TATTATTGTACCATGGATGAGGGGACCCCAGTAACACGCTTCTTAGAATGGGGCTAC
TTCTATTATTATATGGCCGTTTGGGGCAGAGGGACCACGGTCATCGTCTCTTCA

>DH512VK

GACATCGTGATGACCCAGTCTCCGTCCTCCGTGTCTGCATCTGTGGGAGACAGAGTC
ACCATCACTTGCCGGGCAAGTCAGAATATTAGAGACTATTTAAATTGGTATCAACAT
AAACCCGGGGGATCCCCTAGACTCCTAATTTATGCTGCGTCAACTTTGCAAACTGGG
GTCCCGTCCAGATTCAGCGGCAGTGGATCTGGGAACCTTTTCACTCTCACCATTACC
AATCTGCAACCTGAAGATTTTGCAACTTATTATTGTCAAGAGAATTATAATACTATC
CCCTCGCTCAGCTTTGGTCAGGGGACCAAGGTGGACATCAGGC

GAGGTTCAGCTGGTGGAGTCTGGGGGAGGCTTGGTGAAGCCGGGGGGGTCTCTTAGA
CTCTCCTGTGTAGCCTCTGGCTTCACTTTCAGCAACACGTGGATGAGTTGGGTCCGT
CAGGCGCCAGGGAAGGGACTGGAGTGGGTCGGTCGGATTAGCCGGAACAAAGATGGC
GCGAAAACAGAGTACGCCGCACCCGTGAGAGGCAGATTCACCATCTCAAGAGATGAC
TCCAGAGACACATTGTATCTGCAGATGAGCAGCCTGAAAATAGAGGATTCAGGCCGG
TATTTTTGCACCGCAGATCTTGGGGAGGCCGTTGTGTCACGATTTTTGAGTGGGGG
TCCTATTATTACTACATGGACTTCTGGGGCAAGGGGACCACGGTCACCGTCTCTTCA

>DH513VK

GACATTCAGATGACCCAATCTCCATCTCCCCTGTCTGCGTCTGTGGGAGACACAGTC
ACTATCACTTGCCGGGCCAGCCAGAAGATTAGCGACTATTTGAACTGGTACCAACAG
AGGCCGGGGAGAGCCCCCAAGATCCTCATTTACGCTGCGTCCAAGTTGGCAAGCGAC
GTCCCATCAAGATTTAGTGGCAGTGGATATGGCAGAGATTTCACTCTCACCATAACC
GGTCTGCAGCCTGAAGATTTTGCAACCTATTATTGTCAGGAGGCTTACAGTTCTACC
CCCACGTTAACTTTTGGCCAGGGGACCAGGCTGGATCTCAAAC

>DH514VH

GAGGTGCAGCTGGTGGAGTCTGGGGGCGGCTTGATAAAGCCGGGACAGTCACTCACA
CTATTCTGTGTGGGCTTTGGATTCAACTTCGCTAACGACTGGATGGGCTGGGTCCGC
CAGGCTCCAGGGAAGGGACTGGAATGGGTTGGGCGTATAAGGAGACTGAAAGATGGT
GCGAAAGCTGAATATGGATCTTCCGTGAAGGGTAGATTCACCATCTCAAGGGATGAT
TCCAAAAACACCCTATACTTGCACATGAGCAGCCTCAAGGTCGAAGACACAGCCGTC
TACTATTGCACCCGAGACGAGGGGGCCCCAGTTACCCGGTTTCTGGAGTGGGGCTCC
TATTACTACTACATGGCCGTCTGGGGCAAAGGGACCACGGTCACCGTCTCTTCA

>DH514VK

GACATCCAGTTGACCCAGTCTCCAGCCTCTCTGTCTGCATCTGTAGGAGACACAGTG
ACTATCACTTGCCGGGCAAGTCAGAGTATAAAAGATTACATAAATTGGTATCAACAC
AAATCCGGGAGCGCCCCTAGACTCCTGATTTATGCTGCGTCAACCTTACAAAGTGGA
ATCTCGTCAAGGTTCACTGGCAGTGGGTCTGGGACACAGTTCACTCTCACCATTAAC
AGTCTGCAACCTGAAGATTTTGCGACTTATTATTGTCAAGAGGCTTATAACACCAAC
CCCACACTCTCCTTTGGTCAGGGGACCAGGGTGGACAAGAAGC

GAGGTTCAGCTGGTGGAGTCTGGGGGCGGCTTGGTGAAGCCGGGACAGTCACTCACA
CTTTCCTGTGTGGGCTTTGGATTCAATTTCGCTAACGACTGGATGGGCTGGGTCCGC
CAGGCTCCAGGGAAGGGACTGGAATGGGTTGGTCGAATAAGGAGACTAAAAGACGGT
GCGACAACAGAATATTCTTCATCCGTGAAGGGGAGATTCAGTGTCTCAAGAGATGAT
TCAAGGAACACAGTATACTTACACATGAGTAGCCTCAAAGTCCAGGACATTGGCGTC
TATTATTGTACTCGAGACGAGGGGGCCCCGGTTACTCGATTTCTGGAGTGGGGCTCC
TATTACTACTATATGGCCGTCTGGGGCAGAGGGACCACGGTCACCGTCTCTTCA

>DH515VK

GACATCCAGATGACCCAGTCTCCAACCTCTCTGTCTGCATCTGTAGGAGACACAGTT
GCTATCACTTGCCGGGCAAGTCAGAGTGTTAAAGATTATGTGAATTGGTATCAACAC
AAATCCGGGAGCGCCCCTCGACTCCTGATTTATGCTGCCTCAGTCTTACATACTGGA
GTCTCGTCAAGGTTCACTGGCAGTGGGTCTGGGACACAGTTCACTCTCACCATTAGC
AGTCTACAACCTGAAGATTTTGCTACTTATTATTGTCAAGAGGCTTATAACACCTAT
CCCACACTCTCCTTTGGTCAGGGGACCAGGGTGGACAGGAAAC

>DH516VH

GAGGTTCAGCTGGTGGAGTCTGGGGGAGGCTTGGTGAAGCCGGGGGGGTCTCTTAGA
CTCTCCTGTGTAGCCTCTGGCTTCACTTTCAGCAACACGTGGATGAGTTGGGTCCGT
CAGGCGCCAGGGAAGGGACTGGAGTGGGTCGGTCGGATTAGCCGGAACAAAGATGGC
GCGAAAACAGACTACGCCGCACCCGTGAGAGGCAGATTCACCATCTCCAGAGATGAC
TCCAGAGACACATTGTATCTGCAGATGAGCAGCCTGAAAATAGAGGATTCAGGCCGG
TATTTTTGCACCGCAGATCTTGGGGAGGCCGTGGTGTCACGATTTTTGAGTGGGGG
TCCTATTATTACTACATGGACTTCTGGGGCAAGGGGACCACGGTCACCGTCTCTTCA

>DH516VK

GATATTGTGATGACCCAGTCTCCACCTCCCCTGTCTGCGTCTGTGGGAGACACAGTC
ACTATCACTTGCCGGGCCAGCCAGAAGATTAGCGACTATTTGAACTGGTACCAACAG
AGGCCGGGGAGAGCCCCCAAAATACTCATTTACGCTGCGTCCAAGTTGGGAAGCGAC
GTCCCATCAAGGTTCAGTGGCAGTGGATATGGCAGAGATTTCACTCTCACCATCACC
GGTCTGCAGCCTGAAGATTTTGCAACCTATTATTGTCAGGAGGCTTACAGTTCTACT
CCCACGTTAAGTTTTGGCCAGGGGACCAGGCTGGATCTCAAAC

Figure 12 cont.

>DH517VH
GAAAGGCAGGTGGTGGAATATGGGGGAGGCTTGGTGAAGCCGGGGGGGTCTCTTAGA
CTCTCTTGTTTACCGTTTGCCTTTGGGTTCAGGGCCCCCTGGAGGAGTTCTGTCCGT
CACGCGCCTGGGGGCGGAGCGGAGTGGGTCGGTCGGATTAGCCGGAACAAAGATGGC
GCGAAAACAGAGTACGCCGCACCCGTGAGAGGCAGATTCACCATCTCAAGAGATGAC
TCCAGAGACACATTGTATCTGCAGATGACCAGCCTGAAAATAGAGGATTCAGGCCGG
TATTTTTGCACCGCAGATCTTGGGGAGCCCGTGGTGTCACGATTTTTTGAGTGGGGG
TCTTATTATTATTATATGGACCTCTGGGGCAAGGGGACCACGGTCACCGTCTCTTCA

>DH517VL
TCTTCTGAGCTGACTCAGGACCCCACTGTGTCTGTGGCCTTGGGCCAGACAGTCAAG
ATCAGATGCCAAGGAGCCAGCCTCAGAGACTGTTATGCGACCTGGTACCGGCAGAAG
CCAGGACAGGCCCCAACACTTCTCATTTATGATATAAATAAGAGGCCCTCAGGTATC
CCAGACCGATTCTCTGCCTCCTACTCAGGGAGCACTTCTTCCTTGACCATTATTGGG
GCTCAGCCGGAAGATGAGGCTGACTATTTTTGTGCTTCGCGGGACAGGAGTGGTGAC
CGTCTTGGCGTCTTCGGCGGTGGGACCAAACTGACCGTCCTG

>DH518VH
CAGCTGCAGGAGTCGGGTCCCAGACTGGTGAGGCCTTCGGAGACCCTGTCCCTCACC
TGCACTGTATCTGGCTCTGGTGTCTCCGTCAGTCGTGGGAGTTATTATTGGGGCTGG
ATACGCCAGTCCCCAGAAAAGGGACTCGAATGGATTGGAAGTGTCTATTCCACTACT
AGTGGAAAAACCTACTACAACCCGTCCCTCAAGAGTCGAGTCACCTTTTCGAAGGAC
ACGTCCCAGAACGCCTTCTCCCTGACTCTGACGTCTATTACCGCCGCGGACACGGCC
GTCTATTACTGTGCAAGACAATTTGGCTTCATGGGGGGCTTTTTGGAGTGGTATCCG
CACTATTTTGACTTCTGGGGCCCGGGAATCCAGGTCGTCGTGTCTTCT

>DH518VK
GACATTGTGATGACCCAGTCTCCATCCTACCTGTCTACATCTGTCGGTGACAGCATC
ACCATCACTTGCCGGGCAAGTCAGAGTATTAAAACATATGTAAATTGGTATCAACAA
AGACCAGGGAGAGCCCCTAAACTCCTCATCTATTCTTCATCCACTTTGCAACCTGGG
GTCCCGTCAAGATTCAGCGCCAGTGGATCTGGGACAGATTTCGTTCTCTCCATCACC
AATTTGCAGTCTGAAGATTTTGCAACTTACTACTGTCAACAGACCTACTACACCCCC
TCTACTTTTGGCCAGGGGACCACACTGGACATCAAG

CAGGTGCAGCTGGTACAGTCTGGGGCTGAGGTGAAGAAGCCTGGGTCCTCGGTCAAG
GTCTCCTGCAAGGCCTCTGGAGGCTCCTTCTACACCTATACTATCAACTGGGTGCGA
CAGGCCCCTGGACAAGGGCTTGAGTGGATGGGCAGGGTCACCACTATGTTTGGTGTA
ACACTTTACGCACAGAAATTCCAGGGCAGAGTCACACTTACCGCGGACAAATCCACG
AGCACAGCCTACATGGAACTGAGCAGTCTAAGATCTGAGGACACGGCCGTCTATTAT
TGTGCGACAGATGGGCCTGACAATTTTTGGAGTGGCTTGTCTCATGCTTTCGATCTC
TGGGGCCAGGGGACAATGGTCACCGTCTCTTCA

>DH536VL

CAGTCTGCCCTGACTCAGCCTGCCTCCGTGGCTGGGTCTCCTGGACAGTCGATCACC
ATCTCCTGCACTGGAACCAGCAGTGACATTGGTGATTCTAAGTATGTCTCCTGGTAC
CAACAGTTCCCAGGCAAAGCCCCCAAAGTCATGATTTATGAGGTCAGTTATCGGCCC
TCAGGAGTCTCTAGCCGCTTCTCTGGCTCCAAGTCTGGCAACACGGCCTCCCTGACC
ATCTCTGGACTCCAGACTGAGGACGAGGCTGATTATTATTGCATGGCATATACAGGC
ACCTTCACTGCTATTTTCGGCGGAGGGACCAAGCTGACCGTCCTG

>DH537VH

CAGGTGCAGCTGGTGCAGTCTGGGGCTGAGGTGAGGAAGGCTGGGTCGTCGGTGAAG
GTCTCCTGCAAGGCTTCTGGAGGCACCTTCACCAGCTATGGCTTCAGCTGGATACGG
CAGGCCCCTGGCCAAGGGCTTGAGTGGATGGGAAACGTCATCCCTGTCTTTGGTTCA
ACAAACTACGCACAGAAATTTCAGGGCAGAGTCAGTATTACCGCGGACGAAGCCACG
GGCACAGTCCACATGGACCTCACCAGCCTGACATCTGACGACACGGCCGTTTATTAC
TGTGTGAGGTCGAGTAGAGAACTGCCAACGTCAATGGAACGGTGGTTCGACCCCTGG
GGCCAGGGAACCCAGGTCATTGTCTCCTCG

>DH537VK

GACATCCAGATGACCCAGTCTCCATCCTCCCTGTCTGCATCTGTGGGAGACAGCGTC
ACCATTACTTGCCGGGCAAGTCAGAGCATTAACACCTATTTAAATTGGTATCAGCAG
AAACCAGGGAAGGCCCCTAAACTCCTGATCTATTCTGCATCCAATTTACACAATGGG
GTCCCATCGAGGTTCAGTGGCAGTGGATCTGGGACATCTTTCACTCTCACCATCAAC
AATCTACAACCTGAAGATTTTGCAACTTACTACTGTCAACAGAGTTACAGTGCCCCT
TACACTTTTGGCCAGGGGACCAAGTCAGACACCAAA

EVQLVESGGGLVKPGGSLRLPGAASGFTFTNTWMSWVRQAPGKGLEWVGRISRNKDG
AKTEYAAPVRGRFTISRDDSRDTLYLQMTSLKIEDSGRYFCTADLGEPVVSRSIFEW
GSYYYYMDLWGKGTTVTVSS

>DH511VK

DIQLTQSPSPLSASVGDTVTITCRASQKISDYLNWYQQKPGRAPKILIYAASKLGSG
VPSRFSGSGYGRDFTLTITGLQPEDFATYYCQEAYSSTPTLTFGQGTRLDLK

>DH512VH

QVQLVQSGGGLVKPGGSLTLSCSASGFFFDNSWMGWVRQAPGKGLEWVGRIRRLKDG
ATGEYGAAVKDRFTISRDDSRNMLYLHMRTLKTEDSGTYYCTMDEGTPVTRFLEWGY
FYYYMAVWGRGTTVIVSS

>DH512VK

DIVMTQSPSSVSASVGDRVTITCRASQNIRDYLNWYQHKPGGSPRLLIYAASTLQTG
VPSRFSGSGSGNLFTLTITNLQPEDFATYYCQENYNTIPSLSFGQGTKVDIR

>DH513VH

EVQLVESGGGLVKPGGSLRLSCVASGFTFSNTWMSWVRQAPGKGLEWVGRISRNKDG
AKTEYAAPVRGRFTISRDDSRDTLYLQMSSLKIEDSGRYFCTADLGEAVVSRFFEWG
SYYYYMDFWGKGTTVTVSS

>DH513

VKDIQMTQSPSPLSASVGDTVTITCRASQKISDYLNWYQQRPGRAPKILIYAASKLA
SDVPSRFSGSGYGRDFTLTITGLQPEDFATYYCQEAYSSTPTLTFGQGTRLDLK

>DH514VH

EVQLVESGGGLIKPGQSLTLFCVGFGFNFANDWMGWVRQAPGKGLEWVGRIRRLKDG
AKAEYGSSVKGRFTISRDDSKNTLYLHMSSLKVEDTAVYYCTRDEGAPVTRFLEWGS
YYYYMAVWGKGTTVTVSS

>DH514VK

DIQLTQSPASLSASVGDTVTITCRASQSIKDYINWYQHKSGSAPRLLIYAASTLQSG
ISSRFTGSGSGTQFTLTINSLQPEDFATYYCQEAYNTNPTLSFGQGTRVDKK

EVQLVESGGGLVKPGQSLTLSCVGFGFNFANDWMGWVRQAPGKGLEWVGRIRRLKDG
ATTEYSSSVKGRFSVSRDDSRNTVYLHMSSLKVQDIGVYYCTRDEGAPVTRFLEWGS
YYYYMAVWGRGTTVTVSS

>DH515VK

DIQMTQSPTSLSASVGDTVAITCRASQSVKDYVNWYQHKSGSAPRLLIYAASVLHTG
VSSRFTGSGSGTQFTLTISSLQPEDFATYYCQEAYNTYPTLSFGQGTRVDRK

>DH516VH

EVQLVESGGGLVKPGGSLRLSCVASGFTFSNTWMSWVRQAPGKGLEWVGRISRNKDG
AKTDYAAPVRGRFTISRDDSRDTLYLQMSSLKIEDSGRYFCTADLGEAVVSRFFEWG
SYYYYMDFWGKGTTVTVSS

>DH516VK

DIVMTQSPPPLSASVGDTVTITCRASQKISDYLNWYQQRPGRAPKILIYAASKLGSD
VPSRFSGSGYGRDFTLTITGLQPEDFATYYCQEAYSSTPTLSFGQGTRLDLK

>DH517VH

ERQVVEYGGGLVKPGGSLRLSCLPFAFGFRAPWRSSVRHAPGGGAEWVGRISRNKDG
AKTEYAAPVRGRFTISRDDSRDTLYLQMTSLKIEDSGRYFCTADLGEPVVSRFFEWG
SYYYYMDLWGKGTTVTVSS

>DH517VL

SSELTQDPTVSVALGQTVKIRCQGASLRDCYATWYRQKPGQAPTLLIYDINKRPSGI
PDRFSASYSGSTSSLTIIGAQPEDEADYFCASRDRSGDRLGVFGGGTKLTVL

>DH518VH

QLQESGPRLVRPSETLSLTCTVSGSGVSVSRGSYYWGWIRQSPEKGLEWIGSVYSTT
SGKTYYNPSLKSRVTFSKDTSQNAFSLTLTSITAADTAVYYCARQFGFMGGFLEWYP
HYFDFWGPGIQVVVSS

>DH536

VHQVQLVQSGAEVKKPGSSVKVSCKASGGSFYTYTINWVRQAPGQGLEWMGRVTTMF
GVTLYAQKFQGRVTLTADKSTSTAYMELSSLRSEDTAVYYCATDGPDNFWSGLSHAF
DLWGQGTMVTVSS

>DH518VK

DIVMTQSPSYLSTSVGDSITITCRASQSIKTYVNWYQQRPGRAPKLLIYSSSTLQPG
VPSRFSASGSGTDFVLSITNLQSEDFATYYCQQTYYTPSTFGQGTTLDIK

QVQLVQSGAEVKKPGSSVKVSCKASGGSFYTYTINWVRQAPGQGLEWMGRVTTMFGV
TLYAQKFQGRVTLTADKSTSTAYMELSSLRSEDTAVYYCATDGPDNFWSGLSHAFDL
WGQGTMVTVSS

>DH536VL

QSALTQPASVAGSPGQSITISCTGTSSDIGDSKYVSWYQQFPGKAPKVMIYEVSYRP
SGVSSRFSGSKSGNTASLTISGLQTEDEADYYCMAYTGTFTAIFGGGTKLTVL

>DH537VH

QVQLVQSGAEVRKAGSSVKVSCKASGGTFTSYGFSWIRQAPGQGLEWMGNVIPVFGS
TNYAQKFQGRVSITADEATGTVHMDLTSLTSDDTAVYYCVRSSRELPTSMERWFDPW
GQGTQVIVSS

>DH537VK

DIQMTQSPSSLSASVGDSVTITCRASQSINTYLNWYQQKPGKAPKLLIYSASNLHNG
VPSRFSGSGSGTSFTLTINNLQPEDFATYYCQQSYSAPYTFGQGTKSDTK

Figure 13 cont.

```
 DH511VH   EVQLVESGGG LVKPGGSLRL PGAASGFTFT NTWMSWVRQA
DH512VH    Q----Q---- ---------T- SCS----F-D -S--G-----
DH513VH    ---------- ---------- SCV------S ----------
DH514VH    ---------- -I---Q--T- FCVGF--N-A -D--G-----
DH515VH    ---------- -----Q--T- SCVGF--N-A -D--G-----
DH516VH    ---------- ---------- SCV------S ----------

 DH511VH PGKGLEWVGR ISRNKDGAKT EYAAPVRGRF
DH512VH  ---------- -R-L----TG --G-A-KD--
DH513VH  ---------- ---------- ----------
DH514VH  ---------- -R-L-----A --GSS-K---
DH515VH  ---------- -R-L----T- --SSS-K---
DH516VH  ---------- ---------- D--------- 70

DH511VH    TISRDDSRDT LYLQMTSLKI EDSGRYFCTA DLGEPVVSRS
DH512VH    --------NM ---H-RT--T ----T-Y--M -E-T--.T-.
DH513VH    ---------- -----S---- ---------- ----A----.
DH514VH    -------KN- ---H-S---V --TAV-Y--R -E-A--.T-.
DH515VH    SV------N- V--H-S---V Q-I-V-Y--R -E-A--.T-.
DH516VH    ---------- -----S---- ---------- ----A----.

DH511VH    IFEWGSYYYY MDLWGKGTTV TVSS
DH512VH    FL---YF--- -AV--R---- I---
DH513VH    F--------- --F------- ----
DH514VH    FL-------- -AV------- ----
DH515VH    FL-------- -AV--R---- ----
DH516VH    F--------- --F------- ---- 134
```

Figure 14A

```
DH511VK    DIQLTQSPSP LSASVGDTVT ITCRASQKIS DYLNWYQQKP
DH512VK    --VM-----S V------R-- -------N-R -------H--
DH513VK    ---M------ ---------- ---------- --------R-
DH514VK    --------AS ---------- -------S-K --I----H-S
DH515VK    ---M----TS ---------A -------SVK --V----H-S
DH516VK    --VM----P- ---------- ---------- --------R-

DH511VK    GRAPKILIYA ASKLGSGVPS RFSGSGYGRD
DH512VK    -GS-RL---- --T-QT---- ------S-NL
DH513VK    ---------- ----A-D--- ----------
DH514VK    -S--RL---- --T-Q--IS- --T---S-TQ
DH515VK    -S--RL---- --V-HT--S- --T---S-TQ
DH516VK    ---------- ------D--- ---------- 70

DH511VK    FTLTITGLQP EDFATYYCQE AYSSTPTLTF GQGTRLDLK
DH512VK    ------N--- ---------- N-NTI-S-S- ----KV-IR
DH513VK    ---------- ---------- ---------- ---------
DH514VK    -----NS--- ---------- --NTN---S- -----V-K-
DH515VK    -----SS--- ---------- --NTY---S- -----V-R-
DH516VK    ---------- ---------- --------S- --------- 109
```

Figure 14B

| | | | | |
|---|---|---|---|---|
| DH511VH | EVQLVESGGG | LVKPGGSLRL | PGAAS**GFTFT** | **NT**..**W**MSWVR |
| DH512VH | Q----Q---- | --------T- | SCS----F-D | -S..--G--- |
| DH513VH | ---------- | ---------- | SCV------S | --..------ |
| DH514VH | ---------- | -I---Q--T- | FCVGF--N-A | -D..--G--- |
| DH515VH | ---------- | -----Q--T- | SCVGF--N-A | -D..--G--- |
| DH516VH | ---------- | ---------- | SCV------S | --..------ |
| 10E8VH | ---------- | ---------- | SCS----D-D | -A..--T--- |
| 4E10VH | Q----Q--AE | VKR--S-VTV | SCK---GS-S | TY..AL---- |
| 2F5VH | RIT-K---PP | ----TQT-T- | TCSF---SLS | DFGVGVG-I- |

| | | | | |
|---|---|---|---|---|
| DH511VH | QAPGKGLEWV | GR*ISRNKDGA* | *KT*EYAAPVRG | |
| DH512VH | ---------- | ---R-L---- | TG--G-A-KD | |
| DH513VH | ---------- | ---------- | ---------- | |
| DH514VH | ---------- | ---R-L---- | -A--GSS-K- | |
| DH515VH | ---------- | ---R-L---- | T---SSS-K- | |
| DH516VH | ---------- | ---------- | --D------- | |
| 10E8VH | -P-------- | ---TGPGE-W | SVD-----E- | |
| 4E10VH | ----R----M | -GVIPLL..T | I-N--PRFQ- | |
| 2F5VH | -P---A---L | AI-YSDD... | DKR-SPSLNT | 70 |

Figure 15A

```
DH511VH    RFTISRDDSR  DTLYLQMTSL  KIEDSGRYFC  TADLGEPVVS
DH512VH    ----------  NM---H-RT-  -T----T-Y-  -M-E-T--.T
DH513VH    ----------  ------S---  ----------  ------A---
DH514VH    ---------K  N----H-S--  -V--TAV-Y-  -R-E-A--.T
DH515VH    --SV------  N-V--H-S--  -VQ-I-V-Y-  -R-E-A--.T
DH516VH    ----------  ------S---  ----------  ------A---
10E8VH     ------LN-I  NF---E-NN-  RM----L---  ARTGKY....
4E10VH     -I--TA-R-T  S-A--ELN--  RP--TAV-Y-  AREGTT....
2F5VH      -L--TK-T-K  NQVV-V--RV  SPV-TAT---  AHRR-PTT..

DH511VH    RSIFEWGSY.  ..YYYMDLWG  KGTTVTVSS
DH512VH    -.FL---YF-  ------AV--  R-----I---
DH513VH    -.F-------  -------F--  ----------
DH514VH    -.FL------  ------AV--  ----------
DH515VH    -.FL------  ------AV--  R---------
DH516VH    -.F-------  -------F--  ----------
10E8VH     ..YDF-SG-P  PGEE-FQD--  R--L------
4E10VH     ....G--WLG  KPIGAFAH--  Q--L------
2F5VH      ..L-GVPIAR  GPVNA--V--  Q-I---I---
```

Figure 15A cont.

```
DH511VK    DIQLTQSPSP LSASVGDTVT ITCRASQKIS
DH512VK    --VM-----S V------R-- -------N-R
DH513VK    ---M------ ---------- ----------
DH514VK    --------AS ---------- -------S-K
DH515VK    ---M----TS ---------A -------SVK
DH516VK    --VM----P- ---------- ----------
4E10VK     E-V-----GT Q-L-P-ERA- LS-----SVG
2F5VK      AL-------S -------RI- -------GVT
10E8VL     SYE---.ETG V-VAL-R--- ----GDSL.R

DH511VK    .DYLNWYQQK PGRAPKILIY AASKLGSGVP
DH512VK    .-------H- --GS-RL--- ---T-QT---
DH513VK    .--------R ---------- -----A-D--
DH514VK    .--I----H- S-S--RL--- ---T-Q--IS
DH515VK    .--V----H- S-S--RL--- ---V-HT--S
DH516VK    .--------R ---------- -------D--
4E10VK     NNK-A----R --Q--RL--- G--SRP---A
2F5VK      .SA-A--R-- --SP-QL--- D--S-E----
10E8VL     SH-AS---K- --Q--IL-F- GKNNRP----   60
```

Figure 15B

| | | | | |
|---|---|---|---|---|
| DH511VK | SRFSGSGYGR | DFTLTITGLQ | PEDFATYYCQ | |
| DH512VK | -------S-N | L------N-- | ---------- | |
| DH513VK | ---------- | ---------- | ---------- | |
| DH514VK | ---T---S-T | Q-----NS-- | ---------- | |
| DH515VK | ---T---S-T | Q-----SS-- | ---------- | |
| DH516VK | ---------- | ---------- | ---------- | |
| 4E10VK | D------S-T | ------SR-E | -----V---- | |
| 2F5VK | -------S-T | E-----ST-R | ---------- | |
| 10E8VL | D-----AS-N | RAS---S-A- | A--D-E---S | |

| | | | | |
|---|---|---|---|---|
| DH511VK | EAYSST.PTL | TFGQGTRLDL | K | |
| DH512VK | -N-NTI--S- | S-----KV-I | R | |
| DH513VK | ---------- | ---------- | - | |
| DH514VK | ---NTN---- | S------V-K | - | |
| DH515VK | ---NTY---- | S------V-R | - | |
| DH516VK | ---------- | S--------- | - | |
| 4E10VK | QYGQ..-SLS | ------KVEV | - | |
| 2F5VK | QLHF..-YPH | ---G---V-V | R | |
| 10E8VL | SRDK-GSRLS | V--G--K-TV | L | 111 |

Figure 15B cont.

| | AA position | |
|---|---|---|
| MPER-26 | | Biotin-GGG-**QELLELDKWASLWNWFNITNWLWYIK** |
| MPER-26 A1 | 658 | Biotin-GGG-**AELLELDKWASLWNWFNITNWLWYIK** |
| MPER-26 A2 | 659 | Biotin-GGG-**QALLELDKWASLWNWFNITNWLWYIK** |
| MPER-26 A3 | 660 | Biotin-GGG-**QEALELDKWASLWNWFNITNWLWYIK** |
| MPER-26 A4 | 661 | Biotin-GGG-**QELAELDKWASLWNWFNITNWLWYIK** |
| MPER-26 A5 | 662 | Biotin-GGG-**QELLALDKWASLWNWFNITNWLWYIK** |
| MPER-26 A6 | 663 | Biotin-GGG-**QELLEADKWASLWNWFNITNWLWYIK** |
| MPER-26 A7 | 664 | Biotin-GGG-**QELLELAKWASLWNWFNITNWLWYIK** |
| MPER-26 A8 | 665 | Biotin-GGG-**QELLELDAWASLWNWFNITNWLWYIK** |
| MPER-26 A9 | 666 | Biotin-GGG-**QELLELDKAASLWNWFNITNWLWYIK** |
| MPER-26 N10 | 667 | Biotin-GGG-**QELLELDKWNSLWNWFNITNWLWYIK** |
| MPER-26 A11 | 668 | Biotin-GGG-**QELLELDKWAALWNWFNITNWLWYIK** |
| MPER-26 A12 | 669 | Biotin-GGG-**QELLELDKWASAWNWFNITNWLWYIK** |
| MPER-26 A13 | 670 | Biotin-GGG-**QELLELDKWASLANWFNITNWLWYIK** |
| MPER-26 A14 | 671 | Biotin-GGG-**QELLELDKWASLWAWFNITNWLWYIK** |
| MPER-26 A15 | 672 | Biotin-GGG-**QELLELDKWASLWNAFNITNWLWYIK** |
| MPER-26 A16 | 673 | Biotin-GGG-**QELLELDKWASLWNWANITNWLWYIK** |
| MPER-26 A17 | 674 | Biotin-GGG-**QELLELDKWASLWNWFAITNWLWYIK** |
| MPER-26 A18 | 675 | Biotin-GGG-**QELLELDKWASLWNWFNATNWLWYIK** |
| MPER-26 A19 | 676 | Biotin-GGG-**QELLELDKWASLWNWFNIANWLWYIK** |
| MPER-26 A20 | 677 | Biotin-GGG-**QELLELDKWASLWNWFNITAWLWYIK** |
| MPER-26 A21 | 678 | Biotin-GGG-**QELLELDKWASLWNWFNITNALWYIK** |
| MPER-26 A22 | 679 | Biotin-GGG-**QELLELDKWASLWNWFNITNWAWYIK** |
| MPER-26 A23 | 680 | Biotin-GGG-**QELLELDKWASLWNWFNITNWLAYIK** |
| MPER-26 A24 | 681 | Biotin-GGG-**QELLELDKWASLWNWFNITNWLWAIK** |
| MPER-26 A25 | 682 | Biotin-GGG-**QELLELDKWASLWNWFNITNWLWYAK** |
| MPER-26 A26 | 683 | Biotin-GGG-**QELLELDKWASLWNWFNITNWLWYIA** |

Figure 16

| | AA position | |
|---|---|---|
| MPER-26 | | Biotin-GGG-QELLELDKWASLWNWFNITNWLWYIK |
| MPER-26 A1 | 658 | Biotin-GGG-AELLELDKWASLWNWFNITNWLWYIK |
| MPER-26 A2 | 659 | Biotin-GGG-QALLELDKWASLWNWFNITNWLWYIK |
| MPER-26 A3 | 660 | Biotin-GGG-QEALELDKWASLWNWFNITNWLWYIK |
| MPER-26 A4 | 661 | Biotin-GGG-QELAELDKWASLWNWFNITNWLWYIK |
| MPER-26 A5 | 662 | Biotin-GGG-QELLALDKWASLWNWFNITNWLWYIK |
| MPER-26 A6 | 663 | Biotin-GGG-QELLEADKWASLWNWFNITNWLWYIK |
| MPER-26 A7 | 664 | Biotin-GGG-QELLELAKWASLWNWFNITNWLWYIK |
| MPER-26 A8 | 665 | Biotin-GGG-QELLELDAWASLWNWFNITNWLWYIK |
| MPER-26 A9 | 666 | Biotin-GGG-QELLELDKAASLWNWFNITNWLWYIK |
| MPER-26 N10 | 667 | Biotin-GGG-QELLELDKWNSLWNWFNITNWLWYIK |
| MPER-26 A11 | 668 | Biotin-GGG-QELLELDKWAALWNWFNITNWLWYIK |
| MPER-26 A12 | 669 | Biotin-GGG-QELLELDKWASAWNWFNITNWLWYIK |
| MPER-26 A13 | 670 | Biotin-GGG-QELLELDKWASLANWFNITNWLWYIK |
| MPER-26 A14 | 671 | Biotin-GGG-QELLELDKWASLWAWFNITNWLWYIK |
| MPER-26 A15 | 672 | Biotin-GGG-QELLELDKWASLWNAFNITNWLWYIK |
| MPER-26 A16 | 673 | Biotin-GGG-QELLELDKWASLWNWANITNWLWYIK |
| MPER-26 A17 | 674 | Biotin-GGG-QELLELDKWASLWNWFAITNWLWYIK |
| MPER-26 A18 | 675 | Biotin-GGG-QELLELDKWASLWNWFNATNWLWYIK |
| MPER-26 A19 | 676 | Biotin-GGG-QELLELDKWASLWNWFNIANWLWYIK |
| MPER-26 A20 | 677 | Biotin-GGG-QELLELDKWASLWNWFNITAWLWYIK |
| MPER-26 A21 | 678 | Biotin-GGG-QELLELDKWASLWNWFNITNALWYIK |
| MPER-26 A22 | 679 | Biotin-GGG-QELLELDKWASLWNWFNITNWAWYIK |
| MPER-26 A23 | 680 | Biotin-GGG-QELLELDKWASLWNWFNITNWLAYIK |
| MPER-26 A24 | 681 | Biotin-GGG-QELLELDKWASLWNWFNITNWLWAIK |
| MPER-26 A25 | 682 | Biotin-GGG-QELLELDKWASLWNWFNITNWLWYAK |
| MPER-26 A26 | 683 | Biotin-GGG-QELLELDKWASLWNWFNITNWLWYIA |

Figure 16 cont.

| | 656 657 658 659 660 661 662 663 664 665 666 667 668 669 670 671 672 673 674 675 676 677 678 679 680 681 682 683 |
|---|---|
| MPER656-biotin | KKKNEQELLELDKWASLWNWFNITNWLWYIK---biotin |
| MPER656.1-biotin | KKKNEQDLLALDKWASLWNWFDISNWLWYIK---KKK-biotin |
| MPER656.2-biotin | KKKNEKDLLALDSWKNLWNWFSITKWLWYIK---KKK-biotin |
| MPER656.3-biotin | KKKNEQELLALDKWNNLWSWFDITNWLWYIR---KKK-biotin |
| CAP206_0moB5_MPER656-biotin | KKKNEKDLLALDSWKNLWNWFDITKWLWYIK---KKK-biotin |
| MPER656.3dYIK-biotin | KKKNEQELLALDKWNNLWSWFDITNWLWYIR---KKK-biotin |
| MPER656.3YIKd664_6A-biotin | KKKNEQELLALAKANNLWSWFDITNWLWYIRYIKKKK-biotin |
| MPER656.3dYIK664_6A-biotin | KKKNEQELLALAKANNLWSWFDITNWLWYIR---KKK-biotin |
| MPER656.2dYIK683R-biotin | KKKNEKDLLALDSWKNLWNWFSITKWLWYIR---KKK-biotin |
| MPER656.3YIKd664A-biotin | KKKNEQELLALAKWNNLWSWFDITNWLWYIRYIKKKK-biotin |
| CAP206_0moB5_MPER656d683R-biotin | KKKNEKDLLALDSWKNLWNWFDITKWLWYIR---KKK-biotin |
| MPR.03-biotin | KKKNEQELLELDKWASLWNWFDITNWLWYIR---KKK-biotin |

Figure 18

DH270 lineage - Heavy chain nucleotide sequences

```
              ....|....| ....|....| ....|....| ....|....| ....|....|
                     10         20         30         40         50
UCA           CAGGTGCAGC TGGTGCAGTC TGGGGCTGAG GTGAAGAAGC CTGGGGCCTC
I5            CAGGTGCAGC TGGTGCAGTC TGGGGCTGAG RTGAAGAAGC CTGGGGCCTC
I1            CAGGTGCAGC TGGTGCAGTC TGGGGCTGAG DTGAAGAAGC CTGGGGCCTC
DH473H        GAGGTTCAGC TGGTGGAGTC TGGGCCTGAG TTGAAGGAGC CTGGGGCCTC
DH391H        CAGGTGCAGC TGGTGCAGTC TGGGGCTGAA CTGAAGAAGC CTGGGGCCTC
I4            CAGGTGCAGC TGGTGCAGTC TGGGGCTGAG ATGAAGAAGC CTGGGGCCTC
I3            CAGGTGCAGC TGGTGCAGTC TGGGGCTGAA ATGAAGAACC CTGGGGCCTC
DH542H        CAGGTGCAGC TGGTGCAGTC TGGGGCTCAA ATGAAGAACC CTGGGGCCTC
I2            CAGGTGCAGC TGGTGCAGTC TGGGGCTGAA ATGAAGAACC CTGGGGCCTC
DH471H        CAGGTGCAGC TGGTGCAGTC TGGGGCTGAA GTGAAGAACC CTGGGGCCTC
DH429H        GAGGTGCAGC TGGTGCAGTC TGGGGCTGAA ATGAAGAACC CTGGGGCCTC
DH270H        CAGGTGCAGC TGGTGCAGTC TGGGGCTGAG ATGAAGAAGC CTGGGGCCTC

                                        CDR1
              ....|....| ....|....| ....|....| ....|....| ....|....|
                     60         70         80         90        100
UCA           AGTGAAGGTC TCCTGCAAGG CTTCTGGATA CACCTTCACC GGCTACTATA
I5            AGTGAAGGTC TCCTGCAAGG CTTCTGGATA CACCTTCACC GACTACTATA
I1            AGTGAAGGTC TCCTGCAAGG CTTCTGGATA CACCTTCACC GACTACTATA
DH473H        AGTGAAAGTC TCCTGCAAGG CTTCTGGATA CACCTTCACC GACTACTACA
DH391H        AGTGAAGGTC TCCTGCAAGG CTTCTGGATA CACCCTCAGC GACTACTATG
I4            AGTGAAGGTC TCCTGCAAGG CTTCTGGATA CACCTTCACC GACTACTATA
I3            AGTGAAGGTC TCCTGCGCGS CTTCTGGATA TACCTTCACC GACTTCTACA
DH542H        AGTGAAGGTC TCCTGCGCGC CTTCTGGATA TACCTTCACC GACTTTTACA
I2            AGTGAAAGTC TCCTGCGCGS CTTCTGGATA TACCTTCACC GACTTCTACA
DH471H        AGTGAAAGTC TCCTGCGCGC CTTCTGGATA TACCTTCACT GACTTCTACA
DH429H        AGTGAAAGTC TCCTGCGCGG CTTCTGGATA TGGTTTCACC GACTTCTACA
DH270H        AGTGAGGGTC TCCTGCAAGG CTTCTGGATA CACCTTCACC GACTACTATA

              ....|....| ....|....| ....|....| ....|....| ....|....|
                    110        120        130        140        150
UCA           TGCACTGGGT GCGACAGGCC CCTGGACAAG GGCTTGAGTG GATGGGATGG
I5            TACACTGGGT GCGACAGGCC CCTGGACAAG GGCTTGAGTG GATGGGATGG
I1            TACACTGGGT GCGACAGGCC CCTGGACAAG GGCTTGAGTG GATGGCATGG
DH473H        TACACTGGGT GCGACAGGCC CCTGGACAAG GTCTTGAGTG GATGGCATGG
DH391H        TACACTGGCT GCGACAGGCC CCTGGACAGG GGCTTGAGTG GGTGGCTTGG
I4            TACACTGGGT GCGACAGGCC CCTGGACAAG GGCTTGAGTG GATGGGATGG
I3            TACACTGGGT GCGACAGGCC CCTGGACAAG GGCTTSAGTG GATGGGATGG
DH542H        TACATTGGTT GCGCCAGGCC CCTGGCCAGG GGCTTCAGTG GATGGGATGG
I2            TACACTGGGT GCGACTGGCC CCTGGACAAG GGCTTSAGTG GATGGGATGG
DH471H        TACACTGGGT GCGACTGGCC CCTGGACAAG GGCTTGAGTG GCTGGGGTGG
DH429H        TACACTGGGT GCGACTGGCC CCTGGACACG GGCTCCAGTG GATGGGATGG
DH270H        TACACTGGGT GCGACAGGCC CCTGGACAAG GGCCTGAGTG GATGGGATGG
```

Figure 26

CDR2

| | 160 | 170 | 180 | 190 | 200 |
|---|---|---|---|---|---|
| **UCA** | ATCAACCCTA | ACAGTGGTGG | CACAAACTAT | GCACAGAAGT | TTCAGGGCAG |
| **I5** | ATCAACCCTA | ACASTGGTCG | CACAAACTMT | GCACAGAAGT | TTCAGGGCAG |
| **I1** | ATCAACCCTA | CCASTGGTCG | CACAARCTMT | GCACGGAAGT | TTCAGGGCAG |
| **DH473H** | ATCAACCCTA | CCACTGGTCG | CTCTAGCTTT | GCCCGGGGGT | TTCAGGGCAG |
| **DH391H** | ATCAACCCTA | CCAGTGGTCG | CACAATCTCT | CCACGGAAGT | TTCAGGGCAG |
| | | | | | |
| **I4** | ATCAACCCTA | ACACTGGTCG | CACAAACTMT | GCACAGAAGT | TTCAGGGCAG |
| **I3** | ATGAACCCTA | AGACTGGTCG | CACAAACAMT | GCACAAAACT | TTCAGGGCAG |
| **DH542H** | ATGAACCCTC | AGACTGGTCG | CACAAACACT | GCACGAAACT | TTCAGGGGAG |
| **I2** | ATGAACCCTA | AGACTGGTCG | CACAAATAAT | GCACAAAACT | TTCAGGGCAG |
| **DH471H** | ATGAACCCTA | AGACTGGTCG | CACAAATCAA | GGACAAAACT | TTCAGGGCAG |
| **DH429H** | ATGAACCCTA | AGACTGGTCG | CACAAATAAT | GCACAAGATT | TTCAGGGCAG |
| **DH270H** | ATCAACCCTA | GCACTGGTCG | CACAAACTCT | CCACAGAAGT | TTCAGGGCAG |

| | 210 | 220 | 230 | 240 | 250 |
|---|---|---|---|---|---|
| **UCA** | GGTCACCATG | ACCAGGGACA | CGTCCATCAG | CACAGCCTAC | ATGGAGCTGA |
| **I5** | GGTCACCATG | ACCAGGGACA | CGTCCATCAG | CACAGCCTAC | ATGGAGCTGA |
| **I1** | GGTCACCATG | ACCAGGGACA | CGTCCATCAG | CACRGCCTAC | ATGGAACTGA |
| **DH473H** | GGTCACCATG | ACCAGGGAAA | CGTCCGTCAG | CACGGCCTAT | ATGGAACTGA |
| **DH391H** | GGTCACGATG | ACTACGGACA | CGTCCATGAA | TGTTGCCTAC | ATGGAACTGA |
| **I4** | GGTCACCATG | ACCAGGGACA | CGTCCATCAG | CACAGCCTAC | ATGGAGCTGA |
| **I3** | GGTCACCATG | ACCAGGGACA | CGTCCATCGG | CACAGCCTAC | ATGGAGYTGA |
| **DH542H** | GGTCACCATG | ACCAGGGACA | CGTCCATCGG | CACAGCCTAC | ATGGAGTTGA |
| **I2** | GGTCACCATG | ACCAGGGACA | CGTCCATCGG | CACAGCCTAC | ATGGAGYTGA |
| **DH471H** | GGTCACCATG | ACCAGGGACA | CGTCCATCGG | CACAGCCTAC | ATGGAGTTGA |
| **DH429H** | GGTCACCCTG | ACCAGGGACA | CGTCCATCGG | CACAGCCTAC | ATGGAGCTGA |
| **DH270H** | GGTCACCATG | ACCAGGGACA | CGTCCATCAG | CACAGCCTAC | ATGGACCTGA |

CDR3

| | 260 | 270 | 280 | 290 | 300 |
|---|---|---|---|---|---|
| **UCA** | GCAGGCTGAG | ATCTGACGAC | ACGGCCGTGT | ATTACTGTGC | GAGAGGGGGR |
| **I5** | GCAGVCTGAG | ATCTGACGAC | ACGGCCGTGT | ATTACTGTGC | GAGAGGGGGR |
| **I1** | GAAGMCTGAG | ATCTGACGAC | ACGGCCGTCT | ATTACTGTGC | GAGAGGGGGA |
| **DH473H** | GAAGACTGAG | ATCTGACGAC | ACGGCCGTCT | ATTACTGTGC | GAAAGCGGGA |
| **DH391H** | GAGGCTTGAG | ATCTGACGAC | ACGGCCGTCT | ATTTCTGTGC | GAGAGGGGGA |
| **I4** | GCAGVCTGAC | ATCTGACGAC | ACGGCCGTGT | ATTACTGTGC | GACAGGGGGR |
| **I3** | GVAGCCTGAC | ATCTGACGAC | ACGGCCGTVT | ATTACTGTGC | GACAGGGGGR |
| **DH542H** | GAAGCCTGAC | ATCTGACGAC | ACGGCCATAT | ATTACTGTAC | GACAGGGGGA |
| **I2** | GGAGCCTGAC | ATCTGACGAC | ACGGCCGTCT | ATTACTGTGT | GACAGGGGGR |
| **DH471H** | GGAGCCTCAC | ATCTGACGAC | ACGGCCGTCT | ATTACTGTGT | GACAGGGGCC |
| **DH429H** | GGAGGCTGAC | ATCTGACGAC | ACGGCCGTCT | ATTACTGTGT | GACAGGGGGG |
| **DH270H** | ACAGACTGAC | GTCTGACGAC | ACGGCCATGT | ATTACTGTAC | GACCGGGGGG |

Figure 26 cont.

```
             ....|....| ....|....| ....|....| ....|....| ....|....|
                     310        320        330        340        350
UCA          TGGATCRGTC TTTACTATGA TAGTAGTGGT TACCCTAACT TTGACTACTG
I5           TGGATCRGTC TTTACTATGA TAGTAGTGGT TACCCTAACT TTGACTACTG
I1           TGGATCRGTC TTTACGTTGA TTATAGTGGT TACCCTAACT TTGACTCCTG
DH473H       TACATCGCCC TTTACGTTGA CTATAGTGGT TACCCTAACT TTAATTCCTG
DH391H       TGGATCAGTC TCTACGTTGA TTACAGTTAT TACCCTAACT TTGACTCGTG
I4           TGGATCRGTC TTTACTATGA TAGTAGTGGT TACCCTAACT TTGACTACTG
I3           TGGATCAGTC TTTACTATGA TAGTAGTTAT TACCCTAACT TTGACCACTG
DH542H       TGGATCAGTC TTTACTATGA TAGTAGTTAT TACCCCAACT TTGACCACTG
I2           TGGATCAGTC HTTATTATGA TAGTAGTTAT TACCCTAACT TTGACCACTG
DH471H       TGGATCAGTG ATTATTATGA TAGTAGTTAT TATCCTAACT TTGACCACTG
DH429H       TGGATCAGTC CTTATTATGA TAGTAGTTAT TACCCTAATT TTGACCACTG
DH270H       TGGATCGGTC TTTACTCTGA TACTAGTGGT TACCCTAACT TTGACTACTG

             ....|....| ....|....| ....|....| ..
                     360        370        380
UCA          GGGCCAGGGA ACCCTGGTCA CCGTCTCCTC AG
I5           GGGCCAGGGA ACCCTGGTCA CCGTCTCCTC AG
I1           GGGCCAGGGA ACCCTGGTCA CCGTCTCCTC AG
DH473H       GGGCCAGGGA ACCCTGGTCA CCGTCTCCTC AG
DH391H       GGGCCAGGGA ACCCTGGTCT CCGTCTCTTC AG
I4           GGGCCAGGGA ACCCTGGTCA CCGTCTCCTC AG
I3           GGGTCAGGGA ACCCTGGTCA CCGTCTCCTC AG
DH542H       GGGTCAGGGA ACCCTGCTCA CCGTCTCCTC AG
I2           GGGTCAGGGA ACCCTGGTCA CCGTCTCCTC AG
DH471H       GGGTCAGGGA ACCCTGGTCA CCGTCTCCTC AG
DH429H       GGGTCAGGGA ACCCTGATCA CCGTCTCCTC AG
DH270H       GGGCCAGGGA ACCCTGGTCA CCGTCTCCTC AG
```

Figure 26 cont.

DH270 lineage - Heavy chain amino acid sequences

```
                                                CDR1
              ....|....| ....|....| ....|....| ....|....| ....|....|
                      10         20         30         40         50
UCA           QVQLVQSGAE VKKPGASVKV SCKASGYTFT GYYMHWVRQA PGQGLEWMGW
I5            QVQLVQSGAE XKKPGASVKV SCKASGYTFT DYYIHWVRQA PGQGLEWMGW
I1            QVQLVQSGAE XKKPGASVKV SCKASGYTFT DYYIHWVRQA PGQGLEWMAW
DH473H        EVQLVESGPE LKEPGASVKV SCKASGYTFT DYYIHWVRQA PGQGLEWMAW
DH391H        QVQLVQSGAE LKKPGASVKV SCKASGYTLS DYYVHWLRQA PGQGLEWVAW
I4            QVQLVQSGAE MKKPGASVKV SCKASGYTFT DYYIHWVRQA PGQGLEWMGW
I3            QVQLVQSGAE MKNPGASVKV SCAXSGYTFT DFYIHWVRQA PGQGLXWMGW
DH542H        QVQLVQSGAQ MKNPGASVKV SCAPSGYTFT DFYIHWLRQA PGQGLQWMGW
I2            QVQLVQSGAE MKNPGASVKV SCAXSGYTFT DFYIHWVRLA PGQGLXWMGW
DH471H        QVQLVQSGAE VKNPGASVKV SCAPSGYTFT DFYIHWVRLA PGQGLEWLGW
DH429H        EVQLVQSGAE MKNPGASVKV SCAASGYGFT DFYIHWVRLA PGHGLQWMGW
DH270H        QVQLVQSGAE MKKPGASVRV SCKASGYTFT DYYIHWVRQA PGQGPEWMGW

              CDR2                                              CDR3
              ....|....| ....|....| ....|....| ....|....| ....|....|
                      60         70         80         90        100
UCA           INPNSGGTNY AQKFQGRVTM TRDTSISTAY MELSRLRSDD TAVYYCARGX
I5            INPNXGRTNX AQKFQGRVTM TRDTSISTAY MELSXLRSDD TAVYYCARGX
I1            INPTXGRTXX ARKFQGRVTM TRDTSISXAY MELRXLRSDD TAVYYCARGG
DH473H        INPTTGRSSF ARGFQGRVTM TRETSVSTAY MELRRLRSDD TAVYYCAKAG
DH391H        INPTSGRTIS PRKFQGRVTM TTDTSMNVAY MELRGLRSDD TAVYFCARGG
I4            INPNTGRTNX AQKFQGRVTM TRDTSISTAY MELSXLTSDD TAVYYCATGX
I3            MNPKTGRTNX AQNFQGRVTM TRDTSIGTAY MEXXSLTSDD TAXYYCATGX
DH542H        MNPQTGRTNT ARNFQGRVTM TRDTSIGTAY MELRSLTSDD TAIYYCTTGG
I2            MNPKTGRTNN AQNFQGRVTM TRDTSIGTAY MEXRSLTSDD TAVYYCVTGX
DH471H        MNPKTGRTNQ GQNFQGRVTM TRDTSIGTAY MELRSLTSDD TAVYYCVTGA
DH429H        MNPKTGRTNN AQDFQGRVTL TRDTSIGTAY MELRRLTSDD TAVYYCVTGG
DH270H        INPSTGRTNS PQKFQGRVTM TRDTSISTAY MDLNRLTSDD TAMYYCTTGG

              ....|....| ....|....| ....|..
                     110        120
UCA           WIXLYYDSSG YPNFDYWGQG TLVTVSS
I5            WIXLYYDSSG YPNFDYWGQG TLVTVSS
I1            WIXLYVDYSG YPNFDSWGQG TLVTVSS
DH473H        YIALYVDYSG YPNFNSWGQG TLVTVSS
DH391H        WISLYVDYSY YPNFDSWGQG TLVSVSS
I4            WIXLYYDSSG YPNFDYWGQG TLVTVSS
I3            WISLYYDSSY YPNFDHWGQG TLVTVSS
DH542H        WISLYYDSSY YPNFDHWGQG TLLTVSS
I2            WISXYYDSSY YPNFDHWGQG TLVTVSS
DH471H        WISDYYDSSY YPNFDHWGQG TLVTVSS
DH429H        WISPYYDSSY YPNFDHWGQG TLITVSS
DH270H        WIGLYSDTSG YPNFDYWGQG TLVTVSS
```

Figure 26 cont.

DH270 lineage - Light chain nucleotide sequences

```
                ....|....| ....|....| ....|....| ....|....| ....|....|
                        10         20         30         40         50
UCA             CAGTCTGCCC TGACTCAGCC TGCCTCCGTG TCTGGGTCTC CTGGACAGTC
I5              CAGTCTGCCC TGACTCAGCC TGCCTCCGTG TCTGGGTCTC CTGGACAGTC
I1              CAGTCTGCCC TGACTCAGCC TGCCTCCGTG TCTGGGTCTC CTGGACAGTC
DH473H          CAGTCTGCCC TGACTCAGCC TGCCTCCGTG TCTGGGTCTC CTGGCCAGTC
DH391H          CAGCCTGTGC TGACTCAGCC TGCCTCCGTG TCTGGGTCTC CTGGACAGTC
I4              CAGTCTGCCC TGACTCAGCC TGCCTCCGTG TCTGGGTCTC CTGGACAGTC
I3              CAGTCTGYSC TGACTCAGCC TGCCTCCGTG TCTGGGTCTC CTGGACAGTC
DH542H          ACCAGTCTGC TGACTCAGCC TGCCTCCGTG TCTGGGTCTC CTGGACAGTC
I2              CAGTCTGYSC TGACTCAGCC TGCCTCCGTG TCTGGGTCTC CTGGACAGTC
DH471H          CTGCCTGTGC TGACTCAGCC TGCCTCCGTG TCTGGGTCTC CTGGGCAGTC
DH429H          CAGTCTGCCC TGACTCAGCC TGCCTCCGTG TCTGGGTCTC CTGGACAGTC
DH270H          CAGTCTGCCC TGACTCAGCC TGCCTCCGTG TCTGGGTCTC CTGGACAGTC
```

```
                                          CDR1
                ....|....| ....|....| ....|....| ....|....| ....|....|
                        60         70         80         90        100
UCA             GATCACCATC TCCTGCACTG GAACCAGCAG TGATGTTGGG AGTTATAACC
I5              GATCACCATC TCCTGCACTG GAACCAGCWR TGATGTTGGG AGTTATAACC
I1              GATCACCATC TCCTGCACTG GAACCAGCWR TGATGTTGGG AGTTATAACC
DH473H          GATCACCATC TCCTGCACTG GAACCAGCTA TGATGTTGGG AGTTATAATC
DH391H          GATCACCATC TCCTGCACTG GAAGCAGCAG TGATGTTGGG AGTTATAACC
I4              GATCACCATC TCCTGCACTG GAACCAGTTA TGATGTTGGG AGTTATAACC
I3              GATCACCATC TCCTGCACTG GAACCAGTTA TGATGTTGGG AGTTATGACC
DH542H          GATCACCATC TCCTGCACTG GAACCAAGTA TGATGTTGGG AGTCATGACC
I2              GATCACCATC TCCTGCACTG GAACCAGTTA TGATGTTGGG AAGTTTGACC
DH471H          GATCACCATC TCCTGCACTG GGACCATTTA TGATGTTGGG AAGTTTGACC
DH429H          GATCACCATC TCCTGCACTG GAACCAGTTA TGATGTTGCG AAGTTTGACC
DH270H          GATCACCATC TCCTGCACTG GAACCAATTA TGATGTTGGG AGTTATAACC
```

```
                ....|....| ....|....| ....|....| ....|....| ....|....|
                       110        120        130        140        150
UCA             TTGTCTCCTG GTACCAACAG CACCCAGGCA AAGCCCCCAA ACTCATGATT
I5              TTGTCTCCTG GTACCAACAG CACCCAGGCA AAGCCCCCAA ACTCATGATT
I1              TTGTCTCCTG GTACCAACAG CACCCAGGCA AAGCCCCCAA ACTCATGATT
DH473H          TTGTCTCCTG GTACCAACAG CACCCAGGCA AAGCCCCCAA ACTCATTATT
DH391H          TTGTGTCCTG GTACCAGCAG CACCCAGGCA AAGCCCCCAA ACTGATGATT
I4              TTGTCTCCTG GTACCAACAG CACCCAGGCA AAGCCCCCAA ATACATGATT
I3              TTGTCTCCTG GTACCAACAG CACCCAGGCA AAGCCCCCAA ATACATGATT
DH542H          TTGTCTCCTG GTACCAACAG TACCCAGGCA AAGTCCCCAA ATACATGATT
I2              TTGTCTCCTG GTACCAACAG CACCCAGGCA AAGCCCCCAA ATACATGATT
DH471H          TTGTCTCCTG GTACCAGCAC CACCCAGGCA AAGCCCCCAA ATATTTGATT
DH429H          TTGTCTCCTG GTTCCAACAG CACCCAGGCA AAGCCCCCAA ATACATGATT
DH270H          TTGTCTCCTG GTATCAACAG CACCCAGGCA AAGTCCCCAA ATACATAATT
```

Figure 26 cont.

```
                CDR2
           ....|....| ....|....| ....|....| ....|....| ....|....|
                  160        170        180        190        200
UCA        TATGAGGTCA GTAAGCGGCC CTCAGGGGTT TCTAATCGCT TCTCTGGCTC
I5         TATGAGGTCA RTAAGCGGCC CTCAGGGGTT TCTAATCGCT TCTCTGGCTC
I1         TATGAGGTCA RTAAGTGGCC CTCAGGGGTT TCTAATCGCT TCTCTGGCTC
DH473H     TATGAGGTCA GTCAGTGGCC CTCAGGGGTT TCTAAGCGCT TCTCTGGCTC

DH391H     TATGAGGTCA ATAAGTGGGC CTCAGGGGTT TCTGATCGCT TCGCTGGCTC
I4         TATGAGGTCA ATAAGCGGCC CTCAGGGGTT TCTAATCGCT TCTCTGGCTC
I3         TATGAAGTCA ATAAGCGGCC CTCAGGAGTT TCTAATCGCT TCTCTGGCTC
DH542H     TATGAAGTCA ATAAACGGCC CTCAGGAGTT TCTAATCGCT TCTCTGGCTC
I2         TATGAAGTCA ATAAGTGGCC CTCAGGAGTT TCTCATCGCT TCTCTGGCTC
DH471H     TATGAAGTCA AAAAGTGGCC CTCAGGAGTT TCTCATCGCT TCTCTGGCTC
DH429H     TATGAAGTCA ATAAGTGGCC CTCAGGAGTT TCTCATCGCT TCTCTGGTTC
DH270H     TATGAGGTCA ATAAGCGGCC CTCAGGGGTT TCTAATCGCT TCTCTGGCTC

           ....|....| ....|....| ....|....| ....|....| ....|....|
                  210        220        230        240        250
UCA        CAAGTCTGGC AACACGGCCT CCCTGACAAT CTCTGGGCTC CAGGCTGAGG
I5         CAAGTCTGGC AACACGGCCT CCCTGACAAT CTCTGGGCTC CAGGCTGAGG
I1         CAAGTCTGGC AACACGGCCT CCCTGACAAT CTCTGGGCTC CAGGCTGAGG
DH473H     CAAGTCTGGC AACACGGCCT CCCTGACAAT CTCTGGGCTC CAGGCTGAGG
DH391H     CAAGTCTGGC AACACGGCCT CCCTGACAAT CTCTAGACTC CAGGCTGAGG
I4         CAAGTCTGGC AACACGGCCT CCCTGACAAT CTCTGGGCTC CAGGCTGAGG
I3         CAAATCTGGC AACACGGCCT CCCTGACAAT CTCTGGGCTC CAGGCTGAGG
DH542H     CAAATCTGGC AACACGGCCT CCCTGACAAT CTCTGGGCTC CGGGCTGAGG
I2         CAAATCTGGC AACACGGCCT CCCTGACAAT CTCTGGGCTC CAGGCTGAGG
DH471H     CAAATCTGGC AACACGGCCT CCCTGACAAT CTCTGGGCTC CAGGTTGAGG
DH429H     CAAATCTGGC AACACGGCCT CCCTGACAAT CTCTGGGCTC CAGGCTGAGG
DH270H     CAAGTCTGGC AACACGGCCT CCCTGACAAT CTCTGGGCTC CAGGCTGAGG

                                  CDR3
           ....|....| ....|....| ....|....| ....|....| ....|....|
                  260        270        280        290        300
UCA        ACGAGGCTGA TTATTACTGC TGCTCATATG CAGGTAGTAG CACTGTAWTA
I5         ACGAGGCTGA TTATTACTGY TGCTCATATG CAGGTAGTAG CACTGTAWTA
I1         ACGAGGCTVA TTATTACTGT TGCTCATATG CAGGTAGTAG CACTGTAATA
DH473H     ACGAGGCTCA TTATTACTGT TGCTCATATG CAGGCAGTAG CACTGTAATA
DH391H     ACGAGGCTAA TTACTTTTGT TCCTCATCTA CAAATAGTGC CACTGTCATA
I4         ACGAGGCTGA TTATTACTGY TGCTCATATG CAGGTAGTAG CACTGTADTW
I3         ACGAGGCTGA CTATTATTGC TGCTCATTTG GAGGTAGTGC CACTGTRGTC
DH542H     ACGAGGCTGA CTATTATTGC TGTTCATTTG GAGGGAGTGC CACCGTGGTC
I2         ACGAGGCTGA CTATTATTGC TGCTCATTCG GAGGTAGTGC CACTGTRGTC
DH471H     ACGAGGCTGA CTATTATTGC TGCTCATTCG GAGGTAGTGC CGCTGTGGTC
DH429H     ACGAGGCTGA CTATTATTGC TGCTCATTCG GAGGTAGTGC CACTGTAGTC
DH270H     ACGAGGCCAC TTATTACTGT TGTTCATATG CAGGTAGTAG CATTATATTT
```

Figure 26 cont.

```
                 ....|....| ....|....| ....|....| .
                         310        320        330
UCA              TTCGGCGGAG GGACCAAGCT GACCGTCCTA G
I5               TTCGGCGGAG GGACCAAGCT GACCGTCCTA G
I1               TTCGGCGGAG GGACCAAGCT GACCGTCCTA G
DH473H           TTCGGCGGAG GGACCTCGCT GACCGTCCTA G
DH391H           TTCGGCGGAG GGACCAAGCT GACCGTCCTA G
I4               TTCGGCGGAG GGACCAAGCT GACCGTCCTA G
I3               TGCGGCGGAG GGACCAAGGT GACCGTCCTA G
DH542H           TGCGGCGGCG GGACCAAGGT GACCGTCCTA G
I2               TGCGGCGGAG GGACCAAGGT GACCGTCCTA G
DH471H           TGCGGCGGAG GGACCAAGGT GACCGTCCTA G
DH429H           TGCGGCGGAG GGACCAAGGT GACCGTCCTA G
DH270H           TTCGGCGGTG GGACCAAGCT GACCGTCATA G
```

Figure 26 cont.

DH270 lineage - Light chain amino acid sequences

```
                                            CDR1
          ....|....| ....|....| ....|....| ....|....| ....|....|
                  10         20         30         40         50
UCA       QSALTQPASV SGSPGQSITI SCTGTSSDVG SYNLVSWYQQ HPGKAPKLMI
I5        QSALTQPASV SGSPGQSITI SCTGTSXDVG SYNLVSWYQQ HPGKAPKLMI
I1        QSALTQPASV SGSPGQSITI SCTGTSXDVG SYNLVSWYQQ HPGKAPKLMI
DH473H    QSALTQPASV SGSPGQSITI SCTGTSYDVG SYNLVSWYQQ HPGKAPKLII
DH391H    QPVLTQPASV SGSPGQSITI SCTGSSSDVG SYNLVSWYQQ HPGKAPKLMI
I4        QSALTQPASV SGSPGQSITI SCTGTSYDVG SYNLVSWYQQ HPGKAPKYMI
I3        QSXLTQPASV SGSPGQSITI SCTGTSYDVG SYDLVSWYQQ HPGKAPKYMI
DH542H    TSLLTQPASV SGSPGQSITI SCTGTKYDVG SHDLVSWYQQ YPGKVPKYMI
I2        QSXLTQPASV SGSPGQSITI SCTGTSYDVG KFDLVSWYQQ HPGKAPKYMI
DH471H    LPVLTQPASV SGSPGQSITI SCTGTIYDVG KFDLVSWYQH HPGKAPKYLI
DH429H    QSALTQPASV SGSPGQSITI SCTGTSYDVA KFDLVSWFQQ HPGKAPKYMI
DH270H    QSALTQPASV SGSPGQSITI SCTGTNYDVG SYNLVSWYQQ HPGKVPKYII

           CDR2                                            CDR3
          ....|....| ....|....| ....|....| ....|....| ....|....|
                  60         70         80         90        100
UCA       YEVSKRPSGV SNRFSGSKSG NTASLTISGL QAEDEADYYC CSYAGSSTVX
I5        YEVXKRPSGV SNRFSGSKSG NTASLTISGL QAEDEADYYX CSYAGSSTVX
I1        YEVXKWPSGV SNRFSGSKSG NTASLTISGL QAEDEAXYYC CSYAGSSTVI
DH473H    YEVSQWPSGV SKRFSGSKSG NTASLTISGL QAEDEAHYYC CSYAGSSTVI
DH391H    YEVNKWASGV SDRFAGSKSG NTASLTISRL QAEDEANYFC SSSTNSATVI
I4        YEVNKRPSGV SNRFSGSKSG NTASLTISGL QAEDEADYYX CSYAGSSTVX
I3        YEVNKRPSGV SNRFSGSKSG NTASLTISGL QAEDEADYYC CSFGGSATXV
DH542H    YEVNKRPSGV SNRFSGSKSG NTASLTISGL RAEDEADYYC CSFGGSATVV
I2        YEVNKWPSGV SHRFSGSKSG NTASLTISGL QAEDEADYYC CSFGGSATXV
DH471H    YEVKKWPSGV SHRFSGSKSG NTASLTISGL QVEDEADYYC CSFGGSAAVV
DH429H    YEVNKWPSGV SHRFSGSKSG NTASLTISGL QAEDEADYYC CSFGGSATVV
DH270H    YEVNKRPSGV SNRFSGSKSG NTASLTISGL QAEDEATYYC CSYAGSSIIF
```

Figure 26 cont.

>CH557_aa_HC
QVRLAQYGGGVKRLGATMTLSCVASGYTFNDYYIHWVRQAPGQGFEL
LGYIDPANGRPDYAGALRERLSFYRDKSMETLYMDLRSLRYDDTAMY
YCVRNVGTAGSLLHYDHWGSGSPVIVSS
>CH557_aa_LC
EIVLTQSPATLSASPGERVTLTCRASRSVRNNVAWYQHKGGQSPRLL
IYDASTRAAGVPARFSGSASGTEFTLAISNLESEDFTVYFCLQYNNW
WTFGQGTRVDIK

>CH557_nt_HC
CAGGTCCGACTAGCCCAATATGGTGGTGGGGTGAAGAGGCTAGGGGC
CACAATGACCCTTTCCTGCGTGGCATCTGGATACACCTTCAACGACT
ACTACATACATTGGGTGCGGCAGGCCCCTGGACAAGGCTTTGAGTTG
TTGGGATACATCGACCCCGCTAATGGTCGCCCAGACTACGCAGGGGC
GTTGAGGGAGAGACTCTCCTTCTACAGGGACAAGTCCATGGAGACGC
TGTACATGGACCTGAGGAGCCTAAGATATGACGACACGGCCATGTAT
TATTGTGTTAGAAATGTGGGGACCGCTGGCAGCTTGCTGCATTATGA
CCACTGGGGCTCGGGAAGCCCGGTCATCGTCTCCTCC
>CH557_nt_LC
GAAATTGTGTTGACGCAGTCTCCAGCCACCCTGTCCGCGTCTCCAGG
GGAAAGAGTCACCCTAACTTGCAGGGCCAGTCGGAGTGTCCGAAACA
ACGTGGCCTGGTATCAGCACAAGGGTGGCCAGAGTCCCAGGCTCCTC
ATTTATGATGCGTCCACGAGGGCCGCTGGTGTCCCAGCCAGGTTCAG
CGGCAGTGCATCTGGGACAGAGTTCACTCTCGCCATCAGCAACTTGG
AGTCTGAAGATTTTACAGTCTACTTCTGTCTGCAGTATAATAACTGG
TGGACCTTCGGCCAAGGGACCAGGGTGGACATCAAA

Figure 27A

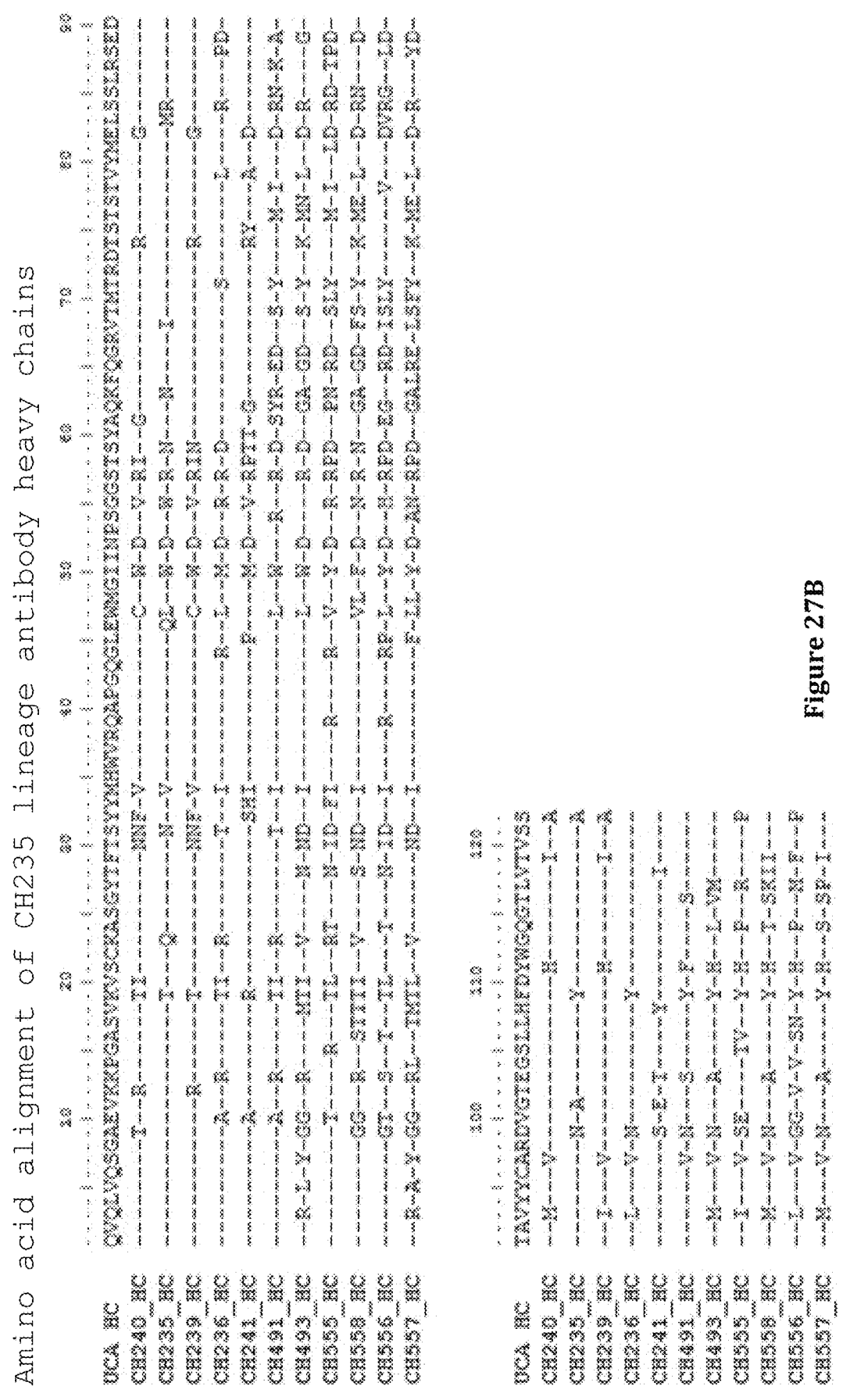

Amino acid alignment of CH235 lineage antibody heavy chains

```
                   10        20        30        40        50        60        70        80        90
           ....|....|....|....|....|....|....|....|....|....|....|....|....|....|....|....|....|....|
UCA_HC     QVQLVQSGAEVKKPGASVKVSCKASGYTFTSYYMHWVRQAPGQGLEWMGIINPSGGSTSYAQKFQGRVTMTRDTSTSTVYMELSSLRSED
CH240_HC   --------T--R------TI---------NNF-V------------C--W-D--V-RI--G------------R-------G--------
CH235_HC   ------------------T---Q-------N--V-----------QL--W-D--W-R-N---N----I--------------MR------
CH239_HC   -----------R------T----------NNF-V------------C--W-D--V-RIN--------------R-------G--------
CH236_HC   ---------A--R-----TI--R-------T--I---------R--L--M-D--R-R-D-----------S-------L----R---FD-
CH241_HC   ---------A--------R------------SHI----------P----M-D--V-RPTT-G-----------RY---A--D--------
CH491_HC   ---------A--R-----TI--R-------T--I------------L--W---R--R-D-SYR-ED--S-Y----M-I---D-RN-K-A-
CH493_HC   --R-L-Y-GG--R----MTI--V----N-ND--I------------L--W-D----R-D--GA-GD--S-Y--K-MN-L--D-R----G-
CH555_HC   ---------T----R---TL--RT---N-ID-FI----R----R--V--Y-D--R-RPD--PN-RD--SLY----M-I--LD-RD-TPD-
CH558_HC   --------GG--R--STTTI--V----S-ND--I------------VL-F-D--N-R-N--GA-GD-FS-Y--K-ME-L--D-RN---D-
CH556_HC   --------GT--S--T--TL---T---N-ID--I----R----RP-L--Y-D--H-RPD-EG--RD-ISLY------V---DVRG--LD-
CH557_HC   --R-A-Y-GG--RL--TMTL--V------ND--I----------F-LL-Y-D-AN-RPD--GALRE-LSFY--K-ME-L--D-R---YD-

                  100       110       120
           ....|....|....|....|....|....|..
UCA_HC     TAVYYCARDVGTEGSLLHFDYWGQGTLVTVSS
CH240_HC   --M---V-------------H-------I--A
CH235_HC   --------N-A-------Y------------A
CH239_HC   --I---V-------------H-------I--A
CH236_HC   --L---V-N---------Y-------------
CH241_HC   --------S-E-T----Y---------I----
CH491_HC   ------V-N---S-----Y-F----S------
CH493_HC   --M---V-N---A-----Y-H--L-VM-----
CH555_HC   --I---V-SE----TV--Y-H--P--R----P
CH558_HC   --M---V-N---A-----Y-H--T-SKII---
CH556_HC   --L---V-GG-V-V-SN-Y-H--P--N-F--F
CH557_HC   --M---V-N---A-----Y-R--S-SP-I---
```

Figure 27B

Amino acid alignment of CH235 lineage antibody light chains

```
            10        20        30        40        50        60        70        80        90
    ....|....|....|....|....|....|....|....|....|....|....|....|....|....|....|....|....|....|
UCA LC   EIVLTQSPATLSVSPGERATLSCRASQSVSSNLAWYQQKPGQAPRLLIYGASTRATGIPARFSGSGSGTEFTLTISSLQSEDFAVYYCQQ
CH236 LC ..................V..........RN.....R..R.....................................M............
CH240 LC .........................T...R.........R.........S...........................V..........L.
CH241 LC .............................R..I...............H..........G........P....A...V............
CH235 LC .............................R........R...........T......V......R........A...M........L.L.
CH239 LC .........................T...R..V................S.........................A.M..........L.
CH558 LC ............A.....V..T....RG.RN.V....HNV..S......D.....P.........A.......A...I.....TL...H.
CH557 LC ............A.....V..T....R..RN.V....H.G..S......D.....A.V.......A.......A.N.E.....T..F.L.
CH555 LC ........D...A.....V..........GTKV...RHVR..P............A........G....N...I.NNF......E.L...
CH556 LC .TT.....D...A.....V......A...G.QV..FRHIR..P.....S......A.V...........D......GM......E.F...

              100
         ....|....|....|.
UCA LC   YNNWWTFGQGTKVEIK
CH236 LC ................
CH240 LC ................
CH241 LC ..D.............
CH235 LC ................
CH239 LC .DD.............
CH558 LC ...........R.D.N
CH557 LC ...........R.D..
CH555 LC .KS..........DN.
CH556 LC .HM........R.DKN
```

Figure 27C

| | $IC_{50}$ (µg/ml) | | | | $IC_{80}$ (µg/ml) | | | |
|---|---|---|---|---|---|---|---|---|
| | Plasma Ab | Plasma Ab | MBC Ab | | Plasma Ab | Plasma Ab | MBC Ab | |
| | DH511 5a | DH511 5b | DH512 | 10E8 | DH511 5a | DH511 5b | DH512 | 10E8 |
| Number of Viruses | 203 | 203 | 208 | 208 | 203 | 203 | 208 | 208 |
| Total Viruses Neutralized | | | | | | | | |
| IC50/IC80 <50ug/ml | 202 | 202 | 206 | 203 | 201 | 201 | 203 | 203 |
| IC50/IC80 <10ug/ml | 196 | 198 | 198 | 202 | 169 | 172 | 147 | 193 |
| IC50/IC80 <1.0ug/ml | 122 | 123 | 103 | 152 | 37 | 37 | 33 | 61 |
| IC50/IC80 <0.1ug/ml | 19 | 18 | 20 | 42 | 5 | 6 | 7 | 10 |
| IC50/IC80 <0.01ug/ml | 4 | 3 | 7 | 10 | 0 | 0 | 3 | 5 |
| Percent of Viruses Neutralized | | | | | | | | |
| IC50/IC80 <50ug/ml | 100 | 100 | 99 | 98 | 99 | 99 | 98 | 98 |
| IC50/IC80 <10ug/ml | 97 | 98 | 95 | 97 | 83 | 85 | 71 | 93 |
| IC50/IC80 <1.0ug/ml | 60 | 61 | 50 | 73 | 18 | 18 | 16 | 29 |
| IC50/IC80 <0.1ug/ml | 9 | 9 | 10 | 20 | 2 | 3 | 3 | 5 |
| IC50/IC80 <0.01ug/ml | 2 | 1 | 3 | 5 | 0 | 0 | 1 | 2 |
| | | | | | | | | |
| Median IC50/IC80 | 0.764 | 0.698 | 1.04 | 0.392 | 3.49 | 3.33 | 5.07 | 1.69 |
| Geometric Mean | 0.684 | 0.634 | 0.792 | 0.299 | 3.02 | 2.80 | 3.73 | 1.34 |

Figure 28A

| | Titer in TZM-bl cells (µg/ml) | | | | | | | | | | | | | | | | | |
|---|---|---|---|---|---|---|---|---|---|---|---|---|---|---|---|---|---|---|
| | Chimeric Ab | | Chimeric Ab | | Chimeric Ab | | Chimeric Ab | | Serum Ab | | Serum Ab | | Serum Ab | | MBC Ab | | | |
| | DH512_K2 | | DH512_K3 | | DH512_K4 | | DH511_2b_K2 | | DH511_5a | | DH511_5b | | DH511_2b | | DH512 | | 10E8 | |
| | IC50 | IC80 | IC50 | IC80 | IC50 | IC80 | IC50 | IC80 | IC50 | IC80 | IC50 | IC80 | IC50 | IC80 | IC50 | IC80 | IC50 | IC80 |
| MEDIAN TITERS | 1.327 | 5.538 | 0.387 | 1.462 | 0.951 | 4.839 | 1.563 | 7.867 | 1.330 | 4.892 | 0.712 | 4.066 | 1.364 | 6.765 | 0.903 | 4.963 | 0.413 | 1.648 |

Figure 28B

| | | | | | | |
|---|---|---|---|---|---|---|
| | | DH512* | | | DH512_K2 | |
| Virus ID | Clade | IC50 | IC80 | | IC50 | IC80 |
| QH0692.42 | B | 3.170 | 15.785 | | 3.385 | 12.499 |
| SC422661.8 | B | 0.532 | 4.018 | | 0.910 | 3.158 |
| AC10.0.29 | B | 0.163 | 1.136 | | 0.348 | 1.619 |
| THRO4156.18 | B | 0.716 | 4.418 | | 1.784 | 7.415 |
| WITO4160.33 | B | 0.136 | 1.850 | | 0.693 | 2.633 |
| Du156.12 | C | 0.058 | 0.290 | | 0.078 | 0.343 |
| Du422.1 | C | 1.024 | 6.146 | | 0.809 | 2.686 |
| ZM53M.PB12 | C | 4.292 | 2.534 | | 6.747 | 21.514 |
| ZM109F.PB4 | C | 0.335 | 5.344 | | 2.387 | 9.154 |
| HIV-0013095-2.11 | C | 0.026 | 0.284 | | <0.023 | 0.617 |
| CNE19 | BC | 0.266 | 3.853 | | 1.403 | 6.256 |
| CNE30 | BC | 3.043 | 19.041 | | 5.780 | 28.975 |
| MS208.A1 | A | 1.770 | 6.902 | | 3.220 | 12.725 |
| Q23.17 | A | 2.113 | 11.185 | | 1.968 | 10.871 |
| Q769.d22 | A | 0.463 | 7.680 | | 1.358 | 10.127 |
| 0330.v4.c3 | A | 1.045 | 10.469 | | 2.370 | 10.334 |
| 191955_A11 | A (T/F) | 0.655 | 3.299 | | 0.981 | 2.691 |
| 928-28 | CRF02_AG | 0.112 | 0.597 | | 0.260 | 1.400 |
| T250-4 | CRF02_AG | 0.377 | 3.496 | | 2.177 | 9.125 |
| 211-9 | CRF02_AG | 0.459 | 3.591 | | 1.020 | 3.622 |
| C1080.c03 | CRF01_AE | 0.103 | 1.305 | | 0.250 | 1.364 |
| R1166.c01 | CRF01_AE | 1.153 | 5.944 | | 2.001 | 5.853 |
| C4118.c09 | CRF01_AE | 1.252 | 18.623 | | 2.753 | 17.337 |
| X2131_C1_B5 | G | 0.174 | 1.096 | | 0.202 | 0.972 |
| P1981_C5_3 | G | 0.049 | 0.331 | | 0.062 | 0.269 |
| X1632_S2_B10 | G | 0.472 | 6.059 | | 0.760 | 4.101 |
| 3016.v5.c45 | D | 0.749 | 3.788 | | 1.437 | 5.222 |
| A07412M1.vrc12 | D | 0.695 | 5.920 | | 1.296 | 6.226 |
| 3817.v2.c59 | CD | 3.570 | 13.097 | | 3.473 | 12.836 |
| 0815.v3.c3 | ACD | 0.158 | 3.334 | | 1.160 | 4.420 |
| | | | | | | |
| MuLV | Neg. Control | >50 | >50 | | >50 | >50 |
| | | | | | | |
| MEDIAN TITERS | | 0.502 | 3.936 | | 1.327 | 5.538 |

Figure 29A

| | | | | | | | | |
|---|---|---|---|---|---|---|---|---|
| | | | | | | | | Titer in TZM.b |
| | DH512_K3 | | | DH512_K4 | | | DH511_5A* | |
| Virus ID | IC50 | IC80 | | IC50 | IC80 | | IC50 | IC80 |
| QH0692.42 | 0.982 | 3.587 | | 2.775 | 9.974 | | 1.614 | 6.942 |
| SC422661.8 | 0.269 | 0.999 | | 0.492 | 2.221 | | 1.327 | 4.239 |
| AC10.0.29 | 0.115 | 0.476 | | 0.207 | 0.987 | | 0.279 | 1.934 |
| THRO4156.18 | 0.584 | 2.617 | | 1.031 | 6.105 | | 0.277 | 2.051 |
| WITO4160.33 | 0.149 | 0.750 | | 0.292 | 1.481 | | 0.294 | 1.546 |
| Du156.12 | <0.023 | 0.108 | | 0.034 | 0.229 | | 0.161 | 0.629 |
| Du422.1 | 0.320 | 1.172 | | 0.638 | 2.357 | | 0.942 | 3.605 |
| ZM53M.PB12 | 2.900 | 11.121 | | 4.429 | 13.276 | | 10.718 | 36.286 |
| ZM109F.PB4 | 0.729 | 2.690 | | 1.966 | 10.797 | | 0.692 | 4.090 |
| HIV-0013095-2.11 | <0.023 | 0.138 | | <0.023 | 0.483 | | 0.077 | 0.606 |
| CNE19 | 0.259 | 1.337 | | 0.462 | 4.989 | | 1.374 | 8.836 |
| CNE30 | 1.499 | 7.869 | | 3.947 | 27.253 | | 2.630 | 15.432 |
| MS208.A1 | 0.683 | 3.312 | | 2.169 | 11.758 | | 1.854 | 6.789 |
| Q23.17 | 0.731 | 3.080 | | 1.828 | 8.227 | | 3.346 | 14.463 |
| Q769.d22 | 0.254 | 1.587 | | 0.596 | 5.661 | | 3.124 | 12.578 |
| 0330.v4.c3 | 0.926 | 3.654 | | 2.245 | 14.007 | | 3.168 | 13.860 |
| 191955_A11 | 0.388 | 1.155 | | 0.956 | 2.555 | | 1.333 | 3.570 |
| 928-28 | 0.033 | 0.513 | | 0.145 | 1.201 | | 0.133 | 0.992 |
| T250-4 | 0.866 | 3.326 | | 2.339 | 9.437 | | 4.869 | 21.225 |
| 211-9 | 0.386 | 1.139 | | 1.040 | 3.680 | | 0.857 | 4.307 |
| C1080.c03 | 0.081 | 0.516 | | 0.173 | 0.988 | | 0.212 | 1.292 |
| R1166.c01 | 0.711 | 2.354 | | 1.925 | 6.129 | | 1.121 | 4.781 |
| C4118.c09 | 0.508 | 4.200 | | 1.173 | 9.343 | | 2.605 | 17.135 |
| X2131_C1_B5 | 0.068 | 0.442 | | 0.126 | 0.750 | | 0.335 | 1.432 |
| P1981_C5_3 | <0.023 | 0.109 | | 0.029 | 0.190 | | 0.138 | 0.571 |
| X1632_S2_B10 | 0.265 | 1.141 | | 0.612 | 2.522 | | 1.351 | 5.682 |
| 3016.v5.c45 | 0.531 | 1.952 | | 1.383 | 6.571 | | 1.435 | 7.036 |
| A07412M1.vrc12 | 0.484 | 1.764 | | 0.946 | 4.688 | | 0.782 | 5.002 |
| 3817.v2.c59 | 1.214 | 4.276 | | 3.210 | 11.531 | | 5.564 | 16.415 |
| 0815.v3.c3 | 0.271 | 1.215 | | 0.568 | 3.551 | | 1.657 | 7.439 |
| | | | | | | | | |
| MuLV | >50 | >50 | | >50 | >50 | | >50 | >50 |
| | | | | | | | | |
| MEDIAN TITERS | 0.387 | 1.462 | | 0.951 | 4.839 | | 1.330 | 4.892 |

Figure 29A cont.

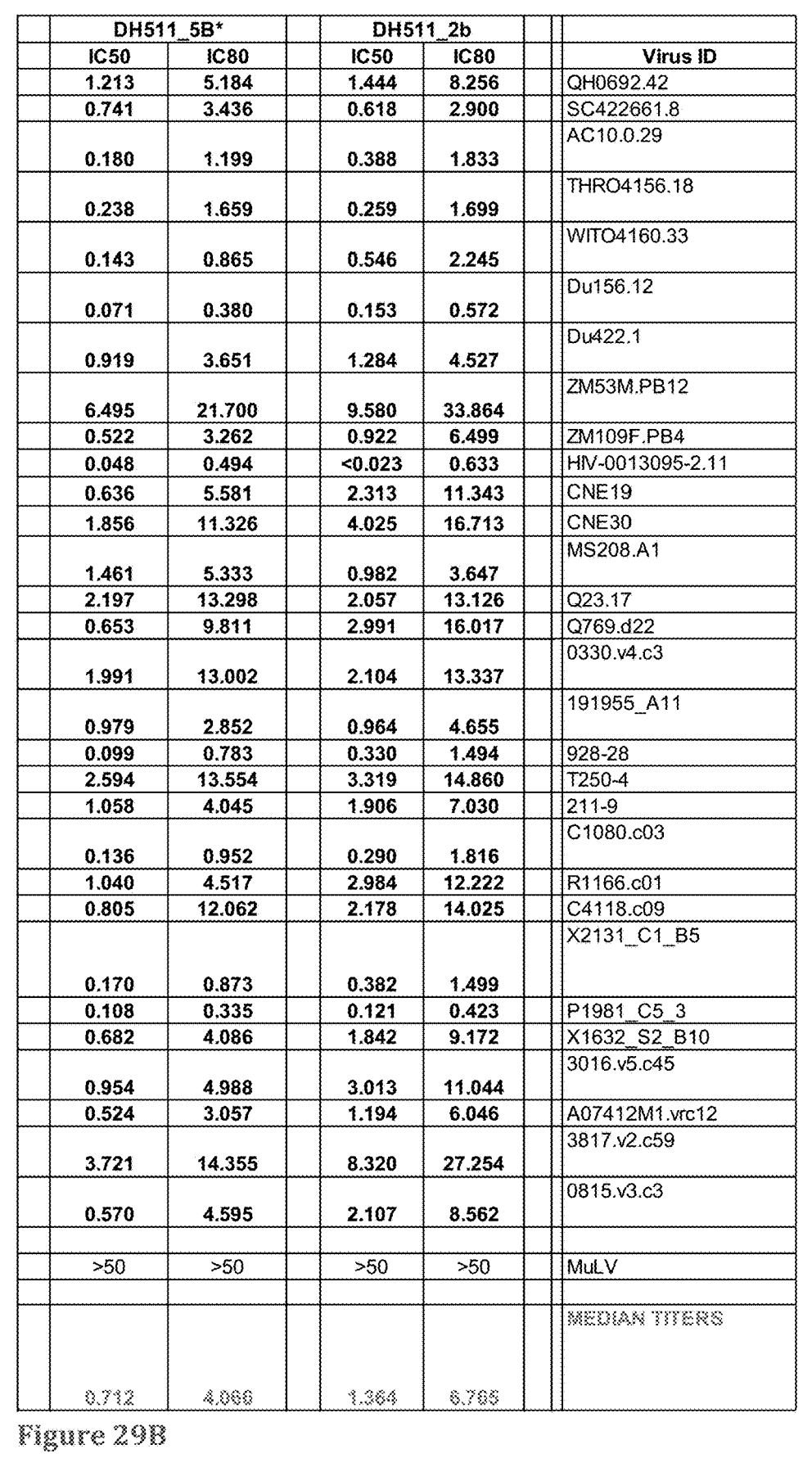

| DH511_5B* | | DH511_2b | | |
|---|---|---|---|---|
| IC50 | IC80 | IC50 | IC80 | Virus ID |
| 1.213 | 5.184 | 1.444 | 8.256 | QH0692.42 |
| 0.741 | 3.436 | 0.618 | 2.900 | SC422661.8 |
| 0.180 | 1.199 | 0.388 | 1.833 | AC10.0.29 |
| 0.238 | 1.659 | 0.259 | 1.699 | THRO4156.18 |
| 0.143 | 0.865 | 0.546 | 2.245 | WITO4160.33 |
| 0.071 | 0.380 | 0.153 | 0.572 | Du156.12 |
| 0.919 | 3.651 | 1.284 | 4.527 | Du422.1 |
| 6.495 | 21.700 | 9.580 | 33.864 | ZM53M.PB12 |
| 0.522 | 3.262 | 0.922 | 6.499 | ZM109F.PB4 |
| 0.048 | 0.494 | <0.023 | 0.633 | HIV-0013095-2.11 |
| 0.636 | 5.581 | 2.313 | 11.343 | CNE19 |
| 1.856 | 11.326 | 4.025 | 16.713 | CNE30 |
| 1.461 | 5.333 | 0.982 | 3.647 | MS208.A1 |
| 2.197 | 13.298 | 2.057 | 13.126 | Q23.17 |
| 0.653 | 9.811 | 2.991 | 16.017 | Q769.d22 |
| 1.991 | 13.002 | 2.104 | 13.337 | 0330.v4.c3 |
| 0.979 | 2.852 | 0.964 | 4.655 | 191955_A11 |
| 0.099 | 0.783 | 0.330 | 1.494 | 928-28 |
| 2.594 | 13.554 | 3.319 | 14.860 | T250-4 |
| 1.058 | 4.045 | 1.906 | 7.030 | 211-9 |
| 0.136 | 0.952 | 0.290 | 1.816 | C1080.c03 |
| 1.040 | 4.517 | 2.984 | 12.222 | R1166.c01 |
| 0.805 | 12.062 | 2.178 | 14.025 | C4118.c09 |
| 0.170 | 0.873 | 0.382 | 1.499 | X2131_C1_B5 |
| 0.108 | 0.335 | 0.121 | 0.423 | P1981_C5_3 |
| 0.682 | 4.086 | 1.842 | 9.172 | X1632_S2_B10 |
| 0.954 | 4.988 | 3.013 | 11.044 | 3016.v5.c45 |
| 0.524 | 3.057 | 1.194 | 6.046 | A07412M1.vrc12 |
| 3.721 | 14.355 | 8.320 | 27.254 | 3817.v2.c59 |
| 0.570 | 4.595 | 2.107 | 8.562 | 0815.v3.c3 |
| | | | | |
| >50 | >50 | >50 | >50 | MuLV |
| | | | | |
| 0.712 | 4.066 | 1.364 | 6.765 | MEDIAN TITERS |

Figure 29B

| DH511_2b_K2 | | | Ab510049 | | | 10E8 (Haynes) | | | |
|---|---|---|---|---|---|---|---|---|---|
| IC50 | IC80 | | IC50 | IC80 | | IC50 | IC80 | | Virus ID |
| 2.111 | 13.660 | | 1.630 | 8.754 | | 0.566 | 2.318 | | QH0692.42 |
| 0.638 | 4.555 | | 0.444 | 2.013 | | 0.302 | 1.233 | | SC422661.8 |
| 0.436 | 2.943 | | 0.153 | 0.823 | | 0.172 | 0.882 | | AC10.0.29 |
| 0.287 | 1.748 | | 0.194 | 1.984 | | 0.120 | 0.566 | | THRO4156.18 |
| 0.371 | 1.900 | | 0.261 | 1.275 | | 0.159 | 0.858 | | WITO4160.33 |
| 0.184 | 0.791 | | 0.064 | 0.336 | | 0.028 | 0.130 | | Du156.12 |
| 2.184 | 7.641 | | 0.758 | 2.880 | | 0.220 | 0.825 | | Du422.1 |
| 12.531 | 47.720 | | 6.127 | 25.371 | | 2.721 | 13.377 | | ZM53M.PB12 |
| 1.529 | 7.978 | | 1.144 | 5.702 | | 0.252 | 1.363 | | ZM109F.PB4 |
| 0.091 | 0.862 | | <0.023 | 0.603 | | <0.023 | 0.127 | | HIV-0013095-2.11 |
| 2.188 | 14.043 | | 1.583 | 7.944 | | 0.582 | 3.268 | | CNE19 |
| 3.817 | 24.186 | | 4.827 | 27.474 | | 0.616 | 4.877 | | CNE30 |
| 0.888 | 4.384 | | 1.480 | 5.405 | | 0.442 | 2.001 | | MS208.A1 |
| 3.327 | 22.256 | | 2.013 | 11.866 | | 0.660 | 3.669 | | Q23.17 |
| 1.095 | 21.724 | | 1.118 | 9.570 | | 1.113 | 4.767 | | Q769.d22 |
| 3.598 | 21.324 | | 1.784 | 9.736 | | 1.405 | 6.461 | | 0330.v4.c3 |
| 1.555 | 5.766 | | 0.956 | 3.362 | | 0.447 | 1.313 | | 191955_A11 |
| 0.553 | 2.272 | | 0.195 | 1.188 | | 0.119 | 0.665 | | 928-28 |
| 5.106 | 25.688 | | 2.599 | 14.555 | | 1.007 | 4.995 | | T250-4 |
| 2.490 | 9.001 | | 1.066 | 3.778 | | 0.635 | 2.174 | | 211-9 |
| 0.388 | 2.146 | | 0.154 | 1.176 | | 0.029 | 0.317 | | C1080.c03 |
| 3.836 | 17.464 | | 1.354 | 5.447 | | 0.384 | 2.914 | | R1166.c01 |
| 2.555 | 32.545 | | 0.801 | 12.004 | | 0.650 | 4.682 | | C4118.c09 |
| 0.440 | 1.646 | | 0.229 | 1.144 | | 0.080 | 0.373 | | X2131_C1_B5 |
| 0.150 | 0.537 | | 0.065 | 0.306 | | <0.023 | 0.106 | | P1981_C5_3 |
| 1.571 | 7.755 | | 0.741 | 4.779 | | 0.494 | 1.932 | | X1632_S2_B10 |
| 3.891 | 14.199 | | 1.811 | 8.529 | | 0.593 | 2.099 | | 3016.v5.c45 |
| 1.407 | 7.393 | | 0.649 | 5.147 | | 0.221 | 1.152 | | A07412M1.vrc12 |
| 11.619 | 41.810 | | 6.004 | 17.824 | | 0.906 | 3.819 | | 3817.v2.c59 |
| 1.989 | 10.166 | | 0.850 | 4.019 | | 0.238 | 1.091 | | 0815.v3.c3 |
| | | | | | | | | | |
| >50 | >50 | | >50 | >50 | | >50 | >50 | | MuLV |
| | | | | | | | | | |
| 1.563 | 7.867 | | 0.903 | 4.963 | | 0.413 | 1.648 | | MEDIAN TITERS |

Figure 29B cont.

| Region | R# | DH511 | DH511 mutation |
|---|---|---|---|
| CDRH3 | 92 | C | |
| | 93 | T | |
| | 94 | A | |
| | 95 | D | |
| | 96 | L | W |
| | 97 | G | W,F |
| | 98 | E | W |
| | 99 | P | W |
| | 100 | V | F,L |
| | 100a | V | W |
| | 100b | S | W |
| | 100c | R | W |
| | 100d | F | W |
| | 100e | F | W |
| | 100f | E | W |
| | 100g | W | |
| | 100h | G | W |
| | 100i | S | W |
| | 100j | Y | W |
| | 100k | Y | |
| | 100k | Y | W |
| | 100l | Y | |
| | 100m | M | |
| | 101 | D | |
| | 102 | L | |
| | 103 | W | |
| | 104 | G | |

Figure 30

| Region | R# | DH512 | DH512 mutation |
|---|---|---|---|
| CDRH3 | 92 | C | |
| | 93 | T | |
| | 94 | M | |
| | 95 | D | |
| | 96 | E | W |
| | 97 | G | W,F |
| | 98 | T | W |
| | 99 | P | W |
| | 100 | V | F,L |
| | 100a | T | W |
| | 100b | R | W |
| | 100c | F | W |
| | 100d | L | W,F |
| | 100e | E | W |
| | 100f | W | |
| | 100g | G | W |
| | 100h | Y | W |
| | 100i | F | W |
| | 100j | Y | |
| | 100k | Y | W |
| | 100l | Y | |
| | 100m | M | |
| | 101 | A | |
| | 102 | V | |
| | 103 | W | |
| | 104 | G | |

Figure 31

Mutations outside of CDRH3

| Region | R# | DH511 | DH511 mutation | Region | R# | DH512 | DH512 mutation |
|---|---|---|---|---|---|---|---|
| CDRH1 | 26 | G | W | CDRH1 | 26 | G | W |
| | 27 | F | | | 27 | F | |
| | 28 | T | W | | 28 | F | W |
| | 29 | F | | | 29 | F | |
| | 30 | S | | | 30 | D | |
| | 31 | N | W | | 31 | N | W |
| | 32 | T | | | 32 | S | |
| | 33 | W | | | 33 | W | |

Figure 32

| Region | R# | DH511 | DH511 mutation | Region | R# | DH512 | DH512 mutation |
|---|---|---|---|---|---|---|---|
| CDRH2 | 51 | I | | CDRH2 | 51 | I | |
| | 52 | S | W | | 52 | R | W |
| | 52a | R | | | 52a | R | |
| | 52b | N | W | | 52b | L | W |
| | 52c | K | W | | 52c | K | W |
| | 53 | D | W | | 53 | D | W |
| | 54 | G | | | 54 | G | |
| | 55 | A | | | 55 | A | |
| | 56 | K | | | 56 | T | |
| | 57 | T | | | 57 | G | |

| Region | R# | DH511 | DH511 mutation | Region | R# | DH512 | DH512 mutation |
|---|---|---|---|---|---|---|---|
| FR3 | 72 | D | | FR3 | 72 | D | |
| | 73 | D | W | | 73 | D | W |
| | 74 | S | W | | 74 | S | W |
| | 75 | R | W | | 75 | R | W |

Figure 32 cont.

DH512 Nucleotide Sequence

CAGGTGCAGCTGGTACAGTCTGGGGGAGGTCTGGTGAAGCCGGGGGGGTCCCTCACACTCTCCTGTTC
AGCCTCTGGATTCTTTTTCGATAATTCATGGATGGGGTGGGTCCGTCAGGCGCCAGGGAAGGGACTGG
AGTGGGTTGGCCGCATTAGAAGGCTCAAAGACGGTGCGACAGGAGAATATGGTGCAGCCGTGAAGGAC
AGATTCACCATTTCAAGAGATGACAGTAGAAATATGCTGTACCTGCACATGAGGACCCTGAAAACCGA
GGACTCAGGCACTTATTATTGTACCATGGATGAGGGGACCCCAGTAACACGCTTCTTAGAATGGGGCT
ACTTCTATTATTATATGGCCGTTTGGGGCAGAGGGACCACGGTCATCGTCTCTTCA

DH512 Translated (Amino Acid) Sequence

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGYFYYYMAVWGRGTTVIVSS

Amino Acid Sequences of DH512 Heavy Chain Mutants

>DH512_E96W

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDWGTPVTRFLEWGYFYYYMAVWGRGTTVIVSS

>DH512_G97W

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEWTPVTRFLEWGYFYYYMAVWGRGTTVIVSS

>DH512_T98W

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGWPVTRFLEWGYFYYYMAVWGRGTTVIVSS

>DH512_P99W

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTWVTRFLEWGYFYYYMAVWGRGTTVIVSS

>DH512_V100F

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPFTRFLEWGYFYYYMAVWGRGTTVIVSS

>DH512_V100I

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPITRFLEWGYFYYYMAVWGRGTTVIVSS

>DH512_T100aW
QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVWRFLEWGYFYYYMAVWGRGTTVIVSS

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTWFLEWGYFYYYMAVWGR
GTTVIVSS

>DH512_F100cW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRWLEWGYFYYYMAVWGRGTTVIVSS

>DH512_L100dW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFWEWGYFYYYMAVWGRGTTVIVSS

>DH512_L100dF

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFFEWGYFYYYMAVWGRGTTVIVSS

>DH512_E100eW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLWWGYFYYYMAVWGRGTTVIVSS

>DH512_G100gW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWWYFYYYMAVWGRGTTVIVSS

>DH512_Y100hW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGWFYYYMAVWGRGTTVIVSS

>DH512_F100iW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGYWYYYMAVWGRGTTVIVSS

>DH512_Y100kW

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGYFYWYMAVWGRGTTVIVSS

Figure 33 cont.

| | | | | IC50 (μg/ml) | IC80 (μg/ml) | IC50 (μg/ml) | IC80 (μg/ml) | IC50 (μg/ml) | IC80 (μg/ml) | IC50 (μg/ml) | IC80 (μg/ml) | IC50 (μg/ml) | IC80 (μg/ml) |
|---|---|---|---|---|---|---|---|---|---|---|---|---|---|
| Antibody ID | Heavy ID | Light ID | Lot Number | BG1168 | BG1168 | CH505.TF | CH505.TF | DU172 | DU172 | MN | MN | SVA | SVA |
| 10E8 | | | | 0.262 | 1.189 | 4.764 | 13.642 | 0.124 | 0.684 | <0.023 | <0.023 | >50 | >50 |
| DH512 (Ab510049_4A) | H510049_4A | K510032 | 314HC | 0.156 | 0.913 | 8.974 | 28.099 | 3.411 | 13.048 | <0.023 | 0.082 | >50 | >50 |
| DH512_K3 | H510049_4A | DH511_2AVK | 132RKR | 0.044 | 0.376 | 2.813 | 13.222 | 3.673 | 11.587 | <0.023 | <0.023 | >50 | >50 |
| DH512_E96W_4A/293i | H510049_4A_E96W | K510032 | 76TCB | 1.918 | 5.716 | 30.990 | >50.32 | 4.775 | 19.394 | 0.051 | 0.276 | >50 | >50 |
| DH512_T98W_4A/293i | H510049_4A_T98W | K510032 | 77TCB | 5.799 | 27.307 | >50 | >50 | 14.417 | >50 | 0.434 | 1.513 | >50 | >50 |
| DH512_P99W_4A/293i | H510049_4A_P99W | K510032 | 78TCB | 2.458 | 12.903 | >50 | >50 | >50 | >50 | 0.232 | 0.729 | >50 | >50 |
| DH512_L100dW_4A/293i | H510049_4A_L100dW | K510032 | 79TCB | 0.398 | 1.299 | 6.823 | 23.220 | 0.606 | 3.308 | <0.023 | 0.100 | >50 | >50 |
| DH512_E100eW_4A/293i | H510049_4A_E100eW | K510032 | 80TCB | 1.411 | 6.738 | >50 | >50 | >50 | >50 | 0.254 | 0.877 | >50 | >50 |
| DH512_Y100hW_4A/293i | H510049_4A_Y100hW | K510032 | 81TCB | 1.568 | 5.143 | 45.094 | >50 | 18.482 | >50 | 0.071 | 0.387 | >50 | >50 |
| DH512_F100iW_4A/293i | H510049_4A_F100iW | K510032 | 135LDW | 1.642 | 7.094 | 39.299 | >50 | >50 | >50 | 0.054 | 0.327 | >50 | >50 |
| DH512_Y100kW_4A/293i | H510049_4A_Y100kW | K510032 | 136LDW | >50 | >50 | >50 | >50 | >50 | >50 | 9.341 | 32.530 | >50 | >50 |
| DH512_V100F_4A/293i | H510049_4A_V100F | K510032 | 137LDW | >50 | >50 | >50 | >50 | >50 | >50 | 20.119 | >50 | >50 | >50 |
| DH512_T100aW_4A/293i | H510049_4A_T100aW | K510032 | 138LDW | 0.099 | 0.696 | 6.240 | 20.059 | 0.134 | 0.950 | <0.023 | <0.023 | >50 | >50 |

Figure 34

| | | | | | | | | | | | | | |
|---|---|---|---|---|---|---|---|---|---|---|---|---|---|
| DH512_R100bW_4A/293i | H510049_4A_R100bW | K510032 | 139LDW | 5.448 | 15.619 | >50 | >50 | >50 | >50 | 0.428 | 1.190 | >50 | >50 |
| DH512_F100cW_4A/293i | H510049_4A_F100cW | K510032 | 140LDW | 1.326 | 6.575 | 30.590 | >50 | >50 | >50 | 0.050 | 0.316 | >50 | >50 |
| DH512_G100gW_4A/293i | H510049_4A_G100gW | K510032 | 141LDW | >50 | >50 | >50 | >50 | >50 | >50 | >50 | >50 | >50 | >50 |
| DH512_V100I_4A/293i | H510049_4A_V100I | K510032 | 142LDW | 2.734 | 10.558 | >50 | >50 | >50 | >50 | 0.304 | 1.107 | >50 | >50 |
| DH512_L100dF_4A/293i | H510049_4A_L100dF | K510032 | 143LDW | 0.048 | 0.349 | 2.733 | 10.178 | 0.229 | 1.673 | <0.023 | <0.023 | >50 | >50 |
| DH512_G97W_4A/293i | H510049_4A_G97W | K510032 | 144LDW | >50 | >50 | >50 | >50 | >50 | >50 | 33.197 | >50 | >50 | >50 |
| Ab82 | | | | >50 | >50 | >50 | >50 | >50 | >50 | >50 | >50 | >50 | >50 |
| CH01+CH31 | | | | 1.441 | 5.337 | <0.011 | 0.059 | 1.515 | 10.121 | 0.575 | 3.315 | >25 | >25 |

Figure 34 cont.

| Ab ID | Old Ab ID | CL | SSA | SSB | Sm | RNP | Scl-70 | Jo-1 | Cent B | Hist | dsDNA | Hep-2 |
|---|---|---|---|---|---|---|---|---|---|---|---|---|
| DH511 | Ab510056 | (-) | (-) | (-) | (-) | (-) | (-) | (-) | (-) | (-) | (-) | (-) |
| DH512 | Ab510049 | (-) | (-) | (-) | (-) | (-) | (-) | (-) | (-) | (-) | (-) | (-) |
| DH513 | Ab570022 | (-) | (-) | (-) | (-) | (-) | (-) | (-) | (-) | (-) | (-) | (-) |
| DH514 | Ab570029 | (+/-) | (-) | (-) | (-) | (-) | (-) | (-) | (-) | (-) | (-) | (-) |
| DH515 | Ab510052 | (-) | (-) | (-) | (-) | (-) | (-) | (-) | +/- | (-) | +/- | (-) |
| DH516 | Ab510048 | (-) | (-) | (-) | (-) | (-) | (-) | (-) | (-) | (-) | (-) | (-) |
| DH517 | Ab510053 | (-) | (-) | (-) | (-) | (-) | (-) | (-) | (-) | (-) | +/- | (-) |
| DH518 | Ab570010 | (+/-) | (-) | (-) | (-) | (-) | (-) | (-) | (-) | (-) | (-) | (-) |
| DH536 | Ab510127 | (-) | (-) | (-) | (-) | (-) | (-) | (-) | (-) | (-) | (-) | (-) |
| DH537 | Ab008587 | (-) | (-) | (-) | (-) | (-) | (-) | (-) | (-) | (-) | (-) | (-) |
| DH511_UCA | | (-) | (-) | (-) | (-) | ++ | (-) | (-) | (-) | (-) | (-) | (-) |
| DH511_I6 | | (+/-) | (-) | (-) | (-) | (-) | (-) | (-) | (-) | (-) | +++ | (-) |
| DH511_I5 | | (+/-) | (-) | (-) | (-) | (-) | (-) | (-) | (-) | (-) | (-) | (-) |
| DH511_I4 | | (+/-) | (-) | (-) | (-) | (-) | (-) | (-) | (-) | (-) | (-) | (-) |
| DH511_I3 | | (+/-) | (-) | (-) | (-) | (-) | (-) | (-) | (-) | (-) | (-) | (-) |
| DH511_I2 | | (+/-) | (-) | (-) | (-) | (-) | (-) | (-) | (-) | (-) | (-) | (-) |
| DH511_I1 | | (+/-) | (-) | (-) | (-) | (-) | (-) | (-) | (-) | (-) | (-) | (-) |

Figure 36

High Throughput Antibody Screen - Panel P

Assay - Luc/TZM-bl values represent IC50 in ug/ml IC50

| |
|---|
| <0.100 |
| 0.100-1.00 |
| 1.00-10.0 |
| >10.0 |

| Virus ID | Clade | DH512 (Panel O) | 10E8 (Panel M) |
|---|---|---|---|
| 0260.v5.c36 | A | 17.0 | 9.87 |
| 0330.v4.c3 | A | 1.42 | 1.12 |
| 0439.v5.c1 | A | 2.36 | 1.23 |
| 3365.v2.c20 | A | 2.29 | 1.60 |
| 3415.v1.c1 | A | 12.6 | 4.69 |
| 3718.v3.c11 | A | 3.80 | 0.838 |
| 398-F1_F6_20 | A | 2.49 | 0.704 |
| BB201.B42 | A | 2.82 | 0.613 |
| BB539.2B13 | A | | |
| BG505.W6M.C2 | A | 1.33 | 0.689 |
| BI369.9A | A | 1.61 | 0.356 |
| BS208.B1 | A | 0.803 | 0.319 |
| KER2008.12 | A | 0.723 | >50 |
| KER2018.11 | A | 4.31 | 1.89 |
| KNH1209.18 | A | 0.410 | 0.406 |
| MB201.A1 | A | 0.844 | 0.411 |
| MB539.2B7 | A | >50 | >50 |
| MI369.A5 | A | 0.510 | 0.671 |
| MS208.A1 | A | 0.927 | 0.187 |
| Q23.17 | A | 1.18 | 0.461 |
| Q259.17 | A | 12.4 | 4.76 |
| Q769.d22 | A | 2.44 | 1.91 |
| Q769.h5 | A | 5.73 | 2.89 |
| Q842.d12 | A | 5.73 | 2.82 |
| QH209.14M.A2 | A | 2.20 | 1.30 |
| RW020.2 | A | 3.46 | 0.902 |
| UG037.8 | A | 0.273 | 0.048 |
| 246-F3.C10.2 | AC | 0.802 | 0.210 |
| 3301.V1.C24 | AC | 12.5 | 2.97 |
| 3589.V1.C4 | AC | 3.26 | 5.77 |
| 6540.v4.c1 | AC | 2.84 | 2.24 |
| 6545.V4.C1 | AC | 7.79 | 2.54 |
| 0815.V3.C3 | ACD | 2.04 | 0.491 |
| 6095.V1.C10 | ACD | 0.0003 | 0.0005 |
| 3468.V1.C12 | AD | 2.00 | 0.381 |
| Q168.a2 | AD | 1.45 | 0.463 |
| Q461.e2 | AD | 2.45 | 2.29 |
| 620345.c1 | AE | 1.77 | 0.989 |
| BJOX009000.02.4 | AE | 0.580 | 0.251 |
| BJOX010000.06.2 | AE | 0.178 | 0.060 |
| BJOX025000.01.1 | AE | 0.751 | 0.228 |
| BJOX028000.10.3 | AE | 0.853 | 0.167 |
| C1080.c3 | AE | 0.521 | 0.108 |

Figure 37

| | | | |
|---|---|---|---|
| C2101.c1 | AE | 4.64 | 1.20 |
| C3347.c11 | AE | 0.046 | 0.019 |
| C4118.09 | AE | 1.66 | 0.421 |
| CM244.ec1 | AE | | 0.365 |
| CNE3 | AE | 2.81 | 1.37 |
| CNE5 | AE | 1.54 | 1.17 |
| CNE55 | AE | 0.287 | 0.038 |
| CNE56 | AE | 0.212 | 0.060 |
| CNE59 | AE | 0.0009 | 0.001 |
| CNE8 | AE | 0.045 | 0.140 |
| M02138 | AE | | |
| R1166.c1 | AE | 0.742 | 0.488 |
| R2184.c4 | AE | 1.12 | 0.576 |
| R3265.c6 | AE | 6.31 | 1.58 |
| TH023.6 | AE | | |
| TH966.8 | AE | 0.081 | 0.039 |
| TH976.17 | AE | 0.762 | 0.392 |
| 235-47 | AG | 0.361 | 0.244 |
| 242-14 | AG | 0.069 | 0.568 |
| 263-8 | AG | 0.407 | 0.229 |
| 269-12 | AG | 0.420 | 0.124 |
| 271-11 | AG | 1.23 | 0.891 |
| 928-28 | AG | 0.215 | 0.079 |
| DJ263.8 | AG | 0.190 | 0.009 |
| T250-4 | AG | 3.54 | 1.07 |
| T251-18 | AG | 7.52 | 0.666 |
| T253-11 | AG | 3.51 | 1.21 |
| T255-34 | AG | 1.40 | 0.228 |
| T257-31 | AG | 3.42 | 0.336 |
| T266-60 | AG | 0.953 | >50 |
| T278-50 | AG | 1.89 | 0.357 |
| T280-5 | AG | 4.21 | |
| T33-7 | AG | 2.34 | 0.818 |
| 3988.25 | B | 0.284 | 0.070 |
| 5768.04 | B | 5.70 | 1.63 |
| 6101.10 | B | 0.012 | 0.001 |
| 6535.3 | B | 1.39 | 0.190 |
| 7165.18 | B | 0.805 | 0.659 |
| 45_01dG5 | B | 0.753 | 0.106 |
| 89.6.DG | B | 0.676 | 0.318 |
| AC10.29 | B | 0.115 | 0.102 |
| ADA.DG | B | 0.042 | 0.055 |
| Bal.01 | B | 0.620 | 0.421 |
| BaL.26 | B | 2.57 | 0.518 |
| BG1168.01 | B | 0.528 | 0.396 |
| BL01.DG | B | 1.08 | 0.362 |
| BR07.DG | B | 0.106 | 0.118 |
| BX08.16 | B | 0.565 | 0.213 |
| CAAN.A2 | B | 5.29 | 1.45 |
| CNE10 | B | 0.121 | 0.014 |
| CNE12 | B | 0.509 | 0.301 |

Figure 37 cont.

| | | | |
|---|---|---|---|
| CNE14 | B | 0.950 | 0.151 |
| CNE4 | B | 0.279 | 0.059 |
| CNE57 | B | 0.120 | 0.059 |
| HO86.8 | B | 2.55 | 0.326 |
| HT593.1 | B | 0.140 | 0.049 |
| HXB2.DG | B | 0.0003 | 0.003 |
| JRCSF.JB | B | 2.04 | 0.429 |
| JRFL.JB | B | 0.862 | 0.174 |
| MN.3 | B | 0.0003 | 0.0003 |
| PVO.04 | B | 2.32 | 1.60 |
| QH0515.01 | B | 4.97 | 2.25 |
| QH0692.42 | B | 2.03 | 0.531 |
| REJO.67 | B | 0.544 | 0.302 |
| RHPA.7 | B | 5.45 | 1.01 |
| SC422.8 | B | 1.63 | 0.343 |
| SF162.LS | B | 1.88 | 0.245 |
| SS1196.01 | B | 0.857 | 0.244 |
| THRO.18 | B | 0.711 | 0.092 |
| TRJO.58 | B | 3.86 | 1.13 |
| TRO.11 | B | 0.228 | 0.028 |
| WITO.33 | B | 0.314 | 0.031 |
| X2278.C2.B6 | B | 3.79 | 0.442 |
| YU2.DG | B | 8.00 | 1.17 |
| BJOX002000.03.2 | BC | 1.17 | 0.384 |
| CH038.12 | BC | 1.57 | 0.271 |
| CH070.1 | BC | 12.1 | 6.65 |
| CH117.4 | BC | 0.458 | 0.270 |
| CH119.10 | BC | 0.916 | 0.591 |
| CH181.12 | BC | 0.959 | 0.754 |
| CNE15 | BC | 1.27 | 0.844 |
| CNE19 | BC | 0.383 | 0.251 |
| CNE20 | BC | 0.370 | 0.131 |
| CNE21 | BC | 1.09 | 0.979 |
| CNE40 | BC | 0.0003 | 0.001 |
| CNE7 | BC | 0.119 | 0.130 |
| 286.36 | C | 3.22 | 1.19 |
| 288.38 | C | 2.19 | 0.435 |
| 0013095-2.11 | C | 0.014 | 0.009 |
| 001428-2.42 | C | 3.33 | 1.71 |
| 0077_V1.C16 | C | 5.56 | 1.86 |
| 00836-2.5 | C | 1.89 | 0.666 |
| 0921.V2.C14 | C | 5.33 | 0.908 |
| 16055-2.3 | C | 2.16 | 1.10 |
| 16845-2.22 | C | 0.016 | 0.020 |
| 16936-2.21 | C | 0.312 | 0.264 |
| 25710-2.43 | C | 0.046 | 0.064 |
| 25711-2.4 | C | 6.14 | 0.516 |
| 25925-2.22 | C | 0.504 | 0.402 |
| 26191-2.48 | C | 1.82 | 1.83 |
| 3168.V4.C10 | C | 2.52 | 2.83 |
| 3637.V5.C3 | C | 2.83 | 2.12 |

Figure 37 cont.

| | | | |
|---|---|---|---|
| 3873.V1.C24 | C | 10.0 | 5.51 |
| 426c | C | | |
| 6322.V4.C1 | C | 2.90 | 0.923 |
| 6471.V1.C16 | C | 11.0 | 4.98 |
| 6631.V3.C10 | C | 7.08 | 0.934 |
| 6644.V2.C33 | C | 0.229 | 0.013 |
| 6785.V5.C14 | C | 1.58 | 0.701 |
| 6838.V1.C35 | C | 0.813 | 0.292 |
| 96ZM651.02 | C | 0.035 | 0.033 |
| BR025.9 | C | 1.10 | 0.307 |
| CAP210.E8 | C | 0.911 | 0.474 |
| CAP244.D3 | C | 1.13 | 0.369 |
| CAP256.206.C9 | C | 0.779 | 0.713 |
| CAP45.G3 | C | 2.84 | 0.722 |
| Ce1176.A3 | C | 0.998 | 0.252 |
| CE703010217.B6 | C | 0.159 | 0.096 |
| CNE30 | C | 3.30 | 0.456 |
| CNE31 | C | 5.23 | 1.32 |
| CNE53 | C | 0.208 | 0.213 |
| CNE58 | C | 0.453 | 0.229 |
| DU123.06 | C | 0.250 | 0.132 |
| DU151.02 | C | 0.928 | 0.461 |
| DU156.12 | C | 0.019 | 0.023 |
| DU172.17 | C | 7.22 | 0.057 |
| DU422.01 | C | 0.821 | 0.224 |
| MW965.26 | C | 0.0003 | 0.001 |
| SO18.18 | C | 7.52 | 1.60 |
| TV1.29 | C | 0.802 | 0.248 |
| TZA125.17 | C | 0.750 | 0.217 |
| TZBD.02 | C | 2.44 | 1.41 |
| ZA012.29 | C | 3.66 | 1.47 |
| ZM106.9 | C | 5.68 | >50 |
| ZM109.4 | C | 0.715 | 0.161 |
| ZM135.10a | C | 0.246 | 0.033 |
| ZM176.66 | C | 1.10 | 0.267 |
| ZM197.7 | C | 0.232 | 0.055 |
| ZM214.15 | C | 5.39 | 2.22 |
| ZM215.8 | C | 0.107 | 0.044 |
| ZM233.6 | C | 0.549 | 0.270 |
| ZM249.1 | C | 1.58 | 0.830 |
| ZM53.12 | C | 6.11 | 2.62 |
| ZM55.28a | C | 7.88 | 2.34 |
| 3326.V4.C3 | CD | 3.62 | 1.40 |
| 3337.V2.C6 | CD | 1.50 | 1.09 |
| 3817.v2.c59 | CD | 2.12 | 0.229 |
| 191821.E6.1 | D | | |
| 231965.c1 | D | 19.6 | 11.0 |
| 247-23 | D | 0.618 | 0.344 |
| 3016.v5.c45 | D | 0.607 | 0.710 |
| 57128.vrc15 | D | 0.352 | 0.212 |
| 6405.v4.c34 | D | 1.93 | 0.461 |

Figure 37 cont.

| | | | |
|---|---|---|---|
| A03349M1.vrc4a | D | 0.402 | 0.270 |
| A07412M1.vrc12 | D | | 0.140 |
| NKU3006.ec1 | D | 0.989 | 0.673 |
| UG021.16 | D | | |
| UG024.2 | D | | |
| P0402.c2.11 | G | 0.094 | 0.057 |
| P1981.C5.3 | G | 0.020 | 0.024 |
| X1193.c1 | G | 0.746 | 0.341 |
| X1254.c3 | G | 2.77 | 3.67 |
| X1632.S2.B10 | G | 0.925 | 0.387 |
| X2088.c9 | G | >50 | >50 |
| X2131.C1.B5 | G | 0.118 | 0.039 |
| SIVmac251.30.SG3 | NA | >50 | >50 |
| SVA.MLV | NA | >50 | >50 |

| | DH512 | 10E8 |
|---|---|---|
| # Viruses | 199 | 200 |
| **Total VS Neutralized** | | |
| IC50 <50ug/ml | 197 | 195 |
| IC50 <10ug/ml | 189 | 194 |
| IC50 <1.0ug/ml | 97 | 145 |
| IC50 <0.1ug/ml | 19 | 38 |
| IC50 <0.01ug/ml | 6 | 9 |
| **% VS Neutralized** | | |
| IC50 <50ug/ml | 99 | 98 |
| IC50 <10ug/ml | 95 | 97 |
| IC50 <1.0ug/ml | 49 | 73 |
| IC50 <0.1ug/ml | 10 | 19 |
| IC50 <0.01ug/ml | 3 | 5 |
| Median IC50 | 1.09 | 0.392 |
| Geometric Mean | 0.802 | 0.315 |

Note: Median and Geometric Mean titers are calculated only for samples with IC50 <50ug/ml Values less than the lowest concentration assayed were assigned a value 2-fold less for calculation purposes. Indicated in italics

Figure 37 cont.

High Throughput Antibody Screen - Panel P

Assay - Luc/TZM-bl values represent IC80 in ug/ml IC80

| |
|---|
| <0.100 |
| 0.100-1.00 |
| 1.00-10.0 |
| >10.0 |

| | | Panel O | Panel M |
|---|---|---|---|
| Virus ID | Clade | DH512 | 10E8 |
| 0260.v5.c36 | A | >50 | 21.7 |
| 0330.v4.c3 | A | 7.37 | 3.64 |
| 0439.v5.c1 | A | 9.57 | 3.95 |
| 3365.v2.c20 | A | 7.89 | 4.56 |
| 3415.v1.c1 | A | 22.1 | 11.5 |
| 3718.v3.c11 | A | 13.5 | 4.42 |
| 398-F1_F6_20 | A | 18.0 | 6.17 |
| BB201.B42 | A | 9.87 | 1.96 |
| BB539.2B13 | A | | |
| BG505.W6M.C2 | A | 5.60 | 2.14 |
| BI369.9A | A | 4.93 | 1.29 |
| BS208.B1 | A | 3.35 | 3.27 |
| KER2008.12 | A | 4.29 | >50 |
| KER2018.11 | A | 17.0 | 7.16 |
| KNH1209.18 | A | 2.25 | 2.39 |
| MB201.A1 | A | 4.22 | 1.36 |
| MB539.2B7 | A | >50 | >50 |
| MI369.A5 | A | 3.41 | 1.77 |
| MS208.A1 | A | 3.56 | 1.14 |
| Q23.17 | A | 5.85 | 1.60 |
| Q259.17 | A | 30.7 | 12.0 |
| Q769.d22 | A | 8.64 | 4.47 |
| Q769.h5 | A | 16.7 | 7.44 |
| Q842.d12 | A | 12.8 | 7.58 |
| QH209.14M.A2 | A | 10.0 | 4.09 |
| RW020.2 | A | 10.0 | 2.92 |
| UG037.8 | A | 1.33 | 0.353 |
| 246-F3.C10.2 | AC | 5.10 | 1.49 |
| 3301.V1.C24 | AC | 33.8 | 9.50 |
| 3589.V1.C4 | AC | 10.2 | 11.7 |
| 6540.v4.c1 | AC | 13.4 | 7.01 |
| 6545.V4.C1 | AC | 15.4 | 7.50 |
| 0815.V3.C3 | ACD | 7.05 | 1.81 |
| 6095.V1.C10 | ACD | 0.001 | 0.004 |
| 3468.V1.C12 | AD | 7.45 | 2.04 |
| Q168.a2 | AD | 5.18 | 2.88 |
| Q461.e2 | AD | 8.68 | 4.68 |
| 620345.c1 | AE | 9.05 | 3.73 |
| BJOX009000.02.4 | AE | 5.03 | 1.47 |
| BJOX010000.06.2 | AE | 1.23 | 0.476 |
| BJOX025000.01.1 | AE | 4.77 | 1.54 |
| BJOX028000.10.3 | AE | 4.59 | 0.876 |
| C1080.c3 | AE | 2.50 | 0.613 |
| C2101.c1 | AE | 15.6 | 4.12 |

Figure 38

| | | | |
|---|---|---|---|
| C3347.c11 | AE | 0.274 | 0.089 |
| C4118.09 | AE | 11.6 | 2.30 |
| CM244.ec1 | AE | | 1.46 |
| CNE3 | AE | 9.17 | 4.01 |
| CNE5 | AE | 7.34 | 2.52 |
| CNE55 | AE | 2.00 | 0.605 |
| CNE56 | AE | 1.18 | 0.314 |
| CNE59 | AE | 0.023 | 0.010 |
| CNE8 | AE | 0.483 | 1.42 |
| M02138 | AE | | |
| R1166.c1 | AE | 3.70 | 2.02 |
| R2184.c4 | AE | 5.40 | 2.20 |
| R3265.c6 | AE | 21.9 | 9.28 |
| TH023.6 | AE | | |
| TH966.8 | AE | 0.611 | 0.291 |
| TH976.17 | AE | 4.08 | 1.75 |
| 235-47 | AG | 1.61 | 0.786 |
| 242-14 | AG | 0.750 | 3.17 |
| 263-8 | AG | 2.63 | 0.991 |
| 269-12 | AG | 2.10 | 0.475 |
| 271-11 | AG | 7.60 | 4.34 |
| 928-28 | AG | 1.28 | 0.365 |
| DJ263.8 | AG | 0.903 | 0.100 |
| T250-4 | AG | 13.1 | 3.45 |
| T251-18 | AG | 20.5 | 2.55 |
| T253-11 | AG | 12.0 | 4.05 |
| T255-34 | AG | 6.11 | 1.14 |
| T257-31 | AG | 10.5 | 1.58 |
| T266-60 | AG | 4.78 | >50 |
| T278-50 | AG | 8.95 | 2.10 |
| T280-5 | AG | 17.0 | |
| T33-7 | AG | 10.2 | 2.83 |
| 3988.25 | B | 0.883 | 0.293 |
| 5768.04 | B | 18.0 | 5.26 |
| 6101.10 | B | 0.137 | 0.005 |
| 6535.3 | B | 7.62 | 1.28 |
| 7165.18 | B | 3.55 | 2.71 |
| 45_01dG5 | B | 4.87 | 0.703 |
| 89.6.DG | B | 2.23 | 1.48 |
| AC10.29 | B | 0.604 | 0.512 |
| ADA.DG | B | 0.482 | 0.358 |
| Bal.01 | B | 4.09 | 1.91 |
| BaL.26 | B | 11.0 | 2.39 |
| BG1168.01 | B | 2.38 | 1.48 |
| BL01.DG | B | 6.87 | 1.57 |
| BR07.DG | B | 1.03 | 0.445 |
| BX08.16 | B | 3.02 | 1.30 |
| CAAN.A2 | B | 16.3 | 5.70 |
| CNE10 | B | 0.932 | 0.169 |
| CNE12 | B | 2.46 | 1.09 |
| CNE14 | B | 4.24 | 0.649 |

Figure 38 cont.

| | | | |
|---|---|---|---|
| CNE4 | B | 2.45 | 0.437 |
| CNE57 | B | 1.28 | 0.317 |
| HO86.8 | B | 10.7 | 1.52 |
| HT593.1 | B | 0.780 | 0.285 |
| HXB2.DG | B | 0.017 | 0.015 |
| JRCSF.JB | B | 9.61 | 1.89 |
| JRFL.JB | B | 5.40 | 0.768 |
| MN.3 | B | 0.004 | 0.001 |
| PVO.04 | B | 15.9 | 6.43 |
| QH0515.01 | B | 15.8 | 5.54 |
| QH0692.42 | B | 11.1 | 2.35 |
| REJO.67 | B | 3.31 | 1.18 |
| RHPA.7 | B | 25.9 | 5.10 |
| SC422.8 | B | 4.60 | 1.15 |
| SF162.LS | B | 7.75 | 1.06 |
| SS1196.01 | B | 4.72 | 1.25 |
| THRO.18 | B | 2.39 | 0.587 |
| TRJO.58 | B | 17.7 | 4.18 |
| TRO.11 | B | 1.22 | 0.286 |
| WITO.33 | B | 1.60 | 0.305 |
| X2278.C2.B6 | B | 14.1 | 2.24 |
| YU2.DG | B | 50 | 5.46 |
| BJOX002000.03.2 | BC | 5.64 | 1.56 |
| CH038.12 | BC | 6.10 | 1.41 |
| CH070.1 | BC | 48.6 | 13.5 |
| CH117.4 | BC | 2.29 | 0.859 |
| CH119.10 | BC | 5.48 | 2.36 |
| CH181.12 | BC | 3.99 | 2.79 |
| CNE15 | BC | 6.77 | 2.97 |
| CNE19 | BC | 3.05 | 1.11 |
| CNE20 | BC | 2.43 | 0.732 |
| CNE21 | BC | 8.40 | 3.25 |
| CNE40 | BC | 0.030 | 0.009 |
| CNE7 | BC | 0.672 | 0.603 |
| 286.36 | C | 14.0 | 5.00 |
| 288.38 | C | 8.90 | 3.08 |
| 0013095-2.11 | C | 0.229 | 0.077 |
| 001428-2.42 | C | 16.3 | 6.28 |
| 0077_V1.C16 | C | 36.0 | 7.11 |
| 00836-2.5 | C | 5.40 | 1.77 |
| 0921.V2.C14 | C | 18.4 | 3.03 |
| 16055-2.3 | C | 9.40 | 3.31 |
| 16845-2.22 | C | 0.238 | 0.172 |
| 16936-2.21 | C | 1.99 | 1.31 |
| 25710-2.43 | C | 0.408 | 0.304 |
| 25711-2.4 | C | 12.6 | 1.69 |
| 25925-2.22 | C | 2.95 | 1.53 |
| 26191-2.48 | C | 8.77 | 4.90 |
| 3168.V4.C10 | C | 19.3 | 8.18 |
| 3637.V5.C3 | C | 11.1 | 6.68 |
| 3873.V1.C24 | C | 13.8 | 15.7 |

Figure 38 cont.

| | | | |
|---|---|---|---|
| 426c | C | | |
| 6322.V4.C1 | C | 9.72 | 3.68 |
| 6471.V1.C16 | C | 41.9 | 14.9 |
| 6631.V3.C10 | C | 15.5 | 3.36 |
| 6644.V2.C33 | C | 1.14 | 0.124 |
| 6785.V5.C14 | C | 6.70 | 2.42 |
| 6838.V1.C35 | C | 3.67 | 1.01 |
| 96ZM651.02 | C | 0.358 | 0.177 |
| BR025.9 | C | 5.33 | 1.11 |
| CAP210.E8 | C | 3.37 | 2.01 |
| CAP244.D3 | C | 4.56 | 1.48 |
| CAP256.206.C9 | C | 3.92 | 2.97 |
| CAP45.G3 | C | 9.41 | 3.41 |
| Ce1176.A3 | C | 4.13 | 1.15 |
| CE703010217.B6 | C | 0.944 | 0.679 |
| CNE30 | C | 16.3 | 2.29 |
| CNE31 | C | 11.5 | 3.57 |
| CNE53 | C | 1.41 | 1.01 |
| CNE58 | C | 2.98 | 1.09 |
| DU123.06 | C | 0.948 | 0.423 |
| DU151.02 | C | 3.60 | 1.71 |
| DU156.12 | C | 0.158 | 0.120 |
| DU172.17 | C | 19.9 | 0.238 |
| DU422.01 | C | 3.95 | 0.812 |
| MW965.26 | C | 0.002 | 0.007 |
| SO18.18 | C | 20.7 | 4.48 |
| TV1.29 | C | 2.66 | 0.719 |
| TZA125.17 | C | 4.05 | 1.19 |
| TZBD.02 | C | 7.78 | 4.31 |
| ZA012.29 | C | 11.3 | 4.12 |
| ZM106.9 | C | 21.8 | >50 |
| ZM109.4 | C | 4.64 | 1.07 |
| ZM135.10a | C | 2.20 | 0.408 |
| ZM176.66 | C | 5.65 | 1.73 |
| ZM197.7 | C | 1.16 | 0.369 |
| ZM214.15 | C | 15.5 | 5.98 |
| ZM215.8 | C | 0.591 | 0.230 |
| ZM233.6 | C | 2.33 | 0.737 |
| ZM249.1 | C | 5.78 | 2.27 |
| ZM53.12 | C | 18.5 | 6.72 |
| ZM55.28a | C | 19.2 | 6.78 |
| 3326.V4.C3 | CD | 13.3 | 4.29 |
| 3337.V2.C6 | CD | 5.60 | 4.87 |
| 3817.v2.c59 | CD | 6.33 | 1.43 |
| 191821.E6.1 | D | | |
| 231965.c1 | D | >50 | 20.4 |
| 247-23 | D | 3.24 | 1.29 |
| 3016.v5.c45 | D | 3.42 | 2.17 |
| 57128.vrc15 | D | 2.59 | 1.50 |
| 6405.v4.c34 | D | 6.76 | 1.80 |
| A03349M1.vrc4a | D | 1.32 | 0.663 |

Figure 38 cont.

| | | | |
|---|---|---|---|
| A07412M1.vrc12 | D | | 0.873 |
| NKU3006.ec1 | D | 4.86 | 2.46 |
| UG021.16 | D | | |
| UG024.2 | D | | |
| P0402.c2.11 | G | 0.815 | 0.460 |
| P1981.C5.3 | G | 0.211 | 0.124 |
| X1193.c1 | G | 3.28 | 1.15 |
| X1254.c3 | G | 14.5 | 15.7 |
| X1632.S2.B10 | G | 3.93 | 1.76 |
| X2088.c9 | G | >50 | >50 |
| X2131.C1.B5 | G | 0.611 | 0.175 |
| SIVmac251.30.SG3 | NA | >50 | >50 |
| SVA.MLV | NA | >50 | >50 |

| | DH512 | 10E8 |
|---|---|---|
| # Viruses | 199 | 200 |
| **Total VS Neutralized** | | |
| IC80 <50ug/ml | 194 | 195 |
| IC80 <10ug/ml | 140 | 186 |
| IC80 <1.0ug/ml | 29 | 57 |
| IC80 <0.1ug/ml | 6 | 9 |
| IC80 <0.01ug/ml | 3 | 5 |
| **% VS Neutralized** | | |
| IC80 <50ug/ml | 97 | 98 |
| IC80 <10ug/ml | 70 | 93 |
| IC80 <1.0ug/ml | 15 | 29 |
| IC80 <0.1ug/ml | 3 | 5 |
| IC80 <0.01ug/ml | 2 | 3 |
| Median IC80 | 5.10 | 1.71 |
| Geometric Mean | 3.82 | 1.37 |

Note: Median and Geometric Mean titers are calculated only for samples with IC80 Values less than the lowest concentration assayed were assigned a value 2-fold less for calculation purposes. Indicated in italics

| PTID | Ab Name | Heavy ID | Light ID | IC50<50 μg/ml BG1168 (20151002) | BG1168 (20151022) | CH505.TF (20151002) | CH505.TF (20151022) | DU172 (20151002) | DU172 (20151022) | MN (20151002) | MN (20151022) |
|---|---|---|---|---|---|---|---|---|---|---|---|
| 704-01-021-0 | DH511_1a_4A/293i | DH511_1AVH_4A | DH511_1AVK | 1.937 | 0.771 | 32.077 | 30.361 | 8.389 | 12.841 | <0.023 | <0.023 |
| 704-01-021-0 | DH511_1b_4A/293i | DH511_1BVH_4A | DH511_1AVK | 1.656 | 0.793 | 20.570 | 25.607 | 6.526 | 8.889 | <0.023 | <0.023 |
| 704-01-021-0 | DH511_2a_4A/293i | DH511_2AVH_4A | DH511_2AVK | 0.898 | 0.813 | 17.790 | 16.482 | 0.224 | 0.185 | <0.023 | <0.023 |
| 704-01-021-0 | DH511_2b_4A/293i | DH511_2BVH_4A | DH511_2AVK | 0.767 | 0.549 | 16.668 | 11.334 | 0.130 | 0.147 | <0.023 | <0.023 |
| 704-01-021-0 | DH511_2c_4A/293i | DH511_2CVH_4A | DH511_2AVK | 10.607 | NT | >50 | NT | 3.056 | NT | 0.610 | NT |
| 704-01-021-0 | DH511_3a_4A/293i | DH511_3AVH_4A | DH511_3AVK | 1.000 | 0.751 | 20.446 | 21.124 | 1.762 | 1.342 | <0.023 | <0.023 |
| 704-01-021-0 | DH511_3b_4A/293i | DH511_3AVH_4A | DH511_3BVK | 1.922 | NT | 43.786 | NT | 2.837 | NT | 0.027 | NT |
| 704-01-021-0 | DH511_3c_4A/293i | DH511_3AVH_4A | DH511_3CVK | 1.199 | 0.458 | 22.369 | 18.698 | 1.498 | 1.193 | <0.023 | <0.023 |
| 704-01-021-0 | DH511_4a_4A/293i | DH511_4AVH_4A | DH511_4A4CVK | 12.294 | 7.089 | >50 | >50 | 17.317 | >50 | 0.468 | 0.149 |
| 704-01-021-0 | DH511_4a_4bK_4A/293i | DH511_4AVH_4A | DH511_4BVK | 5.089 | 5.231 | >50 | >50 | 1.650 | 16.167 | 0.278 | 0.192 |
| 704-01-021-0 | DH511_4b_4aK_4A/293i | DH511_4BVH_4A | DH511_4A4CVK | 30.034 | NT | >50 | NT | >50 | NT | 1.068 | NT |
| 704-01-021-0 | DH511_4b_4A/293i | DH511_4BVH_4A | DH511_4BVK | 26.071 | NT | >50 | NT | >50 | NT | 0.740 | NT |
| 704-01-021-0 | DH511_4c_4A/293i | DH511_4CVH_4A | DH511_4A4CVK | 31.722 | >50 | >50 | >50 | >50 | >50 | 2.063 | 1.328 |
| 704-01-021-0 | DH511_4c_4bK_4A/293i | DH511_4CVH_4A | DH511_4BVK | 33.591 | >50 | >50 | >50 | >50 | >50 | 1.267 | 0.898 |
| 704-01-021-0 | DH511_5a_4A/293i | pDH511_5AVH_4A | pDH511_5AVK | 0.239 | 0.214 | 7.000 | 7.697 | 0.056 | 0.067 | <0.023 | <0.023 |
| 704-01-021-0 | DH511_5b_4A/293i | pDH511_5BVH_4A | pDH511_5AVK | 0.163 | 0.108 | 9.385 | 5.967 | <0.023 | 0.061 | <0.023 | <0.023 |
| 704-01-021-0 | DH512 (Ab510049_4A/293i) | H510049_4A | K510032 | NT | 0.174 | NT | 7.580 | NT | 2.905 | NT | <0.023 |
| | 10E8 | | | 0.188 | 0.098 | 3.314 | 3.178 | <0.023 | <0.023 | <0.023 | <0.023 |
| | 2F5 | | | 0.907 | 0.841 | NT | NT | NT | NT | <0.023 | <0.023 |
| | 4E10 | | | NT | NT | NT | NT | 0.192 | 0.116 | NT | NT |
| | CH31 | | | NT | NT | <0.023 | <0.023 | NT | NT | NT | NT |

Key

<0.2 μg/ml 0.2-2 μg/ml 2-20 μg/ml >20 μg/ml

NT, not tested

Figure 42

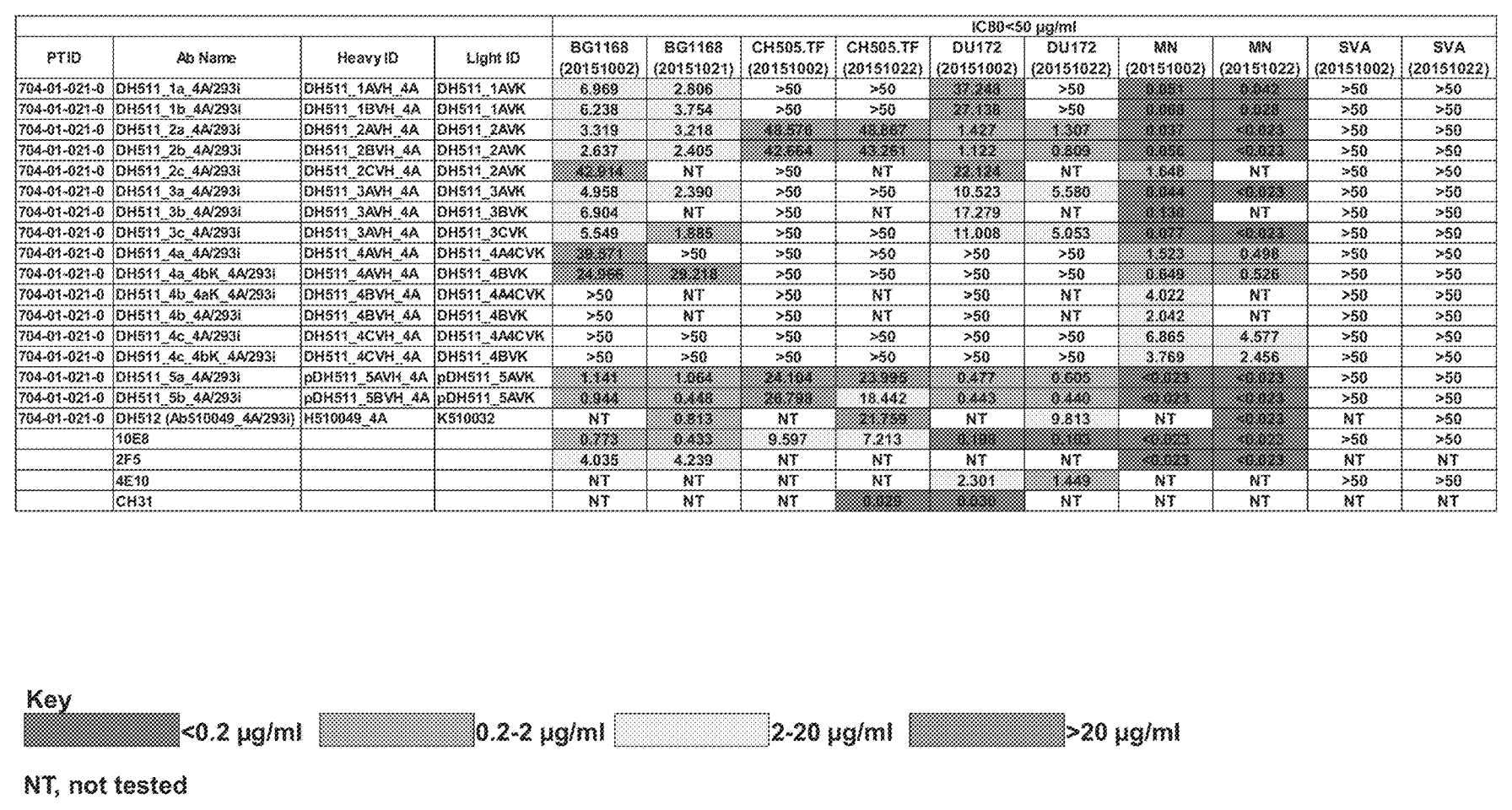

| | | | | IC80<50 µg/ml | | | | | | | | | |
|---|---|---|---|---|---|---|---|---|---|---|---|---|---|
| PTID | Ab Name | Heavy ID | Light ID | BG1168 (20151002) | BG1168 (20151021) | CH505.TF (20151002) | CH505.TF (20151022) | DU172 (20151002) | DU172 (20151022) | MN (20151002) | MN (20151022) | SVA (20151002) | SVA (20151022) |
| 704-01-021-0 | DH511_1a_4A/293i | DH511_1AVH_4A | DH511_1AVK | 6.969 | 2.806 | >50 | >50 | 37.248 | >50 | 0.051 | 0.042 | >50 | >50 |
| 704-01-021-0 | DH511_1b_4A/293i | DH511_1BVH_4A | DH511_1AVK | 6.238 | 3.754 | >50 | >50 | 27.138 | >50 | 0.069 | 0.028 | >50 | >50 |
| 704-01-021-0 | DH511_2a_4A/293i | DH511_2AVH_4A | DH511_2AVK | 3.319 | 3.218 | 48.576 | 48.887 | 1.427 | 1.307 | 0.027 | <0.023 | >50 | >50 |
| 704-01-021-0 | DH511_2b_4A/293i | DH511_2BVH_4A | DH511_2AVK | 2.637 | 2.405 | 42.664 | 43.251 | 1.122 | 0.809 | 0.056 | <0.023 | >50 | >50 |
| 704-01-021-0 | DH511_2c_4A/293i | DH511_2CVH_4A | DH511_2AVK | 42.914 | NT | >50 | NT | 22.124 | NT | 1.648 | NT | >50 | >50 |
| 704-01-021-0 | DH511_3a_4A/293i | DH511_3AVH_4A | DH511_3AVK | 4.958 | 2.390 | >50 | >50 | 10.523 | 5.580 | 0.044 | <0.023 | >50 | >50 |
| 704-01-021-0 | DH511_3b_4A/293i | DH511_3AVH_4A | DH511_3BVK | 6.904 | NT | >50 | NT | 17.279 | NT | 0.130 | NT | >50 | >50 |
| 704-01-021-0 | DH511_3c_4A/293i | DH511_3AVH_4A | DH511_3CVK | 5.549 | 1.885 | >50 | >50 | 11.008 | 5.053 | 0.077 | <0.023 | >50 | >50 |
| 704-01-021-0 | DH511_4a_4A/293i | DH511_4AVH_4A | DH511_4A4CVK | 29.871 | >50 | >50 | >50 | >50 | >50 | 1.523 | 0.498 | >50 | >50 |
| 704-01-021-0 | DH511_4a_4bK_4A/293i | DH511_4AVH_4A | DH511_4BVK | 24.966 | 29.218 | >50 | >50 | >50 | >50 | 0.649 | 0.526 | >50 | >50 |
| 704-01-021-0 | DH511_4b_4aK_4A/293i | DH511_4BVH_4A | DH511_4A4CVK | >50 | NT | >50 | NT | >50 | NT | 4.022 | NT | >50 | >50 |
| 704-01-021-0 | DH511_4b_4A/293i | DH511_4BVH_4A | DH511_4BVK | >50 | NT | >50 | NT | >50 | NT | 2.042 | NT | >50 | >50 |
| 704-01-021-0 | DH511_4c_4A/293i | DH511_4CVH_4A | DH511_4A4CVK | >50 | >50 | >50 | >50 | >50 | >50 | 6.865 | 4.577 | >50 | >50 |
| 704-01-021-0 | DH511_4c_4bK_4A/293i | DH511_4CVH_4A | DH511_4BVK | >50 | >50 | >50 | >50 | >50 | >50 | 3.769 | 2.456 | >50 | >50 |
| 704-01-021-0 | DH511_5a_4A/293i | pDH511_5AVH_4A | pDH511_5AVK | 1.141 | 1.064 | 24.194 | 23.995 | 0.477 | 0.605 | <0.023 | <0.023 | >50 | >50 |
| 704-01-021-0 | DH511_5b_4A/293i | pDH511_5BVH_4A | pDH511_5AVK | 0.944 | 0.448 | 26.798 | 18.442 | 0.443 | 0.440 | <0.023 | <0.023 | >50 | >50 |
| 704-01-021-0 | DH512 (Ab510049_4A/293i) | H510049_4A | K510032 | NT | 0.813 | NT | 21.759 | NT | 9.813 | NT | <0.023 | NT | >50 |
| | 10E8 | | | 0.773 | 0.433 | 9.597 | 7.213 | 0.188 | 0.183 | <0.023 | <0.023 | >50 | >50 |
| | 2F5 | | | 4.035 | 4.239 | NT | NT | NT | NT | <0.023 | <0.023 | NT | NT |
| | 4E10 | | | NT | NT | NT | NT | 2.301 | 1.449 | NT | NT | >50 | >50 |
| | CH31 | | | NT | NT | NT | 0.029 | 0.030 | NT | NT | NT | NT | NT |

Key

<0.2 µg/ml 0.2-2 µg/ml 2-20 µg/ml >20 µg/ml

NT, not tested

Figure 43 cont.

```
                ...
DH512_VH        TCA
DH511_1AVH      ...
DH511_1BVH      ...
DH511_2AVH      ...
DH511_2BVH      ...
DH511_2CVH      ...
DH511_3AVH      C..
DH511_4AVH      ...
DH511_4BVH      ...
DH511_4CVH      ...
DH511_5AVH      ..G
DH511_5BVH      ..G
10E8_VH         ...
```

CDR1
CDR2
CDR3
DH512_VH
DH511_1AVH
DH511_1BVH
DH511_2AVH
DH511_2BVH
DH511_2CVH
DH511_3AVH
DH511_4AVH
DH511_4BVH
DH511_4CVH
DH511_5AVH
DH511_5BVH
10E8_VH

Figure 45 cont.

```
                    210       220       230       240       250       260       270       280       290       300
                ....|....|....|....|....|....|....|....|....|....|....|....|....|....|....|....|....|....|....|
                                                                                         CDR3
DH512_VK        TGGGAACCTTTTCACTCTCACCATTACCAATCTGCAACCTGAAGATTTTGCAACTTATTATTGT---CAAGAGAATTATAATACTATCCCCTCGCTCAGC
DH511_1AVK      .....CAGAC..........T...C.G..G............G..C....G.....C..C..---.......G.....G.T.C.CG...A.A.A..C.
DH511_2AVK      .....CAGAC..T.......T...C.G..G............G..C....G......TC..---.......G.....G.T...CG...A.A.A..TT
DH511_3AVK      ........AA..................A..G........A.......................---.......G...CC.G..CG.T...A.A....C.
DH511_3BVK      ........AA..................A..G........A.......................---.......G...CC.G..CG.T...A.A....C.
DH511_3CVK      ........AA..................A..G........A.......................---.......G...CC.G..CG.T...A.A....C.
DH511_4A4CVK    .....CA.AG..................A..G................................---......GC......C..C.A....A.A...TC.
DH511_4BVK      .....CA.AG..................A..G................................---......GC......C..C.A....A.A...TC.
DH511_5AVK      ....TCGGCC....A..G....C.G..G.....G..............G...............---..G....G...C.GC.GCG.T...AT.TA..TT
10E8_VL         A..A...AGAGCTT.CT.G.....CT.TGGGGCT..GG.G.....CGAC..GGAA.........AGTTCTCG.G.CA.G.G.GGC.G..GTCT.TCGGT.

                    310       320       330
                ....|....|....|....|....|....|.

DH512_VK        TTTGGTCAGGGGACCAAGGTGGACATCAGG-
DH511_1AVK      .....C.T.........AT....G..G.AAC
DH511_2AVK      .....C.T.........AT....G.AG.AAC
DH511_3AVK      .......C........G........GG.A.C
DH511_3BVK      .......C........G........GG.A.C
DH511_3CVK      .......C........G........GG.A.C
DH511_4A4CVK    ................G........GG.AAC
DH511_4BVK      ................G........GG.AAC
DH511_5AVK      ..C..C..................C...AAC
10E8_VL         ..C..CGG.........AC..AC.G..CTCA
```

Figure 46

```
                         10        20        30        40        50        60        70        80        90       100
                 ....|....|....|....|....|....|....|....|....|....|....|....|....|....|....|....|....|....|....|....|
                                              CDR1                 CDR2                                        CDR3
DH512_VK         DIVMTQSPSSVSASVGDRVTITCRASQNIRDYLNWYQHKPGGSPRLLIYAASTLQTGVPSRFSGSGSGNLFTLTITNLQPEDFATYYC~QENYNTIPSLS
DH511_1AVK       ..QI.....FLYG................K.......QR..RA...V....N..S..........Y.TD...I.SS...........~..S.SST.THT
DH511_2AVK       ..Q......FLYG................K.......QR..RA.........N..S..........Y.TD...I.SS..........F.~..S.SST.THI
DH511_3AVK       ..Q...F...L.........M......S.K........T..KA......G.T...R..............Q.....NS............~..S.Q.V.T.T
DH511_3BVK       ..Q...P...L.........M......S.K........T..KA......G.T...R..............Q.....NS............~..S.Q.V.T.T
DH511_3CVK       ..R.......L.........M......S.K........T..KA......G.T...R..............Q.....NS............~..S.Q.V.T.T
DH511_4A4CVK     ..QV....T.L......T.........S.KN.V......S.SA..........A.HS.I....T.....TQ.....NS............~..A...N.T..
DH511_4BVK       ..Q...F.T.L......T.........S.KN.V......S.SA..........A.HS.I....T.....TQ.....NS............~..A...N.T..
DH511_5AVK       ..RL......L.......I........S.K......K.R..EA.K....S..K.RS..S.......Y.SA.....SS............~..S.SSV.MYI
10E8_VL          SYEL..XXTG..VAL.RT......GDSLRSH.AS...K...QA.I..F.GKNNRPS...D.....A...RAS...SGA.A..D.E...SSRDKSGSRLSV

                      110
                 ....|....|

K510032_DH512    FGQGTKVDIR
DH511_1AVK       ..L...LEMK
DH511_2AVK       ..L...LEKK
DH511_3AVK       ..P..R..RK
DH511_3BVK       ..P..R..RK
DH511_3CVK       ..P..R..RK
DH511_4A4CVK     .....R..RK
DH511_4BVK       .....R..RK
DH511_5AVK       ........LK
10E8_VL          ..G...LTVL
```

Figure 47

| PTID | Ab Name | Heavy ID | Light ID | VH | DH | JH | HCDR3 Length | VH Mut (%) | VK | JK | K CDR3 Length | VK Mut (%) |
|---|---|---|---|---|---|---|---|---|---|---|---|---|
| CH0210 | DH511_1a_4A | DH511_1AVH_4A | DH511_1AVK | 3-15*02 | 3-3*01 | 6*03 | 23 | 12.29 | 1-39*01 | 2*01 | 11 | 11.74 |
| CH0210 | DH511_1b_4A | DH511_1BVH_4A | DH511_1AVK | 3-15*02 | 3-3*01 | 6*03 | 23 | 11.60 | 1-39*01 | 2*01 | 11 | 11.74 |
| CH0210 | DH511_2a_4A | DH511_2AVH_4A | DH511_2AVK | 3-15*02 | 3-3*01 | 6*03 | 23 | 13.99 | 1-39*01 | 2*01 | 11 | 11.36 |
| CH0210 | DH511_2b_4A | DH511_2BVH_4A | DH511_2AVK | 3-15*02 | 3-3*01 | 6*03 | 23 | 14.68 | 1-39*01 | 2*01 | 11 | 11.36 |
| CH0210 | DH511_2c_4A | DH511_2CVH_4A | DH511_2AVK | 3-15*02 | 3-3*01 | 6*03 | 23 | 14.97 | 1-39*01 | 2*01 | 11 | 11.36 |
| CH0210 | DH511_3a_4A | DH511_3AVH_4A | DH511_3AVK | 3-15*01 | 3-3*01 | 6*03 | 24 | 20.41 | 1-39*01 | 2*01 | 11 | 13.64 |
| CH0210 | DH511_3b_4A | DH511_3AVH_4A | DH511_3BVK | 3-15*01 | 3-3*01 | 6*03 | 24 | 20.41 | 1-39*01 | 2*01 | 11 | 14.02 |
| CH0210 | DH511_3c_4A | DH511_3AVH_4A | DH511_3CVK | 3-15*01 | 3-3*01 | 6*03 | 24 | 20.41 | 1-39*01 | 2*01 | 11 | 13.64 |
| CH0210 | DH511_4a_4A | DH511_4AVH_4A | DH511_4A4CVK | 3-15*01 | 3-3*01 | 6*03 | 23 | 19.05 | 1-39*01 | 2*01 | 11 | 13.64 |
| CH0210 | DH511_4a_4bK_4A | DH511_4AVH_4A | DH511_4BVK | 3-15*01 | 3-3*01 | 6*03 | 23 | 19.05 | 1-39*01 | 2*01 | 11 | 14.39 |
| CH0210 | DH511_4b_4aK_4A | DH511_4BVH_4A | DH511_4A4CVK | 3-15*01 | 3-3*01 | 6*03 | 23 | 19.80 | 1-39*01 | 2*01 | 11 | 13.64 |
| CH0210 | DH511_4b_4A | DH511_4BVH_4A | DH511_4BVK | 3-15*01 | 3-3*01 | 6*03 | 23 | 19.80 | 1-39*01 | 2*01 | 11 | 14.39 |
| CH0210 | DH511_4c_4A | DH511_4CVH_4A | DH511_4A4CVK | 3-15*01 | 3-3*01 | 6*03 | 23 | 20.48 | 1-39*01 | 2*01 | 11 | 13.64 |
| CH0210 | DH511_4c_4bK_4A | DH511_4CVH_4A | DH511_4BVK | 3-15*01 | 3-3*01 | 6*03 | 23 | 20.48 | 1-39*01 | 2*01 | 11 | 14.39 |
| CH0210 | DH511_5a_4A | DH511_5AVH_4A | DH511_5AVK | 3-15*01 | 3-3*01 | 6*03 | 23 | 10.56 | 1-39*01 | 2*01 | 11 | 15.53 |
| CH0210 | DH511_5b_4A | DH511_5BVH_4A | DH511_5AVK | 3-15*01 | 3-3*01 | 6*03 | 23 | 11.22 | 1-39*01 | 2*01 | 11 | 15.53 |
| | | | | | | | | | | | | |
| | | | | | | | | | | | | |
| | | | | | | | | | | | | |

Figure 55

| | Heavy ID | Light ID |
|---|---|---|
| 1 | DH511_1AVH_4A | DH511_2AVK |
| 2 | DH511_1AVH_4A | DH511_3AVK |
| 3 | DH511_1AVH_4A | DH511_3BVK |
| 4 | DH511_1AVH_4A | DH511_3CVK |
| 5 | DH511_1AVH_4A | DH511_4A4CVK |
| 6 | DH511_1AVH_4A | DH511_4BVK |
| 7 | DH511_1AVH_4A | DH511_5AVK |
| 8 | DH511_1AVH_4A | K510032 (DH512) |
| 9 | DH511_1BVH_4A | DH511_2AVK |
| 10 | DH511_1BVH_4A | DH511_3AVK |
| 11 | DH511_1BVH_4A | DH511_3BVK |
| 12 | DH511_1BVH_4A | DH511_3CVK |
| 13 | DH511_1BVH_4A | DH511_4A4CVK |
| 14 | DH511_1BVH_4A | DH511_4BVK |
| 15 | DH511_1BVH_4A | DH511_5AVK |
| 16 | DH511_1BVH_4A | K510032 (DH512) |
| 17 | DH511_2AVH_4A | DH511_1AVK |
| 18 | DH511_2AVH_4A | DH511_3AVK |
| 19 | DH511_2AVH_4A | DH511_3BVK |
| 20 | DH511_2AVH_4A | DH511_3CVK |
| 21 | DH511_2AVH_4A | DH511_4A4CVK |
| 22 | DH511_2AVH_4A | DH511_4BVK |
| 23 | DH511_2AVH_4A | DH511_5AVK |
| 24 | DH511_2AVH_4A | K510032 (DH512) |
| 25 | DH511_2BVH_4A | DH511_1AVK |
| 26 | DH511_2BVH_4A | DH511_3AVK |
| 27 | DH511_2BVH_4A | DH511_3BVK |
| 28 | DH511_2BVH_4A | DH511_3CVK |
| 29 | DH511_2BVH_4A | DH511_4A4CVK |
| 30 | DH511_2BVH_4A | DH511_4BVK |
| 31 | DH511_2BVH_4A | DH511_5AVK |
| 32 | DH511_2BVH_4A | K510032 (DH512) |

| | Heavy ID | Light ID |
|---|---|---|
| 33 | DH511_2CVH_4A | DH511_1AVK |
| 34 | DH511_2CVH_4A | DH511_3AVK |
| 35 | DH511_2CVH_4A | DH511_3BVK |
| 36 | DH511_2CVH_4A | DH511_3CVK |
| 37 | DH511_2CVH_4A | DH511_4A4CVK |
| 38 | DH511_2CVH_4A | DH511_4BVK |
| 39 | DH511_2CVH_4A | DH511_5AVK |
| 40 | DH511_2CVH_4A | K510032 (DH512) |
| 41 | DH511_3AVH_4A | DH511_1AVK |
| 42 | DH511_3AVH_4A | DH511_2AVK |
| 43 | DH511_3AVH_4A | DH511_4A4CVK |
| 44 | DH511_3AVH_4A | DH511_4BVK |
| 45 | DH511_3AVH_4A | DH511_5AVK |
| 46 | DH511_3AVH_4A | K510032 (DH512) |
| 47 | DH511_4AVH_4A | DH511_1AVK |
| 48 | DH511_4AVH_4A | DH511_2AVK |
| 49 | DH511_4AVH_4A | DH511_3AVK |
| 50 | DH511_4AVH_4A | DH511_3BVK |
| 51 | DH511_4AVH_4A | DH511_3CVK |
| 52 | DH511_4AVH_4A | DH511_5AVK |
| 53 | DH511_4AVH_4A | K510032 (DH512) |
| 54 | DH511_4BVH_4A | DH511_1AVK |
| 55 | DH511_4BVH_4A | DH511_2AVK |
| 56 | DH511_4BVH_4A | DH511_3AVK |
| 57 | DH511_4BVH_4A | DH511_3BVK |
| 58 | DH511_4BVH_4A | DH511_3CVK |
| 59 | DH511_4BVH_4A | DH511_5AVK |
| 60 | DH511_4BVH_4A | K510032 (DH512) |

| | Heavy ID | Light ID |
|---|---|---|
| 61 | DH511_4CVH_4A | DH511_1AVK |
| 62 | DH511_4CVH_4A | DH511_2AVK |
| 63 | DH511_4CVH_4A | DH511_3AVK |
| 64 | DH511_4CVH_4A | DH511_3BVK |
| 65 | DH511_4CVH_4A | DH511_3CVK |
| 66 | DH511_4CVH_4A | DH511_5AVK |
| 67 | DH511_4CVH_4A | K510032 (DH512) |
| 68 | DH511_5AVH_4A | DH511_1AVK |
| 69 | DH511_5AVH_4A | DH511_2AVK |
| 70 | DH511_5AVH_4A | DH511_3AVK |
| 71 | DH511_5AVH_4A | DH511_3BVK |
| 72 | DH511_5AVH_4A | DH511_3CVK |
| 73 | DH511_5AVH_4A | DH511_4A4CVK |
| 74 | DH511_5AVH_4A | DH511_4BVK |
| 75 | DH511_5AVH_4A | K510032 (DH512) |
| 76 | DH511_5BVH_4A | DH511_1AVK |
| 77 | DH511_5BVH_4A | DH511_2AVK |
| 78 | DH511_5BVH_4A | DH511_3AVK |
| 79 | DH511_5BVH_4A | DH511_3BVK |
| 80 | DH511_5BVH_4A | DH511_3CVK |
| 81 | DH511_5BVH_4A | DH511_4A4CVK |
| 82 | DH511_5BVH_4A | DH511_4BVK |
| 83 | DH511_5BVH_4A | K510032 (DH512) |
| 84 | H510049_4A (DH512) | DH511_1AVK |
| 85 | H510049_4A (DH512) | DH511_2AVK |
| 86 | H510049_4A (DH512) | DH511_3AVK |
| 87 | H510049_4A (DH512) | DH511_3BVK |
| 88 | H510049_4A (DH512) | DH511_3CVK |
| 89 | H510049_4A (DH512) | DH511_4A4CVK |
| 90 | H510049_4A (DH512) | DH511_4BVK |
| 91 | H510049_4A (DH512) | DH511_5AVK |

| PTID | Heavy ID | Light ID | IgG Quant (µg/ml) | 1:6 Initial Dilution (µg/ml) |
|---|---|---|---|---|
| 704-01-021-0 | DH511_1AVH_4A | DH511_2AVK | 63 | 10.50 |
| 704-01-021-0 | DH511_1AVH_4A | DH511_3AVK | 67.2 | 11.20 |
| 704-01-021-0 | DH511_1AVH_4A | DH511_3BVK | 62.35 | 10.39 |
| 704-01-021-0 | DH511_1AVH_4A | DH511_3CVK | 109.25 | 18.21 |
| 704-01-021-0 | DH511_1AVH_4A | DH511_4A4CVK | 24.5 | 4.08 |
| 704-01-021-0 | DH511_1AVH_4A | DH511_4BVK | 67 | 11.17 |
| 704-01-021-0 | DH511_1AVH_4A | DH511_5AVK | 38.75 | 6.46 |
| 704-01-021-0 | DH511_1AVH_4A | K510032 (DH512) | 68.35 | 11.39 |
| 704-01-021-0 | DH511_1BVH_4A | DH511_2AVK | 40.85 | 6.81 |
| 704-01-021-0 | DH511_1BVH_4A | DH511_3AVK | 61.9 | 10.32 |
| 704-01-021-0 | DH511_1BVH_4A | DH511_3BVK | 36 | 6.00 |
| 704-01-021-0 | DH511_1BVH_4A | DH511_3CVK | 51.45 | 8.58 |
| 704-01-021-0 | DH511_1BVH_4A | DH511_4A4CVK | 44.5 | 7.42 |
| 704-01-021-0 | DH511_1BVH_4A | DH511_4BVK | 38.75 | 6.46 |
| 704-01-021-0 | DH511_1BVH_4A | DH511_5AVK | 37.5 | 6.25 |
| 704-01-021-0 | DH511_1BVH_4A | K510032 (DH512) | 72.7 | 12.12 |
| 704-01-021-0 | DH511_2AVH_4A | DH511_1AVK | 66.3 | 11.05 |
| 704-01-021-0 | DH511_2AVH_4A | DH511_3AVK | 59.85 | 9.98 |
| 704-01-021-0 | DH511_2AVH_4A | DH511_3BVK | 64.1 | 10.68 |
| 704-01-021-0 | DH511_2AVH_4A | DH511_3CVK | 92.4 | 15.40 |
| 704-01-021-0 | DH511_2AVH_4A | DH511_4A4CVK | 28.5 | 4.75 |
| 704-01-021-0 | DH511_2AVH_4A | DH511_4BVK | 24.1 | 4.02 |
| 704-01-021-0 | DH511_2AVH_4A | DH511_5AVK | 23.2 | 3.87 |
| 704-01-021-0 | DH511_2AVH_4A | K510032 (DH512) | 76.75 | 12.79 |
| 704-01-021-0 | DH511_2BVH_4A | DH511_1AVK | 67.45 | 11.24 |
| 704-01-021-0 | DH511_2BVH_4A | DH511_3AVK | 152.05 | 25.34 |
| 704-01-021-0 | DH511_2BVH_4A | DH511_3BVK | 103.5 | 17.25 |
| 704-01-021-0 | DH511_2BVH_4A | DH511_3CVK | 227.2 | 37.87 |
| 704-01-021-0 | DH511_2BVH_4A | DH511_4A4CVK | 45.9 | 7.65 |
| 704-01-021-0 | DH511_2BVH_4A | DH511_4BVK | 40.65 | 6.78 |
| 704-01-021-0 | DH511_2BVH_4A | DH511_5AVK | 92.65 | 15.44 |
| 704-01-021-0 | DH511_2BVH_4A | K510032 (DH512) | 118.75 | 19.79 |
| 704-01-021-0 | DH511_1AVH_4A | DH511_1AVK | 69.3 | 11.55 |
| 704-01-021-0 | DH511_1BVH_4A | DH511_1AVK | 65 | 10.83 |
| 704-01-021-0 | DH511_2AVH_4A | DH511_2AVK | 68.5 | 11.42 |
| 704-01-021-0 | DH511_2BVH_4A | DH511_2AVK | 85.4 | 14.23 |
| 704-01-021-0 | H510049_4A (DH512) | K510032 (DH512) | 170 | 28.33 |
| Positive Control | HV13221 | HV13501 | 55 | 9.17 |
| Mock Transfection | | | 20 | 3.33 |
| 10E8 | | | | |

Figure 56A

| | IC50 (μg/ml) | IC80 (μg/ml) | IC50 (μg/ml) | IC80 (μg/ml) |
|---|---|---|---|---|
| PTID | BG1168 | BG1168 | SVA | SVA |
| 704-01-021-0 | 1.272 | 6.006 | >10.5 | >10.5 |
| 704-01-021-0 | 9.314 | >11.2 | >11.2 | >11.2 |
| 704-01-021-0 | >10.39 | >10.39 | >10.39 | >10.39 |
| 704-01-021-0 | 8.174 | >18.21 | >18.21 | >18.21 |
| 704-01-021-0 | >4.08 | >4.08 | >4.08 | >4.08 |
| 704-01-021-0 | >11.17 | >11.17 | >11.17 | >11.17 |
| 704-01-021-0 | >6.46 | >6.46 | >6.46 | >6.46 |
| 704-01-021-0 | 2.818 | >11.39 | >11.39 | >11.39 |
| 704-01-021-0 | 1.3 | >6.81 | >6.81 | >6.81 |
| 704-01-021-0 | >10.32 | >10.32 | >10.32 | >10.32 |
| 704-01-021-0 | >6 | >6 | >6 | >6 |
| 704-01-021-0 | 7.843 | >8.58 | >8.58 | >8.58 |
| 704-01-021-0 | >7.42 | >7.42 | >7.42 | >7.42 |
| 704-01-021-0 | >6.46 | >6.46 | >6.46 | >6.46 |
| 704-01-021-0 | >6.25 | >6.25 | >6.25 | >6.25 |
| 704-01-021-0 | 3.458 | >12.12 | >12.12 | >12.12 |
| 704-01-021-0 | 1.047 | 5.776 | >11.05 | >11.05 |
| 704-01-021-0 | 7.925 | >9.98 | >9.98 | >9.98 |
| 704-01-021-0 | >10.65 | >10.68 | >10.68 | >10.68 |
| 704-01-021-0 | 6.174 | >15.4 | >15.4 | >15.4 |
| 704-01-021-0 | >4.75 | >4.75 | >4.75 | >4.75 |
| 704-01-021-0 | >4.02 | >4.02 | >4.02 | >4.02 |
| 704-01-021-0 | >3.87 | >3.87 | >3.87 | >3.87 |
| 704-01-021-0 | 2.091 | >12.79 | >12.79 | >12.79 |
| 704-01-021-0 | 0.513 | 2.523 | >11.24 | >11.24 |
| 704-01-021-0 | 8.241 | >25.34 | >25.34 | >25.34 |
| 704-01-021-0 | 7.890 | >17.25 | >17.25 | >17.25 |
| 704-01-021-0 | 6.789 | >37.87 | >37.87 | >37.87 |
| 704-01-021-0 | >7.65 | >7.65 | >7.65 | >7.65 |
| 704-01-021-0 | >6.78 | >6.78 | >6.78 | >6.78 |
| 704-01-021-0 | 5.087 | >15.44 | >15.44 | >15.44 |
| 704-01-021-0 | 2.002 | 9.339 | >19.79 | >19.79 |
| 704-01-021-0 | 2.236 | >11.55 | >11.55 | >11.55 |
| 704-01-021-0 | 3.239 | >10.83 | >10.83 | >10.83 |
| 704-01-021-0 | 1.023 | 6.96 | >11.42 | >11.42 |
| 704-01-021-0 | 0.244 | 1.503 | >4.23 | >4.23 |
| 704-01-021-0 | 0.522 | 2.750 | >28.33 | >28.33 |
| Positive Control | 1.681 | >9.17 | >9.17 | >9.17 |
| Mock Transfection | >3.33 | >3.33 | >3.33 | >3.33 |
| 10E8 | 0.162 | 0.841 | >50 | >50 |

Figure 56A cont.

| PTID | Heavy ID | Light ID | IgG Quant (µg/ml) | 1:6 Initial Dilution (µg/ml) |
|---|---|---|---|---|
| 704-01-021-0 | DH511_2C VH_4A | DH511_1AVK | 2.511 | 0.419 |
| 704-01-021-0 | DH511_2C VH_4A | DH511_3AVK | 12.819 | 2.137 |
| 704-01-021-0 | DH511_2C VH_4A | DH511_3B VK | 0.397 | 0.066 |
| 704-01-021-0 | DH511_2C VH_4A | DH511_3C VK | 12.785 | 2.131 |
| 704-01-021-0 | DH511_2C VH_4A | DH511_4A4C VK | 0.314 | 0.052 |
| 704-01-021-0 | DH511_2C VH_4A | DH511_4B VK | 0.493 | 0.082 |
| 704-01-021-0 | DH511_2C VH_4A | DH511_5AVK | 5.005 | 0.834 |
| 704-01-021-0 | DH511_2C VH_4A | K510032 (DH512) | 1.826 | 0.304 |
| 704-01-021-0 | DH511_3AVH_4A | DH511_1AVK | 113.8 | 18.967 |
| 704-01-021-0 | DH511_3AVH_4A | DH511_2AVK | 80.144 | 13.357 |
| 704-01-021-0 | DH511_3AVH_4A | DH511_4A4C VK | 0.425 | 0.071 |
| 704-01-021-0 | DH511_3AVH_4A | DH511_4B VK | 1.324 | 0.221 |
| 704-01-021-0 | DH511_3AVH_4A | DH511_5AVK | 35.459 | 5.910 |
| 704-01-021-0 | DH511_3AVH_4A | K510032 (DH512) | 123.19 | 20.532 |
| 704-01-021-0 | DH511_4AVH_4A | DH511_1AVK | 88.918 | 14.820 |
| 704-01-021-0 | DH511_4AVH_4A | DH511_2AVK | 100.574 | 16.762 |
| 704-01-021-0 | DH511_4AVH_4A | DH511_3AVK | 173.528 | 28.921 |
| 704-01-021-0 | DH511_4AVH_4A | DH511_3B VK | 154.783 | 25.797 |
| 704-01-021-0 | DH511_4AVH_4A | DH511_3C VK | 274.865 | 45.811 |
| 704-01-021-0 | DH511_4AVH_4A | DH511_5AVK | 65.743 | 10.957 |
| 704-01-021-0 | DH511_4AVH_4A | K510032 (DH512) | 142.347 | 23.725 |
| 704-01-021-0 | DH511_4B VH_4A | DH511_1AVK | 72.442 | 12.074 |
| 704-01-021-0 | DH511_4B VH_4A | DH511_2AVK | 152.552 | 25.425 |
| 704-01-021-0 | DH511_4B VH_4A | DH511_3AVK | 154.118 | 25.686 |
| 704-01-021-0 | DH511_4B VH_4A | DH511_3B VK | 12.751 | 2.125 |
| 704-01-021-0 | DH511_4B VH_4A | DH511_3C VK | 185.783 | 30.964 |
| 704-01-021-0 | DH511_4B VH_4A | DH511_5AVK | 24.791 | 4.132 |
| 704-01-021-0 | DH511_4B VH_4A | K510032 (DH512) | 139.712 | 23.285 |
| 704-01-021-0 | DH511_4C VH_4A | DH511_1AVK | 123.445 | 20.574 |
| 704-01-021-0 | DH511_4C VH_4A | DH511_2AVK | 169.294 | 28.216 |
| 704-01-021-0 | DH511_4C VH_4A | DH511_3AVK | 253.605 | 42.268 |
| 704-01-021-0 | DH511_4C VH_4A | DH511_3B VK | 451.084 | 75.181 |
| 704-01-021-0 | DH511_4C VH_4A | DH511_3C VK | 444.052 | 74.009 |
| 704-01-021-0 | DH511_4C VH_4A | DH511_5AVK | 93.456 | 15.576 |
| 704-01-021-0 | DH511_4C VH_4A | K510032 (DH512) | 181.158 | 30.193 |
| 704-01-021-0 | DH511_2C VH_4A | DH511_2AVK | 2.124 | 0.354 |
| 704-01-021-0 | DH511_3AVH_4A | DH511_3AVK | 78.025 | 13.004 |
| 704-01-021-0 | DH511_3AVH_4A | DH511_3B VK | 48.033 | 8.006 |
| 704-01-021-0 | DH511_3AVH_4A | DH511_3C VK | 182.475 | 30.413 |
| 704-01-021-0 | DH511_4AVH_4A | DH511_4A4C VK | 3.969 | 0.661 |
| 704-01-021-0 | DH511_4AVH_4A | DH511_4B VK | 11.367 | 1.895 |
| 704-01-021-0 | DH511_4B VH_4A | DH511_4A4C VK | 0.618 | 0.103 |
| 704-01-021-0 | DH511_4B VH_4A | DH511_4B VK | 2.234 | 0.372 |
| 704-01-021-0 | DH511_4C VH_4A | DH511_4A4C VK | 4.813 | 0.802 |
| 704-01-021-0 | DH511_4C VH_4A | DH511_4B VK | 12.499 | 2.083 |
| **704-01-021-0** | **H510049_4A (DH512)** | **K510032 (DH512)** | 119.527 | 19.921 |
| Positive Control | HVI3221 | | 87.846 | 14.641 |
| Mock Transfection | | | 0.003 | 0.001 |
| 10E8 | | | | |
| 2F5 | | | | |

Figure 56B

| | IC 50 (μg/ml) | IC 80 (μg/ml) | IC 50 (μg/ml) | IC 80 (μg/ml) |
|---|---|---|---|---|
| PTID | BG1168 | BG1168 | SVA | SVA |
| 704-01-021-0 | >0.419 | >0.419 | >0.419 | >0.419 |
| 704-01-021-0 | >2.137 | >2.137 | >2.137 | >2.137 |
| 704-01-021-0 | >0.066 | >0.066 | >0.066 | >0.066 |
| 704-01-021-0 | >2.131 | >2.131 | >2.131 | >2.131 |
| 704-01-021-0 | >0.052 | >0.052 | >0.052 | >0.052 |
| 704-01-021-0 | >0.082 | >0.082 | >0.082 | >0.082 |
| 704-01-021-0 | >0.834 | >0.834 | >0.834 | >0.834 |
| 704-01-021-0 | >0.304 | >0.304 | >0.304 | >0.304 |
| 704-01-021-0 | 3.238 | 14.836 | >18.967 | >18.967 |
| 704-01-021-0 | 0.774 | 3.790 | >13.357 | >13.357 |
| 704-01-021-0 | >0.071 | >0.071 | >0.071 | >0.071 |
| 704-01-021-0 | >0.221 | >0.221 | >0.221 | >0.221 |
| 704-01-021-0 | 2.433 | >5.91 | >5.91 | >5.91 |
| 704-01-021-0 | 6.858 | >20.532 | >20.532 | >20.532 |
| 704-01-021-0 | 0.958 | 4.132 | >14.82 | >14.82 |
| 704-01-021-0 | 1.396 | 5.769 | >16.762 | >16.762 |
| 704-01-021-0 | 1.731 | 7.303 | >28.921 | >28.921 |
| 704-01-021-0 | 1.428 | 5.567 | >25.797 | >25.797 |
| 704-01-021-0 | 1.305 | 4.523 | >45.811 | >45.811 |
| 704-01-021-0 | 0.71 | 4.336 | >10.957 | >10.957 |
| 704-01-021-0 | 1.731 | 7.428 | >23.725 | >23.725 |
| 704-01-021-0 | 0.913 | 5.042 | >12.074 | >12.074 |
| 704-01-021-0 | 0.48 | 1.495 | >25.425 | >25.425 |
| 704-01-021-0 | 0.817 | 3.173 | >25.686 | >25.686 |
| 704-01-021-0 | 0.673 | >2.125 | >2.125 | >2.125 |
| 704-01-021-0 | 1.135 | 4.096 | >30.964 | >30.964 |
| 704-01-021-0 | 1.213 | >4.132 | >4.132 | >4.132 |
| 704-01-021-0 | 1.312 | 6.339 | >23.285 | >23.285 |
| 704-01-021-0 | 10.673 | >20.574 | >20.574 | >20.574 |
| 704-01-021-0 | 3.408 | >28.216 | >28.216 | >28.216 |
| 704-01-021-0 | 8.719 | >42.268 | >42.268 | >42.268 |
| 704-01-021-0 | 9.393 | 50.853 | >75.181 | >75.181 |
| 704-01-021-0 | 5.180 | 29.485 | >74.009 | >74.009 |
| 704-01-021-0 | 11.992 | >15.576 | >15.576 | >15.576 |
| 704-01-021-0 | 10.671 | >30.193 | >30.193 | >30.193 |
| 704-01-021-0 | >0.354 | >0.354 | >0.354 | >0.354 |
| 704-01-021-0 | 1.277 | 3.565 | >13.004 | >13.004 |
| 704-01-021-0 | 1.928 | 5.549 | >8.006 | >8.006 |
| 704-01-021-0 | 0.899 | 3.789 | >30.413 | >30.413 |
| 704-01-021-0 | >0.661 | >0.661 | >0.661 | >0.661 |
| 704-01-021-0 | >1.895 | >1.895 | >1.895 | >1.895 |
| 704-01-021-0 | >0.103 | >0.103 | >0.103 | >0.103 |
| 704-01-021-0 | >0.372 | >0.372 | >0.372 | >0.372 |
| 704-01-021-0 | >0.802 | >0.802 | >0.802 | >0.802 |
| 704-01-021-0 | >2.083 | >2.083 | >2.083 | >2.083 |
| 704-01-021-0 | 0.725 | 2.441 | >19.921 | >19.921 |
| Positive Control | 3.686 | >14.641 | >14.641 | >14.641 |
| Mock Transfection | >0.001 | >0.001 | >0.001 | >0.001 |
| 10E8 | 0.262 | 0.779 | >50 | >50 |
| 2F5 | 0.888 | 4.793 | >50 | >50 |

Figure 56B cont.

| PTID | Heavy ID | Light ID | IgG Quant (µg/ml) | 1:6 Initial Dilution (µg/ml) |
|---|---|---|---|---|
| 704-01-021-0 | DH511_5AVH_4A | DH511_1AVK | 199.465 | 33.24 |
| 704-01-021-0 | DH511_5AVH_4A | DH511_2AVK | 218.318 | 36.39 |
| 704-01-021-0 | DH511_5AVH_4A | DH511_3AVK | 427.911 | 71.32 |
| 704-01-021-0 | DH511_5AVH_4A | DH511_3BVK | 333.05 | 55.51 |
| 704-01-021-0 | DH511_5AVH_4A | DH511_3CVK | 134.35 | 22.39 |
| 704-01-021-0 | DH511_5AVH_4A | DH511_4A4CVK | 17.539 | 2.92 |
| 704-01-021-0 | DH511_5AVH_4A | DH511_4BVK | 80.408 | 13.40 |
| 704-01-021-0 | DH511_5AVH_4A | K510032 (DH512) | 155.052 | 25.84 |
| 704-01-021-0 | DH511_5AVH_4A | DH511_5AVK | 178.536 | 29.76 |
| 704-01-021-0 | DH511_5BVH_4A | DH511_1AVK | 18.997 | 3.17 |
| 704-01-021-0 | DH511_5BVH_4A | DH511_2AVK | 11.844 | 1.97 |
| 704-01-021-0 | DH511_5BVH_4A | DH511_3AVK | 169.142 | 28.19 |
| 704-01-021-0 | DH511_5BVH_4A | DH511_3BVK | 2.571 | 0.43 |
| 704-01-021-0 | DH511_5BVH_4A | DH511_3CVK | 111.504 | 18.58 |
| 704-01-021-0 | DH511_5BVH_4A | DH511_4A4CVK | 2.187 | 0.36 |
| 704-01-021-0 | DH511_5BVH_4A | DH511_4BVK | 15.98 | 2.66 |
| 704-01-021-0 | DH511_5BVH_4A | K510032 (DH512) | 50.982 | 8.50 |
| 704-01-021-0 | DH511_5BVH_4A | DH511_5AVK | 204.937 | 34.16 |
| 704-01-021-0 | H510049_4A (DH512) | DH511_1AVK | 130.55 | 21.76 |
| 704-01-021-0 | H510049_4A (DH512) | DH511_2AVK | 145.575 | 24.26 |
| 704-01-021-0 | H510049_4A (DH512) | DH511_3AVK | 597.214 | 99.54 |
| 704-01-021-0 | H510049_4A (DH512) | DH511_3BVK | 1072.598 | 178.77 |
| 704-01-021-0 | H510049_4A (DH512) | DH511_3CVK | 646.48 | 107.75 |
| 704-01-021-0 | H510049_4A (DH512) | DH511_4A4CVK | 3.676 | 0.61 |
| 704-01-021-0 | H510049_4A (DH512) | DH511_4BVK | 14.881 | 2.48 |
| 704-01-021-0 | H510049_4A (DH512) | DH511_5AVK | 156.192 | 26.03 |
| 704-01-021-0 | H510049_4A (DH512) | K510032 (DH512) | 188.551 | 31.43 |
| Positive Control | HV13221 | HV13501 | 100.04 | 16.67 |
| Mock Transfection | | | 0.026 | 0.0043 |
| Ab ID | | | | |
| DH512 (from 20151022) | H510049_4A (DH512) | K510032 (DH512) | 50 | N/A |
| 10E8 (from 20151022) | | | 50 | N/A |

Figure 56C

| | IC 50<50 µg/ml | IC 80<50 µg/ml | IC 50<50 µg/ml | IC 80<50 µg/ml |
|---|---|---|---|---|
| PTID | BG1168 | BG1168 | SVA | SVA |
| 704-01-021-0 | 31.35 | >33.24 | >33.24 | >33.24 |
| 704-01-021-0 | 8.322 | >36.39 | >36.39 | >36.39 |
| 704-01-021-0 | >71.32 | >71.32 | >71.32 | >71.32 |
| 704-01-021-0 | >55.51 | >55.51 | >55.51 | >55.51 |
| 704-01-021-0 | >22.39 | >22.39 | >22.39 | >22.39 |
| 704-01-021-0 | >2.92 | >2.92 | >2.92 | >2.92 |
| 704-01-021-0 | >13.4 | >13.4 | >13.4 | >13.4 |
| 704-01-021-0 | 11.195 | >25.84 | >25.84 | >25.84 |
| 704-01-021-0 | 0.963 | 4.494 | >29.76 | >29.76 |
| 704-01-021-0 | >3.17 | >3.17 | >3.17 | >3.17 |
| 704-01-021-0 | >1.97 | >1.97 | >1.97 | >1.97 |
| 704-01-021-0 | >28.19 | >28.19 | >28.19 | >28.19 |
| 704-01-021-0 | >0.43 | >0.43 | >0.43 | >0.43 |
| 704-01-021-0 | >18.58 | >18.58 | >18.58 | >18.58 |
| 704-01-021-0 | >0.36 | >0.36 | >0.36 | >0.36 |
| 704-01-021-0 | >2.66 | >2.66 | >2.66 | >2.66 |
| 704-01-021-0 | >8.5 | >8.5 | >8.5 | >8.5 |
| 704-01-021-0 | 1.145 | 5.634 | >34.16 | >34.16 |
| 704-01-021-0 | 0.699 | 3.225 | >21.76 | >21.76 |
| 704-01-021-0 | 0.258 | 0.886 | >24.26 | >24.26 |
| 704-01-021-0 | 1.846 | 9.286 | >99.54 | >99.54 |
| 704-01-021-0 | 3.414 | 13.355 | >178.77 | >178.77 |
| 704-01-021-0 | 2.115 | 7.925 | >107.75 | >107.75 |
| 704-01-021-0 | >0.61 | >0.61 | >0.61 | >0.61 |
| 704-01-021-0 | >2.48 | >2.48 | >2.48 | >2.48 |
| 704-01-021-0 | 0.355 | 1.243 | >26.03 | >26.03 |
| 704-01-021-0 | 1.602 | 6.039 | >31.43 | >31.43 |
| Positive Control | 3.674 | 14.218 | >16.67 | >16.67 |
| Mock Transfection | >0 | >0 | >0 | >0 |
| Ab ID | | | | |
| DH512 (from 20151022) | 0.174 | 0.813 | >50 | >50 |
| 10E8 (from 20151022) | 0.099 | 0.433 | >50 | >50 |

Figure 56C cont.

| Description | Antibody ID | Heavy ID | Light ID | IgG Quant (µg/ml) |
|---|---|---|---|---|
| MBC-derived | DH512 | DH512_VH | DH512_VK | 188.551 |
| Chimeric mAb | DH512_K2 | DH512_VH | DH511_1AVK | 130.55 |
| Chimeric mAb | DH512_K3 | DH512_VH | DH511_2AVK | 145.575 |
| Chimeric mAb | DH512_K4 | DH512_VH | DH511_5AVK | 156.192 |
| Chimeric mAb | DH511_2b_K2 | DH511_2BVH | DH511_1AVK | 67.45 |
| Chimeric mAb | DH511_3a_K2 | DH511_3AVH | DH511_2AVK | 80.144 |
| Chimeric mAb | DH511_4a_K2 | DH511_4AVH | DH511_5AVK | 65.743 |
| Chimeric mAb | DH511_4b_K2 | DH511_4BVH | DH511_2AVK | 152.552 |
| Chimeric mAb | DH511_4b_K3 | DH511_4BVH | DH511_3BVK | 12.751 |

MBC, memory B cell

Figure 56D

Key (IC50/IC80 in µg/ml)

| <0.1 | >0.1-1.0 | >1.0-10.0 | >10.0 |
|---|---|---|---|

| | | IC50 (µg/ml) | IC80 (µg/ml) | IC50 (µg/ml) | IC80 (µg/ml) |
|---|---|---|---|---|---|
| Antibody ID | 1:6 Initial Dilution (µg/ml) | BG1168 | BG1168 | SVA | SVA |
| DH512 | 31.43 | 1.602 | 6.039 | >31.43 | >31.43 |
| DH512_K2 | 21.76 | 0.699 | 3.225 | >21.76 | >21.76 |
| DH512_K3 | 24.26 | 0.258 | 0.886 | >24.26 | >24.26 |
| DH512_K4 | 26.03 | 0.355 | 1.243 | >26.03 | >26.03 |
| DH511_2b_K2 | 11.24 | 0.513 | 2.523 | >11.24 | >11.24 |
| DH511_3a_K2 | 13.36 | 0.774 | 3.790 | >13.357 | >13.357 |
| DH511_4a_K2 | 10.96 | 0.710 | 4.336 | >10.957 | >10.957 |
| DH511_4b_K2 | 25.43 | 0.480 | 1.495 | >25.425 | >25.425 |
| DH511_4b_K3 | 2.13 | 0.673 | >2.125 | >2.125 | >2.125 |

Figure 56D cont.

Note that for the AbDH511 series of antibodies, multiple heavy chains will be paired with different light chains and vice-versa. Eleven unique heavy chain and eight unique light chains will be ordered for this antibody series.

Raw Sequences in fasta format

Heavy Chain Sequences

>DH511_1AVH_4A
CAGGTCCAGCTGGTACAGTCTGGGGGAGCCCTGGTAAAGCCCGGGGGGGCCCTTAGACTCTCCTGTGA
AGCCTCTGGATTCACTTTCAGCGATACGTGGATGAGCTGGGTCCGCCATCTTCCCGGGAAGGGACTGG
AGTGGATTGGCCGCATTAGAAGGACCACTGATGGTGGGACAACAGAATACGCTTCACCCGTGAAAGGC
AGATTCACCATCTCAAGAGACGATTCAAGAAACACGCTGTATCTGGAAATGAGTGGCCTGAGAATCGA
CGACACAGCGGTGTATTATTGTACCGCTGATCGGGGGGCCCCAGTCTTACGTTTTTGGGAGTGGGGCT
ACTATGACTACTACATGGAGTTCTGGGGCAGAGGGACCTCGGTCACCGTCTCCTCA

>DH511_1BVH_4A

CAGGTGCAGCTGGTGGAATCTGGGGGAGCCCTGGTAAAGCCCGGGGGGGCCCTTAGACTCTCCTGTGA
AGCCTCTGGATTCACTTTCAGCGATACGTGGATGAGCTGGGTCCGCCATCTTCCCGGGAAGGGACTGG
AGTGGATTGGCCGCATTAGAAGGACCACTGATGGTGGGACAACAGAATACGCTTCACCCGTGAAAGGC
AGATTCACCATCTCAAGAGACGATTCAAGAAACACGCTGTATCTGGAAATGAGTGGCCTGAGAATCGA
CGACACAGCAGTGTATTATTGTACCGCTGATCGGGGGGCCCCAGTCTTACGTTTTTGGGAGTGGGGCT
ACTATGACTACTACATGGAGTTCTGGGGCAGAGGGACCTCGGTCACCGTCTCCTCA

>DH511_2AVH_4A
CAGGTGCAGCTGGTGGAGTCTGGGGGAGCCCTGGTAAAGCCCGGGGGGGCCCTTAGACTCTCCTGTGA
AGCCTCCGGATTCCCTTTCAGCGCTACCTGGATGAGCTGGGTCCGCCATCTCCCCGGAAAGGGACTGG
AGTGGATTGGCCGCATTAGAGCGACCACTAATGGTGGGACAACAGAATACGCTTCACCCGTGAAAGGC
AGATTCACCATCTCAAGGGACGATTCAAGAAACACACTGTATCTGGAGATGAGTGGCCTGAAAATCGA
GGACACTGCCGTGTATTATTGTACCGCTGATCGGGGGGCCCCAGTCTTACGTTTTTGGGAGTGGGGCT
ATTTTGACTACTACATGGAGTTCTGGGGCAAAGGGACCTCGGTCACCGTCTCCTCA

>DH511_2BHV_4A
CAGGTGCAGCTGGTGCAATCTGGGGGAGCCCTGGTAAAGCCCGGGGGGGCCCTTAGACTCTCCTGTGA
AGCCTCCGGATTCCCTTTCAGCGCTACCTGGATGAGCTGGGTCCGCCATCTCCCCGGAAAGGGACTGG
AGTGGATTGGCCGCATTAGAGCGACCACTAATGGTGGGACAACAGAATACGCTTCACCCGTGAAAGGC
AGATTCACCATCTCAAGGGACGATTCAAGAAACACACTGTATCTGGAGATGAGTGGCCTGAAAATCGA
GGACACTGCCGTGTATTATTGTACCGCTGATCGGGGGGCCCCAGTCTTACGTTTTTGGGAGTGGGGCT
ATTTTGACTACTACATGGAGTTCTGGGGCAAAGGGACCTCGGTCACCGTCTCCTCA

Figure 57

>DH511_2CVH_4A

GAAGTGCAGCTGGTGGAGTCTGGGGGAGCCCTGGTAAAGCCCGGGGGGGCCCTTAGACCCTCCTGTGA
AGCCTCCGGATTCCCTTTCAGCGCTACCTGGATGAGCTGGGTCCGCCATCTCCCCGGAAAGGGACTGG
AGTGGATTGGCCGCATTAGAGCGACCACTAATGGTGGGACAACAGAATACGCTTCACCCGTGAAAGGC
AGATTCACAATCTCAAGGGACGATTCAAGAAACACACTGTATCTGGAGATGAGTGGCCTGAAAATCGA
GGACACTGCCGTGTATTATTGTACCGCTGATCGGGGGGCCCCAGTCTTACGTTTTGGGAGTGGGGCT
ATTTTGACTACTACATGGAGTTCTGGGGCAAAGGGACCTCGGTCACCGTCTCCTCA

>DH511_3AVH_4A
GAGGTGCAGTTGGTGGAGTCTGGGGGCGGCTTGGTGAAGGCGGGAGAGAGAGTCACAGTCTCCTGTGA
AGGTTATGGATTCAGATTCGATGACGACTGGATGGGCTGGGTCCGCCAGGCTCCAGGGAGGGGACTGG
AATGGGTTGGTCGTATAAGAAGAGTAAAAGACGGTGCGACGACAGAATATGGTGTACCCGTGAAGGGA
AGATTCACCATCTCAAGGGATGACTCAAAGAACACAGTGTATCTACACATGAATAACCTGAAAATCGA
AGACACAGGTGTATATTATTGTACTAGAGATGAGGGGGCCCCAGTTACACGACGGTTTCTGGAGTGGG
GCTACTTCTACTATTACATGGCCGTCTGGGGCAGAGGGACAACGGTCACCGTCTCTCCA

>DH511_4AVH_4A
GAGGTGCAGCTGGTGCAGTCTGGGGGCGGCTTGGTAAAGCCGGGACAGTCAGTCACACTTTCCTGTGT
GGGCTTTGGATTCAATTTCGCTAATGACTGGATGGGCTGGGTCCGCCAGGCTCCAGGGAAGGGACTGG
AATGGGTTGGTCGTATAAGGAGACTAAAAGATGGTGCGAAAGCGGAATATGGATCATCCGTGAAGGGT
AGATTCACCATCTCAAGAGATGATTCAAGAAACACGCTATATTTGCACATGAATAGCCTCAAGGTCGA
AGACACAGCCGTCTATTATTGTACTCGAGACGAGGGGGCCCCAGTTACCCGATTTCTGGAGTGGGGCT
CCTATTACTACTACATGGCCGTCTGGGGCAGAGGGACCACGGTCATCGTCTCTTCA

>DH511_4BVH_4A
CAGGTGCAGCTGGTGCAATCTGGGGGCGGCTTGGTAAAGCCGGGACAGTCAGTCACACCTTCCTGTGT
GGGCTTTGGATTCAATTTCGCTAATGACTGGATGGGCTGGGTCCGCCAGGCTCCAGGGAAGGGACTGG
AATGGGTTGGTCGTATAAGGAGACTAAAAGATGGTGCGAAAGCGGAATATGGATCATCCGTGAAGGGT
AGATTCACCATCTCAAGAGATGATTCAAGAAACACGCTATATTTGCACATGAATAGCCTCAAGGTCGA
AGACACAGCCGTCTATTATTGTACTCGAGACGAGGGGGCCCCAGTTACCCGATTTCTGGAGTGGGGCT
CCTATTACTACTACATGGCCGTCTGGGGCAGAGGGACCACGGTCATCGTCTCTTCA

>DH511_4CVH_4A
CAGGTCCAGCTTGTACAGTCTGGGGGCGGCTTGGTAGAGCCGGGACAGTCAGTCACACTTTCCTGTGT
GGGCTTTGGATTCAATTTCGCTAATGACTGGATGGGCTGGGTCCGCCAGGCTCCAGGGAAGGGACTGG
AATGGGTTGGTCGTATAAGGAGACTAAAAGATGGTGCGAAAGCGGAATATGGATCATCCGTGAAGGGT
AGATTCACCATCTCAAGAGATGATTCAAGAAACACGCTATATTTGCACATGAATAGCCTCAAGGTCGA
AGACACAGCCGTCTATTATTGTACTCGAGACGAGGGGGCCCCAGTTACCCGACTTCTGGAGTGGGGCT
CCTATTACTACTACATGGCCGTCTGGGGCAGAGGGACCACGGTCATCGTCTCTTCA

>DH511_5AVH_4A
CAGGTCCAGCTGGTACAGTCTGGGGGAGGCTTGGTAAAGCCTGGGGGGTCCCTTACACTCTCCTGTGT
CACCTCTGGATTTACTTTCAGCAACACGTGGATGAGTTGGGTCCGCCAGACTCCAGGGAAGGGACTGG
AGTGGGTTGCCCGTATTAGTAGGGTCGGGGATGGCCCAATAATAGACTACGCTGCTCCCGTGAAAGGC
AGATTCATAATCTCAAGAGATGACTCAAGAAACACACTCTTTCTTCACATGAACAACCTGAAAACCGA
GGACACAGCCGTGTATTATTGTACCGCTGATGAGGGGGCCCCAATTTTAAGATTTTTTGAGTGGGGTT
ATTACAACTACTACATGGACGTCTGGGGCAAGGGGACCACGGTCATCGTCTCCTCG

FIGURE 57 Cont

>DH511_5BVH_4A

CAGGTCCAGCTTGTACAGTCTGGGGGAGGCTTGGTAAAGCCTGGGGGGTCCCTTACACCCTCCTGTGT
CACCTCTGGATTTACTTTCAGCAACACGTGGATGAGTTGGGTCCGCCAGACTCCAGGGAAGGGACTGG
AGTGGGTTGCCCGTATTAGTAGGGTCGGGGATGGCCCAATAATAGACTACGCTGCTCCCGTGAAAGGC
AGATTCATAATCTCAAGAGATGACTCAAGAAACACACTCTTTCTTCACATGAACAACCTGAAAACCGA
GGACACAGCCGTGTATTATTGTACCGCTGATGAGGGGGCCCCAATTTTAAGATTTTTTGAGTGGGGTT
ATTACAACTACTACATGGACGTCTGGGGCAAGGGGACCACGGTCATCGTCTCCTCG

Kappa Chain Sequences

>DH511_1AVK
GACATCCAGATCACGCAGTCTCCGTCTTTCCTGTACGGCTCTGTAGGCGATAGGGTCACCATCACTTG
CCGGGCAAGTCAGAATATTAAGGACTATTTAAATTGGTATCAGCAGAGACCAGGGAGAGCCCCTAGAC
TCCTGGTCTATGCTGCATCCAATTTGCAAAGTGGGGTCCCGTCAAGGTTCAGTGGCAGTGGATATGGG
ACAGACTTCACTCTCATCATCAGCAGTCTGCAACCTGAGGACTTTGCGACTTACTACTGTCAAGAGAG
TTATAGTTCCACGCCCACACACACCTTTGGCCTGGGGACCAAATTGGAGATGAAAC

>DH511_2AVK
GACATCCAGATGACCCAGTCTCCGTCTTTCCTGTACGGCTCTGTAGGCGATAGAGTCACCATCACTTG
CCGGGCAAGTCAGAATATTAAGGACTATTTAAATTGGTATCAGCAGAGACCAGGGAGAGCCCCTAGAC
TCCTGATCTATGCTGCATCCAATTTGCAAAGTGGGGTCCCGTCAAGGTTCAGTGGCAGTGGATATGGG
ACAGACTTTACTCTCATCATCAGCAGTCTGCAACCTGAGGACTTTGCGACTTATTTCTGTCAAGAGAG
TTATAGTTCTACGCCCACACACATTTTTGGCCTGGGGACCAAATTGGAGAAGAAAC

>DH511_3AVK
GACATCCAGATGACCCAGTTTCCATCCTCCCTGTCTGCATCTGTGGGAGACAGAGTCACCATGACTTG
CCGGGCAAGTCAGAGCATTAAGGACTATTTAAATTGGTATCAACACACCCCGGGGAAGGCCCCTCGAC
TCCTGATTTATGGTGCGACGACTTTACAGAGAGGGGTCCCATCAAGATTCAGTGGCAGTGGGTCTGGG
AACCAATTCACTCTCACCATTAACAGTCTGCAACCAGAAGATTTTGCAACTTATTATTGTCAAGAGAG
TTACCAGACCGTTCCCACACTCACCTTTGGTCCGGGGACCAGGGTGGACAGGAAGC

>DH511_3BVK

GACATCCAGATGACTCAGCCTCCATCCTCCCTGTCTGCATCTGTGGGAGACAGAGTCACCATGACTTG
CCGGGCAAGTCAGAGCATTAAGGACTATTTAAATTGGTATCAACACACCCCGGGGAAGGCCCCTCGAC
TCCTGATTTATGGTGCGACGACTTTACAGAGAGGGGTCCCATCAAGATTCAGTGGCAGTGGGTCTGGG
AACCAATTCACTCTCACCATTAACAGTCTGCAACCAGAAGATTTTGCAACTTATTATTGTCAAGAGAG
TTACCAGACCGTTCCCACACTCACCTTTGGTCCGGGGACCAGGGTGGACAGGAAGC

>DH511_3CVK

GACATCCGGATGACCCAGTCTCCATCCTCCCTGTCTGCATCTGTGGGAGACAGAGTCACCATGACTTG
CCGGGCAAGTCAGAGCATTAAGGACTATTTAAATTGGTATCAACACACCCCGGGGAAGGCCCCTCGAC
TCCTGATTTATGGTGCGACGACTTTACAGAGAGGGGTCCCATCAAGATTCAGTGGCAGTGGGTCTGGG
AACCAATTCACTCTCACCATTAACAGTCTGCAACCAGAAGATTTTGCAACTTATTATTGTCAAGAGAG
TTACCAGACCGTTCCCACACTCACCTTTGGTCCGGGGACCAGGGTGGACAGGAAGC

FIGURE 57 Cont

>DH511_4A4CVK

GACATCCAGGTGACCCAGTCTCCAACCTCTCTGTCTGCATCTGTAGGAGACACAGTCACTATCACTTG
CCGGGCAAGTCAGAGCATTAAAAATTATGTAAATTGGTATCAACACAAATCCGGGAGCGCCCCTAGAC
TCCTGATTTATGCTGCGTCAGCCTTACATAGTGGGATCCCGTCAAGGTTCACTGGCAGTGGGTCTGGG
ACACAGTTCACTCTCACCATTAACAGTCTGCAACCTGAAGATTTTGCAACTTATTATTGTCAAGAGGC
TTATAACACCAACCCCACACTCTCCTTTGGTCAGGGGACCAGGGTGGACAGGAAAC

>DH511_4BVK

GACATCCAGATGACACAGTTTCCAACCTCTCTGTCTGCATCTGTAGGAGACACCGTCACTATCACTTG
CCGGGCAAGTCAGAGCATTAAAAATTATGTAAATTGGTATCAACACAAATCCGGGAGCGCCCCTAGAC
TCCTGATTTATGCTGCGTCAGCCTTACATAGTGGGATCCCGTCAAGGTTCACTGGCAGTGGGTCTGGG
ACACAGTTCACTCTCACCATTAACAGTCTGCAACCTGAAGATTTTGCAACTTATTATTGTCAAGAGGC
TTATAACACCAACCCCACACTCTCCTTTGGTCAGGGGACCAGGGTGGACAGGAAAC

>DH511_5AVK
GACATCCGGTTGACCCAGTCTCCATCCTCCCTGTCTGCATCTGTTGGGGACAGAATCACCATCACTTG
TCGGGCCAGCCAAAGCATTAAAGACTATTTAAATTGGTATAAACACCGGCCAGGGGAAGCCCCCAAAC
TCCTCATTTATTCTGCATCCAAGTTGAGAAGTGGGGTCTCATCAAGGTTCAGTGGCAGTGGATATGGG
TCGGCCTTCACACTGACCATCAGCAGTCTGCAGCCTGAAGATTTTGCGACTTATTATTGTCAGGAGAG
TTACAGCAGCGTTCCCATGTACATTTTCGGCCAGGGGACCAAGGTGGACCTCAAAC

Translation of sequences- V(D)J only- in fasta format

Heavy Chain Sequences

>DH511_1AVH_4A

QVQLVQSGGALVKPGGALRLSCEASGFTFSDTWMSWVRHLPGKGLEWIGRIRRTTDGGTTEYASPVK
GRFTISRDDSRNTLYLEMSGLRIDDTAVYYCTADRGAPVLRFWEWGYYDYYMEFWGRGTSVTVSS

>DH511_1BVH_4A

QVQLVESGGALVKPGGALRLSCEASGFTFSDTWMSWVRHLPGKGLEWIGRIRRTTDGGTTEYASPVK
GRFTISRDDSRNTLYLEMSGLRIDDTAVYYCTADRGAPVLRFWEWGYYDYYMEFWGRGTSVTVSS

>DH511_2AVH_4A

QVQLVESGGALVKPGGALRLSCEASGFPFSATWMSWVRHLPGKGLEWIGRIRATTNGGTTEYASPVK
GRFTISRDDSRNTLYLEMSGLKIEDTAVYYCTADRGAPVLRFWEWGYFDYYMEFWGKGTSVTVSS

FIGURE 57 Cont

>DH511_2BHV_4A

QVQLVQSGGALVKPGGALRLSCEASGFPFSATWMSWVRHLPGKGLEWIGRIRATTNGGTTEYASPVK
GRFTISRDDSRNTLYLEMSGLKIEDTAVYYCTADRGAPVLRFWEWGYFDYYMEFWGKGTSVTVSS

>DH511_2CVH_4A

EVQLVESGGALVKPGGALRPSCEASGFPFSATWMSWVRHLPGKGLEWIGRIRATTNGGTTEYASPVK
GRFTISRDDSRNTLYLEMSGLKIEDTAVYYCTADRGAPVLRFWEWGYFDYYMEFWGKGTSVTVSS

>DH511_3AVH_4A

EVQLVESGGGLVKAGERVTVSCEGYGFRFDDDWMGWVRQAPGRGLEWVGRIRRVKDGATTEYGVPVK
GRFTISRDDSKNTVYLHMNNLKIEDTGVYYCTRDEGAPVTRRFLEWGYFYYYMAVWGRGTTVTVSP

>DH511_4AVH_4A

EVQLVQSGGGLVKPGQSVTLSCVGFGFNFANDWMGWVRQAPGKGLEWVGRIRRLKDGAKAEYGSSVK
GRFTISRDDSRNTLYLHMNSLKVEDTAVYYCTRDEGAPVTRFLEWGSYYYYMAVWGRGTTVIVSS

>DH511_4BVH_4A

QVQLVQSGGGLVKPGQSVTPSCVGFGFNFANDWMGWVRQAPGKGLEWVGRIRRLKDGAKAEYGSSVK
GRFTISRDDSRNTLYLHMNSLKVEDTAVYYCTRDEGAPVTRFLEWGSYYYYMAVWGRGTTVIVSS

>DH511_4CVH_4A

QVQLVQSGGGLVEPGQSVTLSCVGFGFNFANDWMGWVRQAPGKGLEWVGRIRRLKDGAKAEYGSSVK
GRFTISRDDSRNTLYLHMNSLKVEDTAVYYCTRDEGAPVTRLLEWGSYYYYMAVWGRGTTVIVSS

>DH511_5AVH_4A

QVQLVQSGGGLVKPGGSLTLSCVTSGFTFSNTWMSWVRQTPGKGLEWVARISRVGDGPIIDYAAPVK
GRFIISRDDSRNTLFLHMNNLKTEDTAVYYCTADEGAPILRFFEWGYYNYYMDVWGKGTTVIVSS

>DH511_5BVH_4A

QVQLVQSGGGLVKPGGSLTPSCVTSGFTFSNTWMSWVRQTPGKGLEWVARISRVGDGPIIDYAAPVK
GRFIISRDDSRNTLFLHMNNLKTEDTAVYYCTADEGAPILRFFEWGYYNYYMDVWGKGTTVIVSS

FIGURE 57 Cont

Kappa Chain Sequences

>DH511_1AVK

DIQITQSPSFLYGSVGDRVTITCRASQNIKDYLNWYQQRPGRAPRLLVYAASNLQSGVPSRFSGSGY
GTDFTLIISSLQPEDFATYYCQESYSSTPTHTFGLGTKLEMKX

>DH511_2AVK
DIQMTQSPSFLYGSVGDRVTITCRASQNIKDYLNWYQQRPGRAPRLLIYAASNLQSGVPSRFSGSGY
GTDFTLIISSLQPEDFATYFCQESYSSTPTHIFGLGTKLEKKX

>DH511_3AVK

DIQMTQFPSSLSASVGDRVTMTCRASQSIKDYLNWYQHTPGKAPRLLIYGATTLQRGVPSRFSGSGS
GNQFTLTINSLQPEDFATYYCQESYQTVPTLTFGPGTRVDRKX

>DH511_3BVK

DIQMTQPPSSLSASVGDRVTMTCRASQSIKDYLNWYQHTPGKAPRLLIYGATTLQRGVPSRFSGSGS
GNQFTLTINSLQPEDFATYYCQESYQTVPTLTFGPGTRVDRKX

>DH511_3CVK

DIRMTQSPSSLSASVGDRVTMTCRASQSIKDYLNWYQHTPGKAPRLLIYGATTLQRGVPSRFSGSGS
GNQFTLTINSLQPEDFATYYCQESYQTVPTLTFGPGTRVDRKX

>DH511_4A4CVK

DIQVTQSPTSLSASVGDTVTITCRASQSIKNYVNWYQHKSGSAPRLLIYAASALHSGIPSRFTGSGS
GTQFTLTINSLQPEDFATYYCQEAYNTNPTLSFGQGTRVDRKX

>DH511_4BVK

DIQMTQFPTSLSASVGDTVTITCRASQSIKNYVNWYQHKSGSAPRLLIYAASALHSGIPSRFTGSGS
GTQFTLTINSLQPEDFATYYCQEAYNTNPTLSFGQGTRVDRKX

>DH511_5AVK

DIRLTQSPSSLSASVGDRITITCRASQSIKDYLNWYKHRPGEAPKLLIYSASKLRSGVSSRFSGSGYGSAFTL
TISSLQPEDFATYYCQESYSSVPMYIFGQGTKVDLKX

FIGURE 57 Cont

Target gene: pDH511_5AVH_4A was made previously as construct #15ACIZXC under Order#:29691872 SQ >pDH511_5AVH_4A
GCTAGCACCATGGAGACAGACACACTCCTGCTATGGGTACTGCTGCTCTGGGTTCCAGGTTCCACTGG
TGACCAGGTCCAGCTGGTACAGTCTGGGGGAGGCTTGGTAAAGCCTGGGGGGTCCCTTACACTCTCCT
GTGTCACCTCTGGATTTACTTTCAGCAACACGTGGATGAGTTGGGTCCGCCAGACTCCAGGGAAGGGA
CTGGAGTGGGTTGCCCGTATTAGTAGGGTCGGGGATGGCCCAATAATAGACTACGCTGCTCCCGTGAA
AGGCAGATTCATAATCTCAAGAGATGACTCAAGAAACACACTCTTTCTTCACATGAACAACCTGAAAA
CCGAGGACACAGCCGTGTATTATTGTACCGCTGATGAGGGGGCCCCAATTTTAAGATTTTTTGAGTGG
GGTTATTACAACTACTACATGGACGTCTGGGGCAAGGGGACCACGGTCATCGTCTCCTCGGCGTCGAC Task 1: Subclone the pDH511_5AVH_4A into HV1301089FabH at NheI-SalI sites (remove the old insert), The resulting product should be called as pDH511_5AFabH that has the gene insert sequence between NheI-XbaI sites in pcDNA3.1(+)/hygromycin backbone as shown below.

>pDH511_5AFabH

GCTAGCACCATGGAGACAGACACACTCCTGCTATGGGTACTGCTGCTCTGGGTTCCAGGTTCCACTGG
TGACCAGGTCCAGCTGGTACAGTCTGGGGGAGGCTTGGTAAAGCCTGGGGGGTCCCTTACACTCTCCT
GTGTCACCTCTGGATTTACTTTCAGCAACACGTGGATGAGTTGGGTCCGCCAGACTCCAGGGAAGGGA
CTGGAGTGGGTTGCCCGTATTAGTAGGGTCGGGGATGGCCCAATAATAGACTACGCTGCTCCCGTGAA
AGGCAGATTCATAATCTCAAGAGATGACTCAAGAAACACACTCTTTCTTCACATGAACAACCTGAAAA
CCGAGGACACAGCCGTGTATTATTGTACCGCTGATGAGGGGGCCCCAATTTTAAGATTTTTTGAGTGG
GGTTATTACAACTACTACATGGACGTCTGGGGCAAGGGGACCACGGTCATCGTCTCCTCGGCGTCGAC
CAAGGGCCCATCGGTCTTCCCCCTGGCACCCTCCTCCAAGAGCACCTCTGGGGGCACAGCGGCCCTGG
GCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTGGTGACCGT
GCCCTCCAGCAGCTTGGGTACCCAGACCTACATCTGCAACGTGAATCACAAGCCCAGCAACACCAAGG
TGGACAAGAGAGTTGAGCCCAAATCTTGTGACAAATGATCTAGA

Target gene: pDH511_5BVH_4A was made previously as construct# 15ACIZYC under the Order ID: 29691872 SQ

>pDH511_5BVH_4A
GCTAGCACCATGGAGACAGACACACTCCTGCTATGGGTACTGCTGCTCTGGGTTCCAGGTTCCACTGG
TGACCAGGTCCAGCTTGTACAGTCTGGGGGAGGCTTGGTAAAGCCTGGGGGGTCCCTTACACCCTCCT
GTGTCACCTCTGGATTTACTTTCAGCAACACGTGGATGAGTTGGGTCCGCCAGACTCCAGGGAAGGGA
CTGGAGTGGGTTGCCCGTATTAGTAGGGTCGGGGATGGCCCAATAATAGACTACGCTGCTCCCGTGAA
AGGCAGATTCATAATCTCAAGAGATGACTCAAGAAACACACTCTTTCTTCACATGAACAACCTGAAAA
CCGAGGACACAGCCGTGTATTATTGTACCGCTGATGAGGGGGCCCCAATTTTAAGATTTTTTGAGTGG
GGTTATTACAACTACTACATGGACGTCTGGGGCAAGGGGACCACGGTCATCGTCTCCTCGGCGTCGAC

Figure 58

Task 2: Subclone the pDH511_5BVH_4A into HV1301089FabH in HV200221 backbone at NheI-SalI sites (remove the old insert), The resulting product should be called as pDH511_5BFabH that has the gene insert sequence between NheI-XbaI sites in pcDNA3.1(+)/hygromycin backbone as shown below.

>pDH511_5BFabH

GCTAGCACCATGGAGACAGACACACTCCTGCTATGGGTACTGCTGCTCTGGGTTCCAGGTTCCACTGG
TGACCAGGTCCAGCTTGTACAGTCTGGGGGAGGCTTGGTAAAGCCTGGGGGGTCCCTTACACCCTCCT
GTGTCACCTCTGGATTTACTTTCAGCAACACGTGGATGAGTTGGGTCCGCCAGACTCCAGGGAAGGGA
CTGGAGTGGGTTGCCCGTATTAGTAGGGTCGGGGATGGCCCAATAATAGACTACGCTGCTCCCGTGAA
AGGCAGATTCATAATCTCAAGAGATGACTCAAGAAACACACTCTTTCTTCACATGAACAACCTGAAAA
CCGAGGACACAGCCGTGTATTATTGTACCGCTGATGAGGGGGCCCCAATTTTAAGATTTTTTGAGTGG
GGTTATTACAACTACTACATGGACGTCTGGGGCAAGGGGACCACGGTCATCGTCTCCTCGGCGTCGAC
CAAGGGCCCATCGGTCTTCCCCCTGGCACCCTCCTCCAAGAGCACCTCTGGGGGCACAGCGGCCCTGG
GCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTGGTGACCGT
GCCCTCCAGCAGCTTGGGTACCCAGACCTACATCTGCAACGTGAATCACAAGCCCAGCAACACCAAGG
TGGACAAGAGAGTTGAGCCCAAATCTTGTGACAAATGATCTAGA

| Antibody ID | Median $IC_{50}$ | Geom. $IC_{50}$ Mean | Percent of Viruses Neutralized: $IC_{50}$ < 50 µg/ml | $IC_{50}$ < 1 µg/ml | $IC_{50}$ < 0.1 µg/ml |
|---|---|---|---|---|---|
| DH511.2 | 1.09 | 0.802 | 99 | 49 | 10 |
| 10E8 | 0.392 | 0.315 | 98 | 73 | 19 |
| VRC01 | 0.281 | 0.287 | 90 | 73 | 26 |

| Antibody ID | Median $IC_{80}$ | Geom. $IC_{80}$ Mean | $IC_{80}$ < 50 µg/ml | $IC_{80}$ < 1 µg/ml | $IC_{80}$ < 0.1 µg/ml |
|---|---|---|---|---|---|
| DH511.2 | 5.1 | 3.82 | 97 | 15 | 3 |
| 10E8 | 1.71 | 1.37 | 98 | 29 | 5 |
| VRC01 | 0.839 | 0.843 | 87 | 49 | 6 |

Key
- < 0.2 µg/ml
- 0.2-2 µg/ml
- 2-20 µg/ml

Key
- 91-100%
- 61-90%
- 31-60%
- 1-30%

Figure 59C

| | FR1 (1–25) | CDR1 | FR2 (–50) |
|---|---|---|---|
| IGHV3-15 | EVQLVESGGGLVKPGGSLRLSCAAS | GFTFSNAW | MSWVRQAPGKGLEWVGR |
| 10E8 VH | EVQLVESGGGLVKPGGSLRLSCSAS | GFDFDNAW | MTWVRQPPGKGLEWVGR |
| DH511.1 VH | EVQLVESGGGLVKPGGSLRLSCAAS | GFTFSNTW | MSWVRQAPGKGLEWVGR |
| DH511.2 VH | QVQLVQSGGGLVKPGGSLTLSCSAS | GFFFDNSW | MGWVRQAPGKGLEWVGR |
| DH511.11P VH | QVQLVQSGGGLVKPGGSLTLSCVTS | GFTFSNTW | MSWVRQTPGKGLEWVAR |
| DH511.12P VH | QVQLVQSGGGLVKPGGSLTPSCVTS | GFTFSNTW | MSWVRQTPGKGLEWVAR |

Figure 60E

| | 52ABC (CDR2) | 60 70 8082ABC 90 (FR3) |
|---|---|---|
| IGHV3-15 | IKSKTDGGTT | DYAAPVKGRFTISRDDSKNTLYLQMNSLKTEDTAVYYCTT |
| 10E8 VH | ITGPGEGWSV | DYAAPVEGRFTISRLNSINFLYLEMNNLRMEDSGLYFCAR |
| DH511.1 VH | ISRNKDGAKT | EYAAPVRGRFTISRDDSRDTLYLQMTSLKIEDSGRYFCTA |
| DH511.2 VH | IRRLKDGATG | EYGAAVKDRFTISRDDSRNMLYLHMRTLKTEDSGTYYCTM |
| DH511.11P VH | ISRVGDGPII | DYAAPVKGRFIISRDDSRNTLFLHMNNLKTEDTAVYYCTA |
| DH511.12P VH | ISRVGDGPII | DYAAPVKGRFIISRDDSRNTLFLHMNNLKTEDTAVYYCTA |

Figure 60E cont.

a
| Donor | MPER C1C Neutralization Titer ($ID_{50}$) |
|---|---|
| CH0210 | 17911 |
b
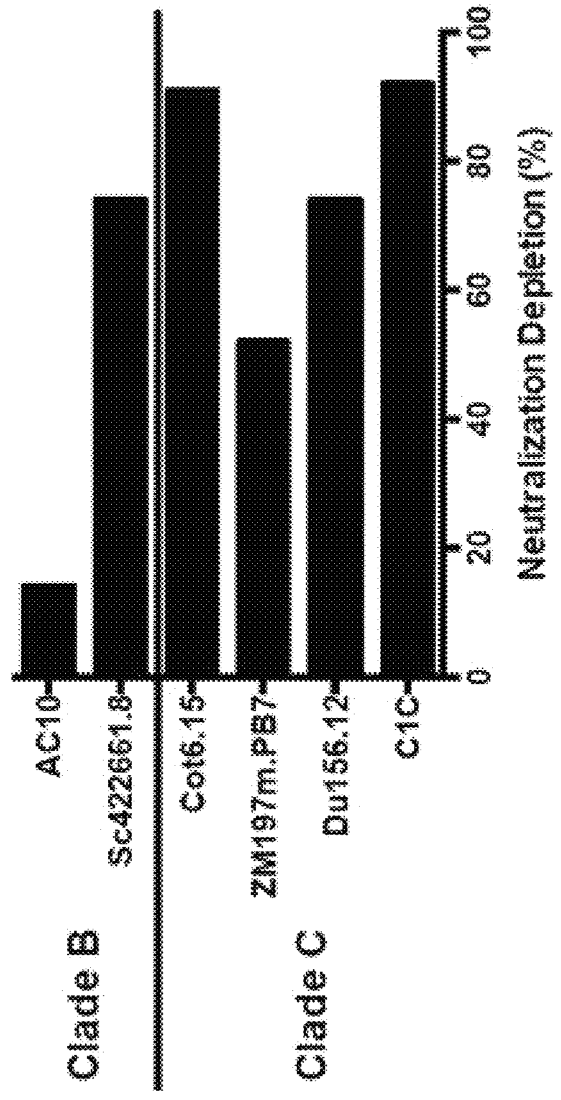
Figures 62A-B b

| Clonotype | V gene | J gene | Mutation rate$^2$ [%] | CDR3 sequence | Comment |
|---|---|---|---|---|---|
| **137** | **3-15** | **6** | **15** | **TADRGAPVLRFWEWGYFDYYMEF** | no complaints |
| **335** | **3-15** | **6** | **15** | **TADEGAPILRFFEWGYYNYYMDV** | no complaints |
| 293 | 3-9 | 4 | 11 | VKGATPSITIFGRVAPFDH | high abundance in FT |
| 289 | 1-69 | 2 | 9 | ARVERPGDSDWYFDL | CDR1 peptide only |
| 2413 | 4-16 | 4 | 4 | ARTAVAGTNYFDY | low confidence |
| 373 | 3-9 | 3 | 6 | TKDIVWRYSLSEGAFDL | low confidence |
| **195** | **3-15** | **6** | **21** | **TRDEGAPVTRFLEWGSYYYYMAV** | no complaints |
| 2284 | 3-7 | 3 | 7 | ARDGPATFRLLEYVFMSSFDM | rel. high abundance in FT |
| 2765 | 3-74 | 4 | 12 | ARGGSGIFRFPNY | low confidence |
| 92 | 3-9 | 3 | 10 | AKDTMGHCSSAFCFAFDF | no CDR3 peptide |

Figure 63B

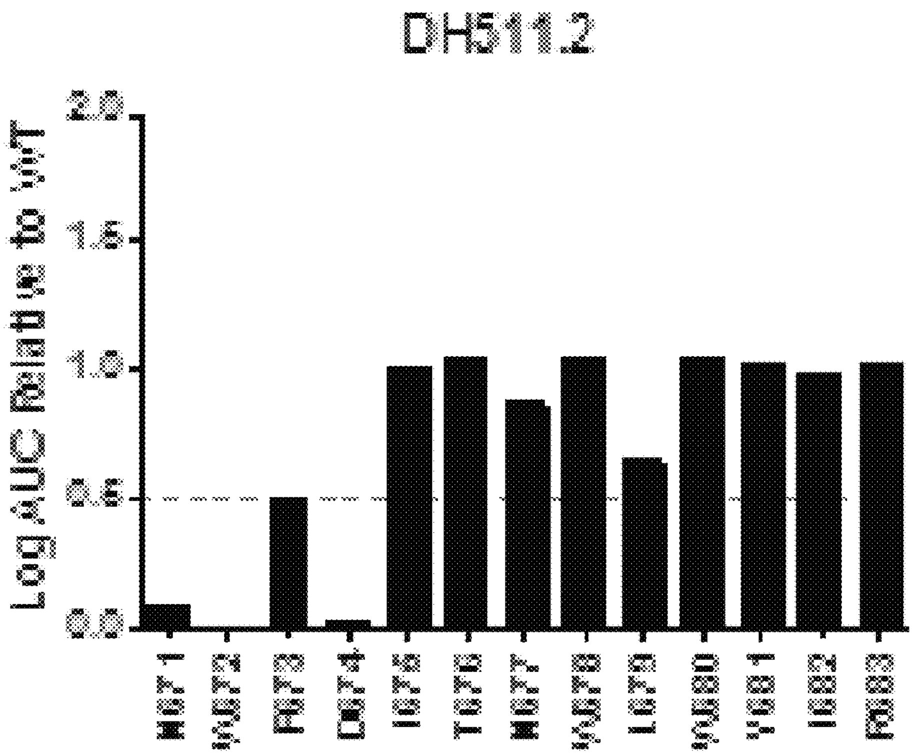
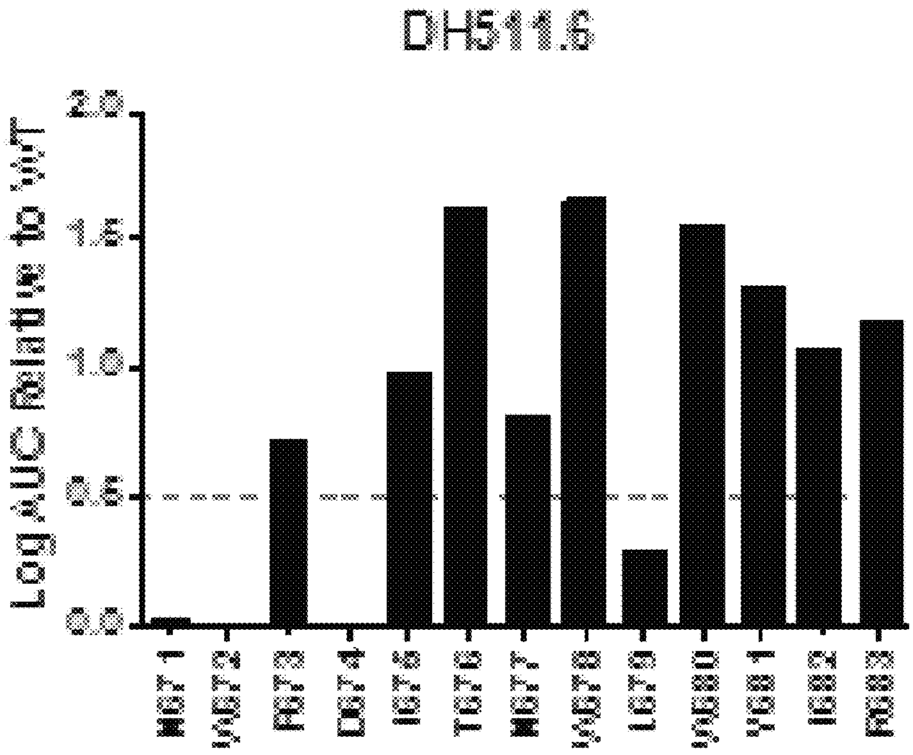
Figure 65A cont.

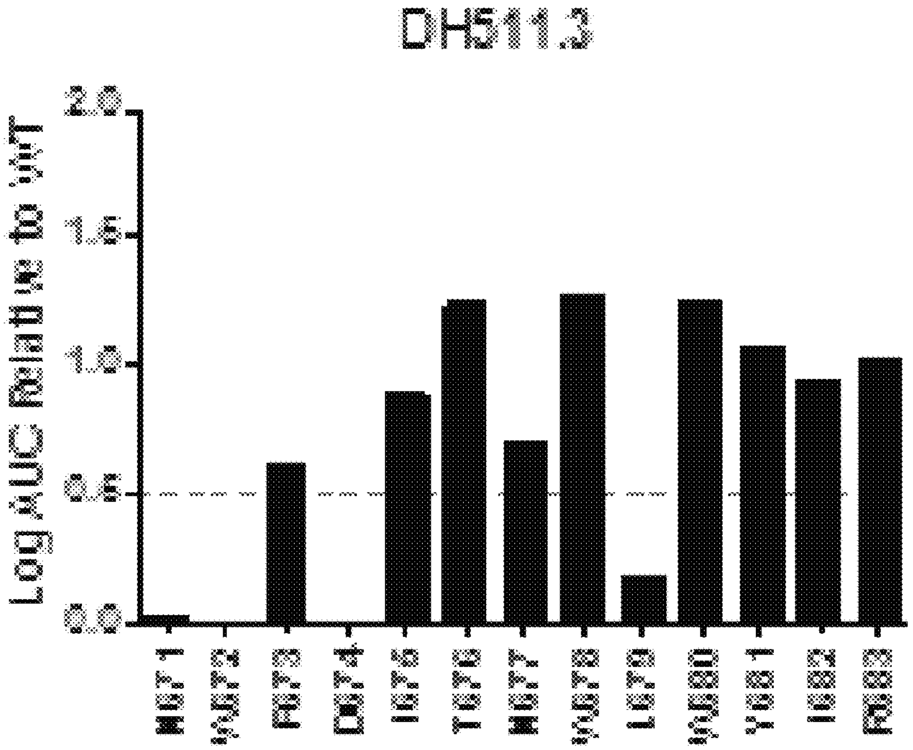
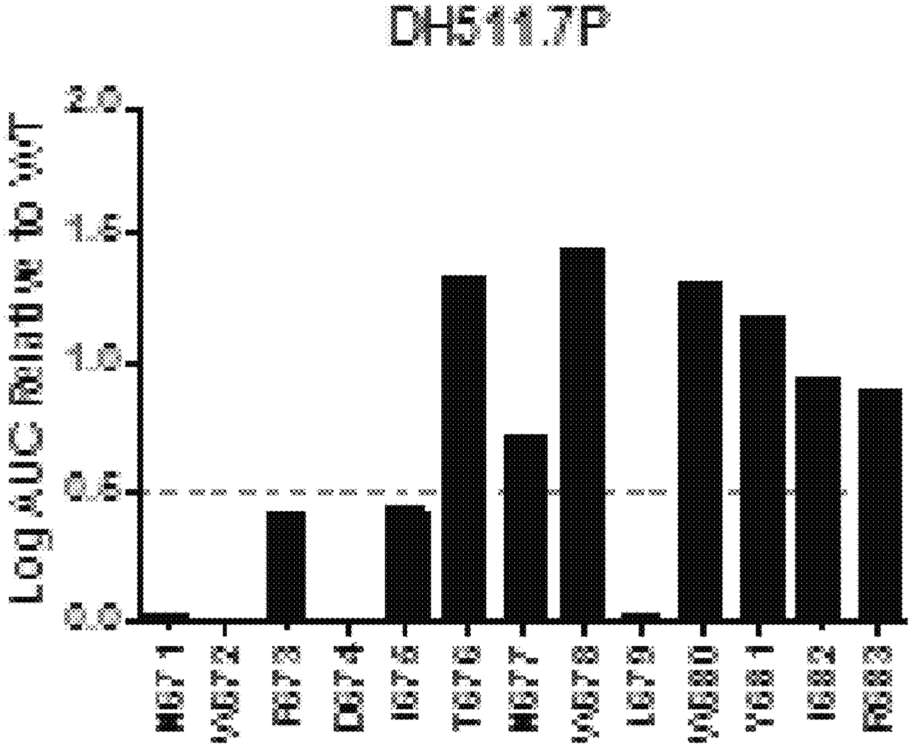
Figure 65A cont.

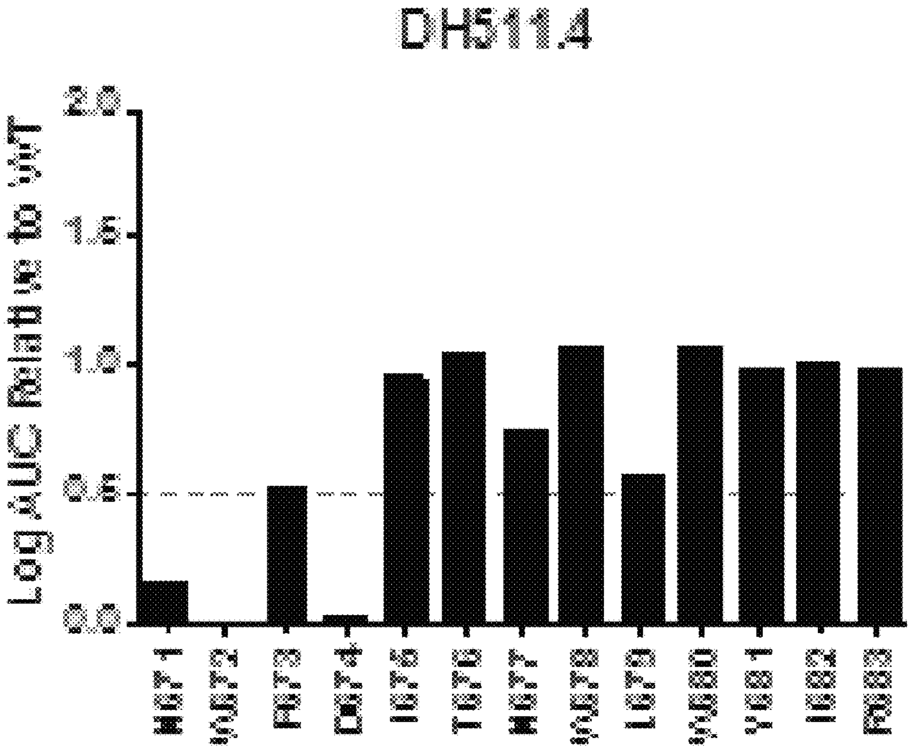
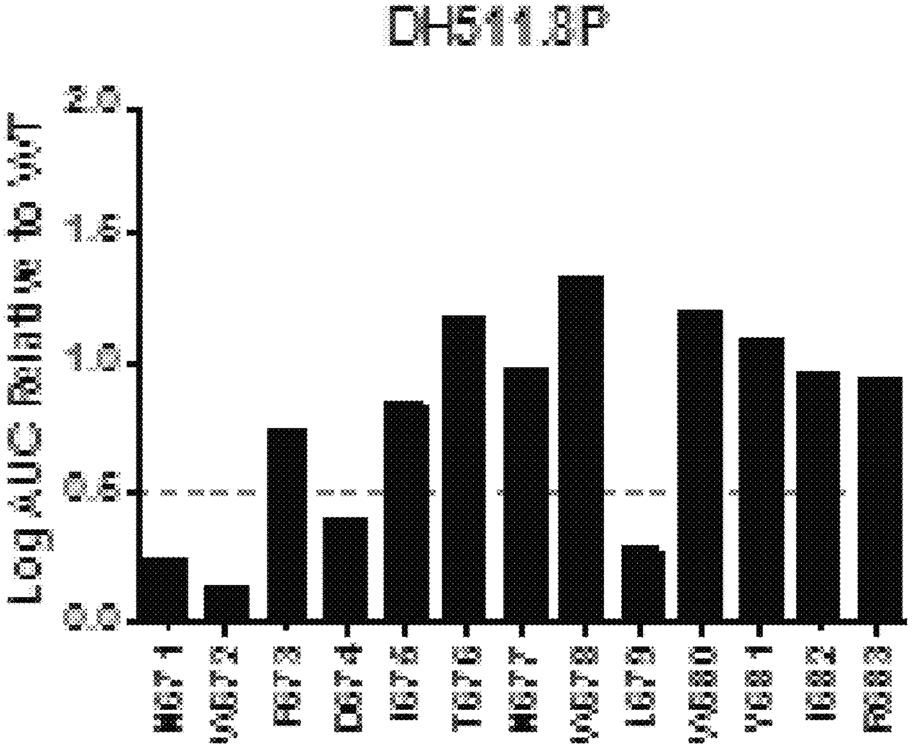
Figure 65A cont.

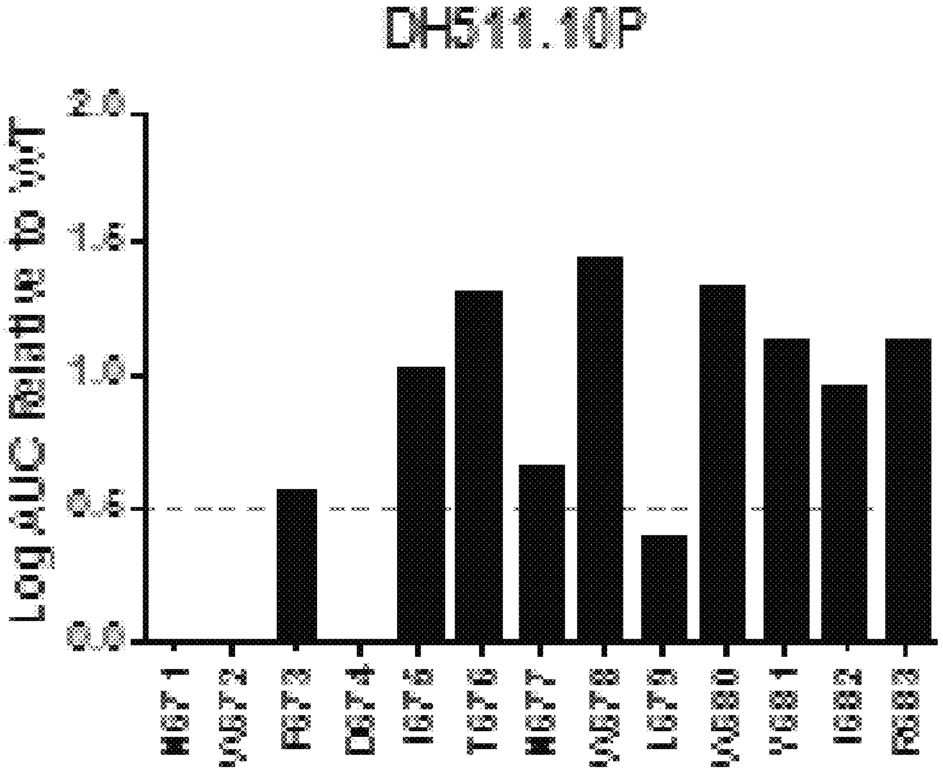
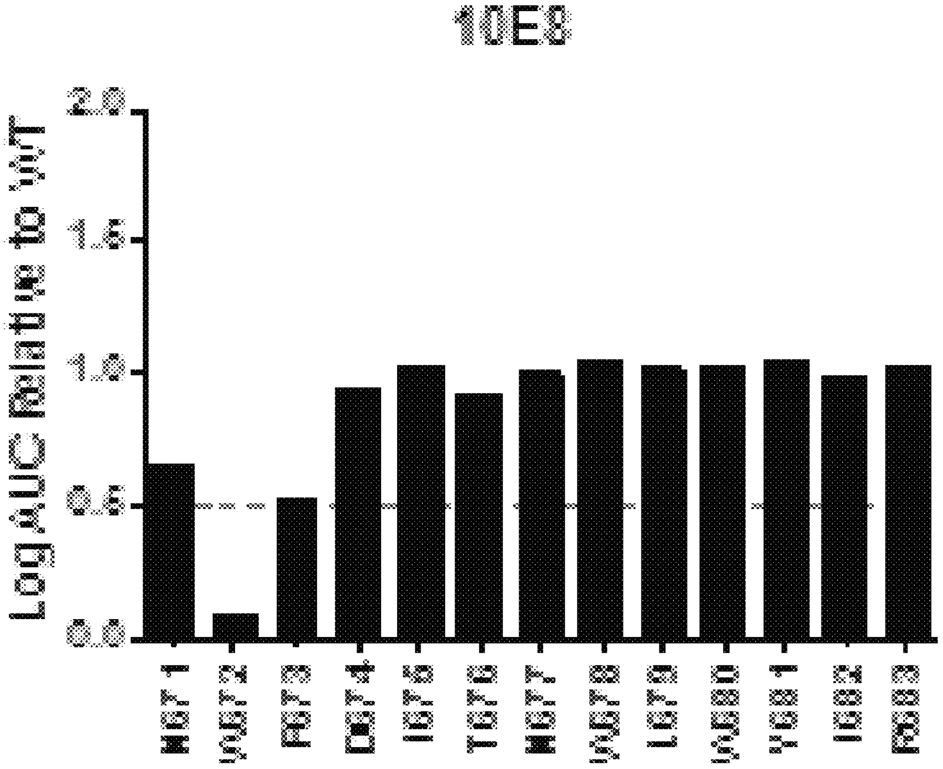
Figure 65B cont.

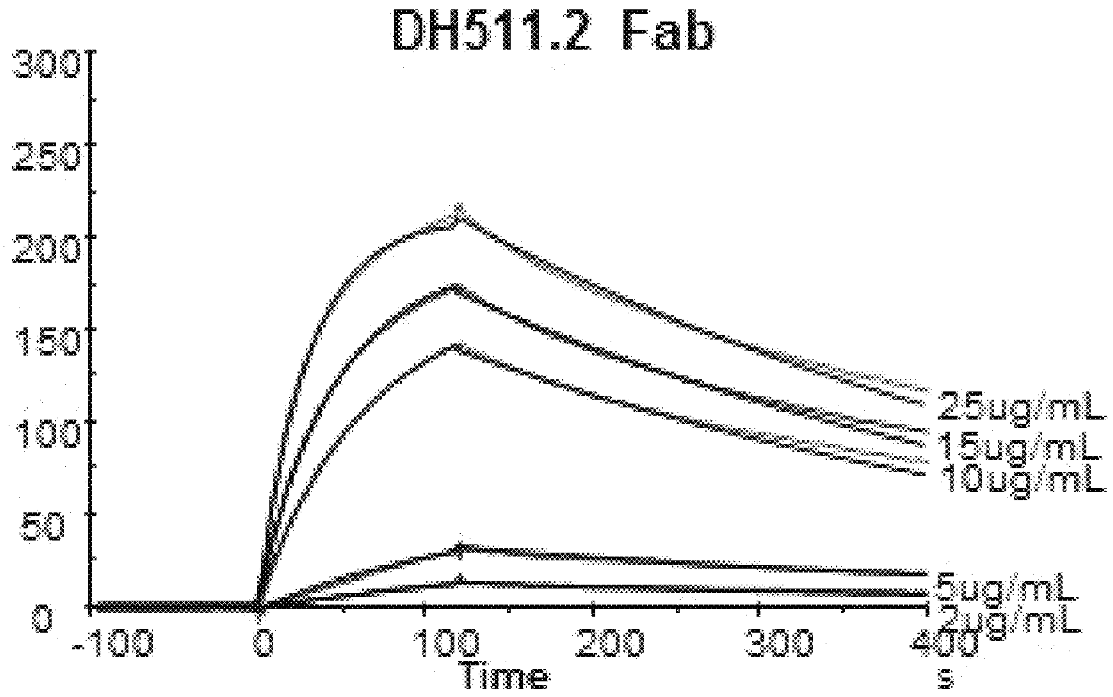
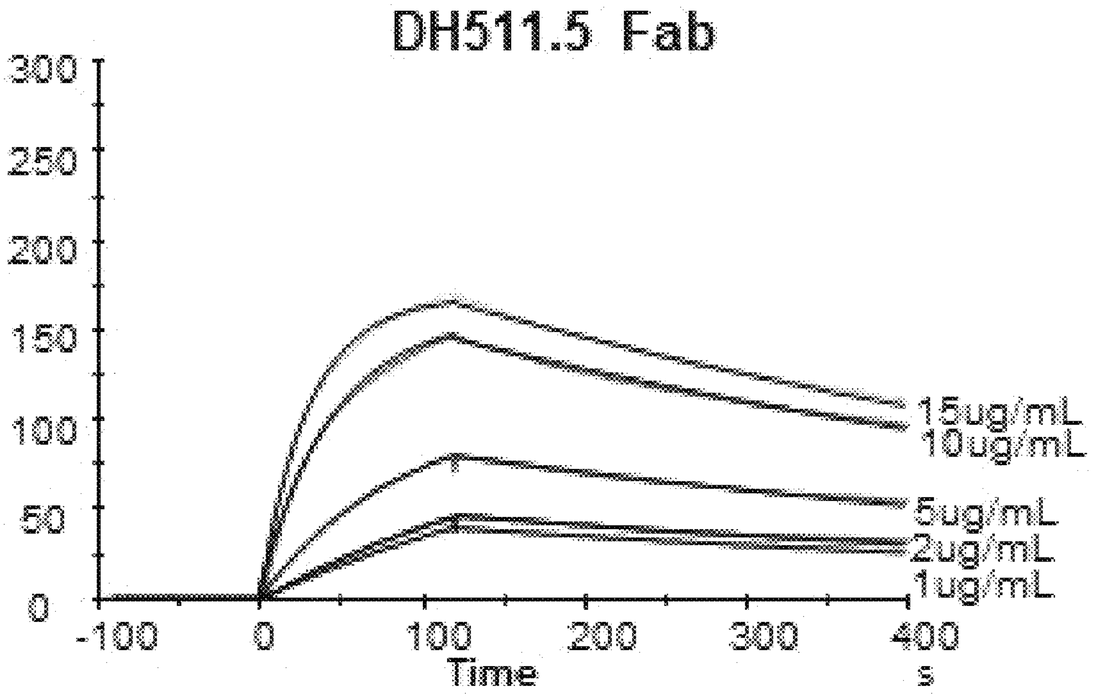
Figure 66A cont.

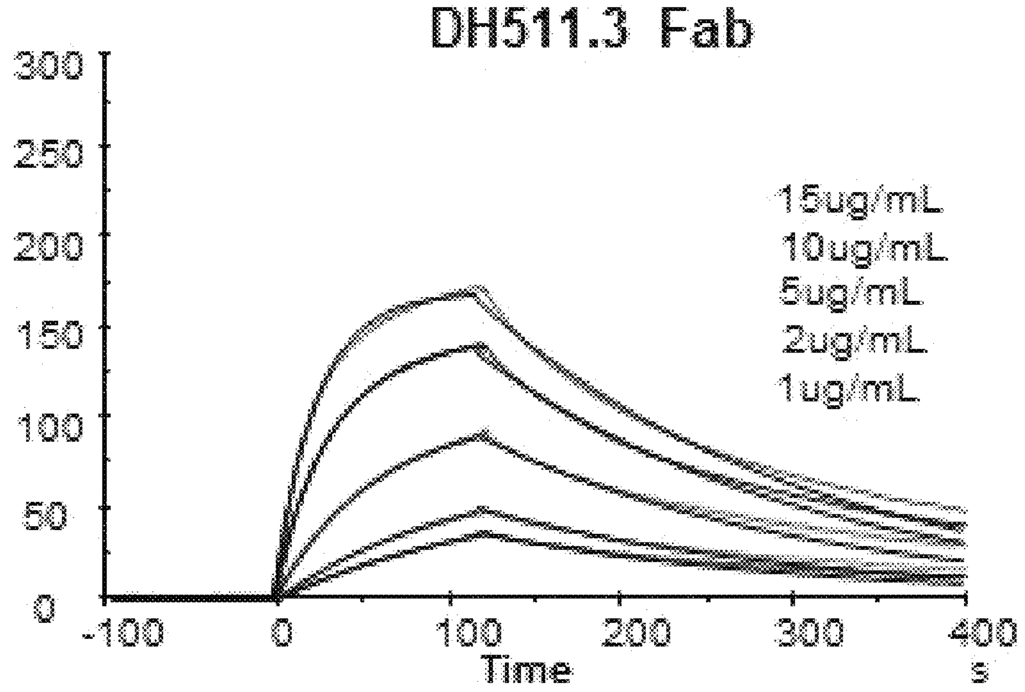
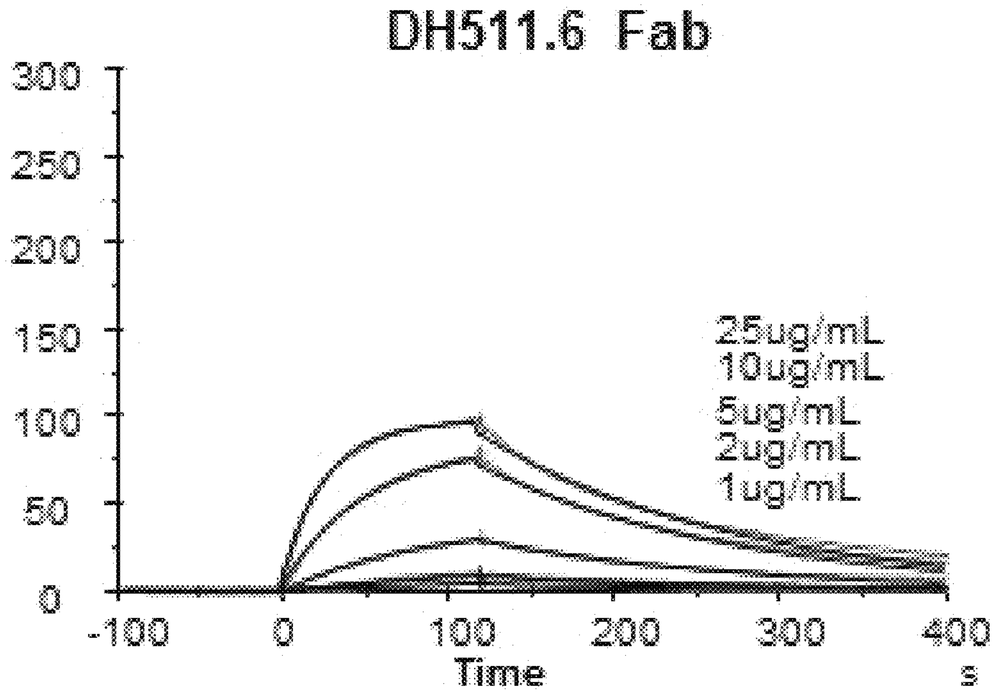
Figure 66A cont.

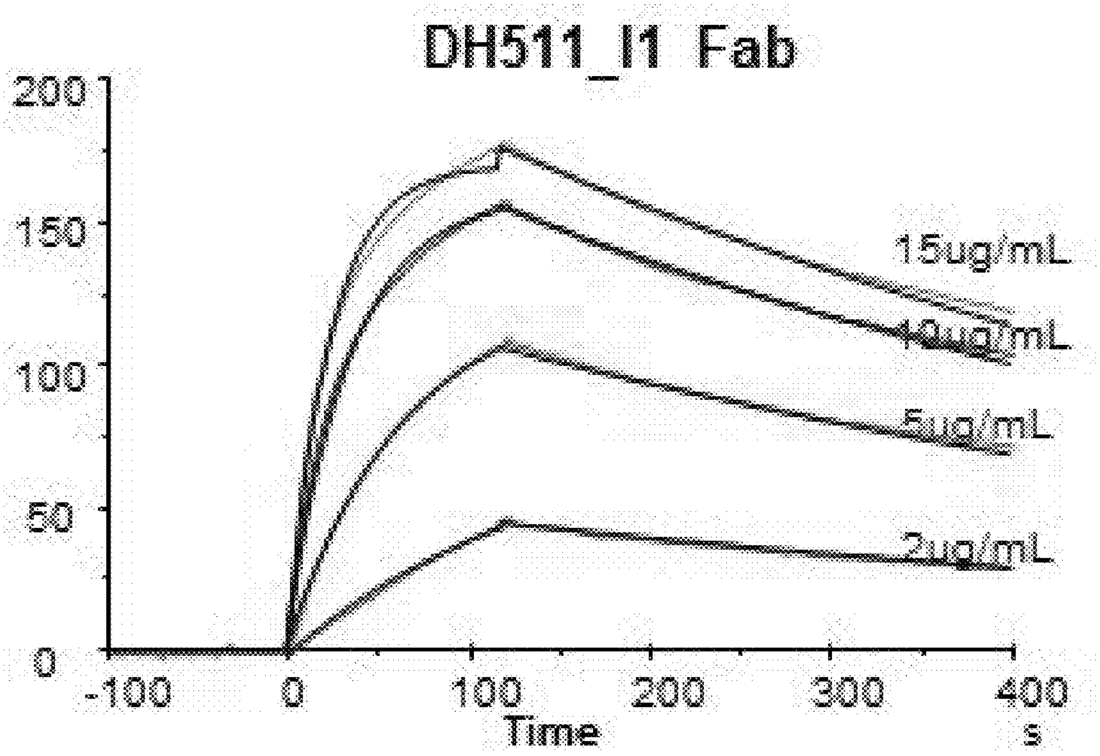
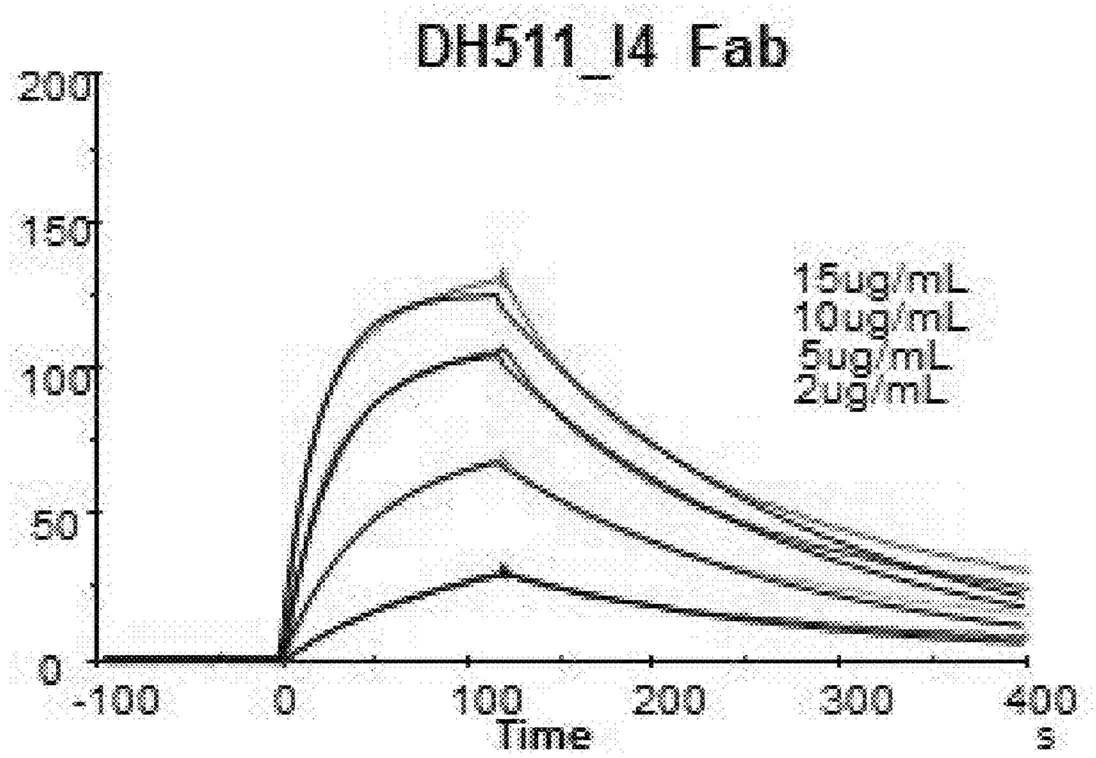
Figure 66B cont.

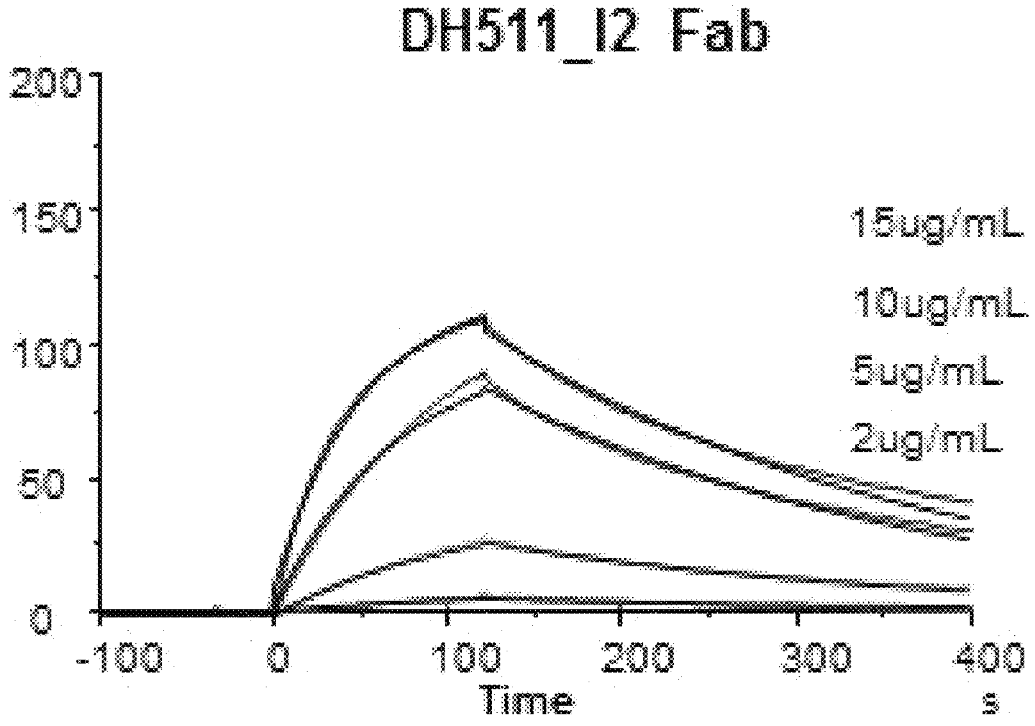
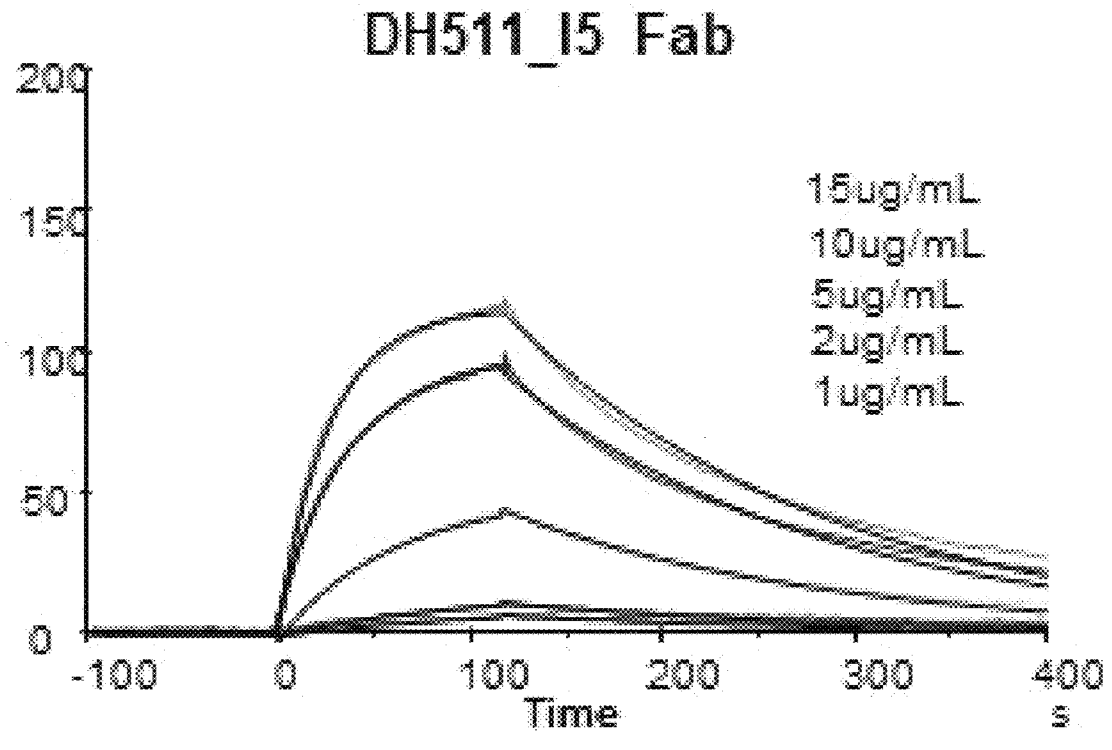
Figure 66B cont.

| Fab ID | ka ($Ms^{-1}$) x $10^4$ | kd ($s^{-1}$) x $10^{-4}$ | Kd (nM) |
|---|---|---|---|
| DH511.1 Fab | 10.4 | 35.8 | 34.4 |
| DH511.2 Fab | 6.35 | 23.6 | 37.2 |
| DH511.3 Fab | 11.9 | 52.8 | 44.4 |
| DH511.4 Fab | 10.2 | 21.1 | 20.6 |
| DH511.5 Fab | 10.5 | 15.2 | 14.5 |
| DH511.6 Fab | 6.4 | 64 | 99.9 |
| DH511_UCA Fab | | No binding | |
| DH511_I1 Fab | 13.9 | 15.5 | 11.1 |
| DH511_I2 Fab | 5.3 | 39.8 | 75.1 |
| DH511_I3 Fab | 12.6 | 57.4 | 45.6 |
| DH511_I4 Fab | 14.3 | 59.6 | 41.8 |
| DH511_I5 Fab | 10.5 | 61 | 58.1 |
| DH511_I6 Fab | | No binding | |

Figure 66C

| Peptide name | Sequence |
|---|---|
| MPER656-biotin | NEQELLELDKWASLWNWFNITNWLWYIK-GTH1 |
| MPER656.1-biotin | NEQDLLALDKWASLWNWFDISNWLWYIK-GTH1 |
| MPER656.2-biotin | NEKDLLALDSWKNLWNWFSITKWLWYIK-GTH1 |
| MPER656.3-biotin | NEQELLALDKWNNLWSWFDITNWLWYIR-GTH1 |
| CAP206 OmoB5 MPER656-biotin | NEKDLLALDSWKNLWNWFDITKWLWYIK-GTH1 |

Figure 67C

HCDR3 Sequence Alignment

```
         92                         104
         |                          |
10E8     CARTGK---YYDFWSGYPPEEYFQDWG
DH511    CTADLGEPVVSRFFEWGSYYYYMDLWG
DH512    CTMDEGTPV-TRFLEWGYFYYYMAVWG
```

Figure 73A-D

Heavy Chain Sequences
Mature Monoclonal Antibodies

| Donor | Antibody ID | IGHV | IGHD | IGHJ | CDR3 length (Amino Acids)[a] | CDR3 Sequence (Amino Acids) | Somatic Mutations (Nucleotides)[b] | Mutation Frequency (Nucleotides)[b] | Mutation Frequency (Amino Acids)[b] |
|---|---|---|---|---|---|---|---|---|---|
| CH0210 | DH511.1 | 3-15*01 | 3-3*01 | 6*04 | 24 | TADLGEPVVSRFFEWGSYYYYMDL | 46 | 15.7% | 17.7% |
| CH0210 | DH511.2 | 3-15*01 | 4-4*01 | 6*03 | 23 | TMDEGTPVTRFLEWGYFYYYMAV | 52 | 17.6% | 27.5% |
| CH0210 | DH511.3 | 3-15*01 | 3-3*01 | 6*03 | 24 | TADLGEAVVSRFFEWGSYYYYMDF | 47 | 16.0% | 18.7% |
| CH0210 | DH511.4 | 3-15*01 | 3-3*01 | 6*03 | 23 | TRDEGAPVTRFLEWGSYYYYMAV | 63 | 21.4% | 26.5% |
| CH0210 | DH511.5 | 3-15*01 | 3-3*01 | 6*03 | 23 | TRDEGAPVTRFLEWGSYYYYMAV | 64 | 21.8% | 29.5% |
| CH0210 | DH511.6 | 3-15*01 | 3-3*01 | 6*03 | 24 | TADLGEAVVSRFFEWGSYYYYMDF | 47 | 16.0% | 17.7% |
| CH0210 | DH517 | 4-34*01 | 3-16*01 | 6*01 | 24 | ARGTGVVVGGSWTVPPGMAYYLDV | 54 | 18.1% | |

Figure 75

Inferred UCA and Intermediate Antibodies

| Donor | Antibody ID | IGHV | IGHD | IGHJ | CDR3 length (Amino Acids)[a] | CDR3 Sequence (Amino Acids) | Somatic Mutations (Nucleotides)[b] | Mutation Frequency (Nucleotides)[b] | Mutation Frequency (Amino Acids)[b] |
|---|---|---|---|---|---|---|---|---|---|
| CH0210 | DH511_UCA | 3-15*01 | 3-3*01 | 6*03 | 24 | TTDLEGAPVLRFLEWGYYYYYMDV | 0 | 0.0% | 0.0% |
| CH0210 | DH511_I6 | 3-15*01 | 3-3*01 | 6*03 | 24 | TTDLEGAPVSRFLEWGYYYYYMDV | 12 | 4.1% | 6.9% |
| CH0210 | DH511_I5 | 3-15*01 | 3-3*01 | 6*03 | 24 | TADLGEAVVSRFFEWGSYYYYMDF | 45 | 15.3% | 16.7% |
| CH0210 | DH511_I4 | 3-15*01 | 3-3*01 | 6*03 | 24 | TADLGEAVVSRFFEWGSYYYYMDF | 46 | 15.6% | 17.7% |
| CH0210 | DH511_I3 | 3-15*01 | 3-3*01 | 6*03 | 24 | TADLGEAVVSRFFEWGSYYYYMDF | 46 | 15.6% | 17.7% |
| CH0210 | DH511_I2 | 3-15*01 | 3-3*01 | 6*03 | 23 | TTDEGAPVTRFLEWGYYYYYMAV | 18 | 6.1% | 13.8% |
| CH0210 | DH511_I1 | 3-15*01 | 3-3*01 | 6*03 | 23 | TRDEGAPVTRFLEWGSYYYYMAV | 50 | 17.0% | 23.6% |

Figure 75 cont.

Light Chain Sequences
Mature Monoclonal Antibodies

| Donor | Antibody ID | IGKV | IGKJ | CDR3 length (Amino Acids)[a] | CDR3 Sequence (Amino Acids) | Somatic Mutations (Nucleotides)[b] | Mutation Frequency (Nucleotides)[b] | Mutation Frequency (Amino Acids)[b] |
|---|---|---|---|---|---|---|---|---|
| CH0210 | DH511.1 | 1-39*01 | 2*01 | 11 | QEAYSSTPTLT | 43 | 16.3% | 17.6% |
| CH0210 | DH511.2 | 1-39*01 | 2*03 | 11 | QENYNTIPSLS | 37 | 14.0% | 20.7% |
| CH0210 | DH511.3 | 1-39*01 | 2*01 | 11 | QEAYSSTPTLT | 45 | 17.1% | 19.6% |
| CH0210 | DH511.4 | 1-39*01 | 2*01 | 11 | QEAYNTNPTLS | 42 | 15.9% | 21.7% |
| CH0210 | DH511.5 | 1-39*01 | 2*01 | 11 | QEAYNTYPTLS | 45 | 17.1% | 22.7% |
| CH0210 | DH511.6 | 1-39*01 | 2*03 | 11 | QEAYSSTPTLS | 45 | 17.6% | 21.7% |
| CH0210 | DH517 | 3-19*01 | 2*01 | 12 | ASRDRSGDRLGV | 35 | 13.4% | |

Figure 75 cont.

Inferred UCA and intermediate antibodies

| Donor | Antibody ID | IGKV | IGKJ | CDR3 length (Amino Acids)[a] | CDR3 Sequence (Amino Acids) | Somatic Mutations (Nucleotides)[b] | Mutation Frequency (Nucleotides)[b] | Mutation Frequency (Amino Acids)[b] |
|---|---|---|---|---|---|---|---|---|
| CH0210 | DH511_UCA | 1-39*01 | 2-1*01 | 11 | QQSYSTPPTCT | 0 | 0.0% | 1.1% |
| CH0210 | DH511_I6 | 1-39*01 | 2-1*01 | 11 | QETYSTTPTFT | 10 | 3.8% | 6.2% |
| CH0210 | DH511_I5 | 1-39*01 | 2-1*01 | 11 | QEAYSSTPTLT | 41 | 15.5% | 17.6% |
| CH0210 | DH511_I4 | 1-39*01 | 2-1*01 | 11 | QEAYSSTPTLT | 44 | 16.7% | 19.6% |
| CH0210 | DH511_I3 | 1-39*01 | 2-1*01 | 11 | QEAYSSTPTLT | 44 | 16.7% | 19.6% |
| CH0210 | DH511_I2 | 1-39*01 | 2-1*01 | 11 | QETYNTTPTLT | 19 | 7.2% | 12.4% |
| CH0210 | DH511_I1 | 1-39*01 | 2-1*01 | 11 | QEAYNTNPTLS | 37 | 14.0% | 18.6% |

[a]CDR3 length listed according to the IMGT definition.
[b]Somatic mutations were determined over the entire variable region and are reported as the number/frequency of nucleotides or amino acids that differed from the putative germ line V-gene sequences.

Figure 75 cont.

Key ($IC_{50}$ in µg/ml): <0.100 | 0.100-1.00 | 1.00-10.0 | >10.0

| | | $IC_{50}$ (µg/ml) | | | | | | | | |
|---|---|---|---|---|---|---|---|---|---|---|
| Virus | Clade | DH511.1 | DH511.2 | DH511.3 | DH511.4 | DH511.5 | DH511.6 | DH517 | VRC01 | 10E8 |
| KER2018.11 | A | 8.15 | 4.63 | 18.5 | 15.4 | 15.8 | 18.7 | >50 | 0.701 | 22.0 |
| Q23.17 | | 4.46 | 2.52 | 9.50 | 9.00 | 9.55 | 13.4 | >50 | 0.064 | 0.783 |
| Q769.h5 | | 0.029 | 0.014 | 0.075 | 1.40 | 0.037 | 0.008 | >50 | 0.005 | 2.67 |
| RW020.2 | | 2.77 | 1.30 | 8.92 | 6.18 | 4.73 | 7.17 | >50 | 0.109 | 1.36 |
| 6540.v4.c1 | AC | 4.41 | 1.46 | 10.3 | 7.83 | 14.7 | 12.5 | >50 | >50 | 3.01 |
| Q168.a2 | AD | 5.07 | 1.04 | 8.94 | 10.1 | 11.8 | 7.86 | >50 | 0.059 | 1.93 |
| C1080.c3 | AE | 0.029 | 0.017 | 0.040 | 0.239 | 0.091 | 0.032 | 0.406 | 0.195 | 0.008 |
| CNE59 | | 0.009 | 0.003 | 0.028 | 0.064 | 0.036 | 0.015 | 0.558 | 0.344 | 0.001 |
| TH966.8 | | 0.017 | 0.011 | 0.015 | 0.156 | 0.031 | 0.010 | 0.094 | 0.026 | 0.024 |
| DJ263.8 | AG | 0.027 | 0.066 | 0.140 | 0.732 | 0.218 | 0.318 | 0.070 | 0.068 | 0.015 |
| 6101.10 | B | 0.074 | 0.045 | 0.175 | 0.310 | 0.282 | 0.205 | 3.54 | 0.045 | 0.007 |
| Bal.01 | | 0.517 | 0.063 | 0.918 | 2.47 | 1.11 | 0.239 | 47.9 | 0.012 | 0.638 |
| BG1168.01 | | 0.283 | 0.219 | 0.705 | 1.32 | 1.07 | 0.609 | 5.54 | 0.218 | 0.405 |
| CAAN.A2 | | 4.52 | 3.15 | 9.30 | 11.3 | 9.89 | 14.8 | >50 | 1.59 | 1.14 |
| JRCSF.JB | | 1.59 | 0.674 | 3.98 | 5.09 | 2.79 | 2.50 | >50 | 0.097 | 0.523 |
| JRFL.JB | | 1.56 | 0.619 | 2.64 | 5.02 | 3.20 | 1.88 | 28.3 | 0.037 | 0.155 |
| PVO.04 | | 4.04 | 1.29 | 9.26 | 11.8 | 7.08 | 8.27 | >50 | 0.254 | 2.81 |
| THRO.18 | | 0.112 | 0.146 | 0.275 | 0.688 | 0.639 | 0.851 | 10.2 | 1.49 | 0.100 |
| TRJO.58 | | 6.25 | 2.80 | 8.96 | 6.52 | 7.50 | 8.53 | >50 | 0.078 | 0.980 |
| TRO.11 | | 0.442 | 0.235 | 1.12 | 0.921 | 0.932 | 0.941 | 7.82 | 0.409 | 0.023 |
| YU2.DG | | 2.75 | 1.30 | 6.36 | 5.33 | 4.08 | 3.67 | >50 | 0.024 | 2.23 |
| CNE58 | C | 2.68 | 0.682 | 5.83 | 4.60 | 3.74 | 8.16 | >50 | 0.171 | 0.501 |
| DU156.12 | | 0.134 | 0.035 | 0.206 | 0.167 | 0.396 | 0.327 | 5.70 | 0.053 | 0.004 |
| DU172.17 | | 0.457 | 2.71 | 6.92 | 4.63 | 2.24 | 9.07 | 15.4 | >50 | 0.026 |
| DU422.01 | | 0.909 | 0.565 | 2.83 | 1.84 | 2.10 | 3.57 | 18.1 | >50 | 0.189 |
| ZA012.29 | | 2.18 | 0.690 | 3.67 | 3.75 | 3.21 | 0.880 | >50 | 0.542 | 3.09 |
| ZM106.9 | | 10.1 | 3.35 | 20.8 | 14.5 | 16.8 | 16.3 | >50 | 0.173 | >25 |
| ZM55.28a | | 10.9 | 5.95 | 16.6 | 10.0 | 24.9 | 33.9 | >50 | 0.313 | 2.85 |
| 57128.vrc.15 | D | 0.156 | 0.051 | 0.333 | 0.898 | 1.18 | 0.274 | 0.945 | >50 | 0.611 |
| X1632.S2.B10 | G | 0.314 | 0.159 | 0.409 | 0.323 | 0.705 | 0.671 | 18.8 | 0.023 | 0.579 |
| AC10.29 | B | ND | ND | ND | ND | ND | ND | ND | 0.138 | 0.171 |
| AC10.29Δ332(S334A) | | ND | ND | ND | ND | ND | ND | ND | 0.562 | ND |
| 6644.V2.C33 | C | ND | ND | ND | ND | ND | ND | ND | 0.202 | 0.007 |

| | DH511.1 | DH511.2 | DH511.3 | DH511.4 | DH511.5 | DH511.6 | DH517 | VRC01 | 10E8 |
|---|---|---|---|---|---|---|---|---|---|
| # Viruses | 30 | 30 | 30 | 30 | 30 | 30 | 30 | 30 | 30 |
| **Total Viruses Neutralized** | | | | | | | | | |
| **IC50 <50ug/ml** | 30 | 30 | 30 | 30 | 30 | 30 | 15 | 26 | 29 |
| **IC50 <1ug/ml** | 15 | 18 | 12 | 10 | 10 | 14 | 5 | 24 | 19 |
| **IC50 <0.1ug/ml** | 6 | 9 | 4 | 1 | 4 | 4 | 2 | 13 | 8 |
| **Percent of Viruses Neutralized** | | | | | | | | | |
| **IC50 <50ug/ml** | 100 | 100 | 100 | 100 | 100 | 100 | 50 | 87 | 97 |
| **IC50 <1ug/ml** | 50 | 60 | 40 | 33 | 33 | 47 | 17 | 80 | 63 |
| **IC50 <0.1ug/ml** | 20 | 30 | 13 | 3 | 13 | 13 | 7 | 43 | 27 |
| **Median IC50** | 1.23 | 0.647 | 3.25 | 4.18 | 2.52 | 2.19 | 5.70 | 0.103 | 0.579 |
| **Geometric Mean** | 0.669 | 0.336 | 1.50 | 2.17 | 1.64 | 1.34 | 3.39 | 0.107 | 0.290 |

Figure 76

Key (IC80 in μg/ml)

| <0.100 | 0.100-1.00 | 1.00-10.0 | >10.0 |
|---|---|---|---|

| | | IC80 (μg/ml) | | | | | | | | |
|---|---|---|---|---|---|---|---|---|---|---|
| Virus | Clade | DH511.1 | DH511.2 | DH511.3 | DH511.4 | DH511.5 | DH511.6 | DH517 | VRC01 | 10E8 |
| KER2018.11 | A | 30.1 | 16.4 | 48.0 | 39.5 | >50 | >50 | >50 | 2.19 | 6.38 |
| Q23.17 | | 17.0 | 11.6 | 37.0 | 27.7 | 29.7 | 43.8 | >50 | 0.265 | 3.02 |
| Q769.h5 | | 3.01 | 0.697 | 8.02 | 13.5 | 23.8 | 49.5 | >50 | 0.046 | 6.62 |
| RW020.2 | | 16.1 | 7.75 | 34.2 | 18.3 | 25.7 | 43.5 | >50 | 0.689 | 4.10 |
| 6540.v4.c1 | AC | 32.7 | 24.5 | >50 | >50 | >50 | >50 | >50 | >50 | 7.86 |
| Q168.a2 | AD | 34.6 | 12.7 | >50 | >50 | >50 | >50 | >50 | 0.351 | 5.23 |
| C1080.c3 | AE | 0.543 | 0.333 | 1.06 | 1.97 | 1.34 | 0.776 | 13.6 | 2.91 | 0.683 |
| CNE59 | | 0.065 | 0.033 | 0.181 | 0.262 | 0.247 | 0.125 | 3.06 | 2.48 | 0.030 |
| TH966.8 | | 0.196 | 0.178 | 0.475 | 1.08 | 1.24 | 0.360 | >50 | 0.423 | 0.315 |
| DJ263.8 | AG | 0.297 | 0.697 | 2.16 | 4.93 | 5.01 | 5.91 | 10.5 | 0.434 | 0.176 |
| 6101.10 | B | 0.620 | 0.574 | 1.32 | 2.04 | 1.98 | 1.85 | 25.4 | 0.215 | 0.021 |
| Bal.01 | | 8.37 | 3.23 | 19.3 | 19.3 | 23.2 | 49.7 | >50 | 0.097 | 2.49 |
| BG1168.01 | | 2.40 | 1.94 | 5.46 | 6.79 | 7.86 | 6.83 | 28.7 | 1.64 | 1.52 |
| CAAN.A2 | | 27.3 | 18.2 | 49.4 | >50 | >50 | >50 | >50 | 5.62 | 5.97 |
| JRCSF.JB | | 13.7 | 5.99 | 28.1 | 24.7 | 19.1 | 30.0 | >50 | 0.660 | 2.38 |
| JRFL.JB | | 10.1 | 6.91 | 22.9 | 21.9 | 17.4 | 22.9 | >50 | 0.050 | 0.824 |
| PVO.04 | | 35.2 | 13.0 | >50 | >50 | >50 | >50 | >50 | 1.31 | 8.54 |
| THRO.18 | | 2.23 | 1.86 | 3.54 | 4.32 | 8.87 | 18.1 | >50 | 27.0 | 0.715 |
| TRJO.58 | | 21.5 | 11.1 | 20.6 | 28.5 | 33.9 | 45.2 | >50 | 0.293 | 4.33 |
| TRO.11 | | 2.17 | 1.27 | 4.68 | 3.92 | 3.69 | 4.28 | 30.3 | 1.67 | 0.398 |
| YU2.DG | | 28.6 | 18.2 | >50 | >50 | >50 | >50 | >50 | 0.179 | 9.46 |
| CNE58 | C | 11.3 | 4.25 | 29.5 | 22.1 | 21.2 | 46.9 | >50 | 0.556 | 2.52 |
| DU156.12 | | 0.828 | 0.309 | 1.37 | 0.928 | 1.66 | 1.75 | 31.3 | 0.248 | 0.061 |
| DU172.17 | | 4.09 | 11.6 | 19.3 | 15.6 | 17.8 | >50 | >50 | >50 | 0.300 |
| DU422.01 | | 5.67 | 2.93 | 10.6 | 7.58 | 8.28 | 13.0 | >50 | >50 | 1.10 |
| ZA012.29 | | 13.3 | 6.70 | 28.9 | 18.5 | 28.2 | >50 | >50 | 2.86 | 6.43 |
| ZM106.9 | | 43.1 | 24.0 | >50 | >50 | >50 | >50 | >50 | 0.979 | >25 |
| ZM55.28a | | 28.8 | 12.0 | >50 | >50 | >50 | >50 | >50 | 1.37 | 11.8 |
| 57128.vrc.15 | D | 7.32 | 2.23 | 9.06 | 8.04 | 9.76 | 8.71 | >50 | >50 | 2.46 |
| X1632.S2.B10 | G | 3.54 | 1.82 | 6.60 | 4.68 | 7.00 | 9.37 | >50 | 0.344 | 2.35 |
| AC10.29 | B | ND | ND | ND | ND | ND | ND | ND | 4.40 | 0.947 |
| AC10.29Δ332(S334A) | | ND | ND | ND | ND | ND | ND | ND | 5.75 | ND |
| 6644.V2.C33 | C | ND | ND | ND | ND | ND | ND | ND | 1.31 | 0.115 |

| | DH511.1 | DH511.2 | DH511.3 | DH511.4 | DH511.5 | DH511.6 | DH517 | VRC01 | 10E8 |
|---|---|---|---|---|---|---|---|---|---|
| # Viruses | 30 | 30 | 30 | 30 | 30 | 30 | 30 | 30 | 30 |
| Total Viruses Neutralized | | | | | | | | | |
| IC50 <50ug/ml | 30 | 30 | 24 | 23 | 22 | 20 | 7 | 26 | 29 |
| IC50 <1ug/ml | 6 | 7 | 2 | 2 | 1 | 3 | 0 | 16 | 10 |
| IC50 <0.1ug/ml | 1 | 1 | 0 | 0 | 0 | 0 | 0 | 3 | 3 |
| Percent of Viruses Neutralized | | | | | | | | | |
| IC50 <50ug/ml | 100 | 100 | 80 | 77 | 73 | 67 | 23 | 87 | 97 |
| IC50 <1ug/ml | 20 | 23 | 7 | 7 | 3 | 10 | 0 | 53 | 33 |
| IC50 <0.1ug/ml | 3 | 3 | 0 | 0 | 0 | 0 | 0 | 10 | 10 |
| Median IC50 | 9.24 | 5.12 | 9.83 | 8.04 | 9.32 | 9.74 | 20.3 | 0.608 | 2.460 |
| Geometric Mean | 5.64 | 3.24 | 7.73 | 7.36 | 7.86 | 8.09 | 15.4 | 0.670 | 1.444 |

Figure 77

Key ($IC_{50}$/$IC_{80}$ in μg/ml)

| <0.100 | 0.100-1.00 | 1.00-10.0 | >10.0 |
|---|---|---|---|

| | | $IC_{50}$ (μg/ml) | | | $IC_{80}$ (μg/ml) | | |
|---|---|---|---|---|---|---|---|
| Virus | Clade | DH511.2 | 10E8 | VRC01 | DH511.2 | 10E8 | VRC01 |
| 0260.v5.c36 | A | 17.8 | 9.87 | 0.502 | >50 | 21.7 | 1.24 |
| 0330.v4.c3 | A | 1.42 | 1.12 | 0.056 | 7.37 | 3.64 | 0.184 |
| 0439.v5.c1 | A | 2.36 | 1.23 | 0.113 | 9.57 | 3.95 | 0.369 |
| 3365.v2.c20 | A | 2.29 | 1.60 | 0.054 | 7.89 | 4.56 | 0.129 |
| 3415.v1.c1 | A | 12.8 | 4.69 | 0.081 | 22.1 | 11.5 | 0.238 |
| 3718.v3.c11 | A | 3.80 | 0.838 | 0.572 | 13.5 | 4.42 | >50 |
| 398-F1_F6_20 | A | 2.49 | 0.704 | 0.134 | 18.0 | 6.17 | 0.493 |
| BB201.B42 | A | 2.82 | 0.613 | 0.338 | 9.87 | 1.96 | 0.926 |
| BG505.W6M.C2 | A | 1.33 | 0.689 | 0.049 | 5.60 | 2.14 | 0.164 |
| BI369.9A | A | 1.61 | 0.356 | 0.220 | 4.93 | 1.29 | 0.769 |
| BS208.B1 | A | 0.803 | 0.319 | 0.030 | 3.35 | 3.27 | 0.080 |
| KER2008.12 | A | 0.723 | >50 | 0.485 | 4.29 | >50 | 1.58 |
| KER2018.11 | A | 4.31 | 1.89 | 0.674 | 17.0 | 7.16 | 1.73 |
| KNH1209.18 | A | 0.410 | 0.406 | 0.068 | 2.25 | 2.39 | 0.213 |
| MB201.A1 | A | 0.844 | 0.411 | 0.170 | 4.22 | 1.36 | 0.496 |
| MB539.2B7 | A | >50 | >50 | 0.326 | >50 | >50 | 0.890 |
| MI369.A5 | A | 0.510 | 0.671 | 0.228 | 3.41 | 1.77 | 0.742 |
| MS208.A1 | A | 0.927 | 0.187 | 0.195 | 3.56 | 1.14 | 0.661 |
| Q23.17 | A | 1.18 | 0.461 | 0.056 | 5.85 | 1.60 | 0.166 |
| Q259.17 | A | 12.4 | 4.76 | 0.060 | 30.7 | 12.0 | 0.182 |
| Q769.d22 | A | 2.44 | 1.91 | 0.033 | 8.64 | 4.47 | 0.102 |
| Q769.h5 | A | 5.73 | 2.89 | 0.055 | 16.7 | 7.44 | 0.149 |
| Q842.d12 | A | 5.73 | 2.82 | 0.025 | 12.8 | 7.58 | 0.082 |
| QH209.14M.A2 | A | 2.20 | 1.30 | 0.033 | 10.0 | 4.09 | 0.093 |
| RW020.2 | A | 3.46 | 0.902 | 0.366 | 10.8 | 2.92 | 0.947 |
| UG037.8 | A | 0.273 | 0.048 | 0.087 | 1.33 | 0.353 | 0.282 |
| 246-F3.C10.2 | AC | 0.802 | 0.210 | 0.215 | 5.10 | 1.49 | 0.760 |
| 3301.V1.C24 | AC | 12.5 | 2.97 | 0.087 | 33.8 | 9.50 | 0.234 |
| 3589.V1.C4 | AC | 3.26 | 5.77 | 0.079 | 10.2 | 11.7 | 0.222 |
| 6540.v4.c1 | AC | 2.84 | 2.24 | >50 | 13.4 | 7.01 | >50 |
| 6545.V4.C1 | AC | 7.79 | 2.54 | >50 | 15.4 | 7.50 | >50 |
| 0815.V3.C3 | ACD | 2.04 | 0.491 | 0.023 | 7.05 | 1.81 | 0.072 |
| 6095.V1.C10 | ACD | 0.0003 | 0.0005 | 0.674 | 0.0010 | 0.004 | 2.42 |
| 3468.V1.C12 | AD | 2.00 | 0.381 | 0.040 | 7.45 | 2.04 | 0.135 |
| Q168.a2 | AD | 1.45 | 0.463 | 0.064 | 5.18 | 2.88 | 0.193 |
| Q461.e2 | AD | 2.45 | 2.29 | 0.398 | 8.68 | 4.68 | 1.14 |
| 620345.c1 | AE | 1.77 | 0.989 | >50 | 9.05 | 3.73 | >50 |
| BJOX009000.02.4 | AE | 0.580 | 0.251 | 2.27 | 5.03 | 1.47 | 5.95 |
| BJOX010000.06.2 | AE | 0.178 | 0.060 | 8.13 | 1.23 | 0.476 | 23.3 |
| BJOX025000.01.1 | AE | 0.751 | 0.228 | 7.50 | 4.77 | 1.54 | 18.6 |
| BJOX028000.10.3 | AE | 0.853 | 0.167 | 0.181 | 4.59 | 0.876 | 0.811 |
| C1080.c3 | AE | 0.521 | 0.108 | 3.26 | 2.50 | 0.613 | 10.8 |
| C2101.c1 | AE | 4.64 | 1.20 | 0.243 | 15.6 | 4.12 | 0.678 |
| C3347.c11 | AE | 0.048 | 0.019 | 0.119 | 0.274 | 0.089 | 0.333 |
| C4118.09 | AE | 1.66 | 0.421 | 0.149 | 11.6 | 2.30 | 0.633 |
| CM244.ec1 | AE | | 0.365 | | | 1.46 | |
| CNE3 | AE | 2.81 | 1.37 | 1.37 | 9.17 | 4.01 | 8.70 |
| CNE5 | AE | 1.54 | 1.17 | 0.233 | 7.34 | 2.52 | 0.890 |
| CNE55 | AE | 0.287 | 0.038 | 0.264 | 2.00 | 0.605 | 0.902 |
| CNE56 | AE | 0.212 | 0.060 | 0.295 | 1.18 | 0.314 | 1.25 |

Figure 78

Key ($IC_{50}$/$IC_{80}$ in μg/ml)

| <0.100 | 0.100-1.00 | 1.00-10.0 | >10.0 |
|---|---|---|---|

| | | $IC_{50}$ (μg/ml) | | | $IC_{80}$ (μg/ml) | | |
|---|---|---|---|---|---|---|---|
| Virus | Clade | DH511.2 | 10E8 | VRC01 | DH511.2 | 10E8 | VRC01 |
| CNE59 | AE | 0.0003 | 0.0010 | 0.498 | 0.023 | 0.010 | 1.71 |
| CNE8 | AE | 0.045 | 0.140 | 0.414 | 0.483 | 1.42 | 1.27 |
| R1166.c1 | AE | 0.742 | 0.488 | 1.93 | 3.70 | 2.02 | 6.61 |
| R2184.c4 | AE | 1.12 | 0.576 | 0.098 | 5.40 | 2.20 | 0.311 |
| R3265.c6 | AE | 6.31 | 1.58 | 0.443 | 21.9 | 9.28 | 1.61 |
| TH966.8 | AE | 0.081 | 0.039 | 0.482 | 0.611 | 0.291 | 1.39 |
| TH976.17 | AE | 0.762 | 0.392 | 0.360 | 4.08 | 1.75 | 1.11 |
| 235-47 | AG | 0.361 | 0.244 | 0.042 | 1.61 | 0.786 | 0.122 |
| 242-14 | AG | 0.068 | 0.568 | >50 | 0.750 | 3.17 | >50 |
| 263-8 | AG | 0.407 | 0.229 | 0.108 | 2.63 | 0.991 | 0.415 |
| 269-12 | AG | 0.420 | 0.124 | 0.211 | 2.10 | 0.475 | 0.537 |
| 271-11 | AG | 1.23 | 0.891 | 0.042 | 7.60 | 4.34 | 0.147 |
| 928-28 | AG | 0.215 | 0.079 | 0.353 | 1.28 | 0.365 | 1.08 |
| DJ263.8 | AG | 0.190 | 0.009 | 0.057 | 0.903 | 0.100 | 0.305 |
| T250-4 | AG | 3.54 | 1.07 | >50 | 13.1 | 3.45 | >50 |
| T251-18 | AG | 7.52 | 0.666 | 5.67 | 20.5 | 2.55 | 12.7 |
| T253-11 | AG | 3.51 | 1.21 | 0.403 | 12.0 | 4.05 | 0.994 |
| T255-34 | AG | 1.40 | 0.228 | 0.773 | 6.11 | 1.14 | 2.54 |
| T257-31 | AG | 3.42 | 0.336 | 2.23 | 10.5 | 1.58 | 6.43 |
| T266-60 | AG | 0.953 | >50 | 3.39 | 4.78 | >50 | 11.9 |
| T278-50 | AG | 1.89 | 0.357 | >50 | 8.95 | 2.10 | >50 |
| T280-5 | AG | 4.21 | | 0.029 | 17.0 | | 0.080 |
| T33-7 | AG | 2.34 | 0.818 | 0.016 | 10.2 | 2.83 | 0.057 |
| 3988.25 | B | 0.284 | 0.070 | 0.475 | 0.883 | 0.293 | 1.25 |
| 5768.04 | B | 5.70 | 1.63 | 0.323 | 16.0 | 5.26 | 0.824 |
| 6101.10 | B | 0.012 | 0.0010 | 0.055 | 0.137 | 0.005 | 0.153 |
| 6535.3 | B | 1.39 | 0.190 | 1.78 | 7.62 | 1.28 | 4.60 |
| 7165.18 | B | 0.805 | 0.659 | 16.1 | 3.55 | 2.71 | >50 |
| 45_01dG5 | B | 0.753 | 0.106 | 0.013 | 4.87 | 0.703 | 0.030 |
| 89.6.DG | B | 0.676 | 0.318 | 0.975 | 2.23 | 1.48 | 3.29 |
| AC10.29 | B | 0.115 | 0.102 | 0.973 | 0.604 | 0.512 | 2.98 |
| ADA.DG | B | 0.042 | 0.055 | 0.322 | 0.482 | 0.358 | 1.29 |
| Bal.01 | B | 0.620 | 0.421 | 0.067 | 4.09 | 1.91 | 0.259 |
| BaL.26 | B | 2.57 | 0.518 | 0.081 | 11.0 | 2.39 | 0.203 |
| BG1168.01 | B | 0.528 | 0.396 | 0.977 | 2.38 | 1.48 | 3.45 |
| BL01.DG | B | 1.08 | 0.362 | >50 | 6.87 | 1.57 | >50 |
| BR07.DG | B | 0.106 | 0.118 | 1.36 | 1.03 | 0.445 | 5.14 |
| BX08.16 | B | 0.565 | 0.213 | 0.429 | 3.02 | 1.30 | 1.03 |
| CAAN.A2 | B | 5.29 | 1.45 | 1.29 | 16.3 | 5.70 | 3.48 |
| CNE10 | B | 0.121 | 0.014 | 0.782 | 0.932 | 0.189 | 1.99 |
| CNE12 | B | 0.509 | 0.301 | 0.553 | 2.46 | 1.09 | 1.93 |
| CNE14 | B | 0.950 | 0.151 | 0.218 | 4.24 | 0.649 | 0.742 |
| CNE4 | B | 0.279 | 0.058 | 0.600 | 2.45 | 0.437 | 2.43 |
| CNE57 | B | 0.120 | 0.059 | 0.507 | 1.28 | 0.317 | 1.43 |
| HO86.8 | B | 2.55 | 0.326 | >50 | 10.7 | 1.52 | >50 |
| HT593.1 | B | 0.140 | 0.049 | 0.647 | 0.780 | 0.285 | 2.04 |
| HXB2.DG | B | 0.0003 | 0.003 | 0.039 | 0.012 | 0.015 | 0.116 |
| JRCSF.JB | B | 2.04 | 0.429 | 0.254 | 9.61 | 1.89 | 0.840 |
| JRFL.JB | B | 0.862 | 0.174 | 0.024 | 5.40 | 0.768 | 0.068 |
| MN.3 | B | 0.0003 | 0.0003 | 0.016 | 0.004 | 0.0010 | 0.037 |

Figure 78 cont.

Key ($IC_{50}$/$IC_{80}$ in µg/ml)

| <0.100 | 0.100-1.00 | 1.00-10.0 | >10.0 |
|---|---|---|---|

| | | $IC_{50}$ (µg/ml) | | | $IC_{80}$ (µg/ml) | | |
|---|---|---|---|---|---|---|---|
| Virus | Clade | DH511.2 | 10E8 | VRC01 | DH511.2 | 10E8 | VRC01 |
| PVO.04 | B | 2.32 | 1.60 | 0.395 | 15.9 | 6.43 | 1.03 |
| QH0515.01 | B | 4.97 | 2.25 | 1.17 | 15.6 | 5.54 | 3.58 |
| QH0692.42 | B | 2.03 | 0.531 | 1.77 | 11.1 | 2.35 | 4.92 |
| REJO.67 | B | 0.544 | 0.302 | 0.078 | 3.31 | 1.18 | 0.203 |
| RHPA.7 | B | 5.45 | 1.01 | 0.040 | 25.9 | 5.10 | 0.132 |
| SC422.8 | B | 1.63 | 0.343 | 0.197 | 4.60 | 1.15 | 0.501 |
| SF162.LS | B | 1.88 | 0.245 | 0.367 | 7.75 | 1.06 | 0.875 |
| SS1196.01 | B | 0.857 | 0.244 | 0.408 | 4.72 | 1.25 | 1.08 |
| THRO.18 | B | 0.711 | 0.092 | 6.24 | 2.39 | 0.587 | 23.2 |
| TRJO.58 | B | 3.86 | 1.13 | 0.111 | 17.7 | 4.18 | 0.292 |
| TRO.11 | B | 0.228 | 0.028 | 0.541 | 1.22 | 0.286 | 1.54 |
| WITO.33 | B | 0.314 | 0.031 | 0.125 | 1.60 | 0.305 | 0.372 |
| X2278.C2.B1 | B | 3.79 | 0.442 | 0.116 | 14.1 | 2.24 | 0.320 |
| YU2.DG | B | 8.00 | 1.17 | 0.087 | 50 | 5.46 | 0.238 |
| BJOX002000.03.2 | BC | 1.17 | 0.384 | >50 | 5.64 | 1.56 | >50 |
| CH038.12 | BC | 1.57 | 0.271 | 0.378 | 6.10 | 1.41 | 0.939 |
| CH070.1 | BC | 12.1 | 6.65 | 8.57 | 44.6 | 13.5 | >50 |
| CH117.4 | BC | 0.458 | 0.270 | 0.062 | 2.29 | 0.859 | 0.194 |
| CH119.10 | BC | 0.916 | 0.591 | 0.577 | 5.48 | 2.36 | 1.84 |
| CH181.12 | BC | 0.959 | 0.754 | 0.407 | 3.99 | 2.79 | 1.21 |
| CNE15 | BC | 1.27 | 0.844 | 0.078 | 6.77 | 2.97 | 0.282 |
| CNE19 | BC | 0.363 | 0.251 | 0.141 | 3.05 | 1.11 | 0.577 |
| CNE20 | BC | 0.378 | 0.131 | 7.20 | 2.43 | 0.732 | >50 |
| CNE21 | BC | 1.09 | 0.979 | 0.232 | 8.40 | 3.25 | 0.882 |
| CNE40 | BC | 0.0003 | 0.0010 | 0.301 | 0.030 | 0.009 | 3.54 |
| CNE7 | BC | 0.119 | 0.130 | 0.183 | 0.672 | 0.603 | 0.837 |
| 286.36 | C | 3.22 | 1.19 | 0.325 | 14.0 | 5.00 | 0.748 |
| 288.38 | C | 2.19 | 0.435 | 1.31 | 8.90 | 3.08 | 4.05 |
| 0013095-2.11 | C | 0.014 | 0.009 | 0.111 | 0.229 | 0.077 | 0.316 |
| 001428-2.42 | C | 3.33 | 1.71 | 0.010 | 16.3 | 6.28 | 0.038 |
| 0077_V1.C16 | C | 5.56 | 1.86 | 0.655 | 36.0 | 7.11 | 2.37 |
| 00836-2.5 | C | 1.89 | 0.666 | 0.126 | 5.40 | 1.77 | 0.639 |
| 0921.V2.C14 | C | 5.33 | 0.908 | 0.220 | 18.4 | 3.03 | 0.727 |
| 16055-2.3 | C | 2.16 | 1.10 | 0.094 | 9.40 | 3.31 | 0.244 |
| 16845-2.22 | C | 0.018 | 0.020 | 4.69 | 0.238 | 0.172 | 17.7 |
| 16936-2.21 | C | 0.312 | 0.264 | 0.179 | 1.99 | 1.31 | 0.474 |
| 25710-2.43 | C | 0.046 | 0.064 | 0.577 | 0.408 | 0.304 | 1.83 |
| 25711-2.4 | C | 6.14 | 0.516 | 0.496 | 12.6 | 1.69 | 1.59 |
| 25925-2.22 | C | 0.504 | 0.402 | 0.469 | 2.95 | 1.53 | 1.32 |
| 26191-2.48 | C | 1.82 | 1.83 | 0.139 | 8.77 | 4.90 | 0.490 |
| 3168.V4.C10 | C | 2.52 | 2.83 | 0.139 | 19.3 | 8.18 | 0.394 |
| 3637.V5.C3 | C | 2.83 | 2.12 | 3.84 | 11.1 | 6.68 | 8.30 |
| 3873.V1.C24 | C | 10.0 | 5.51 | 0.767 | 13.8 | 15.7 | 2.64 |
| 6322.V4.C1 | C | 2.90 | 0.923 | >50 | 9.72 | 3.68 | >50 |
| 6471.V1.C16 | C | 11.0 | 4.98 | >50 | 41.9 | 14.9 | >50 |
| 6631.V3.C10 | C | 7.08 | 0.934 | >50 | 15.5 | 3.36 | >50 |
| 6644.V2.C33 | C | 0.229 | 0.013 | 0.182 | 1.14 | 0.124 | 0.731 |
| 6785.V5.C14 | C | 1.58 | 0.701 | 0.281 | 6.70 | 2.42 | 0.900 |
| 6838.V1.C35 | C | 0.813 | 0.292 | 0.181 | 3.67 | 1.01 | 0.694 |
| 96ZM651.02 | C | 0.035 | 0.033 | 0.979 | 0.358 | 0.177 | 2.27 |

Figure 78. cont

Key ($IC_{50}$/$IC_{80}$ in μg/ml)

| <0.100 | 0.100-1.00 | 1.00-10.0 | >10.0 |
|---|---|---|---|

| | | $IC_{50}$ (μg/ml) | | | $IC_{80}$ (μg/ml) | | |
|---|---|---|---|---|---|---|---|
| Virus | Clade | DH511.2 | 10E8 | VRC01 | DH511.2 | 10E8 | VRC01 |
| BR025.9 | C | 1.10 | 0.307 | 0.222 | 5.33 | 1.11 | 1.61 |
| CAP210.E8 | C | 0.911 | 0.474 | >50 | 3.37 | 2.01 | >50 |
| CAP244.D3 | C | 1.13 | 0.369 | 1.21 | 4.56 | 1.48 | 3.37 |
| CAP256.206.C9 | C | 0.779 | 0.713 | 0.915 | 3.92 | 2.97 | 2.10 |
| CAP45.G3 | C | 2.84 | 0.722 | 7.52 | 9.41 | 3.41 | 45.3 |
| Ce1176.A3 | C | 0.998 | 0.252 | 2.64 | 4.13 | 1.15 | 7.56 |
| CE703010217.B6 | C | 0.159 | 0.086 | 0.295 | 0.944 | 0.679 | 0.758 |
| CNE30 | C | 3.30 | 0.456 | 0.808 | 16.3 | 2.29 | 2.10 |
| CNE31 | C | 5.23 | 1.32 | 0.947 | 11.5 | 3.57 | 2.02 |
| CNE53 | C | 0.208 | 0.213 | 0.062 | 1.41 | 1.01 | 0.221 |
| CNE58 | C | 0.453 | 0.229 | 0.132 | 2.98 | 1.09 | 0.436 |
| DU123.06 | C | 0.250 | 0.132 | 9.08 | 0.948 | 0.423 | 25.5 |
| DU151.02 | C | 0.928 | 0.461 | 17.3 | 3.60 | 1.71 | >50 |
| DU156.12 | C | 0.019 | 0.023 | 0.081 | 0.158 | 0.120 | 0.230 |
| DU172.17 | C | 7.22 | 0.057 | >50 | 19.9 | 0.238 | >50 |
| DU422.01 | C | 0.821 | 0.224 | >50 | 3.95 | 0.812 | >50 |
| MW965.26 | C | 0.0003 | 0.0010 | 0.023 | 0.002 | 0.007 | 0.065 |
| SO18.18 | C | 7.52 | 1.60 | 0.067 | 20.7 | 4.48 | 0.162 |
| TV1.29 | C | 0.802 | 0.248 | >50 | 2.66 | 0.719 | >50 |
| TZA125.17 | C | 0.750 | 0.217 | >50 | 4.05 | 1.19 | >50 |
| TZBD.02 | C | 2.44 | 1.41 | 0.068 | 7.78 | 4.31 | 0.198 |
| ZA012.29 | C | 3.66 | 1.47 | 0.296 | 11.3 | 4.12 | 0.755 |
| ZM106.9 | C | 5.68 | >50 | 0.208 | 21.8 | >50 | 0.627 |
| ZM109.4 | C | 0.715 | 0.161 | 0.144 | 4.64 | 1.07 | 0.410 |
| ZM135.10a | C | 0.246 | 0.033 | 1.38 | 2.20 | 0.408 | 4.26 |
| ZM176.66 | C | 1.10 | 0.267 | 0.063 | 5.65 | 1.73 | 0.266 |
| ZM197.7 | C | 0.232 | 0.055 | 0.729 | 1.16 | 0.369 | 2.00 |
| ZM214.15 | C | 5.39 | 2.22 | 1.37 | 15.5 | 5.98 | 4.95 |
| ZM215.8 | C | 0.107 | 0.044 | 0.344 | 0.591 | 0.230 | 1.32 |
| ZM233.6 | C | 0.549 | 0.270 | 2.27 | 2.33 | 0.737 | 7.04 |
| ZM249.1 | C | 1.58 | 0.630 | 0.077 | 5.78 | 2.27 | 0.283 |
| ZM53.12 | C | 6.11 | 2.62 | 1.17 | 18.5 | 6.72 | 3.59 |
| ZM55.28a | C | 7.88 | 2.34 | 0.334 | 19.8 | 6.78 | 1.01 |
| 3326.V4.C3 | CD | 3.62 | 1.40 | 0.088 | 13.3 | 4.29 | 17.6 |
| 3337.V2.C6 | CD | 1.50 | 1.09 | 0.086 | 5.60 | 4.87 | 0.203 |
| 3817.v2.c59 | CD | 2.12 | 0.229 | >50 | 6.33 | 1.43 | >50 |
| 231965.c1 | D | 19.6 | 11.0 | 0.448 | >50 | 20.4 | 1.12 |
| 247-23 | D | 0.618 | 0.344 | 1.53 | 3.24 | 1.29 | 9.17 |
| 3016.v5.c45 | D | 0.607 | 0.710 | 0.121 | 3.42 | 2.17 | 0.272 |
| 57128.vrc15 | D | 0.352 | 0.212 | >50 | 2.59 | 1.50 | >50 |
| 6405.v4.c34 | D | 1.93 | 0.461 | 1.82 | 6.76 | 1.80 | 3.05 |
| A03349M1.vrc4a | D | 0.402 | 0.270 | 3.48 | 1.32 | 0.663 | 11.7 |
| A07412M1.vrc12 | D | | 0.140 | | | 0.873 | |
| NKU3006.ec1 | D | 0.989 | 0.673 | 0.441 | 4.86 | 2.46 | 1.23 |
| P0402.c2.11 | G | 0.084 | 0.057 | 0.085 | 0.815 | 0.460 | 0.288 |
| P1981.C5.3 | G | 0.020 | 0.024 | 0.187 | 0.211 | 0.124 | 0.683 |
| X1193.c1 | G | 0.746 | 0.341 | 0.092 | 3.28 | 1.15 | 0.388 |
| X1254.c3 | G | 2.77 | 3.67 | 0.041 | 14.5 | 15.7 | 0.128 |
| X1632.S2.B10 | G | 0.925 | 0.387 | 0.096 | 3.93 | 1.76 | 0.632 |
| X2088.c9 | G | >50 | >50 | >50 | >50 | >50 | >50 |

Figure 78. cont

Key ($IC_{50}$/$IC_{80}$ in μg/ml)

| <0.100 | 0.100-1.00 | 1.00-10.0 | >10.0 |
|---|---|---|---|

| | | $IC_{50}$ (μg/ml) | | | $IC_{80}$ (μg/ml) | | |
|---|---|---|---|---|---|---|---|
| Virus | Clade | DH511.2 | 10E8 | VRC01 | DH511.2 | 10E8 | VRC01 |
| X2131.C1.B5 | G | 0.118 | 0.039 | 0.466 | 0.611 | 0.175 | 1.64 |
| SIVmac251.30.SG3 | Control | >50 | >50 | >50 | >50 | >50 | >50 |
| SVA.MLV | Control | >50 | >50 | >50 | >50 | >50 | >50 |
| | | | | | | | |
| | | DH511.2 | 10E8 | VRC01 | DH511.2 | 10E8 | VRC01 |
| Number of Viruses | | 199 | 200 | 199 | 199 | 200 | 199 |
| Total Viruses Neutralized | | | | | | | |
| IC50/80 <50ug/ml | | 197 | 195 | 179 | 194 | 195 | 174 |
| IC50/80 <10ug/ml | | 189 | 194 | 177 | 140 | 186 | 163 |
| IC50/80 <1.0ug/ml | | 97 | 145 | 146 | 29 | 57 | 98 |
| IC50/80 <0.1ug/ml | | 19 | 38 | 51 | 6 | 9 | 11 |
| IC50/80 <0.01ug/ml | | 6 | 9 | 0 | 3 | 5 | 0 |
| Percent of Viruses Neutralized | | | | | | | |
| IC50/80 <50ug/ml | | 99 | 98 | 90 | 97 | 98 | 87 |
| IC50/80 <10ug/ml | | 95 | 97 | 89 | 70 | 93 | 82 |
| IC50/80 <1.0ug/ml | | 49 | 73 | 73 | 15 | 29 | 49 |
| IC50/80 <0.1ug/ml | | 10 | 19 | 26 | 3 | 5 | 6 |
| IC50/80 <0.01ug/ml | | 3 | 5 | 0 | 2 | 3 | 0 |
| | | | | | | | |
| Median IC50/80 | | 1.09 | 0.392 | 0.281 | 5.10 | 1.71 | 0.839 |
| Geometric Mean | | 0.802 | 0.315 | 0.287 | 3.82 | 1.37 | 0.843 |

Figure 78. cont

| Virus ID | DH511.2 | | | Virus ID | DH511.2 | | |
|---|---|---|---|---|---|---|---|
| | $IC_{50}$ | $IC_{80}$ | MPI* | | $IC_{50}$ | $IC_{80}$ | MPI* |
| Du156.12 | 0.092 | 0.475 | 100 | 21261106_C12_H2 | 3.53 | 17.7 | 98 |
| Du172.17 | 1.65 | 8.54 | 98 | 21369737_G11_F2 | 6.80 | 33.3 | 90 |
| Du422.1 | 0.749 | 4.80 | 100 | 21399975_E2_B3 | 3.29 | 15.7 | 97 |
| ZM197M.PB7 | 0.053 | 0.601 | 99 | 21492713_B11_E3 | 2.18 | 10.6 | 98 |
| ZM214M.PL15 | 0.385 | 4.95 | 99 | 21502011_F12_E2 | 0.587 | 4.07 | 99 |
| ZM233M.PB6 | 0.590 | 4.08 | 100 | 21561324_D3_B5 | 7.84 | 24.9 | 93 |
| ZM53M.PB12 | 5.64 | 22.6 | 96 | 19314479_A2_5 | 0.943 | 5.35 | 99 |
| ZM109F.PB4 | 0.682 | 6.08 | 98 | 98-F4_H5-13 | 12.7 | 41.1 | 85 |
| ZM135M.PL10a | 0.690 | 3.36 | 100 | 234-F1-16-57 | 1.33 | 7.19 | 99 |
| CAP45.2.00.G3 | 0.268 | 6.84 | 98 | 541-F1_A7_2 | 20.8 | >50 | 75 |
| Du151.2 | 1.27 | 6.60 | 99 | 569-F1_37_10 | 9.21 | 36.6 | 86 |
| CAP244.2.00.D3 | 1.07 | 3.08 | 100 | 304_F2_1_11 | 7.21 | 31.9 | 91 |
| ZM215F.PB8 | 0.065 | 0.400 | 100 | 346_F4_D2_12 | 0.147 | 1.08 | 99 |
| ZM55F.PB28a | 3.27 | 15.4 | 98 | 556_F2_3_25 | 1.93 | 10.4 | 97 |
| ZM106F.PB9 | 6.18 | 36.9 | 92 | CAP69.1.12_TA7.1 | 0.799 | 6.48 | 99 |
| 6644.v2.c33 | 0.231 | 0.965 | 100 | CAP136.1.16_E6_1 | 0.243 | 5.92 | 97 |
| 0077.v1.c16 | 1.91 | 18.9 | 93 | CAP174.1.06_F3_1B | 0.085 | 1.31 | 99 |
| 3728.v2.c6 | 2.17 | 11.2 | 97 | CAP220.2.00_A8_5B | 2.10 | 11.2 | 98 |
| 6838.v1.c35 | 1.12 | 5.00 | 100 | CAP224.1.18_C7_3 | 0.962 | 3.09 | 99 |
| 6785.v5.c14 | 2.89 | 13.3 | 98 | CAP225.1.06_A2_18 | 2.31 | 10.9 | 99 |
| 0041.v3.c18 | 1.56 | 7.99 | 99 | CAP269.2.00_F11_1 | 1.24 | 7.87 | 99 |
| 3168.v4.c10 | 1.64 | 14.3 | 97 | CAP37.1.18_D2_19 | 11.2 | 40.4 | 87 |
| 3873.v1.c24 | 4.14 | 21.3 | 94 | CAP40.2.01_A3_5 | 0.189 | 2.48 | 100 |
| 6322.v4.c1 | 2.96 | 16.6 | 98 | CAP129.1.15_B2_13 | 1.60 | 13.9 | 96 |
| 0921.v2.c14 | 2.66 | 10.5 | 98 | CAP237.1.22_B2_2_39 | 0.546 | 4.11 | 99 |
| 3637.v5.c3 | 3.31 | 16.8 | 94 | CAP258.2.00_X_23 | 0.512 | 3.93 | 99 |
| 6471.v1.c16 | 8.00 | 47.3 | 91 | CAP260.2.00_TA1_1B | 3.38 | 19.5 | 95 |
| 0984.v2.c2 | 14.4 | 42.8 | 84 | CAP266.2.00_E9_h6 | 3.78 | 14.3 | 95 |
| 6040.v4.c15 | 1.50 | 12.7 | 95 | TRP290.2.00_23_6 | 0.650 | 4.83 | 100 |
| 6631.v3.c10 | 2.43 | 12.4 | 98 | TRP292.2.00_12_4 | 0.430 | 2.30 | 100 |
| 933.v4.c4 | 3.27 | 9.32 | 100 | TRP307.2.00_24_1 | 0.741 | 5.87 | 98 |
| 6980.v0.c31 | 5.10 | 17.5 | 98 | TRP310.2.00_20_2 | 0.070 | 0.544 | 99 |
| 3426.v5.c17 | 0.087 | 0.459 | 100 | TRP343.2.00_21_2 | 2.20 | 16.8 | 86 |
| 377.v4.c09 | 6.33 | 23.6 | 94 | TRP347.2.00_B1_1 | 0.818 | 5.91 | 99 |
| Ce1086_B2 | 0.176 | 2.29 | 99 | TRP363.2.00_10_3 | 0.208 | 2.30 | 100 |
| Ce0393_C3 | 1.22 | 7.00 | 100 | 722_G4_16 | 0.762 | 2.54 | 100 |
| Ce1176_A3 | 0.868 | 5.10 | 99 | So431_C1_1 | 0.157 | 2.34 | 98 |
| Ce2010_F5 | >50 | >50 | 35 | CT885_H3_2 | 2.69 | 13.2 | 98 |
| Ce0682_E4 | 0.574 | 4.85 | 99 | So186_H6_5 | 1.09 | 5.21 | 99 |
| Ce1172_H1 | 0.141 | 1.71 | 100 | So405_T24_5 | 0.054 | 0.272 | 100 |
| Ce2060_G9 | 2.67 | 14.7 | 97 | So225_H11_12 | >50 | >50 | 29 |
| Ce2103_E8 | 13.3 | 45.7 | 89 | So706_T10b_3 | 23.6 | >50 | 69 |
| Ce0985_H7(Rev-) | 17.7 | 43.1 | 85 | CT072_56_7 | 0.353 | 2.30 | 100 |
| Ce703010131_1E2 | 2.95 | 18.0 | 94 | CT966_E1-7 | 0.831 | 3.80 | 100 |
| Ce703010054_2A2 | 2.05 | 8.71 | 100 | CT977_69_12 | 0.372 | 2.64 | 100 |
| Ce703010217_B6 | 0.172 | 1.27 | 100 | CT140_140_B6 | 1.50 | 6.59 | 100 |
| Ce703010228_1C4 | 1.53 | 7.19 | 99 | CT349_39_16 | 0.142 | 1.37 | 100 |
| Ce704010083_B8 | 0.538 | 3.13 | 100 | CT431_G6_6 | 0.410 | 1.84 | 100 |
| Ce704809221_1B3 | 0.104 | 0.640 | 100 | CT823_B6_1 | 0.939 | 4.55 | 100 |
| Ce0626_E6 | 0.708 | 3.23 | 99 | Ko426_T78_10 | 1.30 | 5.79 | 100 |

*MPI: Maximum Percent Inhibition

Figure 79

| Virus ID | DH511.2 | | |
|---|---|---|---|
| | $IC_{50}$ | $IC_{80}$ | MPI* |
| Ce0665_F2 | 0.026 | 0.117 | 100 |
| Ce0089_G2 | 2.32 | 10.2 | 100 |
| Ce2052_G10 | 0.813 | 4.86 | 100 |
| Ce704010069_C6 | 1.30 | 6.44 | 98 |
| Ce703010010_C4 | 1.46 | 7.23 | 100 |
| Ce704810053_2B7 | 1.50 | 7.02 | 100 |
| CeCAP210_TA5 | 1.28 | 5.75 | 100 |
| CeCAP200_B8a | 3.40 | 15.7 | 98 |
| CeCAP221_B14 | 5.07 | 16.9 | 98 |
| CeCAP188_1_D1_14(Rev-) | 2.34 | 11.2 | 98 |
| CeCAP177_1A3 | 1.16 | 5.78 | 100 |
| 246F C1G | 2.66 | 12.8 | 99 |
| ZM249M.PL1 | 1.03 | 8.38 | 100 |
| ZM247v1(Rev-) | 1.83 | 10.1 | 98 |
| 7060101641A7(Rev-) | 0.245 | 2.95 | 100 |
| 7030102001E5(Rev-) | 6.53 | 37.4 | 87 |
| 1394C9G1(Rev-) | 1.08 | 8.48 | 98 |
| 235080_3G7env2(Rev-) | 4.16 | 18.0 | 98 |
| BF1266.431a | 3.73 | 24.4 | 91 |
| 704010042 | 0.548 | 2.40 | 100 |
| 705010185 | 5.05 | 19.0 | 96 |
| 705010198 | 4.39 | 21.8 | 97 |
| 705010067 | 1.73 | 10.3 | 99 |
| 2833264 | 1.82 | 13.8 | 99 |
| 1245045 | 9.09 | 34.6 | 93 |
| 19157834_V1 | 0.511 | 4.06 | 100 |
| 2969249 | 1.61 | 9.57 | 97 |
| 3514597 | 8.15 | 28.0 | 93 |
| 20258279_V2 | 7.89 | 27.9 | 91 |
| 20721190 | 5.06 | 17.9 | 96 |
| 20803520 | 6.19 | 27.1 | 93 |
| 20915593 | 0.210 | 1.33 | 100 |
| 20927783 | 7.92 | 28.4 | 96 |
| 20965238 | 11.1 | 44.2 | 91 |
| 21197826_V1 | 11.1 | 36.5 | 90 |
| 21283649 | 15.3 | 45.5 | 83 |
| 2759058_F10_B6 | 1.75 | 8.49 | 98 |
| 2768732_C5_16 | 13.4 | 50.0 | 87 |
| 2869751_A4_D3 | 6.06 | 18.4 | 96 |
| 2891391_A2_E1 | 6.05 | 17.2 | 98 |
| 3545883_G1_E1 | 1.47 | 9.71 | 99 |
| 18814602_H8_F3 | 0.234 | 2.56 | 100 |
| 19252094_A5_G2 | 5.32 | 34.6 | 92 |
| 19707346_E8_C6 | 1.47 | 8.58 | 100 |
| 19715820_A10_H2 | 0.389 | 2.76 | 99 |
| 20104663_E11_D2 | 0.960 | 4.37 | 99 |
| 20198102_E9_G1 | 1.33 | 9.90 | 99 |
| 20286961_C1_H8 | 0.442 | 2.68 | 100 |
| 20883229_C9_H6 | 0.549 | 4.24 | 100 |
| 21203310_G7_C3 | 1.09 | 8.49 | 98 |

| Virus ID | DH511.2 | | |
|---|---|---|---|
| | $IC_{50}$ | $IC_{50}$ | MPI* |
| Ko459_T68_4 | 1.20 | 6.53 | 99 |
| Ko870_C2_10 | 0.837 | 4.31 | 100 |
| Ko224_T87_2_4 | 0.697 | 10.8 | 95 |
| Ko756_38_Tb12 | 0.314 | 2.50 | 100 |
| CA327_D2_2 | 0.677 | 3.57 | 100 |
| CA392_H2_6 | 0.692 | 2.36 | 100 |
| CA457_H1_1 | 1.18 | 5.36 | 100 |
| ME067_A10-15 | 2.85 | 13.2 | 98 |
| CA146_H3_3 | 0.070 | 0.504 | 100 |
| CA240_A5.5 | 3.96 | 20.3 | 97 |
| 1811_B3.23 | 2.59 | 9.22 | 99 |
| 2865_A11.12 | 4.99 | 18.9 | 97 |
| 3603_C11.13 | 1.17 | 5.18 | 99 |
| 3312_D6.2 | 5.44 | 49.7 | 85 |
| CAP301.2.00_C3.20 | 1.36 | 10.3 | 99 |
| CAP340.2.00_B3.16 | 0.303 | 4.32 | 99 |
| CAP382.2.00_D7.19 | 4.07 | 22.9 | 96 |
| CAP317.2.00_D4.10 | 0.786 | 12.5 | 95 |
| CAP341.2.00.C10.18 | 0.145 | 0.675 | 98 |
| CAP304.2.00_F6.6 | 6.77 | 30.7 | 91 |
| CAP306.2.00_F9.1 | 2.68 | 14.8 | 96 |
| CAP308.2.00_E11.35 | >50 | >50 | 40 |
| CAP323.2.00_B6.45 | 2.04 | 10.0 | 98 |
| CAP330.2.00_F2.41 | 1.52 | 6.65 | 100 |
| CAP326.2.00_D9.2 | 18.4 | 43.8 | 90 |
| 20417927.07 | 2.79 | 17.6 | 93 |
| 20355851.20 | 39.1 | >50 | 57 |
| 20358510.01 | 9.71 | 36.7 | 94 |
| 1107356.07 | 1.03 | 7.01 | 100 |
| 1143465.14 | 0.133 | 0.494 | 100 |
| 1170887.08 | 6.50 | 20.5 | 94 |
| B005582-7_G7.8 | >50 | >50 | 38 |
| B005018-8_F6.3 | 0.269 | 2.15 | 100 |
| CT810_G4-7 | 0.721 | 6.37 | 100 |
| CT184_D3.15 | 1.86 | 10.4 | 99 |
| SO607_B6.9 | 13.8 | 45.4 | 84 |
| Me178_G6.16 | 1.48 | 7.98 | 100 |
| CAP291.2.00_H2.15 | 1.08 | 4.46 | 100 |
| CAP327.2.00_C6.37 | 2.88 | 12.3 | 98 |
| CAP378.2.00_D2.5 | 3.06 | 22.0 | 94 |
| SO032_A2.8-1 | 0.085 | 0.909 | 100 |
| CT565_C7.48 | 2.87 | 13.0 | 99 |
| Ko243_H6.3 | 4.25 | 19.2 | 96 |
| CAP331.2.00_D7.39 | 4.29 | 34.1 | 95 |
| CAP332.2.00_C10.1 | 2.06 | 10.4 | 99 |
| CAP206.1.B5.Y681D | 0.895 | 4.28 | 99 |
| CH0505.w4.3 | 0.020 | 0.131 | 100 |
| 6022.v7.c24 | 2.45 | 10.6 | 99 |
| 6146.v7.c23 | 14.6 | 44.4 | 84 |
| CH0694.env | 12.0 | 47.0 | 84 |

Figure 79 cont.

| | | Early/Acute Clade C Virus Panel (n=200) | | | | | | | |
|---|---|---|---|---|---|---|---|---|---|
| | | Highest Concentration | % Viruses Neutralized Highest Concentration | | Median Titers (All viruses) | | Median Titers (Sensitive Viruses Only) | |
| bnAb | Epitope Target | Tested (ug/ml) | IC50 Cut-off | IC80 Cut-off | IC50 | IC80 | IC50 | IC80 |
| VRC01 | CD4bs | 50 | 84.0 | 77.5 | 0.748 | 2.970 | 0.553 | 1.750 |
| 10E8 | MPER | 25 | 97.5 | 96.5 | 0.570 | 3.468 | 0.559 | 3.399 |
| DH511.2 | MPER | 50 | 98.0 | 96.5 | 1.547 | 9.443 | 1.510 | 8.580 |

Figure 79 cont.

Key ($IC_{50}/IC_{80}$ in µg/ml)

| <0.100 | 0.100-1.00 | 1.00-10.0 | >10.0 |
|---|---|---|---|

| | | | | IC50 (µg/ml) | IC50 (µg/ml) | IC50 (µg/ml) | IC50 (µg/ml) | IC50 (µg/ml) |
|---|---|---|---|---|---|---|---|---|
| PTID | Antibody ID | Heavy ID | Light ID | BG1168 | CH505.TF | DU172 | MN | SVA |
| | 10E8 | | | 0.262 | 4.76 | 0.124 | <0.023 | >50 |
| 704-01-021-0 | DH511.2 (Ab510049) | DH511.2 VH_4A | DH511.2 VK | 0.156 | 8.97 | 3.41 | <0.023 | >50 |
| 704-01-021-0 | DH511.2_K3 | DH511.2 VH_4A | DH511.3 VK | 0.044 | 2.81 | 3.67 | <0.023 | >50 |
| 704-01-021-0 | DH511.2_E96W | DH511.2 VH_4A_E96W | DH511.2 VK | 1.92 | 31.0 | 4.78 | 0.051 | >50 |
| 704-01-021-0 | DH511.2_T98W | DH511.2 VH_4A_T98W | DH511.2 VK | 5.80 | >50 | 14.4 | 0.434 | >50 |
| 704-01-021-0 | DH511.2_P99W | DH511.2 VH_4A_P99W | DH511.2 VK | 2.46 | >50 | >50 | 0.232 | >50 |
| 704-01-021-0 | DH511.2_L100dW | DH511.2 VH_4A_L100dW | DH511.2 VK | 0.398 | 6.82 | 0.606 | <0.023 | >50 |
| 704-01-021-0 | DH511.2_E100eW | DH511.2 VH_4A_E100eW | DH511.2 VK | 1.41 | >50 | >50 | 0.254 | >50 |
| 704-01-021-0 | DH511.2_Y100hW | DH511.2 VH_4A_Y100hW | DH511.2 VK | 1.57 | 45.1 | 18.5 | 0.071 | >50 |
| 704-01-021-0 | DH511.2_F100lW | DH511.2 VH_4A_F100lW | DH511.2 VK | 1.64 | 39.3 | >50 | 0.054 | >50 |
| 704-01-021-0 | DH511.2_Y100kW | DH511.2 VH_4A_Y100kW | DH511.2 VK | >50 | >50 | >50 | 9.34 | >50 |
| 704-01-021-0 | DH511.2_V100F | DH511.2 VH_4A_V100F | DH511.2 VK | >50 | >50 | >50 | 20.1 | >50 |
| 704-01-021-0 | DH511.2_T100aW | DH511.2 VH_4A_T100aW | DH511.2 VK | 0.098 | 6.24 | 0.134 | <0.023 | >50 |
| 704-01-021-0 | DH511.2_R100bW | DH511.2 VH_4A_R100bW | DH511.2 VK | 5.45 | >50 | >50 | 0.428 | >50 |
| 704-01-021-0 | DH511.2_F100cW | DH511.2 VH_4A_F100cW | DH511.2 VK | 1.33 | 30.6 | >50 | 0.090 | >50 |
| 704-01-021-0 | DH511.2_G100gW | DH511.2 VH_4A_G100gW | DH511.2 VK | >50 | >50 | >50 | >50 | >50 |
| 704-01-021-0 | DH511.2_V100I | DH511.2 VH_4A_V100I | DH511.2 VK | 2.73 | >50 | >50 | 0.304 | >50 |
| 704-01-021-0 | DH511.2_L100dF | DH511.2 VH_4A_L100dF | DH511.2 VK | 0.048 | 2.73 | 0.229 | <0.023 | >50 |
| 704-01-021-0 | DH511.2_G97W | DH511.2 VH_4A_G97W | DH511.2 VK | >50 | >50 | >50 | 33.2 | >50 |
| Control | Ab82 | | | >50 | >50 | >50 | >50 | >50 |
| Control | CH01+CH31 | | | 1.44 | <0.011 | 1.52 | 0.575 | >25 |

Figure 80

| | | | | IC80 (μg/ml) | IC80 (μg/ml) | IC80 (μg/ml) | IC80 (μg/ml) | IC80 (μg/ml) |
|---|---|---|---|---|---|---|---|---|
| PTID | Antibody ID | Heavy ID | Light ID | BG1168 | CH505.TF | DU172 | MN | SVA |
| | 10E8 | | | 1.19 | 13.6 | 0.684 | <0.023 | >50 |
| 704-01-021-0 | DH511.2 (Ab510049) | DH511.2 VH_4A | DH511.2 VK | 0.913 | 28.1 | 13.0 | 0.082 | >50 |
| 704-01-021-0 | DH511.2_K3 | DH511.2 VH_4A | DH511.8 VK | 0.376 | 13.2 | 11.6 | <0.023 | >50 |
| 704-01-021-0 | DH511.2_E98W | DH511.2 VH_4A_E98W | DH511.2 VK | 5.72 | >50.32 | 19.4 | 0.276 | >50 |
| 704-01-021-0 | DH511.2_T99W | DH511.2 VH_4A_T99W | DH511.2 VK | 27.3 | >50 | >50 | 1.51 | >50 |
| 704-01-021-0 | DH511.2_P99W | DH511.2 VH_4A_P99W | DH511.2 VK | 12.9 | >50 | >50 | 0.729 | >50 |
| 704-01-021-0 | DH511.2_L100dW | DH511.2 VH_4A_L100dW | DH511.2 VK | 1.30 | 23.2 | 3.31 | 0.100 | >50 |
| 704-01-021-0 | DH511.2_E100eW | DH511.2 VH_4A_E100eW | DH511.2 VK | 6.74 | >50 | >50 | 0.877 | >50 |
| 704-01-021-0 | DH511.2_Y100hW | DH511.2 VH_4A_Y100hW | DH511.2 VK | 5.14 | >50 | >50 | 0.387 | >50 |
| 704-01-021-0 | DH511.2_F100iW | DH511.2 VH_4A_F100iW | DH511.2 VK | 7.09 | >50 | >50 | 0.327 | >50 |
| 704-01-021-0 | DH511.2_Y100kW | DH511.2 VH_4A_Y100kW | DH511.2 VK | >50 | >50 | >50 | 32.5 | >50 |
| 704-01-021-0 | DH511.2_V100F | DH511.2 VH_4A_V100F | DH511.2 VK | >50 | >50 | >50 | >50 | >50 |
| 704-01-021-0 | DH511.2_T100aW | DH511.2 VH_4A_T100aW | DH511.2 VK | 0.696 | 20.1 | 0.950 | <0.023 | >50 |
| 704-01-021-0 | DH511.2_R100bW | DH511.2 VH_4A_R100bW | DH511.2 VK | 15.6 | >50 | >50 | 1.19 | >50 |
| 704-01-021-0 | DH511.2_F100cW | DH511.2 VH_4A_F100cW | DH511.2 VK | 6.58 | >50 | >50 | 0.316 | >50 |
| 704-01-021-0 | DH511.2_G100gW | DH511.2 VH_4A_G100gW | DH511.2 VK | >50 | >50 | >50 | >50 | >50 |
| 704-01-021-0 | DH511.2_V100I | DH511.2 VH_4A_V100I | DH511.2 VK | 10.6 | >50 | >50 | 1.11 | >50 |
| 704-01-021-0 | DH511.2_L100dF | DH511.2 VH_4A_L100dF | DH511.2 VK | 0.349 | 10.2 | 1.67 | <0.023 | >50 |
| 704-01-021-0 | DH511.2_G97W | DH511.2 VH_4A_G97W | DH511.2 VK | >50 | >50 | >50 | >50 | >50 |
| Control | Ab82 | | | >50 | >50 | >50 | >50 | >50 |
| Control | CH01+CH31 | | | 5.34 | 0.059 | 10.1 | 3.32 | >25 |

Figure 80 cont.

Heavy Chain Sequences
Plasma monoclonal antibodies

| Donor | HeAvy ChAin ID | IGHV | IGHD | IGHJ | CDR3 length (Amino Acids)[a] | CDR3 Sequence (Amino Acids) | Somatic Mutations (Nucleotides)[b] | Mutation Frequency (Nucleotides)[b] | Mutation Frequency (Amino Acids)[b] |
|---|---|---|---|---|---|---|---|---|---|
| CH0210 | DH511.7AP VH | 3-15*02 | 3-3*01 | 6*03 | 23 | TADRGAPVLRFWEWGYYDYYMEF | 36 | 12.3% | in progress |
| CH0210 | DH511.7BP VH | 3-15*02 | 3-3*01 | 6*03 | 23 | TADRGAPVLRFWEWGYYDYYMEF | 34 | 11.6% | in progress |
| CH0210 | DH511.8AP VH | 3-15*02 | 3-3*01 | 6*03 | 23 | TADRGAPVLRFWEWGYFDYYMEF | 41 | 14.0% | in progress |
| CH0210 | DH511.8BP VH | 3-15*02 | 3-3*01 | 6*03 | 23 | TADRGAPVLRFWEWGYFDYYMEF | 43 | 14.7% | in progress |
| CH0210 | DH511.8CP VH | 3-15*02 | 3-3*01 | 6*03 | 23 | TADRGAPVLRFWEWGYFDYYMEF | 44 | 15.0% | in progress |
| CH0210 | DH511.9AP VH | 3-15*01 | 3-3*01 | 6*03 | 24 | TRDEGAPVTRRFLEWGYFYYYMAV | 60 | 20.4% | in progress |
| CH0210 | DH511.10AP VH | 3-15*01 | 3-3*01 | 6*03 | 23 | TRDEGAPVTRFLEWGSYYYYMAV | 56 | 19.1% | in progress |
| CH0210 | DH511.10BP VH | 3-15*01 | 3-3*01 | 6*03 | 23 | TRDEGAPVTRFLEWGSYYYYMAV | 58 | 19.8% | in progress |
| CH0210 | DH511.10CP VH | 3-15*01 | 3-3*01 | 6*03 | 23 | TRDEGAPVTRLLEWGSYYYYMAV | 60 | 20.5% | in progress |
| CH0210 | DH511.11AP VH | 3-15*01 | 3-3*01 | 6*03 | 23 | TADEGAPILRFFEWGYYNYYMDV | 32 | 10.6% | in progress |
| CH0210 | DH511.12AP VH | 3-15*01 | 3-3*01 | 6*03 | 23 | TADEGAPILRFFEWGYYNYYMDV | 34 | 11.2% | in progress |

Figure 81

Light Chain Sequences
Plasma monoclonal antibodies

| Donor | Light Chain ID | IGKV | IGKJ | CDR3 length (Amino Acids)[a] | CDR3 Sequence (Amino Acids) | Somatic Mutations (Nucleotides)[b] | Mutation Frequency (Nucleotides)[b] | Mutation Frequency (Amino Acids)[b] |
|---|---|---|---|---|---|---|---|---|
| CH0210 | DH511. 7PA VK | 1-39*01 | 2*01 | 11 | QESYSSTPTHT | 31 | 11.7% | in progress |
| CH0210 | DH511. 8PA VK | 1-39*01 | 2*01 | 11 | QESYSSTPTHI | 30 | 11.4% | in progress |
| CH0210 | DH511. 9A VK | 1-39*01 | 2*01 | 11 | QESYQTVPTLT | 36 | 13.6% | in progress |
| CH0210 | DH511. 9BP VK | 1-39*01 | 2*01 | 11 | QESYQTVPTLT | 37 | 14.0% | in progress |
| CH0210 | DH511. 9CP VK | 1-39*01 | 2*01 | 11 | QESYQTVPTLT | 36 | 13.6% | in progress |
| CH0210 | DH511. 10P VK | 1-39*01 | 2*01 | 11 | QEAYNTNPTLS | 36 | 13.6% | in progress |
| CH0210 | DH511. 10BP VK | 1-39*01 | 2*01 | 11 | QEAYNTNPTLS | 38 | 14.4% | in progress |
| CH0210 | DH511. 11A P VK | 1-39*01 | 2*01 | 11 | QESYSSVPMYI | 41 | 15.5% | in progress |

[a]CDR3 length listed according to the IMGT definition.
[b]Somatic mutations were determined over the entire variable region and are reported as the number/frequency of nucleotides or amino acids that differed from the putative germ line V-gene sequence.

Figure 81 cont.

Pairing of Plasma-derived Heavy and Light Chains for Expression of 16 Recombinant Monoclonal Antibodies

| | Ab Name | Heavy ID | Light ID |
|---|---|---|---|
| 1 | DH511.7P | DH511.7AP VH | DH511.7AP VK |
| 2 | DH511.7bP | DH511.7BP VH | DH511.7AP VK |
| 3 | DH511.8P | DH511.8AP VH | DH511.8AP VK |
| 4 | DH511.8bP | DH511.8BP VH | DH511.8AP VK |
| 5 | DH511.8cP | DH511.8CP VH | DH511.8AP VK |
| 6 | DH511.9P | DH511.9AP VH | DH511.9AP VK |
| 7 | DH511.9bP | DH511.9AP VH | DH511.9BP VK |
| 8 | DH511.9cP | DH511.9AP VH | DH511.9CP VK |
| 9 | DH511.10P | DH511.10AP VH | DH511.10AP VK |
| 10 | DH511.10a10bVKP | DH511.10AP VH | DH511.10BP VK |
| 11 | DH511.10b10aVKP | DH511.10BP VH | DH511.10AP VK |
| 12 | DH511.10bP | DH511.10BP VH | DH511.10BP VK |
| 13 | DH511.10cP | DH511.10CP VH | DH511.10AP VK |
| 14 | DH511.10c10bVKP | DH511.10CP VH | DH511.10BP VK |
| 15 | DH511.11P | DH511.11AP VH | DH511.11AP VK |
| 16 | DH511.12P | DH511.12P VH | DH511.11AP VK |

Figure 81 cont.

Key ($IC_{50}/IC_{80}$ in µg/ml)

| <0.100 | 0.100-1.00 | 1.00-10.0 | >10.0 |
|---|---|---|---|

| | $IC_{50}$ (µg/ml) | | | | | | | | | |
|---|---|---|---|---|---|---|---|---|---|---|
| Ab Name | BG1168 (Assay 1) | BG1168 (Assay 2) | CH505.TF (Assay 1) | CH505.TF (Assay 2) | DU172 (Assay 1) | DU172 (Assay 2) | MN (Assay 1) | MN (Assay 2) | SVA (Assay 1) | SVA (Assay 2) |
| 10E8 | 0.188 | 0.099 | 3.31 | 3.18 | <0.023 | <0.023 | <0.023 | <0.023 | >50 | >50 |
| DH511.2 | NT | 0.174 | NT | 7.58 | NT | 2.91 | NT | <0.023 | NT | >50 |
| DH511.7P | 1.94 | 0.771 | 32.1 | 30.4 | 8.39 | 12.8 | <0.023 | <0.023 | >50 | >50 |
| DH511.7bP | 1.66 | 0.793 | 20.6 | 25.6 | 6.53 | 8.89 | <0.023 | <0.023 | >50 | >50 |
| DH511.8P | 0.898 | 0.813 | 17.8 | 16.5 | 0.224 | 0.185 | <0.023 | <0.023 | >50 | >50 |
| DH511.8bP | 0.767 | 0.549 | 16.7 | 11.3 | 0.130 | 0.147 | <0.023 | <0.023 | >50 | >50 |
| DH511.8cP | 10.6 | NT | >50 | NT | 3.06 | NT | 0.610 | NT | >50 | >50 |
| DH511.9P | 1.00 | 0.751 | 20.4 | 21.1 | 1.76 | 1.34 | <0.023 | <0.023 | >50 | >50 |
| DH511.9bP | 1.92 | NT | 43.8 | NT | 2.84 | NT | 0.027 | NT | >50 | >50 |
| DH511.9cP | 1.20 | 0.458 | 22.4 | 18.7 | 1.50 | 1.19 | <0.023 | <0.023 | >50 | >50 |
| DH511.10P | 12.3 | 7.09 | >50 | >50 | 17.3 | >50 | 0.468 | 0.149 | >50 | >50 |
| DH511.10a10bVKP | 5.09 | 5.23 | >50 | >50 | 1.65 | 16.2 | 0.278 | 0.152 | >50 | >50 |
| DH511.10b10aVKP | 30.8 | NT | >50 | NT | >50 | NT | 1.07 | NT | >50 | >50 |
| DH511.10bP | 26.1 | NT | >50 | NT | >50 | NT | 0.740 | NT | >50 | >50 |
| DH511.10cP | 31.7 | >50 | >50 | >50 | >50 | >50 | 2.06 | 1.33 | >50 | >50 |
| DH511.10c10bVKP | 33.6 | >50 | >50 | >50 | >50 | >50 | 1.27 | 0.898 | >50 | >50 |
| DH511.11P | 0.239 | 0.214 | 7.00 | 7.70 | 0.055 | 0.067 | <0.023 | <0.023 | >50 | >50 |
| DH511.12P | 0.163 | 0.108 | 9.39 | 5.97 | <0.023 | 0.061 | <0.023 | <0.023 | >50 | >50 |
| 2F5 | 0.907 | 0.841 | NT | NT | NT | NT | <0.023 | <0.023 | NT | NT |
| 4E10 | NT | NT | NT | NT | 0.192 | 0.116 | NT | NT | >50 | >50 |
| CH31 | NT | NT | <0.023 | <0.023 | NT | NT | NT | NT | NT | NT |

Figure 82

| Ab Name | IC$_{50}$ (μg/ml) | | | | | | | | | |
|---|---|---|---|---|---|---|---|---|---|---|
| | BG1168 (Assay 1) | BG1168 (Assay 2) | CH505.TF (Assay 1) | CH505.TF (Assay 2) | DU172 (Assay 1) | DU172 (Assay 2) | MN (Assay 1) | MN (Assay 2) | SVA (Assay 1) | SVA (Assay 2) |
| 10E8 | 0.773 | 0.433 | 9.60 | 7.21 | 0.198 | 0.103 | <0.023 | <0.023 | >50 | >50 |
| DH511.2 | NT | 0.813 | NT | 21.8 | NT | 9.81 | NT | <0.023 | NT | >50 |
| DH511.7P | 6.97 | 2.81 | >50 | >50 | 37.2 | >50 | 0.051 | 0.042 | >50 | >50 |
| DH511.7bP | 6.24 | 3.75 | >50 | >50 | 27.1 | >50 | 0.068 | 0.028 | >50 | >50 |
| DH511.8P | 3.32 | 3.22 | 48.6 | 48.9 | 1.43 | 1.31 | 0.037 | <0.023 | >50 | >50 |
| DH511.8bP | 2.64 | 2.41 | 42.7 | 43.3 | 1.12 | 0.809 | 0.056 | <0.023 | >50 | >50 |
| DH511.8cP | 42.9 | NT | >50 | NT | 22.1 | NT | 1.65 | NT | >50 | >50 |
| DH511.9P | 4.96 | 2.39 | >50 | >50 | 10.5 | 5.58 | 0.044 | <0.023 | >50 | >50 |
| DH511.9bP | 6.90 | NT | >50 | NT | 17.3 | NT | 0.130 | NT | >50 | >50 |
| DH511.9cP | 5.55 | 1.89 | >50 | >50 | 11.0 | 5.05 | 0.077 | <0.023 | >50 | >50 |
| DH511.10P | 39.6 | >50 | >50 | >50 | >50 | >50 | 1.52 | 0.498 | >50 | >50 |
| DH511.10a10bVKP | 25.0 | 29.2 | >50 | >50 | >50 | >50 | 0.649 | 0.526 | >50 | >50 |
| DH511.10b10aVKP | >50 | NT | >50 | NT | >50 | NT | 4.02 | NT | >50 | >50 |
| DH511.10bP | >50 | NT | >50 | NT | >50 | NT | 2.04 | NT | >50 | >50 |
| DH511.10cP | >50 | >50 | >50 | >50 | >50 | >50 | 6.87 | 4.58 | >50 | >50 |
| DH511.10c10bVKP | >50 | >50 | >50 | >50 | >50 | >50 | 3.77 | 2.46 | >50 | >50 |
| DH511.11P | 1.14 | 1.06 | 24.1 | 24.0 | 0.477 | 0.605 | <0.023 | <0.023 | >50 | >50 |
| DH511.12P | 0.944 | 0.448 | 26.8 | 18.4 | 0.443 | 0.440 | <0.023 | <0.023 | >50 | >50 |
| 2F5 | 4.04 | 4.24 | NT | NT | NT | NT | <0.023 | <0.023 | NT | NT |
| 4E10 | NT | NT | NT | NT | 2.30 | 1.45 | NT | NT | >50 | >50 |
| CH31 | NT | NT | NT | 0.029 | 0.030 | NT | NT | NT | NT | NT |

Results shown are derived from two independent experiments. NT, not tested.

Figure 82 cont.

Key ($IC_{50}$/$IC_{80}$ in μg/ml)

| <0.100 | 0.100-1.00 | 1.00-10.0 | >10.0 |
|---|---|---|---|

| | | $IC_{50}$ (μg/ml) | | | | $IC_{80}$ (μg/ml) | | | |
|---|---|---|---|---|---|---|---|---|---|
| Virus | Clade | DH511.11P | DH511.12P | DH511.2 | 10E8 | DH511.11P | DH511.12P | DH511.2 | 10E8 |
| 0260.v5.c36 | A | 10.9 | 12.0 | 17.0 | 9.87 | 28.4 | 30.6 | >50 | 21.7 |
| 0330.v4.c3 | A | 0.798 | 0.785 | 1.42 | 1.12 | 4.75 | 5.17 | 7.37 | 3.64 |
| 0439.v5.c1 | A | 2.02 | 1.74 | 2.36 | 1.23 | 6.99 | 5.83 | 9.57 | 3.95 |
| 3365.v2.c20 | A | 1.23 | 1.43 | 2.29 | 1.60 | 6.52 | 5.78 | 7.89 | 4.56 |
| 3415.v1.c1 | A | 10.7 | 9.89 | 12.6 | 4.69 | 17.5 | 19.2 | 22.1 | 11.5 |
| 3718.v3.c11 | A | 3.48 | 3.34 | 3.80 | 0.838 | 13.7 | 10.7 | 13.5 | 4.42 |
| 398-F1_F6_20 | A | 2.84 | 2.26 | 2.49 | 0.704 | 16.9 | 10.7 | 18.0 | 6.17 |
| BB201.B42 | A | 1.97 | 2.61 | 2.82 | 0.613 | 8.09 | 8.37 | 9.87 | 1.96 |
| BB539.2B13 | A | 2.16 | 2.08 | 6.73 | 0.591 | 6.32 | 7.16 | 43.0 | 13.0 |
| BG505.W6MC2 | A | 0.915 | 0.907 | 1.33 | 0.689 | 4.93 | 4.03 | 5.60 | 2.14 |
| BI369.9A | A | 0.850 | 1.10 | 1.61 | 0.356 | 3.37 | 3.62 | 4.93 | 1.29 |
| BS208.B1 | A | 0.425 | 0.398 | 0.803 | 0.319 | 2.03 | 1.76 | 3.35 | 3.27 |
| KER2008.12 | A | 0.544 | 0.548 | 0.723 | >50 | 2.76 | 2.30 | 4.29 | >50 |
| KER2018.11 | A | 3.73 | 3.73 | 4.31 | 1.89 | 13.4 | 14.1 | 17.0 | 7.16 |
| KNH1209.18 | A | 0.359 | 0.313 | 0.410 | 0.406 | 1.87 | 1.53 | 2.25 | 2.39 |
| MB201.A1 | A | 0.679 | 0.657 | 0.844 | 0.411 | 3.31 | 3.02 | 4.22 | 1.36 |
| MB539.2B7 | A | 10.2 | 13.8 | >50 | >50 | >50 | >50 | >50 | >50 |
| MI369.A5 | A | 0.562 | 0.347 | 0.510 | 0.671 | 2.55 | 2.50 | 3.41 | 1.77 |
| MS208.A1 | A | 0.700 | 0.496 | 0.927 | 0.187 | 2.41 | 2.36 | 3.56 | 1.14 |
| Q23.17 | A | 1.50 | 1.59 | 1.18 | 0.461 | 6.34 | 6.98 | 5.85 | 1.60 |
| Q259.17 | A | 7.94 | 7.31 | 12.4 | 4.76 | 24.5 | 21.7 | 30.7 | 12.0 |
| Q769.d22 | A | 1.65 | 1.60 | 2.44 | 1.91 | 6.21 | 6.05 | 8.64 | 4.47 |
| Q769.h5 | A | 3.39 | 4.09 | 5.73 | 2.89 | 13.7 | 14.0 | 16.7 | 7.44 |

Figure 83

| | | | | | | | | | |
|---|---|---|---|---|---|---|---|---|---|
| Q842.d12 | A | 3.50 | 4.56 | 5.73 | 2.82 | 14.7 | 13.5 | 12.8 | 7.58 |
| QH209.14M.A2 | A | 1.22 | 1.03 | 2.20 | 1.30 | 5.63 | 5.10 | 10.0 | 4.09 |
| RW020.2 | A | 3.41 | 3.19 | 3.46 | 0.902 | 8.77 | 8.34 | 10.0 | 2.92 |
| UG037.8 | A | 0.210 | 0.250 | 0.273 | 0.048 | 0.931 | 0.844 | 1.33 | 0.353 |
| 246-F3.C10.2 | AC | 0.777 | 0.589 | 0.802 | 0.210 | 3.33 | 3.37 | 5.10 | 1.49 |
| 3301.V1.C24 | AC | 11.4 | 6.79 | 12.5 | 2.97 | 30.0 | 22.3 | 33.8 | 9.50 |
| 3589.V1.C4 | AC | 0.431 | 0.194 | 3.26 | 5.77 | 3.19 | 2.18 | 10.2 | 11.7 |
| 6540.v4.c1 | AC | 5.84 | 6.24 | 2.84 | 2.24 | 24.0 | 23.7 | 13.4 | 7.01 |
| 6545.V4.C1 | AC | 6.97 | 6.71 | 7.79 | 2.54 | 14.7 | 19.5 | 15.4 | 7.50 |
| 0815.V3.C3 | ACD | 1.31 | 0.944 | 2.04 | 0.491 | 5.04 | 4.72 | 7.05 | 1.81 |
| 8095.V1.C10 | ACD | 0.005 | 0.004 | 0.0006 | 0.0005 | 0.022 | 0.018 | 0.0010 | 0.004 |
| 3468.V1.C12 | AD | 0.560 | 0.480 | 2.00 | 0.381 | 2.98 | 2.45 | 7.45 | 2.04 |
| Q168.a2 | AD | 1.53 | 1.42 | 1.45 | 0.463 | 6.39 | 5.63 | 5.18 | 2.88 |
| Q461.e2 | AD | 1.90 | 1.65 | 2.45 | 2.29 | 6.48 | 5.68 | 8.68 | 4.68 |
| 620345.c1 | AE | 1.82 | 1.38 | 1.77 | 0.989 | 7.31 | 6.10 | 9.05 | 3.73 |
| BJOX009000.02.4 | AE | 0.743 | 0.726 | 0.580 | 0.251 | 4.00 | 3.33 | 5.03 | 1.47 |
| BJOX010000.06.2 | AE | 0.247 | 0.231 | 0.178 | 0.060 | 1.58 | 1.40 | 1.23 | 0.476 |
| BJOX025000.01.1 | AE | 0.431 | 0.479 | 0.751 | 0.228 | 3.05 | 3.03 | 4.77 | 1.54 |
| BJOX028000.10.3 | AE | 0.321 | 0.322 | 0.853 | 0.167 | 2.41 | 2.26 | 4.59 | 0.876 |
| C1080.c3 | AE | 0.360 | 0.310 | 0.521 | 0.108 | 1.54 | 1.59 | 2.50 | 0.613 |
| C2101.c1 | AE | 1.37 | 1.30 | 4.64 | 1.20 | 7.26 | 6.64 | 15.6 | 4.12 |
| C3347.c11 | AE | 0.086 | 0.098 | 0.045 | 0.019 | 0.377 | 0.376 | 0.274 | 0.089 |
| C4118.09 | AE | 0.857 | 0.851 | 1.66 | 0.421 | 6.07 | 5.90 | 11.6 | 2.30 |
| CM244.ec1 | AE | 0.477 | 0.413 | 0.863 | 0.365 | 3.33 | 3.00 | 6.02 | 1.46 |
| CNE3 | AE | 2.63 | 2.94 | 2.81 | 1.37 | 8.80 | 9.99 | 9.17 | 4.01 |
| CNE5 | AE | 1.85 | 1.40 | 1.54 | 1.17 | 8.25 | 6.84 | 7.34 | 2.52 |
| CNE55 | AE | 0.363 | 0.310 | 0.287 | 0.038 | 1.99 | 1.45 | 2.00 | 0.605 |
| CNE56 | AE | 0.175 | 0.170 | 0.212 | 0.060 | 0.944 | 0.715 | 1.18 | 0.314 |

Figure 83 cont.

| | | | | | | | | | | |
|---|---|---|---|---|---|---|---|---|---|---|
| CNE59 | AE | 0.013 | 0.017 | 0.0006 | 0.0010 | | 0.062 | 0.068 | 0.023 | 0.010 |
| CNE8 | AE | 0.310 | 0.322 | 0.045 | 0.140 | | 1.63 | 1.71 | 0.483 | 1.42 |
| M02138 | AE | 0.045 | 0.061 | 0.125 | 0.014 | | 0.162 | 0.172 | 0.669 | 0.126 |
| R1166.c1 | AE | 0.764 | 0.681 | 0.742 | 0.488 | | 2.87 | 2.70 | 3.70 | 2.02 |
| R2184.c4 | AE | 0.881 | 0.708 | 1.12 | 0.576 | | 3.99 | 3.25 | 5.40 | 2.20 |
| R3265.c6 | AE | 3.92 | 3.10 | 6.31 | 1.58 | | 15.7 | 14.8 | 21.9 | 9.28 |
| TH023.6 | AE | | | 0.0010 | 0.0003 | | | | 0.022 | 0.034 |
| TH966.8 | AE | 0.132 | 0.172 | 0.081 | 0.039 | | 0.590 | 0.502 | 0.611 | 0.291 |
| TH976.17 | AE | 0.437 | 0.480 | 0.762 | 0.392 | | 2.84 | 2.46 | 4.08 | 1.75 |

Figure 83 cont.

| Key | ($IC_{50}$/$IC_{80}$ in μg/ml) | | |
|---|---|---|---|
| <0.100 | 0.100-1.00 | 1.00-10.0 | >10.0 |

| | | $IC_{80}$ (μg/ml) | | | | $IC_{50}$ (μg/ml) | | | |
|---|---|---|---|---|---|---|---|---|---|
| Virus | Clade | DH511.11P | DH511.12P | DH511.2 | 10E8 | DH511.11P | DH511.12P | DH511.2 | 10E8 |
| 235-47 | AG | 0.332 | 0.313 | 0.361 | 0.244 | 1.38 | 1.28 | 1.61 | 0.786 |
| 242-14 | AG | 0.107 | 0.132 | 0.069 | 0.568 | 0.643 | 0.618 | 0.750 | 3.17 |
| 263-8 | AG | 0.279 | 0.263 | 0.407 | 0.229 | 1.98 | 1.85 | 2.63 | 0.991 |
| 269-12 | AG | 0.226 | 0.208 | 0.420 | 0.124 | 0.804 | 0.810 | 2.10 | 0.475 |
| 271-11 | AG | 0.672 | 0.601 | 1.23 | 0.891 | 6.43 | 5.33 | 7.60 | 4.34 |
| 928-28 | AG | 0.243 | 0.210 | 0.215 | 0.079 | 1.06 | 1.20 | 1.28 | 0.365 |
| DJ263.8 | AG | 0.052 | 0.046 | 0.190 | 0.009 | 0.348 | 0.344 | 0.903 | 0.100 |
| T250-4 | AG | 1.83 | 1.82 | 3.54 | 1.07 | 7.96 | 8.05 | 13.1 | 3.45 |
| T251-18 | AG | 5.12 | 3.57 | 7.52 | 0.666 | 12.2 | 10.1 | 20.5 | 2.55 |
| T253-11 | AG | 2.00 | 1.47 | 3.51 | 1.21 | 9.32 | 7.78 | 12.0 | 4.05 |
| T255-34 | AG | 0.284 | 0.274 | 1.40 | 0.228 | 2.22 | 1.83 | 6.11 | 1.14 |
| T257-31 | AG | 1.33 | 1.74 | 3.42 | 0.336 | 5.08 | 5.46 | 10.5 | 1.58 |
| T266-60 | AG | 0.803 | 1.10 | 0.953 | >50 | 3.58 | 3.91 | 4.78 | >50 |
| T278-50 | AG | 0.987 | 1.11 | 1.89 | 0.357 | 5.95 | 5.84 | 8.95 | 2.10 |
| T280-5 | AG | 14.9 | 13.6 | 4.21 | 0.715 | 40.4 | 29.0 | 17.0 | 4.77 |
| T33-7 | AG | 2.38 | 2.25 | 2.34 | 0.818 | 8.61 | 8.51 | 10.2 | 2.83 |
| 3988.25 | B | 0.261 | 0.220 | 0.284 | 0.070 | 0.961 | 0.756 | 0.883 | 0.293 |
| 5768.04 | B | 4.52 | 4.32 | 5.70 | 1.63 | 16.5 | 15.2 | 16.0 | 5.26 |
| 6101.10 | B | 0.035 | 0.018 | 0.012 | 0.0010 | 0.106 | 0.076 | 0.137 | 0.005 |
| 6535.3 | B | 0.755 | 0.603 | 1.39 | 0.190 | 4.81 | 3.67 | 7.62 | 1.28 |
| 7165.18 | B | 1.18 | 1.01 | 0.805 | 0.659 | 5.63 | 5.45 | 3.55 | 2.71 |
| 45_01dG5 | B | 0.803 | 0.678 | 0.753 | 0.106 | 4.64 | 4.21 | 4.87 | 0.703 |

Figure 83 cont.

| | | | | | | | | | |
|---|---|---|---|---|---|---|---|---|---|
| 89.6.DG | B | 0.989 | 0.970 | 0.676 | 0.318 | 3.43 | 3.24 | 2.23 | 1.48 |
| AC10.29 | B | 0.323 | 0.294 | 0.115 | 0.102 | 1.29 | 1.30 | 0.604 | 0.512 |
| ADA.DG | B | 0.160 | 0.151 | 0.042 | 0.055 | 0.757 | 0.649 | 0.482 | 0.358 |
| Bal.01 | B | 0.859 | 0.740 | 0.620 | 0.421 | 4.69 | 3.92 | 4.09 | 1.91 |
| BaL.26 | B | 0.786 | 0.908 | 2.57 | 0.518 | 4.45 | 4.41 | 11.0 | 2.39 |
| BG1168.01 | B | 0.424 | 0.544 | 0.528 | 0.396 | 1.44 | 1.63 | 2.38 | 1.48 |
| BL01.DG | B | | | 1.08 | 0.362 | | | 6.87 | 1.57 |
| BR07.DG | B | 0.287 | 0.237 | 0.106 | 0.118 | 1.18 | 1.08 | 1.03 | 0.445 |
| BX08.16 | B | | | 0.565 | 0.213 | | | 3.02 | 1.30 |
| CAAN.A2 | B | 2.75 | 2.18 | 5.29 | 1.45 | 13.8 | 11.1 | 16.3 | 5.70 |
| CNE10 | B | 0.047 | 0.040 | 0.121 | 0.014 | 0.415 | 0.401 | 0.932 | 0.169 |
| CNE12 | B | 0.395 | 0.363 | 0.509 | 0.301 | 1.63 | 1.73 | 2.46 | 1.09 |
| CNE14 | B | 0.725 | 0.697 | 0.950 | 0.151 | 3.37 | 3.82 | 4.24 | 0.649 |
| CNE4 | B | 0.152 | 0.155 | 0.279 | 0.059 | 1.14 | 1.05 | 2.45 | 0.437 |
| CNE57 | B | 0.233 | 0.361 | 0.120 | 0.059 | 1.14 | 1.67 | 1.28 | 0.317 |
| HO86.8 | B | 2.19 | 2.46 | 2.55 | 0.326 | 8.38 | 7.94 | 10.7 | 1.52 |
| HT593.1 | B | 0.125 | 0.116 | 0.140 | 0.049 | 0.678 | 0.643 | 0.780 | 0.285 |
| HXB2.DG | B | 0.007 | 0.008 | 0.0006 | 0.003 | 0.041 | 0.060 | 0.012 | 0.015 |
| JRCSF.JB | B | 1.99 | 1.75 | 2.04 | 0.429 | 8.51 | 7.59 | 9.61 | 1.89 |
| JRFL.JB | B | 0.948 | 0.791 | 0.862 | 0.174 | 3.95 | 3.48 | 5.40 | 0.768 |
| MN.3 | B | 0.005 | 0.007 | 0.0006 | 0.0003 | 0.019 | 0.025 | 0.004 | 0.0010 |
| PVO.04 | B | 2.10 | 1.72 | 2.32 | 1.60 | 8.94 | 7.91 | 15.9 | 6.43 |
| QH0515.01 | B | 4.18 | 3.55 | 4.97 | 2.25 | 13.6 | 13.4 | 15.8 | 5.54 |
| QH0692.42 | B | 1.47 | 1.20 | 2.03 | 0.531 | 5.71 | 5.30 | 11.1 | 2.35 |
| REJO.67 | B | 0.699 | 0.699 | 0.544 | 0.302 | 3.11 | 3.29 | 3.31 | 1.18 |
| RHPA.7 | B | 3.69 | 3.03 | 5.45 | 1.01 | 15.8 | 13.3 | 25.9 | 5.10 |
| SC422.8 | B | 1.01 | 1.00 | 1.63 | 0.343 | 3.79 | 3.87 | 4.60 | 1.15 |

Figure 83 cont.

| | | | | | | | | | |
|---|---|---|---|---|---|---|---|---|---|
| SF162.LS | B | 0.620 | 0.843 | 1.88 | 0.245 | 4.08 | 3.98 | 7.75 | 1.06 |
| SS1196.01 | B | 0.174 | 0.232 | 0.857 | 0.244 | 1.21 | 1.18 | 4.72 | 1.25 |
| THRO.18 | B | 0.326 | 0.291 | 0.711 | 0.092 | 1.52 | 1.26 | 2.39 | 0.587 |
| TRJO.58 | B | 5.73 | 4.78 | 3.86 | 1.13 | 22.3 | 19.8 | 17.7 | 4.18 |
| TRO.11 | B | 0.240 | 0.214 | 0.228 | 0.028 | 0.984 | 0.848 | 1.22 | 0.286 |
| WITO.33 | B | 0.186 | 0.240 | 0.314 | 0.031 | 0.876 | 0.873 | 1.60 | 0.305 |
| X2278.C2.B6 | B | 1.26 | 1.36 | 3.79 | 0.442 | 6.93 | 6.16 | 14.1 | 2.24 |
| YU2.DG | B | 4.54 | 5.06 | 8.00 | 1.17 | 37.7 | 32.1 | 50 | 5.46 |
| BJOX002000.03.2 | BC | 0.763 | 0.651 | 1.17 | 0.384 | 4.28 | 3.99 | 5.64 | 1.56 |
| CH038.12 | BC | 0.979 | 0.827 | 1.57 | 0.271 | 4.21 | 3.57 | 6.10 | 1.41 |
| CH070.1 | BC | 8.22 | 5.55 | 12.1 | 6.65 | 34.8 | 36.8 | 44.6 | 13.5 |

Figure 83 cont.

Key ($IC_{50}/IC_{80}$ in μg/ml)

| <0.100 | 0.100-1.00 | 1.00-10.0 | >10.0 |
|---|---|---|---|

| | | $IC_{50}$ (μg/ml) | | | | $IC_{80}$ (μg/ml) | | | |
|---|---|---|---|---|---|---|---|---|---|
| Virus | Clade | DH511.11P | DH511.12P | DH511.2 | 10E8 | DH511.11P | DH511.12P | DH511.2 | 10E8 |
| CH117.4 | BC | 0.412 | 0.353 | 0.458 | 0.270 | 1.58 | 1.57 | 2.29 | 0.859 |
| CH119.10 | BC | 0.598 | 0.656 | 0.916 | 0.591 | 3.49 | 3.35 | 5.48 | 2.36 |
| CH181.12 | BC | 1.04 | 1.02 | 0.969 | 0.754 | 3.97 | 3.46 | 3.99 | 2.79 |
| CNE15 | BC | 0.657 | 0.786 | 1.27 | 0.844 | 4.38 | 3.42 | 6.77 | 2.97 |
| CNE19 | BC | 0.392 | 0.264 | 0.383 | 0.251 | 2.27 | 2.33 | 3.05 | 1.11 |
| CNE20 | BC | 0.345 | 0.391 | 0.370 | 0.131 | 2.08 | 1.81 | 2.43 | 0.732 |
| CNE21 | BC | 0.873 | 0.808 | 1.09 | 0.979 | 5.24 | 5.26 | 8.40 | 3.25 |
| CNE40 | BC | 0.007 | 0.012 | 0.0006 | 0.0010 | 0.042 | 0.044 | 0.030 | 0.009 |
| CNE7 | BC | 0.170 | 0.206 | 0.119 | 0.130 | 0.911 | 0.814 | 0.672 | 0.603 |
| 286.36 | C | 0.497 | 0.232 | 3.22 | 1.19 | 3.50 | 2.77 | 14.0 | 5.00 |
| 288.38 | C | 0.883 | 0.715 | 2.19 | 0.435 | 3.72 | 3.90 | 8.90 | 3.08 |
| 0013095-2.11 | C | 0.018 | 0.025 | 0.014 | 0.009 | 0.184 | 0.156 | 0.229 | 0.077 |
| 001428-2.42 | C | 3.68 | 3.32 | 3.33 | 1.71 | 16.2 | 17.2 | 16.3 | 6.28 |
| 0077_V1.C16 | C | 2.00 | 2.74 | 5.56 | 1.86 | 10.8 | 11.3 | 36.0 | 7.11 |
| 00836-2.5 | C | 1.38 | 1.35 | 1.89 | 0.666 | 4.14 | 3.69 | 5.40 | 1.77 |
| 0921.V2.C14 | C | 2.56 | 1.59 | 5.33 | 0.908 | 7.42 | 4.47 | 18.4 | 3.03 |
| 16055-2.3 | C | 0.433 | 0.403 | 2.16 | 1.10 | 3.13 | 2.75 | 9.40 | 3.31 |
| 16845-2.22 | C | 0.014 | 0.020 | 0.016 | 0.020 | 0.121 | 0.139 | 0.238 | 0.172 |
| 16936-2.21 | C | 0.117 | 0.116 | 0.312 | 0.264 | 0.803 | 0.872 | 1.99 | 1.31 |
| 25710-2.43 | C | 0.056 | 0.078 | 0.046 | 0.064 | 0.303 | 0.374 | 0.408 | 0.304 |
| 25711-2.4 | C | 1.26 | 0.899 | 6.14 | 0.616 | 4.22 | 3.25 | 12.6 | 1.69 |
| 25925-2.22 | C | 0.567 | 0.443 | 0.504 | 0.402 | 2.83 | 1.92 | 2.95 | 1.53 |

Figure 83 cont.

| | | | | | | | | | |
|---|---|---|---|---|---|---|---|---|---|
| 26191-2.48 | C | 1.88 | 1.34 | 1.82 | 1.83 | 9.86 | 8.46 | 8.77 | 4.90 |
| 3168.V4.C10 | C | 2.16 | 1.14 | 2.52 | 2.83 | 12.3 | 8.42 | 19.3 | 8.18 |
| 3637.V5.C3 | C | 2.26 | 1.58 | 2.83 | 2.12 | 9.21 | 8.78 | 11.1 | 6.68 |
| 3873.V1.C24 | C | 7.38 | 6.39 | 10.0 | 5.51 | 24.1 | 19.6 | 13.8 | 15.7 |
| 426c | C | 0.821 | 0.497 | 2.22 | 0.445 | 2.98 | 2.12 | 7.87 | 1.60 |
| 6322.V4.C1 | C | 2.40 | 1.75 | 2.90 | 0.923 | 11.1 | 9.07 | 9.72 | 3.68 |
| 6471.V1.C16 | C | 8.01 | 5.50 | 11.0 | 4.98 | 23.2 | 29.2 | 41.9 | 14.9 |
| 6631.V3.C10 | C | 2.96 | 2.62 | 7.08 | 0.934 | 11.3 | 9.65 | 15.5 | 3.36 |
| 6644.V2.C33 | C | 0.502 | 0.498 | 0.229 | 0.013 | 1.73 | 1.65 | 1.14 | 0.124 |
| 6785.V5.C14 | C | 1.74 | 1.96 | 1.58 | 0.701 | 6.48 | 6.03 | 6.70 | 2.42 |
| 6838.V1.C35 | C | 0.562 | 0.634 | 0.813 | 0.292 | 2.30 | 2.50 | 3.67 | 1.01 |
| 96ZM651.02 | C | 0.094 | 0.094 | 0.035 | 0.033 | 0.396 | 0.345 | 0.358 | 0.177 |
| BR025.9 | C | 1.11 | 0.965 | 1.10 | 0.307 | 3.85 | 3.39 | 5.33 | 1.11 |
| CAP210.E8 | C | 0.818 | 0.619 | 0.911 | 0.474 | 2.46 | 2.35 | 3.37 | 2.01 |
| CAP244.D3 | C | 0.538 | 0.601 | 1.13 | 0.369 | 2.18 | 2.23 | 4.56 | 1.48 |
| CAP256.206.C9 | C | 0.585 | 0.545 | 0.779 | 0.713 | 2.93 | 2.93 | 3.92 | 2.97 |
| CAP45.G3 | C | 1.18 | 1.23 | 2.84 | 0.722 | 5.04 | 4.61 | 9.41 | 3.41 |
| Ce1176.A3 | C | 0.458 | 0.489 | 0.998 | 0.252 | 1.95 | 1.79 | 4.13 | 1.15 |
| CE703010217.B6 | C | 0.121 | 0.107 | 0.159 | 0.096 | 0.811 | 0.653 | 0.944 | 0.679 |
| CNE30 | C | 1.42 | 1.03 | 3.30 | 0.456 | 5.95 | 4.32 | 16.3 | 2.29 |
| CNE31 | C | 2.00 | 1.64 | 5.23 | 1.32 | 5.87 | 5.68 | 11.5 | 3.57 |
| CNE53 | C | 0.240 | 0.214 | 0.208 | 0.213 | 1.18 | 1.20 | 1.41 | 1.01 |
| CNE58 | C | 0.202 | 0.112 | 0.453 | 0.229 | 1.07 | 0.776 | 2.98 | 1.09 |
| DU123.06 | C | 0.145 | 0.128 | 0.250 | 0.132 | 0.665 | 0.604 | 0.948 | 0.423 |
| DU151.02 | C | 0.591 | 0.480 | 0.928 | 0.461 | 2.67 | 2.32 | 3.60 | 1.71 |
| DU156.12 | C | 0.037 | 0.039 | 0.019 | 0.023 | 0.177 | 0.165 | 0.158 | 0.120 |
| DU172.17 | C | 0.161 | 0.143 | 7.22 | 0.057 | 0.789 | 0.721 | 19.9 | 0.238 |

Figure 83 cont.

| | | | | | | | | | |
|---|---|---|---|---|---|---|---|---|---|
| DU422.01 | C | 0.583 | 0.575 | 0.821 | 0.224 | 2.53 | 2.05 | 3.95 | 0.812 |
| MW965.26 | C | | | 0.0006 | 0.0010 | | | 0.002 | 0.007 |
| SO18.18 | C | 1.43 | 1.54 | 7.52 | 1.60 | 7.80 | 6.63 | 20.7 | 4.48 |
| TV1.29 | C | 0.618 | 0.487 | 0.802 | 0.248 | 1.75 | 1.40 | 2.66 | 0.719 |
| TZA125.17 | C | 0.466 | 0.407 | 0.750 | 0.217 | 1.93 | 2.12 | 4.05 | 1.19 |
| TZBD.02 | C | 2.40 | 2.17 | 2.44 | 1.41 | 8.18 | 7.56 | 7.78 | 4.31 |
| ZA012.29 | C | 2.29 | 1.73 | 3.66 | 1.47 | 7.59 | 7.01 | 11.3 | 4.12 |
| ZM106.9 | C | 5.40 | 4.17 | 5.68 | >50 | 13.8 | 17.6 | 21.8 | >50 |
| ZM109.4 | C | 0.296 | 0.223 | 0.715 | 0.161 | 1.99 | 1.70 | 4.64 | 1.07 |
| ZM135.10a | C | 0.156 | 0.106 | 0.246 | 0.033 | 1.05 | 0.913 | 2.20 | 0.408 |
| ZM176.66 | C | 0.563 | 0.443 | 1.10 | 0.267 | 3.21 | 2.80 | 5.65 | 1.73 |

Figure 83 cont.

Key ($IC_{50}/IC_{80}$ in μg/ml)

| <0.100 | 0.100-1.00 | 1.00-10.0 | >10.0 |
|---|---|---|---|

| | | $IC_{50}$ (μg/ml) | | | | $IC_{80}$ (μg/ml) | | | |
|---|---|---|---|---|---|---|---|---|---|
| Virus | Clade | DH511.11P | DH511.12P | DH511.2 | 10E8 | DH511.11P | DH511.12P | DH511.2 | 10E8 |
| ZM197.7 | C | 0.098 | 0.109 | 0.232 | 0.056 | 0.523 | 0.520 | 1.16 | 0.369 |
| ZM214.15 | C | 2.52 | 1.84 | 5.39 | 2.22 | 9.67 | 6.40 | 15.5 | 5.98 |
| ZM215.8 | C | 0.077 | 0.066 | 0.107 | 0.044 | 0.343 | 0.246 | 0.591 | 0.230 |
| ZM233.6 | C | 0.253 | 0.192 | 0.549 | 0.270 | 0.983 | 1.08 | 2.33 | 0.737 |
| ZM249.1 | C | 1.78 | 1.66 | 1.58 | 0.830 | 4.94 | 5.11 | 5.78 | 2.27 |
| ZM53.12 | C | 8.95 | 8.14 | 6.11 | 2.62 | 22.2 | 20.3 | 18.5 | 6.72 |
| ZM55.28a | C | 6.32 | 4.10 | 7.88 | 2.34 | 15.8 | 17.0 | 19.8 | 6.78 |
| 3326.V4.C3 | CD | 1.89 | 1.64 | 3.62 | 1.40 | 8.13 | 6.90 | 13.3 | 4.29 |
| 3337.V2.C6 | CD | 1.06 | 0.763 | 1.50 | 1.09 | 6.34 | 4.46 | 5.60 | 4.87 |
| 3817.v2.c59 | CD | 2.08 | 1.84 | 2.12 | 0.229 | 8.07 | 6.31 | 6.33 | 1.43 |
| 191821.E6.1 | D | 2.48 | 2.47 | 6.82 | 1.91 | 7.70 | 6.83 | 18.3 | 5.89 |
| 231965.c1 | D | 13.6 | 12.6 | 19.6 | 11.0 | 33.1 | 31.8 | >50 | 20.4 |
| 247-23 | D | 0.652 | 0.500 | 0.618 | 0.344 | 2.35 | 2.08 | 3.24 | 1.29 |
| 3016.v5.c45 | D | 0.826 | 0.749 | 0.607 | 0.710 | 3.12 | 2.90 | 3.42 | 2.17 |
| 57128.vrc15 | D | 0.417 | 0.496 | 0.352 | 0.212 | 1.96 | 2.14 | 2.59 | 1.50 |
| 6405.v4.c34 | D | 0.981 | 0.870 | 1.93 | 0.461 | 4.91 | 4.20 | 6.76 | 1.80 |
| A03349M1.vrc4a | D | 0.508 | 0.532 | 0.402 | 0.270 | 1.33 | 1.39 | 1.32 | 0.663 |
| A07412M1.vrc12 | D | 0.425 | 0.375 | 0.851 | 0.140 | 2.45 | 2.13 | 4.55 | 0.873 |
| NKU3006.ec1 | D | 0.625 | 0.713 | 0.989 | 0.673 | 2.72 | 2.69 | 4.86 | 2.46 |
| UG021.16 | D | | | 0.100 | 0.046 | | | 0.774 | 0.362 |
| UG024.2 | D | 0.109 | 0.106 | 0.154 | 0.063 | 0.451 | 0.523 | 0.745 | 0.241 |
| P0402.c2.11 | G | 0.151 | 0.149 | 0.094 | 0.057 | 0.953 | 1.04 | 0.815 | 0.460 |
| P1981.C5.3 | G | 0.071 | 0.073 | 0.020 | 0.024 | 0.280 | 0.221 | 0.211 | 0.124 |

Figure 83 cont.

| | | | | | | | | | | |
|---|---|---|---|---|---|---|---|---|---|---|
| X1193.c1 | G | 0.324 | 0.360 | 0.746 | 0.341 | | 1.46 | 1.54 | 3.28 | 1.15 |
| X1254.c3 | G | 1.34 | 1.06 | 2.77 | 3.67 | | 6.12 | 6.13 | 14.5 | 15.7 |
| X1632.S2.B10 | G | 0.728 | 0.675 | 0.925 | 0.387 | | 3.47 | 3.22 | 3.93 | 1.76 |
| X2088.c9 | G | >50 | >50 | >50 | >50 | | >50 | >50 | >50 | >50 |
| X2131.C1.B5 | G | 0.079 | 0.089 | 0.118 | 0.039 | | 0.382 | 0.386 | 0.611 | 0.175 |
| SIVmac251.30.SG3 | NA | 10.3 | 29.9 | >50 | >50 | | >50 | >50 | >50 | >50 |
| SVA.MLV | NA | >50 | >50 | >50 | >50 | | >50 | >50 | >50 | >50 |

| | DH511.11P | DH511.12P | DH511.2 | 10E8 | | DH511.11P | DH511.12P | DH511.2 | 10E8 |
|---|---|---|---|---|---|---|---|---|---|
| Number of Viruses | 203 | 203 | 208 | 208 | | 203 | 203 | 208 | 208 |
| Total Viruses Neutralized | | | | | | | | | |
| IC50/IC80 <50ug/ml | 202 | 202 | 206 | 203 | | 201 | 201 | 203 | 203 |
| IC50/IC80 <10ug/ml | 196 | 198 | 198 | 202 | | 169 | 172 | 147 | 193 |
| IC50/IC80 <1.0ug/ml | 122 | 123 | 103 | 152 | | 37 | 37 | 33 | 61 |
| IC50/IC80 <0.1ug/ml | 19 | 18 | 20 | 42 | | 5 | 6 | 7 | 10 |
| IC50/IC80 <0.01ug/ml | 4 | 3 | 7 | 10 | | 0 | 0 | 3 | 5 |
| Percent of Viruses Neutralized | | | | | | | | | |
| IC50/IC80 <50ug/ml | 100 | 100 | 99 | 98 | | 99 | 99 | 98 | 98 |
| IC50/IC80 <10ug/ml | 97 | 98 | 95 | 97 | | 83 | 85 | 71 | 93 |
| IC50/IC80 <1.0ug/ml | 60 | 61 | 50 | 73 | | 18 | 18 | 16 | 29 |
| IC50/IC80 <0.1ug/ml | 9 | 9 | 10 | 20 | | 2 | 3 | 3 | 5 |
| IC50/IC80 <0.01ug/ml | 2 | 1 | 3 | 5 | | 0 | 0 | 1 | 2 |
| | | | | | | | | | |
| Median IC50/IC80 | 0.764 | 0.698 | 1.04 | 0.392 | | 3.49 | 3.33 | 5.07 | 1.69 |
| Geometric Mean | 0.684 | 0.634 | 0.792 | 0.299 | | 3.02 | 2.80 | 3.73 | 1.34 |

Figure 83 cont.

| Peptide | Sequence |
|---|---|
| MPR.03-biotin | KKK-NEQELLELDKWASLWNWFDITNWLWYIR-KKK-biotin |
| MPR.03 N671A-biotin | KKK-NEQELLELDKWASLWAWFDITNWLWYIR-KKK-biotin |
| MPR.03 W672A-biotin | KKK-NEQELLELDKWASLWNAFDITNWLWYIR-KKK-biotin |
| MPR.03 F673A-biotin | KKK-NEQELLELDKWASLWNWADITNWLWYIR-KKK-biotin |
| MPR.03 D674A-biotin | KKK-NEQELLELDKWASLWNWFAITNWLWYIR-KKK-biotin |
| MPR.03 I675A-biotin | KKK-NEQELLELDKWASLWNWFDATNWLWYIR-KKK-biotin |
| MPR.03 T676A-biotin | KKK-NEQELLELDKWASLWNWFDIANWLWYIR-KKK-biotin |
| MPR.03 N677A-biotin | KKK-NEQELLELDKWASLWNWFDITAWLWYIR-KKK-biotin |
| MPR.03 W678A-biotin | KKK-NEQELLELDKWASLWNWFDITNALWYIR-KKK-biotin |
| MPR.03 L679A-biotin | KKK-NEQELLELDKWASLWNWFDITNWAWYIR-KKK-biotin |
| MPR.03 W680A-biotin | KKK-NEQELLELDKWASLWNWFDITNWLAYIR-KKK-biotin |
| MPR.03 Y681A-biotin | KKK-NEQELLELDKWASLWNWFDITNWLWAIR-KKK-biotin |
| MPR.03 I682A-biotin | KKK-NEQELLELDKWASLWNWFDITNWLWYAR-KKK-biotin |
| MPR.03 R683A-biotin | KKK-NEQELLELDKWASLWNWFDITNWLWYIA-KKK-biotin |

Figure 84

| Virus | Sequence |
|---|---|
| COT6.15 WT | QELLALDSWKNLWSWFDITKWLWYIKIFI |
| A662G | QELLGLDSWKNLWSWFDITKWLWYIKIFI |
| L663A | QELLAADSWKNLWSWFDITKWLWYIKIFI |
| D664A | QELLALASWKNLWSWFDITKWLWYIKIFI |
| S665A | QELLALDAWKNLWSWFDITKWLWYIKIFI |
| W666A | QELLALDSAKNLWSWFDITKWLWYIKIFI |
| K667A | QELLALDSWANLWSWFDITKWLWYIKIFI |
| N668A | QELLALDSWKALWSWFDITKWLWYIKIFI |
| L669A | QELLALDSWKNAWSWFDITKWLWYIKIFI |
| W670A | QELLALDSWKNLASWFDITKWLWYIKIFI |
| S671A | QELLALDSWKNLWAWFDITKWLWYIKIFI |
| W672A | QELLALDSWKNLWSAFDITKWLWYIKIFI |
| F673A | QELLALDSWKNLWSWADITKWLWYIKIFI |
| D674A | QELLALDSWKNLWSWFAITKWLWYIKIFI |
| D674S | QELLALDSWKNLWSWFSITKWLWYIKIFI |
| D674N | QELLALDSWKNLWSWFNITKWLWYIKIFI |
| I675A | QELLALDSWKNLWSWFDATKWLWYIKIFI |
| T676A | QELLALDSWKNLWSWFDIAKWLWYIKIFI |
| K677A | QELLALDSWKNLWSWFDITAWLWYIKIFI |
| W678A | QELLALDSWKNLWSWFDITKALWYIKIFI |
| L679A | QELLALDSWKNLWSWFDITKWAWYIKIFI |
| W680A | QELLALDSWKNLWSWFDITKWLAYIKIFI |

Figure 85

$IC_{50}$ (μg/ml) in TZM-bl cells[1]

| Antibody | COT6 WT | A662G | L663A | D664A | S665A | W666A | K667A | N668A | L669A | W670A | S671A |
|---|---|---|---|---|---|---|---|---|---|---|---|
| DH511.1 | 0.21 | <0.023 | <0.023 | 0.36 | 0.08 | <0.023 | <0.023 | 0.62 | <0.023 | 0.17 | <0.023 |
| DH511.2 | 0.10 | <0.023 | <0.023 | 0.12 | 0.03 | <0.023 | <0.023 | 0.24 | <0.023 | <0.023 | <0.023 |
| DH511.3 | 0.30 | <0.023 | <0.023 | 0.44 | 0.18 | <0.023 | 0.09 | 0.95 | 0.04 | 0.34 | 0.06 |
| DH511.4 | 0.32 | <0.023 | <0.023 | 0.58 | 0.22 | <0.023 | 0.10 | 0.84 | <0.023 | 0.35 | 0.09 |
| DH511.5 | 0.46 | 0.05 | 0.03 | 0.81 | 0.25 | <0.023 | 0.08 | 1.2 | 0.08 | 0.38 | 0.10 |
| DH511.6 | 0.40 | 0.04 | <0.023 | 0.44 | 0.23 | <0.023 | 0.08 | 1.3 | 0.07 | 0.45 | 0.10 |
| DH511.11P | 0.08 | <0.023 | <0.023 | 0.12 | 0.05 | <0.023 | <0.023 | 0.25 | <0.023 | 0.06 | <0.023 |
| DH511.12P | 0.09 | <0.023 | <0.023 | 0.12 | 0.05 | <0.023 | <0.023 | 0.26 | <0.023 | 0.05 | <0.023 |
| 2F5 | >50 | >50 | >50 | >50 | >50 | >50 | >50 | >50 | >50 | >50 | >50 |
| 10E8 | 0.03 | <0.023 | <0.023 | 0.04 | <0.023 | <0.023 | <0.023 | 0.10 | <0.023 | <0.023 | <0.023 |
| 4E10 | 0.54 | 0.04 | <0.023 | 0.89 | 0.30 | <0.023 | 0.18 | 2.2 | 0.06 | 0.57 | 0.19 |
| CH01-31 | 0.12 | 0.14 | 0.10 | 0.13 | 0.13 | 0.04 | 0.10 | 0.10 | 0.06 | 0.09 | 0.11 |

[1]Values are the antibody concentration (μg/ml)at which relative luminescence units (RLUs) were reduced 50% compared to virus control wells (no test sample).

Note: Values in bold are considered positive for neutralizing antibody activity when compared against background.

Values highlighted in yellow indicate resistance to neutralization.

Figure 86

$IC_{50}$ (μg/ml) in TZM-bl cells[1]

| Antibody | D664A | F673A | D674A | D674S | I675A | T676A | K677A | W678A | L679A | W680A | D674N |
|---|---|---|---|---|---|---|---|---|---|---|---|
| DH511.1 | >50* | 1.0 * | 2.5* | 1.9* | <0.023 | 0.09 | <0.023 | <0.023 | 0.35 | <0.023 | 0.21 |
| DH511.2 | 0.19 | 0.31 | 0.71* | 0.55* | <0.023 | <0.023 | <0.023 | <0.023 | <0.023 | <0.023 | 0.07 |
| DH511.3 | >50* | 1.6* | 4.2* | 3.4* | <0.023 | 0.15 | 0.05 | 0.03 | 0.97 | <0.023 | 0.44 |
| DH511.4 | 15* | 1.4* | 5.5* | 3.6* | 0.03 | 0.14 | 0.06 | 0.06 | 0.14 | 0.05 | 0.71 |
| DH511.5 | 31* | 1.6* | 8.2* | 2.0* | 0.06 | 0.24 | 0.14 | 0.10 | 0.19 | 0.10 | 0.72 |
| DH511.6 | >50* | 1.9* | 7.1* | 5.1* | 0.03 | 0.15 | 0.09 | 0.08 | 2.6 | 0.05 | 1.0 |
| DH511.11P | 1.5* | 0.27 | 0.56* | 0.27 | <0.023 | <0.023 | <0.023 | <0.023 | 0.03 | <0.023 | 0.05 |
| DH511.12P | 0.87* | 0.24 | 0.53* | 0.23 | <0.023 | 0.02 | <0.023 | <0.023 | 0.03 | <0.023 | 0.04 |
| 2F5 | >50 | >50 | >50 | >50 | >50 | >50 | >50 | >50 | >50 | >50 | >50 |
| 10E8 | 10* | 0.72* | 0.30* | 0.18* | <0.023 | <0.023 | <0.023 | <0.023 | <0.023 | <0.023 | 0.03 |
| 4E10 | >50* | >50* | 5.5* | 4.1* | 0.09 | >50* | 0.16 | 0.07 | 0.53 | 17* | 0.60 |
| CH01-31 | 0.07 | 0.07 | 0.09 | 0.10 | 0.09 | 0.07 | 0.07 | 0.06 | 0.10 | 0.08 | 0.11 |

[1]Values are the antibody concentration (μg/ml)at which relative luminescence units (RLUs) were reduced 50% compared to virus control wells (no test sample).

Note: Values in bold are considered positive for neutralizing antibody activity when compared against background.

Values marked with asterix (*) indicate resistance to neutralization.

Figure 86 cont.

| Antibody | Peptide | gp41 Residue Range | Peptide Sequence |
|---|---|---|---|
| DH511.1 | $MPER_{656-683}$ | 656-683 | $RRR^{656}NEQELLELDKWASLWNWFDITNWLWYIR^{683}RRR$ |
| DH511.2 | MPR.03.DN4 | 662-683 | $KKK^{662}ELDKWASLWNWFDITNWLWYIR^{683}KKK$ |
| DH511.2 | MPR.03.DN14 | 670-683 | $KKK\ ^{670}WNWFDITNWLWYIR^{683}\ KKK$ |

Figure 87

| | DH511.1 Fab + $MPER_{656-683}$ | DH511.2 Fab + $MPER_{662-683}$ | DH511.2 Fab + $MPER_{670-683}$ | DH511.4 Fab |
|---|---|---|---|---|
| **PDB Accession Code** | | | | |
| **Data Collection** | | | | |
| Space group | I222 | C2 | C2 | P1 |
| Cell constants | | | | |
| *a*, *b*, *c* (Å) | 64.1, 134.0, 179.6 | 109.5, 75.8, 122.8 | 110.1, 75.6, 123.4 | 42.5, 48.2, 57.1 |
| a, b, g (°) | 90.0, 90.0, 90.0 | 90.0, 94.5, 90.0 | 90.0 94.1 90.0 | 86.1, 82.3, 82.3 |
| Wavelength (Å) | 1.0000 | 1.0000 | 1.0000 | 1.0000 |
| Resolution (Å) | 50 - 2.70 (2.80 - 2.70) | 50 - 2.65 (2.74 - 2.65) | 50 - 2.17 (2.23 - 2.17) | 50 - 1.50 (1.53 - 1.50) |
| $R_{merge}$ | 0.133 (0.809) | 0.085 (0.467) | 0.077 (0.483) | 0.055 (0.519) |
| *I* / s*I* | 12.1 (1.66) | 6.54 (1.70) | 15.6 (1.65) | 16.1 (3.7) |
| Completeness (%) | 99.7 (98.4) | 96.9 (97.9) | 93.5 (52.5) | 93.3 (93.1) |
| Multiplicity | 6.3 (4.6) | 1.7 (1.7) | 5.1 (2.6) | 2.5 (2.3) |
| **Refinement** | | | | |
| Resolution (Å) | 37.3 - 2.74 (2.83 - 2.74) | 40.8 - 2.64 (2.73 - 2.64) | 42.5 - 2.17 (2.24 - 2.17) | 27.3 – 1.50 (1.53 – 1.50) |
| Unique reflections | 20466 (1711) | 28726 (2832) | 51031 (3495) | 64453 (3551) |
| $R_{work}$ / $R_{free}$ (%) | 21.28/25.57 | 25.61/28.99 | 19.03/22.63 | 18.80/21.11 |
| No. atoms | 3750 | 7332 | 7403 | 3655 |
| Protein | 3723 | 7124 | 7135 | 3464 |
| Ligand/ion | - | 2 | 1 | 0 |

Figure 88

| | | | | |
|---|---|---|---|---|
| Water | 27 | 206 | 267 | 191 |
| *B*-factors (Å$^2$) | 80.5 | 58.5 | 55.8 | 28.2 |
| Protein | 80.6 | 58.9 | 56.0 | 28.0 |
| Ligand/ion | - | 61.6 | 29.6 | - |
| Water | 57.7 | 45.8 | 51.0 | 31.3 |
| R.m.s. deviations | | | | |
| Bond lengths (Å) | 0.003 | 0.002 | 0.006 | 0.006 |
| Bond angles (°) | 0.68 | 0.62 | 0.88 | 1.121 |
| Ramachandran | | | | |
| Most favored regions (%) | 94.0 | 97.0 | 98.0 | 98.5 |
| Additional allowed regions (%) | 5.37 | 3.0 | 2 | 1.6 |
| Disallowed regions (%) | 0.63 | 0 | 0 | 0 |

Numbers in parentheses represent highest resolution shell.

Figure 88 cont.

Antibody contact interfaces by HCDR loop (Å$^2$)

| | DH511.1 + $MPER_{656-683}$ | DH511.2 + $MPER_{662-683}$ | DH511.12P + $MPER_{662-683}$ |
|---|---|---|---|
| HCDR1 | 207.53 | 138.02 | 130.8 |
| HCDR2 | 122.54 | 148.85 | 106.55 |
| FWR3 | 58.57 | 3.25 | 0 |
| HCDR3 | 362.48 | 391.28 | 403.71 |
| Total | 751.12 | 681.4 | 641.06 |

Figure 89

Hydrogen bonds

| | Atom 1: Atom no. | Atom 1: Atom name | Atom 1: Res name | Atom 1: Res no. | Atom 1: Chain | | Atom 2: Atom no. | Atom 2: Atom name | Atom 2: Res name | Atom 2: Res no. | Atom 2: Chain | Distance |
|---|---|---|---|---|---|---|---|---|---|---|---|---|
| 1. | 3574 | O | TRP | 670 | A | <--> | 214 | ND2 | ASN | 31 | H | 3.14 |
| 2. | 3625 | OD2 | ASP | 674 | A | <--> | 397 | NH2 | ARG | 53 | H | 3.32 |
| 3. | 3624 | OD1 | ASP | 674 | A | <--> | 414 | NZ | LYS | 55 | H | 2.97 |
| 4. | 3712 | NE | ARG | 683 | A | <--> | 873 | O | TRP | 113 | H | 3.15 |
| 5. | 3715 | NH2 | ARG | 683 | A | <--> | 873 | O | TRP | 113 | H | 3.09 |

Salt bridges

| | Atom 1: Atom no. | Atom 1: Atom name | Atom 1: Res name | Atom 1: Res no. | Atom 1: Chain | | Atom 2: Atom no. | Atom 2: Atom name | Atom 2: Res name | Atom 2: Res no. | Atom 2: Chain | Distance |
|---|---|---|---|---|---|---|---|---|---|---|---|---|
| 1. | 3625 | OD2 | ASP | 674 | A | <--> | 397 | NH2 | ARG | 53 | H | 3.32 |
| 2. | 3624 | OD1 | ASP | 674 | A | <--> | 414 | NZ | LYS | 55 | H | 2.97 |

Figure 90

Non-bonded contacts

| Distance | Atom 1 Atom no. | Atom 1 Atom name | Atom 1 Res name | Atom 1 Res no. | Atom 1 Chain | | Atom 2 Atom no. | Atom 2 Atom name | Atom 2 Res name | Atom 2 Res no. | Atom 2 Chain | |
|---|---|---|---|---|---|---|---|---|---|---|---|---|
| 1. | 3460 | CB | ALA | 656 | A | <--> | 184 | CA | THR | 28 | H | 3.78 |
| 2. | 3460 | CB | ALA | 656 | A | <--> | 187 | CB | THR | 28 | H | 3.80 |
| 3. | 3460 | CB | ALA | 656 | A | <--> | 188 | OG1 | THR | 28 | H | 3.30 |
| 4. | 3460 | CB | ALA | 656 | A | <--> | 189 | CG2 | THR | 28 | H | 3.74 |
| 5. | 3569 | CD1 | LEU | 669 | A | <--> | 189 | CG2 | THR | 28 | H | 3.61 |
| 6. | 3467 | CD | GLU | 657 | A | <--> | 205 | CB | SER | 30 | H | 3.85 |
| 7. | 3468 | OE1 | GLU | 657 | A | <--> | 205 | CB | SER | 30 | H | 3.82 |
| 8. | 3466 | CG | GLU | 657 | A | <--> | 206 | OG | SER | 30 | H | 3.85 |
| 9. | 3467 | CD | GLU | 657 | A | <--> | 206 | OG | SER | 30 | H | 3.67 |
| 10. | 3589 | CB | ASN | 671 | A | <--> | 210 | O | ASN | 31 | H | 3.89 |
| 11. | 3592 | ND2 | ASN | 671 | A | <--> | 210 | O | ASN | 31 | H | 3.89 |
| 12. | 3569 | CD1 | LEU | 669 | A | <--> | 211 | CB | ASN | 31 | H | 3.70 |
| 13. | 3567 | CB | LEU | 669 | A | <--> | 212 | CG | ASN | 31 | H | 3.68 |
| 14. | 3589 | CB | ASN | 671 | A | <--> | 212 | CG | ASN | 31 | H | 3.89 |
| 15. | 3567 | CB | LEU | 669 | A | <--> | 213 | OD1 | ASN | 31 | H | 3.68 |
| 16. | 3573 | C | TRP | 670 | A | <--> | 213 | OD1 | ASN | 31 | H | 3.87 |
| 17. | 3585 | N | ASN | 671 | A | <--> | 213 | OD1 | ASN | 31 | H | 3.90 |

Figure 90 cont.

| | | | | | | | | | | | | |
|---|---|---|---|---|---|---|---|---|---|---|---|---|
| 18. | 3589 | CB | ASN | 671 | A | <--> | 213 | OD1 | ASN | 31 | H | 3.64 |
| 19. | 3573 | C | TRP | 670 | A | <--> | 214 | ND2 | ASN | 31 | H | 3.60 |
| 20. | 3574 | O | TRP | 670 | A | <--> | 214 | ND2 | ASN | 31 | H | 3.14 |
| 21. | 3589 | CB | ASN | 671 | A | <--> | 214 | ND2 | ASN | 31 | H | 3.63 |
| 22. | 3604 | CZ2 | TRP | 672 | A | <--> | 229 | CD2 | TRP | 33 | H | 3.66 |
| 23. | 3604 | CZ2 | TRP | 672 | A | <--> | 232 | CE3 | TRP | 33 | H | 3.83 |
| 24. | 3612 | CG | PHE | 673 | A | <--> | 233 | CZ2 | TRP | 33 | H | 3.75 |
| 25. | 3613 | CD1 | PHE | 673 | A | <--> | 233 | CZ2 | TRP | 33 | H | 3.69 |
| 26. | 3615 | CE1 | PHE | 673 | A | <--> | 233 | CZ2 | TRP | 33 | H | 3.84 |
| 27. | 3606 | CH2 | TRP | 672 | A | <--> | 234 | CZ3 | TRP | 33 | H | 3.87 |
| 28. | 3615 | CE1 | PHE | 673 | A | <--> | 235 | CH2 | TRP | 33 | H | 3.83 |
| 29. | 3590 | CG | ASN | 671 | A | <--> | 393 | CD | ARG | 53 | H | 3.88 |
| 30. | 3592 | ND2 | ASN | 671 | A | <--> | 393 | CD | ARG | 53 | H | 3.35 |
| 31. | 3590 | CG | ASN | 671 | A | <--> | 394 | NE | ARG | 53 | H | 3.83 |
| 32. | 3591 | OD1 | ASN | 671 | A | <--> | 394 | NE | ARG | 53 | H | 3.78 |
| 33. | 3592 | ND2 | ASN | 671 | A | <--> | 394 | NE | ARG | 53 | H | 3.80 |
| 34. | 3590 | CG | ASN | 671 | A | <--> | 395 | CZ | ARG | 53 | H | 3.54 |
| 35. | 3591 | OD1 | ASN | 671 | A | <--> | 395 | CZ | ARG | 53 | H | 3.08 |
| 36. | 3592 | ND2 | ASN | 671 | A | <--> | 395 | CZ | ARG | 53 | H | 3.87 |
| 37. | 3625 | OD2 | ASP | 674 | A | <--> | 395 | CZ | ARG | 53 | H | 3.74 |
| 38. | 3590 | CG | ASN | 671 | A | <--> | 396 | NH1 | ARG | 53 | H | 3.20 |
| 39. | 3591 | OD1 | ASN | 671 | A | <--> | 396 | NH1 | ARG | 53 | H | 2.46 |
| 40. | 3592 | ND2 | ASN | 671 | A | <--> | 396 | NH1 | ARG | 53 | H | 3.50 |
| 41. | 3623 | CG | ASP | 674 | A | <--> | 396 | NH1 | ARG | 53 | H | 3.90 |
| 42. | 3624 | OD1 | ASP | 674 | A | <--> | 396 | NH1 | ARG | 53 | H | 3.86 |
| 43. | 3625 | OD2 | ASP | 674 | A | <--> | 396 | NH1 | ARG | 53 | H | 3.39 |

Figure 90 cont.

| | | | | | | | | | | | | |
|---|---|---|---|---|---|---|---|---|---|---|---|---|
| 44. | 3566 | O | LEU | 669 | A | <--> | 397 | NH2 | ARG | 53 | H | 3.62 |
| 45. | 3591 | OD1 | ASN | 671 | A | <--> | 397 | NH2 | ARG | 53 | H | 3.67 |
| 46. | 3625 | OD2 | ASP | 674 | A | <--> | 397 | NH2 | ARG | 53 | H | 3.32 |
| 47. | 3566 | O | LEU | 669 | A | <--> | 413 | CE | LYS | 55 | H | 3.70 |
| 48. | 3623 | CG | ASP | 674 | A | <--> | 414 | NZ | LYS | 55 | H | 3.86 |
| 49. | 3624 | OD1 | ASP | 674 | A | <--> | 414 | NZ | LYS | 55 | H | 2.97 |
| 50. | 3614 | CD2 | PHE | 673 | A | <--> | 420 | CG | ASP | 56 | H | 3.76 |
| 51. | 3614 | CD2 | PHE | 673 | A | <--> | 421 | OD1 | ASP | 56 | H | 3.84 |
| 52. | 3614 | CD2 | PHE | 673 | A | <--> | 422 | OD2 | ASP | 56 | H | 3.58 |
| 53. | 3598 | CG | TRP | 672 | A | <--> | 788 | N | GLY | 103 | H | 3.62 |
| 54. | 3599 | CD1 | TRP | 672 | A | <--> | 788 | N | GLY | 103 | H | 3.54 |
| 55. | 3600 | CD2 | TRP | 672 | A | <--> | 788 | N | GLY | 103 | H | 3.55 |
| 56. | 3601 | NE1 | TRP | 672 | A | <--> | 788 | N | GLY | 103 | H | 3.43 |
| 57. | 3602 | CE2 | TRP | 672 | A | <--> | 788 | N | GLY | 103 | H | 3.43 |
| 58. | 3598 | CG | TRP | 672 | A | <--> | 789 | CA | GLY | 103 | H | 3.75 |
| 59. | 3600 | CD2 | TRP | 672 | A | <--> | 789 | CA | GLY | 103 | H | 3.41 |
| 60. | 3602 | CE2 | TRP | 672 | A | <--> | 789 | CA | GLY | 103 | H | 3.69 |
| 61. | 3603 | CE3 | TRP | 672 | A | <--> | 789 | CA | GLY | 103 | H | 3.62 |
| 62. | 3598 | CG | TRP | 672 | A | <--> | 790 | C | GLY | 103 | H | 3.86 |
| 63. | 3597 | CB | TRP | 672 | A | <--> | 791 | O | GLY | 103 | H | 3.12 |
| 64. | 3598 | CG | TRP | 672 | A | <--> | 791 | O | GLY | 103 | H | 3.34 |
| 65. | 3600 | CD2 | TRP | 672 | A | <--> | 791 | O | GLY | 103 | H | 3.83 |
| 66. | 3640 | CG2 | THR | 676 | A | <--> | 802 | CA | PRO | 105 | H | 3.79 |
| 67. | 3640 | CG2 | THR | 676 | A | <--> | 805 | CB | PRO | 105 | H | 3.66 |
| 68. | 3640 | CG2 | THR | 676 | A | <--> | 806 | CG | PRO | 105 | H | 3.77 |
| 69. | 3711 | CD | ARG | 683 | A | <--> | 839 | O | PHE | 110 | H | 3.13 |

Figure 90 cont.

| | | | | | | | | | | | | |
|---|---|---|---|---|---|---|---|---|---|---|---|---|
| 70. | 3712 | NE | ARG | 683 | A | <--> | 839 | O | PHE | 110 | H | 3.42 |
| 71. | 3710 | CG | ARG | 683 | A | <--> | 847 | CE1 | PHE | 110 | H | 3.70 |
| 72. | 3711 | CD | ARG | 683 | A | <--> | 848 | CE2 | PHE | 110 | H | 3.73 |
| 73. | 3710 | CG | ARG | 683 | A | <--> | 849 | CZ | PHE | 110 | H | 3.51 |
| 74. | 3711 | CD | ARG | 683 | A | <--> | 849 | CZ | PHE | 110 | H | 3.69 |
| 75. | 3712 | NE | ARG | 683 | A | <--> | 853 | O | PHE | 111 | H | 3.89 |
| 76. | 3713 | CZ | ARG | 683 | A | <--> | 853 | O | PHE | 111 | H | 3.83 |
| 77. | 3715 | NH2 | ARG | 683 | A | <--> | 853 | O | PHE | 111 | H | 3.71 |
| 78. | 3712 | NE | ARG | 683 | A | <--> | 870 | N | TRP | 113 | H | 3.60 |
| 79. | 3677 | CD1 | TRP | 680 | A | <--> | 873 | O | TRP | 113 | H | 3.43 |
| 80. | 3712 | NE | ARG | 683 | A | <--> | 873 | O | TRP | 113 | H | 3.15 |
| 81. | 3713 | CZ | ARG | 683 | A | <--> | 873 | O | TRP | 113 | H | 3.50 |
| 82. | 3715 | NH2 | ARG | 683 | A | <--> | 873 | O | TRP | 113 | H | 3.09 |
| 83. | 3665 | C | LEU | 679 | A | <--> | 874 | CB | TRP | 113 | H | 3.86 |
| 84. | 3666 | O | LEU | 679 | A | <--> | 874 | CB | TRP | 113 | H | 3.36 |
| 85. | 3667 | CB | LEU | 679 | A | <--> | 874 | CB | TRP | 113 | H | 3.85 |
| 86. | 3710 | CG | ARG | 683 | A | <--> | 874 | CB | TRP | 113 | H | 3.81 |
| 87. | 3711 | CD | ARG | 683 | A | <--> | 874 | CB | TRP | 113 | H | 3.84 |
| 88. | 3712 | NE | ARG | 683 | A | <--> | 874 | CB | TRP | 113 | H | 3.65 |
| 89. | 3667 | CB | LEU | 679 | A | <--> | 875 | CG | TRP | 113 | H | 3.84 |
| 90. | 3667 | CB | LEU | 679 | A | <--> | 877 | CD2 | TRP | 113 | H | 3.79 |
| 91. | 3666 | O | LEU | 679 | A | <--> | 880 | CE3 | TRP | 113 | H | 3.31 |
| 92. | 3667 | CB | LEU | 679 | A | <--> | 880 | CE3 | TRP | 113 | H | 3.80 |
| 93. | 3670 | CD2 | LEU | 679 | A | <--> | 880 | CE3 | TRP | 113 | H | 3.87 |
| 94. | 3670 | CD2 | LEU | 679 | A | <--> | 882 | CZ3 | TRP | 113 | H | 3.83 |
| 95. | 3637 | O | THR | 676 | A | <--> | 884 | N | GLY | 114 | H | 3.89 |

Figure 90 cont.

| | | | | | | | | | | | | |
|---|---|---|---|---|---|---|---|---|---|---|---|---|
| 96. | 3637 | O | THR | 676 | A | <--> | 885 | CA | GLY | 114 | H | 3.42 |
| 97. | 3675 | CB | TRP | 680 | A | <--> | 885 | CA | GLY | 114 | H | 3.64 |
| 98. | 3677 | CD1 | TRP | 680 | A | <--> | 885 | CA | GLY | 114 | H | 3.87 |
| 99. | 3638 | CB | THR | 676 | A | <--> | 887 | O | GLY | 114 | H | 3.55 |
| 100. | 3605 | CZ3 | TRP | 672 | A | <--> | 899 | CG | TYR | 116 | H | 3.67 |
| 101. | 3605 | CZ3 | TRP | 672 | A | <--> | 900 | CD1 | TYR | 116 | H | 3.69 |
| 102. | 3605 | CZ3 | TRP | 672 | A | <--> | 901 | CD2 | TYR | 116 | H | 3.82 |
| 103. | 3605 | CZ3 | TRP | 672 | A | <--> | 902 | CE1 | TYR | 116 | H | 3.88 |

Figure 90 cont.

Hydrogen bonds

| | <------ A T O M 1 ------> | | | | | | <------ A T O M 2 ------> | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 209 | O | ASN | 31 | H | <--> | 6804 | ND2 | ASN | 671 | P | 3.17 |
| 2. | 213 | ND2 | ASN | 31 | H | <--> | 6786 | O | TRP | 670 | P | 2.86 |
| 3. | 397 | NH1 | ARG | 53 | H | <--> | 6837 | OD2 | ASP | 674 | P | 2.93 |
| 4. | 415 | NZ | LYS | 55 | H | <--> | 6750 | O | TRP | 666 | P | 3.29 |
| 5. | 415 | NZ | LYS | 55 | H | <--> | 6778 | O | LEU | 669 | P | 3.02 |
| 6. | 864 | O | TRP | 112 | H | <--> | 6924 | NE | ARG | 683 | P | 2.94 |
| 7. | 864 | O | TRP | 112 | H | <--> | 6927 | NH2 | ARG | 683 | P | 2.97 |

Salt bridges

| | <----- A T O M 1 -----> | | | | | | <----- A T O M 2 -----> | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 397 | NH1 | ARG | 53 | H | <--> | 6837 | OD2 | ASP | 674 | P | 2.93 |
| 2. | 415 | NZ | LYS | 55 | H | <--> | 6836 | OD1 | ASP | 674 | P | 3.30 |

Figure 91

Non-bonded contacts

| | <----- ATOM 1 -----> | | | | | | <----- ATOM 2 -----> | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 185 | CE2 | PHE | 28 | H | <--> | 6782 | CD2 | LEU | 669 | P | 3.35 |
| 2. | 186 | CZ | PHE | 28 | H | <--> | 6782 | CD2 | LEU | 669 | P | 3.46 |
| 3. | 209 | O | ASN | 31 | H | <--> | 6804 | ND2 | ASN | 671 | P | 3.17 |
| 4. | 211 | CG | ASN | 31 | H | <--> | 6786 | O | TRP | 670 | P | 3.77 |
| 5. | 212 | OD1 | ASN | 31 | H | <--> | 6777 | C | LEU | 669 | P | 3.87 |
| 6. | 212 | OD1 | ASN | 31 | H | <--> | 6779 | CB | LEU | 669 | P | 3.51 |
| 7. | 212 | OD1 | ASN | 31 | H | <--> | 6783 | N | TRP | 670 | P | 3.68 |
| 8. | 212 | OD1 | ASN | 31 | H | <--> | 6785 | C | TRP | 670 | P | 3.86 |
| 9. | 212 | OD1 | ASN | 31 | H | <--> | 6786 | O | TRP | 670 | P | 3.86 |
| 10. | 212 | OD1 | ASN | 31 | H | <--> | 6801 | CB | ASN | 671 | P | 3.78 |
| 11. | 212 | OD1 | ASN | 31 | H | <--> | 6804 | ND2 | ASN | 671 | P | 3.90 |
| 12. | 213 | ND2 | ASN | 31 | H | <--> | 6785 | C | TRP | 670 | P | 3.57 |
| 13. | 213 | ND2 | ASN | 31 | H | <--> | 6786 | O | TRP | 670 | P | 2.86 |
| 14. | 213 | ND2 | ASN | 31 | H | <--> | 6801 | CB | ASN | 671 | P | 3.76 |
| 15. | 225 | CG | TRP | 33 | H | <--> | 6816 | CZ2 | TRP | 672 | P | 3.76 |
| 16. | 227 | CD2 | TRP | 33 | H | <--> | 6816 | CZ2 | TRP | 672 | P | 3.50 |
| 17. | 227 | CD2 | TRP | 33 | H | <--> | 6818 | CH2 | TRP | 672 | P | 3.71 |
| 18. | 229 | CE2 | TRP | 33 | H | <--> | 6816 | CZ2 | TRP | 672 | P | 3.72 |
| 19. | 229 | CE2 | TRP | 33 | H | <--> | 6818 | CH2 | TRP | 672 | P | 3.74 |

Figure 91 cont.

| | | | | | | | | | | | | |
|---|---|---|---|---|---|---|---|---|---|---|---|---|
| 20. | 230 | CE3 | TRP | 33 | H | <--> | 6816 | CZ2 | TRP | 672 | P | 3.83 |
| 21. | 230 | CE3 | TRP | 33 | H | <--> | 6818 | CH2 | TRP | 672 | P | 3.69 |
| 22. | 231 | CZ2 | TRP | 33 | H | <--> | 6818 | CH2 | TRP | 672 | P | 3.79 |
| 23. | 231 | CZ2 | TRP | 33 | H | <--> | 6824 | CG | PHE | 673 | P | 3.51 |
| 24. | 231 | CZ2 | TRP | 33 | H | <--> | 6825 | CD1 | PHE | 673 | P | 3.45 |
| 25. | 231 | CZ2 | TRP | 33 | H | <--> | 6826 | CD2 | PHE | 673 | P | 3.67 |
| 26. | 231 | CZ2 | TRP | 33 | H | <--> | 6827 | CE1 | PHE | 673 | P | 3.58 |
| 27. | 231 | CZ2 | TRP | 33 | H | <--> | 6828 | CE2 | PHE | 673 | P | 3.79 |
| 28. | 231 | CZ2 | TRP | 33 | H | <--> | 6829 | CZ | PHE | 673 | P | 3.75 |
| 29. | 232 | CZ3 | TRP | 33 | H | <--> | 6818 | CH2 | TRP | 672 | P | 3.70 |
| 30. | 233 | CH2 | TRP | 33 | H | <--> | 6818 | CH2 | TRP | 672 | P | 3.75 |
| 31. | 233 | CH2 | TRP | 33 | H | <--> | 6825 | CD1 | PHE | 673 | P | 3.82 |
| 32. | 233 | CH2 | TRP | 33 | H | <--> | 6827 | CE1 | PHE | 673 | P | 3.68 |
| 33. | 386 | NH1 | ARG | 52 | H | <--> | 6829 | CZ | PHE | 673 | P | 3.70 |
| 34. | 394 | CD | ARG | 53 | H | <--> | 6804 | ND2 | ASN | 671 | P | 3.32 |
| 35. | 395 | NE | ARG | 53 | H | <--> | 6804 | ND2 | ASN | 671 | P | 3.36 |
| 36. | 396 | CZ | ARG | 53 | H | <--> | 6802 | CG | ASN | 671 | P | 3.48 |
| 37. | 396 | CZ | ARG | 53 | H | <--> | 6803 | OD1 | ASN | 671 | P | 3.23 |
| 38. | 396 | CZ | ARG | 53 | H | <--> | 6804 | ND2 | ASN | 671 | P | 3.41 |
| 39. | 396 | CZ | ARG | 53 | H | <--> | 6837 | OD2 | ASP | 674 | P | 3.36 |
| 40. | 397 | NH1 | ARG | 53 | H | <--> | 6777 | C | LEU | 669 | P | 3.88 |
| 41. | 397 | NH1 | ARG | 53 | H | <--> | 6778 | O | LEU | 669 | P | 3.72 |

Figure 91 cont.

| | | | | | | | | | | | | |
|---|---|---|---|---|---|---|---|---|---|---|---|---|
| 42. | 397 | NH1 | ARG | 53 | H | <--> | 6779 | CB | LEU | 669 | P | 3.86 |
| 43. | 397 | NH1 | ARG | 53 | H | <--> | 6797 | N | ASN | 671 | P | 3.76 |
| 44. | 397 | NH1 | ARG | 53 | H | <--> | 6801 | CB | ASN | 671 | P | 3.90 |
| 45. | 397 | NH1 | ARG | 53 | H | <--> | 6802 | CG | ASN | 671 | P | 3.16 |
| 46. | 397 | NH1 | ARG | 53 | H | <--> | 6803 | OD1 | ASN | 671 | P | 3.13 |
| 47. | 397 | NH1 | ARG | 53 | H | <--> | 6804 | ND2 | ASN | 671 | P | 3.35 |
| 48. | 397 | NH1 | ARG | 53 | H | <--> | 6837 | OD2 | ASP | 674 | P | 2.93 |
| 49. | 398 | NH2 | ARG | 53 | H | <--> | 6803 | OD1 | ASN | 671 | P | 3.37 |
| 50. | 398 | NH2 | ARG | 53 | H | <--> | 6835 | CG | ASP | 674 | P | 3.28 |
| 51. | 398 | NH2 | ARG | 53 | H | <--> | 6836 | OD1 | ASP | 674 | P | 3.05 |
| 52. | 398 | NH2 | ARG | 53 | H | <--> | 6837 | OD2 | ASP | 674 | P | 2.97 |
| 53. | 403 | CB | LEU | 54 | H | <--> | 6761 | CZ2 | TRP | 666 | P | 3.41 |
| 54. | 403 | CB | LEU | 54 | H | <--> | 6763 | CH2 | TRP | 666 | P | 3.83 |
| 55. | 408 | CA | LYS | 55 | H | <--> | 6760 | CE3 | TRP | 666 | P | 3.72 |
| 56. | 411 | CB | LYS | 55 | H | <--> | 6754 | CB | TRP | 666 | P | 3.78 |
| 57. | 411 | CB | LYS | 55 | H | <--> | 6755 | CG | TRP | 666 | P | 3.75 |
| 58. | 411 | CB | LYS | 55 | H | <--> | 6757 | CD2 | TRP | 666 | P | 3.73 |
| 59. | 411 | CB | LYS | 55 | H | <--> | 6760 | CE3 | TRP | 666 | P | 3.78 |
| 60. | 413 | CD | LYS | 55 | H | <--> | 6750 | O | TRP | 666 | P | 3.85 |
| 61. | 413 | CD | LYS | 55 | H | <--> | 6779 | CB | LEU | 669 | P | 3.74 |
| 62. | 414 | CE | LYS | 55 | H | <--> | 6750 | O | TRP | 666 | P | 3.79 |
| 63. | 415 | NZ | LYS | 55 | H | <--> | 6750 | O | TRP | 666 | P | 3.29 |
| 64. | 415 | NZ | LYS | 55 | H | <--> | 6778 | O | LEU | 669 | P | 3.02 |
| 65. | 415 | NZ | LYS | 55 | H | <--> | 6836 | OD1 | ASP | 674 | P | 3.30 |
| 66. | 421 | CG | ASP | 56 | H | <--> | 6826 | CD2 | PHE | 673 | P | 3.53 |

Figure 91 cont.

| | | | | | | | | | | | | |
|---|---|---|---|---|---|---|---|---|---|---|---|---|
| 67. | 421 | CG | ASP | 56 | H | <--> | 6828 | CE2 | PHE | 673 | P | 3.67 |
| 68. | 422 | OD1 | ASP | 56 | H | <--> | 6826 | CD2 | PHE | 673 | P | 3.36 |
| 69. | 422 | OD1 | ASP | 56 | H | <--> | 6828 | CE2 | PHE | 673 | P | 3.57 |
| 70. | 423 | OD2 | ASP | 56 | H | <--> | 6826 | CD2 | PHE | 673 | P | 3.60 |
| 71. | 782 | CA | GLU | 102 | H | <--> | 6813 | NE1 | TRP | 672 | P | 3.79 |
| 72. | 783 | C | GLU | 102 | H | <--> | 6813 | NE1 | TRP | 672 | P | 3.84 |
| 73. | 790 | N | GLY | 103 | H | <--> | 6810 | CG | TRP | 672 | P | 3.53 |
| 74. | 790 | N | GLY | 103 | H | <--> | 6811 | CD1 | TRP | 672 | P | 3.32 |
| 75. | 790 | N | GLY | 103 | H | <--> | 6812 | CD2 | TRP | 672 | P | 3.55 |
| 76. | 790 | N | GLY | 103 | H | <--> | 6813 | NE1 | TRP | 672 | P | 3.20 |
| 77. | 790 | N | GLY | 103 | H | <--> | 6814 | CE2 | TRP | 672 | P | 3.35 |
| 78. | 791 | CA | GLY | 103 | H | <--> | 6810 | CG | TRP | 672 | P | 3.64 |
| 79. | 791 | CA | GLY | 103 | H | <--> | 6812 | CD2 | TRP | 672 | P | 3.45 |
| 80. | 791 | CA | GLY | 103 | H | <--> | 6814 | CE2 | TRP | 672 | P | 3.70 |
| 81. | 791 | CA | GLY | 103 | H | <--> | 6815 | CE3 | TRP | 672 | P | 3.83 |
| 82. | 792 | C | GLY | 103 | H | <--> | 6809 | CB | TRP | 672 | P | 3.76 |
| 83. | 792 | C | GLY | 103 | H | <--> | 6810 | CG | TRP | 672 | P | 3.71 |
| 84. | 793 | O | GLY | 103 | H | <--> | 6809 | CB | TRP | 672 | P | 3.27 |
| 85. | 793 | O | GLY | 103 | H | <--> | 6810 | CG | TRP | 672 | P | 3.44 |
| 86. | 793 | O | GLY | 103 | H | <--> | 6811 | CD1 | TRP | 672 | P | 3.81 |
| 87. | 802 | CA | PRO | 105 | H | <--> | 6852 | CG2 | THR | 676 | P | 3.79 |
| 88. | 805 | CB | PRO | 105 | H | <--> | 6845 | CG2 | ILE | 675 | P | 3.73 |
| 89. | 805 | CB | PRO | 105 | H | <--> | 6852 | CG2 | THR | 676 | P | 3.72 |

Figure 91 cont.

| | | | | | | | | | | | | |
|---|---|---|---|---|---|---|---|---|---|---|---|---|
| 90. | 806 | CG | PRO | 105 | H | <--> | 6845 | CG2 | ILE | 675 | P | 3.75 |
| 91. | 836 | O | PHE | 109 | H | <--> | 6923 | CD | ARG | 683 | P | 3.38 |
| 92. | 847 | O | LEU | 110 | H | <--> | 6925 | CZ | ARG | 683 | P | 3.77 |
| 93. | 847 | O | LEU | 110 | H | <--> | 6926 | NH1 | ARG | 683 | P | 3.69 |
| 94. | 861 | N | TRP | 112 | H | <--> | 6924 | NE | ARG | 683 | P | 3.81 |
| 95. | 863 | C | TRP | 112 | H | <--> | 6924 | NE | ARG | 683 | P | 3.86 |
| 96. | 864 | O | TRP | 112 | H | <--> | 6884 | CA | TRP | 680 | P | 3.69 |
| 97. | 864 | O | TRP | 112 | H | <--> | 6924 | NE | ARG | 683 | P | 2.94 |
| 98. | 864 | O | TRP | 112 | H | <--> | 6925 | CZ | ARG | 683 | P | 3.38 |
| 99. | 864 | O | TRP | 112 | H | <--> | 6927 | NH2 | ARG | 683 | P | 2.97 |
| 100. | 865 | CB | TRP | 112 | H | <--> | 6878 | O | LEU | 679 | P | 3.78 |
| 101. | 865 | CB | TRP | 112 | H | <--> | 6879 | CB | LEU | 679 | P | 3.68 |
| 102. | 865 | CB | TRP | 112 | H | <--> | 6924 | NE | ARG | 683 | P | 3.85 |
| 103. | 866 | CG | TRP | 112 | H | <--> | 6879 | CB | LEU | 679 | P | 3.78 |
| 104. | 868 | CD2 | TRP | 112 | H | <--> | 6879 | CB | LEU | 679 | P | 3.82 |
| 105. | 871 | CE3 | TRP | 112 | H | <--> | 6878 | O | LEU | 679 | P | 3.63 |
| 106. | 871 | CE3 | TRP | 112 | H | <--> | 6879 | CB | LEU | 679 | P | 3.83 |
| 107. | 875 | N | GLY | 113 | H | <--> | 6849 | O | THR | 676 | P | 3.70 |
| 108. | 876 | CA | GLY | 113 | H | <--> | 6849 | O | THR | 676 | P | 3.15 |
| 109. | 876 | CA | GLY | 113 | H | <--> | 6887 | CB | TRP | 680 | P | 3.52 |
| 110. | 878 | O | GLY | 113 | H | <--> | 6850 | CB | THR | 676 | P | 3.74 |
| 111. | 882 | O | TYR | 114 | H | <--> | 6852 | CG2 | THR | 676 | P | 3.58 |
| 112. | 895 | CB | PHE | 115 | H | <--> | 6852 | CG2 | THR | 676 | P | 3.80 |
| 113. | 896 | CG | PHE | 115 | H | <--> | 6817 | CZ3 | TRP | 672 | P | 3.50 |
| 114. | 897 | CD1 | PHE | 115 | H | <--> | 6817 | CZ3 | TRP | 672 | P | 3.48 |
| 115. | 898 | CD2 | PHE | 115 | H | <--> | 6817 | CZ3 | TRP | 672 | P | 3.72 |
| 116. | 899 | CE1 | PHE | 115 | H | <--> | 6817 | CZ3 | TRP | 672 | P | 3.70 |
| 117. | 899 | CE1 | PHE | 115 | H | <--> | 6818 | CH2 | TRP | 672 | P | 3.87 |

Figure 91 cont.

Hydrogen bonds

| | <----- A T O M 1 -----> | | | | | | <----- A T O M 2 -----> | | | | |
|---|---|---|---|---|---|---|---|---|---|---|---|
| Distance | Atom no. | Atom name | Res name | Res no. | Chain | | Atom no. | Atom name | Res name | Res no. | Chain | |
| 1. | 3574 | OD1 | ASP | 674 | A | <--> | 399 | NH1 | ARG | 53 | H | 2.43 |
| 2. | 3664 | NH1 | ARG | 683 | A | <--> | 844 | O | PHE | 110 | H | 2.83 |

Salt bridges

| | <----- A T O M 1 -----> | | | | | | <----- A T O M 2 -----> | | | | |
|---|---|---|---|---|---|---|---|---|---|---|---|
| Distance | Atom no. | Atom name | Res name | Res no. | Chain | | Atom no. | Atom name | Res name | Res no. | Chain | |
| 1. | 3574 | OD1 | ASP | 674 | A | <--> | 399 | NH1 | ARG | 53 | H | 2.43 |

Figure 92

Non-bonded contacts

| | <----- A T O M 1 -----> | | | | | | <----- A T O M 2 -----> | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 3519 | CD1 | LEU | 669 | A | <--> | 189 | CG2 | THR | 28 | H | 3.66 |
| 2. | 3519 | CD1 | LEU | 669 | A | <--> | 206 | OG | SER | 30 | H | 3.23 |
| 3. | 3540 | CG | ASN | 671 | A | <--> | 210 | O | ASN | 31 | H | 3.59 |
| 4. | 3541 | OD1 | ASN | 671 | A | <--> | 210 | O | ASN | 31 | H | 3.79 |
| 5. | 3542 | ND2 | ASN | 671 | A | <--> | 210 | O | ASN | 31 | H | 3.57 |
| 6. | 3517 | CB | LEU | 669 | A | <--> | 211 | CB | ASN | 31 | H | 3.76 |
| 7. | 3519 | CD1 | LEU | 669 | A | <--> | 211 | CB | ASN | 31 | H | 3.57 |
| 8. | 3541 | OD1 | ASN | 671 | A | <--> | 211 | CB | ASN | 31 | H | 3.71 |
| 9. | 3519 | CD1 | LEU | 669 | A | <--> | 212 | CG | ASN | 31 | H | 3.73 |
| 10. | 3517 | CB | LEU | 669 | A | <--> | 214 | ND2 | ASN | 31 | H | 3.55 |
| 11. | 3518 | CG | LEU | 669 | A | <--> | 214 | ND2 | ASN | 31 | H | 3.75 |
| 12. | 3519 | CD1 | LEU | 669 | A | <--> | 214 | ND2 | ASN | 31 | H | 3.75 |
| 13. | 3520 | CD2 | LEU | 669 | A | <--> | 214 | ND2 | ASN | 31 | H | 3.44 |
| 14. | 3554 | CZ2 | TRP | 672 | A | <--> | 227 | CG | TRP | 33 | H | 3.79 |
| 15. | 3554 | CZ2 | TRP | 672 | A | <--> | 229 | CD2 | TRP | 33 | H | 3.67 |
| 16. | 3554 | CZ2 | TRP | 672 | A | <--> | 231 | CE2 | TRP | 33 | H | 3.78 |
| 17. | 3562 | CG | PHE | 673 | A | <--> | 233 | CZ2 | TRP | 33 | H | 3.51 |
| 18. | 3563 | CD1 | PHE | 673 | A | <--> | 233 | CZ2 | TRP | 33 | H | 3.57 |
| 19. | 3564 | CD2 | PHE | 673 | A | <--> | 233 | CZ2 | TRP | 33 | H | 3.66 |

Figure 92 cont.

| | | | | | | | | | | | | |
|---|---|---|---|---|---|---|---|---|---|---|---|---|
| 20. | 3565 | CE1 | PHE | 673 | A | <--> | 233 | CZ2 | TRP | 33 | H | 3.81 |
| 21. | 3566 | CE2 | PHE | 673 | A | <--> | 233 | CZ2 | TRP | 33 | H | 3.89 |
| 22. | 3565 | CE1 | PHE | 673 | A | <--> | 235 | CH2 | TRP | 33 | H | 3.86 |
| 23. | 3541 | OD1 | ASN | 671 | A | <--> | 396 | CD | ARG | 53 | H | 3.61 |
| 24. | 3542 | ND2 | ASN | 671 | A | <--> | 396 | CD | ARG | 53 | H | 3.53 |
| 25. | 3541 | OD1 | ASN | 671 | A | <--> | 397 | NE | ARG | 53 | H | 3.51 |
| 26. | 3541 | OD1 | ASN | 671 | A | <--> | 398 | CZ | ARG | 53 | H | 3.23 |
| 27. | 3574 | OD1 | ASP | 674 | A | <--> | 398 | CZ | ARG | 53 | H | 3.45 |
| 28. | 3540 | CG | ASN | 671 | A | <--> | 399 | NH1 | ARG | 53 | H | 3.49 |
| 29. | 3541 | OD1 | ASN | 671 | A | <--> | 399 | NH1 | ARG | 53 | H | 2.96 |
| 30. | 3542 | ND2 | ASN | 671 | A | <--> | 399 | NH1 | ARG | 53 | H | 3.40 |
| 31. | 3573 | CG | ASP | 674 | A | <--> | 399 | NH1 | ARG | 53 | H | 3.48 |
| 32. | 3574 | OD1 | ASP | 674 | A | <--> | 399 | NH1 | ARG | 53 | H | 2.43 |
| 33. | 3575 | OD2 | ASP | 674 | A | <--> | 399 | NH1 | ARG | 53 | H | 3.82 |
| 34. | 3574 | OD1 | ASP | 674 | A | <--> | 400 | NH2 | ARG | 53 | H | 3.70 |
| 35. | 3575 | OD2 | ASP | 674 | A | <--> | 400 | NH2 | ARG | 53 | H | 3.77 |
| 36. | 3564 | CD2 | PHE | 673 | A | <--> | 417 | CG | ASP | 56 | H | 3.82 |
| 37. | 3564 | CD2 | PHE | 673 | A | <--> | 418 | OD1 | ASP | 56 | H | 3.76 |
| 38. | 3567 | CZ | PHE | 673 | A | <--> | 438 | CD1 | ILE | 59 | H | 3.64 |
| 39. | 3549 | CD1 | TRP | 672 | A | <--> | 785 | OE1 | GLU | 102 | H | 3.63 |
| 40. | 3551 | NE1 | TRP | 672 | A | <--> | 785 | OE1 | GLU | 102 | H | 3.90 |
| 41. | 3548 | CG | TRP | 672 | A | <--> | 787 | N | GLY | 103 | H | 3.66 |
| 42. | 3549 | CD1 | TRP | 672 | A | <--> | 787 | N | GLY | 103 | H | 3.60 |
| 43. | 3550 | CD2 | TRP | 672 | A | <--> | 787 | N | GLY | 103 | H | 3.48 |

Figure 92 cont.

| | | | | | | | | | | | | |
|---|---|---|---|---|---|---|---|---|---|---|---|---|
| 44. | 3551 | NE1 | TRP | 672 | A | <--> | 787 | N | GLY | 103 | H | 3.41 |
| 45. | 3552 | CE2 | TRP | 672 | A | <--> | 787 | N | GLY | 103 | H | 3.32 |
| 46. | 3554 | CZ2 | TRP | 672 | A | <--> | 787 | N | GLY | 103 | H | 3.86 |
| 47. | 3550 | CD2 | TRP | 672 | A | <--> | 788 | CA | GLY | 103 | H | 3.47 |
| 48. | 3552 | CE2 | TRP | 672 | A | <--> | 788 | CA | GLY | 103 | H | 3.70 |
| 49. | 3553 | CE3 | TRP | 672 | A | <--> | 788 | CA | GLY | 103 | H | 3.60 |
| 50. | 3547 | CB | TRP | 672 | A | <--> | 790 | O | GLY | 103 | H | 3.24 |
| 51. | 3548 | CG | TRP | 672 | A | <--> | 790 | O | GLY | 103 | H | 3.40 |
| 52. | 3550 | CD2 | TRP | 672 | A | <--> | 790 | O | GLY | 103 | H | 3.72 |
| 53. | 3660 | CG | ARG | 683 | A | <--> | 830 | O | PHE | 109 | H | 3.60 |
| 54. | 3661 | CD | ARG | 683 | A | <--> | 830 | O | PHE | 109 | H | 3.21 |
| 55. | 3658 | O | ARG | 683 | A | <--> | 839 | CE2 | PHE | 109 | H | 3.86 |
| 56. | 3658 | O | ARG | 683 | A | <--> | 840 | CZ | PHE | 109 | H | 3.21 |
| 57. | 3664 | NH1 | ARG | 683 | A | <--> | 843 | C | PHE | 110 | H | 3.46 |
| 58. | 3664 | NH1 | ARG | 683 | A | <--> | 844 | O | PHE | 110 | H | 2.83 |
| 59. | 3664 | NH1 | ARG | 683 | A | <--> | 861 | N | TRP | 112 | H | 3.88 |
| 60. | 3622 | CA | TRP | 680 | A | <--> | 864 | O | TRP | 112 | H | 3.62 |
| 61. | 3625 | CB | TRP | 680 | A | <--> | 864 | O | TRP | 112 | H | 3.90 |
| 62. | 3661 | CD | ARG | 683 | A | <--> | 864 | O | TRP | 112 | H | 3.40 |
| 63. | 3662 | NE | ARG | 683 | A | <--> | 864 | O | TRP | 112 | H | 3.50 |
| 64. | 3663 | CZ | ARG | 683 | A | <--> | 864 | O | TRP | 112 | H | 3.56 |
| 65. | 3664 | NH1 | ARG | 683 | A | <--> | 864 | O | TRP | 112 | H | 3.48 |
| 66. | 3615 | C | LEU | 679 | A | <--> | 865 | CB | TRP | 112 | H | 3.82 |
| 67. | 3616 | O | LEU | 679 | A | <--> | 865 | CB | TRP | 112 | H | 3.27 |
| 68. | 3617 | CB | LEU | 679 | A | <--> | 865 | CB | TRP | 112 | H | 3.85 |

Figure 92 cont.

| | | | | | | | | | | | | |
|---|---|---|---|---|---|---|---|---|---|---|---|---|
| 69. | 3661 | CD | ARG | 683 | A | <--> | 865 | CB | TRP | 112 | H | 3.87 |
| 70. | 3616 | O | LEU | 679 | A | <--> | 871 | CE3 | TRP | 112 | H | 3.74 |
| 71. | 3587 | O | THR | 676 | A | <--> | 875 | N | GLY | 113 | H | 3.80 |
| 72. | 3587 | O | THR | 676 | A | <--> | 876 | CA | GLY | 113 | H | 3.24 |
| 73. | 3625 | CB | TRP | 680 | A | <--> | 876 | CA | GLY | 113 | H | 3.54 |
| 74. | 3588 | CB | THR | 676 | A | <--> | 878 | O | GLY | 113 | H | 3.81 |
| 75. | 3664 | NH1 | ARG | 683 | A | <--> | 885 | CD2 | TYR | 114 | H | 3.89 |
| 76. | 3664 | NH1 | ARG | 683 | A | <--> | 887 | CE2 | TYR | 114 | H | 3.38 |
| 77. | 3590 | CG2 | THR | 676 | A | <--> | 895 | CB | TYR | 115 | H | 3.83 |
| 78. | 3555 | CZ3 | TRP | 672 | A | <--> | 896 | CG | TYR | 115 | H | 3.61 |
| 79. | 3555 | CZ3 | TRP | 672 | A | <--> | 897 | CD1 | TYR | 115 | H | 3.62 |
| 80. | 3555 | CZ3 | TRP | 672 | A | <--> | 898 | CD2 | TYR | 115 | H | 3.82 |
| 81. | 3555 | CZ3 | TRP | 672 | A | <--> | 899 | CE1 | TYR | 115 | H | 3.85 |

Figure 92 cont.

Hydrogen bonds

| | <----- A T O M 1 -----> | | | | | | <----- A T O M 2 -----> | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 3537 | ND2 | ASN | 671 | A | <--> | 210 | O | ASN | 31 | H | 2.84 |
| 2. | 3519 | O | TRP | 670 | A | <--> | 214 | ND2 | ASN | 31 | H | 3.17 |
| 3. | 3570 | OD2 | ASP | 674 | A | <--> | 399 | NH1 | ARG | 53 | H | 2.83 |
| 4. | 3657 | NE | ARG | 683 | A | <--> | 864 | O | TRP | 112 | H | 3.05 |
| 5. | 3660 | NH2 | ARG | 683 | A | <--> | 864 | O | TRP | 112 | H | 3.15 |

Salt bridges

| | <----- A T O M 1 -----> | | | | | | <----- A T O M 2 -----> | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 3570 | OD2 | ASP | 674 | A | <--> | 399 | NH1 | ARG | 53 | H | 2.83 |

Figure 93

Non-bonded contacts

| | ATOM 1 | | | | | | ATOM 2 | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 3514 | CD1 | LEU | 669 | A | <--> | 189 | CG2 | THR | 28 | H | 3.35 |
| 2. | 3537 | ND2 | ASN | 671 | A | <--> | 209 | C | ASN | 31 | H | 3.81 |
| 3. | 3534 | CB | ASN | 671 | A | <--> | 210 | O | ASN | 31 | H | 3.84 |
| 4. | 3535 | CG | ASN | 671 | A | <--> | 210 | O | ASN | 31 | H | 3.79 |
| 5. | 3537 | ND2 | ASN | 671 | A | <--> | 210 | O | ASN | 31 | H | 2.84 |
| 6. | 3512 | CB | LEU | 669 | A | <--> | 211 | CB | ASN | 31 | H | 3.64 |
| 7. | 3514 | CD1 | LEU | 669 | A | <--> | 211 | CB | ASN | 31 | H | 3.71 |
| 8. | 3514 | CD1 | LEU | 669 | A | <--> | 212 | CG | ASN | 31 | H | 3.36 |
| 9. | 3514 | CD1 | LEU | 669 | A | <--> | 213 | OD1 | ASN | 31 | H | 3.45 |
| 10. | 3514 | CD1 | LEU | 669 | A | <--> | 214 | ND2 | ASN | 31 | H | 3.76 |
| 11. | 3515 | CD2 | LEU | 669 | A | <--> | 214 | ND2 | ASN | 31 | H | 3.75 |
| 12. | 3518 | C | TRP | 670 | A | <--> | 214 | ND2 | ASN | 31 | H | 3.81 |
| 13. | 3519 | O | TRP | 670 | A | <--> | 214 | ND2 | ASN | 31 | H | 3.17 |
| 14. | 3534 | CB | ASN | 671 | A | <--> | 214 | ND2 | ASN | 31 | H | 3.40 |
| 15. | 3549 | CZ2 | TRP | 672 | A | <--> | 227 | CG | TRP | 33 | H | 3.78 |
| 16. | 3549 | CZ2 | TRP | 672 | A | <--> | 228 | CD1 | TRP | 33 | H | 3.85 |
| 17. | 3549 | CZ2 | TRP | 672 | A | <--> | 229 | CD2 | TRP | 33 | H | 3.67 |
| 18. | 3549 | CZ2 | TRP | 672 | A | <--> | 230 | NE1 | TRP | 33 | H | 3.84 |
| 19. | 3549 | CZ2 | TRP | 672 | A | <--> | 231 | CE2 | TRP | 33 | H | 3.71 |
| 20. | 3557 | CG | PHE | 673 | A | <--> | 233 | CZ2 | TRP | 33 | H | 3.62 |

Figure 93 cont.

| | | | | | | | | | | | | |
|---|---|---|---|---|---|---|---|---|---|---|---|---|
| 21. | 3558 | CD1 | PHE | 673 | A | <--> | 233 | CZ2 | TRP | 33 | H | 3.62 |
| 22. | 3559 | CD2 | PHE | 673 | A | <--> | 233 | CZ2 | TRP | 33 | H | 3.73 |
| 23. | 3560 | CE1 | PHE | 673 | A | <--> | 233 | CZ2 | TRP | 33 | H | 3.75 |
| 24. | 3561 | CE2 | PHE | 673 | A | <--> | 233 | CZ2 | TRP | 33 | H | 3.88 |
| 25. | 3562 | CZ | PHE | 673 | A | <--> | 233 | CZ2 | TRP | 33 | H | 3.88 |
| 26. | 3537 | ND2 | ASN | 671 | A | <--> | 396 | CD | ARG | 53 | H | 3.48 |
| 27. | 3535 | CG | ASN | 671 | A | <--> | 397 | NE | ARG | 53 | H | 3.90 |
| 28. | 3536 | OD1 | ASN | 671 | A | <--> | 397 | NE | ARG | 53 | H | 3.88 |
| 29. | 3537 | ND2 | ASN | 671 | A | <--> | 397 | NE | ARG | 53 | H | 3.52 |
| 30. | 3535 | CG | ASN | 671 | A | <--> | 398 | CZ | ARG | 53 | H | 3.51 |
| 31. | 3536 | OD1 | ASN | 671 | A | <--> | 398 | CZ | ARG | 53 | H | 3.27 |
| 32. | 3537 | ND2 | ASN | 671 | A | <--> | 398 | CZ | ARG | 53 | H | 3.62 |
| 33. | 3570 | OD2 | ASP | 674 | A | <--> | 398 | CZ | ARG | 53 | H | 3.24 |
| 34. | 3511 | O | LEU | 669 | A | <--> | 399 | NH1 | ARG | 53 | H | 3.54 |
| 35. | 3530 | N | ASN | 671 | A | <--> | 399 | NH1 | ARG | 53 | H | 3.56 |
| 36. | 3535 | CG | ASN | 671 | A | <--> | 399 | NH1 | ARG | 53 | H | 3.37 |
| 37. | 3536 | OD1 | ASN | 671 | A | <--> | 399 | NH1 | ARG | 53 | H | 3.37 |
| 38. | 3537 | ND2 | ASN | 671 | A | <--> | 399 | NH1 | ARG | 53 | H | 3.70 |
| 39. | 3570 | OD2 | ASP | 674 | A | <--> | 399 | NH1 | ARG | 53 | H | 2.83 |
| 40. | 3536 | OD1 | ASN | 671 | A | <--> | 400 | NH2 | ARG | 53 | H | 3.34 |
| 41. | 3568 | CG | ASP | 674 | A | <--> | 400 | NH2 | ARG | 53 | H | 3.31 |

Figure 93 cont.

| | | | | | | | | | | | | |
|---|---|---|---|---|---|---|---|---|---|---|---|---|
| 42. | 3569 | OD1 | ASP | 674 | A | <--> | 400 | NH2 | ARG | 53 | H | 3.29 |
| 43. | 3570 | OD2 | ASP | 674 | A | <--> | 400 | NH2 | ARG | 53 | H | 2.85 |
| 44. | 3559 | CD2 | PHE | 673 | A | <--> | 417 | CG | ASP | 56 | H | 3.89 |
| 45. | 3559 | CD2 | PHE | 673 | A | <--> | 419 | OD2 | ASP | 56 | H | 3.87 |
| 46. | 3561 | CE2 | PHE | 673 | A | <--> | 438 | CD1 | ILE | 59 | H | 3.85 |
| 47. | 3562 | CZ | PHE | 673 | A | <--> | 438 | CD1 | ILE | 59 | H | 3.54 |
| 48. | 3546 | NE1 | TRP | 672 | A | <--> | 779 | CA | GLU | 102 | H | 3.85 |
| 49. | 3544 | CD1 | TRP | 672 | A | <--> | 785 | OE1 | GLU | 102 | H | 3.62 |
| 50. | 3543 | CG | TRP | 672 | A | <--> | 787 | N | GLY | 103 | H | 3.54 |
| 51. | 3544 | CD1 | TRP | 672 | A | <--> | 787 | N | GLY | 103 | H | 3.53 |
| 52. | 3545 | CD2 | TRP | 672 | A | <--> | 787 | N | GLY | 103 | H | 3.36 |
| 53. | 3546 | NE1 | TRP | 672 | A | <--> | 787 | N | GLY | 103 | H | 3.36 |
| 54. | 3547 | CE2 | TRP | 672 | A | <--> | 787 | N | GLY | 103 | H | 3.27 |
| 55. | 3549 | CZ2 | TRP | 672 | A | <--> | 787 | N | GLY | 103 | H | 3.83 |
| 56. | 3545 | CD2 | TRP | 672 | A | <--> | 788 | CA | GLY | 103 | H | 3.48 |
| 57. | 3547 | CE2 | TRP | 672 | A | <--> | 788 | CA | GLY | 103 | H | 3.75 |
| 58. | 3548 | CE3 | TRP | 672 | A | <--> | 788 | CA | GLY | 103 | H | 3.58 |
| 59. | 3542 | CB | TRP | 672 | A | <--> | 790 | O | GLY | 103 | H | 3.31 |
| 60. | 3543 | CG | TRP | 672 | A | <--> | 790 | O | GLY | 103 | H | 3.49 |
| 61. | 3545 | CD2 | TRP | 672 | A | <--> | 790 | O | GLY | 103 | H | 3.81 |
| 62. | 3585 | CG2 | THR | 676 | A | <--> | 800 | CB | PRO | 105 | H | 3.72 |
| 63. | 3585 | CG2 | THR | 676 | A | <--> | 801 | CG | PRO | 105 | H | 3.75 |
| 64. | 3656 | CD | ARG | 683 | A | <--> | 830 | O | PHE | 109 | H | 2.96 |
| 65. | 3657 | NE | ARG | 683 | A | <--> | 830 | O | PHE | 109 | H | 3.59 |
| 66. | 3655 | CG | ARG | 683 | A | <--> | 840 | CZ | PHE | 109 | H | 3.65 |

Figure 93 cont.

| | | | | | | | | | | | | |
|---|---|---|---|---|---|---|---|---|---|---|---|---|
| 67. | 3685 | CD | LYS | 686 | A | <---> | 840 | CZ | PHE | 109 | H | 3.81 |
| 68. | 3656 | CD | ARG | 683 | A | <---> | 842 | CA | PHE | 110 | H | 3.83 |
| 69. | 3656 | CD | ARG | 683 | A | <---> | 844 | O | PHE | 110 | H | 3.85 |
| 70. | 3657 | NE | ARG | 683 | A | <---> | 844 | O | PHE | 110 | H | 3.46 |
| 71. | 3658 | CZ | ARG | 683 | A | <---> | 844 | O | PHE | 110 | H | 3.21 |
| 72. | 3659 | NH1 | ARG | 683 | A | <---> | 844 | O | PHE | 110 | H | 3.29 |
| 73. | 3660 | NH2 | ARG | 683 | A | <---> | 844 | O | PHE | 110 | H | 3.68 |
| 74. | 3657 | NE | ARG | 683 | A | <---> | 861 | N | TRP | 112 | H | 3.78 |
| 75. | 3617 | CA | TRP | 680 | A | <---> | 864 | O | TRP | 112 | H | 3.66 |
| 76. | 3622 | CD1 | TRP | 680 | A | <---> | 864 | O | TRP | 112 | H | 3.84 |
| 77. | 3657 | NE | ARG | 683 | A | <---> | 864 | O | TRP | 112 | H | 3.05 |
| 78. | 3658 | CZ | ARG | 683 | A | <---> | 864 | O | TRP | 112 | H | 3.54 |
| 79. | 3660 | NH2 | ARG | 683 | A | <---> | 864 | O | TRP | 112 | H | 3.15 |
| 80. | 3611 | O | LEU | 679 | A | <---> | 865 | CB | TRP | 112 | H | 3.72 |
| 81. | 3611 | O | LEU | 679 | A | <---> | 871 | CE3 | TRP | 112 | H | 3.65 |
| 82. | 3582 | O | THR | 676 | A | <---> | 875 | N | GLY | 113 | H | 3.86 |
| 83. | 3616 | N | TRP | 680 | A | <---> | 875 | N | GLY | 113 | H | 3.86 |
| 84. | 3582 | O | THR | 676 | A | <---> | 876 | CA | GLY | 113 | H | 3.30 |
| 85. | 3616 | N | TRP | 680 | A | <---> | 876 | CA | GLY | 113 | H | 3.86 |
| 86. | 3617 | CA | TRP | 680 | A | <---> | 876 | CA | GLY | 113 | H | 3.88 |
| 87. | 3620 | CB | TRP | 680 | A | <---> | 876 | CA | GLY | 113 | H | 3.46 |
| 88. | 3583 | CB | THR | 676 | A | <---> | 878 | O | GLY | 113 | H | 3.80 |
| 89. | 3660 | NH2 | ARG | 683 | A | <---> | 888 | CE1 | TYR | 114 | H | 3.63 |
| 90. | 3585 | CG2 | THR | 676 | A | <---> | 895 | CB | TYR | 115 | H | 3.88 |
| 91. | 3550 | CZ3 | TRP | 672 | A | <---> | 896 | CG | TYR | 115 | H | 3.53 |
| 92. | 3550 | CZ3 | TRP | 672 | A | <---> | 897 | CD1 | TYR | 115 | H | 3.49 |
| 93. | 3551 | CH2 | TRP | 672 | A | <---> | 897 | CD1 | TYR | 115 | H | 3.87 |
| 94. | 3550 | CZ3 | TRP | 672 | A | <---> | 898 | CD2 | TYR | 115 | H | 3.75 |
| 95. | 3550 | CZ3 | TRP | 672 | A | <---> | 899 | CE1 | TYR | 115 | H | 3.68 |
| 96. | 3551 | CH2 | TRP | 672 | A | <---> | 899 | CE1 | TYR | 115 | H | 3.65 |
| 97. | 3550 | CZ3 | TRP | 672 | A | <---> | 901 | CZ | TYR | 115 | H | 3.87 |
| 98. | 3549 | CZ2 | TRP | 672 | A | <---> | 919 | CE1 | TYR | 117 | H | 3.89 |

Figure 93 cont.

IC50 (µg/ml) in TZM-bl cells[1]

| Ab Name | 398-F1-F6_20 | CNE8 | X2278_C2_B6 | 246-F3_C10_2 | TRO.11 | CNE55 | CH119.10 |
|---|---|---|---|---|---|---|---|
| DH511_UCA4A | >50.0 | >50.0 | >50.0 | >50.0 | >50.0 | >50.0 | >50.0 |
| DH511_I6_4A | >50.0 | >50.0 | >50.0 | >50.0 | >50.0 | >50.0 | >50.0 |
| DH511_I5_4A | 23.682 | 4.959 | 11.236 | 1.782 | 0.289 | 4.176 | 2.413 |
| DH511_I4_4A | 22.127 | 4.758 | 11.862 | 2.791 | 0.298 | 4.409 | 3.209 |
| DH511_I3_4A | 24.865 | 4.821 | 12.594 | 2.744 | 0.292 | 2.822 | 2.916 |
| DH511_I2_4A | 43.109 | 6.616 | 19.674 | 3.300 | 0.485 | 5.542 | 3.224 |
| DH511_I1_4A | 26.974 | 6.222 | 12.837 | 2.935 | 0.435 | 4.819 | 1.789 |
| DH511.1 | 2.9 | 0.03 | 1.0 | 1.1 | 0.25 | 0.63 | 0.85 |
| DH511.2 | 1.2 | <0.011 | 0.36 | 0.39 | 0.13 | 0.32 | 0.44 |
| DH511.3 | 4.7 | 0.05 | 1.4 | 1.6 | 0.36 | 0.92 | 1.5 |
| DH511.4 | 8.8 | 0.07 | 2.5 | 1.5 | 0.39 | 2.1 | 0.74 |
| DH511.5 | 9.4 | 0.12 | 4.0 | 1.2 | 0.63 | 3.4 | 1.2 |
| DH511.6 | 12 | 0.07 | 4.7 | 1.7 | 0.46 | 1.3 | 2.1 |
| CH01-31 | 0.162 | 0.253 | 0.124 | 0.155 | 0.333 | 0.211 | 1.003 |
| 10E8* | 0.73 | 0.03 | 0.29 | 0.5 | 0.02 | 0.14 | 0.5 |

[1]Values are the antibody concentration (µg/ml)at which relative luminescence units (RLUs) were reduced 50% compared to virus control wells (no test sample).

Note: Values in bold are considered positive for neutralizing antibody activity when compared against background.

*Reference data.

Figure 94

| | IC50 (µg/ml) in TZM-bl cells[1] | | | | |
|---|---|---|---|---|---|
| Ab Name | BJOX002000.03.2 | 25710-2.43 | X1632_S2_B10 | Ce703010217_B6 | Ce1176_A3 |
| DH511_UCA4A | >50.0 | >50.0 | >50.0 | >50.0 | >50.0 |
| DH511_I6_4A | >50.0 | >50.0 | >50.0 | >50.0 | >50.0 |
| DH511_I5_4A | 6.513 | 1.132 | 4.426 | 0.952 | 4.601 |
| DH511_I4_4A | 7.364 | 1.498 | 5.668 | 0.851 | 4.979 |
| DH511_I3_4A | 6.235 | 1.283 | 5.528 | 0.941 | 4.024 |
| DH511_I2_4A | 13.004 | 2.120 | 5.523 | 4.963 | 9.617 |
| DH511_I1_4A | 10.444 | 1.548 | 5.963 | 1.213 | 4.102 |
| DH511.1 | 1.2 | 0.16 | 0.85 | 0.20 | 1.3 |
| DH511.2 | 0.52 | 0.10 | 0.42 | 0.16 | 0.59 |
| DH511.3 | 1.5 | 0.43 | 1.3 | 0.55 | 2.2 |
| DH511.4 | 1.7 | 0.46 | 1.0 | 0.67 | 2.7 |
| DH511.5 | 2.8 | 0.39 | 1.6 | 0.58 | 1.5 |
| DH511.6 | 2.2 | 0.56 | 1.6 | 0.89 | 3.2 |
| CH01-31 | 7.819 | 0.244 | 0.110 | 0.108 | 0.134 |
| 10E8* | 0.55 | 0.05 | 0.4 | 0.22 | 0.36 |

[1]Values are the antibody concentration (µg/ml)at which relative luminescence units (RLUs) were reduced 50% compared to virus control wells (no test sample).

Note: Values in bold are considered positive for neutralizing antibody activity when compared against background.

*Reference data.

Figure 94 cont.

A: Overlap extension oligonucleotides for framework region 1 (5' - 3')

| | |
|---|---|
| VH1 | TATTCCCATCGCGGCGCCAGGTCCAGCTKGTRCAGTCTGG |
| VH157 | TATTCCCATCGCGGCGCCAGGTGCAGCTGGTGSARTCTGG |
| VH2 | TATTCCCATCGCGGCGCCAGRTCACCTTGAAGGAGTCTG |
| VH3 | TATTCCCATCGCGGCGCGAGGTGCAGCTGKTGGAGWCY |
| VH4 | TATTCCCATCGCGGCGCCAGGTGCAGCTGCAGGAGTCSG |
| VH4-DP63 | TATTCCCATCGCGGCGCCAGGTGCAGCTACAGCAGTGGG |
| VH6 | TATTCCCATCGCGGCGCCAGGTACAGCTGCAGCAGTCA |
| VH3N | TATTCCCATCGCGGCGCTCAACACAACGGTTCCCAGTTA |
| VK1 | GCGCCGCGATGGGAATAGCTAGCCGACATCCRGDTGACCCAGTCTCC |
| VK2 | GCGCCGCGATGGGAATAGCTAGCCGATATTGTGMTGACBCAGWCTCC |
| VK3 | GCGCCGCGATGGGAATAGCTAGCCGAAATTGTRWTGACRCAGTCTCC |
| VK5 | GCGCCGCGATGGGAATAGCTAGCCGAAACGACACTCACGCAGTCTC |
| VL1 | GCGCCGCGATGGGAATAGCTAGCCCAGTCTGTSBTGACGCAGCCGCC |
| VL1459 | GCGCCGCGATGGGAATAGCTAGCCCAGCCTGTGCTGACTCARYC |
| VL15910 | GCGCCGCGATGGGAATAGCTAGCCCAGCCWGKGCTGACTCAGCCMCC |
| VL2 | GCGCCGCGATGGGAATAGCTAGCCCAGTCTGYYCTGAYTCAGCCT |
| VL3 | GCGCCGCGATGGGAATAGCTAGCCTCCTATGWGCTGACWCAGCCAA |
| VL-DPL16 | GCGCCGCGATGGGAATAGCTAGCCTCCTCTGAGCTGASTCAGGASCC |
| VL3-38 | GCGCCGCGATGGGAATAGCTAGCCTCCTATGAGCTGAYRCAGCYACC |
| VL6 | GCGCCGCGATGGGAATAGCTAGCCAATTTTATGCTGACTCAGCCCC |
| VL78 | GCGCCGCGATGGGAATAGCTAGCCCAGDCTGTGGTGACYCAGGAGCC |

Figure 95A

B: Overlap extension oligonucleotides for leader peptide (5' - 3')

| | |
|---|---|
| VH1 | TATTCCCATCGCGGCGCACAGGTGCCCACTCCCAGGTGCAG |
| VH3 | TATTCCCATCGCGGCGCAAGGTGTCCAGTGTGARGTGCAG |
| VH4/6 | TATTCCCATCGCGGCGCCCCAGATGGGTCCTGTCCCAGGTGCAG |
| VH5 | TATTCCCATCGCGGCGCCAAGGAGTCTGTTCCGAGGTGCAG |
| VL1 | GCGCCGCGATGGGAATATCTGCTCGAGTTCGGTCA GGTCCTGGGCCCAGTCTGTGCTG |
| VL2 | GCGCCGCGATGGGAATATCTGCTCGAGTTCGGTCA GGTCCTGGGCCCAGTCTGCCCTG |
| VL3 | GCGCCGCGATGGGAATATCTGCTCGAGTTCGGTCA YWCTGCACAGGCTCTGTGACCTCCTAT |
| VL4/5 | GCGCCGCGATGGGAATATCTGCTCGAGTTCGGTCA GGTCTCTCTCSCAGCYTGTGCTG |
| VL6 | GCGCCGCGATGGGAATATCTGCTCGAGTTCGGTCA GTTCTTGGGCCAATTTTATGCTG |
| VL7 | GCGCCGCGATGGGAATATCTGCTCGAGTTCGGTCA GGTCCAATTCYCAGGCTGTGGTG |
| VL8 | GCGCCGCGATGGGAATATCTGCTCGAGTTCGGTCA GAGTGGATTCTCAGACTGTGGTG |
| VK1/2 | GCGCCGCGATGGGAATATCTGCTCGAGTTCGGTCA ATGAGGSTCCCYGCTCAGCTGCTGG |
| VK3 | GCGCCGCGATGGGAATATCTGCTCGAGTTCGGTCA CTCTTCCTCCTGCTACTCTGGCTCCCAG |
| VK4 | GCGCCGCGATGGGAATATCTGCTCGAGTTCGGTCA ATTTCTCTGTTGCTCTGGATCTCTG |

C: Nested constant region oligonucleotides (5' - 3')

| | |
|---|---|
| IgG nested | NNNNATGGGCCCTGSGATGGGCCCTTGGTGGARGC |
| IgM nested | NNNNATGGGCCCTGGGTTGGGGCGGATGCACTCC |
| IgA nested | NNNNATGGGCCCTGCTTGGGGCTGGTCGGGGATG |
| IgKC nested | NNNNGTGCGGCCGCAGATGGTGCAGCCACAGTTC |
| IgLC nested | NNNNGTGCGGCCGCGAGGGYGGGAACAGAGTGAC |

Figures 95B-C

| Antibody ID | CDR3 | IMGT Length | Membrane Insertion Score[a] |
|---|---|---|---|
| DH511.1 | CTADLGEPVVSRFFEWGSYYYYMDLW | 24 | 1.36 |
| DH511.2 | CTMDEGTP-VTRFLEWGYFYYYMAVW | 23 | 2.11 |
| DH511.3 | CTADLGEAVVSRFFEWGSYYYYMDFW | 24 | 1.64 |
| DH511.4 | CTRDEGAP-VTRFLEWGSYYYYMAVW | 23 | 0.85 |
| DH511.5 | CTRDEGAP-VTRFLEWGSYYYYMAVW | 23 | 0.85 |
| DH511.6 | CTADLGEAVVSRFFEWGSYYYYMDFW | 24 | 1.64 |
| DH511.7P | | | |
| DH511.8P | | | |
| DH511.9P | | | |
| DH511.10P | | | |
| DH511.11P | | | |
| DH511.12P | | | |
| 2F5 | CAHRRGPTTLFGVPIARGPVNAMDVW | 24 | -0.25 |
| 4E10 | CAREGTTGWGWLGKPIGAFAHW | 20 | 2.96 |
| 10E8 | CARTGKYYDFWSGYPPGEEYFQDW | 22 | 1.5 |

*a: Membrane insertion score is calculated as sum of Wimley-White Interfacial Hydrophobicity Scale values over the middle 50% of the HCDR3 amino acids. Positive scores are favorable for membrane insertion.*

*Phe or Trp residues are highlighted in red.*

*Pro are highlighted in blue.*

Figure 96

| Ab ID | OD 450 nm (33 μg/ml) |
|---|---|
| DH511.1 | 0.075 |
| DH511.2 | 0.069 |
| DH511.3 | 0.080 |
| DH511.4 | 0.116 |
| DH511.5 | 0.073 |
| DH511.6 | 0.072 |
| DH511.7P | |
| DH511.8P | |
| DH511.9P | |
| DH511.10P | |
| DH511.11P | |
| DH511.12P | |
| DH511_UCA | 0.061 |
| DH511_I6 | 0.118 |
| DH511_I5 | 0.089 |
| DH511_I4 | 0.111 |
| DH511_I3 | 0.129 |
| DH511_I2 | 0.126 |
| DH511_I1 | 0.160 |
| Synagis | 0.043 |
| 4E10 | 2.068 |

Data shown are an average of two independent experiments. OD values above 0.15 were considered positive.

Figure 97

| Key | (IC50/IC80 in µg/ml) | | |
|---|---|---|---|
| <0.100 | 0.100-1.00 | 1.00-10.0 | >10.0 |

| | | | | | IC50 (µg/ml) | IC80 (µg/ml) | IC50 (µg/ml) | IC80 (µg/ml) |
|---|---|---|---|---|---|---|---|---|
| Antibody Number | Heavy-chain ID | Light-chain ID | IgG Quant (µg/ml) | 1:6 Initial Dilution (µg/ml) | BG1168 | BG1168 | SVA | SVA |
| 1 | DH511.7AVHP_4A | DH511.2AVKP | 63 | 10.50 | 1.272 | 6.006 | >10.5 | >10.5 |
| 2 | DH511.7AVHP_4A | DH511.9AVKP | 67.2 | 11.20 | 9.314 | >11.2 | >11.2 | >11.2 |
| 3 | DH511.7AVHP_4A | DH511.9BVKP | 62.35 | 10.39 | >10.39 | >10.39 | >10.39 | >10.39 |
| 4 | DH511.7AVHP_4A | DH511.9CVKP | 109.25 | 18.21 | 8.174 | >18.21 | >18.21 | >18.21 |
| 5 | DH511.7AVHP_4A | DH511.10AVKP | 24.5 | 4.08 | >4.08 | >4.08 | >4.08 | >4.08 |
| 6 | DH511.7AVHP_4A | DH511.10BVKP | 67 | 11.17 | >11.17 | >11.17 | >11.17 | >11.17 |
| 7 | DH511.7AVHP_4A | DH511.11AVKP | 38.75 | 6.46 | >6.46 | >6.46 | >6.46 | >6.46 |
| 8 | DH511.7AVHP_4A | DH511.2VKP | 68.35 | 11.39 | 2.818 | >11.39 | >11.39 | >11.39 |
| 9 | DH511.7BVHP_4A | DH511.8AVKP | 40.85 | 6.81 | 1.3 | >6.81 | >6.81 | >6.81 |
| 10 | DH511.7BVHP_4A | DH511.9AVKP | 61.9 | 10.32 | >10.32 | >10.32 | >10.32 | >10.32 |
| 11 | DH511.7BVHP_4A | DH511.9BVKP | 36 | 6.00 | >6 | >6 | >6 | >6 |
| 12 | DH511.7BVHP_4A | DH511.9CVKP | 51.45 | 8.58 | 7.843 | >8.58 | >8.58 | >8.58 |
| 13 | DH511.7BVHP_4A | DH511.10AVKP | 44.5 | 7.42 | >7.42 | >7.42 | >7.42 | >7.42 |
| 14 | DH511.7BVHP_4A | DH511.10BVKP | 38.75 | 6.46 | >6.46 | >6.46 | >6.46 | >6.46 |
| 15 | DH511.7BVHP_4A | DH511.11AVKP | 37.5 | 6.25 | >6.25 | >6.25 | >6.25 | >6.25 |
| 16 | DH511.7BVHP_4A | DH511.2VKP | 72.7 | 12.12 | 3.458 | >12.12 | >12.12 | >12.12 |
| 17 | DH511.8AVHP_4A | DH511.7AVKP | 66.3 | 11.05 | 1.047 | 5.776 | >11.05 | >11.05 |
| 18 | DH511.8AVHP_4A | DH511.9AVKP | 59.85 | 9.98 | 7.925 | >9.98 | >9.98 | >9.98 |
| 19 | DH511.8AVHP_4A | DH511.9BVKP | 64.1 | 10.68 | >10.65 | >10.68 | >10.68 | >10.68 |
| 20 | DH511.8AVHP_4A | DH511.9CVKP | 92.4 | 15.40 | 6.174 | >15.4 | >15.4 | >15.4 |
| 21 | DH511.8AVHP_4A | DH511.10AVKP | 28.5 | 4.75 | >4.75 | >4.75 | >4.75 | >4.75 |
| 22 | DH511.8AVHP_4A | DH511.10BVKP | 24.1 | 4.02 | >4.02 | >4.02 | >4.02 | >4.02 |
| 23 | DH511.8AVHP_4A | DH511.11AVKP | 23.2 | 3.87 | >3.87 | >3.87 | >3.87 | >3.87 |
| 24 | DH511.8AVHP_4A | DH511.2VKP | 76.75 | 12.79 | 2.091 | >12.79 | >12.79 | >12.79 |
| 25 | DH511.8BVHP_4A | DH511.7AVKP | 67.45 | 11.24 | 0.513 | 2.523 | >11.24 | >11.24 |
| 26 | DH511.8BVHP_4A | DH511.9AVKP | 152.05 | 25.34 | 8.241 | >25.34 | >25.34 | >25.34 |
| 27 | DH511.8BVHP_4A | DH511.9BVKP | 103.5 | 17.25 | 7.890 | >17.25 | >17.25 | >17.25 |
| 28 | DH511.8BVHP_4A | DH511.9CVKP | 227.2 | 37.87 | 6.789 | >37.87 | >37.87 | >37.87 |

Figure 98

| | | | | | | | | |
|---|---|---|---|---|---|---|---|---|
| 29 | DH511.8BVHP_4A | DH511.10AVKP | 45.9 | 7.65 | >7.65 | >7.65 | >7.65 | >7.65 |
| 30 | DH511.8BVHP_4A | DH511.10BVKP | 40.65 | 6.78 | >6.78 | >6.78 | >6.78 | >6.78 |
| 31 | DH511.8BVHP_4A | DH511.11AVKP | 92.65 | 15.44 | 5.087 | >15.44 | >15.44 | >15.44 |
| 32 | DH511.8BVHP_4A | DH511.2VKP | 118.75 | 19.79 | 2.002 | 9.339 | >19.79 | >19.79 |
| 33 | DH511.8CVHP_4A | DH511.7AVKP | 2.511 | 0.419 | >0.419 | >0.419 | >0.419 | >0.419 |
| 34 | DH511.8CVHP_4A | DH511.9AVKP | 12.819 | 2.137 | >2.137 | >2.137 | >2.137 | >2.137 |
| 35 | DH511.8CVHP_4A | DH511.9BVKP | 0.397 | 0.066 | >0.066 | >0.066 | >0.066 | >0.066 |
| 36 | DH511.8CVHP_4A | DH511.9CVKP | 12.785 | 2.131 | >2.131 | >2.131 | >2.131 | >2.131 |
| 37 | DH511.8CVHP_4A | DH511.10AVKP | 0.314 | 0.052 | >0.052 | >0.052 | >0.052 | >0.052 |
| 38 | DH511.8CVHP_4A | DH511.10BVKP | 0.493 | 0.082 | >0.082 | >0.082 | >0.082 | >0.082 |
| 39 | DH511.8CVHP_4A | DH511.11AVKP | 5.005 | 0.834 | >0.834 | >0.834 | >0.834 | >0.834 |
| 40 | DH511.8CVHP_4A | DH511.2VKP | 1.825 | 0.304 | >0.304 | >0.304 | >0.304 | >0.304 |
| 41 | DH511.9AVHP_4A | DH511.7AVKP | 113.8 | 18.967 | 3.238 | 14.836 | >18.967 | >18.967 |
| 42 | DH511.9AVHP_4A | DH511.8AVKP | 80.144 | 13.357 | 0.774 | 3.790 | >13.357 | >13.357 |
| 43 | DH511.9AVHP_4A | DH511.10AVKP | 0.425 | 0.071 | >0.071 | >0.071 | >0.071 | >0.071 |
| 44 | DH511.9AVHP_4A | DH511.10BVKP | 1.324 | 0.221 | >0.221 | >0.221 | >0.221 | >0.221 |
| 45 | DH511.9AVHP_4A | DH511.11AVKP | 35.459 | 5.910 | 2.433 | >5.91 | >5.91 | >5.91 |
| 46 | DH511.9AVHP_4A | DH511.2VKP | 123.19 | 20.532 | 6.858 | >20.532 | >20.532 | >20.532 |
| 47 | DH511.10AVHP_4A | DH511.7AVKP | 88.918 | 14.820 | 0.958 | 4.132 | >14.82 | >14.82 |
| 48 | DH511.10AVHP_4A | DH511.8AVKP | 100.574 | 16.762 | 1.396 | 5.769 | >16.762 | >16.762 |
| 49 | DH511.10AVHP_4A | DH511.9AVKP | 173.528 | 28.921 | 1.731 | 7.303 | >28.921 | >28.921 |
| 50 | DH511.10AVHP_4A | DH511.9BVKP | 154.783 | 25.797 | 1.428 | 5.567 | >25.797 | >25.797 |
| 51 | DH511.10AVHP_4A | DH511.9CVKP | 274.865 | 45.811 | 1.305 | 4.523 | >45.811 | >45.811 |
| 52 | DH511.10AVHP_4A | DH511.11AVKP | 65.743 | 10.957 | 0.71 | 4.336 | >10.957 | >10.957 |
| 53 | DH511.10AVHP_4A | DH511.2VKP | 142.347 | 23.725 | 1.731 | 7.428 | >23.725 | >23.725 |
| 54 | DH511.10BVHP_4A | DH511.7AVKP | 72.442 | 12.074 | 0.913 | 5.042 | >12.074 | >12.074 |
| 55 | DH511.10BVHP_4A | DH511.8AVKP | 152.552 | 25.425 | 0.48 | 1.495 | >25.425 | >25.425 |
| 56 | DH511.10BVHP_4A | DH511.9AVKP | 154.118 | 25.686 | 0.817 | 3.173 | >25.686 | >25.686 |
| 57 | DH511.10BVHP_4A | DH511.9BVKP | 12.751 | 2.125 | 0.673 | >2.125 | >2.125 | >2.125 |
| 58 | DH511.10BVHP_4A | DH511.9CVKP | 185.783 | 30.964 | 1.135 | 4.096 | >30.964 | >30.964 |
| 59 | DH511.10BVHP_4A | DH511.11AVKP | 24.791 | 4.132 | 1.213 | >4.132 | >4.132 | >4.132 |
| 60 | DH511.10BVHP_4A | DH511.2VKP | 139.712 | 23.285 | 1.312 | 6.239 | >23.285 | >23.285 |

Antibody highlighted in red showed comparable potency to DH512.

Figure 98 cont.

| Key | (IC50/IC80 in µg/ml) | | |
|---|---|---|---|
| <0.100 | 0.100-1.00 | 1.00-10.0 | >10.0 |

| | | | | | IC50 (µg/ml) | IC80 (µg/ml) | IC50 (µg/ml) | IC80 (µg/ml) |
|---|---|---|---|---|---|---|---|---|
| Antibody Number | Heavy-chain ID | Light-chain ID | IgG Quant (µg/ml) | 1:6 Initial Dilution (µg/ml) | BG1168 | BG1168 | SVA | SVA |
| 61 | DH511.10CVHP_4A | DH511.7AVKP | 123.445 | 20.574 | 10.673 | >20.574 | >20.574 | >20.574 |
| 62 | DH511.10CVHP_4A | DH511.8AVKP | 169.294 | 28.216 | 3.408 | >28.216 | >28.216 | >28.216 |
| 63 | DH511.10CVHP_4A | DH511.9AVKP | 253.605 | 42.268 | 8.719 | >42.268 | >42.268 | >42.268 |
| 64 | DH511.10CVHP_4A | DH511.9BVKP | 451.084 | 75.181 | 9.393 | 50.853 | >75.181 | >75.181 |
| 65 | DH511.10CVHP_4A | DH511.9CVKP | 444.052 | 74.009 | 5.180 | 29.485 | >74.009 | >74.009 |
| 66 | DH511.10CVHP_4A | DH511.11AVKP | 93.456 | 15.576 | 11.992 | >15.576 | >15.576 | >15.576 |
| 67 | DH511.10CVHP_4A | DH511.2VKP | 181.158 | 30.193 | 10.671 | >30.193 | >30.193 | >30.193 |
| 68 | DH511.11AVHP_4A | DH511.7AVKP | 199.455 | 33.24 | 31.35 | >33.24 | >33.24 | >33.24 |
| 69 | DH511.11AVHP_4A | DH511.8AVKP | 218.318 | 36.39 | 8.322 | >36.39 | >36.39 | >36.39 |
| 70 | DH511.11AVHP_4A | DH511.9AVKP | 427.911 | 71.32 | >71.32 | >71.32 | >71.32 | >71.32 |
| 71 | DH511.11AVHP_4A | DH511.9BVKP | 333.05 | 55.51 | >55.51 | >55.51 | >55.51 | >55.51 |
| 72 | DH511.11AVHP_4A | DH511.9CVKP | 134.35 | 22.39 | >22.39 | >22.39 | >22.39 | >22.39 |
| 73 | DH511.11AVHP_4A | DH511.10AVKP | 17.539 | 2.92 | >2.92 | >2.92 | >2.92 | >2.92 |
| 74 | DH511.11AVHP_4A | DH511.10BVKP | 80.408 | 13.40 | >13.4 | >13.4 | >13.4 | >13.4 |
| 75 | DH511.11AVHP_4A | DH511.2VKP | 155.052 | 25.84 | 11.195 | >25.84 | >25.84 | >25.84 |
| 76 | DH511.12AVHP_4A | DH511.7AVKP | 18.957 | 3.17 | >3.17 | >3.17 | >3.17 | >3.17 |
| 77 | DH511.12AVHP_4A | DH511.8AVKP | 11.844 | 1.97 | >1.97 | >1.97 | >1.97 | >1.97 |
| 78 | DH511.12AVHP_4A | DH511.9AVKP | 169.142 | 28.19 | >28.19 | >28.19 | >28.19 | >28.19 |
| 79 | DH511.12AVHP_4A | DH511.9BVKP | 2.571 | 0.43 | >0.43 | >0.43 | >0.43 | >0.43 |
| 80 | DH511.12AVHP_4A | DH511.9CVKP | 111.504 | 18.58 | >18.58 | >18.58 | >18.58 | >18.58 |
| 81 | DH511.12AVHP_4A | DH511.10AVKP | 2.187 | 0.36 | >0.36 | >0.36 | >0.36 | >0.36 |
| 82 | DH511.12AVHP_4A | DH511.10BVKP | 15.98 | 2.66 | >2.66 | >2.66 | >2.66 | >2.66 |
| 83 | DH511.12AVHP_4A | DH511.2VKP | 50.982 | 8.50 | >8.5 | >8.5 | >8.5 | >8.5 |
| 84 | DH511.2VH | DH511.7AVKP | 130.55 | 21.76 | 0.639 | 3.225 | >21.76 | >21.76 |
| 85 | DH511.2VH | DH511.8AVKP | 145.575 | 24.26 | 0.258 | 0.886 | >24.26 | >24.26 |
| 86 | DH511.2VH | DH511.9AVKP | 597.214 | 99.54 | 1.846 | 9.286 | >99.54 | >99.54 |

Figure 98 cont.

| | | | | | | | | |
|---|---|---|---|---|---|---|---|---|
| 87 | DH511.2VH | DH511.9BVKP | 1072.598 | 178.77 | 3.414 | 13.356 | >178.77 | >178.77 |
| 88 | DH511.2VH | DH511.9CVKP | 646.48 | 107.75 | 2.115 | 7.926 | >107.75 | >107.75 |
| 89 | DH511.2VH | DH511.10AVKP | 3.676 | 0.61 | >0.61 | >0.61 | >0.61 | >0.61 |
| 90 | DH511.2VH | DH511.10BVKP | 14.881 | 2.48 | >2.48 | >2.48 | >2.48 | >2.48 |
| 91 | DH511.2VH | DH511.11AVKP | 156.192 | 26.03 | 0.355 | 1.243 | >26.03 | >26.03 |
| DH511.2 | DH511.2VH | DH511.2VKP | 188.551 | 31.43 | 1.602 | 6.039 | >31.43 | >31.43 |
| | DH511.2VH | DH511.2VKP | 119.527 | 19.921 | 0.725 | 2.441 | >19.921 | >19.921 |
| | DH511.2VH | DH511.2VKP | 170 | 28.33 | 0.522 | 2.750 | >28.33 | >28.33 |
| 10E8 mAb | | | | | 0.152 | 0.841 | >50 | >50 |
| | | | | | 0.262 | 0.779 | >50 | >50 |
| 2F5 mAb | | | 100.04 | 16.67 | 3.674 | 14.218 | >16.67 | >16.67 |
| | | | 87.846 | 14.641 | 3.686 | >14.641 | >14.641 | >14.641 |
| | | | 55 | 9.17 | 1.581 | >9.17 | >9.17 | >9.17 |
| Mock Transfection | | | 0.026 | 0.0043 | >0 | >0 | >0 | >0 |
| | | | 0.003 | 0.001 | >0.001 | >0.001 | >0.001 | >0.001 |
| | | | 20 | 3.33 | >3.33 | >3.33 | >3.33 | >3.33 |

Antibody highlighted in red showed comparable potency to DH512.

Figure 98 cont.

| | | Titer in TZM.bl cells (ug/ml) | | | | | |
|---|---|---|---|---|---|---|---|
| | | DH511.2_K3* | | DH511.2 | | 10E8 | |
| Virus ID | Clade | $IC_{50}$ | $IC_{80}$ | $IC_{50}$ | $IC_{80}$ | $IC_{50}$ | $IC_{80}$ |
| QH0692.42 | B | 0.982 | 3.59 | 1.63 | 8.75 | 0.566 | 2.32 |
| SC422661.8 | B | 0.269 | 0.999 | 0.444 | 2.01 | 0.302 | 1.23 |
| AC10.0.29 | B | 0.115 | 0.476 | 0.153 | 0.823 | 0.172 | 0.882 |
| THRO4156.18 | B | 0.584 | 2.62 | 0.194 | 1.98 | 0.120 | 0.566 |
| WITO4160.33 | B | 0.149 | 0.750 | 0.261 | 1.28 | 0.159 | 0.858 |
| Du156.12 | C | <0.023 | 0.108 | 0.064 | 0.336 | 0.028 | 0.130 |
| Du422.1 | C | 0.320 | 1.17 | 0.758 | 2.88 | 0.220 | 0.825 |
| ZM53M.PB12 | C | 2.90 | 11.1 | 6.13 | 25.4 | 2.72 | 13.4 |
| ZM109F.PB4 | C | 0.729 | 2.69 | 1.14 | 5.70 | 0.252 | 1.36 |
| HIV-0013095-2.11 | C | <0.023 | 0.138 | <0.023 | 0.603 | <0.023 | 0.127 |
| CNE19 | BC | 0.259 | 1.34 | 1.58 | 7.94 | 0.582 | 3.27 |
| CNE30 | BC | 1.50 | 7.87 | 4.83 | 27.5 | 0.616 | 4.88 |
| MS208.A1 | A | 0.683 | 3.31 | 1.48 | 5.41 | 0.442 | 2.00 |
| Q23.17 | A | 0.731 | 3.08 | 2.01 | 11.9 | 0.660 | 3.67 |
| Q769.d22 | A | 0.254 | 1.59 | 1.12 | 9.57 | 1.11 | 4.77 |
| 0330.v4.c3 | A | 0.926 | 3.65 | 1.78 | 9.74 | 1.41 | 6.46 |
| 191955_A11 | A (T/F) | 0.388 | 1.16 | 0.956 | 3.36 | 0.447 | 1.31 |
| 928-28 | CRF02_AG | 0.033 | 0.513 | 0.195 | 1.19 | 0.119 | 0.665 |
| T250-4 | CRF02_AG | 0.866 | 3.33 | 2.60 | 14.6 | 1.01 | 5.00 |
| 211-9 | CRF02_AG | 0.386 | 1.14 | 1.07 | 3.78 | 0.635 | 2.17 |
| C1080.c03 | CRF01_AE | 0.081 | 0.516 | 0.154 | 1.18 | 0.029 | 0.317 |
| R1166.c01 | CRF01_AE | 0.711 | 2.35 | 1.35 | 5.45 | 0.384 | 2.91 |
| C4118.c09 | CRF01_AE | 0.508 | 4.20 | 0.801 | 12.0 | 0.650 | 4.68 |
| X2131_C1_B5 | G | 0.068 | 0.442 | 0.229 | 1.14 | 0.080 | 0.373 |
| P1981_C5_3 | G | <0.023 | 0.109 | 0.065 | 0.306 | <0.023 | 0.106 |
| X1632_S2_B10 | G | 0.265 | 1.14 | 0.741 | 4.78 | 0.494 | 1.93 |
| 3016.v5.c45 | D | 0.531 | 1.95 | 1.81 | 8.53 | 0.593 | 2.10 |
| A07412M1.vrc12 | D | 0.484 | 1.76 | 0.649 | 5.15 | 0.221 | 1.15 |
| 3817.v2.c59 | CD | 1.21 | 4.28 | 6.00 | 17.8 | 0.906 | 3.82 |
| 0815.v3.c3 | ACD | 0.271 | 1.22 | 0.850 | 4.02 | 0.238 | 1.09 |
| | | | | | | | |
| MuLV | Neg. Control | >50 | >50 | >50 | >50 | >50 | >50 |
| | | | | | | | |
| MEDIAN TITERS | | 0.387 | 1.462 | 0.903 | 4.963 | 0.413 | 1.648 |

*DH511.2_K3 is comprised of the DH511.2 heavy-chain reconstituted with the light chain DH511.8AVK.

Figure 99

A: PCR conditions for isotype specific amplification

| Amplicon | Primers | Expected Length | Extension Y (s) | Cycles X (#) |
|---|---|---|---|---|
| Paired IgG, IgA, IgK, IgL | IgG, IgA, IgK, IgL | 1100 | 33 | 8 |
| Paired IgM, IgK, IgL | IgM, IgK, IgL | 1100 | 33 | 5 |
| VH only IgG, IgA | IgG, IgA, VH_linker | 600 | 20 | 8 |
| VH only IgM | IgM, VH_linker | 600 | 20 | 5 |
| VL only | IgK, IgL, VL_linker | 550 | 20 | 5 |

B: Oligonucleotides for isotype specific amplification (5' - 3')

| | |
|---|---|
| IgG | GTCTCGTGGGCTCGGAGATGTGTATAAGAGACAGNNNNNATGGGCCCTG SGATGGGCCCTTGGTGGARGC |
| IgM | GTCTCGTGGGCTCGGAGATGTGTATAAGAGACAGNNNNNATGGGCCCTG GGTTGGGGCGGATGCACTCC |
| IgA | GTCTCGTGGGCTCGGAGATGTGTATAAGAGACAGNNNNNATGGGCCCTG CTTGGGGCTGGTCGGGGATG |
| IgK | TCGTCGGCAGCGTCAGATGTGTATAAGAGACAGNNNNNGTGCGGCCGC AGATGGTGCAGCCACAGTTC |
| IgL | TCGTCGGCAGCGTCAGATGTGTATAAGAGACAGNNNNNGTGCGGCCGC GAGGGYGGGAACAGAGTGAC |
| VL_linker | GTCTCGTGGGCTCGGAGATGTGTATAAGAGACAGNNNNNGCGCCGCGATGGGAAT |
| VH_linker | TCGTCGGCAGCGTCAGATGTGTATAAGAGACAGNNNNNGCTAGCTATTCCCATCGCGG |

C: PCR conditions for MiSeq Barcoding

| Amplicon | Expected Length | Extension Y (s) | Cycles X (#) |
|---|---|---|---|
| Paired IgG, IgA, IgK, IgL | 1100 | 33 | 8 |
| Paired IgM, IgK, IgL | 1100 | 33 | 8 |
| VH only IgG, IgA | 600 | 20 | 8 |
| VH only IgM | 600 | 20 | 8 |
| VL only | 550 | 20 | 8 |

Figures 100A-C

HIV-1 NEUTRALIZING ANTIBODIES AND USES THEREOF

This application is a continuation application of U.S. application Ser. No. 15/559,314 filed on Sep. 18, 2017, which is a U.S. National Stage application under 35 U.S.C. § 371 of International Patent Application No. PCT/US16/23488, filed Mar. 21, 2016, which application claims the benefit of and priority to U.S. Application Ser. No. 62/135,309 filed Mar. 19, 2015, U.S. Application Ser. No. 62/222,057 filed Sep. 22, 2015, and U.S. Application Ser. No. 62/260,100 filed Nov. 25, 2015, U.S. Application Ser. No. 62/191,095 filed Jul. 10, 2015, U.S. Application Ser. No. 62/191,054 filed Jul. 10, 2015 and U.S. Application Ser. No. 62/261,233 filed Nov. 30, 2015 the content of each application is hereby incorporated by reference in its entirety.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as known to those skilled therein as of the date of the invention described herein.

GOVERNMENT SUPPORT

This invention was made with government support under Center for HIV/AIDS Vaccine Immunology-Immunogen Design grant UM1-A1100645 from the NIH, NIAID, Division of AIDS. The government has certain rights in the invention.

SEQUENCE LISTING

The instant application contains a Sequence Listing which has been filed electronically in ASCII format and is hereby incorporated by reference in its entirety. Said ASCII copy, created on May 5, 2020, is named 1234300_00338US2_SL.txt and is 343,838 bytes in size.

FIELD OF THE INVENTION

The invention relates to the identification of monoclonal HIV-1 neutralizing antibodies, such as, but not limited to, antibodies that bind to the membrane-proximal region of HIV-1 gp41, their recombinant expression and purification and uses.

BACKGROUND

A number of neutralizing monoclonal antibodies (mAbs) have been isolated from HIV-1 infected individuals and these mAbs define specific regions (epitopes) on the virus that are vulnerable to NAbs.

Broadly neutralizing antibodies have been isolated only from natural HIV infection. See e.g. Mascola and Haynes, Immunological Reviews (2013) Vol. 254: 225-244. Some examples of broadly neutralizing antibodies (bnAbs) that bind gp41 at gp41bnAb sites within the membrane proximal region are 2F5, 4E10 and 10E8. These gp41 neutralizing antibodies recognize the membrane-proximal region (MPER) of the HIV-1 gp41 glycoprotein. The advantage of gp41 bnAbs is that they are generally quite broad in their neutralization coverage yet the antibodies to date, have not been developed for prevention or treatment. This is because 2F5 and 4E10 are quite polyreactive and autoreactive, and while mAb 10E8 is less polyreactive, it is autoreactive and is not stable (Haynes B F et al. Science 308: 1906-8, 2005; Yang G, et al. JEM 210: 241-56, 2013; Huang J et al nature 491: 406-412, 2012). Unfortunately, so far none of these antibodies have been developed for HIV prevention or treatment. Thus, the need exists for monoclonal broadly neutralizing antibodies that can be developed and used for prevention and treatment for an infectious agent, such as HIV.

SUMMARY OF THE INVENTION

In certain aspects the invention provides an antibody or fragment thereof with the binding specificity of an MPER antibody as described herein. In non-limiting embodiments the MPER antibody from FIG. 13, FIG. 55, FIG. 56 or FIGS. 30-33 (antibodies with mutations in the DH512 or DH511 VH chain). In non-limiting embodiments, combination mutations in the DH512 or DH511 VHCDR3 could include VH_L100dF together with T100aW FIGS. 31 and 32); VH_L100dW together with T100aW (FIGS. 31 and 32).

Non-limiting examples include antibodies comprising VH or VL chains from DH511, DH512, DH512_K3, DH512-L100dF, DH513, DH514, DH515, DH516, DH517, DH518, lineage members.

In certain embodiments, the antibody or fragment thereof is fully human and recombinantly produced. In certain embodiments, some of the VH and/VL chains are isolated from human subject who have been naturally infected with HIV. In certain embodiments the antibody is not naturally occurring. In certain embodiments the antibody comprises naturally occurring pair of VH and VL chains. In certain embodiments the antibody comprises naturally occurring pair of VH and VL chains wherein the Fc portion of the antibody is not the natural isotype or portion of the naturally occurring pair of VH and VL chains. In certain embodiments the antibody is computationally designed, for example based on some naturally isolated VH and VL sequences. In certain embodiments the antibody is computationally designed, e.g., UCA, Intermediates in the antibody lineages. In certain embodiments the antibody comprises a non-naturally occurring pairing of VH and VL chains, wherein the VH or VL individually could be isolated from a subject. In some embodiments, the antibody comprises VH chain or HCDRs of a VH chain of one clonal member, and VL or LCDRs of another clonal member, i.e., a non-naturally occurring antibody comprising sequences derived from natural pairs.

In certain embodiments, the antibody or fragment thereof comprises a VH chain that is 90%, 91%, 92%, 93%, 94%, 95%, 96%, 97%, 98%, 99% or 100% identical to the VH chain of antibody DH511, DH512, DH513, DH514, DH515, DH516, DH517, DH518, DH536, DH537, DH491 or DH493, or an antibody from Example 10, 11 or 12.

In certain embodiments, the antibody or fragment thereof comprises a VL chain that is 90%, 91%, 92%, 93%, 94%, 95%, 96%, 97%, 98%, 99% or 100% identical to the VL chain of antibody DH511, DH512, DH513, DH514, DH515, DH516, DH517, DH518, DH536, DH537, DH491 or DH493, or an antibody from Example 10, 11 or 12.

In certain embodiments, the antibody or fragment thereof comprises a VH chain that is 90%, 91%, 92%, 93%, 94%, 95%, 96%, 97%, 98%, 99% or 100% identical to the VH chain of antibody DH511, DH512, DH513, DH514, DH515, DH516, DH517, DH518, DH536, DH537, DH491 or DH493 and further comprises a VL chain that is 90%, 91%, 92%, 93%, 94%, 95%, 96%, 97%, 98%, 99% or 100% identical to the VL chain of antibody DH511, DH512, DH513, DH514, DH515, DH516, DH517, DH518, DH536, DH537, DH491 or DH493, or an antibody from Example 10, 11 or 12.

In certain embodiments, the antibody or fragment thereof comprises a VH which comprises the HCDR1, HCDR2, and HCDR3 of antibody DH511, DH512, DH513, DH514, DH515, DH516, DH517, DH518, DH536, DH537, DH491 or DH493, or an antibody from Example 10, 11 or 12.

In certain embodiments, the antibody or fragment thereof comprises a VL which comprises the LCDR1, LCDR2, and LCDR3 of antibody DH511, DH512, DH513, DH514, DH515, DH516, DH517, DH518, DH536, DH537, DH491 or DH493, or an antibody from Example 10, 11 or 12.

In certain embodiments, the antibody or fragment thereof comprises a VH which comprises the HCDR1, HCDR2, and HCDR3 of antibody DH511, DH512, DH513, DH514, DH515, DH516, DH517, DH518, DH536, DH537, DH491 or DH493, or an antibody from Example 10, 11 or 12 and further comprises the complementary VL which comprises the LCDR1, LCDR2, LCDR3 of antibody DH511, DH512, DH513, DH514, DH515, DH516, DH517, DH518, DH536, DH537, DH491 or DH493, or an antibody from Example 10, 11 or 12.

In certain embodiments, the antibody or fragment thereof comprises VH and VL of antibody DH511, DH512, DH513, DH514, DH515, DH516, DH517, DH518, DH536, DH537, DH491 or DH493, or an antibody from Example 10, 11 or 12.

In certain embodiments, the antibody is DH511, DH512, DH513, DH514, DH515, DH516, DH517, DH518, DH536, DH537, DH491 or DH493, or an antibody from Example 10, 11 or 12, e.g. without limitation DH511_5a_ or DH511_5b, DH512_K3.

In certain aspects, the invention provides a pharmaceutical composition comprising anyone of the antibodies of the invention or fragments thereof or any combination thereof.

In certain aspects, the invention provides a pharmaceutical composition comprising anyone of the antibodies of the invention, or a combination thereof.

In certain embodiments, the composition comprises an antibody or a fragment thereof which is recombinantly produced in CHO cells.

In certain aspects, the invention provides a pharmaceutical composition comprising a vector comprising a nucleic acid encoding anyone of inventive antibodies or fragments. In certain embodiments, the nucleic acids are optimized for expression in human host cells. In certain embodiments, the vector is suitable for gene delivery and expression. Non-limiting examples of such vectors include adenoviral vectors (Ads), adeno associated virus based vectors (AAVs), or a combination thereof.

In certain embodiments, the compositions further comprise an antibody or a fragment thereof comprising the VH and VL chains of antibody DH540.

In certain embodiments, the compositions further comprise an antibody or a fragment thereof comprising VH and VL chain of antibody CH557 or DH270 lineage antibody, for example without limitation DH542, DH542-QSA, DH542_L4.

In certain aspects the invention provides a bispecific antibody which comprises gp41 MPER binding specificity.

In some embodiments the MPER binding portion of the bispecific antibody comprises VH and/or VL chains, variants or fragments thereof.

In certain aspects the invention provides methods to treat or prevent HIV-1 infection in a subject comprising administering to the subject the pharmaceutical composition of any one of the preceding claims in a therapeutically effective amount.

In certain embodiments of the methods, the pharmaceutical composition is administered in a therapeutically effective regimen.

BRIEF DESCRIPTION OF THE DRAWINGS

FIG. 4 shows V(D)J Rearrangement of MPER Antibodies Isolated from Four HIV-1 Infected Individuals. * indicates that these mAbs neutralized the tier 1 isolate MN in TZM-bl cells. Mutation refers to VH nucleotide sequence somatic mutation percentages in the variable heavy (VH) immunoglobulin (Ig) genes.

FIG. 5 shows Neutralization Titers of MPER Antibodies Isolated from Four HIV-1 Infected Individuals using a small panel of HIV-1 isolates in the TZMbl pseudovirus inhibition assay.

FIG. 7 shows summary results of neutralization of gp41 antibodies against a panel of 30 HIV-1 tier 2 isolates in the TZMbl pseudovirus neutralization assay. Data show that antibodies in the DH511 B cell clonal lineage (DH511-DH516) all neutralize 100% of 30 HIV-1 isolates tested in the TZMbl Env pseudovirus neutralization assay.

FIG. 8 shows Neutralizing Breadth and Potency of DH512, DH517 and DH518 HIV-1 BnAbs compared to 10E8, VRC01 and a mixture of CH01 and CH31 bnAbs. DH512 neutralizes 100% of HIV strains and is as at least as potent as 10E8.

FIG. 9 shows Neutralizing Breadth and Potency of various HIV-1 BnAbs that are candidates for being combined with DH512 or other antibodies in FIG. 4 for a potent mixture of bnAbs. DH270IA1 is I1 in the DH270 lineage (See FIG. 26, and U.S. Ser. No. 62/056,568 filed Sep. 28, 2014)

FIG. 10 shows Neutralizing Breadth and Potency of some candidate bnAbs for single or combination use.

FIG. 11 shows summary of Clone DH511 binding to the indicated peptides (SEQ ID NOs: 3-14) in ELISA. Clone DH511 antibodies bind at the C-terminus of the MPER. "+" indicates that antibodies in the Clone DH511 bind to the peptide. The summary shows that DH511 clone antibodies do not bind the peptides when D674 is mutated to 5674. The twelve sequences of the peptides (without the three lysines at the N— and C— end) are shown in SEQ ID NOs: _ to _. The twelve sequences of the peptides (with the three lysines at the N— and C— end) are shown in SEQ ID NOs: 3 to 14. Thus, antibody DH511 requires an aspartic acid at amino acid position 674 for binding.

FIG. 12 shows nucleic acid sequences of antibodies DH511-518, DH536 and 537 (SEQ ID Nos: 15 to 34).

FIG. 13 shows amino acid sequences of antibodies DH511-518, DH536 and 537. (SEQ ID Nos: 35 to 55)

FIGS. 14A-B show Alignment of VH (FIG. 14A; (SEQ ID Nos: 56-61)) and VL (FIG. 14B (SEQ ID Nos: 62-67)) Sequences of BnAb DH511 Clonal Lineage. Bolded is the sequence of CDR1, underlined is the sequence of CDR2 and italicized is the sequence of CDR3 of the DH511 VH chain and DH511 VL chain. The CDRs of the VH and VL sequences of the other antibodies DH512, DH513, DH514, DH515, and DH516 can be readily determined based on the sequence alignment.

FIGS. 15A-B show Alignment of VH (FIG. 15A (SEQ ID Nos: 68-76)) and VL (FIG. 15B (SEQ ID Nos: 77-85)) sequences of MPER BnAbs. Bolded is the sequence of CDR1, italicized is the sequence of CDR2 and underlined is the sequence of CDR3 of VH or VL of the listed MPER antibodies.

FIG. 16 shows sequences of MPER alanine mutants (SEQ ID NOs: 86-112) screened in ELISA. All antibodies in the DH51 clone showed weak binding to this peptide set. DH517 (Ab510053) strongly bound to MPER656 peptide and showed decreased binding to several residues (A4, A6-A13, A16-A18, A20, A23, A24, A26) using the ala substituted peptides in table.

FIG. 18 shows MPER656 variants (SEQ ID NOs: 113-124) screened in ELISA. Residues shown in light blue (underlined) indicate positions that differ from MPER656-biotin.

FIG. 26 shows the amino acids sequences of VH (SEQ ID NOs: 137-148) and VL (SEQ ID NOs: 161-172) chains of antibodies of the DH270 lineage, and nucleic acid sequences (SEQ ID NOs: 125-136 (VH); SEQ ID NOs: 149-160 (VL)) encoding these amino acids. CDRs are highlighted and underlined in the UCA.

FIG. 27A shows amino acid (SEQ ID Nos: 173 and 174) and nucleic acid sequences (SEQ ID Nos: 175 and 176) of CD4bs antibody CH557. FIG. 27B shows amino acid sequences of VH chains of antibodies from CH235 lineage (SEQ ID NOs:177-188). FIG. 27C shows amino acid sequences of VL chains of antibodies from CH235 lineage (SEQ ID NOs: 189-198).

FIG. 28A shows neutralization Breadth and Potency of Plasma and Memory B cell (MBC)-derived MPER bnAbs. FIG. 28B shows neutralization Breadth and Potency of chimeric MPER bnAbs (n=30 cross-clade HIV-1 isolates)

FIGS. 29A and B show neutralization data from TZM-bl assay (Titer in TZM.bl cells (ug/ml) for DH512_K3 and other chimeric antibodies compared to DH512 and 10E8. The data in the first column is historic data when DH512 was run in this panel previously. DH512 was run at the same time as DH512_K3 but is listed as Ab510049 in this assay; therefore, data from columns DH512_K3 and AA&AB DH512/Ab510049 should be compared.

FIG. 30 shows positions in the VHCDR3 chain of DH511 (SEQ ID NO: 471) which could be mutated. Amino acid positions refer to Kabat numbering. Most mutations are to changes to W, but F, L or possibly other substitutions can be tried.

FIG. 31 shows positions in the VHCDR3 chain of DH512 (SEQ ID NO: 472) which could be mutated. Amino acid positions refer to Kabat numbering for the DH512VH chain: QVQLVQSGGGLVKPGGSLTLSCSASGFFFDN-SWMGWVRQAPGKGLEWVGRIRRLK DGAT-GEYGAAVKDRFTISRDDSRNMLYLHMRTLKTED-SGTYYCTMDEGTPVTRFLE WGYFYYYMAVWGRGTTVIVSS (SEQ ID NO: 469). Most mutations are to changes to W, but F, L or possibly other substitutions can also be tried. Position V100 can be changed to I. Position L100d can be changed to F.

FIG. 32 shows positions outside of VHCDR3 which could be mutated (SEQ ID NOs: 473-478, respectively, in order of appearance). Most mutations are to changes to W, but F, L or possibly other substitutions can also be tried.

FIG. 33 shows amino acid sequences (SEQ ID NOs: 199-216) of some of the DH512 mutants from FIG. 31.

FIG. 34 shows neutralization data for a set of 16 mutations from FIG. 31. In this figure DH512 is referred to as DH512 (Ab510049_4A): its heavy chain is H510049_4 and its light chain is K510032

FIG. 36 shows a summary of self-reactivity data of MPER antibodies.

FIG. 37 shows summary results of neutralization data of DH512 and 10E8 against a panel of HIV-1 isolates in the TZMbl pseudovirus neutralization assay. Values represent IC50 in μg/ml. FIG. 37 also shows the mean IC50 and percent of isolates neutralized at different IC50 values.

FIG. 38 shows summary results of neutralization data of DH512 and 10E8 against a panel of HIV-1 isolates in the TZMbl pseudovirus neutralization assay. Values represent IC80 in μg/ml. FIG. 38 also shows the mean IC80 and percent of isolates neutralized at different IC80 values.

FIG. 41 shows Neutralization Activity (IC50) of MPER Antibodies Identified by Paired VH:VL Sequencing Technology (Example 10). Summary data of two independent assays.

FIG. 42 shows Neutralization Activity (IC80) of MPER Antibodies Identified by Paired VH:VL Sequencing Technology (Example 10). Summary data of two independent assays.

FIG. 46 shows Amino Acid Alignment of MPER Antibody Light Chain Sequences (SEQ ID NOs: 253-262).

FIG. 47 shows Immunogenetic Characteristics of MPER Antibodies—Original Pairings.

FIG. 55 shows Antibody Pairings—Heavy and Light Chain Chimeric Antibodies from Example 11.

FIG. 56A shows neutralization activity of Heavy and Light Chain Chimeric Antibodies chimeric pairings 1-32 (from FIG. 55). FIG. 56B shows Neutralization Activity on New Pairings in rows 33-67 (from FIG. 55). FIG. 56C shows Neutralization Activity on New Pairings in rows 68-91 (from FIG. 55). FIG. 56D shows that 8 chimeric antibodies were selected for large scale expression and neutralization activity analysis.

FIG. 57 shows nucleic acid and amino acid sequences of VH and VL sequences of antibodies from Example 10 (SEQ ID NOs: 263-300).

FIG. 58 shows sequences of DH511_5a and 5b as Fabs (SEQ ID NOs: 301-304).

FIGS. 59A-F show isolation of MPER-directed broadly neutralizing antibodies. (a) Fluorescently-labeled MPR.03 peptide tetramers were used to stain peripheral blood mononuclear cells from donor CH0210. A representative flow cytometric plot is shown. Square represents frequency of MPR.03 double positive memory B cells that were single-cell sorted for Ig gene amplification and expression. Colored dots within the square show individual cells that yielded MPER-specific monoclonal antibodies DH511.1-DH511.6 as revealed by index sorting. Memory B cells were gated as live CD16-CD14-CD3-CD235-CD19+IgD-CD38hi. (b) Phylogenetic tree of VHDHJH sequences of the DH511 clonal lineage. Ancestral reconstruction of the evolutionary pathway from the inferred unmutated common ancestor (UCA) to the mature mAbs including 6 maturational intermediates (circles, 11-16) is indicated. (c) Neutralization activity of probe-identified MPER antibodies against a panel of 199 cross-clade HIV-1 isolates. Median and geometric mean neutralization potency against viruses neutralized with a median IC50/IC80<50 μg/ml is indicated. Percentage of 199 viruses neutralized by mAbs DH511.1-DH511.6, 10E8, and VRC01 at IC50<50 μg/ml, IC50<1 μg/ml, and IC50<0.1 μg/ml. (d) Neutralization potency and breadth of DH511.2 compared to 10E8 and VRC01 against a 199 HIV-1 Env pseudovirus panel displayed as potency-breadth curves. Percentage of isolates neutralized at IC50 (top panel) and IC80 (bottom panel) values is plotted against mAb concentration. (e) Percent maximum neutralization of each isolate by DH511.2 is shown. (f) Identification of MPER-directed broadly neutralizing plasma antibodies by proteomics. Phylogenetic tree of heavy chain sequences identified in the plasma (black) and in the memory B cell compartment (grey, see FIG. 59*b*). The bar on the right shows the relative abundance of the three identified clonotypes in serum (IV: 95%, II: 4%, III: 1%).

FIGS. 60A-E shows structural analysis of the DH511 lineage. (a) Ribbon model of crystal structures of DH511.1 and DH511.2 Fabs in complex with gp41 MPER peptides 656-683 and 662-683, respectively, oriented based on Ca-atom superposition of distal MPER residues 671-683. (b) Close-up view of antibody-peptide contacts. gp41 residues that interact with antibody VH3-15 region residues, HCDR3 residues, or both, are shown in cyan, red, and brown, respectively. (c) Ribbon model of crystal structures of Fabs of plasma-derived variants DH511.11P and DH511.12P are shown in complex with gp41 MPER peptide 662-683 [511.11P is placeholder here]. Residues shown in surface representation differ in sequence from DH511.1 or DH511.2. Of the residues that are unique to DH511.11P and DH511.12P, those at the interface with gp41 are colored red and are predominantly located within their HCDR3 loops. (d) Close-up view of DH511.11P and DH511.12P antibody-peptide contacts, with gp41 contacting residues colored as in b. (e) Sequence alignment of DH511 lineage antibodies (SEQ ID NOs: 305-310), antibody 10E8, and their shared VH3-15 germ line gene precursor. Residues that contact gp41 are labeled with closed circles, and somatically-mutated residues shaded red, orange blue, and green, for 10E8, DH511.1, DH511.2, and DH511.11P and DH511.12P, respectively.

FIGS. 62A-C show standard experimental mapping and neutralization-based epitope prediction analysis to delineate the specificities that mediate plasma neutralization breadth. (a) Plasma from donor CH0210 showed potent MPER-directed neutralizing activity against the HIV-2/HIV-1 MPER chimeric pseudovirus C1C. Neutralization titer is reported as median inhibitory dilution (ID50). (b) Neutralization activity adsorbed with MPER peptide. Anti-MPER antibodies were depleted from plasma using MPER peptide-coated magnetic beads. The depleted fraction was tested for neutralization activity against the indicated heterologous viruses. Neutralization was considerably diminished by removal of anti-MPER from both plasmas, indicating that MPER antibodies were largely responsible for neutralization breadth. ND, not determined. (c) Neutralization-based epitope prediction (NEP) analysis. The predicted relative prevalence of antibody clusters [(10 epitopes targeting sites of vulnerability (CD4 binding site, V1/V2, MPER, glycan V3)] is shown as a heat map, with dark color intensity (higher fractional number) corresponding to a stronger neutralization signal. Plasma neutralization breadth is shown, and numbers in each row add up to 1.00. Shown below are the locations on the Env trimer of the epitopes identified by NEP for this donor and confirmed to be targeted by standard experimental mapping methods.

FIGS. 63A-B show frequency and identity of CDR3 peptides from MPER affinity chromatography. (a) Representative histogram of antibody clonotype frequencies identified proteomically in the F(ab)'2 elution and flow through fractions following MPER affinity purification. Clonotypes were defined as genes with the same V- and J-gene usage and >85% sequence identity in the HCDR3. Frequencies of the identified clonotypes were based on the average peak areas of the detected CDR peptides. (b) Identified clonotypes and gene usage (SEQ ID NOs: 311-320).

FIG. 66A-C show Surface-plasmon resonance analysis of binding of the DH511 clonal lineage to MPR.03 peptide.

FIG. 66C shows Association (ka) and dissociation (kd) rate constants and binding affinities (Kd) for each Fab.

FIG. 67A-C show Surface-plasmon resonance analysis of binding of the DH511 clonal lineage to MPER liposomes (SEQ ID NOs: 321-325).

FIG. 73A-D shows Structural Comparison of DH511 (A), DH512 (B), and 10E8 (C)HCDR3 Loops. Conserved DH511/DH512 and 10E8 hydrophobic residue doublets at apex of HCDR3 loops are spatially co-localized (D), relative to MPER. Comparison is based on Ca superposition of MPER residues 671-683.

FIG. 75 shows sequence characteristics of MPER antibodies isolated from memory B cells (SEQ ID NOs: 332-359). FIG. 75 corresponds to Supplementary Table 1 as referenced in Example 12.

FIG. 76 shows neutralization activity of MPER mAbs against a cross-clade 30 isolate HIV-1 Env-pseudovirus panel (IC50 values). FIG. 76 corresponds to Supplementary Table 2a as referenced in Example 12.

FIG. 77 shows neutralization activity of MPER mAbs against a cross-clade 30 isolate HIV-1 Env-pseudovirus panel (IC80 values). FIG. 77 corresponds to Supplementary Table 2b as referenced in Example 12.

FIG. 78 shows neutralization activity of DH511.2 against a cross-clade 199 isolate HIV-1 Env-pseudovirus panel. FIG. 78 corresponds to Supplementary Table 3 as referenced in Example 12.

FIG. 79 shows neutralization activity of DH511.2 against a panel of 200 clade C HIV-1 primary isolates. FIG. 79 corresponds to Supplementary Table 4 as referenced in Example 12.

FIG. 80 shows neutralization activity of 16 DH511.2 heavy chain mutant antibodies. FIG. 80 corresponds to Supplementary Table 27 as referenced in Example 12.

FIG. 81 shows sequence characteristics and pairing of plasma-derived heavy and light chains identified by mass spectrometry and paired VH-VL next-generation sequencing (SEQ ID NOs: 360-367 and 479-489, respectively, in order of appearance). FIG. 81 corresponds to Supplementary Table 6 as referenced in Example 12.

FIG. 82 shows neutralization activity of 16 plasma mAbs against a 4 indicator HIV-1 Env pseudovirus panel. FIG. 82 corresponds to Supplementary Table 7 as referenced in Example 12.

FIG. 83 shows neutralization activity of plasma mAbs DH511.11P and DH511.12P against a cross-clade 203 isolate HIV-1 Env-pseudovirus panel. FIG. 83 corresponds to Supplementary Table 8 as referenced in Example 12.

FIG. 84 shows sequences of alanine substituted MPR.03 peptides (SEQ ID NOs: 368-381). FIG. 84 corresponds to Supplementary Table 9 as referenced in Example 12.

FIG. 85 shows sequences of COT6.15 MPER mutant viruses (SEQ ID NOs: 382-403). FIG. 85 corresponds to Supplementary Table 10 as referenced in Example 12.

FIG. 86 shows neutralization Activity Against a series of MPER alanine mutant pseudoviruses in the COT6.15 Env background. FIG. 86 corresponds to Supplementary Table 11 as referenced in Example 12.

FIG. 87 shows crystallization peptides (SEQ ID NOs: 404-406). FIG. 87 corresponds to Supplementary Table 12 as referenced in Example 12.

FIG. 88 shows crystallographic data collection and refinement statistics. FIG. 88 corresponds to Supplementary Table 13 as referenced in Example 12.

FIG. 89 shows antibody contact interfaces by CDR loop. FIG. 89 corresponds to Supplementary Table 14 as referenced in Example 12.

FIG. 90 shows bonded and non-bonded contacts DH511.1-MPER. (Non-Kabat numbering). FIG. 90 corresponds to Supplementary Table 15 as referenced in Example 12.

FIG. 91 shows bonded and non-bonded contacts DH511.2-MPER. (Non-Kabat numbering). FIG. 91 corresponds to Supplementary Table 16 as referenced in Example 12.

FIG. 92 shows bonded and non-bonded contacts DH511.11P-MPER. FIG. 92 corresponds to Supplementary Table 17 as referenced in Example 12.

FIG. 93 shows bonded and non-bonded contacts DH511.12P-MPER. (Non-Kabat numbering). FIG. 93 corresponds to Supplementary Table 18 as referenced in Example 12.

FIG. 94 shows neutralization of the DH511 clonal lineage against a panel of 12 global HIV-1 reference strains. FIG. 94 corresponds to Supplementary Table 19 as referenced in Example 12.

FIGS. 95A-C show primers and PCR conditions for paired VH:VL NGS. FIG. 95A shows overlap extension oligonucleotides for framework region 1 (5'-3') (SEQ ID NOs: 407-427). FIG. 95B shows overlap extension oligonucleotides for leader peptide (5'-3') (SEQ ID NOs: 428-441). FIG. 95C shows nested constant region oligonucleotides (5'-3') (SEQ ID NOs: 442-446). FIG. 95A corresponds to Supplementary Table 28 as referenced in Example 12. FIG. 95B corresponds to Supplementary Table 29 as referenced in Example 12. FIG. 95C corresponds to Supplementary Table 30 as referenced in Example 12.

FIG. 96 shows DH511 clonal lineage membrane insertion scores and HCDR3 analysis (SEQ ID NOs: 447-455). The membrane insertion scores can be recalculated to exclude the C in the CDR3. HCDR3s score for the .P antibodies will be calculated. FIG. 96 corresponds to Supplementary Table 21 as referenced in Example 12.

FIG. 97 shows cardiolipin reactivity of the DH511 clonal lineage. FIG. 97 corresponds to Supplementary Table 22 as referenced in Example 12.

FIG. 98 shows neutralization activity of 91 chimeric MPER mAbs against the tier 2 HIV-1 isolate B.BG1168. FIG. 98 corresponds to Supplementary Table 23 as referenced in Example 12.

FIG. 99 shows neutralization activity of chimeric mAb DH511.2_K3 against a cross-clade 30 isolate Env-pseudovirus panel. FIG. 99 corresponds to Supplementary Table 24 as referenced in Example 12.

FIGS. 100A-C show primers and PCR conditions for paired VH:VL NGS. FIG. 100A shows PCR conditions for isotype specific amplification. FIG. 100B shows oligonucleotides for isotype specific amplification (5'-3') (SEQ ID NOs: 456-462). FIG. 100C shows PCR conditions for MiSeq Barcoding. FIG. 100A corresponds to Supplementary Table 30 as referenced in Example 12. FIG. 100B corresponds to Supplementary Table 31 as referenced in Example 12. FIG. 100C corresponds to Supplementary Table 32 as referenced in Example 12.

DETAILED DESCRIPTION

Figure 1:
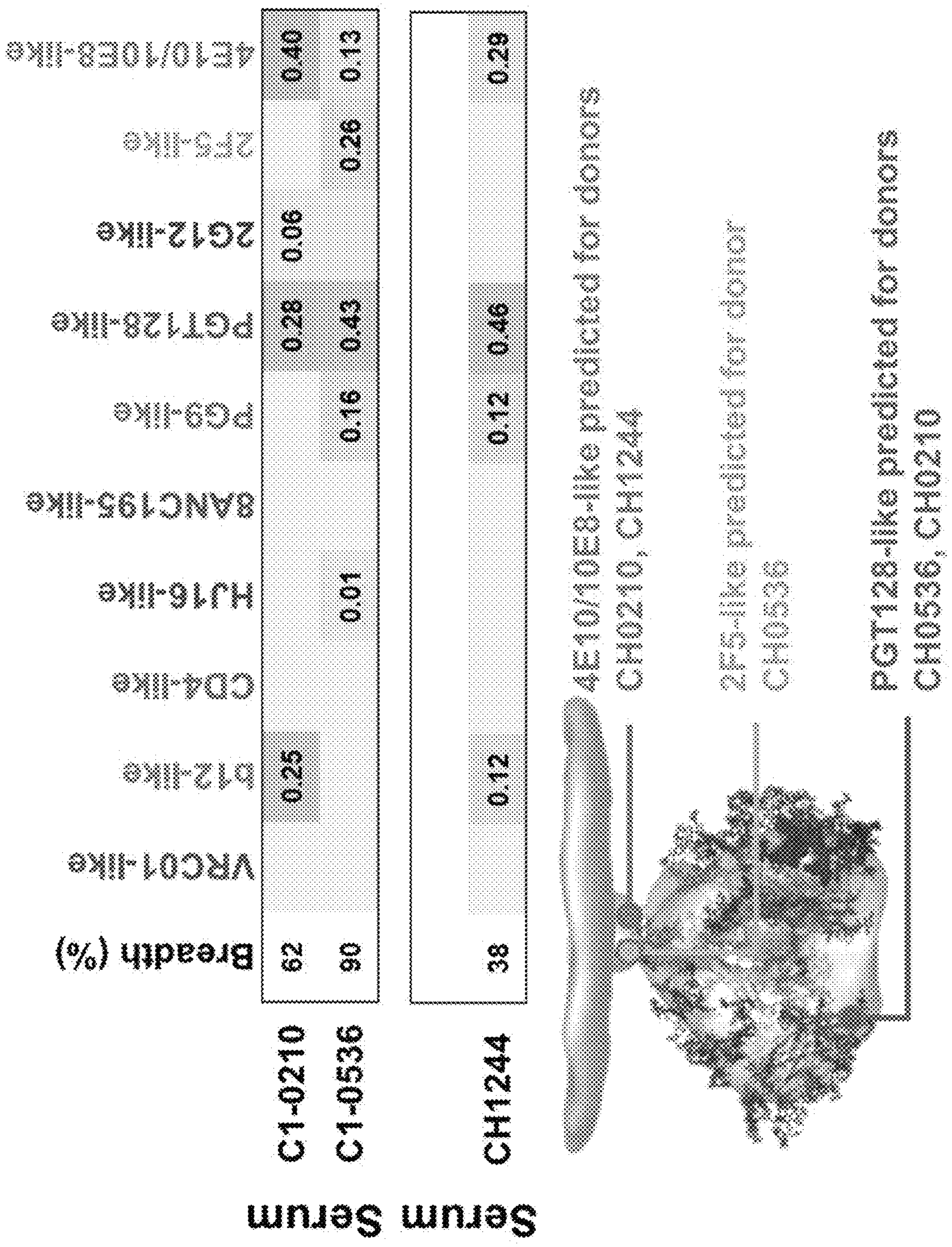
FIG. 1 shows Neutralization-based Epitope Prediction (NEP) Analysis. Neutralization-based epitope prediction analysis. The predicted relevant prevalence of antibody clusters [(10 epitopes targeting sites of vulnerability (CD4 binding site, V1/V2, MPER, glycan V3)] is shown as a heat map, with dark color intensity (higher fractional number) corresponding to a stronger neutralization signal. Plasma neutralization breadth is shown, and numbers in each row add up to 1.00. NEP algorithm reference: [Georgiev I S et al *Science* 340: 751-756].

Broadly neutralizing and potent HIV envelope antibodies are now being developed for both prevention of HIV (Rudicell R S et al. J. Virol 88: 12669-82, 2014) and for treatment of HIV infected individuals (Barouch D H, et al. Nature 503: 224-8, 2013; Shingai M et al. Nature 503: 277-80, 2013). Thus, human recombinant antibodies either alone or in combinations have great prophylactic and therapeutic potential for the prevention and treatment of HIV. Moreover, antibodies that bind with high affinity to Env may be useful in eliminating the latent pool of HIV-infected CD4 T cells and curing HIV, when either used to sensitize HIV expressing target cells with bispecific bnAbs for NK or CD8 T cell killing or when bnAbs are conjugated with toxins or radionucleotides.

In certain aspects the invention provides fully human antibodies and fragments that specifically bind to and potently neutralize various isolates of HIV-1. In some embodiments, the antibodies bind to HIV-1 gp41. In some embodiments, the antibodies of the invention specifically bind the membrane-proximal extracellular region (MPER) of gp41.

In certain aspects the invention provides pharmaceutical compositions including these human antibodies and a pharmaceutically acceptable carrier. In certain aspects the invention provides antibodies for passive immunization against HIV/AIDS. Nucleic acids encoding these antibodies, expression cassettes and vectors including these nucleic acids, and isolated cells that express the nucleic acids which encode the antibodies of the invention are also provided.

In some embodiments, the invention provides antibodies which are clonal variants (See e.g., Examples 11, and 12). In some embodiments, clonal variants are sequences that differ by one or more nucleotides or amino acids, and have a V region with shared mutations compared to the germline, identical VDJ or VJ gene usage, identical the same or similar HCDR3 length, and the same VL and JL usage. The germline sequence (unmutated common ancestor "UCA") is intended to be the sequence coding for the antibody/immunoglobulin (or of any fragment thereof) deprived of mutations, for example somatic mutations. Antibodies in a clone that are designate as UCA and/or I (for "Intermediate") are typically not isolated from a biological sample, but are derived computationally based on VH and/or VL sequences isolated from subjects infected with HIV-1.

Compositions including the human antibodies of the invention, including antibodies specific for gp41, can be used for any purpose including but not limited to research, diagnostic and therapeutic purposes. In non-limiting embodiments, the human monoclonal antibodies disclosed herein can be used to detect HIV-1 in a biological sample or interfere with the HIV-1 activity, for example to diagnose or treat a subject having an HIV-1 infection and/or AIDS. For example, the antibodies can be used to determine HIV-1 titer in a subject. The antibodies disclosed herein also can be used to study the biology of the human immunodeficiency virus. The antibodies of the invention can be used for therapeutic purposes for treatment or prevention of HIV-1 infection, alone or in combination with other therapeutic modalities, including ART and/or combination with other HIV-1 targeting antibodies, neutralizing antibodies and/or ADCC inducing antibodies.

Figures 2, 3:
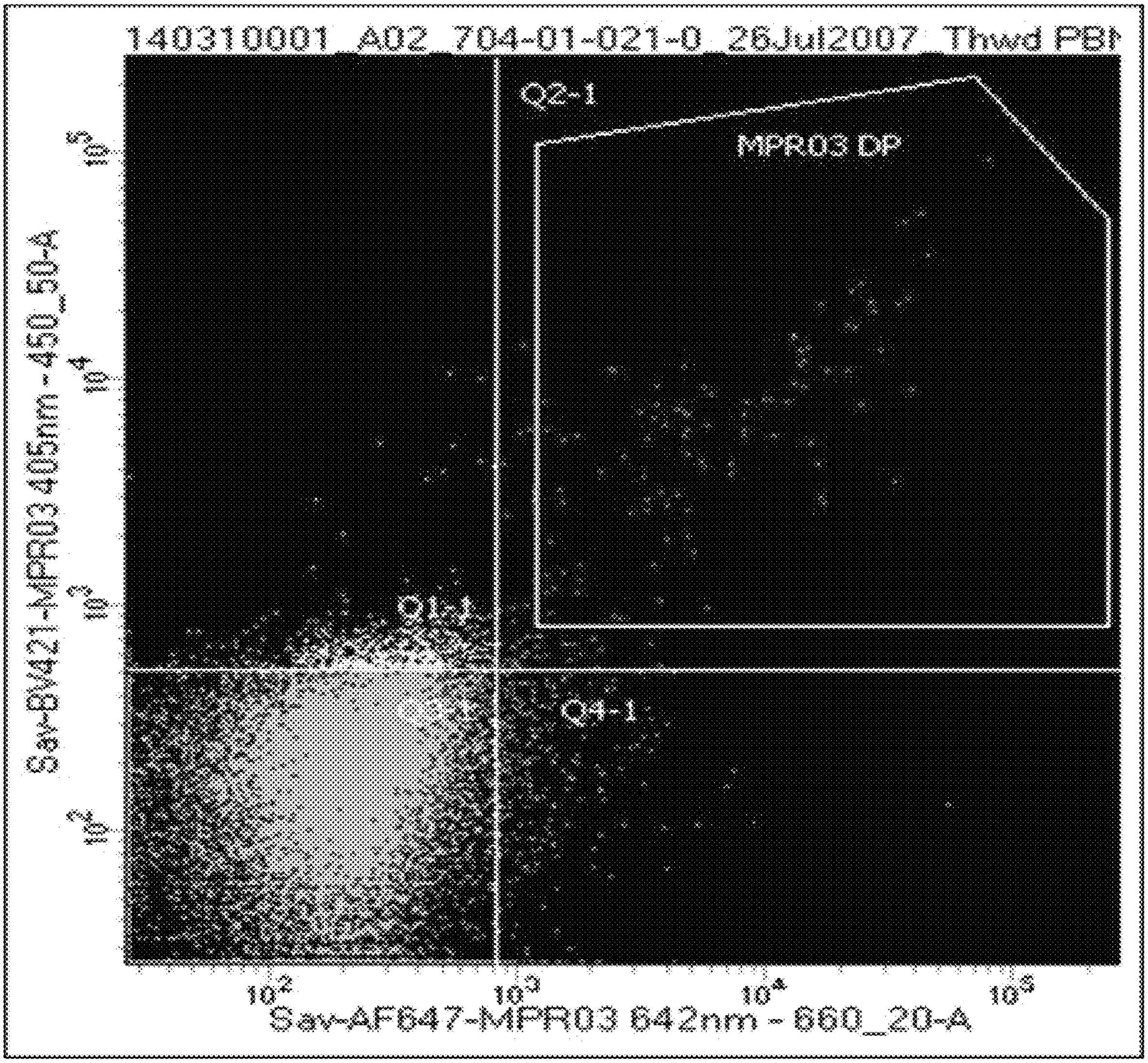
FIG. 2 shows MPR.03 Hook sequence (SEQ ID NOs: 1-2). MPR.03 is a biotinylated peptide containing lysines at both ends for solubility (KKKNEQELLELDK-WASLWNWFDITNWLWYIRKKK-biotin) (SEQ ID NO: 463) used to pull out gp41 antibodies from blood memory B cell sorts See Morris L. et al. (2011) PLoS ONE 6(9): e23532.
FIG. 3 shows a representative CH0210 mper03 sort (sort #1).

In some embodiments, the disclosed MPER antibodies specifically bind to a polypeptide disclosed in for example but not limited to FIG. 3, FIG. 11, and FIG. 16, and Example 12. The person of ordinary skill in the art will understand that the antibodies of the invention can also bind to gp41MPER residues extending N-terminal or C-terminal to the above sequences.

In some embodiments, residues believed to make contacts with the antibodies of the invention include resides identified in the mapping studies described in for example but not limited to FIGS. 11, 16-15. In some embodiments, the antibodies of the invention are expected to make contact with additional gp41 MPER residues. In some embodiments, the antibodies of the invention are expected to make contact with some of the gp41 MPER residues as previously described for the 10E8 antibody.

In some embodiments, the disclosed antibodies are referred to as 10E8-like antibodies because their binding to the MPER maps to a region similar to the MPER region bound by the 10E8 antibody previously described (See US Pub 20140348785). The 10E8 antibody specifically binds the membrane proximal extracellular region (MPER) of gp41 at an epitope that is designated as the 10E8 epitope. The crystal structure of the 10E8 antibody was solved in complex with a gp41 peptide (See 20140348785 Example 1), which allowed for detailed analysis of the binding of the 10E8 antibody and gp41, and describe at the atomic level the binding of 10E8 antibody to the 10E8 epitope. This epitope, and thus the antibodies of this class (10E8-like antibodies), can be distinguished from other antibodies that bound gp41 at other epitopes. The 10E8 epitope, e.g., KWASLWNWFDITNWLWYIR (SEQ ID NO: 464), extends C-terminal to the 2F5 epitope (although there is some overlap) on the gp41 ectodomain and is distinguished from the 4E10 and Z13E1 epitope by expanding the binding to C-terminal residues previously thought to be inaccessible (e.g. these residues were believed to be buried in the lipid bilayer).

In some embodiments, an MPER antibody of the invention is not the 10E8, 4E10, 2F5 or any other MPER antibody as previously described. Some of the difference between certain antibodies of the invention and the 10E8, 4E10 and 2F5 antibodies are demonstrated in FIG. 15 (VH sequence alignment) and FIGS. 6, and 7 (neutralization breadth and potency), and for example but not limited to FIGS. 11, 16-25 (epitope mapping studies), Example 12. In certain embodiments, the inventive antibodies bind an MPER epitope which comprises D674 (See FIG. 11). In certain embodiments, the 10E8 antibody (See US Pub 20140348785) MPER binding is not sensitive to D674S mutation. The DH511 lineage antibodies (FIG. 6) neutralize 100% of isolates whereas 10E8 did not (FIG. 7).

Figure 35:
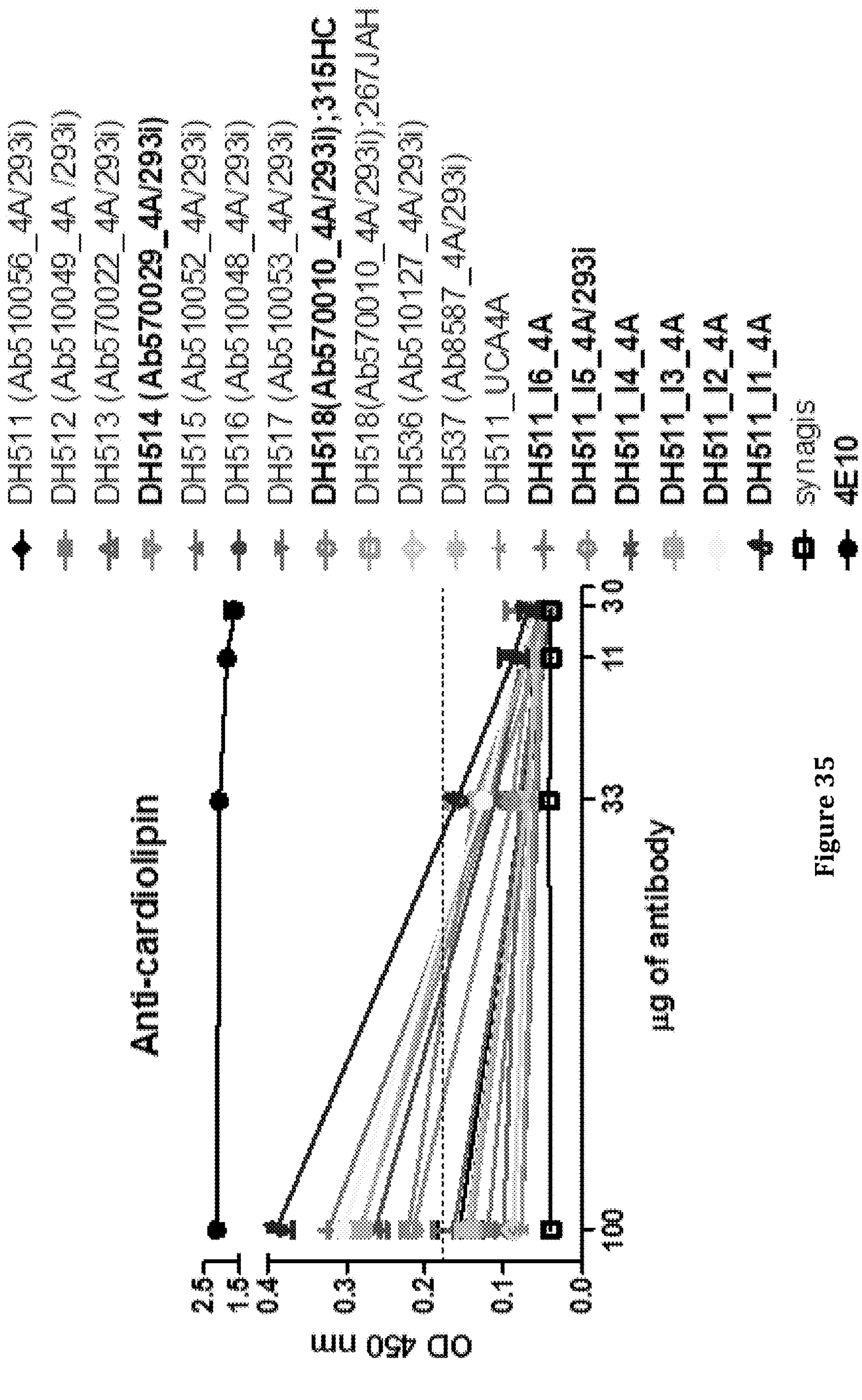
FIG. 35 shows summary of anti-cardiolipin activity of various antibodies as measured by QUANTA Lite® ACA IgG III kit. Data plotted are representative of 2 independent experiments. mAb were run in duplicate in the second assay. Mean error and standard deviation are shown. Data were consistent between assays. Dotted line indicates positivity cut-off of 0.18. mAbs with OD values above 0.18 are bolded in the figure legend (DH514, DH518-315 HC, DH511-I6-4a through DH511_I1_4A; 4E10).

In some embodiments, the antibodies of the invention are expected not to exhibit self-reactivity—they do not bind or bind very weakly to self-antigens, such as human protein. For use as preventive or therapeutic agents, what matters is whether the mature antibody will be polyreactive or not (FIGS. 35-36, Example 12). Various assays to determine poly and autoreactivity are known in the art.

The neutralization breadth of the inventive antibodies is demonstrated by the diversity of viruses which are neutralized in the TZMbl Env pseudovirus inhibition assay. In certain embodiments, the neutralization breadth and/or binding of the antibodies of the invention can be maintained in the presence of tolerate changes to the epitope. Comparing the sequences of the neutralized viruses, versus viruses that are not neutralized, a skilled artisan can readily determine the % virus changes, including changes in the MPER region and the epitope, which can be tolerated while neutralization and/or binding is maintained.

Comparing the sequences of the antibodies (e.g. FIGS. 4, 12, 13, 14 and 15) and their neutralization properties (e.g. FIGS. 6-9), a skilled artisan can readily determine sequence identity, compare sequence length and determine the % sequence identity and/or changes, including % sequence identity and/or changes in the VH and VL sequences, including % sequence identity and/or changes in the CDRs, as well as the specific positions and types of substitutions which can be tolerated while neutralization potency and breadth is maintained.

Various algorithms for sequence alignment are known in the art. The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a VL or a VH of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the VH and VL amino acid sequences of the antibodies described herein and still maintain the neutralization breadth, biding and/or potency. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the CDR1, 2, and/or 3 of VH and CDR1, 2, and/or 3 VL amino acid sequences of the antibodies described herein and still maintain the neutralization breadth, biding and/or potency.

In certain embodiments, the invention provides antibodies which can tolerate a larger percent variation in the sequences outside of the VH and/VL sequences of the antibodies. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65% identical, wherein the identity is outside of the VH or VL regions, or the CDRs of the VH or VL chains of the antibodies described herein.

Antibodies exist, for example as intact immunoglobulins and antigen binding variants or fragments e.g. as a number of well characterized produced by digestion with various peptidases. For instance, Fabs, Fvs, scFvs that specifically bind to gp41 or fragments of gp41 would be gp41-specific binding agents. Binding specificity can be determined by any suitable assay in the art, for example but not limited competition binding assays, epitope mapping, etc. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. Provided are also genetically engineered forms such as chimeric antibodies and heteroconjugate antibodies such as bispecific antibodies. See also, Pierce Catalog and Handbook, 1994-1995 (Pierce Chemical Co., Rockford, Ill.); Kuby, Immunology, 3.sup.rd Ed., W.H. Freeman & Co., New York, 1997.

In certain embodiments the invention provides antibody fragments, which have the binding specificity and/or properties of the inventive antibodies. Non-limiting examples include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab').sub.2, the fragment of the antibody obtained by treating whole antibody with the enzyme pepsin without subsequent reduction; (4) F(ab').sub.2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. In certain embodiments, the antibody fragments can be produces recombinantly.

In certain embodiments, VH refers to the variable region of an immunoglobulin heavy chain, including but not limited to that of an antibody fragment, such as Fv, scFv, dsFv or Fab. In certain embodiments, VL refers to the variable region of an immunoglobulin light chain, including but not limited to that of an Fv, scFv, dsFv or Fab.

Any of the nucleic acids encoding any of the antibodies, or fragment thereof can be expressed in a recombinantly engineered cell such as bacteria, plant, yeast, insect and mammalian cells. The nucleic acid sequences include any sequence necessary for expression, including but not limited to a promoter, a leader sequence. These antibodies can be expressed as individual VH and/or VL chain, or can be expressed as a fusion protein. In certain embodiments, the antibodies can be expressed by viral vector mediated delivery of genes encoding the antibodies of the invention (See e.g. Yang et al. Viruses 2014, 6, 428-447).

To create a single chain antibody, (scFv) the VH- and VL-encoding DNA fragments are operatively linked to another fragment encoding a flexible linker, e.g., encoding the amino acid sequence $(Gly_4\text{-}Ser)_3$ (SEQ ID NO: 470), such that the VH and VL sequences can be expressed as a contiguous single-chain protein, with the VH and VL domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

In some embodiments, a single chain antibody may be monovalent, if only a single VH and VL are used, bivalent, if two VH and VL are used, or polyvalent, if more than two VH and VL are used. Bispecific or polyvalent antibodies may be generated that bind specifically to gp120 and to another molecule, such as gp41.

There are numerous expression systems available for expression of proteins including *E. coli*, other bacterial hosts, yeast, and various higher eukaryotic cells such as the COS, CHO, HeLa and myeloma cell lines.

In certain embodiments, the invention provides monoclonal antibodies. In certain embodiments the monoclonal antibodies are produced by a clone of B-lymphocytes. In certain embodiments the monoclonal antibody is a recombinant and is produced by a host cell into which the light and heavy chain genes of a single antibody have been transfected. Any suitable cell could be used for transfection and expression of the antibodies of the invention. Suitable cell lines include without limitation 293T cells or CHO cells.

Monoclonal antibodies are produced by any suitable method known to those of skill in the art. In some embodiments, monoclonal antibodies are produced by immortalizing B-cell expressing an antibody. Methods for immortalizing B-cells are known in the art, for example but not limited to using EBV transformation, treatment with various stimulants, and/or apoptotic inhibitors (Bonsignori et al. J. Virol. 85: 9998-10009, 2011). In some embodiments, monoclonal antibodies are produced by making hybrid antibody-forming cells from a fusion of myeloma cells with immune spleen cells to make hybridomas. In some embodiments monoclonal antibodies are isolated from a subject, for example but not limited as described in Example 1 (Liao H X et al. J Virol Methods. 2009 June; 158(1-2):171-9). The amino acid and nucleic acid sequences of such monoclonal antibodies can be determined.

The antibodies described herein, or fragments thereof, may be recombinantly produced in prokaryotic or eukaryotic expression systems. These systems are well described in the art. In general, protein therapeutics are produced from mammalian cells. The most widely used host mammalian cells are Chinese hamster ovary (CHO) cells and mouse myeloma cells, including NS0 and Sp2/0 cells. Two derivatives of the CHO cell line, CHO-K1 and CHO pro-3, gave rise to the two most commonly used cell lines in large scale production, DUKX-X11 and DG44. (See, e.g., Kim, J., et al., "CHO cells in biotechnology for production of recombinant proteins: current state and further potential," *Appl. Microbiol. Biotechnol.*, 2012, 93:917-30, which is hereby incorporated-by-reference.) Other mammalian cell lines for recombinant antibody expression include, but are not limited to, COS, HeLa, HEK293T, U2O5, A549, HT1080, CAD, P19, NIH 3T3, L929, N2a, HEK 293, MCF-7, Y79, SO-Rb50, HepG2, J558L, and BHK. If the aim is large-scale production, the most currently used cells for this application are CHO cells. Guidelines to cell engineering for mAbs production were also reported. (Costa et al., "Guidelines to cell engineering for monoclonal antibody production," *Eur J Pharm Biopharm,* 2010, 74:127-38, which is hereby incorporated-by-reference.) Using heterologous promoters, enhancers and amplifiable genetic markers, the yields of antibody and antibody fragments can be increased. Thus, in certain embodiments, the invention provides an antibody, or antibody fragment, that is recombinantly produced from a mammalian cell-line, including a CHO cell-line. In certain embodiments, the invention provides a composition comprising an antibody, or antibody fragment, wherein the antibody or antibody fragment was recombinantly produced in a mammalian cell-line, and wherein the antibody or antibody fragment is present in the composition at a concentration of at least 1, 10, 100, 1000 micrograms/mL, or at a concentration of at least 1, 2, 3, 4, 5, 6, 7, 8, 9, 10, 20, 50, or 100 milligrams/mL.

Furthermore, large-scale production of therapeutic-grade antibodies are much different than those for laboratory scale. There are extreme purity requirements for therapeutic-grade. Large-scale production of therapeutic-grade antibodies requires multiples steps, including product recovery for cell-culture harvest (removal of cells and cell debris), one or more chromatography steps for antibody purification, and formulation (often by tangential filtration). Because mammalian cell culture and purification steps can introduce antibody variants that are unique to the recombinant production process (i.e., antibody aggregates, N- and C-terminal variants, acidic variants, basic variants, different glycosylation profiles), there are recognized approaches in the art for analyzing and controlling these variants. (See, Fahrner, et al., Industrial purification of pharmaceutical antibodies: Development, operation, and validation of chromatography processes, *Biotech. Gen. Eng. Rev.,* 2001, 18:301-327, which is hereby incorporated-by-reference.) In certain embodiments of the invention, the antibody composition comprises less than 1, 2, 3, 4, 5, 10, 15, 20, 25, 30, 35, 50, or 100 nanograms of host cell protein (i.e., proteins from the cell-line used to recombinantly produce the antibody)). In other embodiments, the antibody composition comprises less than 1, 2, 3, 4, 5, 6, 7, 8, 9, 10, 15, 20, or 25 ng of protein A per milligram of antibody or antibody fragment (i.e., protein A is a standard approach for purifying antibodies from recombinant cell culture, but steps should be done to limit the amount of protein A in the composition, as it may be immunogenic). (See, e.g., U.S. Pat. No. 7,458,704, Reduced protein A leaching during protein A affinity chromatography; which is hereby incorporated-by-reference.)

The antibodies of the invention can be of any isotype. In certain embodiments, the antibodies of the invention can be used as IgG1, IgG2, IgG3, IgG4, whole IgG1 or IgG3s, whole monomeric IgAs, dimeric IgAs, secretory IgAs, IgMs as monomeric, pentameric or other polymer forms of IgM. The class of an antibody comprising the VH and VL chains described herein can be specifically switched to a different class of antibody by methods known in the art.

In some embodiments, the nucleic acid encoding the VH and VL can encode an Fc domain (immunoadhesin). The Fc domain can be an IgA, IgM or IgG Fc domain. The Fc domain can be an optimized Fc domain, as described in U.S. Published Patent Application No. 20100093979, incorporated herein by reference. In one example, the immunoadhesin is an IgG1 Fc. In one example, the immunoadhesin is an IgG3 Fc.

In certain embodiments the antibodies comprise amino acid alterations, or combinations thereof, for example in the Fc region outside of epitope binding, which alterations can improve their properties. Various Fc modifications are known in the art. Amino acid numbering is according to the EU Index in Kabat. In some embodiments, the invention contemplates antibodies comprising mutations that affect neonatal Fc receptor (FcRn) binding, antibody half-life, and localization and persistence of antibodies at mucosal sites. See e.g. Ko S Y et al., Nature 514: 642-45, 2014, at FIG. 1a and citations therein; Kuo, T. and Averson, V., mAbs 3(5): 422-430, 2011, at Table 1, US Pub 20110081347 (an aspartic acid at Kabat residue 288 and/or a lysine at Kabat residue 435), US Pub 20150152183 for various Fc region mutation, incorporated by reference in their entirety. In certain embodiments, the antibodies comprise AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the $4^{th}$ A (N434A) is to enhance FcR neonatal mediated transport of the IgG to mucosal sites (Shields R I et al. ibid). Other antibody mutations have been reported to improve antibody half-life or function or both and can be incorporated in sequences of the antibodies. These include the DLE set of mutations (Romain G, et al. Blood 124: 3241, 2014), the LS mutations M428L/N434S, alone or in a combination with other Fc region mutations, (Ko S Y et al. Nature 514: 642-45, 2014, at FIG. 1a and citations therein; Zlevsky et al., Nature Biotechnology, 28(2): 157-159, 2010; US Pub 20150152183); the YTE Fc mutations (Robbie G et al Antimicrobial Agents and Chemotherapy 12: 6147-53, 2013) as well as other engineered mutations to the antibody such as QL mutations, IHH mutations (Ko S Y et al. Nature 514: 642-45, 2014, at FIG. 1a and relevant citations; See also Rudicell R et al. J. Virol 88: 12669-82, 201). In some embodiments, modifications, such as but not limited to antibody fucosylation, may affect interaction with Fc receptors (See e.g. Moldt, et al. JVI 86(11): 66189-6196, 2012). In some embodiments, the antibodies can comprise modifications, for example but not limited to glycosylation, which reduce or eliminate polyreactivity of an antibody. See e.g. Chuang, et al. Protein Science 24: 1019-1030, 2015. In some embodiments the antibodies can comprise modifications in the Fc domain such that the Fc domain exhibits, as compared to an unmodified Fc domain enhanced antibody dependent cell mediated cytotoxicity (ADCC); increased binding to Fc.gamma.RIIA or to Fc.gamma.RIIIA; decreased binding to Fc.gamma.RIIB; or increased binding to Fc.gamma.RIIB. See e.g. US Pub 20140328836.

In certain embodiments, antibodies of the invention including but not limited to antibodies comprising a CDR(s) of VH and/or VL chains, or antibody fragments of the inventive antibodies can be used as the HIV-1 binding arm(s) of a bispecific molecule, e.g. DARTS, diabodies, toxin labeled HIV-1 binding molecules.

In accordance with the methods of the present invention, either the intact antibody or a fragment thereof can be used. Either single chain Fv, bispecific antibody for T cell engagement, or chimeric antigen receptors can be used (Chow et al, Adv. Exp. Biol. Med. 746:121-41 (2012)). That is, in non-limiting embodiments, intact antibody, a Fab fragment, a diabody, or a bispecific whole antibody can be used to inhibit HIV-1 infection in a subject (e.g., a human). A bispecific F(ab)2 can also be used with one arm a targeting molecule like CD3 to deliver it to T cells and the other arm the arm of the native antibody (Chow et al, Adv. Exp. Biol. Med. 746:121-41 (2012)). Toxins that can be bound to the antibodies or antibody fragments described herein include unbound antibody, radioisotopes, biological toxins, boronated dendrimers, and immunoliposomes (Chow et al, Adv. Exp. Biol. Med. 746:121-41 (2012)). Toxins (e.g., radionucleotides or other radioactive species) can be conjugated to the antibody or antibody fragment using methods well known in the art (Chow et al, Adv. Exp. Biol. Med. 746: 121-41 (2012)). The invention also includes variants of the antibodies (and fragments) disclosed herein, including variants that retain the ability to bind to recombinant Env protein, the ability to bind to the surface of virus-infected cells and/or ADCC-mediating properties of the antibodies specifically disclosed, and methods of using same to, for example, reduce HIV-1 infection risk. Combinations of the antibodies, or fragments thereof, disclosed herein can also be used in the methods of the invention.

Antibodies of the invention and fragments thereof can be produced recombinantly using nucleic acids comprising nucleotide sequences encoding VH and VL sequences selected from those shown in the figures and examples.

In certain embodiments the invention provides intact/whole antibodies. In certain embodiments the invention provides antigen binding fragments thereof. Typically, fragments compete with the intact antibody from which they were derived for specific binding to the target including separate heavy chains, light chains Fab, Fab', F(ab').sub.2, F(ab)c, diabodies, Dabs, nobodies, and Fv. Fragments can be produced by recombinant DNA techniques, or by enzymatic or chemical separation of intact immunoglobulins.

In certain embodiments the invention provides a bispecific antibody. A bispecific or bifunctional/dual targeting antibody is an artificial hybrid antibody having two different heavy/light chain pairs and two different binding sites (see, e.g., Romain Rouet & Daniel Christ "Bispecific antibodies with native chain structure" Nature Biotechnology 32, 136-137 (2014); Garber "Bispecific antibodies rise again" Nature Reviews Drug Discovery 13, 799-801 (2014), FIG. 1a; Byrne et al. "A tale of two specificities: bispecific antibodies for therapeutic and diagnostic applications" Trends in Biotechnology, Volume 31, Issue 11, November 2013, Pages 621-632 Songsivilai and Lachmann, Clin. Exp. Immunol., 79:315-321 (1990); Kostelny et al., J. Immunol. 148:1547-53 (1992) (and references therein)). In certain embodiments the bispecific antibody is a whole antibody of any isotype. In other embodiments it is a bispecific fragment, for example but not limited to $F(ab)_2$ fragment. In some embodiments, the bispecific antibodies do not include Fc portion, which makes these diabodies relatively small in size and easy to penetrate tissues.

In certain embodiments, the bispecific antibodies could include Fc region. Fc bearing diabodies, for example but not limited to Fc bearing DARTs are heavier, and could bind neonatal Fc receptor, increasing their circulating half-life. See Garber “Bispecific antibodies rise again” Nature Reviews Drug Discovery 13, 799-801 (2014), FIG. 1a; See US Pub 20130295121, incorporated by reference in their entirety. In certain embodiments, the invention encompasses diabody molecules comprising an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In some embodiments, the Fc domain (or portion thereof) is derived from IgG. In some embodiments, the IgG isotype is IgG1, IgG2, IgG3 or IgG4 or an allotype thereof. In some embodiments, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). In some embodiments, the Fc domain may be engineered into a polypeptide chain comprising the diabody molecule of the invention in any position relative to other domains or portions of the polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotype thereof. The hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of the polypeptide chain. In certain embodiments, a polypeptide chain of the invention comprises a hinge domain, which hinge domain is at the C-terminus of the polypeptide chain, wherein the polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

In some embodiments, the invention encompasses multimers of polypeptide chains, each of which polypeptide chains comprise a VH and VL domain, comprising CDRs as described herein. In certain embodiments, the VL and VH domains comprising each polypeptide chain have the same specificity, and the multimer molecule is bivalent and monospecific. In other embodiments, the VL and VH domains comprising each polypeptide chain have differing specificity and the multimer is bivalent and bispecific. In some embodiments, the polypeptide chains in multimers further comprise an Fc domain. Dimerization of the Fc domains leads to formation of a diabody molecule that exhibits immunoglobulin-like functionality, i.e., Fc mediated function (e.g., Fc-Fc.gamma.R interaction, complement binding, etc.).

In yet other embodiments, diabody molecules of the invention encompass tetramers of polypeptide chains, each of which polypeptide chain comprises a VH and VL domain. In certain embodiments, two polypeptide chains of the tetramer further comprise an Fc domain. The tetramer is therefore comprised of two ‘heavier’ polypeptide chains, each comprising a VL, VH and Fc domain, and two ‘lighter’ polypeptide chains, comprising a VL and VH domain. Interaction of a heavier and lighter chain into a bivalent monomer coupled with dimerization of the monomers via the Fc domains of the heavier chains will lead to formation of a tetravalent immunoglobulin-like molecule. In certain aspects the monomers are the same, and the tetravalent diabody molecule is monospecific or bispecific. In other aspects the monomers are different, and the tetra valent molecule is bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to increase the probability of mispairings, is to engineer “knobs-into-holes” type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a ‘knob’, e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., ‘the hole’ (e.g., a substitution with glycine). Such sets of mutations can be engineered into any pair of polypeptides comprising the diabody molecule, and further, engineered into any portion of the polypeptides chains of the pair. Methods of protein engineering to favor heterodimerization over homodimerization are well known in the art, in particular with respect to the engineering of immunoglobulin-like molecules, and are encompassed herein (see e.g., Ridgway et al. (1996) “‘Knobs-Into-Holes’ Engineering Of Antibody CH3 Domains For Heavy Chain Heterodimerization,” Protein Engr. 9:617-621, Atwell et al. (1997) “Stable Heterodimers From Remodeling The Domain Interface Of A Homodimer Using A Phage Display Library,” J. Mol. Biol. 270: 26-35, and Xie et al. (2005) “A New Format Of Bispecific Antibody: Highly Efficient Heterodimerization, Expression And Tumor Cell Lysis,” J. Immunol. Methods 296:95-101; each of which is hereby incorporated herein by reference in its entirety).

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain variants identified as altering effector function are known in the art. For example International Application WO04/063351, U.S. Patent Application Publications 2005/0037000 and 2005/0064514.

The bispecific diabodies of the invention can simultaneously bind two separate and distinct epitopes. In certain embodiments the epitopes are from the same antigen. In other embodiments, the epitopes are from different antigens. In preferred embodiments, at least one epitope binding site is specific for a determinant expressed on an immune effector cell (e.g. CD3, CD16, CD32, CD64, etc.) which are expressed on T lymphocytes, natural killer (NK) cells or other mononuclear cells. In one embodiment, the diabody molecule binds to the effector cell determinant and also activates the effector cell. In this regard, diabody molecules of the invention may exhibit Ig-like functionality independent of whether they further comprise an Fc domain (e.g., as assayed in any effector function assay known in the art or exemplified herein (e.g., ADCC assay).

Non-limiting examples of bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to BiTE (Micromet), DART (MacroGenics) (e.g. U.S. Pat. No. 8,795,667; U.S. Publication Nos. 2014-0099318; 2013-0295121; 2010-0174053 and 2009-0060910; European Patent Publication No. EP 2714079; EP 2601216; EP 2376109; EP 2158221 and PCT Publications No. WO 2015/026894; WO 2015/026892; WO 2015/021089; WO 2014/159940; WO 2012/162068; WO 2012/018687; WO 2010/080538), the content of each of these publications in herein incorporated by reference in its entirety), Fcab and Mab2 (F-star), Fc-engineered IgG1 (Xencor) or DuoBody (based on Fab arm exchange, Genmab).

In certain embodiments, the bispecific antibody comprises an HIV envelope binding fragment, for example but not limited to an HIV envelope binding fragment from any of the antibodies described herein. In other embodiments, the bispecific antibody further comprises a second antigen-interaction-site/fragment. In other embodiments, the bispecific antibody further comprises at least one effector domain.

In certain embodiments the bispecific antibodies engage cells for Antibody-Dependent Cell-mediated Cytotoxicity (ADCC). In certain embodiments the bispecific antibodies engage natural killer cells, neutrophil polymorphonuclear leukocytes, monocytes and macrophages. In certain embodiments the bispecific antibodies are T-cell engagers. In certain embodiments, the bispecific antibody comprises an HIV envelope binding fragment and CD3 binding fragment. Various CD3 antibodies are known in the art. See for example U.S. Pat. No. 8,784,821. In certain embodiments, the bispecific antibody comprises an HIV envelope binding fragment and CD16 binding fragment.

In certain embodiments the invention provides antibodies with dual targeting specificity. In certain aspects the invention provides bi-specific molecules that are capable of localizing an immune effector cell to an HIV-1 envelope expressing cell, so as facilitate the killing of the HIV-1 envelope expressing cell. In this regard, bispecific antibodies bind with one "arm" to a surface antigen on target cells, and with the second "arm" to an activating, invariant component of the T cell receptor (TCR) complex. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bauerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). DART (dual affinity retargeting) molecules are based on the diabody format but feature a C-terminal disulfide bridge for additional stabilization (Moore et al., Blood 117, 4542-51 (2011)). The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The invention also contemplates bispecific molecules with enhanced pharmacokinetic properties. In some embodiments, such molecules are expected to have increased serum half-life. In some embodiments, these are Fc-bearing DARTs (see supra).

In certain embodiments, such bispecific molecules comprise one portion which targets HIV-1 envelope and a second portion which binds a second target. In certain embodiments, the first portion comprises VH and VL sequences, or CDRs from the antibodies described herein. In certain embodiments, the second target could be, for example but not limited to an effector cell. In certain embodiments the second portion is a T-cell engager. In certain embodiments, the second portion comprises a sequence/paratope which targets CD3. In certain embodiments, the second portion is an antigen-binding region derived from a CD3 antibody, optionally a known CD3 antibody. In certain embodiments, the anti-CD antibody induce T cell-mediated killing. In certain embodiments, the bispecific antibodies are whole antibodies. In other embodiments, the dual targeting antibodies consist essentially of Fab fragments. In other embodiments, the dual targeting antibodies comprise a heavy chain constant region (CH1. In certain embodiments, the bispecific antibody does not comprise Fc region. In certain embodiments, the bispecific antibodies have improved effector function. In certain embodiments, the bispecific antibodies have improved cell killing activity. Various methods and platforms for design of bispecific antibodies are known in the art. See for example US Pub. 20140206846, US Pub. 20140170149, US Pub. 20090060910, US Pub 20130295121, US Pub. 20140099318, US Pub. 20140088295 which contents are herein incorporated by reference in their entirety.

In certain embodiments the invention provides human, humanized and/or chimeric antibodies.

Pharmaceutical Compositions

In certain aspects the invention provides a pharmaceutical composition comprising an antibody of the invention wherein the composition is used for therapeutic purposes such as but not limited to prophylaxis, treatments, prevention, and/or cure. In certain aspects the invention provides a pharmaceutical composition comprising an antibody of the invention in combination with any other suitable antibody. In certain embodiments, the pharmaceutical compositions comprise nucleic acids which encode the antibodies of the invention. In certain embodiments, these nucleic acids can be expressed by any suitable vector for expression of antibodies. Non-limiting examples include attenuated viral hosts or vectors or bacterial vectors, recombinant vaccinia virus, adenovirus, adeno-associated virus (AAV), herpes virus, retrovirus, cytomegalovirus or other viral vectors can be used to express the antibody.

Various methods to make pharmaceutical compositions are known in the art and are contemplated by the invention. In some embodiments, the compositions include excipient suitable for a biologic molecule such as the antibodies of the invention. In some embodiments, the antibodies could be produced in specific cell lines and conditions so as to control glycosylation of the antibody. In some embodiments, the antibody framework for example, could comprise specific modification so as to increase stability of the antibody.

In certain aspects, the invention provides that the antibodies, and fragments thereof, described herein can be formulated as a composition (e.g., a pharmaceutical composition). Suitable compositions can comprise an inventive antibody (or antibody fragment) dissolved or dispersed in a pharmaceutically acceptable carrier (e.g., an aqueous medium). The compositions can be sterile and can be in an injectable form (e.g. but not limited to a form suitable for intravenous injection, intramascular injection). The antibodies (and fragments thereof) can also be formulated as a composition appropriate for topical administration to the skin or mucosa. Such compositions can take the form of liquids, ointments, creams, gels and pastes. The antibodies (and fragments thereof) can also be formulated as a composition appropriate for intranasal administration. The antibodies (and fragments thereof) can be formulated so as to be administered as a post-coital douche or with a condom. Standard formulation techniques can be used in preparing suitable compositions.

The antibody (and fragments thereof), described herein have utility, for example, in settings including but not limited to the following:

i) in the setting of anticipated known exposure to HIV-1 infection, the antibodies described herein (or fragments thereof) and be administered prophylactically (e.g., IV, topically or intranasally) as a microbiocide, ii) in the setting of known or suspected exposure, such as occurs in the setting of rape victims, or commercial sex workers, or in any homosexual or heterosexual transmission without condom protection, the antibodies described herein (or fragments thereof) can be administered as post-exposure prophylaxis, e.g., IV or topically, and iii) in the setting of Acute HIV infection (AHI), the antibodies described herein (or fragments thereof) can be administered as a treatment for AHI to control the initial viral load or for the elimination of virus-infected CD4 T cells.

In accordance with the invention, the antibodies (or antibody fragments) described herein can be administered prior to contact of the subject or the subject's immune system/cells with HIV-1 or within about 48 hours of such contact. Administration within this time frame can maximize inhibition of infection of vulnerable cells of the subject with HIV-1.

In addition, various forms of the antibodies described herein can be administered to chronically or acutely infected HIV patients and used to kill remaining virus infected cells by virtue of these antibodies binding to the surface of virus infected cells and being able to deliver a toxin to these reservoir cells.

Suitable dose ranges can depend on the antibody (or fragment) and on the nature of the formulation and route of administration. Optimum doses can be determined by one skilled in the art without undue experimentation. For example, doses of antibodies in the range of 1-50 mg/kg of unlabeled or labeled antibody (with toxins or radioactive moieties) can be used. If antibody fragments, with or without toxins are used or antibodies are used that can be targeted to specific CD4 infected T cells, then less antibody can be used (e.g., from 5 mg/kg to 0.01 mg/kg).

In certain aspects the invention provides use of the antibodies of the invention, including bispecific antibodies, in methods of treating and preventing HIV-1 infection in an individual, comprising administering to said individual a therapeutically effective amount of a composition comprising the antibodies of the invention in a pharmaceutically acceptable form. In certain embodiment, the methods include a composition which includes more than one HIV-1 targeting antibody. In certain embodiments, the HIV-1 targeting antibodies in such combination bind different epitopes on the HIV-1 envelope. In certain embodiments, such combinations of bispecific antibodies targeting more than one HIV-1 epitope provide increased killing of HIV-1 infected cells. In other embodiments, such combinations of bispecific antibodies targeting more than one HIV-1 epitope provide increased breadth in recognition of different HIV-1 subtypes.

In certain embodiments, the composition comprising the antibodies of the invention alone or in any combination can be administered via IM, subcutaneous, or IV delivery, or could be deposited at mucosal sites, such as the oral cavity to prevent maternal to child transmission, the rectal space or the vagina as a microbicide. In certain embodiments, the antibodies can be administered locally in the rectum, vagina, or in the oral cavity, and can be formulated as a microbiocide (Hladik F et al ELIFE Elife. 2015 Feb. 3; 4. doi: 10.7554/eLife.04525; Multipurpose prevention technologies for reproductive and sexual health. Stone A. Reprod Health Matters. 2014 November; 22(44):213-7. doi: 10.1016/S0968-8080(14)44801-8). In other embodiments, antibodies can be formulated such that the therapeutic antibody or combination thereof is impregnated on a vaginal ring (Chen Y et al. Drug Des. Devel. Ther 8: 1801-15, 2014; Malcolm R K et al BJOG 121 Suppl 5: 62-9, 2014). Antibodies can be administered alone or with anti-retroviral drugs for a combination microbiocide (Hladik F et al ELIFE Elife. 2015 Feb. 3; 4. doi: 10.7554/eLife.04525)

Alternatively they can be administered in complex with a form of HIV Env, optimally gp120, but also an Env trimer, to enhance Env immunogenicity. In certain embodiments, the antibodies can be delivered by viral vector mediated delivery of genes encoding the antibodies of the invention (See e.g. Yang et al. Viruses 2014, 6, 428-447). In certain embodiments, the antibodies can be administered in viral vector, for example but not limited to adenoassociated viral vector, for expression in muscle and plasma.

In certain embodiments, antibodies with different binding specificities are combined for use in pharmaceutical compositions and therapeutic methods. For example: CD4 binding site antibodies are combined with V3 antibodies, MPER antibodies and so forth. FIGS. 8, 9 and 10 show a selection of potent HIV-1 neutralizing antibodies which can be used in pharmaceutical compositions, and therapeutic methods. Non-limiting examples of selections of combinations of certain antibodies include: DH542, DH542_L4, DH542_QSA, DH429 and DH512 (or any of the DH512 variants); DH512 and CH31 (See US Publication 20140205607); DH512 (or any of the other DH512 variants) and DH540 (See Example 8, and this antibody will be described elsewhere); DH542, DH542_L4, DH542_QSA, DH429, DH512 and DH540; DH542, DH542_L4, DH542_QSA, DH429 and CH557; CH557 and DH512 (or any of the DH512 variants). These combinations are expected to give a greater overall potency and breadth. A polyclonal mixture of Abs is expected reduce or eliminate viral escape. It is readily understood by skilled artisans that in some embodiments a combination therapy envisions a composition which combines various antibodies. In other embodiments a combination therapy is provided wherein antibodies are administered as individual compositions, for example at different times, by different means, or at administered at different locations. In other embodiments, a combination therapy is provides wherein a therapeutic antibody or antibodies is combined with other therapeutic means, for example anti-retroviral drug cocktails, or drugs which activate latently infected HIV-1 cells.

In some embodiments, the disclosed antibodies or antigen binding fragments thereof are used to determine whether HIV-1 envelope(s) is a suitable antigen for inclusion in a vaccine composition. For example the antibodies can be used to determine whether an antigen in a vaccine composition including a gp41 immunogen assumes a conformation including an epitope bound by the inventive antibodies or fragments thereof. This can be readily determined by a method which includes contacting a sample containing the vaccine, such as a gp120 antigen, with a disclosed antibody or antigen binding fragment under conditions sufficient for formation of an immune complex, and detecting the immune complex, to detect an HIV-1 antigen including an epitope of an inventive antibody in the sample. In one example, the detection of the immune complex in the sample indicates that vaccine component, such as a HIV-1 Env antigen assumes a conformation capable of binding the antibody or antigen binding fragment.

Antibodies Names Correlation

Various antibodies names are used throughout the application. Antibodies names correlation is as follows:

Memory B cell antibodies: DH511=DH511.1; DH512=DH511.2; DH513=DH511.3; DH514=DH511.4; DH515=DH511.5; DH516=DH511.6;

Plasma antibodies: DH511_1a=DH511.7P; DH511_2a=DH511.8P; DH511_3a=DH511.9P; DH511_4a=DH511.10P; DH511_5a=DH511.11P; DH511_5a=DH511.12P.

Chimeric antibodies which combine a heavy and light chain from different antibodies are typically indicated by the designation of the heavy and light chain of each parent antibody.

Mutations in the VH chain are referenced with respect to Kabat numbering of the indicated VH chain.

The following examples are provided to illustrate particular features of certain embodiments, but the scope of the claims should not be limited to those features exemplified.

EXAMPLES

Example 1: MPER Antibodies

FIG. 1 shows the three HIV infected individual plasma that was evaluated for HIV neutralizing activity and the specificities profiled by the Georgiev algorithm (Georgiev I S et al Science 340: 751-6, 2013). From this analysis we found three subjects (CH0210, CH0536, CH1244) with gp41 bnAb activity (FIG. 1).

Methods to identify and isolate MPER reactive antibodies were carried out as described in Liao H X et al. J. Virol. Methods 158: 171-9, 2009. MPER specific hooks were designed to identify to antibodies which bind to HIV-1 gp41 MPER region. Using one such hook, the MPR.03-biotin hook tetramerized (FIG. 2), with fluorophor labeled streptavidin in two colors (FIG. 3), we sorted by flow cytometry into single wells, the diagonally (that reacted with both colors hooks) reactive memory B cells (FIG. 3). B cells from 10 million PBMC were sorted and PCR was carried out according to the protocol in Liao H X et al. J. Virol. Methods 158: 171-9, 2009. PCR amplifications were carried out to amplify rearranged VH and VL fragment pairs from the diagonally sorted memory B cells (Liao et al JVM). Overlapping PCR was used to construct full length Ig heavy and Ig light linear genes comprising the rearranged VH and VL fragment pairs. RT-PCR and PCR reactions was carried out essentially as described in Liao H X et al. J. Virol. Methods 158: 171-9, 2009, see for example FIG. 1, Section 3.3. Sequence analysis of the VH and VL genes was carried out to determine the VH and VL gene usage, CDR lengths, the % mutation of HCDR3 and LCDR3. Based on this sequence analysis, one to two pairs of linear VH and VL genes were selected and made in linear cassettes (essentially as described in Liao H X et al. J. Virol. Methods 158: 171-9, 2009, see for example FIG. 1, Section 3.3) to produce recombinant monoclonal antibodies by transient transfection in 293T cells.

Pairs of VH and VL genes as selected above can also be used to produce plasmids for stable expression of recombinant antibodies.

In certain embodiments, the plasmids or linear constructs for recombinant antibody expression also comprise AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the 4$^{th}$ A (N434A) is to enhance FcR neonatal mediated transport of the IgG to mucosal sites (Shields R I et al. ibid).

The antibodies of the invention were selected based on a combination of criteria including sequence analyses, and functional analyses including but not limited as neutralization breadth, and potency.

Figure 6:
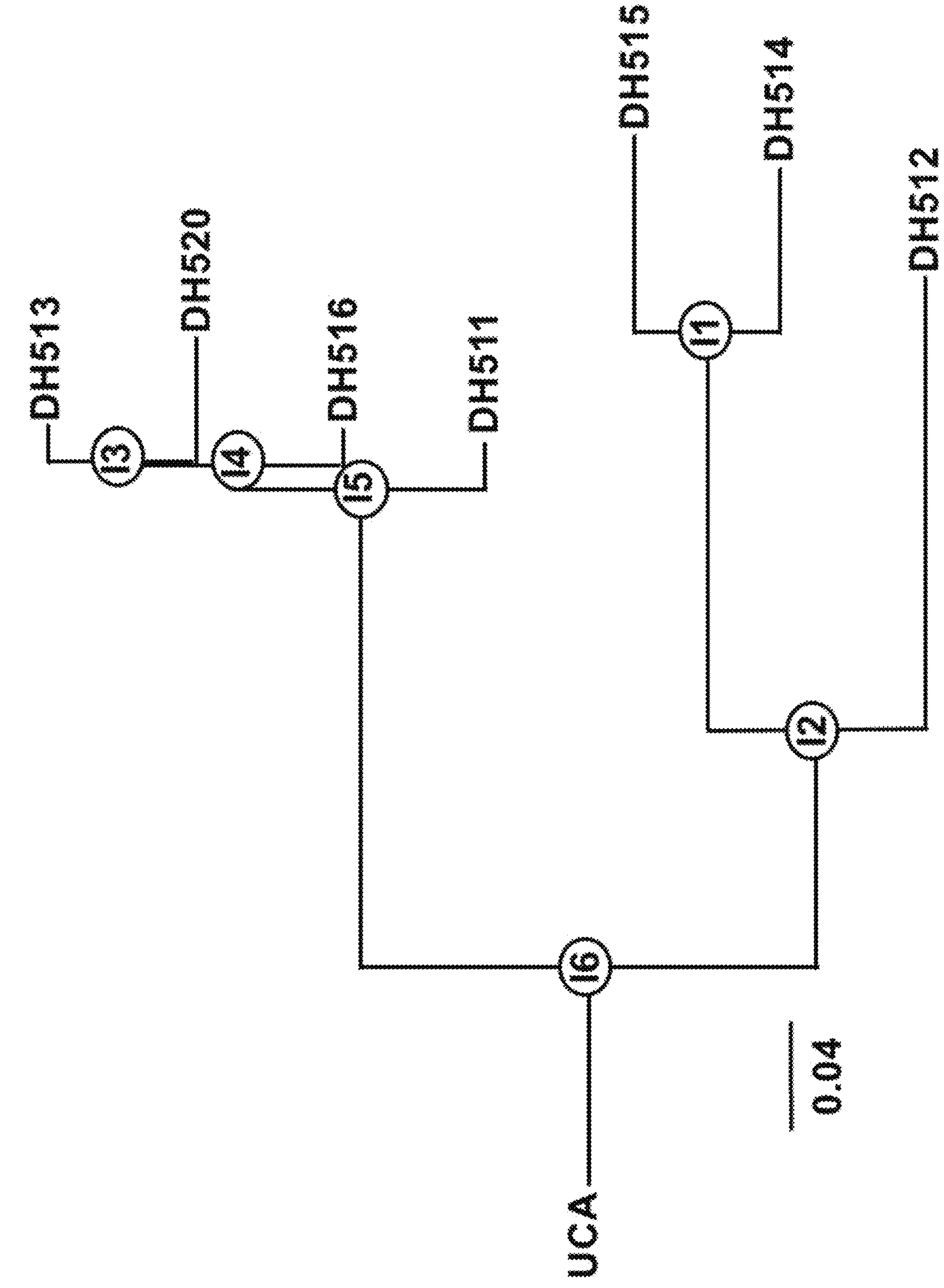
FIG. 6 shows the MPER BnAb DH511 VH Phylogram of the B Cell Clonal Lineage Derived from Subject 0210. Antibodies in clone DH511 include the following: DH511, DH512, DH513, DH514, DH515, DH516 and DH520.
Figure 17:
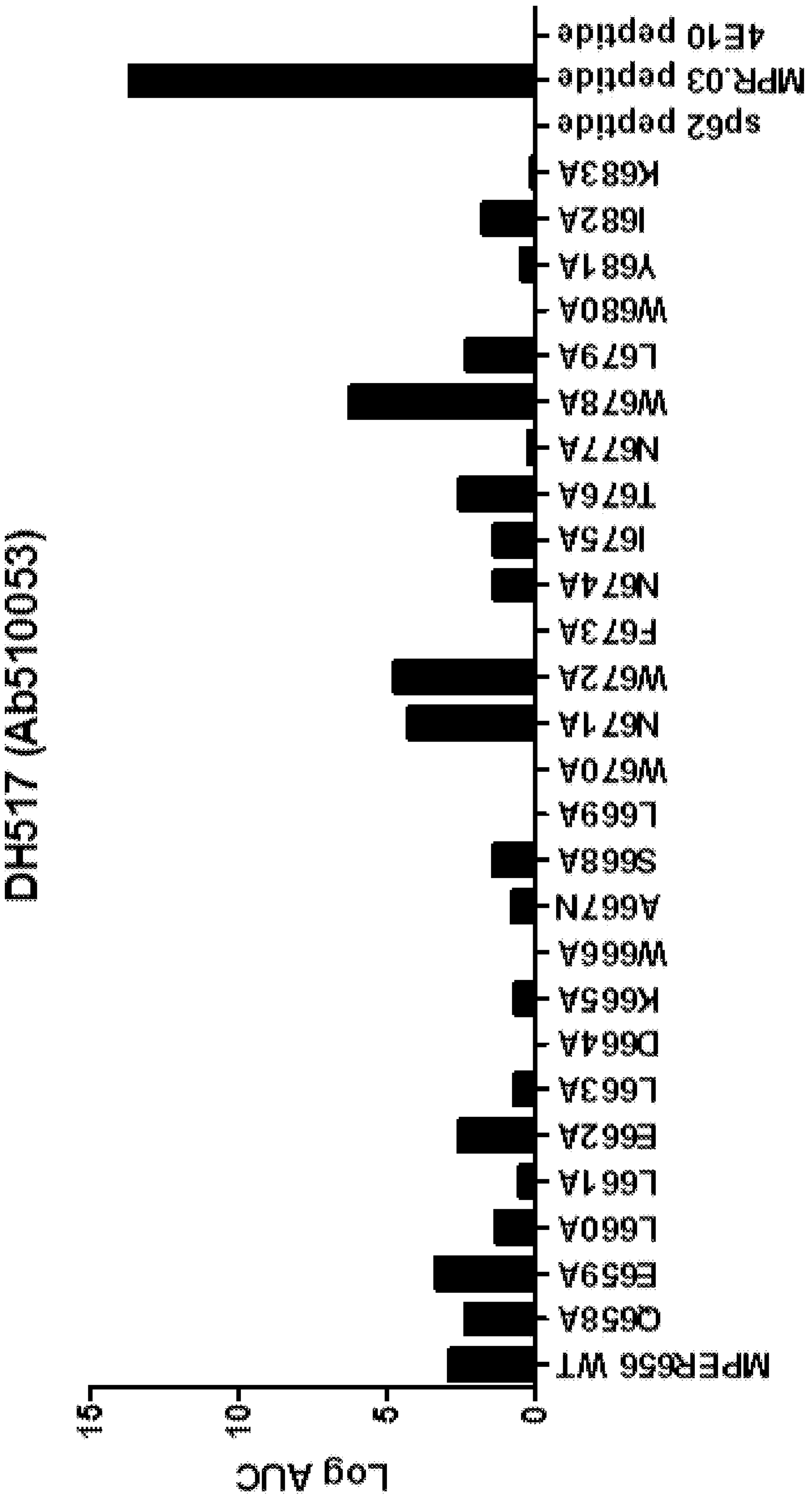
FIG. 17 shows Binding of DH517 (Ab510053) to alanine substituted MPER-26 peptides. The binding studies do not conclusively map the DH517 epitope.
Figure 19:
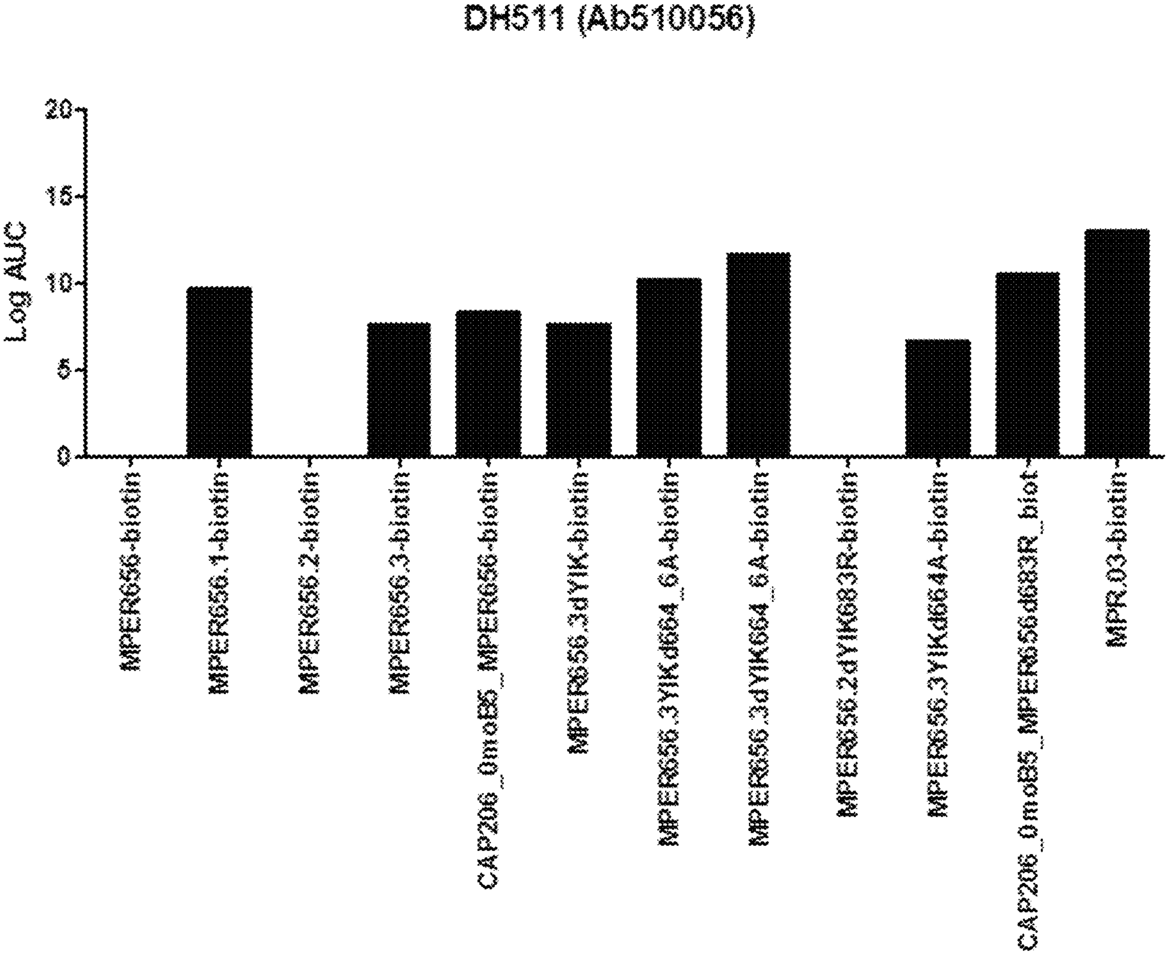
FIG. 19 shows Binding of DH511 (Ab510056) to MPER656 variants
Figure 20:
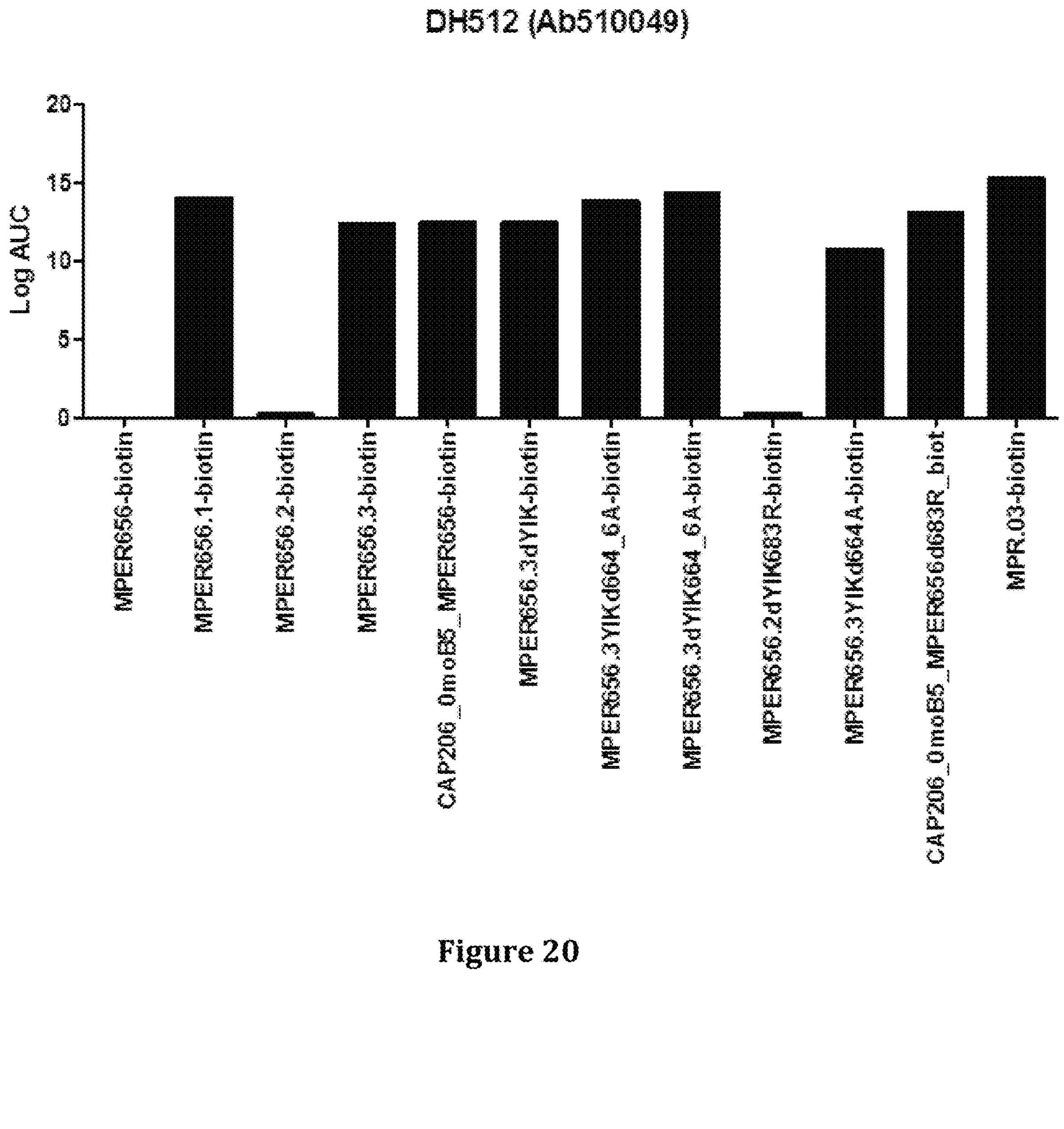
FIG. 20 shows Binding of DH512 (Ab510049) to MPER656 variants
Figure 21:
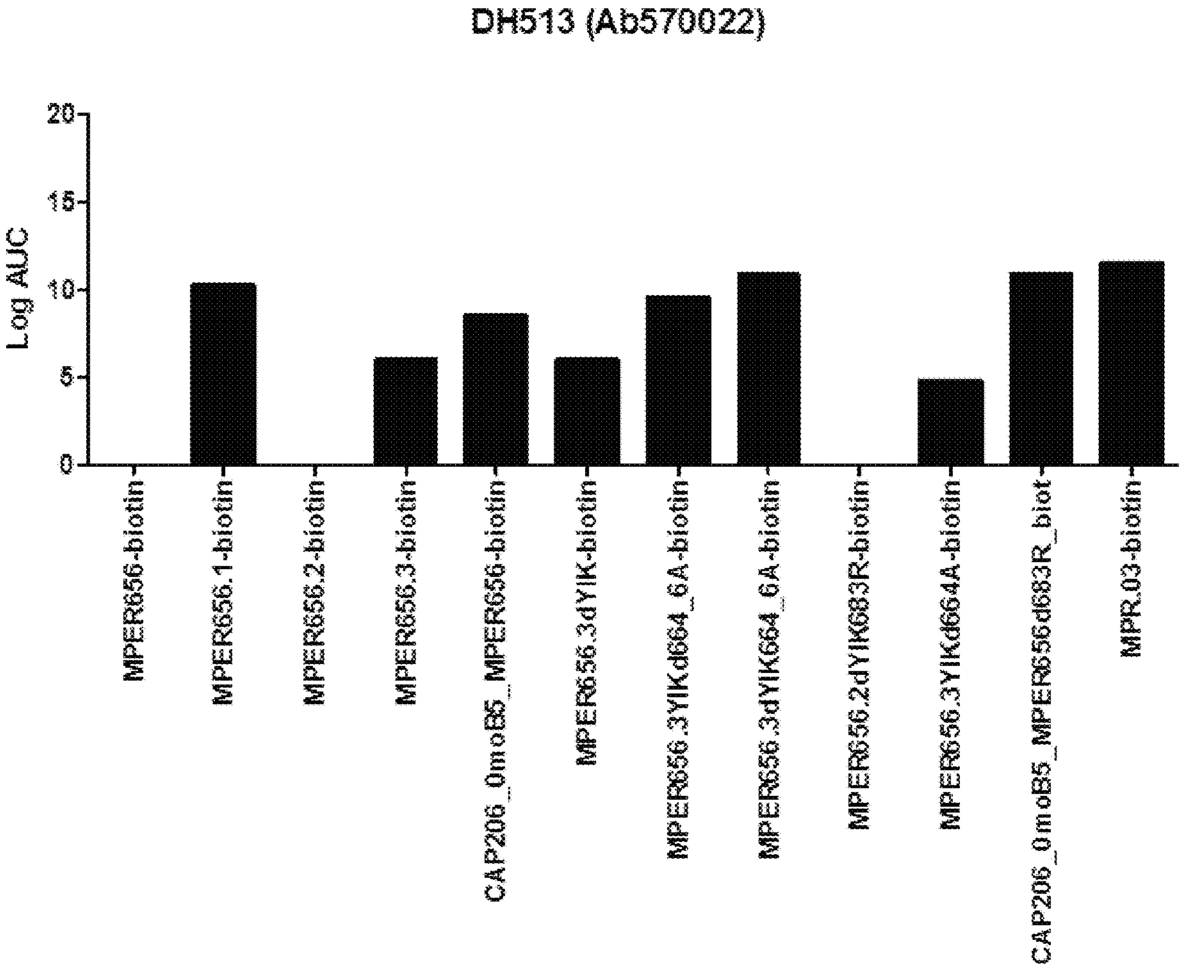
FIG. 21 shows Binding of DH513 (Ab570022) to MPER656 variants
Figure 22:
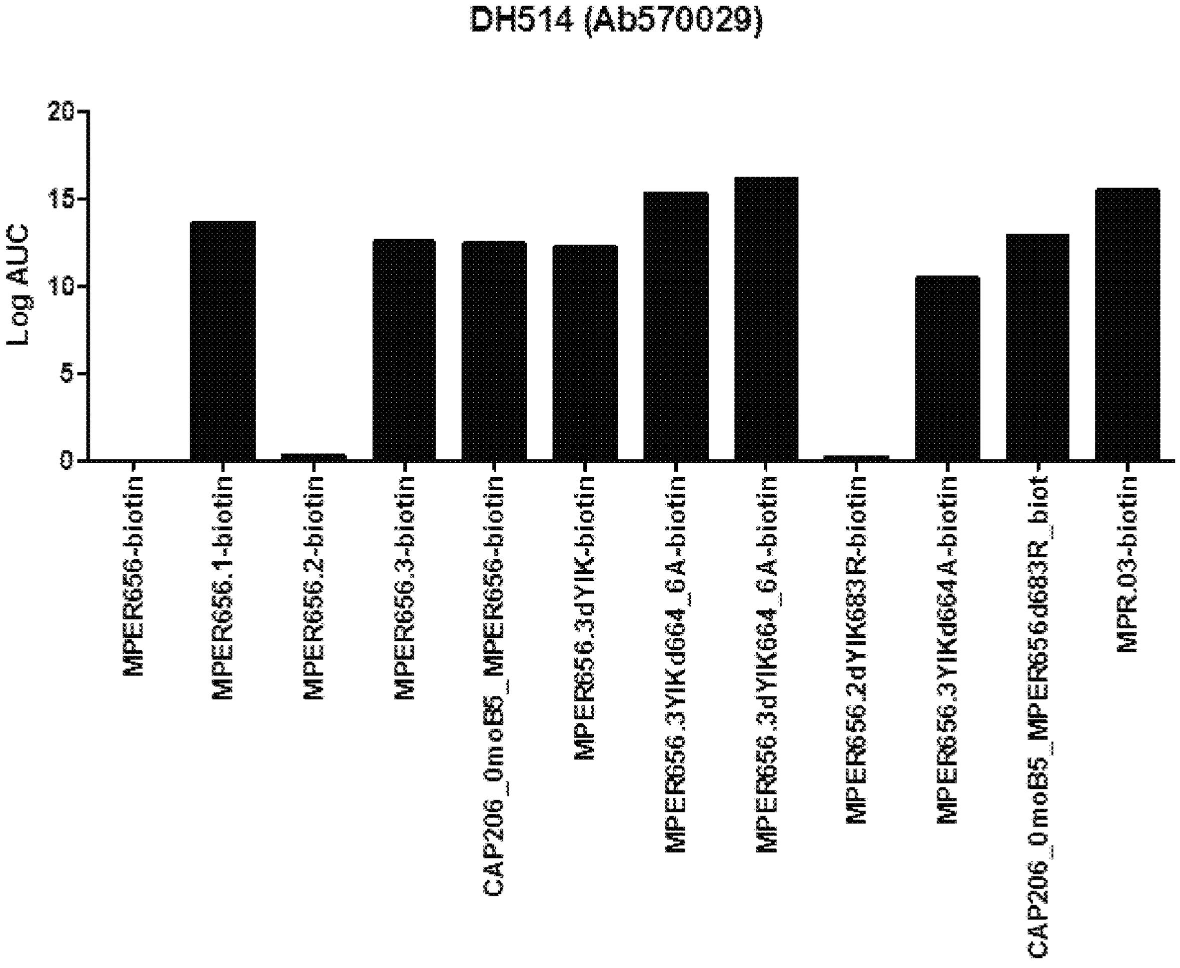
FIG. 22 shows Binding of DH514 (Ab570029) to MPER656 variants
Figure 23:
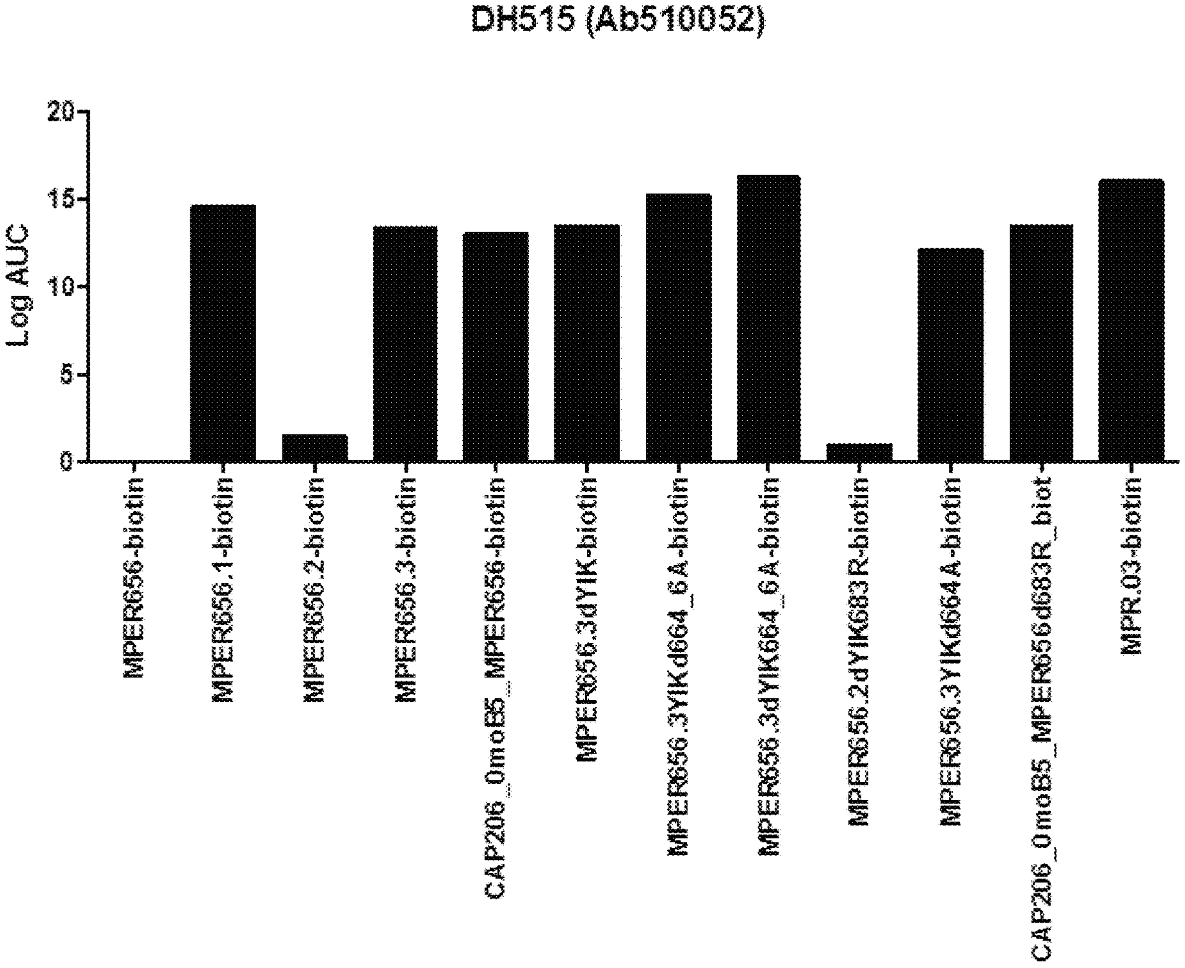
FIG. 23 shows Binding of DH515 (Ab510052) to MPER656 variants
Figure 24:
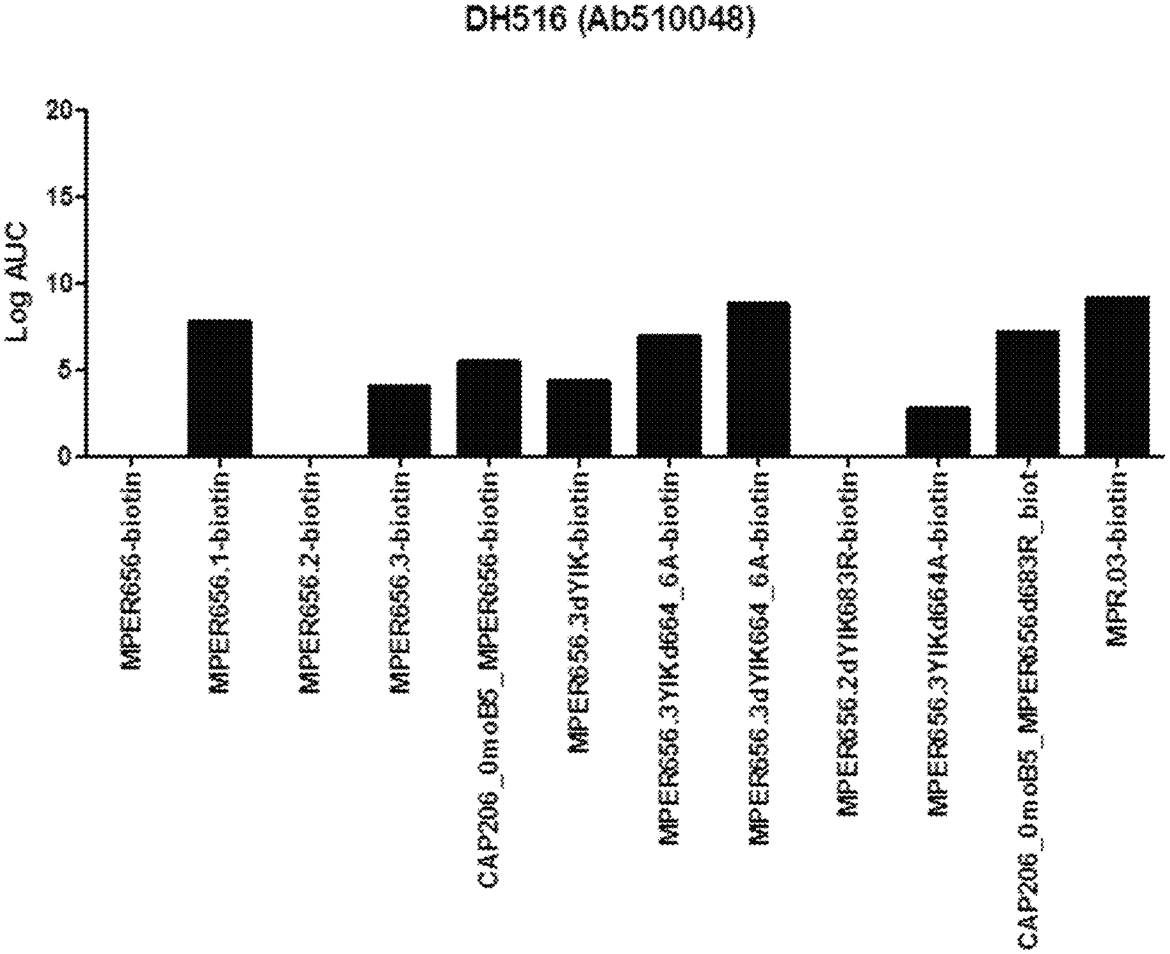
FIG. 24 shows Binding of DH516 (Ab510048) to MPER656 variants
Figure 25:
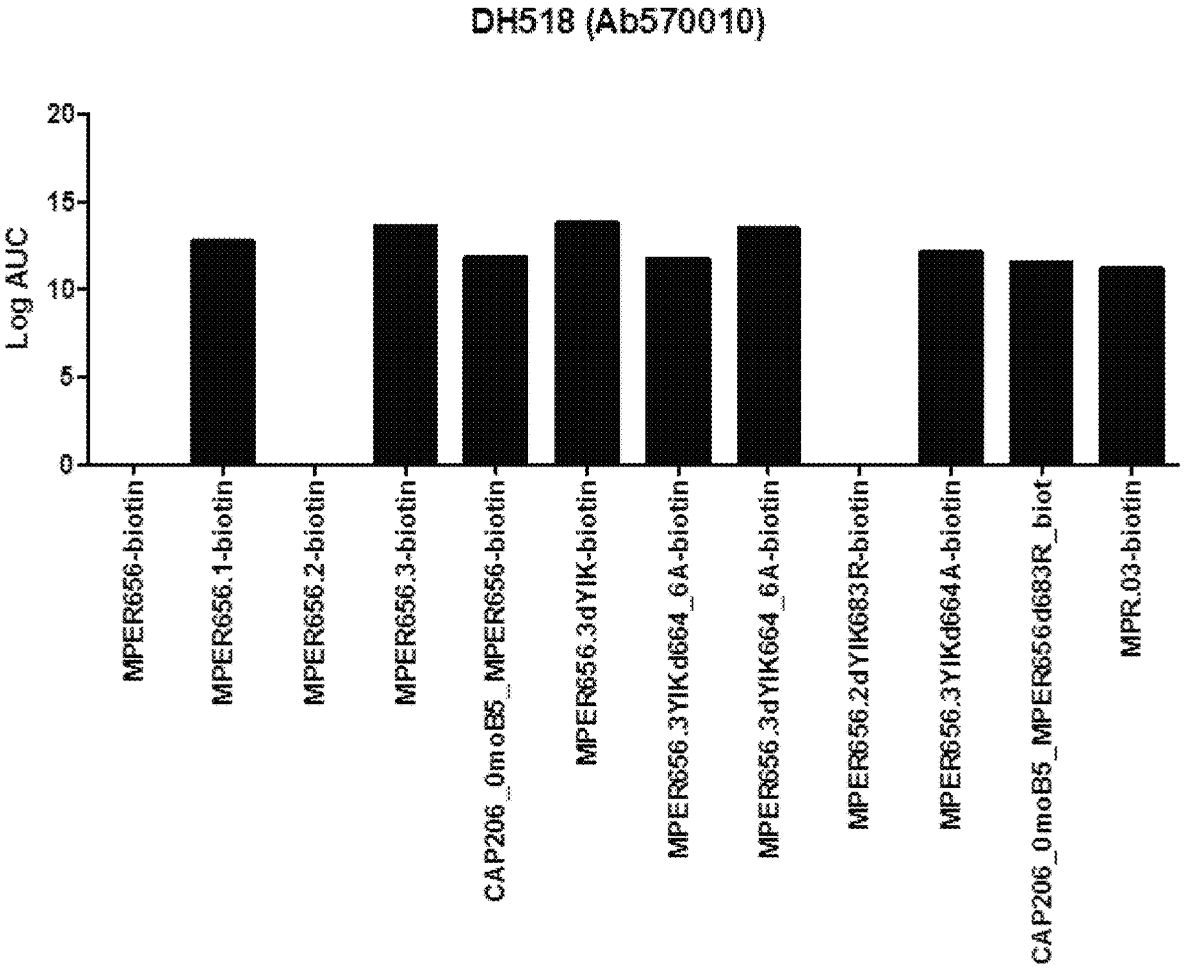
FIG. 25 shows Binding of DH518 (Ab570010) to MPER656 variants.

In certain embodiments, the antibodies of the invention comprise naturally rearranged VH and VL fragment pairs, wherein the rest of the Ig gene is not naturally occurring with the isolated rearranged VH and VL fragments. In certain embodiments, the antibodies of the invention are recombinantly produced by synth FIG. 4 and Example 12 shows a summary of some of the characteristics of the recombinant MPER antibodies of the invention. DH511-DH517 are antibodies with VH and VL chains from individual CH0210. DH518 is an antibody with VH and VL chains from individual CH0536. DH536 is an antibody with VH and VL chains from individual CH1244. CH537 is an antibody with VH and VL chains from individual CH0585. DH 511-DH516 antibodies are all members of the same B cell clonal lineage (FIG. 6). FIG. 5 shows the neutralizing capacity of these antibodies with all but DH536 and DH537 able to neutralize difficult to neutralized (tier 2) HIV strains B.BG1168, C.CH505, and C.DU172). FIG. 6 shows the phylogram of the DH511 clonal lineage.

Example 2: TZMbl Neutralization Assay

TZMbl neutralization assay is a standard way to evaluate antibody breadth and potency. See Montefiori, D. Methods Mol Biol. 2009; 485:395-405; HIV-1 Env-pseudoviruses infection of TZM-bl cells. Exemplary pseudovirus neutralization assays and panels of HIV-1 pseudovirus are described for example, in Li et al., J Virol 79, 10108-10125, 2005, Seaman et al, J. Virol., 84:1439-1452, 2010; Sarzotti-Kelsoe et al., J. Immunol. Methods, 409:131-46, 2014; and WO2011/038290, each of which is incorporated by reference herein. Various HIV-1 isolates, both Tier 1 and Tier 2 viruses can be included in this assay.

The TZMbl assay was conducted to determine neutralization potency and breadth of the various antibodies of the invention on different HIV-1 pseudoviruses.

FIG. 7 shows the results of neutralization of 8 of the gp41 antibodies against a panel of 30 HIV tier 2 isolates in the TZMbl pseudovirus neutralization assay. The DH511 clonal lineage members all neutralized 100% (30/30) isolates while DH517 neutralized 50% and DH518 neutralized 83%. This in contrast to 10E8 gp41 antibody that only neutralized 29/30 isolates. FIG. 8 shows the mean IC50, IC80 and percent of isolates neutralized at an IC50<50 ug/ml and at an IC80 of <5 ug/ml (confirm). Thus, mAb DH512 is equally as potent and slightly more broad in neutralization breadth than the mAb 10E8. FIG. 9 shows other mAbs and their breadth and potency. Various figures, including without limitation, FIGS. 37, 38, 28, 56 and 34, and Figures from Example 12 show neutralization data of various antibodies against various panels of pseudoviruses.

Example 3: Epitope Mapping of MPER Antibodies

Binding of antibodies to various MPER peptides in an ELISA assay was used to map the epitopes of the MPER antibodies.

FIG. 11 shows that Antibody epitopes maps to the C-terminus of gp41 to a similar region where 10E8 binds (Huang J et al. Nature 491 406, 2012; See US Pub 20140348785). FIGS. 11, 15-25 show binding of antibodies to MPER peptide variants. These mapping studies show that the antibodies of the invention are 10E8 like Abs. In non-limiting embodiments, DH512 shows the broadest and most potent neutralization among the antibodies tested.

FIG. 12 shows an alanine substituted gp41 peptide set used to map DH517 mab and FIG. 13 shows a summary of ala mutants to which the antibody is sensitive for binding to gp41. FIGS. 14 and 15 show the VH and VL sequences of the DH511-DH516 antibodies.

FIGS. 12-13 show the nucleotide and amino acid sequences of all the certain antibodies of the invention.

FIGS. 16-25 show that DH517 displayed a unique mapping pattern in that it depends on DKW at the N terminus and several residues at the C terminus important for 10E8 binding and neutralization. Clone DH511 mAbs bound strongly to the majority of the MPER656 variants, showing decreased binding to MPER656.2 and MPER656.2dYIK683R-biotin. These data indicate that the asparagine at position 674 is critical for binding, thus providing evidence that these mAbs bind at the C-terminus.

All the antibodies used in the above Examples had the AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the 4$^{th}$ A (N434A) is to enhance FcR neonatal mediated transport of the IgG to mucosal sites (Shields R I et al. ibid).

Epitope mapping studies are also described in Example 12.

Example 4: Binding Assays and Kd Determination

Kd measurements of antibody binding to HIV-1 envelope, e.g. gp41 or any other suitable peptide for the MPER antibodies, will be determined by Surface Plasmon Resonance measurements, for example using Biacore, or any other suitable technology which permits detection of interaction between two molecules in a quantitative way.

Example 5: Various Assays

Various assays for self-reactivity of human antibodies are known in the art. AtheNA Multi-Lyte ANA Plus Test System is one such assay. ELISA cardiolipin assay is another assay to measure autoreactivity.

The stability and properties of the antibodies, for example as formulated in a composition for treatment will be tested.

Animal studies (PK and PD studies) could be conducted to determine the distribution and half-life of the antibodies.

Various assays and experiments can be designed to analyze prevention, treatment and/or cure.

Example 6: Antibodies from CH235 Lineage

CH557 is one example of a CD4bs broad neutralizing HIV-1 antibody, from a series of clonal antibodies (FIG. 28) which can be used in combination with the antibodies of the invention.

Example 7: V3 Glycan Antibodies from DH270 Lineage

Antibodies from DH270 lineage are shown in FIG. 26. I1 (DH270IA1), I2, I4, I3 and UCA in FIG. 26 are not isolated from human subjects but are derived computationally based on VH and VL sequences of other observed antibodies from the clone: DH471, DH429, DH473, DH391 and DH270. The VH and VL sequences of DH471, DH429, DH473, DH391 and DH270 are derived from a human subject infected with HIV-1.

The VH and VL sequences of DH471, DH429, DH473, DH391 and DH270 are derived essentially as described in Example 1, except that cell were sorted with a different hook.

Neutralization data for antibodies I1 (DH270IA1) and DH429 is summarized in FIG. 9, and FIG. 10.

DH542, DH542-QSA, DH542_K3 are non-limiting examples of V3 antibodies, which can be used in combination with the antibodies of the invention. The nucleotide and amino acid sequences of the VH and VL of DH542 QSA are shown below. DH542 QSA antibody has the VH of DH542 and the VL called DH542-QSA

```
>DH542_HC_nt
                                   (SEQ ID NO: 465)
CAGGTGCAGCTGGTGCAGTCTGGGGCTCAAATGAA

GAACCCTGGGGCCTCAGTGAAGGTCTCCTGCGCGC

CTTCTGGATATACCTTCACCGACTTTTACATACAT

TGGTTGCGCCAGGCCCCTGGCCAGGGGCTTCAGTG

GATGGGATGGATGAACCCTCAGACTGGTCGCACAA

ACACTGCACGAAACTTTCAGGGGAGGGTCACCATG

ACCAGGGACACGTCCATCGGCACAGCCTACATGGA

GTTGAGAAGCCTGACATCTGACGACACGGCCATAT

ATTACTGTACGACAGGGGGATGGATCAGTCTTTAC

TATGATAGTAGTTATTACCCCAACTTTGACCACTG

GGGTCAGGGAACCCTGCTCACCGTCTCCTCAG

>DH542_HC_aa
                                   (SEQ ID NO: 466)
QVQLVQSGAQMKNPGASVKVSCAPSGYTFTDFYIH

WLRQAPGQGLQWMGWMNPQTGRTNTARNFQGRVTM

TRDTSIGTAYMELRSLTSDDTAIYYCTTGGWISLY

YDSSYYPNFDHWGQGTLLTVSS

>DH542_LC_nt_corrected (DH542_QSA)
                                   (SEQ ID NO: 467)
CAGTCTGCCCTGACTCAGCCTGCCTCCGTGTCTGG

GTCTCCTGGACAGTCGATCACCATCTCCTGCACTG

GAACCAAGTATGATGTTGGGAGTCATGACCTTGTC

TCCTGGTACCAACAGTACCCAGGCAAAGTCCCCAA

ATACATGATTTATGAAGTCAATAAACGGCCCTCAG

GAGTTTCTAATCGCTTCTCTGGCTCCAAATCTGGC

AACACGGCCTCCCTGACAATCTCTGGGCTCCGGGC

TGAGGACGAGGCTGACTATTATTGCTGTTCATTTG

GAGGGAGTGCCACCGTGGTCTGCGGCGGCGGGACC

AAGGTGACCGTCCTAg
```

-continued

```
>DH542_LC_aa_corrected (DH542_QSA)
                                   (SEQ ID NO: 468)
QSALTQPASVSGSPGQSITISCTGTKYDVGSHDLV

SWYQQYPGKVPKYMIYEVNKRPSGVSNRFSGSKSG

NTASLTISGLRAEDEADYYCCSFGGSATWCGGGTK

VTVL
```

DH542-L4 is an antibody that has a VH of DH542 and VL of DH429 (FIG. 26)

Example 8: DH540 Antibody is Described Elsewhere

DH540 antibody is described in detail in U.S. Ser. No. 62/170,558, filed Jun. 3, 2015.

Example 9: TZMbl Neutralization Assay

TZMbl neutralization assay was conducted to determine neutralization potency and breadth of different HIV-1 viral species by DH512 and mAb 10E8. FIGS. 37 and 38 show the results of neutralization against a panel of HIV isolates in the TZMbl pseudovirus neutralization assay. FIGS. 37 and 38 also show the mean IC50, IC80 and percent of isolates neutralized at different IC50 or IC80 values.

Example 10: Isolation of Additional Antibodies from the DH511 Lineage

High Throughput Native VH:VL Sequencing from Single B Cells

Figure 39:
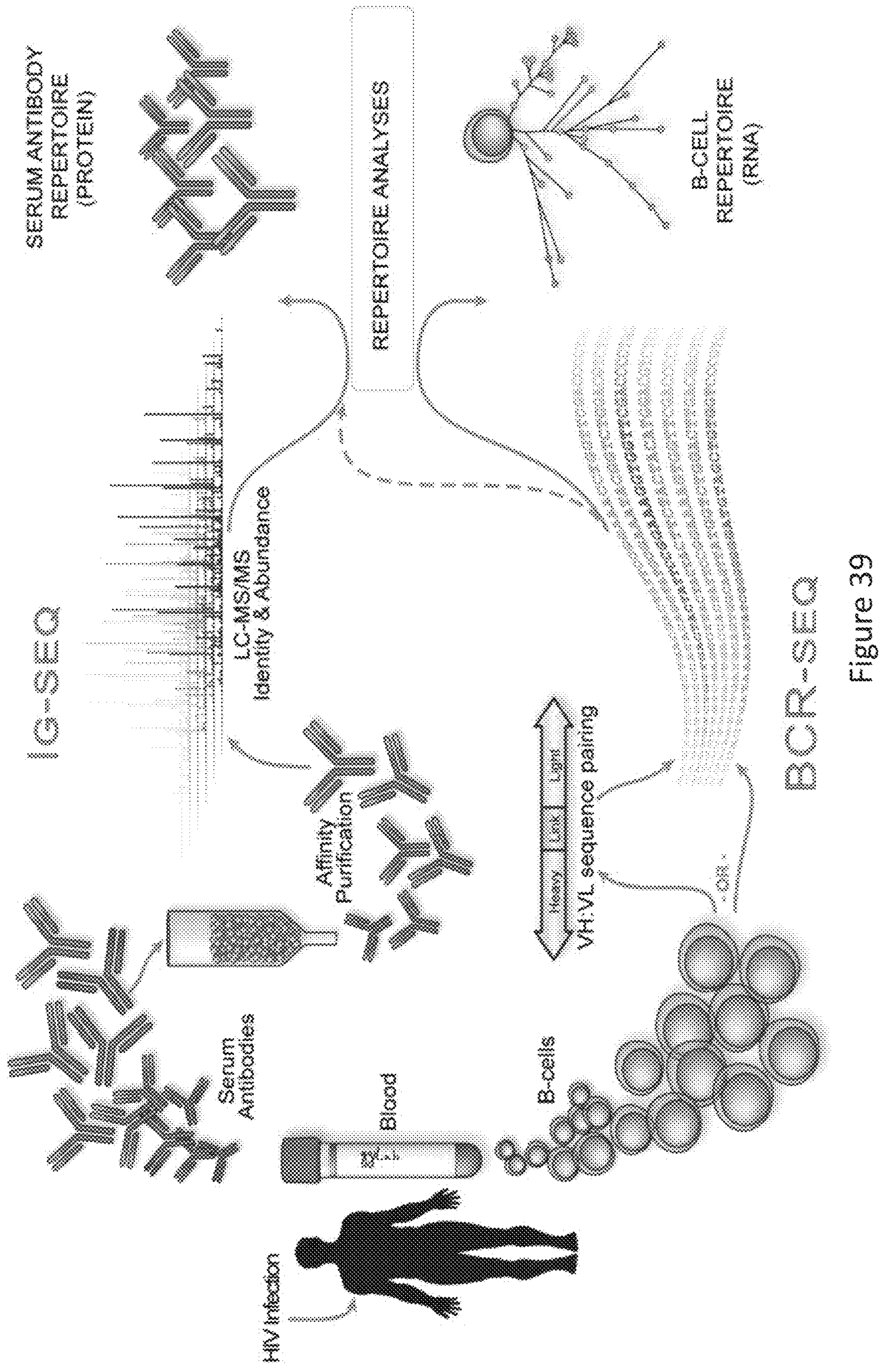
FIG. 39 shows Experimental Overview of Paired VH-VL Sequencing and antibody identification (Example 10). V gene repertoire sequencing. Identification of individual monoclonal antibodies requires the generation of a sample-specific database of IgG VH sequences constructed by next-generation sequencing of mature B cells isolated from the PBMCs of the donor. Reads are processed bioinformatically to obtain a database of unique VH sequences, which then are clustered into clonotypes according to their CDR3 sequences. The obtained database is used to interpret the MS spectra. F(ab)2 purification and proteomic analysis. F(ab)2 fragments are prepared from total serum IgG and subjected to antigen-affinity chromatography (monomeric gp120). Proteins in the elution and flow-through are denatured and reduced, alkylated, trypsin-digested and analyzed by high resolution LC-MS/MS. Spectra are interpreted with the sample-specific VH database and peptides uniquely associated with a single CDR3 are used to identify full-length VH sequences.
Figure 40:
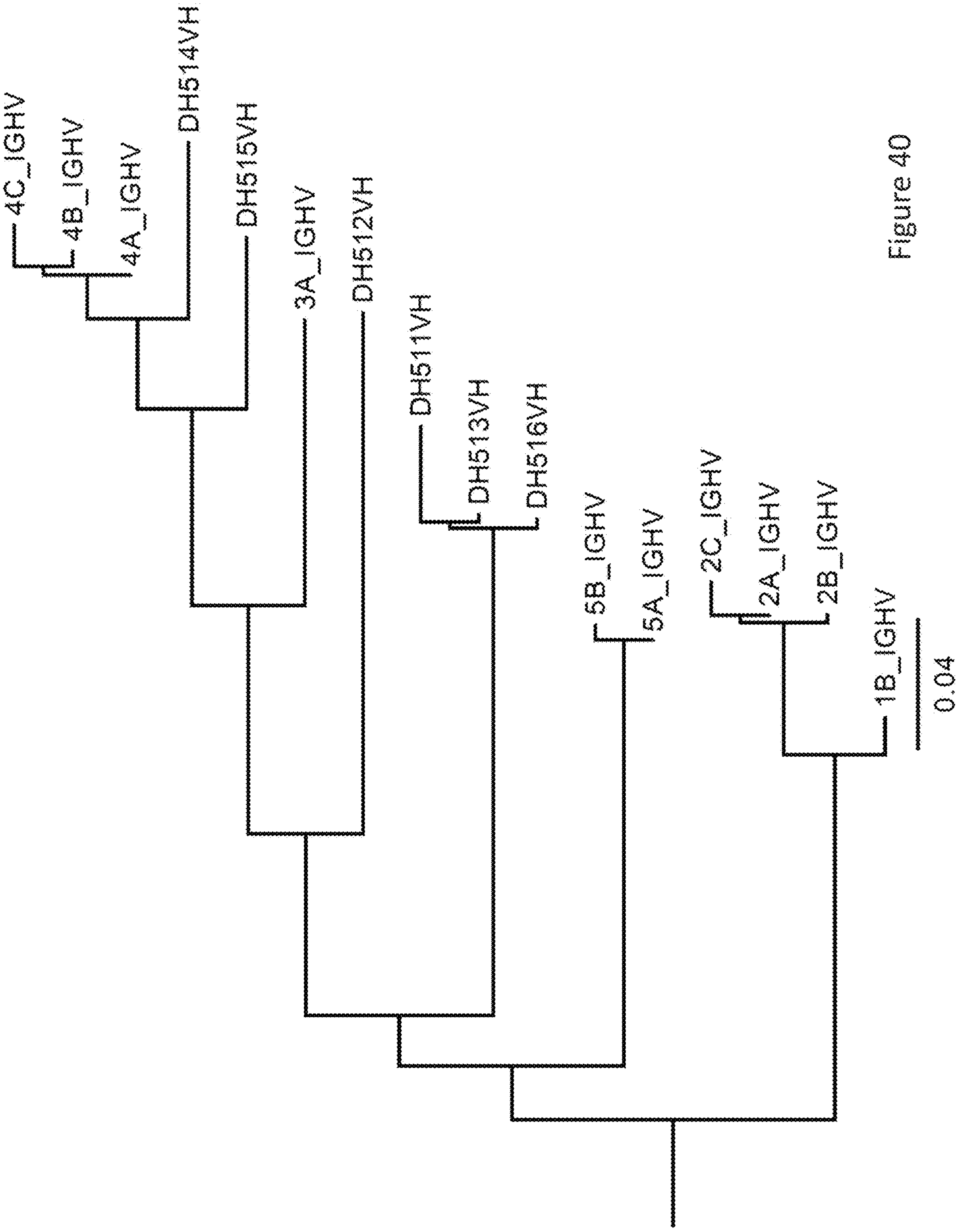
FIG. 40 shows MPER BnAb DH511 Clonal Lineage Derived from African Individual CH0210 (the heavy chain for DH511_1A is not included).
Figure 43:
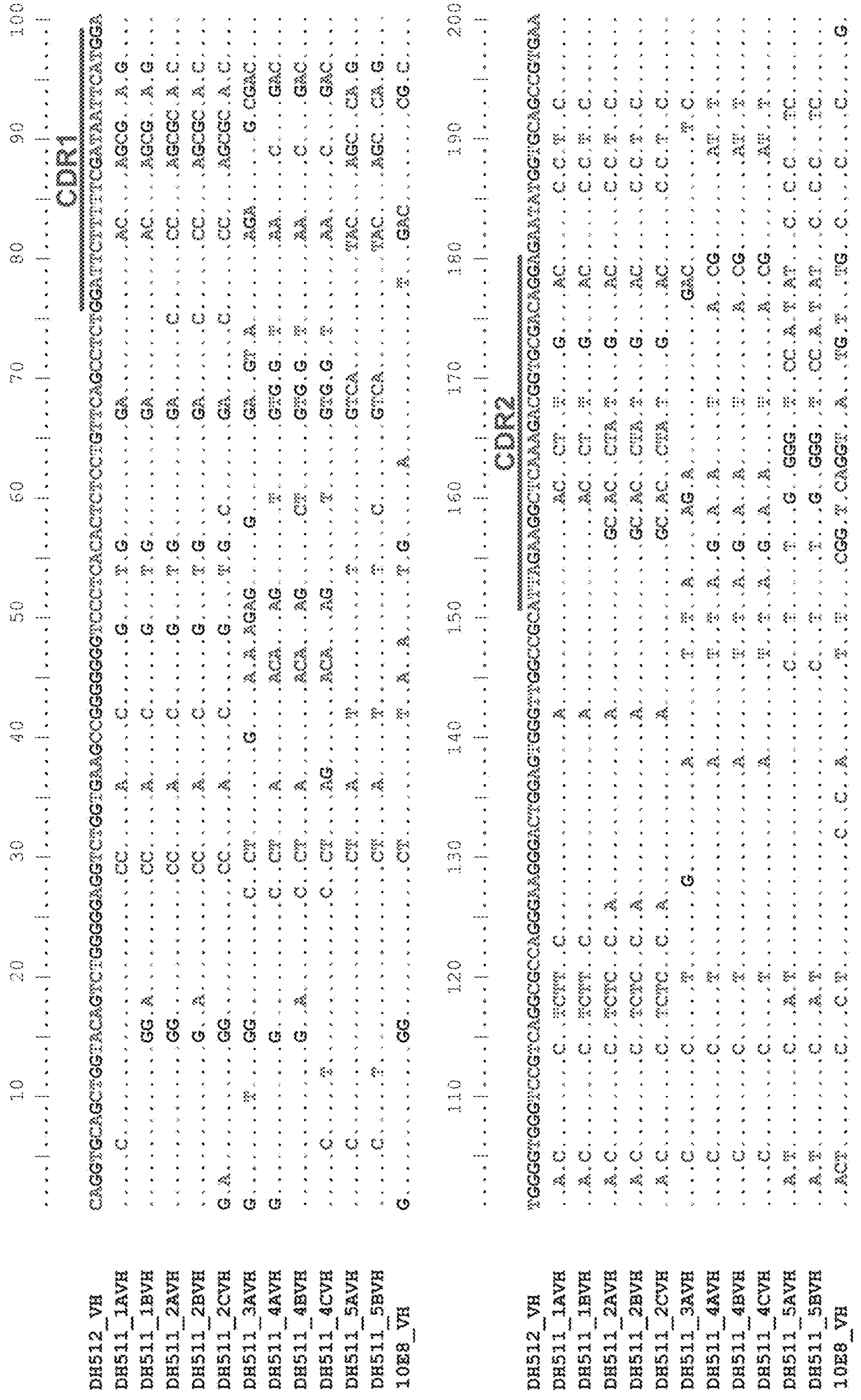
FIG. 43 shows Nucleotide Alignment of MPER Antibody Heavy Chain Sequences (SEQ ID NOs: 217-229).
Figure 43:
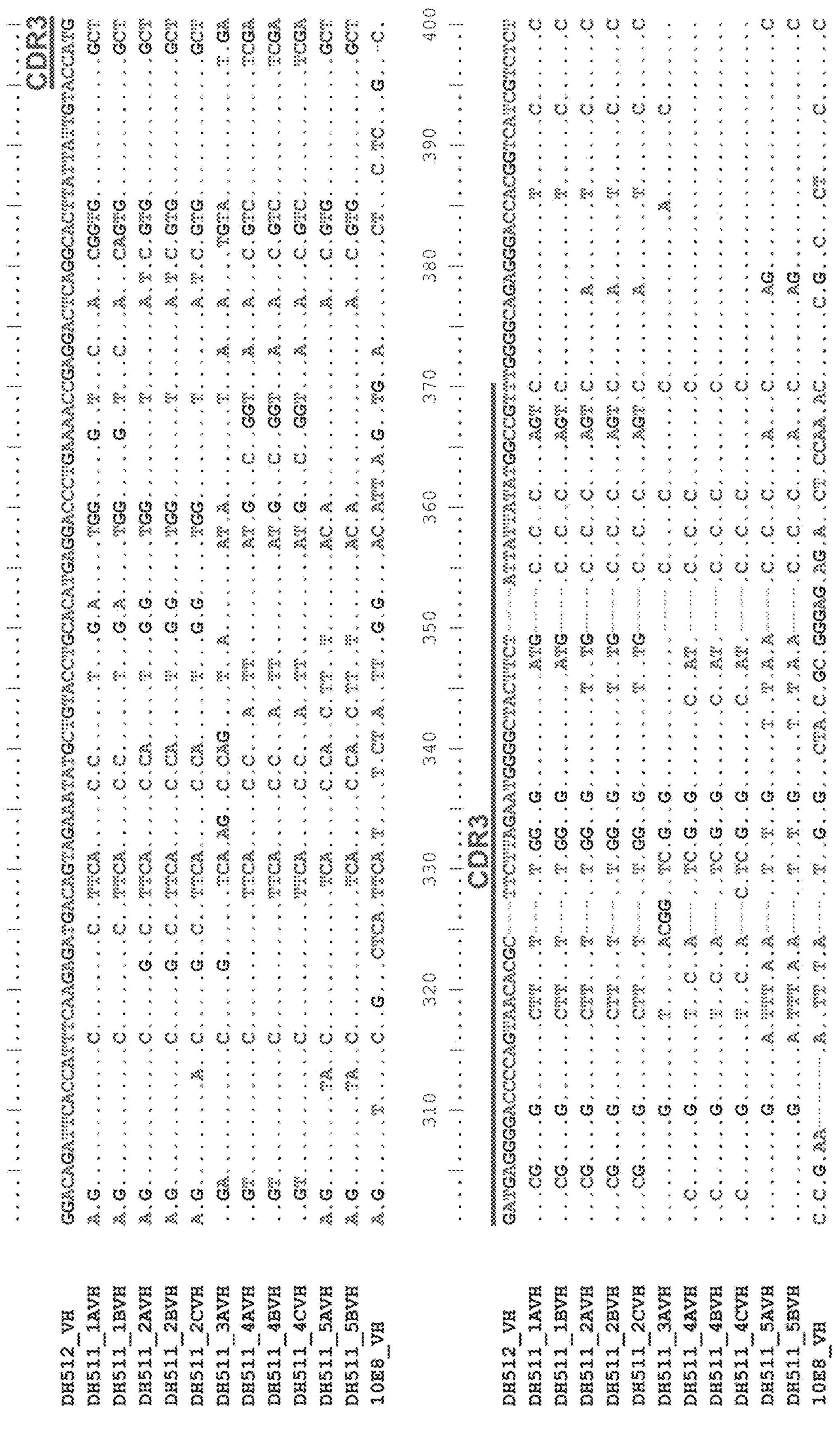
Figure 44:
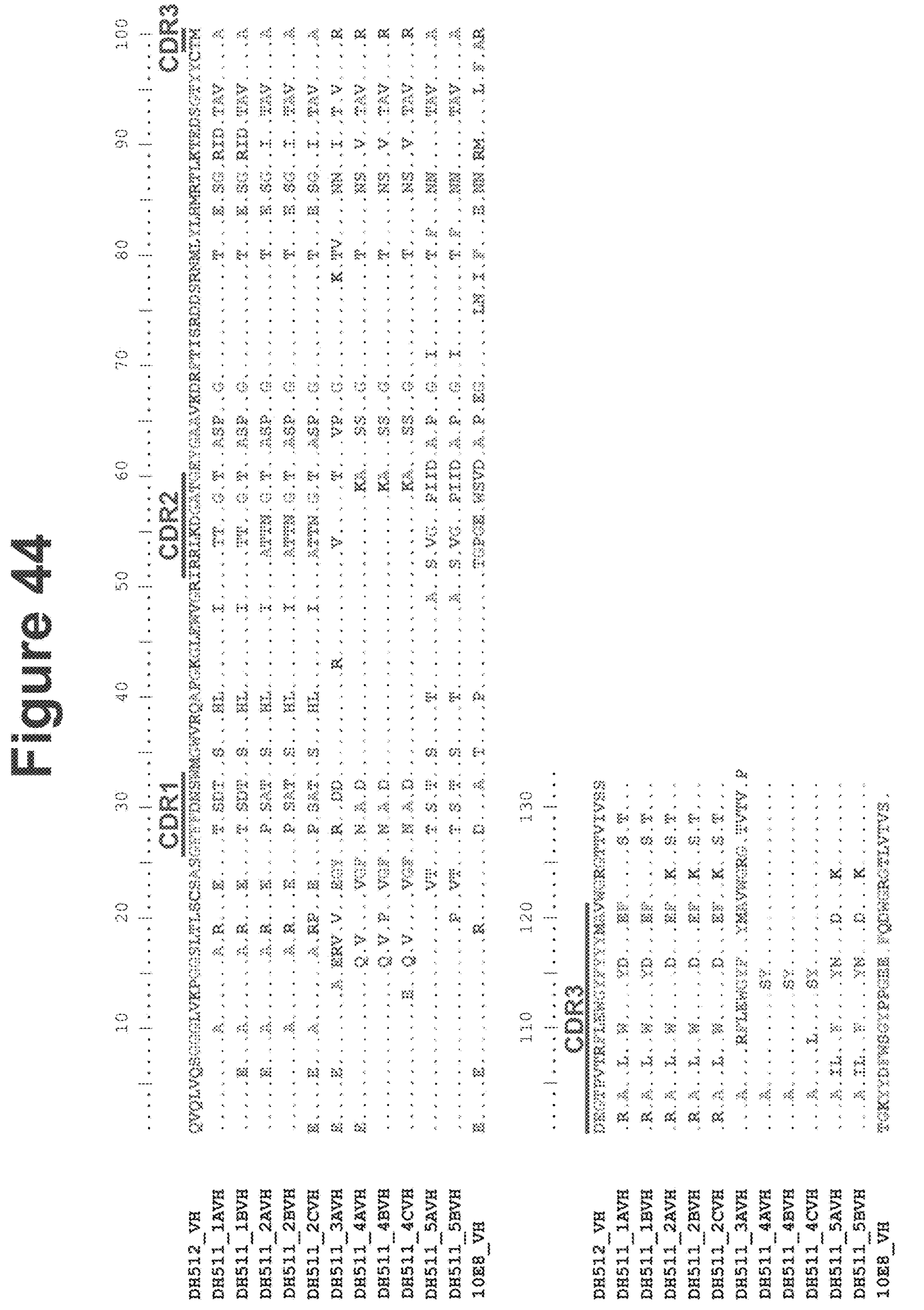
FIG. 44 shows Amino Acid Alignment of MPER Antibody Heavy Chain Sequences (SEQ ID NOs: 230-242).
Figure 45:
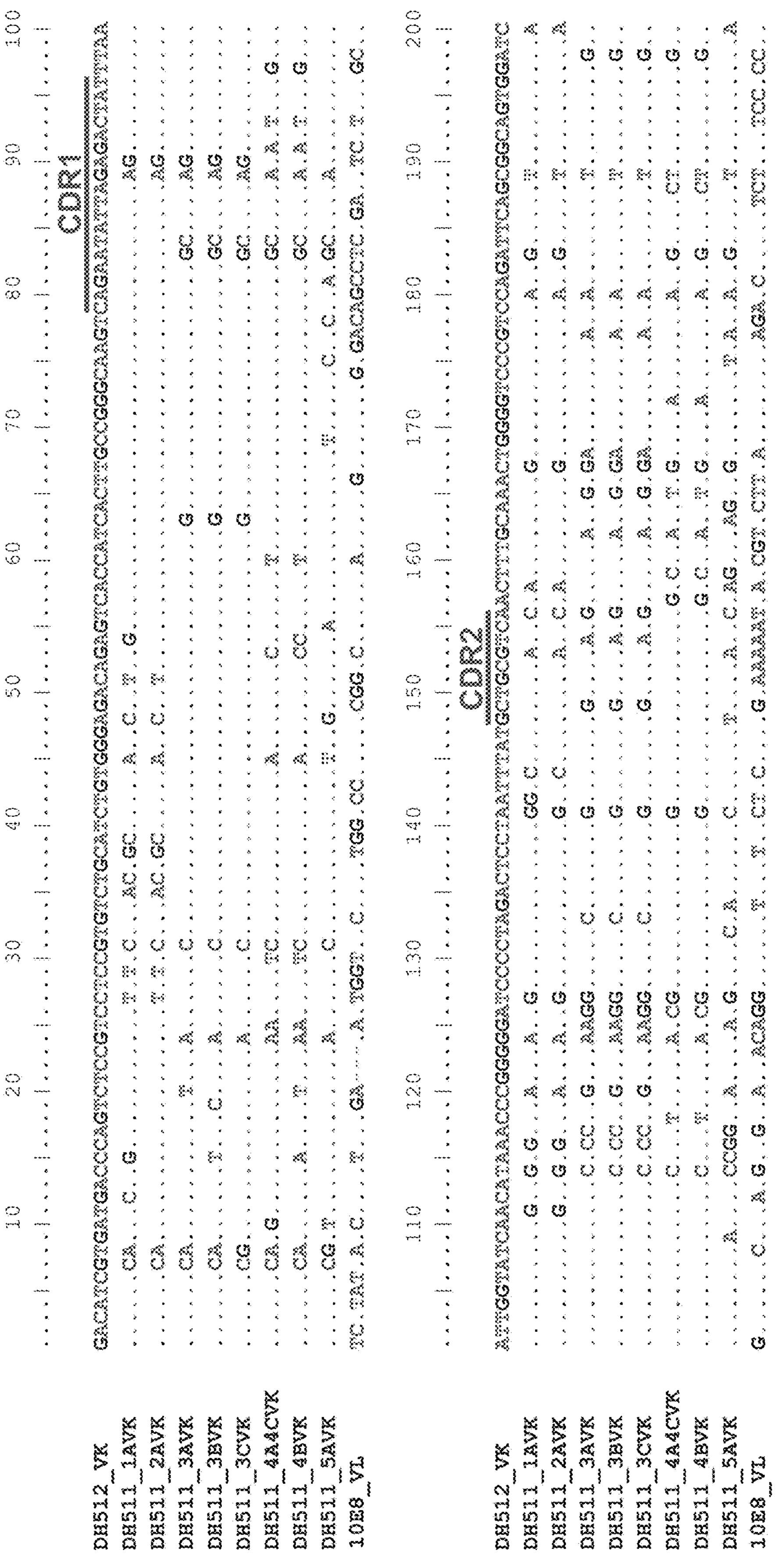
FIG. 45 shows Nucleotide Alignment of MPER Antibody Light Chain Sequences (SEQ ID NOs: 243-252).
Figure 48:
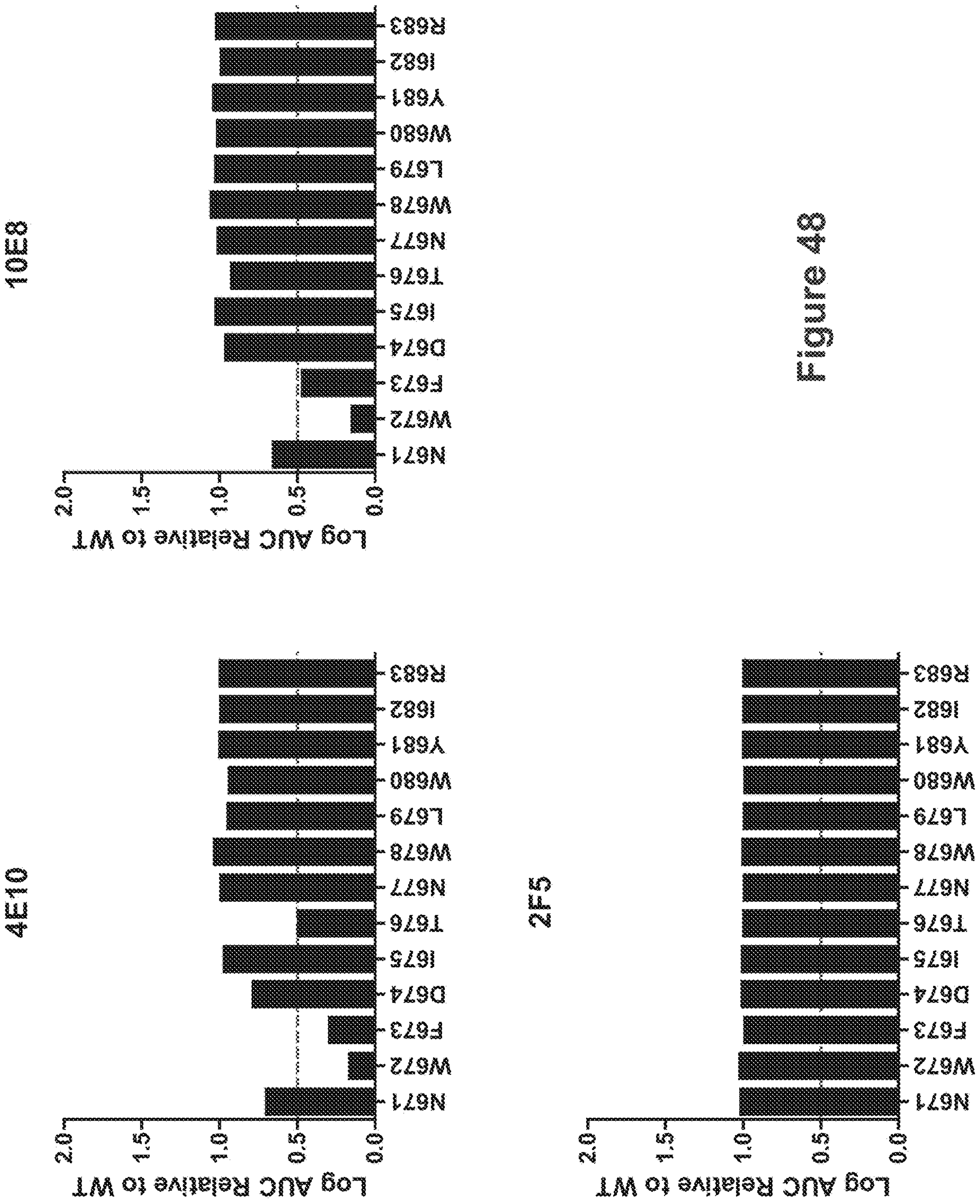
FIG. 48 shows epitope mapping of antibodies of Example 10. Binding to various MPER peptides in an ELISA assay was used to map the epitopes of these MPER antibodies.
Figure 49:
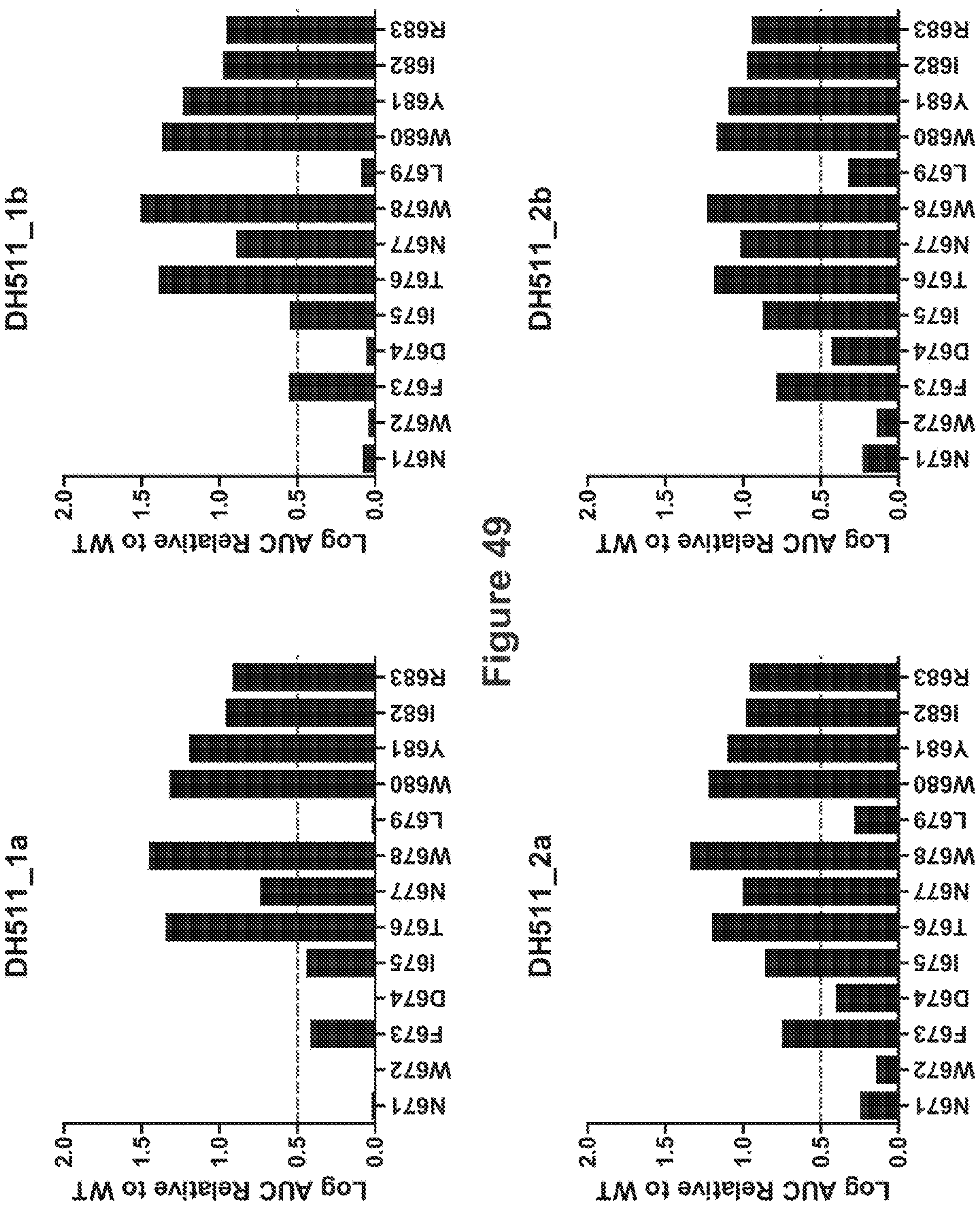
FIG. 49 show epitope mapping of antibodies of Example 10. Binding to various MPER peptides in an ELISA assay was used to map the epitopes of these MPER antibodies.
Figure 50:
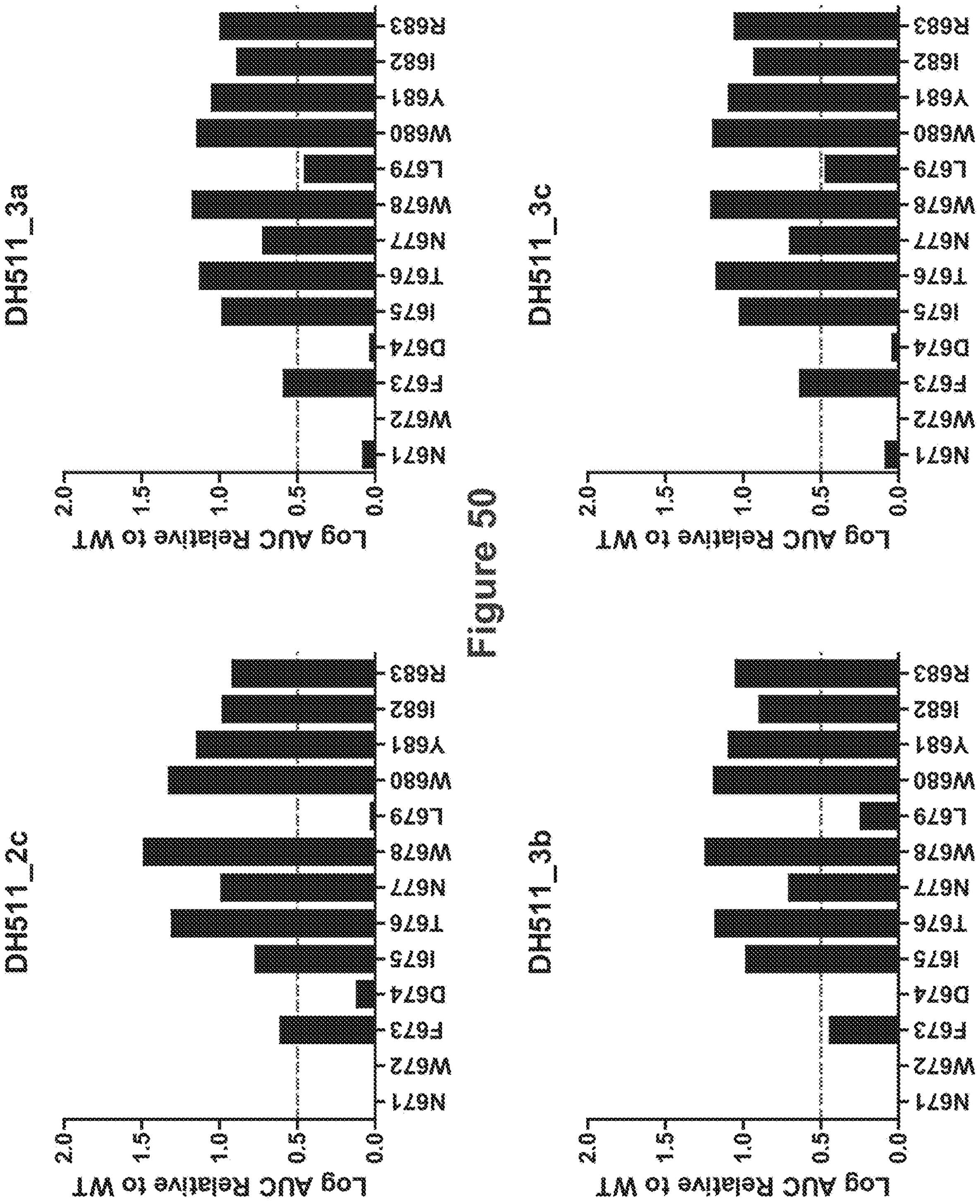
FIG. 50 show epitope mapping of antibodies of Example 10. Binding to various MPER peptides in an ELISA assay was used to map the epitopes of these MPER antibodies.
Figure 51:
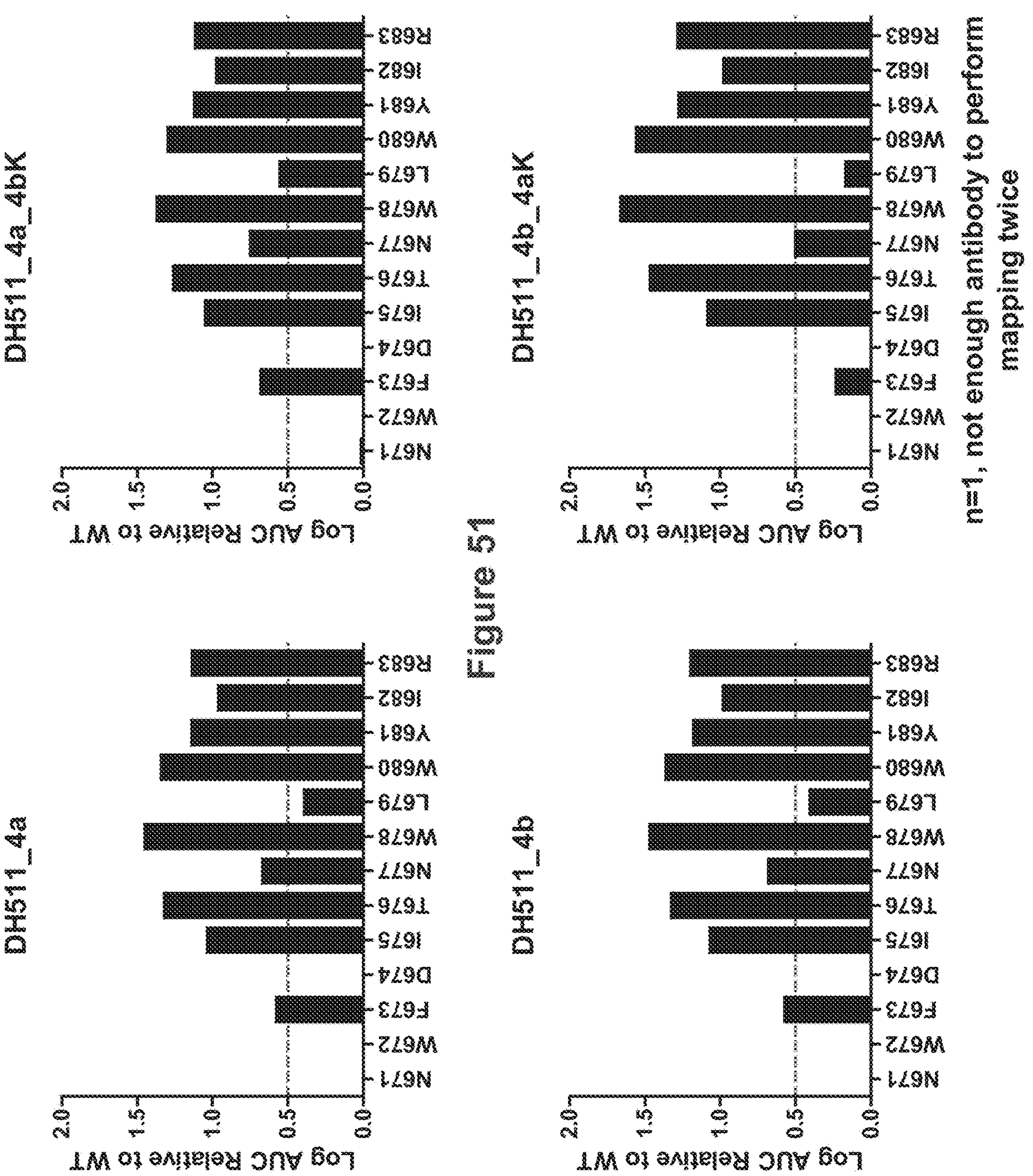
FIG. 51 show epitope mapping of antibodies of Example 10. Binding to various MPER peptides in an ELISA assay was used to map the epitopes of these MPER antibodies.
Figure 52:
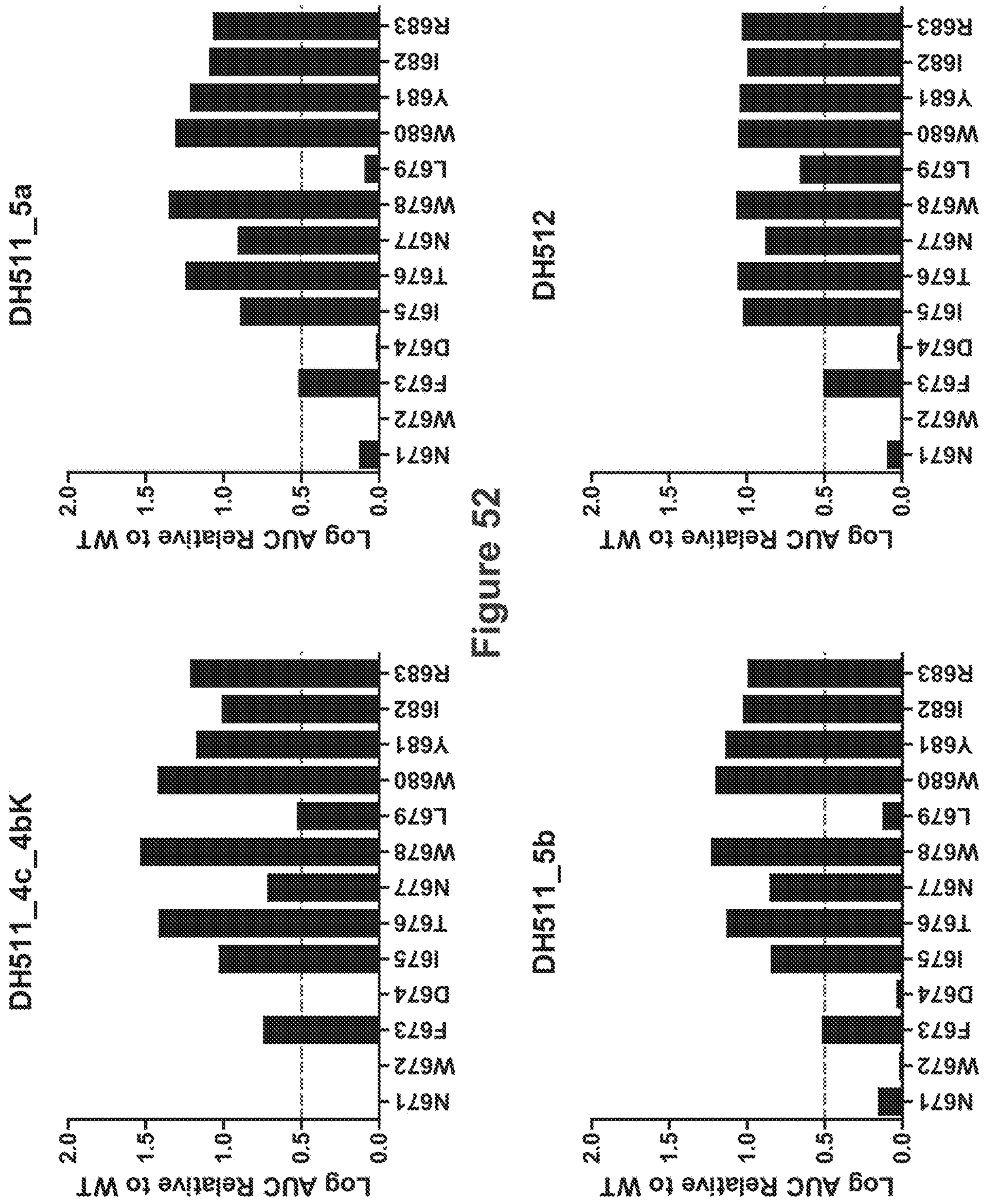
FIG. 52 show epitope mapping of antibodies of Example 10. Binding to various MPER peptides in an ELISA assay was used to map the epitopes of these MPER antibodies.
Figure 53:
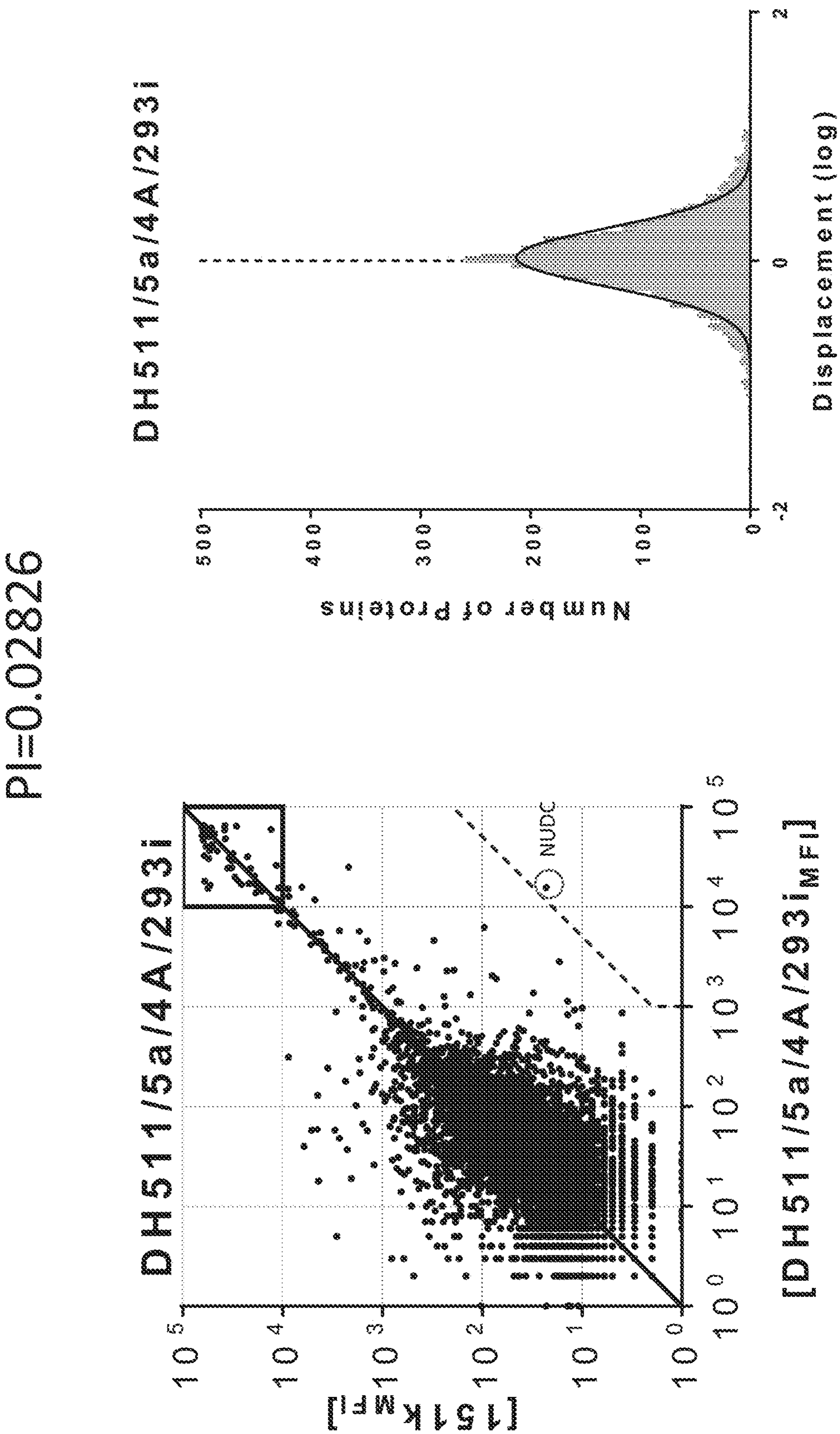
FIG. 53 shows Poly/Autoreactivity analysis of DH511_5a. Antibody DH511_5a appears to be autoreactive with one protein (NUDC).
Figure 54:
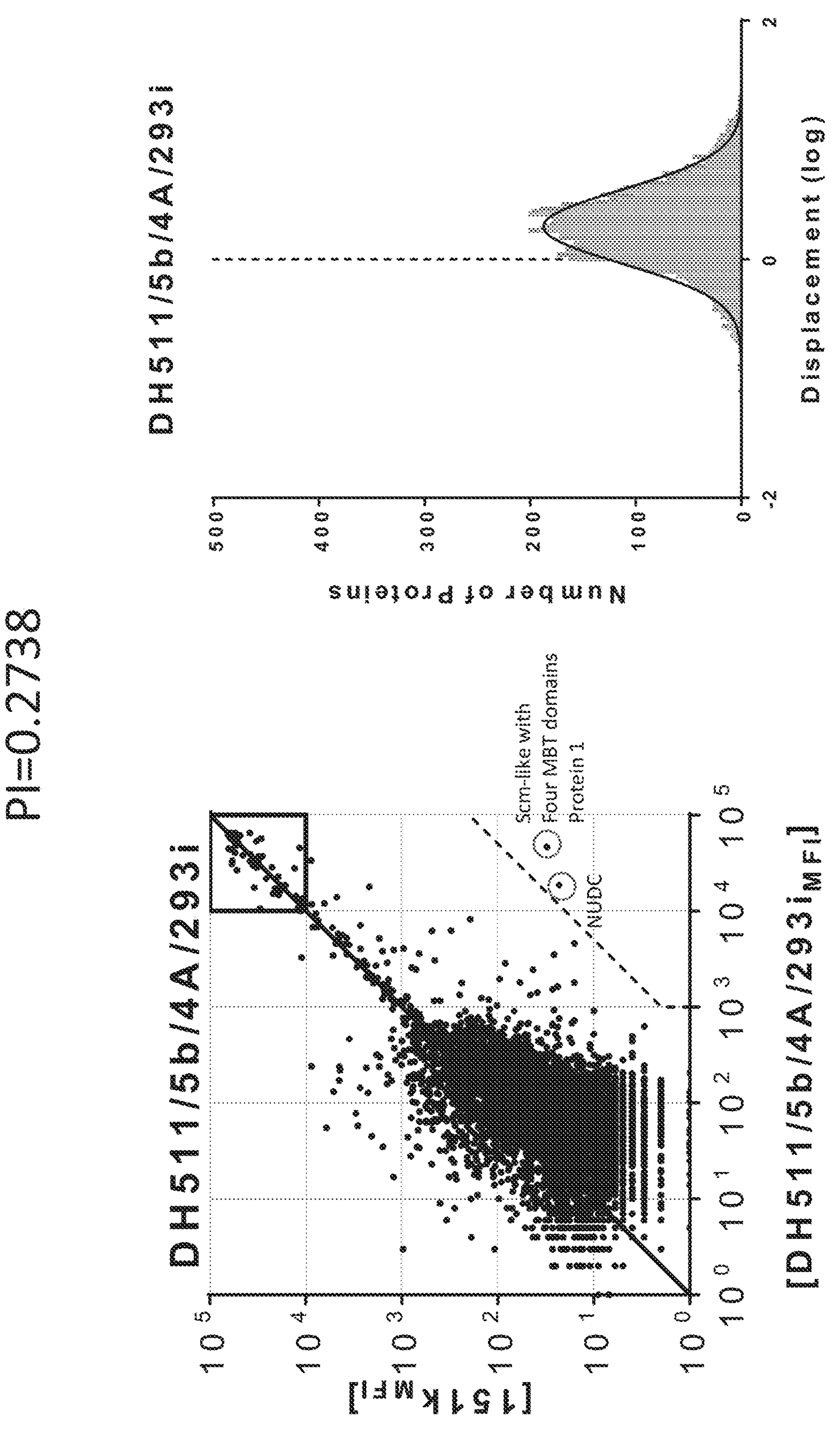
FIG. 54 shows Poly/Autoreactivity analysis of DH511_5b. Antibody DH511_5b appears to be polyreactive.

Additional antibodies were isolated from the individual CH0210 by high-throughput sequencing of the paired human immunoglobulin heavy and light chain repertoire. See FIG. 39. For detailed methods, see DeKosky et al. Nature Biotechnology, 31, 166-169 (2013), and DeKosky et al. Nature Medicine, 21, 86-91 (2015). Briefly B cells were isolated from PBMCs via negative depletion. The heavy and light chain transcripts were co-localized on RNA binding beads, and then physically tied together using overlap extension RT-PCR. The paired VH:VL amplicons were then used to generate 3 libraries for sequencing: a heavy chain database, a light chain database, and a paired database. The necessity for three databases stems from the fact that MiSeq currently limits the forward and reverse reads to ~300 bp each (approximate read lengths are shown below as arrows). As the heavy and light chains are both longer than 300 nucleotides, the full length heavy and full length light chains were sequenced separately and the paired database was used as a key to stitch the heavy and light chains together by matching unique CDR3 sequences.

F(ab)2 fragments were prepared from total serum IgG and subjected to antigen-affinity chromatography using the MPER peptide. Proteins in the elution and flow-through were denatured and reduced, alkylated, trypsin-digested and analyzed by high resolution LC-MS/MS. Spectra were interpreted with the heavy chain database obtained from next-generation sequencing, and peptides uniquely associated with a single CDR ("informative peptides") were used to identify full-length VH sequences. Clonotypes are defined as VH sequences having the same germline V and J and at least 85% aa identity in the CDRH3. To identify the MPER-binding antibodies, the focus was on the clonotypes that contain the identified CDR3 peptides and were highly enriched in the elution. This identified three clonotypes: 137, 335 and 195. All three clonotypes use the same VDJ combination (VH3-15, DH3-3, and JH6), which was also utilized by the DH511 series MPER lineages.

Based on VH sequences it was apparent that the antibodies pulled out by the paired VH:VL sequencing technology were members of the DH511 clonal lineage. Therefore, all of the antibodies are named starting with DH511. The numbers after the underscore correspond to the cluster names that were designated by the VH:VL sequencing. Antibodies were clustered by 96% nucleotide identity in the CDR3.

The above analysis identified additional MPER antibodies listed below:

| PTID | Ab ID | H ID | K/L ID |
|---|---|---|---|
| 704-01-021-0 | DH511_1a_4A | DH511_1AVH_4A | DH511_1AVK |
| 704-01-021-0 | DH511_1b_4A | DH511_1BVH_4A | DH511_1AVK |
| 704-01-021-0 | DH511_2a_4A | DH511_2AVH_4A | DH511_2AVK |
| 704-01-021-0 | DH511_2b_4A | DH511_2BVH 4A | DH511_2AVK |
| 704-01-021-0 | DH511_2c_4A | DH511_2CVH_4A | DH511_2AVK |
| 704-01-021-0 | DH511_3a 4A | DH511_3AVH_4A | DH511_3AVK |
| 704-01-021-0 | DH511_3b_4A | DH511_3AVH_4A | DH511_3BVK |
| 704-01-021-0 | DH511_3c_4A | DH511_3AVH_4A | DH511_3CVK |
| 704-01-021-0 | DH511_4a_4A | DH511_4AVH_4A | DH511_4A4CVK |
| 704-01-021-0 | DH511_4a_4bK_4A | DH511_4AVH_4A | DH511_4BVK |
| 704-01-021-0 | DH511_4b_4aK_4A | DH511_4BVH_4A | DH511_4A4CVK |
| 704-01-021-0 | DH511_4b_4A | DH511_4BVH 4A | DH511_4BVK |
| 704-01-021-0 | DH511_4c_4A | DH511_4CVH_4A | DH511_4A4CVK |
| 704-01-021-0 | DH511_4c_4bK_4A | DH511_4CVH_4A | DH511_4BVK |
| 704-01-021-0 | DH511_5a_4A | DH511_5AVH_4A | DH511_5AVK |
| 704-01-021-0 | DH511_5b_4A | DH511_5BVH_4A | DH511_5AVK |

VH and VL genes were selected and made in linear cassettes (essentially as described in Liao H X et al. J. Virol. Methods 158: 171-9, 2009, see for example FIG. 1, Section 3.3) to produce recombinant monoclonal antibodies by transient transfection in 293T cells. See also Example 1 for variations in the backbone.

Example 11: Heavy and Light Chain Chimeric Antibodies; Antibodies with Changes in the Amino Acids of the VH Chain This example describes chimeric antibodies comprising non-natural VH and VL chain pairs. Naturally occurring VH or VL chain are combined in non-natural pairs as described in FIG. 55, chimeras 1-91.

Chimeras 1-91 were recombinantly expressed and their neutralization profile was determined in the TZMB1 assay (FIG. 56). Based on neutralization data for chimeras 68-91 as shown in FIG. 56, three antibodies DH512_K2_4A (VH: H510049_4A (DH512) and VL: DH511_1AVK), DH512_K3_4A (VH: H510049_4A (DH512) and VL: DH511_2AVK) and DH512_K4_4A (VH: H510049_4A (DH512) and VL: DH511_5AVK) antibodies were produced large scale and will be tested for neutralization against a larger panel of viruses (see panels for DU512).

The invention contemplates antibodies which comprise amino acid changes, or combination of such changes, in the VH chains of antibodies form the DH511 lineage. Non-limiting examples of antibodies with mutations are provided in FIGS. 30-33, or any combination thereof. Most mutations are to changes to W, but can also try F, L or possibly other substitutions, e.g. without limitation I, V, A. Additional mutations include without limitation the following: T100aF; T100aL; T100aI; T100aV; T100aA; L100dW, or any combination thereof.

In some embodiment, such double mutants: T100aW-L100dF; T100aW-L100dW; T100aF-L100dF; T100aL-L100dF; T100aL-L100dW.

Neutralization data for a subset of these antibodies is provided in FIG. 34. The data show that some of the mutations abrogate neutralization while others enhance potency. One candidate, DH512 L100dF_4A, is more potent than 10E8 and has similar potency to DH512_K3.

In some embodiments, L100d could be changed to Trp. Data in FIGS. 34 and 80 show that single mutant L100dF, and single mutant T100aW have improved neutralization. These single mutants will be tested against a panel of additional viruses (see panel for DH512, DH512_K3).

Contemplated are also combination mutations, for example but not limited combination T100aW with L100dF, combination L100dW with T100aW.

Mutated VH chain as contemplated above could be combined with VH chain from DH512, or with VH chain from DH512_K3 (DH511_2AVK).

Example 12: Shared Memory and Plasma Repertoires of HIV-1 Neutralizing Antibodies Shared Memory and Plasma Repertoires of HIV-1 Neutralizing Antibodies Understanding the relationship of the memory B cell and plasma immunoglobulin repertoires of HIV-1-infected individuals who develop broadly neutralizing antibodies (bnAbs) is important, since plasma antibody responses are required to achieve maximum protection from infectious agents. Using HIV-1 envelope gp41 membrane-proximal external region (MPER)-specific memory B cell sorting and next-generation sequencing, coupled with mass spectrometry analysis of plasma antibodies, we probed the memory B cell and plasma antibody repertoires of an HIV-1-infected donor with a plasma bnAb signature that mapped to Env gp41 distal MPER. We found potent IgG bnAbs from the same B cell clonal lineage in memory B cells and plasma that neutralized 99% of HIV-1 isolates. Structural analysis demonstrated clonal lineage antibodies from memory B cells and plasma both recognized the envelope gp41 epitope identically in an alpha helical conformation. Thus, a major source of potentially protective plasma HIV-1 bnAbs is the memory B cell pool.

Introduction

Inducing broadly reactive neutralizing antibodies (bnAbs) is critical for developing a protective HIV-1 vaccine. Some of the broadest bnAbs isolated are to the envelope gp41 membrane proximal external region (MPER), with two of these, 10E8 and 4E10, the most broad (1, 2). Monoclonal antibody (mAb) 4E10, while extremely broad in neutralization breadth, is not potent, and is highly polyreactive with many non-HIV-1 proteins and autoreactive with the human protein splicing factor 3b subunit 3 (SF3B3) (3) as well as with lipids (4). In contrast, mAb 10E8 is not as polyreactive as 4E10, and is both more broad and potent (1), although it does have a degree of lipid reactivity (5) and is autoreactive with the host protein family of sequence similarity 84 member A (FAM84A) (6).

To date, all HIV-1 broadly neutralizing antibodies have been isolated from memory B cells, either with clonal memory B cell cultures or using fluorophore-labeled Env and flow cytometry cell sorting. However, most correlates of protection for infectious agents with successful vaccines are the levels of plasma neutralizing antibodies. Moreover, the correlate of decreased transmission risk in the only HIV-1 vaccine trial to demonstrate a degree of efficacy was plasma antibodies to the second variable loop (V2) region (7).

In HIV-1 infection, 60% of HIV-1-specific antibodies derive from abnormal B cell subsets, that are either activated or exhausted and express Fc receptor-like-4 (FcRL4) (8, 9). However, many of the antibodies reflected in HIV-1 memory B cells are not expressed in plasma (8). Similarly, many of the memory B cell specificities of antibodies in other settings are also not represented in plasma (10-12). Thus, it is not known if envelope-reactive memory B cells with bnAb B cell receptors are a major source of plasma broad neutralizing activity.

Here we have isolated memory B cell and plasma broad and potent envelope gp41 bnAbs from an African donor and demonstrated broad and potent plasma gp41 bnAbs to be in the same B cell clonal lineage as those isolated from memory B cells. Chimeric antibodies consisting of memory bnAb $V_H$ and plasma bnAb $V_L$ as well as engineering memory bnAb heavy chain complementary determining regions yield antibodies with greater potency than naturally paired antibodies. Thus, the class-switched memory B cell pool contributes to plasma bnAbs.

Results

Isolation of Memory B Cell gp41 Neutralizing Antibodies

Figure 59A:
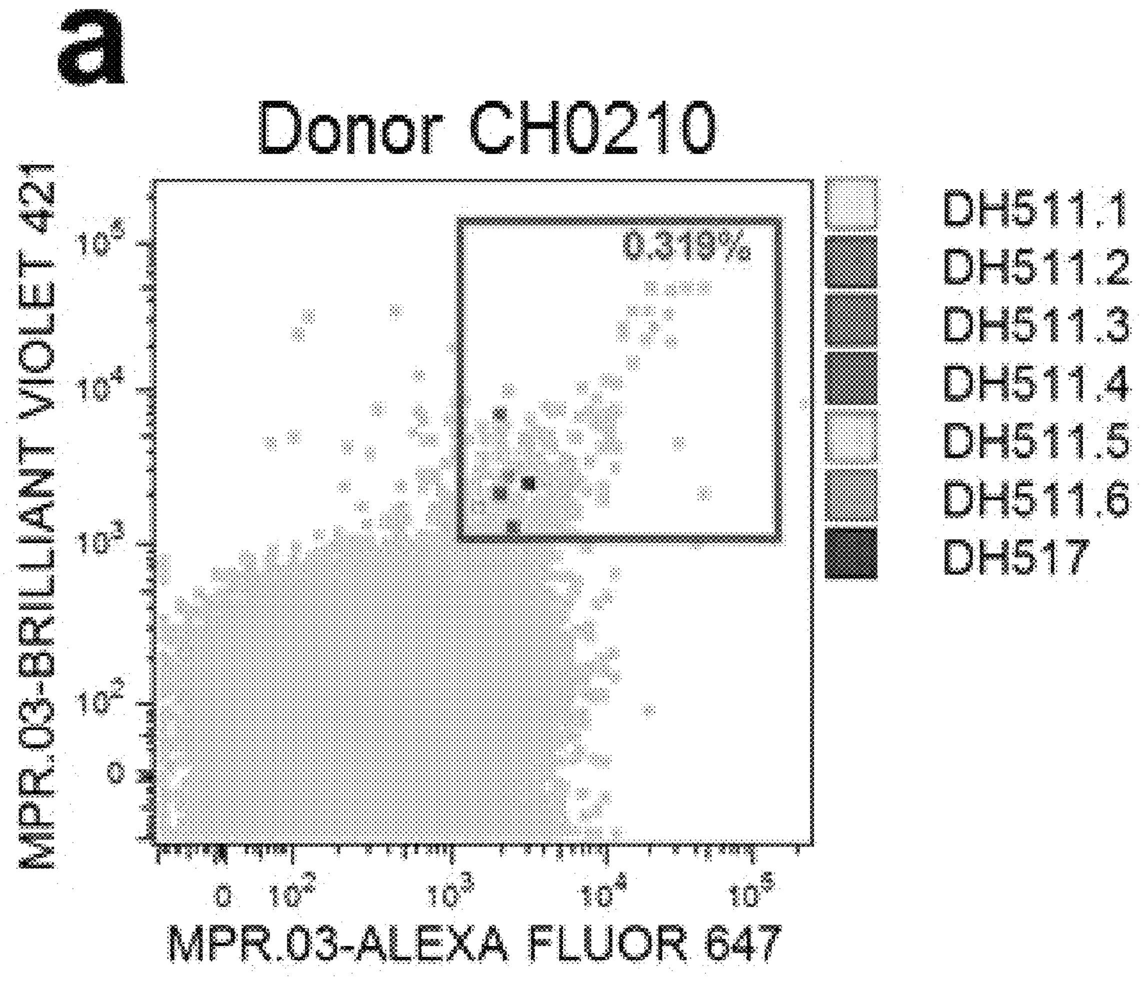
Figure 59B:
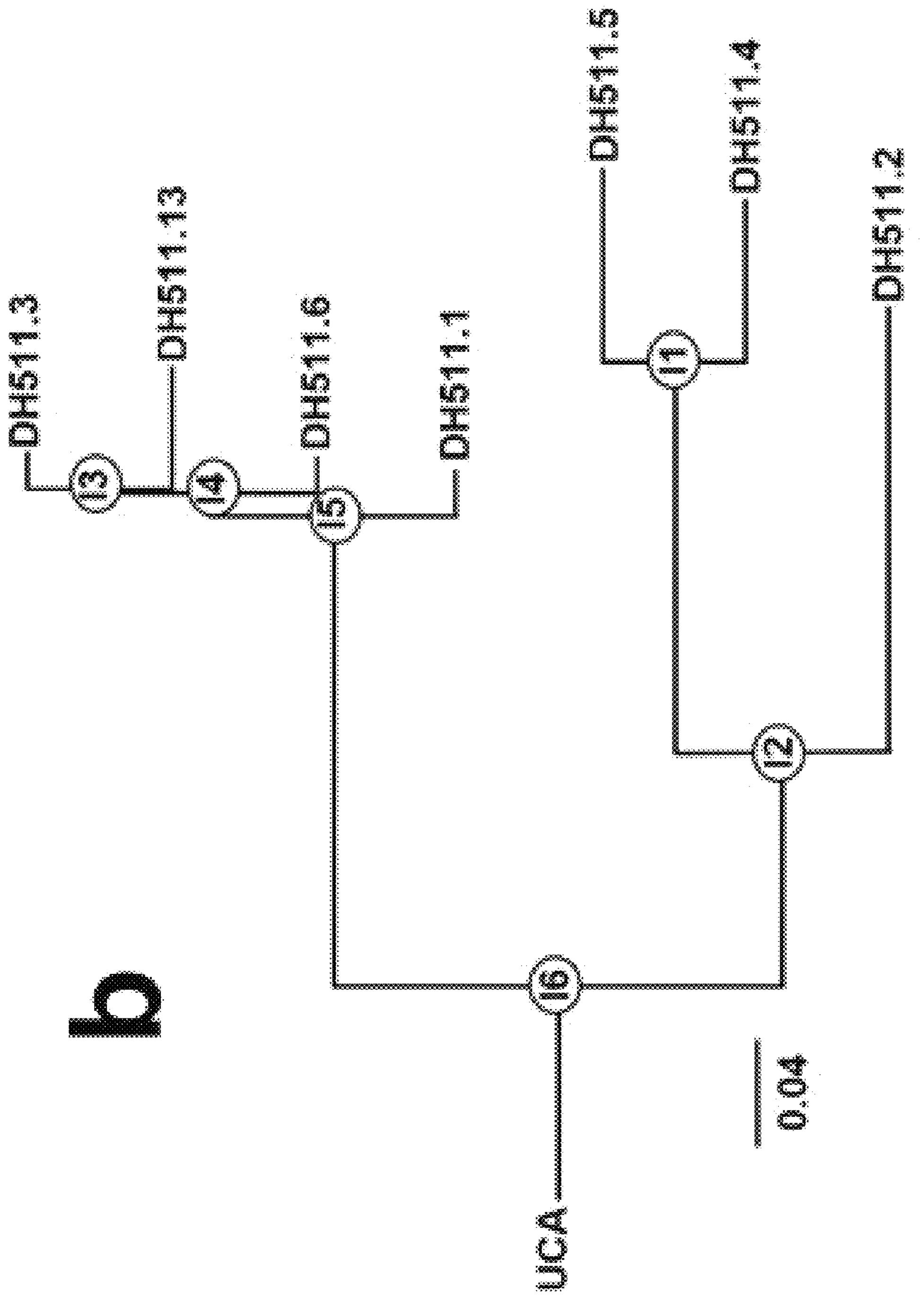
Figure 62C:
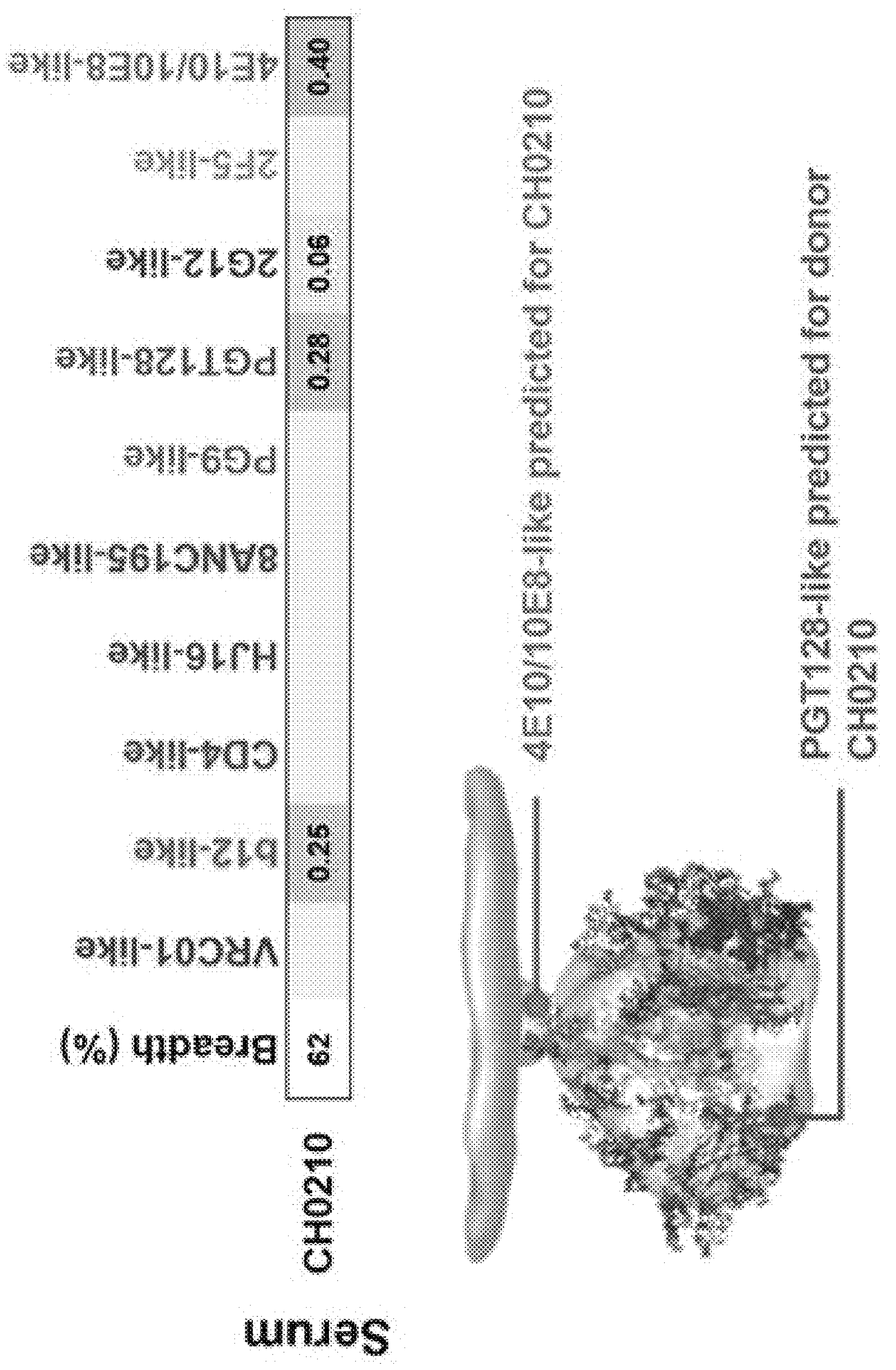

Neutralization-based epitope prediction analysis revealed that plasma from HIV-1 clade C-infected individual CH0210 contained C-terminal MPER bnAb activity (13) (FIG. 62). Six clonally-related mAbs, designated DH511.1-DH511.6, were isolated by antigen-specific single memory B cell sorting using MPER peptide fluorophore-labeled probes (14) (FIG. 59*a*, 59*b*, and Supplementary Table 1). The DH511 B cell clonal lineage was distinguished by HCDR3 loops of 24 amino acids in DH511.1, DH511.3, and DH511.6, while DH511.2, DH511.4, and DH511.5 antibodies had a one amino acid deletion in the HCDR3, resulting in a length of 23 amino acids (Supplementary Table 1). $V_H$ and $V_L$ somatic mutation rates were 15-22% and 14-18%, respectively. The DH511 clonal lineage was derived from the same heavy-chain germ line gene as previously isolated gp41 neutralizing antibody 10E8 ($V_H$3-15), but utilized a different $V_L$ germ line gene (DH511: $V_K$1-39, 10E8: $V_L$3-19) (1) (Supplementary Table 1). Antibody DH517, derived from a second clonal lineage arising from the same donor, was similarly isolated. DH517 utilized $V_H$ 4-34 and $V_L$3-19 germ line genes, was 22.8% and 14.3% mutated, respectively, and had a long HCDR3 comprised of 24 amino acids.

Figure 59D:
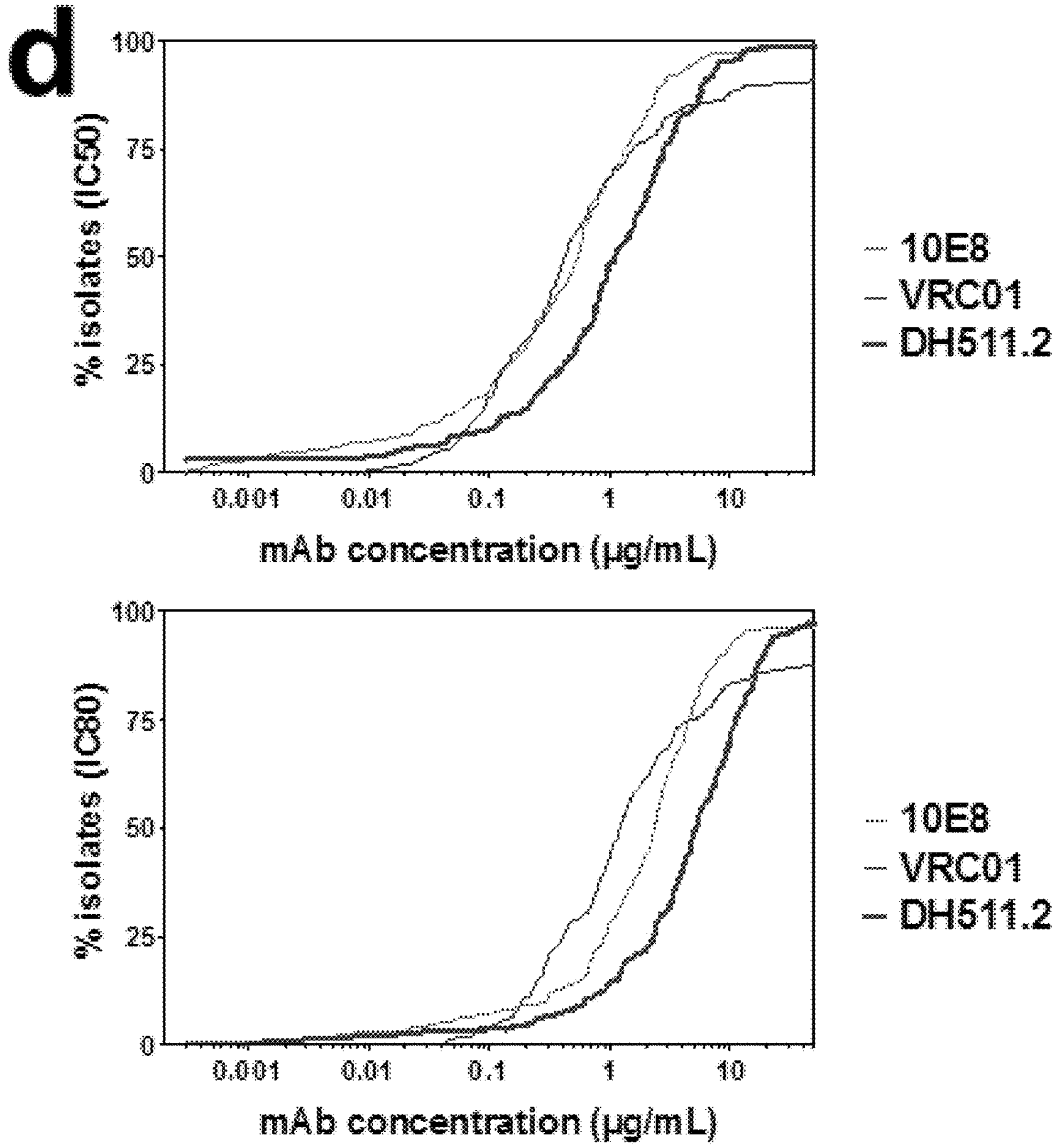
Figure 59E:
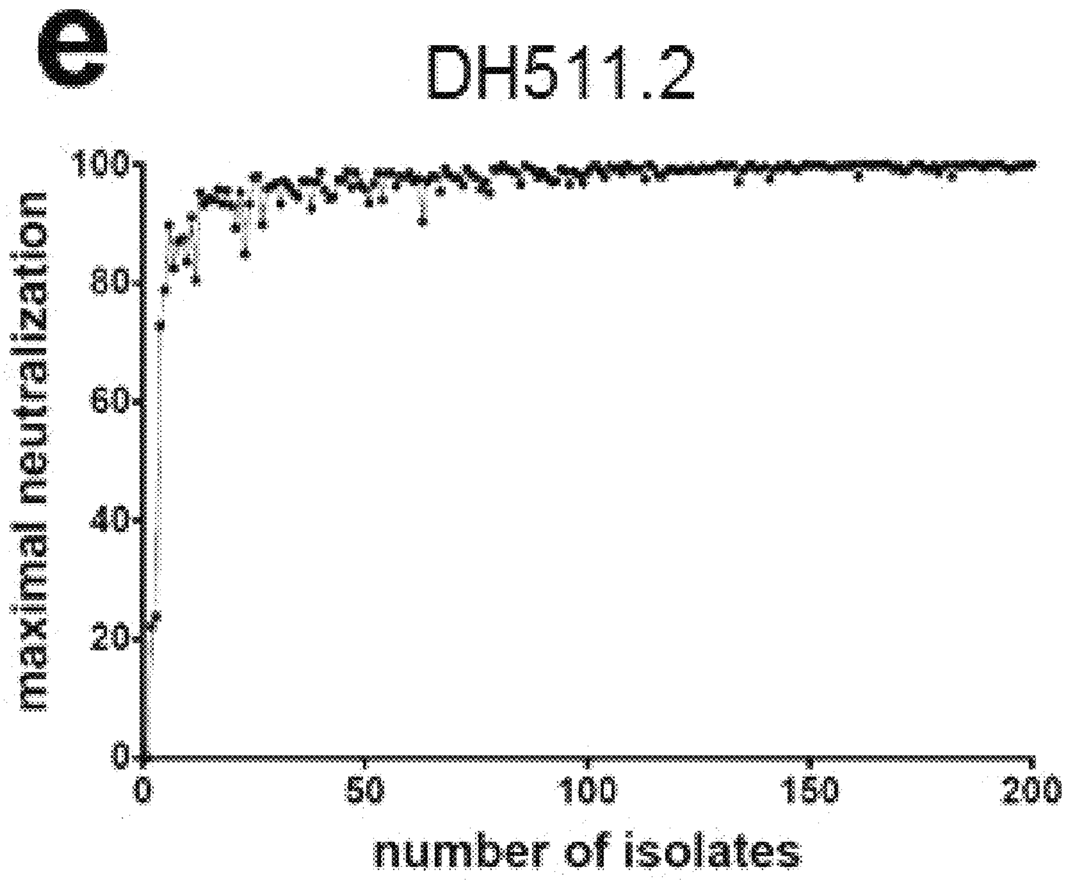

DH511.1-DH511.6 and DH517 mAbs were assessed for neutralization breadth and potency against a panel of 30 cross-clade HIV-1 isolates. All six DH511 clonal members neutralized 30 of 30 isolates tested with median 50% inhibitory concentrations ($IC_{50}$) ranging from 0.7 to 4.2 μg/ml (Supplementary Table 2a). DH517 had less breadth than DH511 clone antibodies, neutralizing 15 of 30 isolates with a median $IC_{50}$ of 5.7 μg/ml (Supplementary Table 2a). The most potent DH511 clone bnAb (DH511.2) in a large cross-clade panel of 199 geographically and genetically diverse HIV-1 Env pseudoviruses, neutralized 197/199 (99%) viruses but was less potent than 10E8 (195/200, 98%) (median $IC_{50}$, DH511.2=1.1 μg/ml and 10E8=0.4 μg/ml) (FIG. 59*c*, 59*d*, and Supplementary Table 3). Neutralization curves revealed that DH511.2 achieved >99% maximal neutralization for 93% of the isolates (FIG. 59*e*), and showed similar potency and breadth of neutralization against a second panel of 200 clade C primary HIV-1 isolates (Supplementary Table 4).

Isolation of Plasma Gp41 Neutralizing Antibodies

We next analyzed the MPER-specific plasma antibody repertoire from donor CH0210 using an independent proteomics-based approach for the identification and semi-quantitative determination of antigen-specific antibodies in human serum (15, 16). MPER-specific antibodies were isolated from a 2 ml plasma sample by affinity chromatography, processed for proteomics (10) and subjected to liquid chromatography high-resolution tandem mass spectrometry (LC-MS/MS) analysis. For peptide identification, a donor-specific VH database comprising 98,413 unique high quality sequences was derived from a natively paired $V_H$:$V_L$ repertoire from 845,000 peripheral single B cells from total PBMCs (isolated using MACS negative selection: $CD2^-$ $CD14^-CD16^-CD43^-CD235a^-$) (17-19). These $V_H$ sequences were then clustered into 4,428 clonotypes, using a cut-off of ≥85% amino acid identity in the HCDR3 region.

Using stringent data filtering protocols (10), high confidence peptide-spectrum matches (PSMs) from HCDR3 peptides were identified and their respective LC peak intensities were used for relative quantification. As we have shown previously, an estimated >80% of all HCDR3 peptides within a sample are typically identified in this manner (detection limit approximately 0.4 ng/ml), and peak intensities correlate well with absolute peptide concentrations (10, 15). Plasma Ig clonotypes were defined as VH sequences having the same germline V and J and 85% aa identity in the HCDR3.

Figure 59F:
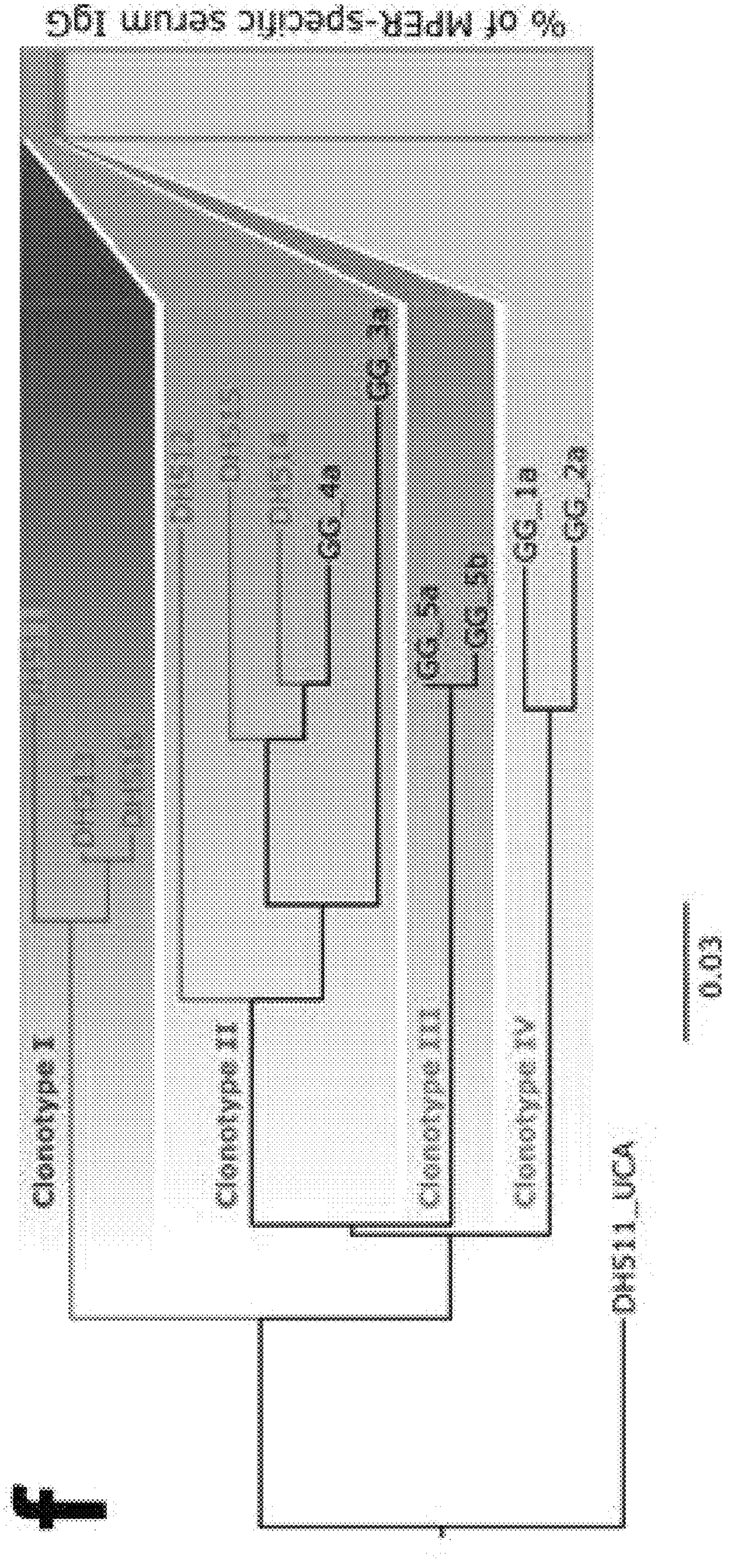
Figure 63A:
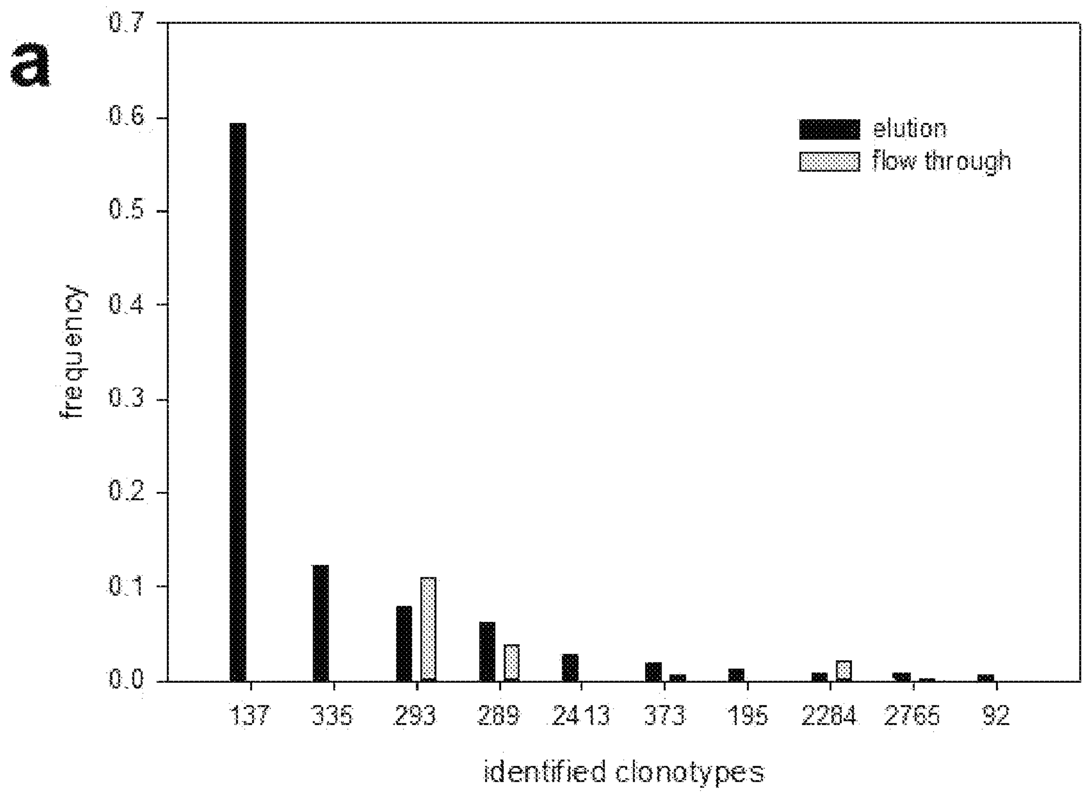
Figure 64:
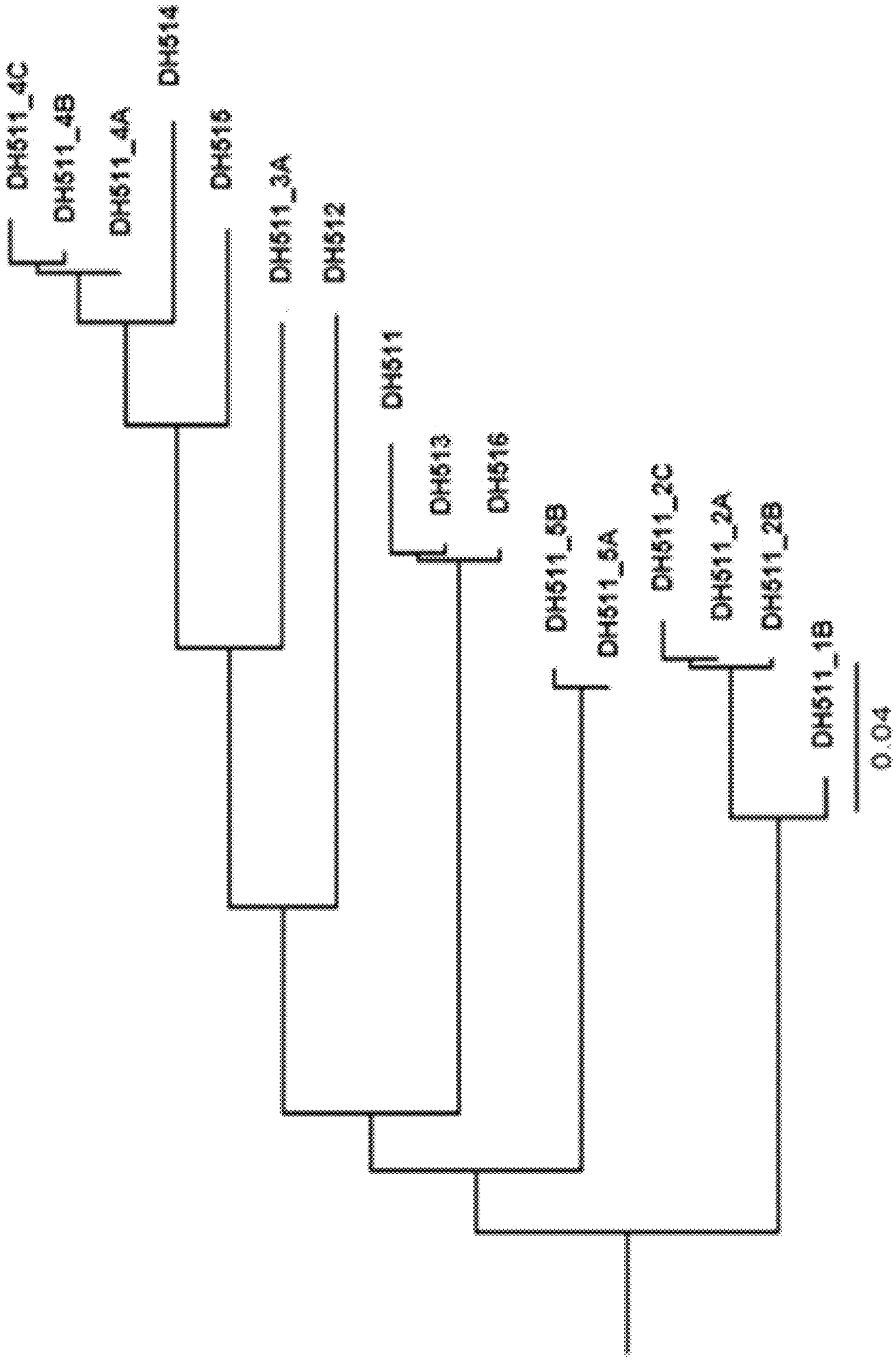
FIG. 64 shows Phylogenetic tree of VHDHJH sequences of memory B cell and plasma-derived DH511 clonal lineage members.
Figure 65A:
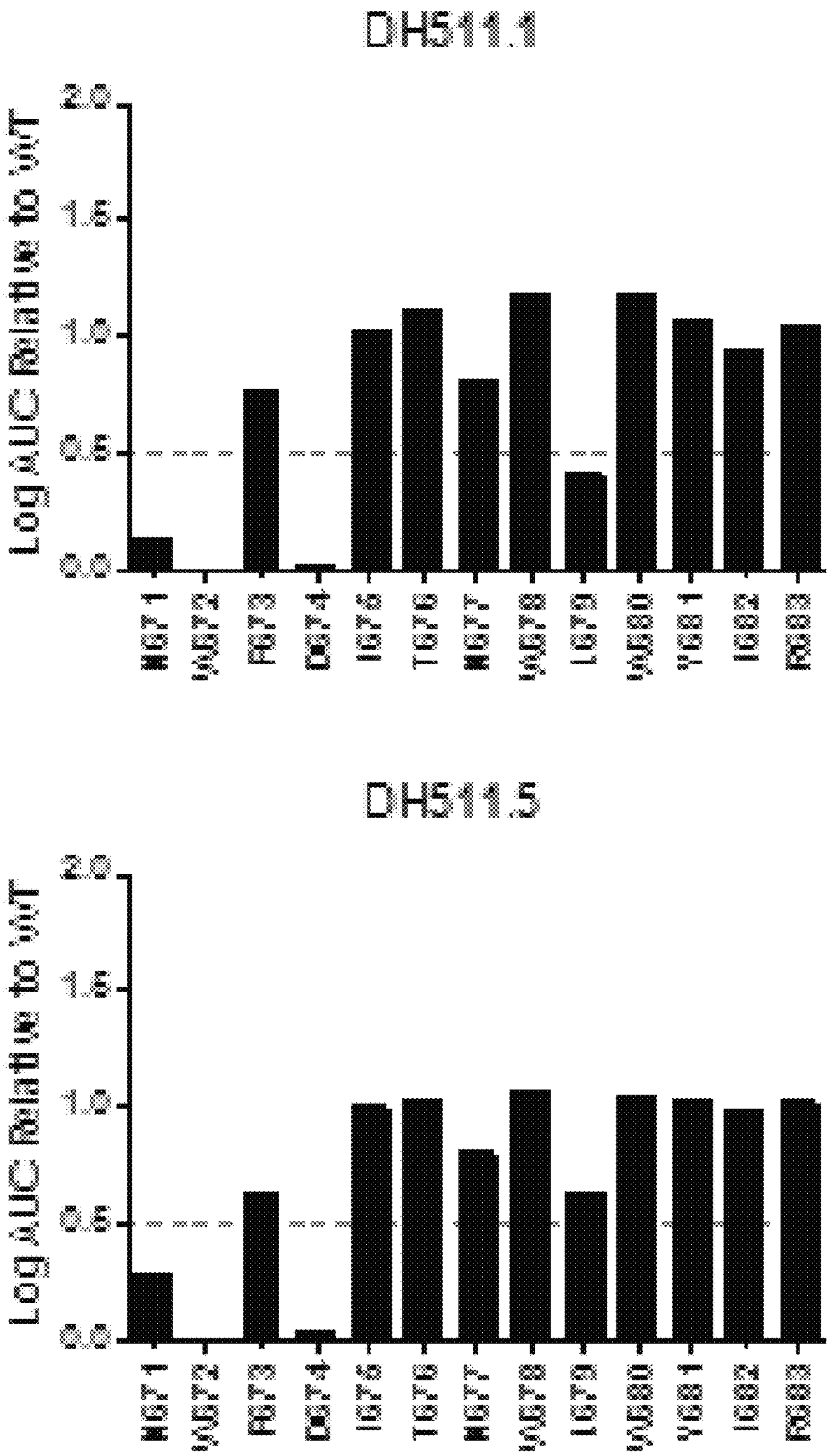
FIGS. 65A and 65B show Epitope mapping by alanine scanning mutagenesis of C-terminal MPER residues. Values listed are mean measurements from two independent experiments. Epitope residues were defined as residues where log AUC relative to wild-type (WT) for alanine mutations was reduced by 50%.
Figure 65B:
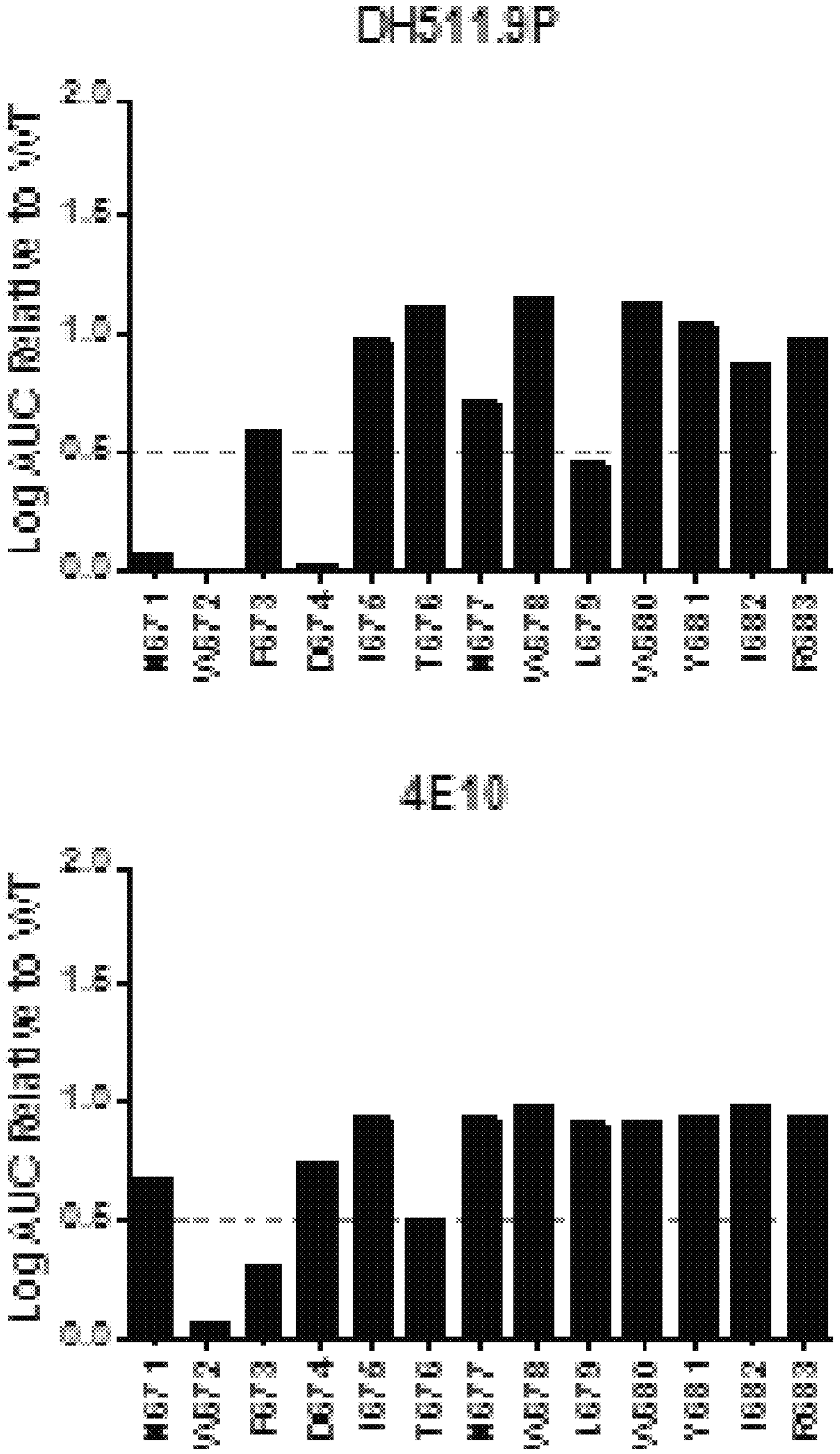
Figure 65B:
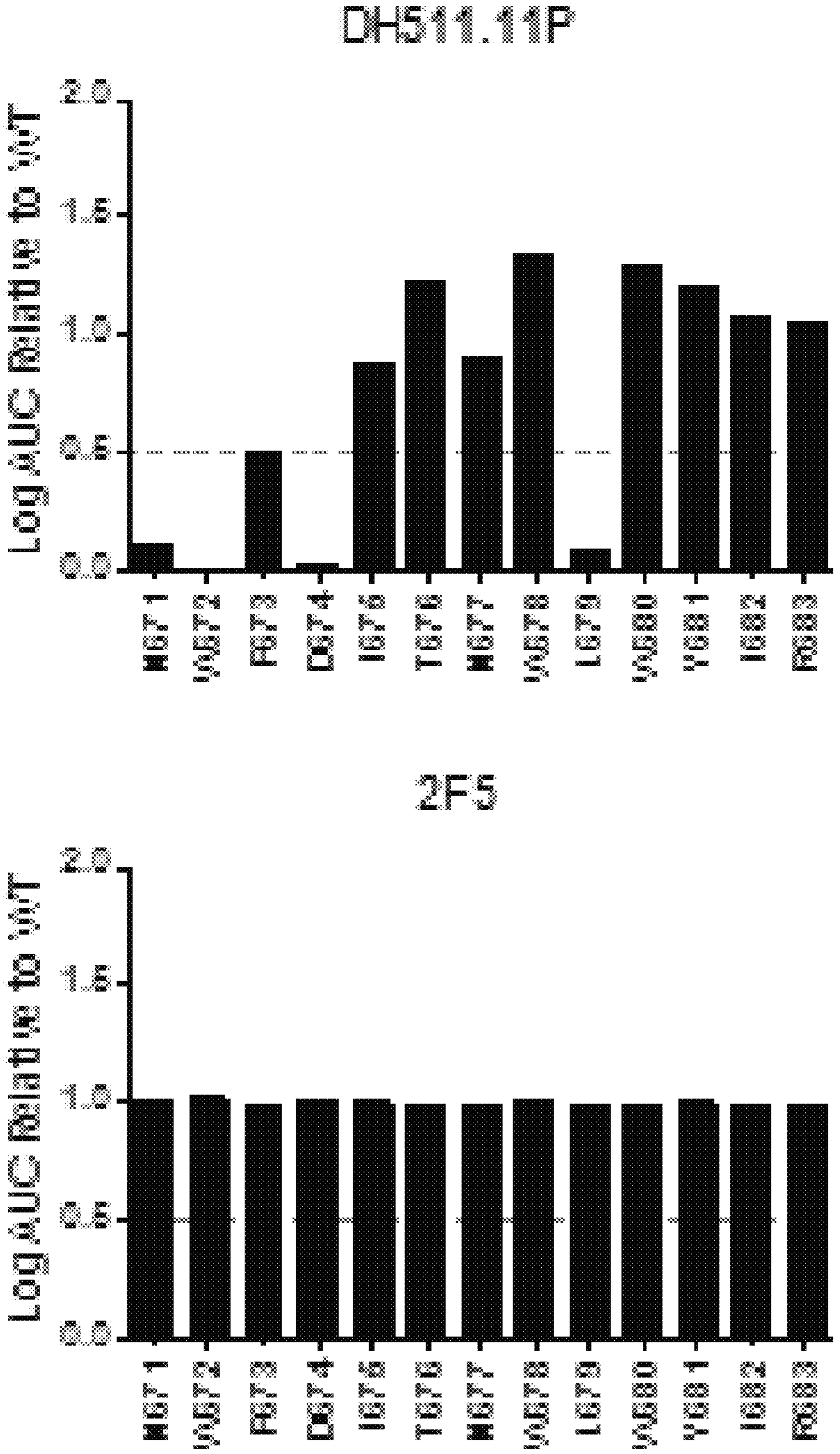
Figure 65B:
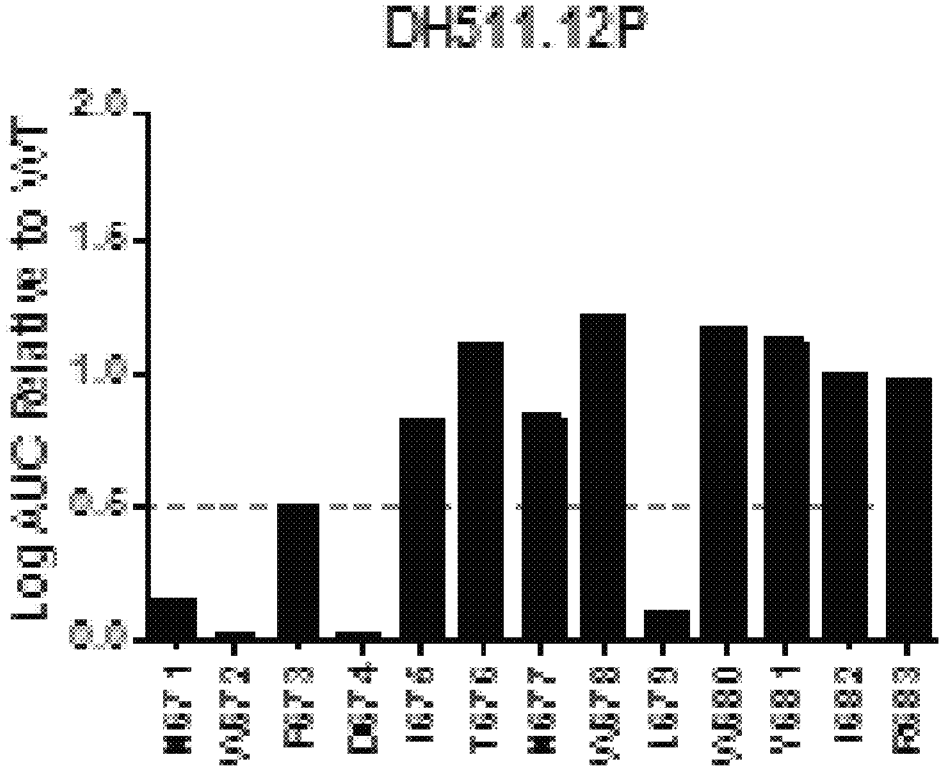

We found that the MPER-specific plasma antibody repertoire consisted of 10 clonotypes, three of which used the same VDJ combination ($V_H$3-15, $D_H$3-3, $J_H$6) as the DH511 clonal lineage (FIG. 63). Clonotype IV comprised 95% of the total intensity of HCDR3 peptides detected in the MPER-specific antibody repertoire (i.e. in antibodies eluted following affinity chromatography with immobilized MPR.03 peptide); we noted that detection of HCDR1 and HCDR2 peptides unique to Clonotype IV provided further unambiguous support for the prevalence of these antibodies in the CH0210 plasma (FIG. 59*f*). Clonotype II, which included antibodies DH511.2, DH511.4 and DH511.5 isolated by single-cell sorting, and Clonotype III were detected at 4% and 1% relative abundancy, respectively (FIG. 59*f*). All three HCDR3 clonotypes utilized the same VDJ genes ($V_H$3-15, $D_H$3-3 and $J_H$6), displayed similar HCDR3 lengths of 23-24 amino acids and $V_H$ gene mutation rates of 15-20% (Supplementary Table 6). Whereas 11 VH DH511 clonal lineage members were found by mass spectrometry (Supplementary Table 6, FIG. 64), the phylogram was collapsed to represent the most prevalent members (FIG. 59*f*). It is noteworthy that Clonotype I (FIG. 59*g*), that includes DH511.1, DH511.3 and DH511.6, was isolated by memory B cell sorting but was not detected in the plasma; we validated that recombinant DH511.1, DH511.3 and DH511.6 antibodies were readily detectable by mass spectrometry, indicating that their absence from the CH0210 plasma was not a technical artifact.

Using the proteomically identified HCDR3 sequences, we searched the native $V_H$:$V_L$ sequence database comprising ~200,000 heavy-light chain pairs from single B cells to determine the respective full-length light-chain sequence belonging to each clonotype (Supplementary Table 6). For clonotypes in which multiple $V_H$:$V_L$ somatic variants were detected, only the two most frequent variants, as quantified by the number of sequencing reads, were selected for expression and characterization (Supplementary Table 6). The light-chains belonging to these three clonotypes all shared the same V- and J-gene identity (IGKV1-39, IGKJ2) as the light-chains of the DH511 clonal lineage isolated by memory B cell single-cell sorting. Six plasma mAbs belonging to the DH511 clonal lineage (designated DH511.7P-DH511.12P), showed potent tier 2 neutralizing activity against a panel of four HIV-1 isolates (Supplementary Table 7), with mAbs DH511.11P and DH511.12P demonstrating the most potent neutralizing activity. DH511.11P and DH511.12P were selected for further characterization of their neutralization breadth and potency against a panel of 203 cross-clade isolates and had slightly more breadth (99.5% of isolates tested) and greater potency than memory B cell-derived DH511.2 but were less potent than 10E8 (median $IC_{50}$: 0.7 μg/ml for DH511.11P and DH511.12P versus 0.4 μg/ml for 10E8) (Supplementary Table 8).

Structural Analysis of DH511 Lineage Antibodies

We used a panel of alanine substituted MPER peptides that span gp41 residues 671-683 (Supplementary Table 9) to define the epitopes of DH511.1-DH511.12P by enzyme linked immunosorbent assay (ELISA). Similar to the epitopes of 4E10 and 10E8 (1), DH511.1-DH511.12P binding was sensitive to alanine mutations at $Asn671_{gp41}$ and $Trp672_{gp41}$, but unlike 4E10 and 10E8, was also sensitive to $Asp674Ala_{gp41}$, and to a lesser extent $Leu679Ala_{gp41}$ mutations (FIG. 63). Assessment of the neutralization activity of DH511.1-DH511.12P (not DH511.7-DH511.10) mAbs against clade C COT6.15 Env pseudoviruses bearing alanine substitutions across the MPER (20, 21) (Supplementary Table 10) demonstrated sensitivity of neutralization to Env mutations of $Phe673Ala_{gp41}$, $Asp674Ala_{gp41}$, and $Asp674Ser_{gp41}$, with the most prominent resistance observed against the $Trp672Ala_{gp41}$ mutant virus (Supplementary Table 11). These data demonstrated that the epitope recognized by DH511 lineage antibodies was similar to but distinct with those of gp41 bnAbs 4E10 and 10E8, requiring the aspartic acid at position 674 for binding and neutralization.

Figure 60A:
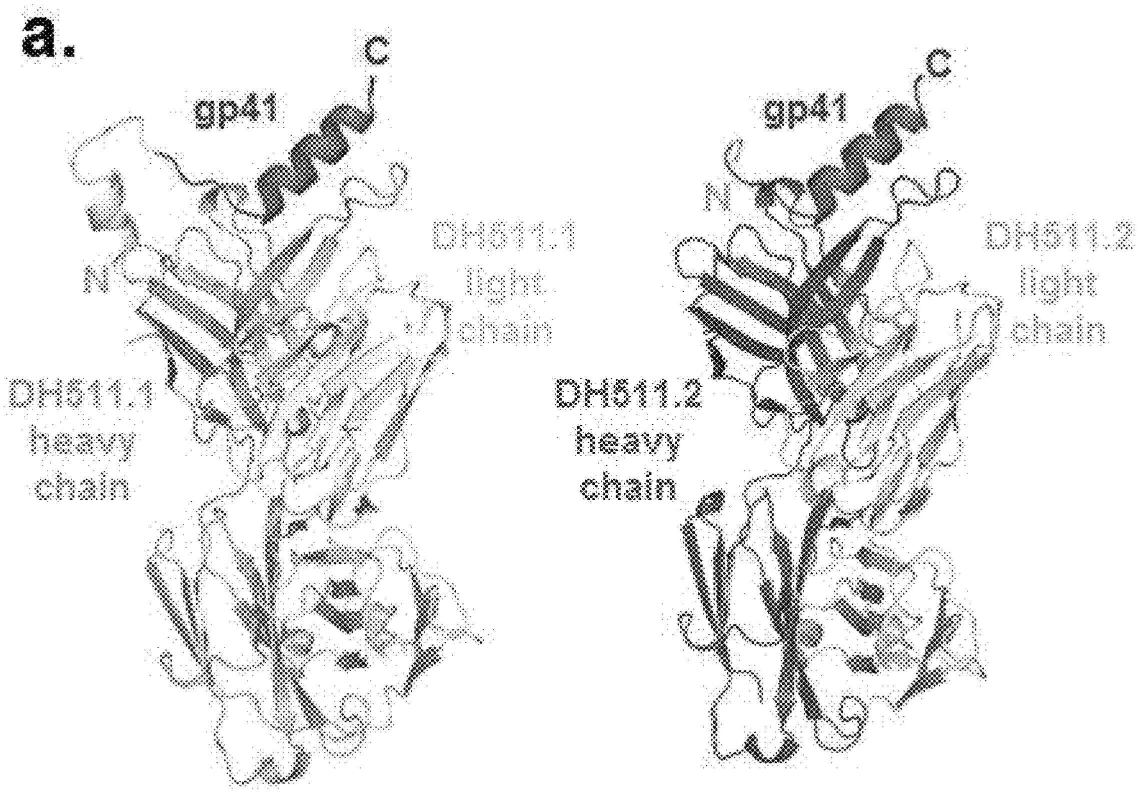
Figure 60B:
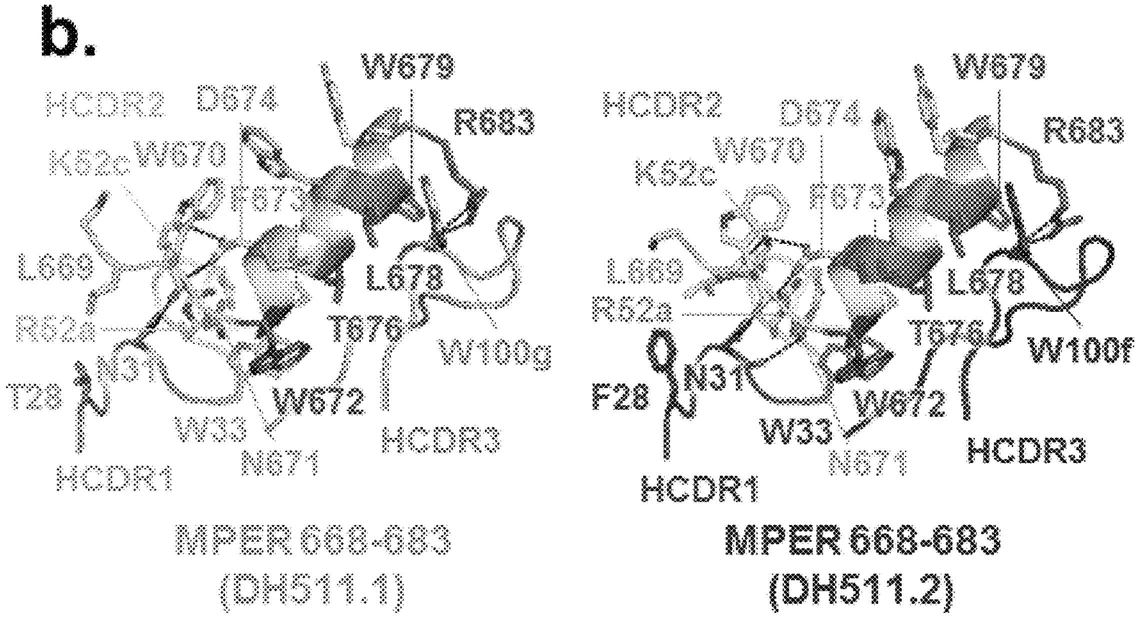
Figure 60C:
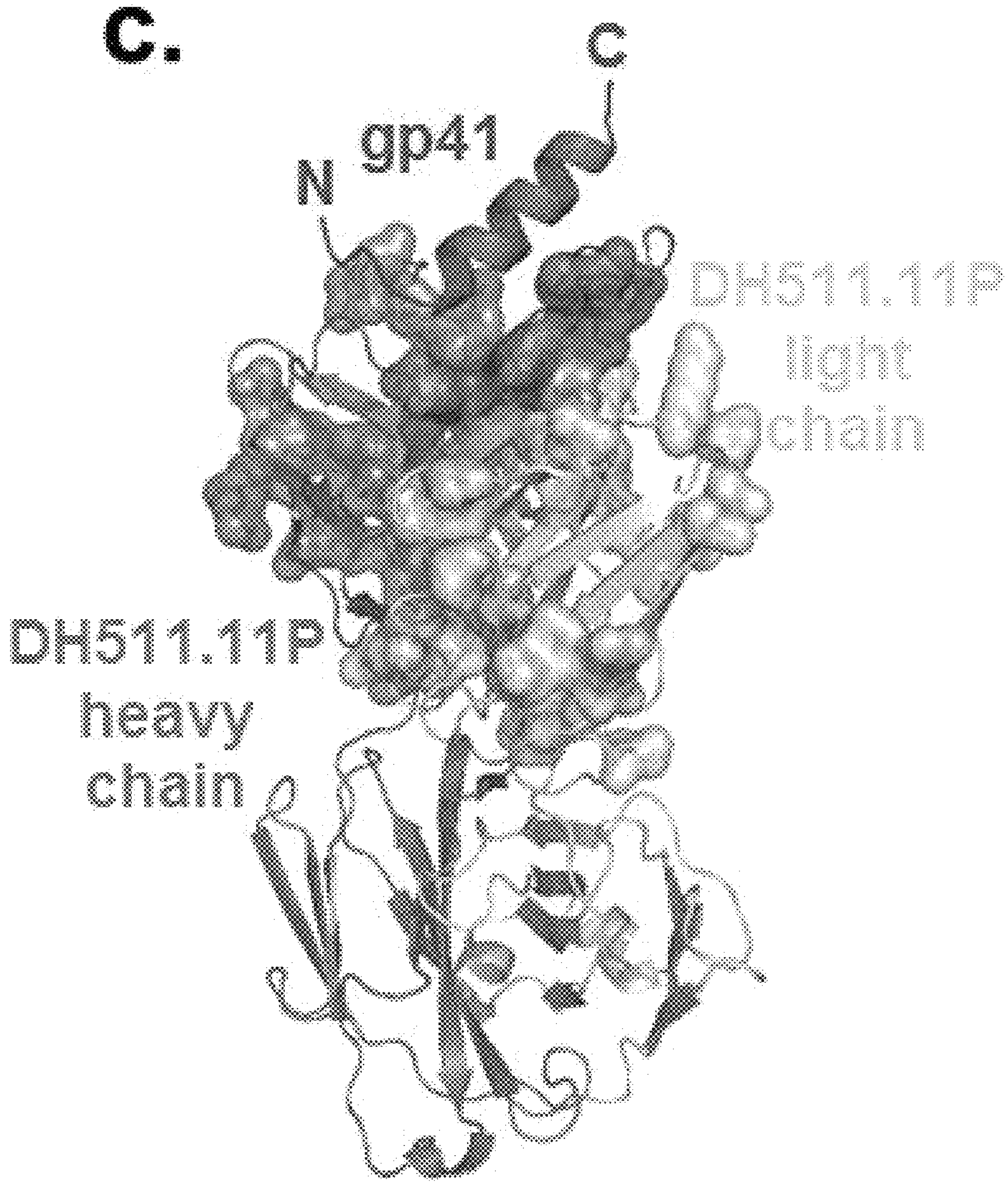
Figure 60D:
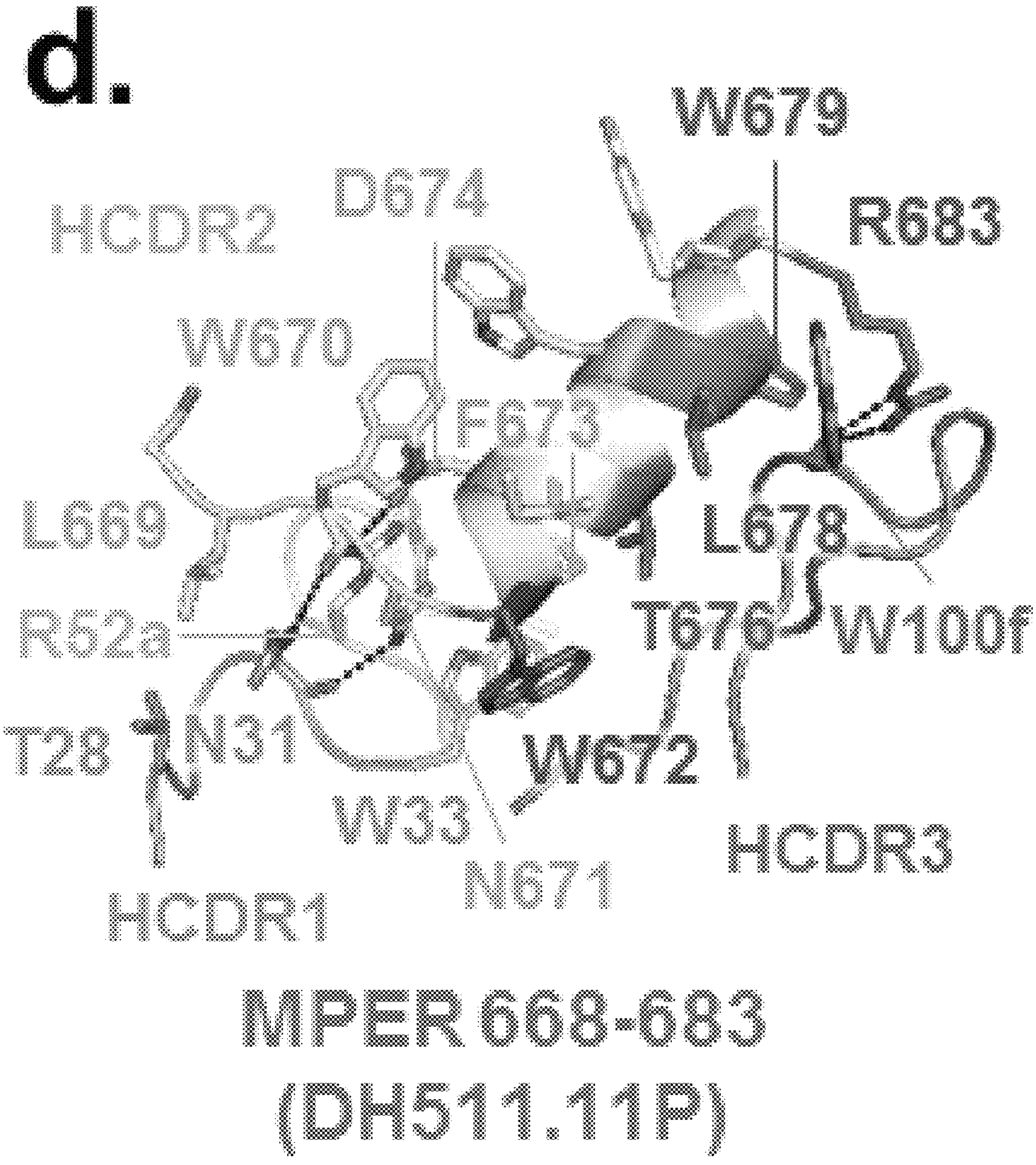

Crystal structures of the antigen-binding fragments (Fab) of the DH511.1 antibody in complex with a peptide spanning the full gp41 MPER (residues 656-683) and of the DH511.2 antibody in complex with gp41 peptides spanning residues 662-683 and 670-683 were determined to 2.7 Å, 2.6 Å and 2.2 Å resolution, respectively (FIG. 60, FIG. 62 and Supplementary Tables 12 and 13). Both DH511.1 and DH511.2 recognized an alpha-helical conformation of the distal portion of the gp41 MPER (residues 671-683) (FIG. 60*a*), similar to the conformation recognized by neutralizing antibodies 10E8 and 4E10 (FIG. 61*b*). C□ RMSDs for this region of gp41 across all four antibody-bound structures did not exceed 0.46 Å. Ordered electron density for the bound peptides was also observed upstream of the distal gp41 MPER helix. In the case of DH511.1, an additional □-helix was present between residues 656-661, followed by an extended conformation between residues 662-670 (FIG. 60*a*). DH511.2-bound MPER also adopted an extended conformation between residues 662-670, upstream of the distal helix, with the highest degree of overall structural homology to DH511.1-bound MPER occurring between gp41 residues 668-683 (C□ RMSD=0.39 Å) (FIG. 60*a*). Interactions between DH511.1 and DH511.2 and gp41 MPER were mediated exclusively by their heavy chains, with $V_H$3-15-encoded regions accounting for 45-50% of the antibody contact interface with gp41, and HCDR3 loops accounting for 50% or more of the remaining interface (FIGS. 60*b* and 61*c*, Supplementary Table 14). A total of 751.1 and 681.4 $Å^2$ interactive surface area was buried on DH511.1 and DH511.2, respectively, and 797.2 and 780.1 $Å^2$ on gp41 MPER in the two respective structures (Supplementary Table 14). The larger interface observed for the DH511.1 complex was due to the longer gp41 MPER peptide of that complex and the additional interface observed between its N-terminus and the antibody. It is likely that this additional interface is due to crystal lattice constraints, since alanine scan mutagenesis of N-terminal gp41 MPER residues did not result in reduction of antibody binding (FIG. 65). Contacts between DH511.1 and DH511.2 and gp41 MPER were highly conserved in both structures (FIG. 60*c* and Supplementary Tables 15-16). VH3-15-encoded residues of both DH511.1 and DH511.2 mediated interactions with gp41 residues L669, W670, N671, W672, F673, and D674, while their HCDR3 loop residues contacted gp41 residues W672, T676, L678, W679 and R683, as well as I675 in the case of DH511.2 (FIG. 60*c* and Supplementary Tables 15-16). The interactions observed in the structures were consistent with alanine scan analyses that revealed reduced antibody binding upon mutation of gp41 residues 671-674 and 679 (FIG. 65). Interactions between DH511.1 and DH511.2 and main-chain atoms of gp41, which would be difficult to detect in alanine scan analyses, were also observed, including between antibody residue N31 and the carbonyl oxygen of gp41 W670 (FIG. 60*c* and Supplementary Tables 15-16).

To compare atomic-level recognition of gp41 MPER by plasma-derived versus memory B-cell-derived antibodies, structural studies of the plasma-derived DH511-lineage antibodies DH511.11P and DH511.12P were undertaken in complex with gp41 MPER peptides. Crystal structures of DH511.11P and DH511.12P Fabs were determined in complex with a peptide spanning gp41 MPER residues 662-683, to 2.47 and 1.88 Å, respectively (FIG. 60*c* and Supplementary Tables 12 and 13). The structures revealed that both plasma derived variants recognized a conformation of the MPER similar to that recognized by DH511.1 and DH511.2, adopting an □-helix between residues 671-683 and an extended conformation upstream, between residues 662-670. The highest degree of structural homology occurred between residues 668-683. As in the case of DH511.1 and DH511.2, interactions between DH511.11P and DH511.12P and gp41 were mediated exclusively by their heavy chains (FIG. 60*d* and Supplementary Table 14). The plasma-derived variants recognized the very same gp41 residues as those recognized in common by DH511.1 and DH511.2, although the respective antibody residues that mediated these contacts with gp41 differed in some cases (FIG. 60*b*, 60*d*, 60*e* and Supplementary Tables 15-18). While contacts between HCDR1 loop residues of the DH511.11P and DH511.12P and gp41 were largely conserved relative to those of DH511.1 and DH511.2, gp41 contacts mediated by their HCDR2 loops diverged relative to those of DH511.1 and DH511.2 (FIG. 60). The substitution of DH511.1 and DH511.2 HCDR2 residue K52c with a glycine in DH511.11P and DH511.12P, led to the loss of a salt bridge mediated by K52c and gp41 residue D674—one that was replaced by an additional salt bridge mediated by conserved residue R52a (FIGS. 60*b*, 60*d*, 60*e* and Supplementary Tables 15-18). Examination of additional gp41-contacting residues that were unique to the plasma-derived variants revealed that unique residues of their HCDR3 loops, which differed from the DH511.1 and DH511.2 HCDR3 loops at ~7 residue positions, mediated many of these contacts (FIG. 60*c* and Supplementary Tables 17-18). Despite their overall sequence divergence from DH511.1 and DH511.2, ~26-28% in heavy chain variable regions, the structures of the DH511.11P and DH511.12P were highly homologous to those of DH511.1 and DH511.2. In sum, the plasma-derived variants examined here recognized a similar conformation of the gp41 MPER as that recognized by memory B-cell derived variants, contacted a similar set of gp41 residues, and did so through modified antibody contacts that did not significantly alter the backbone conformations of their paratopes or common epitope.

Figure 61A:
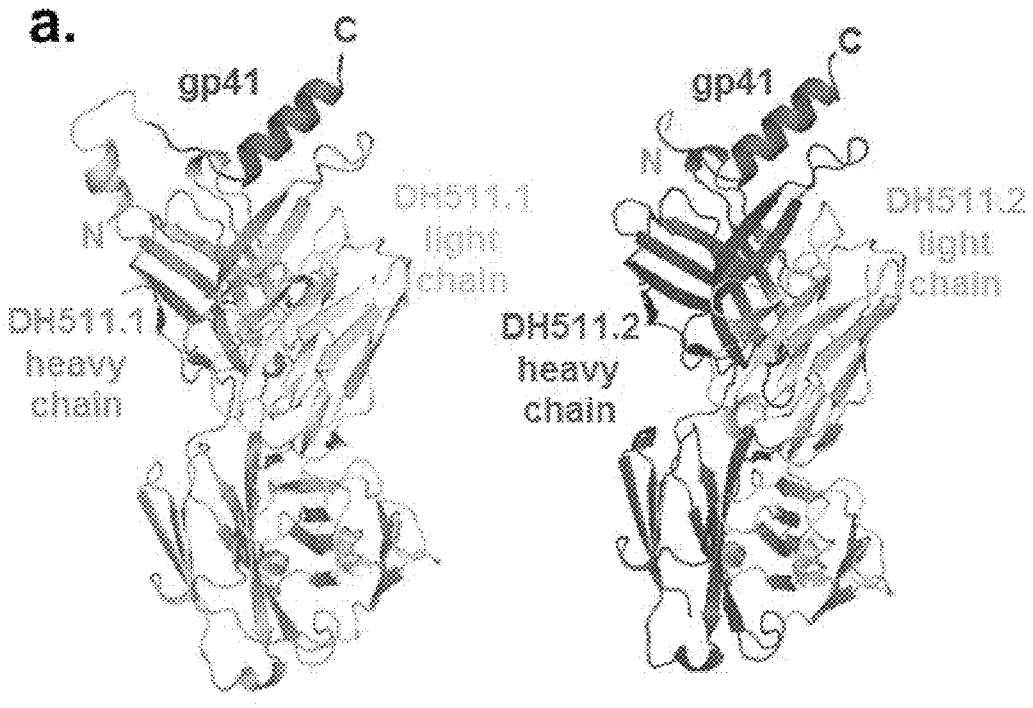
FIGS. 61A-E shows comparison with other MPER-specific antibodies. (a) Crystal structures of DH511.1 and DH511.2 Fab in complex with gp41 MPER peptides 656-683 and 662-683, respectively, oriented based on Ca-atom superposition of distal MPER residues 671-683. (b) Crystal structures of antibodies 10E8 and 4E10 in complex with MPER peptide epitopes, oriented as in (a). (c) Surface representations of antibodies DH511.1, DH511.2, and 10E8, colored as in (a) and (b) and rotated by 60°. gp41 contact footprints within the HCDR3 loops are colored red and those within the variable heavy chain VH3-15 regions are colored green. VH3-15 contacting residues positions that are shared by antibodies DH511.1 and DH511.2 and antibody 10E8 are colored cyan. (d) Angles of approach to distal gp41 MPER by antibodies DH511.1, DH511.2, 10E8, and 4E10. Shown is a superposition of the structures of antibody-bound gp41 MPER, with lines representing the longitudinal and latitudinal axes of antibody variable regions colored as in (a) and (b). The longitudinal axis is drawn to the Ca atom of gp41 residue 672 from the center of the latitudinal axis, defined as the point midway between heavy and light chain intra-chain disulfide bonds (spheres).
Figure 61B:
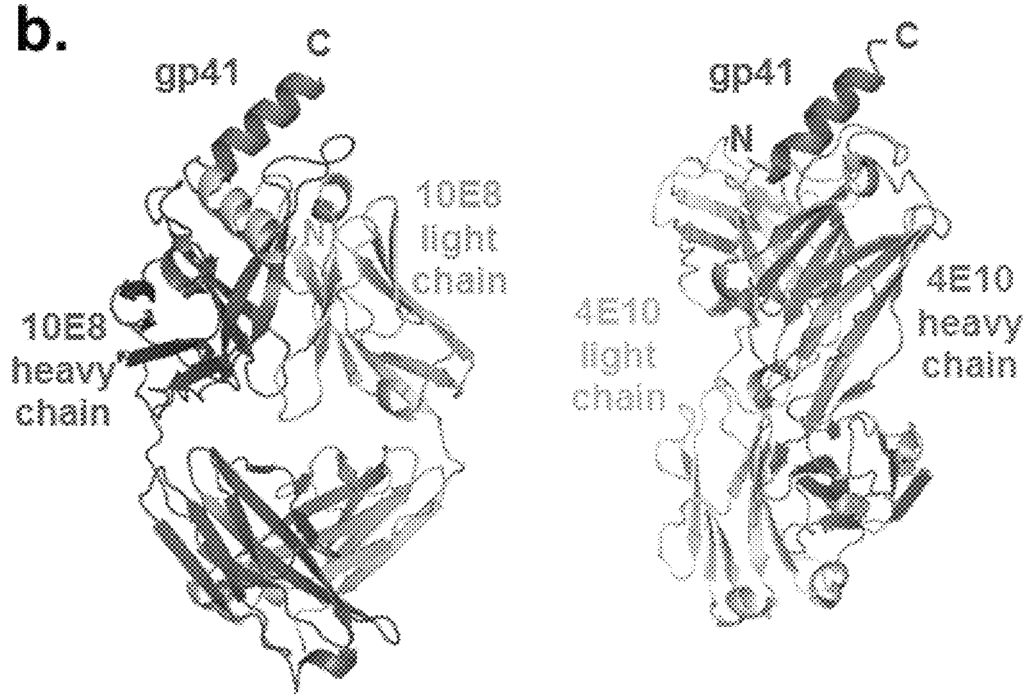
Figure 61C:
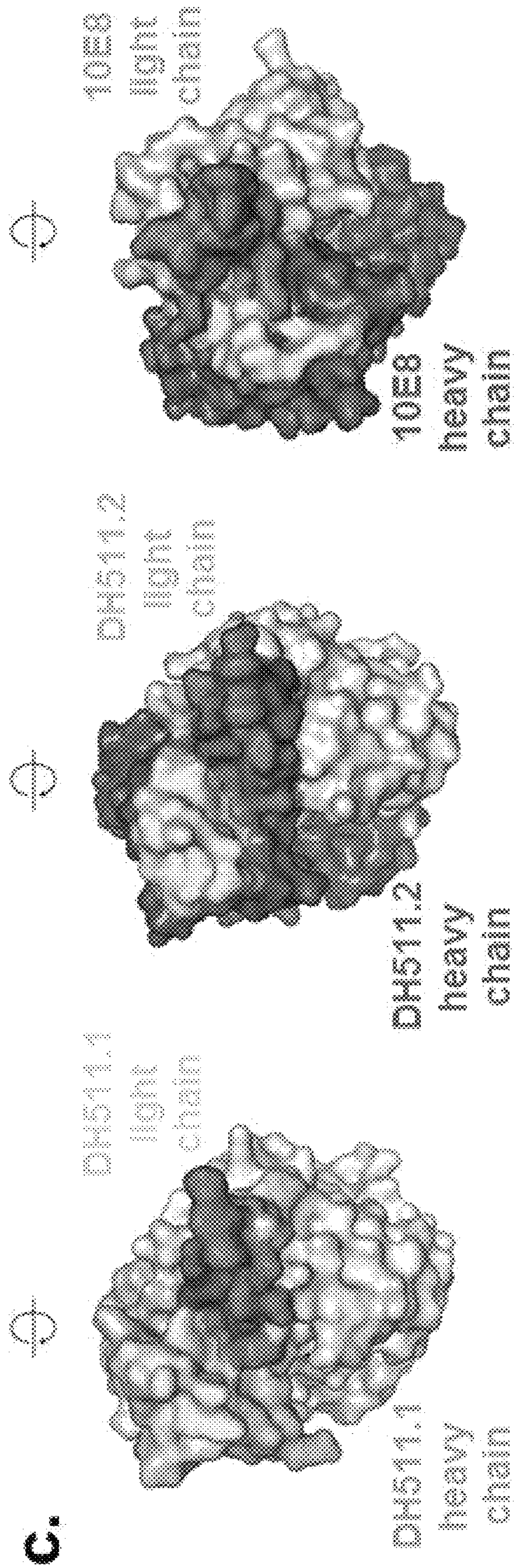
Figure 61D:
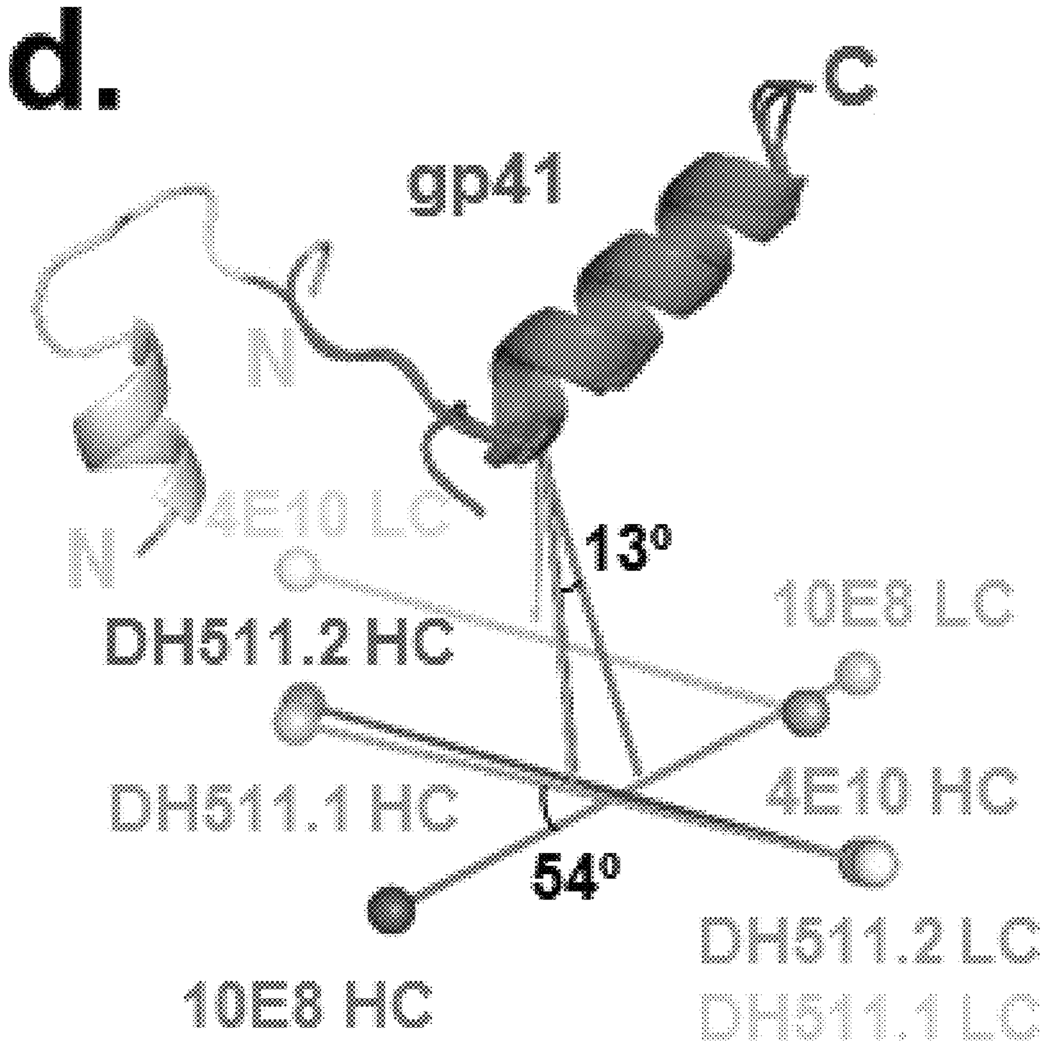

We next compared the structures of DH511 lineage antibodies to those of other antibodies that target the distal gp41 MPER (FIGS. 61*a* and 61*b*). Since the DH511 lineage shares a common VH3-15 heavy chain precursor as the 10E8 lineage, we were especially interested in determining if a structural basis for usage of this precursor to target the MPER could be discerned. As a first step, we compared the directions of approach of DH511 lineage antibodies to the distal MPER helix, relative to those of 10E8 and 4E10. All four antibodies were oriented by superimposing residues 671-683 of their respective epitopes, and their directions of approach were defined by a line drawn from the Ca atom of epitope residue 672 to a point midway between the variable region intra-chain heavy and light chain disulfide bonds, which represented the longitudinal axis of the antibody variable regions. Pairwise comparison of the directions of approach of DH511.1 versus those of DH511.2, 10E8 and 4E10 yielded differences of 4.7°, 13.4° and 25.2°, respectively, suggesting the DH511 lineage most closely resembled 10E8 in its approach to the epitope (FIG. 61*d*). While the longitudinal axes of the DH511.1 and DH511.2 variable regions and that of 10E8 were highly similar, the orientations of their heavy and light chains relative to this longitudinal axis differed more substantially—by ~54° (FIG. 61*d*). This difference resulted in a rotational shift of the gp41 footprint on 10E8 relative to the footprint on DH511 lineage antibodies (FIG. 61*c*). Thus, while DH511 lineage antibodies share an identical heavy chain $V_H$3-15 precursor as antibody 10E8, and approached gp41 MPER from similar angles, the orientations of their heavy and light chains relative to the epitope differed more substantially.

Figure 61E:
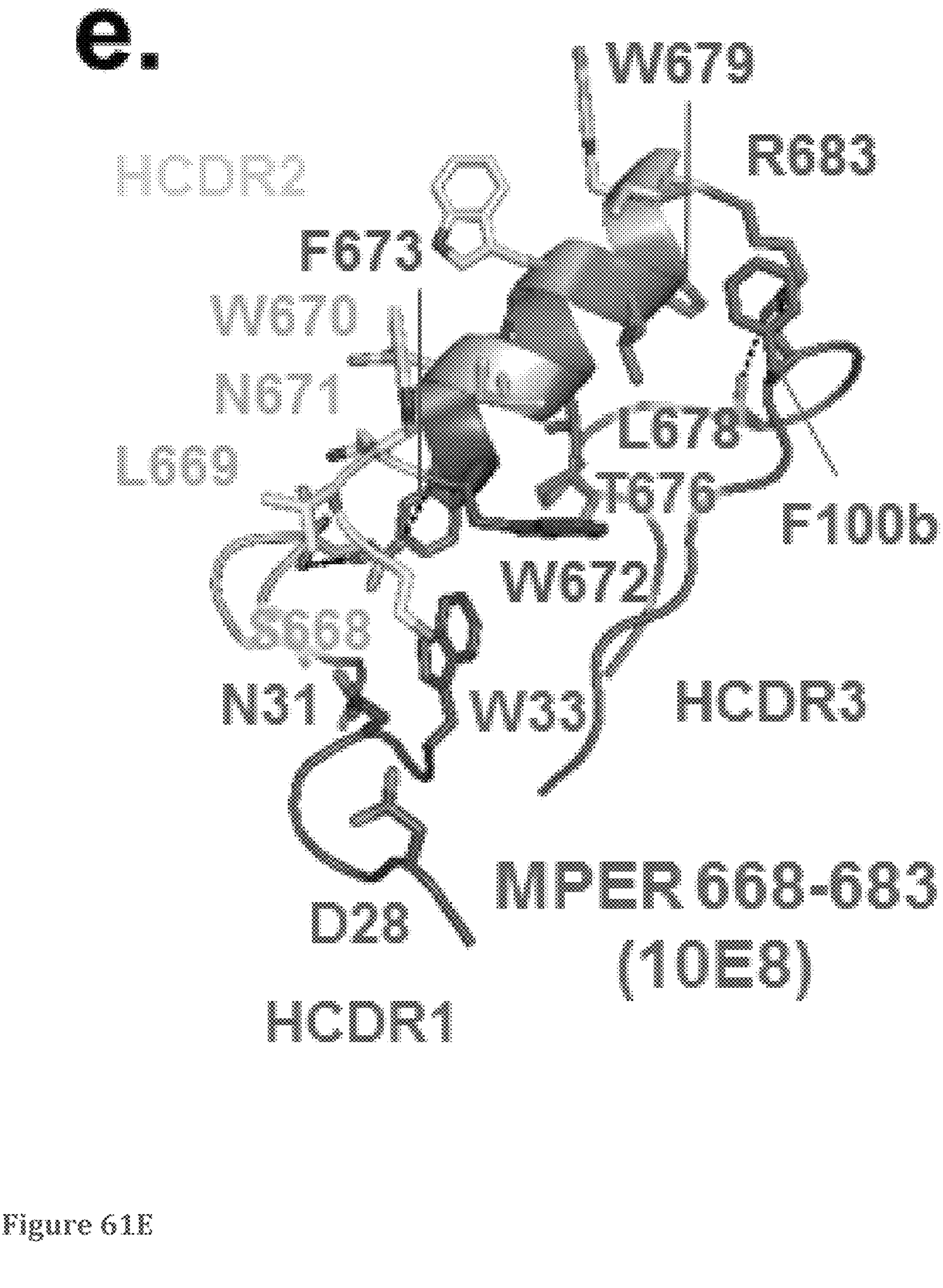

To determine if a common structural basis for $V_H$3-15 precursor usage could nonetheless be discerned between the two lineages, we compared $V_H$3-15-encoded gp41-contacting residues in DH511.1, DH511.2 and 10E8. Of the total number of residue interactions that exist between the VH3-15 regions of three respective antibodies and gp41 (8 for DH511.1, 10 for DH511.2, and 10 for 10E8), five common residue positions were involved interactions with gp41 in all three antibodies: 28, 31, and 33 within the HCDR1 and 52c and 53 within the HCDR2 (FIGS. 61*c* and 60*e*). Heavy chain residues 31 and 33 are asparagine and tryptophan in all three antibodies and are un-mutated from the germ-line precursor. Residue 53 is aspartate in DH511.1 and DH511.2, as it is in the germ-line precursor, and a chemically similar glutamate in 10E8. Residue positions 28 and 52c are somatically mutated from germ-line in all three antibodies, to disparate amino acids (FIG. 61*e*). While all five residues maintain contact with gp41 in both the DH511.1 and 10E8 lineages, the rotational shift in the orientations of the heavy and light chains between the two lineages results in distinct modes of gp41 recognition (FIGS. 60*b* and 61*e*). Yet, the five common $V_H$3-15 encoded gp41-contacting residues in both lineages end up interacting with many of the same gp41 MPER residues, including L669, W670, N671, W672, and F673 (FIGS. 60*b*, 60*e*, and 61*e*). $V_H$3-15 germ line encoded residue W33, shown in previous studies to be required for 10E8 recognition of gp41 (1), interacts with gp41 residues W672 and F673 in both the DH511.1 and 10E8 lineages, although from a distinct spatial position in each case (FIGS. 60*b* and 61*e*). Thus, despite a relative shift in heavy and light chain orientations, a common subset of DH511.1 and 10E8 lineage $V_H$3-15 residues interact with the same subset of distal MPER residues. It remains to be determined if the observed differences in the heavy and light chain orientations of two lineages, relative to gp41 MPER, were determined at inception of naïve antibody recognition or if they were added during antibody development and maturation.

Origin and Development of the DH511 Clonal Lineage

Figure 66A:
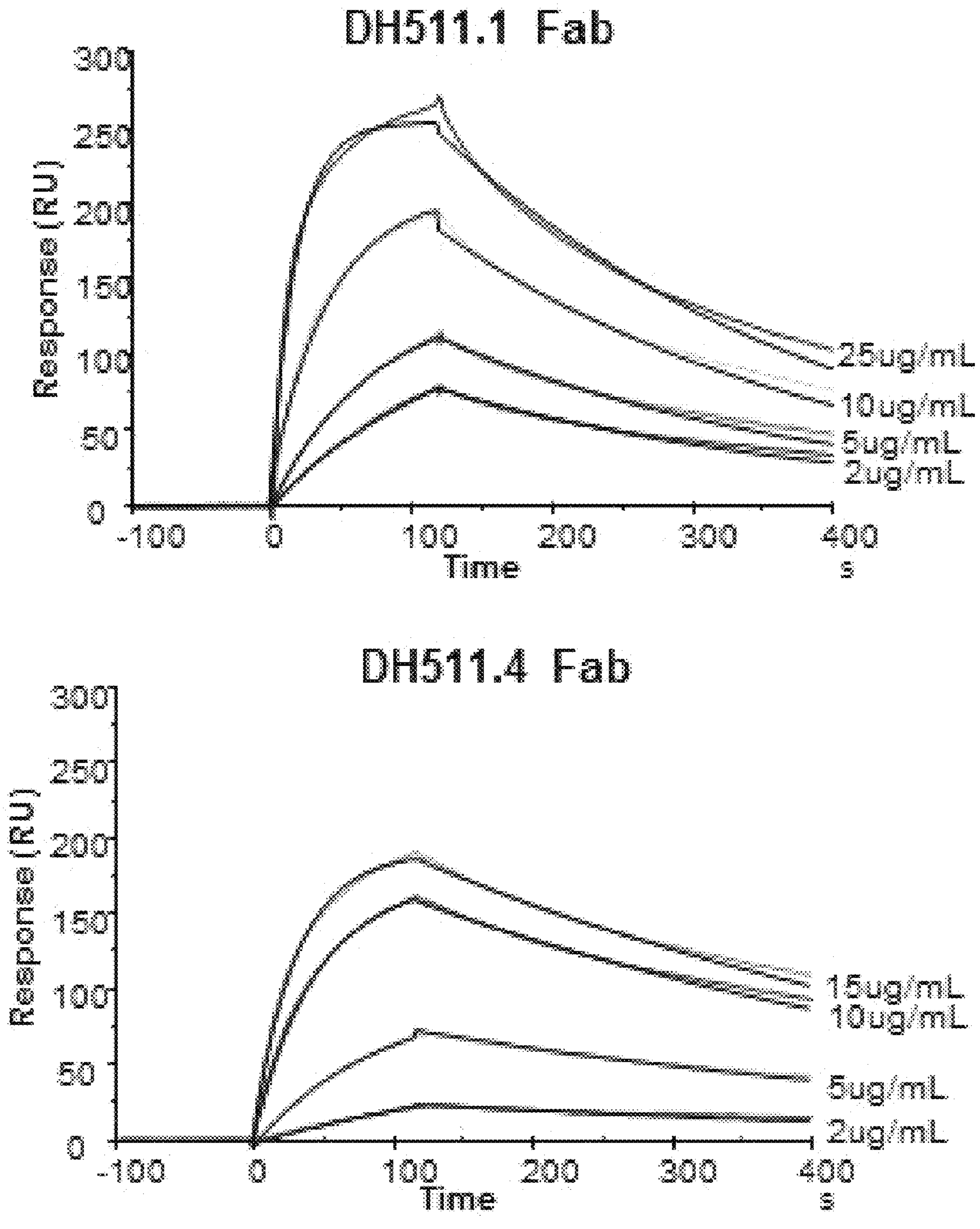
Figure 66B:
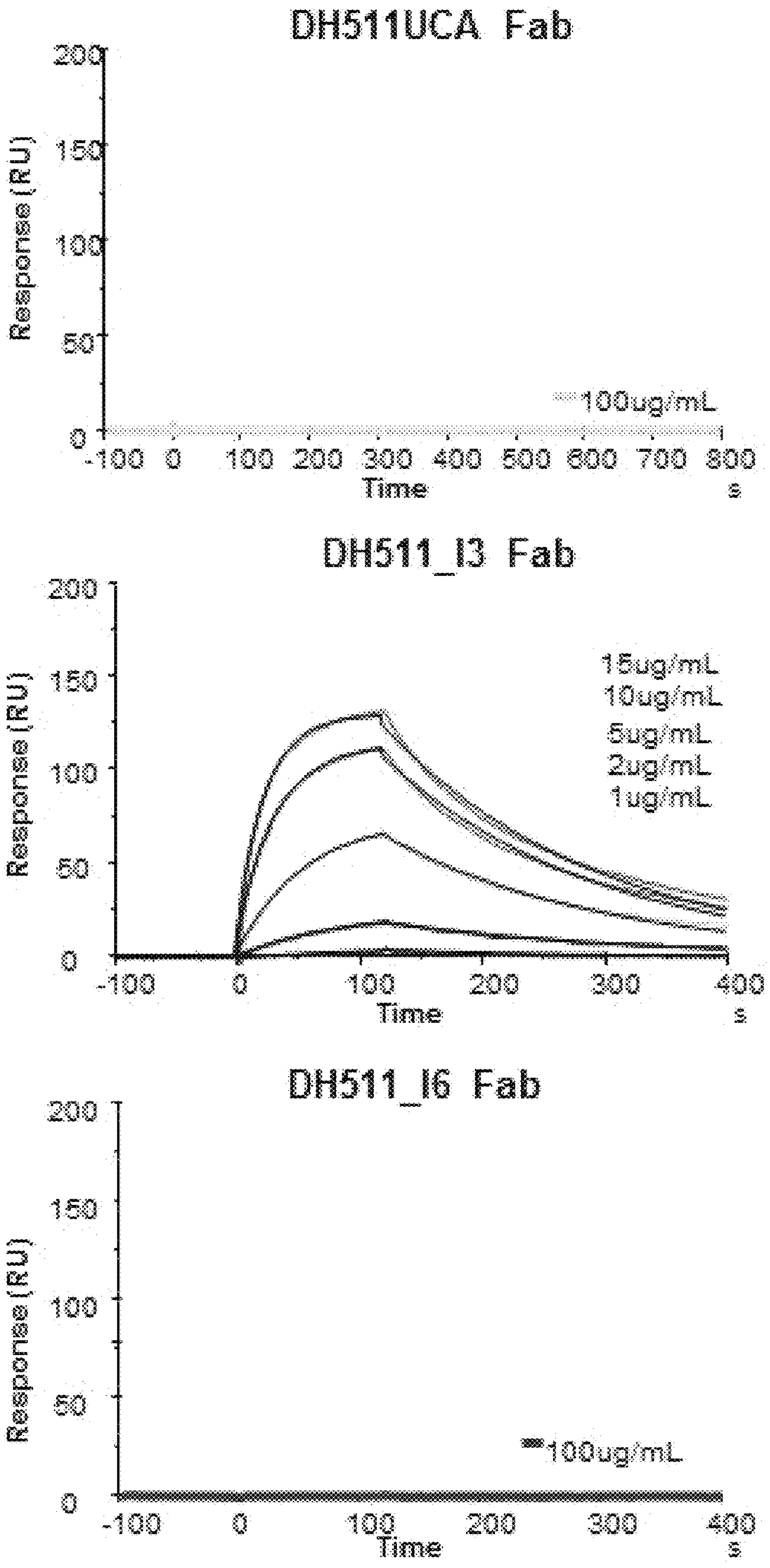
Figure 67A:
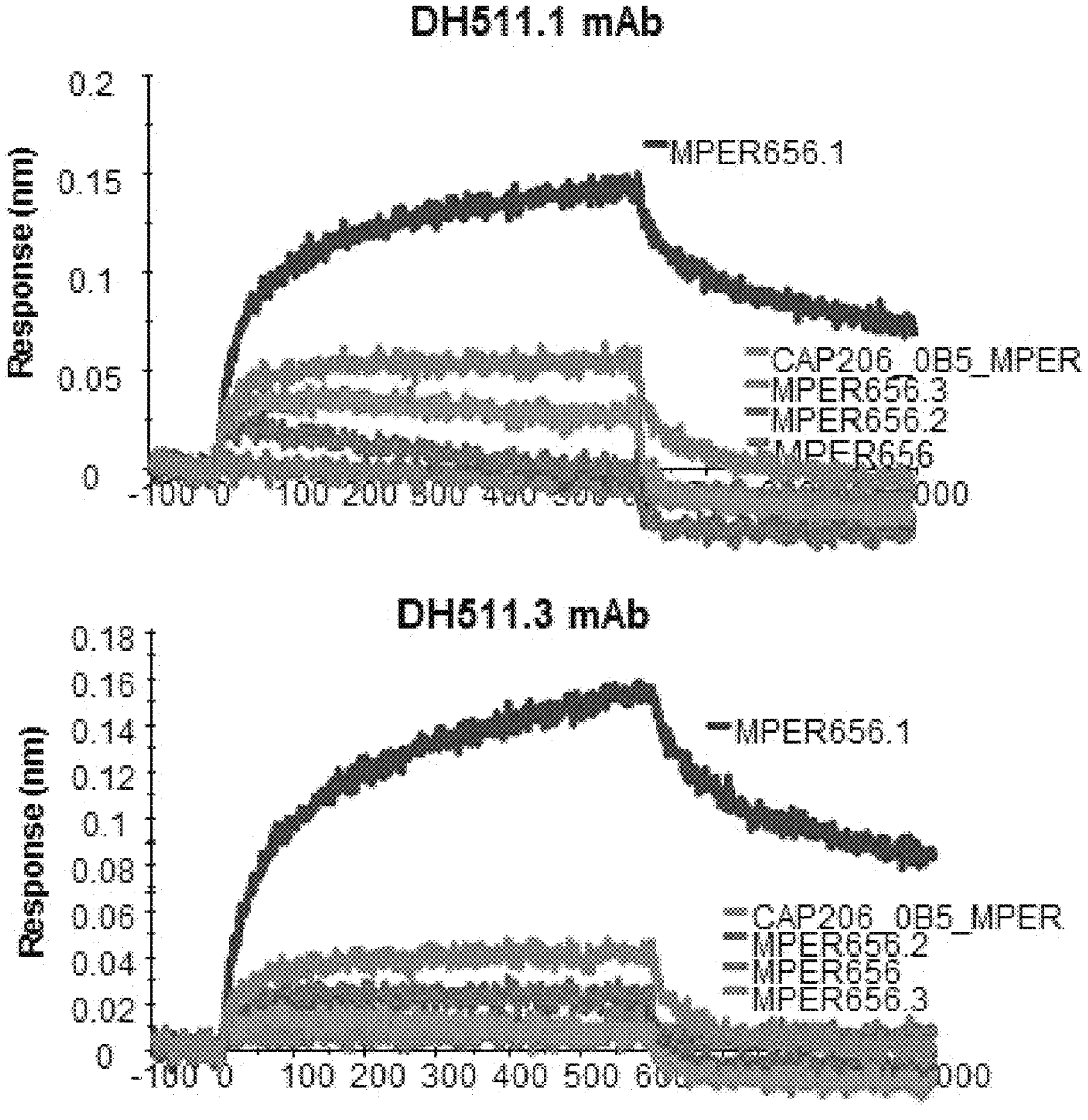
Figure 67A:
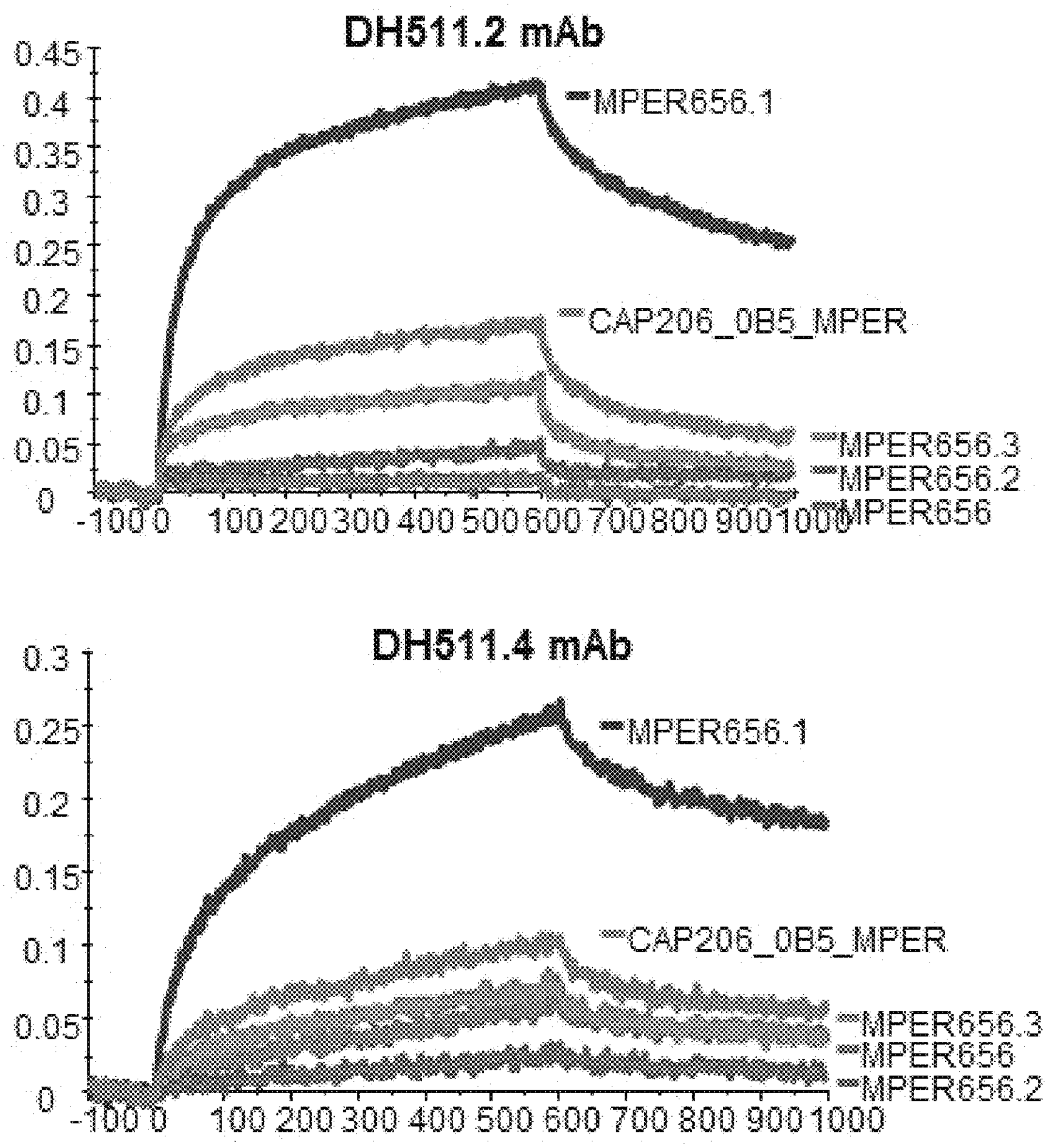
Figure 67B:
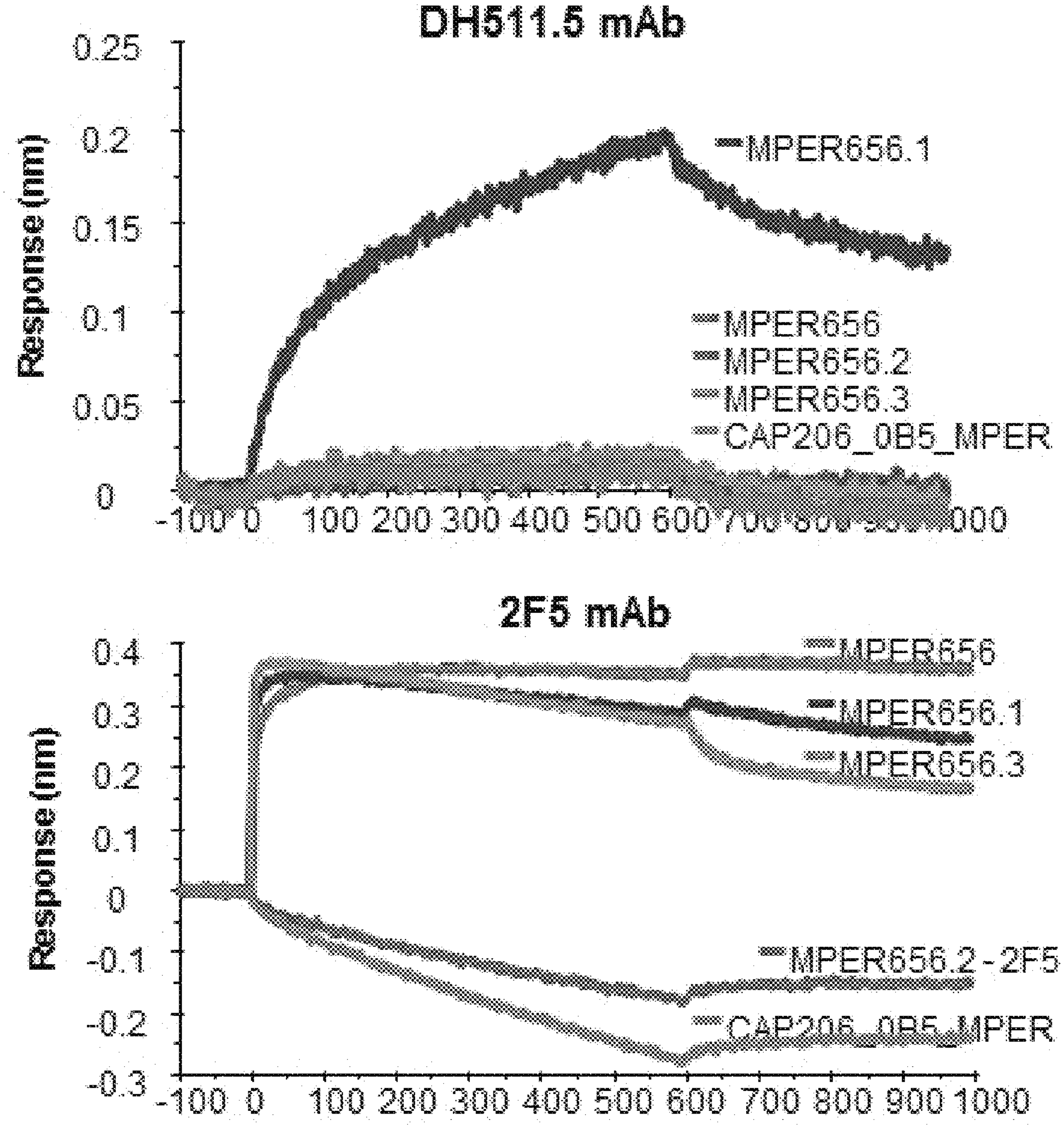
Figure 67B:
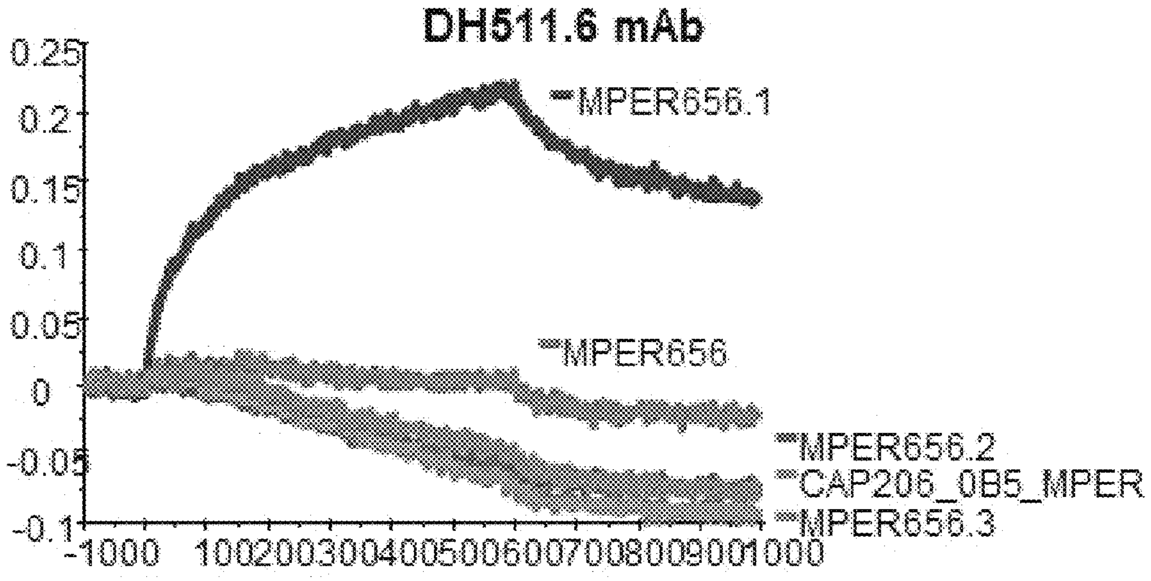
Figure 68A:
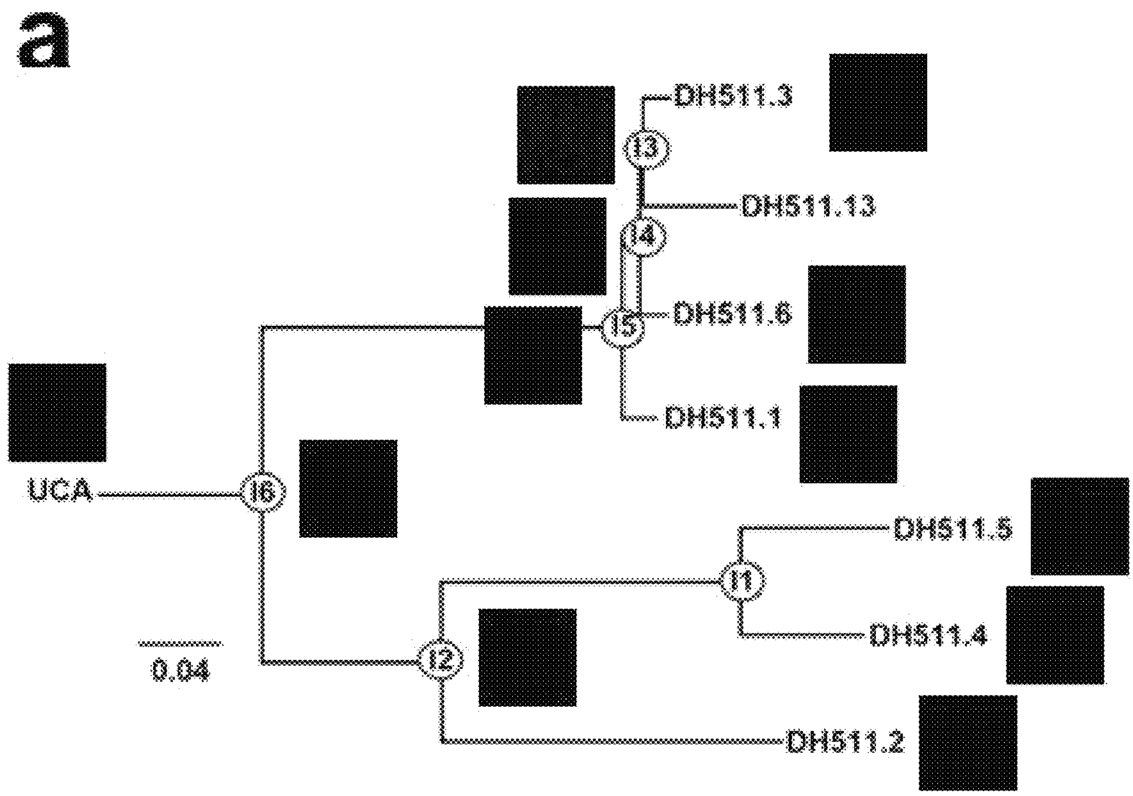
FIG. 68A-C show poly/autoreactivity analysis of MPER bNAbs. Reactivity of DH511 clonal lineage members with self-antigens as measured by indirect immunofluorescence Hep-2 cell staining (b) and a multiplex bead array anti-nuclear antibody (ANA) assay (a) panel consisting of several autoantigens: SSA, SSB, Smith antigen (Sm), ribonucleoprotein (RNP), Scl-70, Jo-1, double-stranded DNA (dsDNA), Cent B, Histone, and anti-cardiolipin. None of the antibodies were identified as reactive with Hep-2 cells. DH511.1 UCA reacted with ribonucleoprotein, and DH511 I6 reacted with dsDNA. (c) Protein microarrays were used to assess binding to >9400 human proteins. Autoantigens identified: PPP1R1C (protein phosphatase 1, regulatory (inhibitor) subunit 1C) [DH511.1]; FYN (FYN oncogene related to SRC, FGR, YES, transcription variant 1 [DH511.1, DH511.3, DH511.6, DH511_I3, DH511_I4]; NECAP endocytosis associated 1 (NECAP1) [DH511.1, DH11.6]; SIAHBP1 (fuse-binding protein-interacting repressor, transcription variant 1, mRNA) [DH511.11]; STUB 1 (STIP1 homology and U-box containing protein 1) [DH511.2, DH511.6] STIP1 (stress-induced phosphoprotein 1) [DH511 DH511_I2]; OR1F1 (olfactory receptor, family 1, subfamily F, member 1) [DH511]; C6orf145 (Px-domain containing protein) [DH511.1]; FLJ36032 [DH511_UCA]; TTC1 (tetratricopeptide repeat domain 1) [DH511_I1], nuclear distribution gene C homolog (*A. nidulans*) (NUDC) [DH511.11P, DH511.12P], Scm-like with four MBT domains protein 1 [DH511.12P].
Figure 68B:
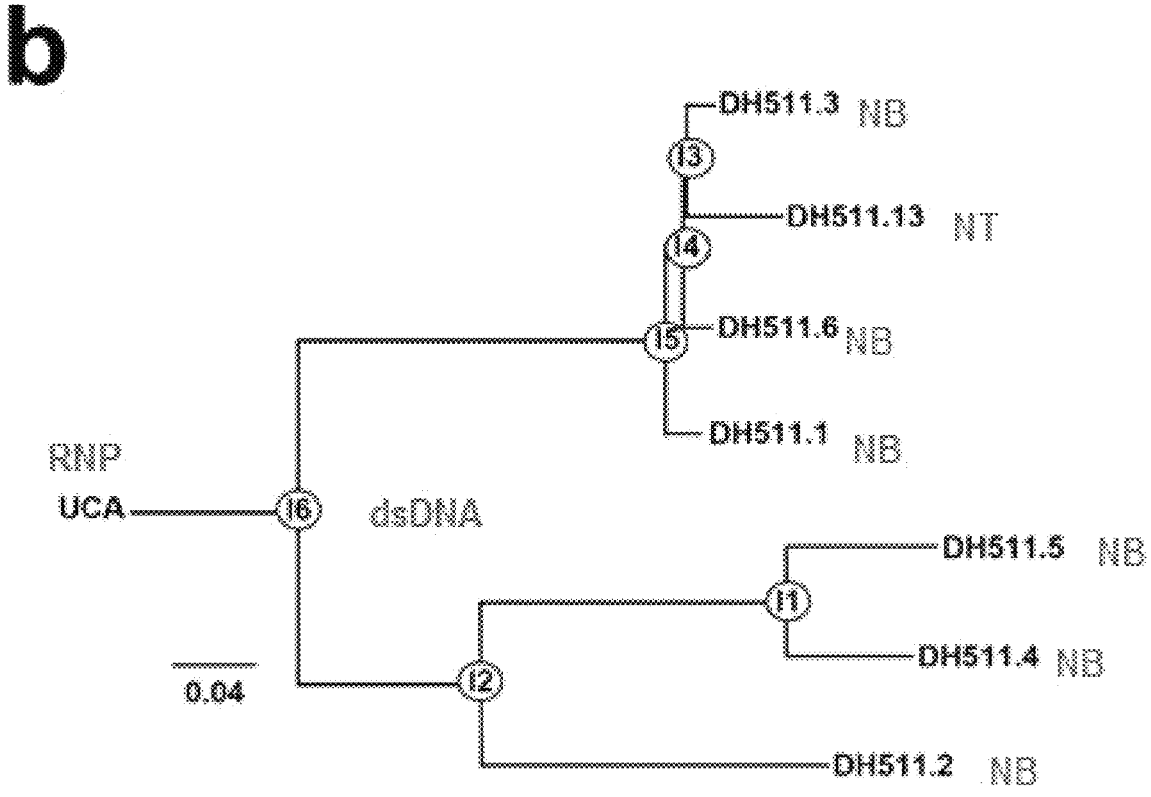
Figure 68C:
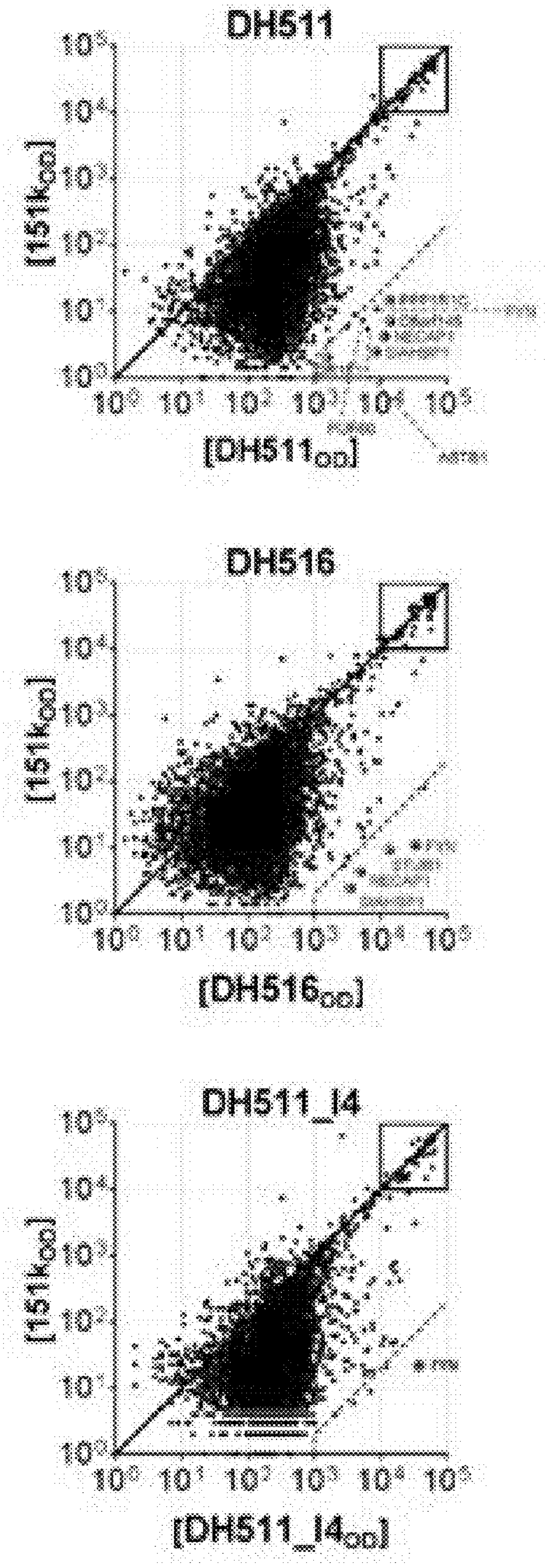
Figure 68C:
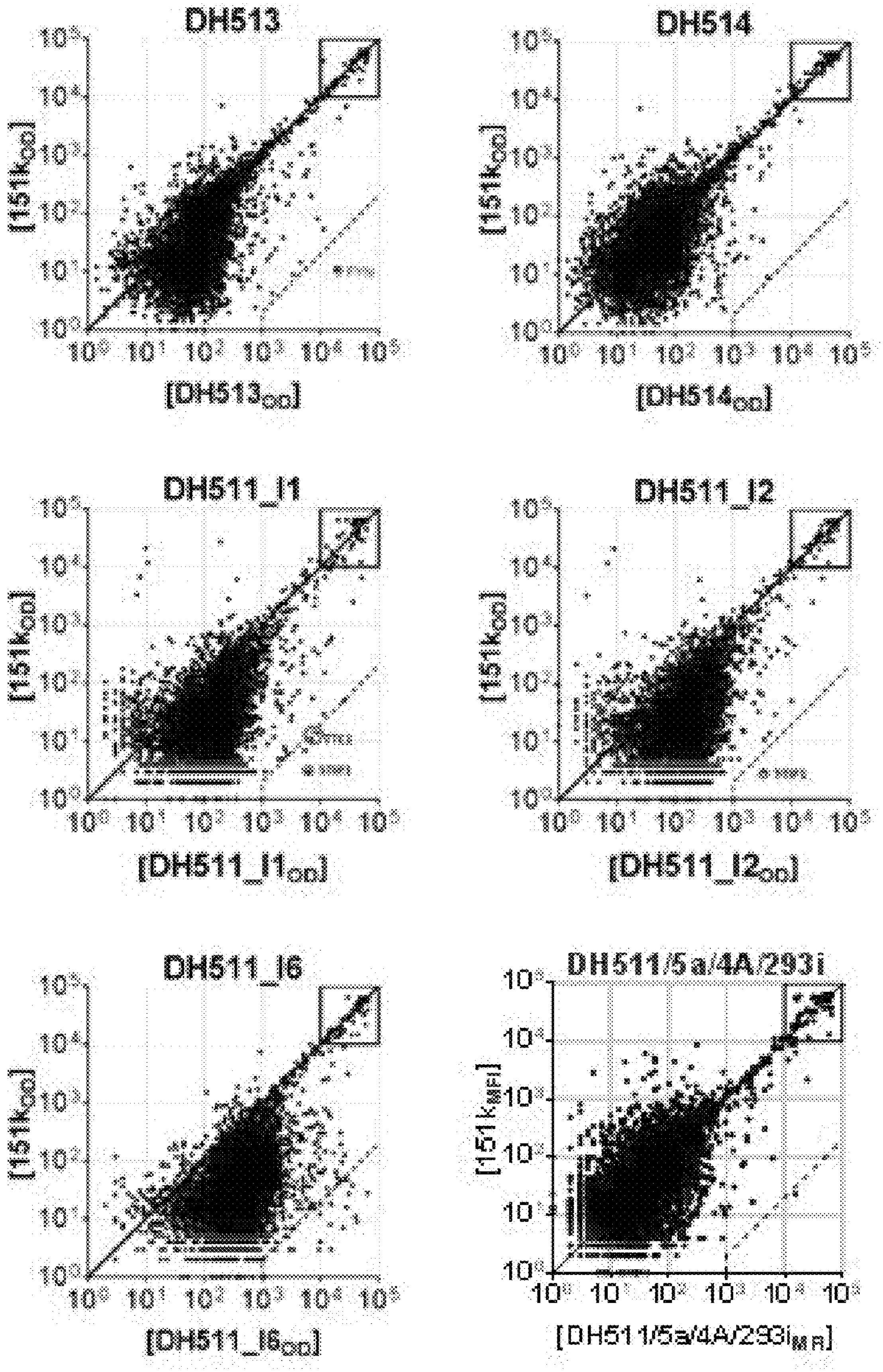
Figure 68C:
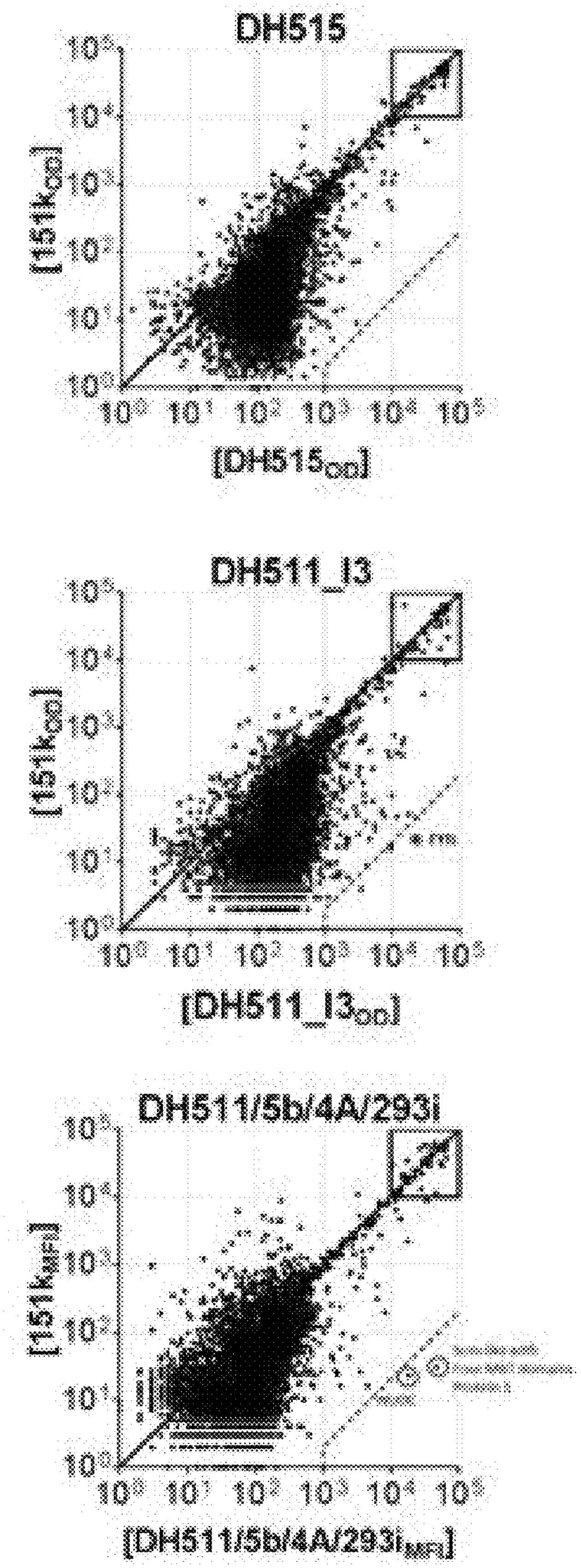

A maximum likelihood phylogenetic tree was constructed from the VDJ sequences recovered from memory B cell sorting and was used to infer the unmutated common ancestor (UCA) of clone DH511 and six maturational intermediate antibodies (FIG. 59*b*). A global panel of 12 HIV-1 isolates was used to assess the development of neutralization breadth in the DH511 clonal lineage. None of the isolates were neutralized by the UCA or intermediate (I) 6 antibody that was most closely related to the DH511 UCA. Antibody I2 and later members of the lineage acquired the ability to neutralize 12/12 isolates (Supplementary Table 19). DH511 clone acquisition of breadth was associated with the accumulation of somatic mutations, but neutralization potency did not directly correlate with percent VH mutation frequency. Analysis of a panel of MPER peptides and MPER peptide liposomes did not reveal constructs that bound to the UCA. Binding to the MPER peptides was acquired at the 15 stage of maturation (FIGS. 66 and 67).

Polyreactivity/Autoreactivity of the DH511 Clonal Lineage

Figure 69:
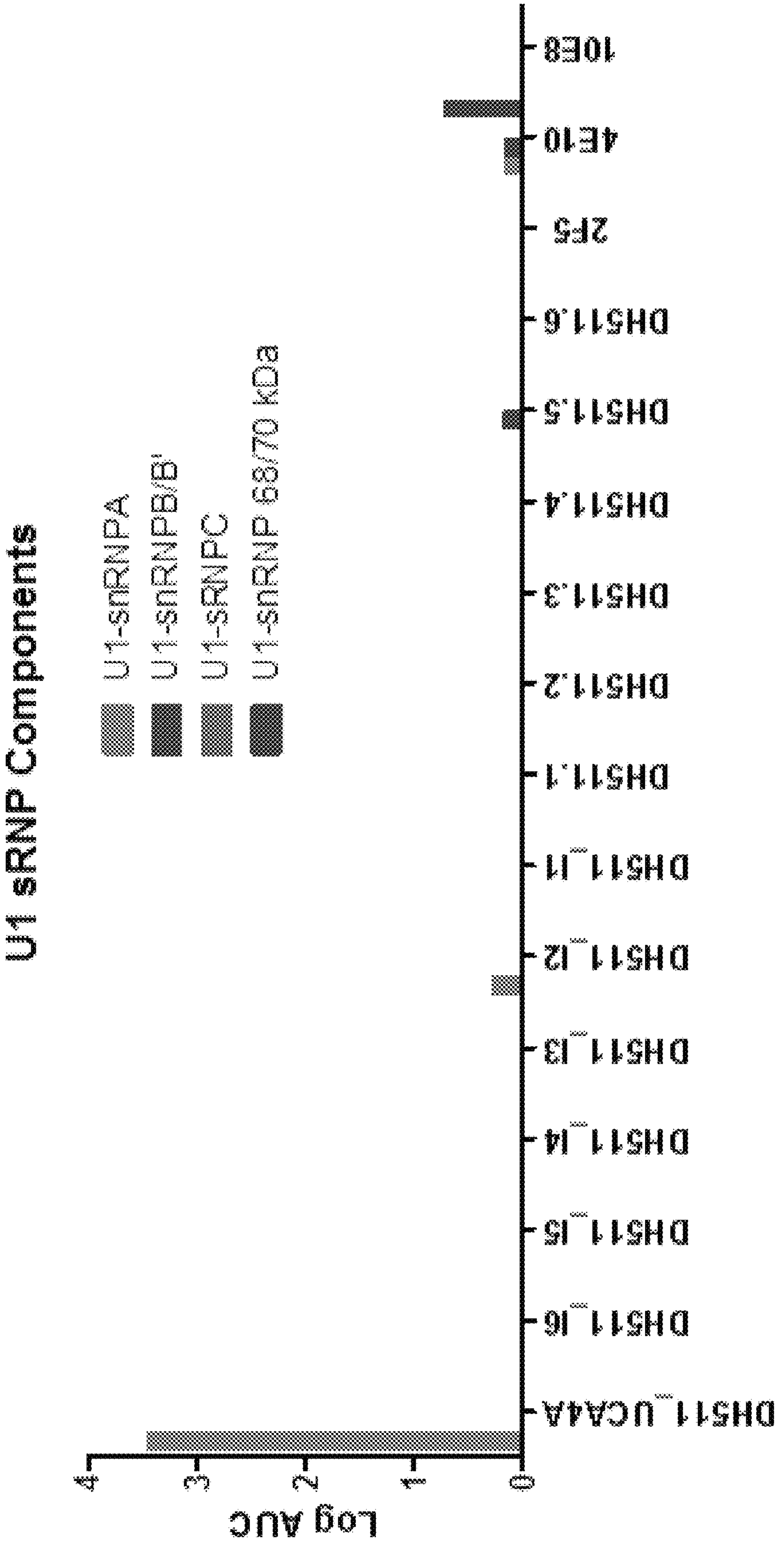
FIG. 69 shows ELISA binding of DH511 lineage members to U1 snRNP components. The DH511_UCA bound specifically to U1-snRNPA while no binding was observed to the other components. Results shown represent one experiment.
Figure 70:
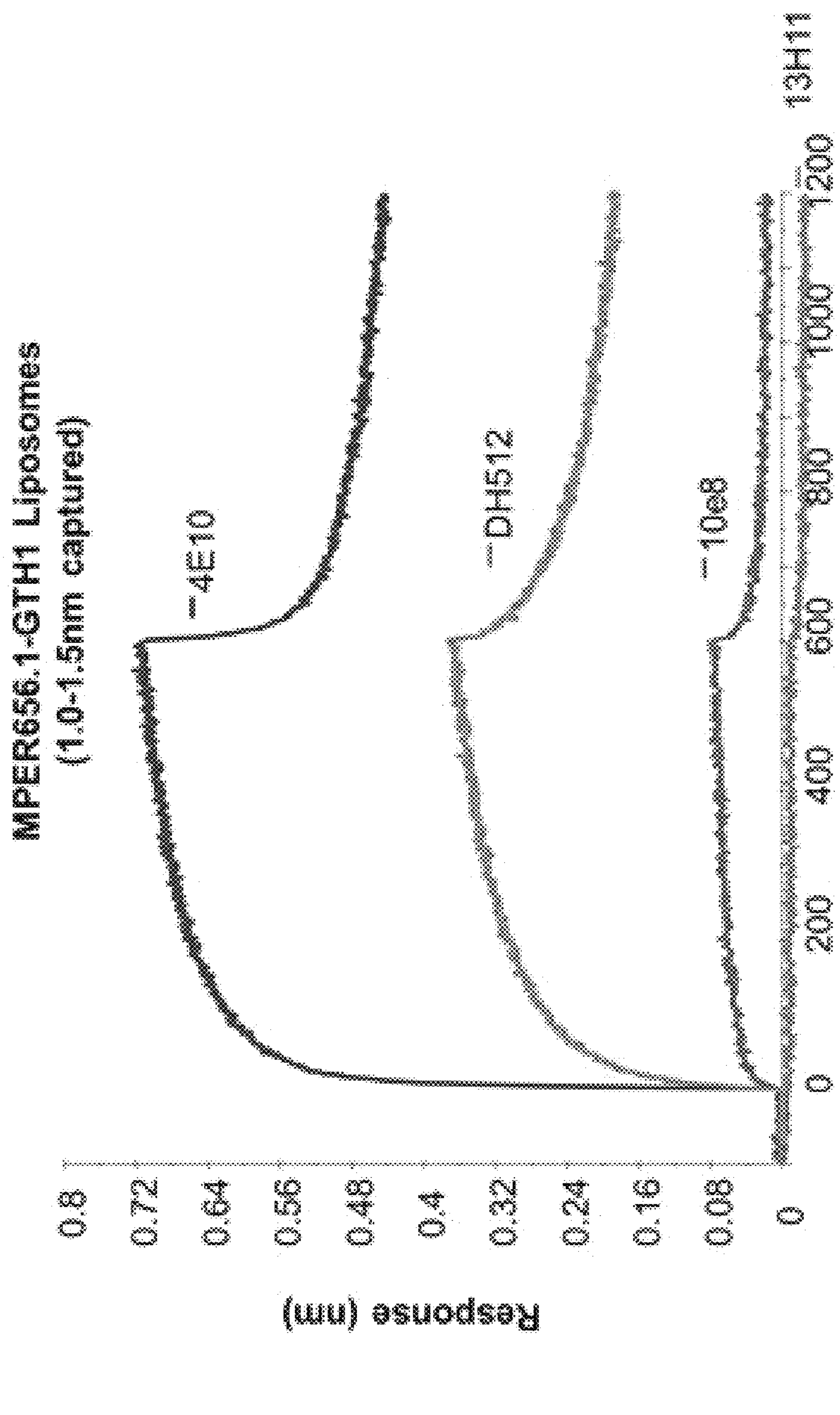
FIG. 70 shows potential mechanistic differences in binding of 4E10 versus DH511.2/10E8 to MPER liposomes. 4E10 bound to MPER656.1 in a biphasic association/dissociation mode and the binding could be fit to a 2-step conformational change model. DH512 appears to have a different mechanistic mode and its binding could be fit to a 1:1 Langmuir model.
Figure 70:
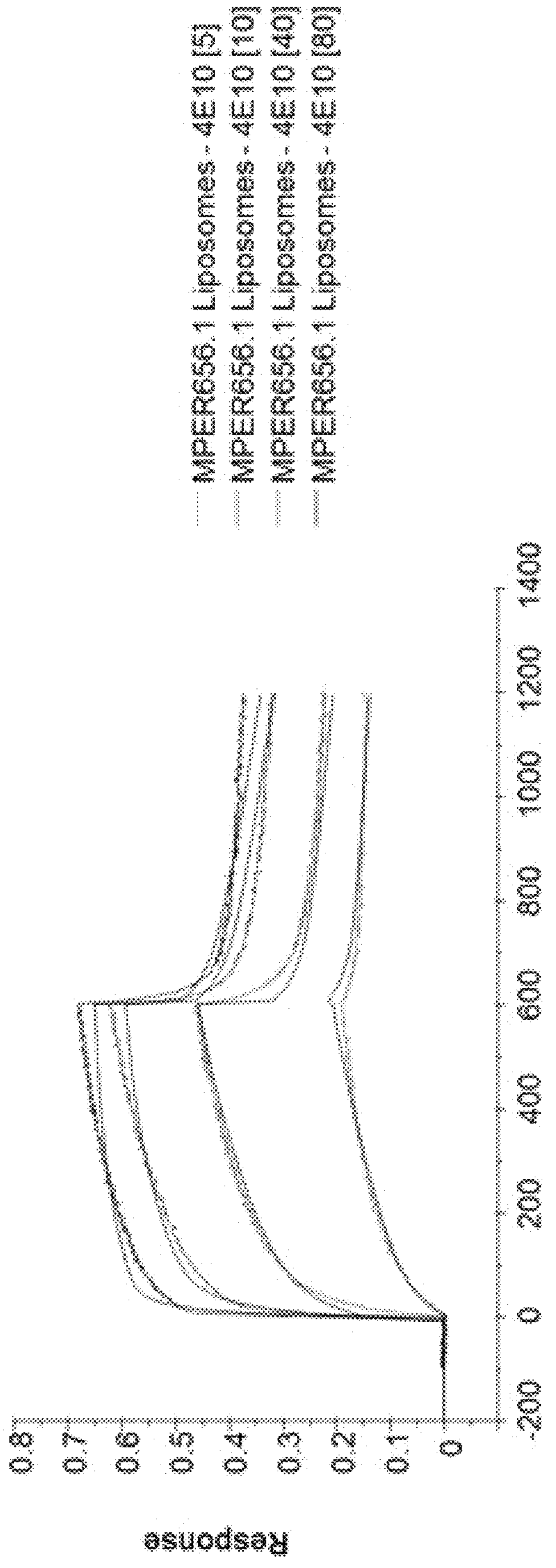
Figure 70:
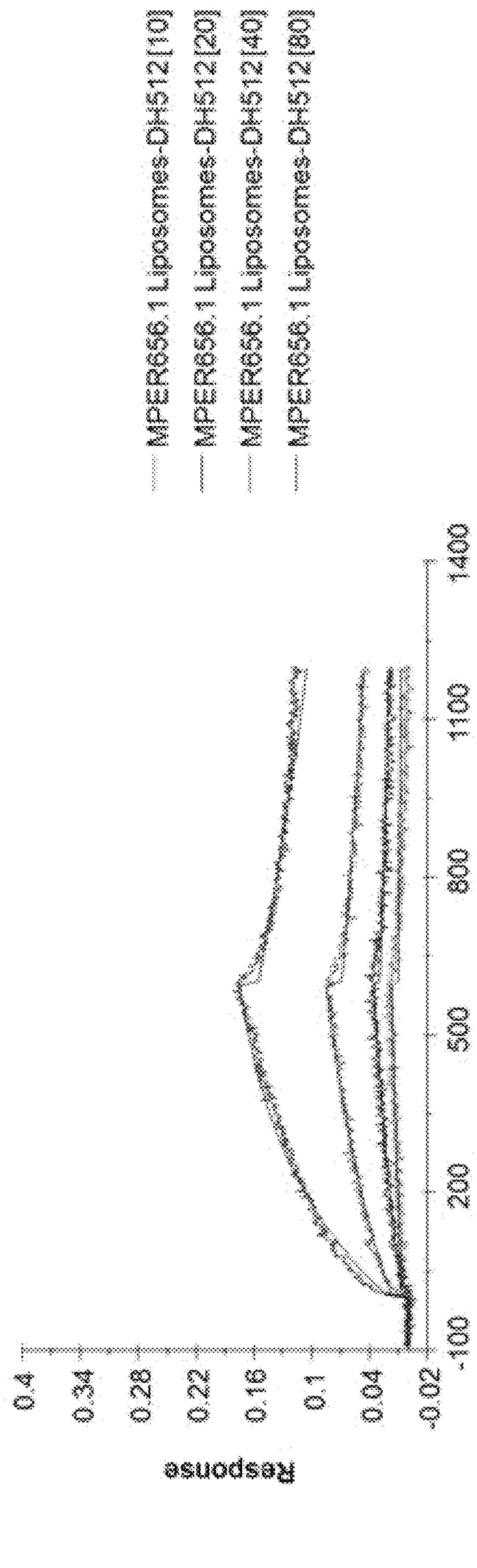

The DH511 inferred UCA and intermediates 11-13 and 16 reacted with several autoantigens as measured by ELISA (FIGS. 68-69) and were found to exhibit polyreactivity in a protein microarray against 9,400 human proteins (3) (FIG. 68). The mature members of the lineage were not polyreactive by ELISA, although some members demonstrated polyreactivity by microarray analysis (DH511.1, DH511.5, DH511.6, and DH511.12P). All DH511 lineage members lacked reactivity by indirect immunofluorescence human epithelial (HEp-2) cell staining assay. Regarding higher affinity autoreactivity with single proteins, mature bnAb DH511.2 reacted with the E3 ubiquitin ligase STIP1 Homology and U-Box Containing Protein 1 (STUB1) while both DH511.11P and DH511.12P reacted with nuclear distribution gene C homolog (*A. nidulans*) (NUDC); DH511.12 also reacted with Scm-like with four MBT domains protein 1 (SFMBT1) (FIG. 68).

To characterize the lipid reactivity of the DH511 clonal lineage, we first determined propensity for lipid membrane binding/insertion of DH511.1-DH511.6 based on HCDR3 hydrophobicity. Three or more Phe or Trp amino acid residues were contained within the HCDR3 sequences of each DH511 clonal lineage member, and several members were found to have at least one Pro, with the exception of DH511.3 and DH511.6. A membrane insertion score was calculated based on the Wimley-White hydrophobicity scale, which measures the propensity of amino acids to sit at the interface of the head and tail group in a lipid bilayer. Notably, membrane insertion scores were similar between the most potent neutralizer DH511.2 and 4E10/10E8 but differed from 2F5 (Supplementary Table 21).

Figure 71A:
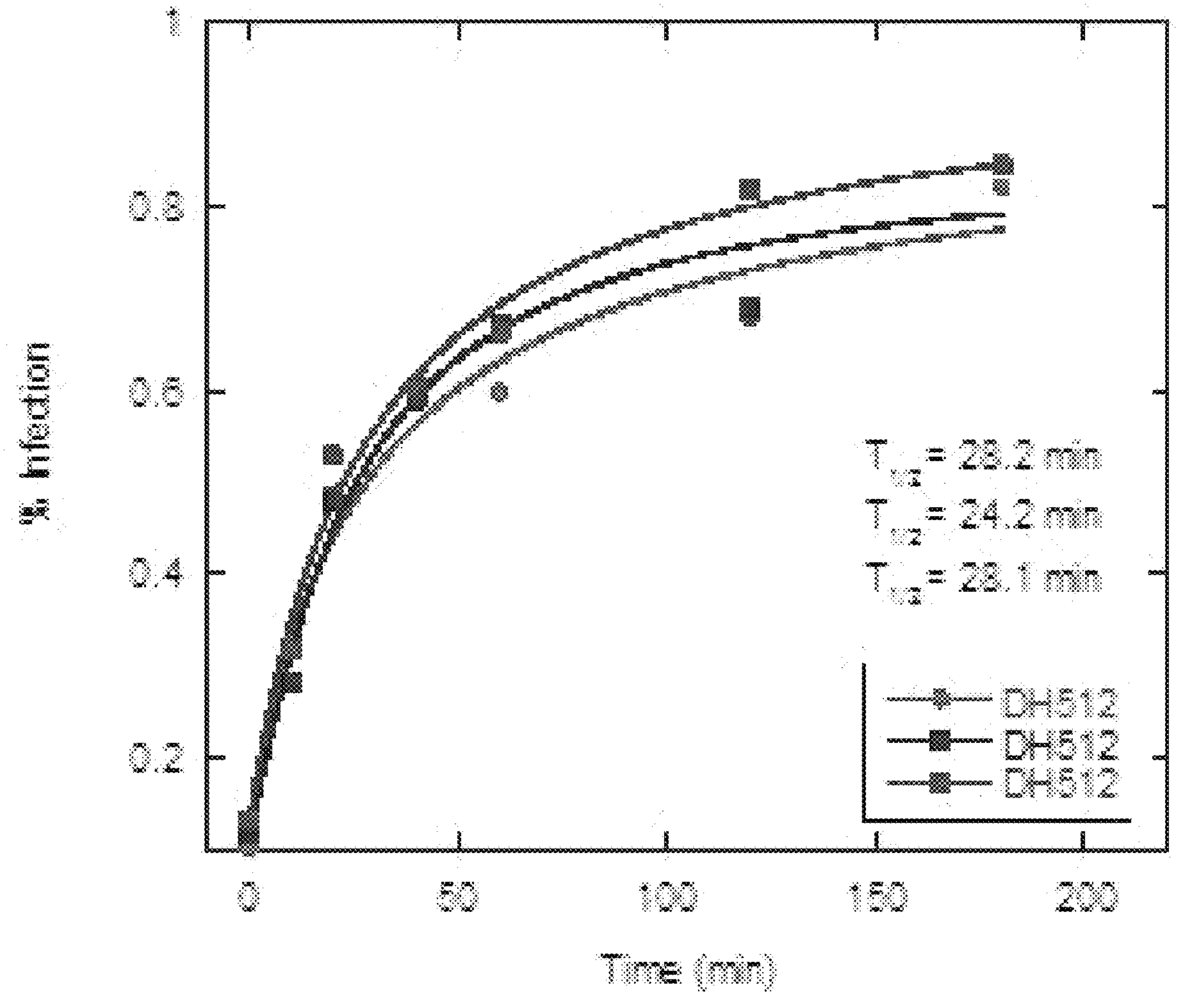
FIG. 71A-C show DH511.2 recognizes a transiently exposed intermediate state of gp41, and the lifetime of DH511.2 epitope exposure is the same as that of 10E8 and 4E10. Time course of neutralization of tier 2 HIV-1 isolate B.BG1168 was measured by addition of mAbs to TZM-bl cells pre-incubated with virus. Half-life values were similar among the three antibodies.
Figure 71B:
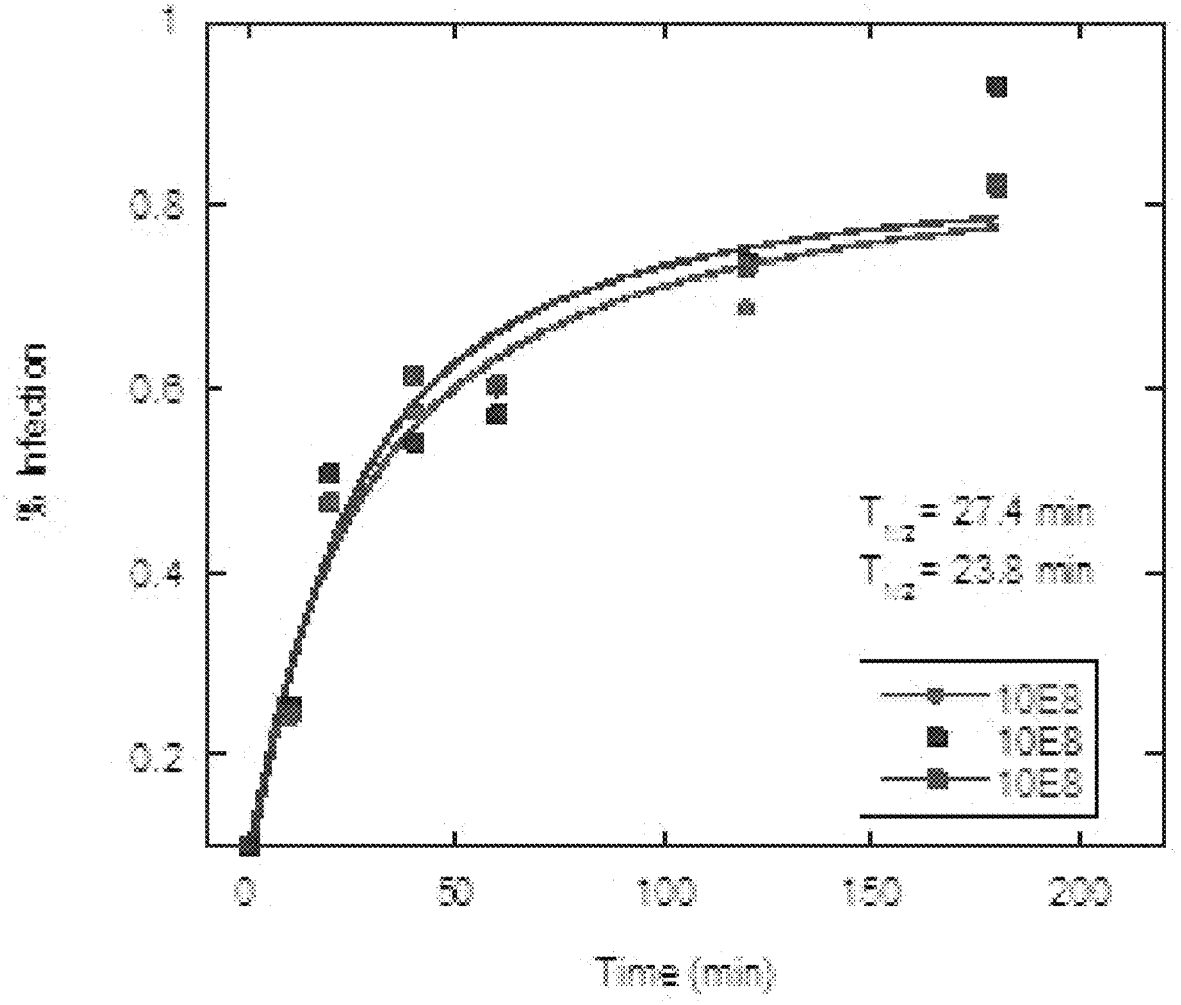
Figure 71C:
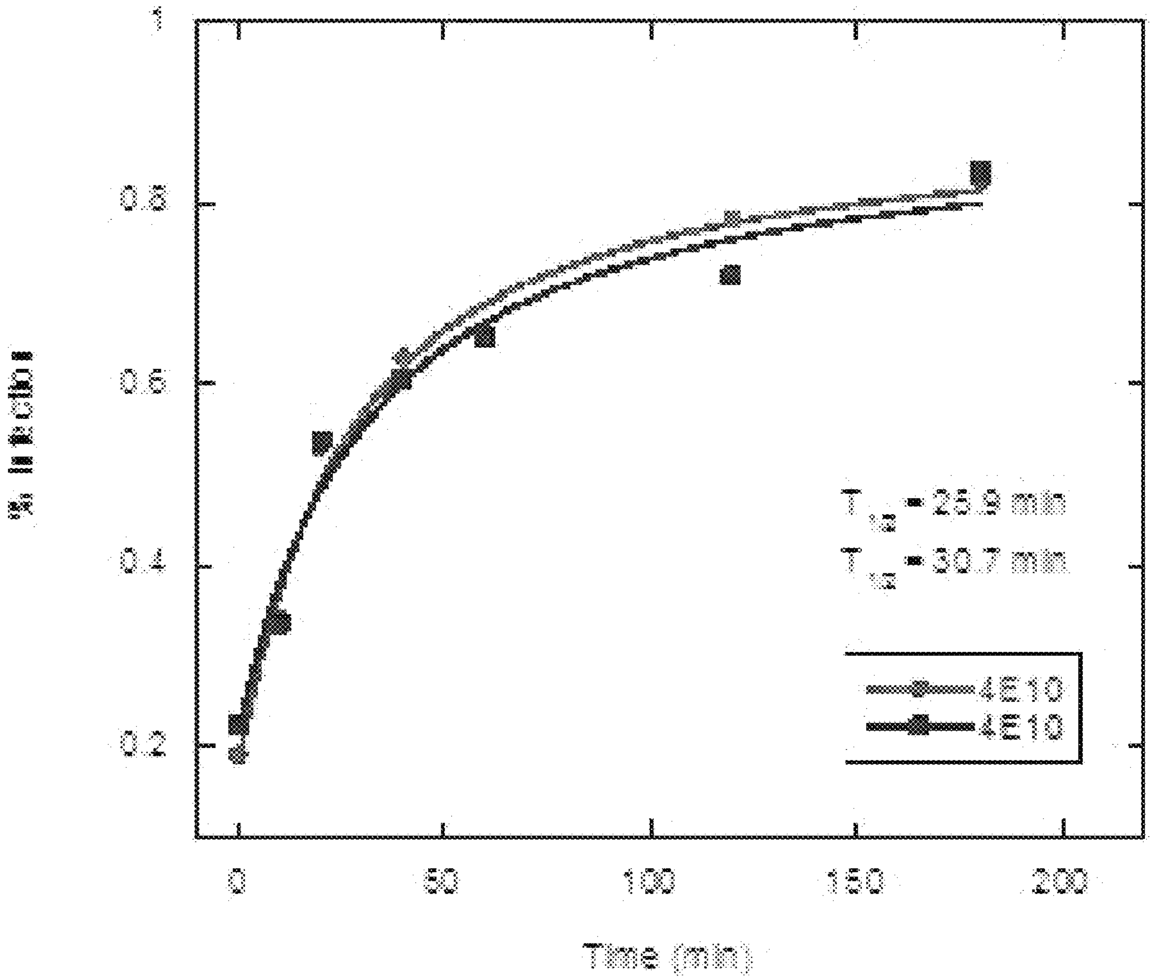
Figure 72:
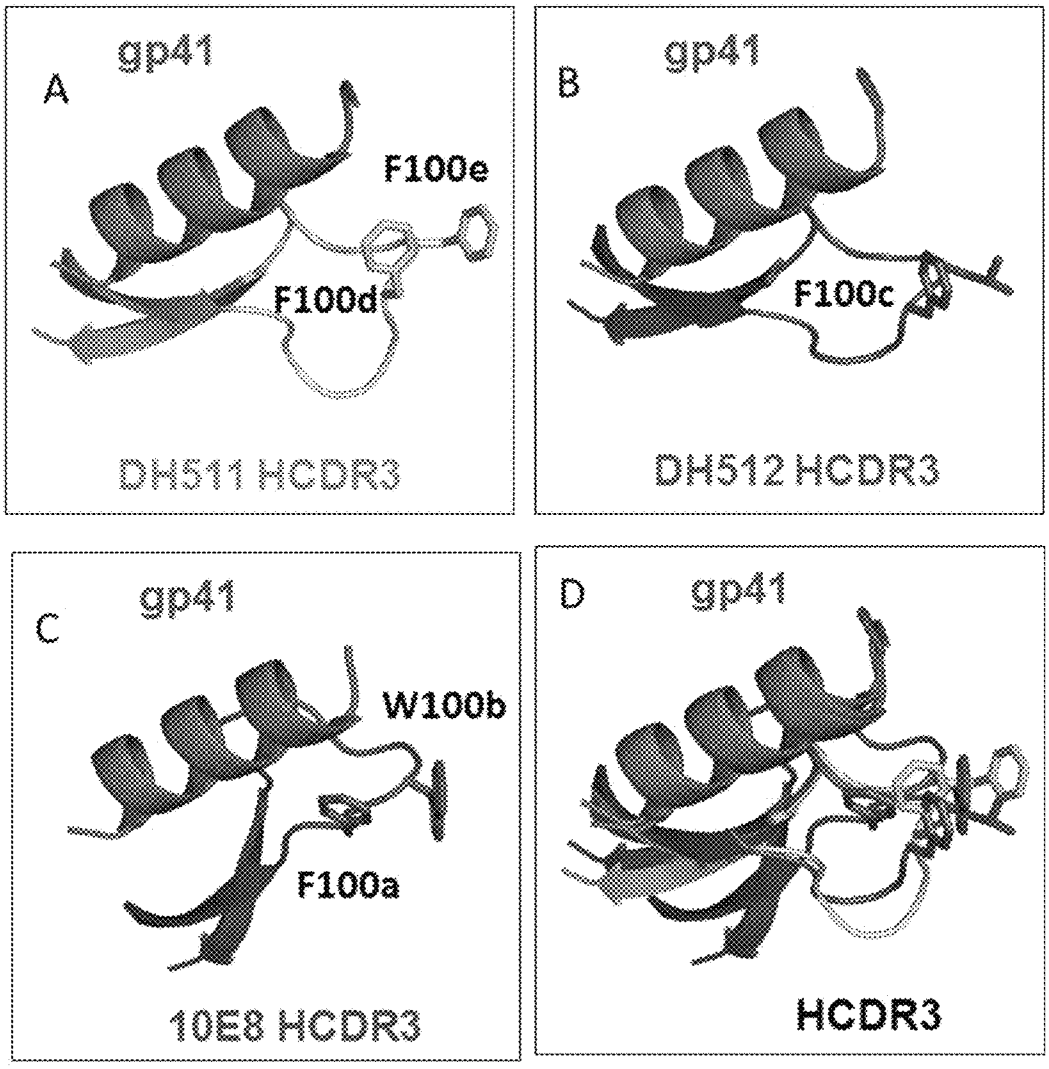
FIG. 72 shows Sequence Comparison of DH511, DH512, and 10E8 HCDR3 Loops (SEQ ID NOs: 326-328). The figure shows that while HCDR3 loops of DH511 and 10E8 lineages are both encoded by D3-3 precursor, substantial differences are observed in their final matured lengths and sequences. One conserved sequence motif between DH511/DH512 and 10E8 HCDR3s appears to be a hydrophobic residue doublet at the center of the loop (boxed).
Figures 74A, 74B:
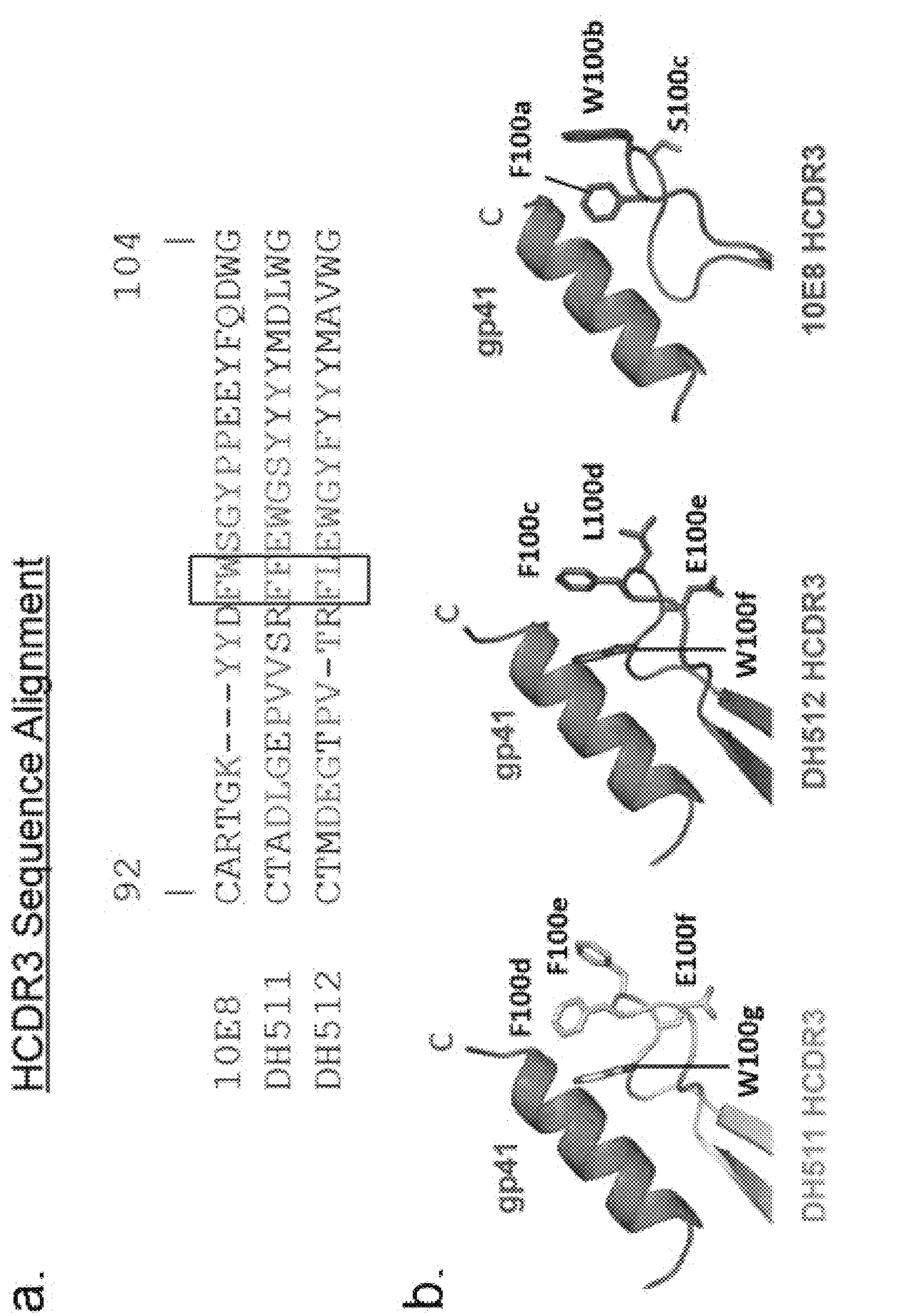
FIGS. 74A-B shows Comparison of DH511, DH512, and 10E8 HCDR3 Loops. (a) Sequence alignment of HCDR3 loops of DH511, DH512, and 10E8 (SEQ ID NOs: 329-331). (b) Structural comparison of HCDR3 loops based on alignment of distal MPER gp41 residues (that CDRH3 orientation differs from FIG. 73). The HCDR3 loops of bNabs that target the gp41 MPER have been shown to be critical for their capacity to neutralize the HIV-1 virus, largely through interactions with the viral membrane. Mutations that reduce hydrophobicity of the HCDR3 loops ablate virus neutralization, while mutations that augment hydrophobicity in turn augment neutralization potency. Given that the DH511 lineage shares a common D3-3 gene with 10E8, we sought to compare the sequences and structures of their respective HCDR3 loops to assess whether common characteristics could be discerned. While sequence alignment of their matured amino acid sequences were quite different, as were their lengths, a conserved hydrophobic residue doublet at the centers of both loops was observed. These two residues have previously been shown to be critical for 10E8 epitope binding and neutralization. Remarkably, despite the overall differences in sequence and length of the DH511/12 and 10E8 HCDR3 loops, when they were compared structurally based on an alignment of MPER distal residues, the conserved hydrophobic residue doublets at their tips ended up spatially co-localized relative to MPER. Studies are underway to assess the importance of these two residues in the DH511 context, and the structures are being utilized to introduce additional mutations that are aimed at improving the neutralization potency of DH511-lineage antibodies as immunotherapeutics. 1Huang, J. et al. Broad and potent neutralization of HIV-1 by a gp41-specific human antibody. Nature 491, 406-412, doi:10.1038/nature11544 (2012).

To further delineate the interaction of DH511 clonal members with the lipid bilayer interface, we determined cardiolipin reactivity and kinetics of binding to MPER peptide versus MPER peptide-liposome conjugates. The UCA and members of the memory B cell clonal lineage did not bind cardiolipin in ELISA (Supplementary Table 22). The binding of gp41 bnAbs 2F5 and 4E10 to gp41-lipid complex has been proposed as a sequential two-step process, in which encountering the lipid membrane takes place first, presumably to aid in docking of the antibody with the transiently exposed gp41 intermediate neutralizing epitope during the virion-host cell fusion process (4, 22, 23). Surface plasmon resonance (SPR) analysis of DH511 lineage fragments of antigen binding (Fabs) demonstrated that DH511.1-DH511.6 and intermediates I1-I5 bound the MPER peptide (NEQELLELDK-WASLWNWFDITNWLWYIR (SEQ ID NO: 2)) with nanomolar affinity (Kd range: 11.1-99.9 nm), while the inferred UCA and intermediate 6 (most closely related to the UCA) did not bind (FIG. 66). Binding kinetics studies as show in FIG. 71), support the hypothesis that like 2F5 and 4E10, DH511 lineage antibodies bind in a two-step conformational change model.

To determine the impact of timing of the gp41 intermediate epitope exposure on HIV-1 neutralization (24), we compared the window of time in which bnAbs DH511.2, 10E8, and 4E10 could neutralize the tier 2 HIV-1 strain B.BG1168 after virus addition to TZM-bl cells. The lifetime of neutralization for DH511.2 ($t_{1/2}$: 26.8±2.3 min) was the same as that for bnAbs 10E8 ($t_{1/2}$: 25.6±2.5 min) and 4E10 ($t_{1/2}$: 28.2±3.5 min), similar to the published half-life of fusion inhibition by the gp41 intermediate mimic T20 (20.2±0.5 min) (24). These results suggest that DH511.2 recognizes a transiently exposed intermediate state of gp41 (25).

Engineering DH511 Clonal Lineage Members for Enhanced Potency

To identify more potent variants of the DH511 clonal lineage, we generated 91 chimeric mAbs by swapping the heavy and light-chains of DH511.2 with those of DH511 lineage members derived from the plasma. Of the 91 chimeric antibodies, one variant, DH511.2_K3 (comprised of the DH511.2 heavy-chain reconstituted with the plasma light-chain of DH511.8P), showed greater potency than 10E8 (Supplementary Table 24). DH511.2_K3 neutralization data are shown in FIGS. 28 and 58.

Sixteen HCDR3 mutations of DH511.2 were made (FIGS. 30-33) to determine effect on DH511.2 potency. FIG. 34 shows neutralization data for sixteen of these antibodies. Additional mutations will be made, including combinations of mutations, from the mutations listed in FIGS. 30-31.

Discussion

We have used a combination of memory B cell sorting (26, 27) and plasma antigen-specific antibody characterization by HCDR3 mass spectrometry sequencing to simultaneously characterize class-switched memory B cell antibodies and plasma antibodies (15, 28-30). The memory B cell repertoire contains multiple specificities of antibodies reflective of an individual's immune history (30) whereas primary contributors to plasma antibodies are both long lived plasma cells as well as shorter lived plasma cells derived from terminally differentiated memory B cells in response to current antigens (16). However, evidence exists that for non-HIV-1 antigens such as influenza (11) and West Nile virus (12), not all of the memory B cell repertoire is found in plasma. Here we demonstrate that class-switched memory B cells and plasma shared the same clonal lineage members of highly broad and potent HIV-1 gp41 neutralizing antibodies.

In the case of HIV-1 antibody responses, the relationship of the memory B cell and plasma antibody pools is complicated by the damage that HIV-1 inflicts on the B cell lineage with disruption of the germinal center in the earliest stages of infection (31), and the accumulation of FcRL4+ memory B cells in chronic infection (8). Interestingly, HIV-1-specific B cell responses are enriched in the FcRL4+ memory B cell compartment and exhibit many features of premature exhaustion (8). Regarding antibodies that target the Env bnAb epitope at the CD4 binding site, it has been shown that ~60% of this response is contained within the exhausted FcRL4+ memory B cell compartment, thus preventing their progression to plasma cells and production of secreted antibody (8, 9). In contrast, Scheid and colleagues studied antigen-specific memory B cell repertoires in HIV-1 infected individuals and found broad diversity of neutralizing antibodies (32). Moreover, analysis has demonstrated bnAb activity in plasma can predict isolation of bnAb variable heavy ($V_H$) and variable light ($V_L$) from memory B cells from the same individual (13, 33-38). Moreover, only a limited number of bnAb specificities are generally present in HIV-1-infected plasma (38, 39), and when bnAbs are isolated from memory B cells in clonal memory B cell cultures, the bnAbs are the minority of the Env specifities isolated (26, 37, 40). Thus, in spite of early damage to B cell follicles and accumulation of memory B cells with an exhaustion phenotype, HIV-1 infected individuals can make productive, albeit subdominant, bnAb responses that progress to plasma cell differentiation and secretion into blood plasma.

A critical question is whether memory B cells in HIV-1 infected individuals are differentiating into the long-lived plasma cell pool that resides in bone marrow and is responsible for long-lived plasma antibody responses (41). We have previously studied the effect of anti-retroviral treatment in HIV-1 infection on the half-lives of Env gp120 and gp41 as well as Gag antibody responses, and demonstrated whereas Env antibody half-life was short for gp120 (81 weeks) and gp41 (33 weeks), antibody half-life was longer for Gag (648 weeks). In contrast, in the same individuals, the half-life of influenza antibodies did not decay over the time studied (42). These data demonstrate that in chronic HIV-1-infection, the cells making plasma gp41 antibodies are not long-lived plasma cells.

Thus, by directly measuring the gp41 broad neutralizing repertoire in memory B cells and plasma, we have directly demonstrated the survival from immune damage of memory B cells to produce plasma broadly neutralizing antibodies. Finally, we show that blood plasma is a rich source for isolation of potent bnAbs for recombinant antibody production and for constructing chimeric memory B cell/plasma antibodies for enhancing antibody potency and breadth.

REFERENCES

1. Huang J, Ofek G, Laub L, Louder M K, Doria-Rose N A, Longo N S, Imamichi H, Bailer R T, Chakrabarti B, Sharma S K, Alam S M, Wang T, Yang Y, Zhang B, Migueles S A, Wyatt R, Haynes B F, Kwong P D, Mascola J R, Connors M. 2012. Broad and potent neutralization of HIV-1 by a gp41-specific human antibody. Nature 491: 406-412.

2. Zwick M B, Labrijn A F, Wang M, Spenlehauer C, Saphire E O, Binley J M, Moore J P, Stiegler G, Katinger H, Burton D R, Parren P W. 2001. Broadly neutralizing antibodies targeted to the membrane-proximal external region of human immunodeficiency virus type 1 glycoprotein gp41. Journal of virology 75:10892-10905.
3. Yang G, Holl T M, Liu Y, Li Y, Lu X, Nicely N I, Kepler T B, Alam S M, Liao H X, Cain D W, Spicer L, VandeBerg J L, Haynes B F, Kelsoe G. 2013. Identification of autoantigens recognized by the 2F5 and 4E10 broadly neutralizing HIV-1 antibodies. The Journal of experimental medicine 210:241-256.
4. Alam S M, McAdams M, Boren D, Rak M, Scearce R M, Gao F, Camacho Z T, Gewirth D, Kelsoe G, Chen P, Haynes B F. 2007. The role of antibody polyspecificity and lipid reactivity in binding of broadly neutralizing anti-HIV-1 envelope human monoclonal antibodies 2F5 and 4E10 to glycoprotein 41 membrane proximal envelope epitopes. Journal of immunology 178:4424-4435.
5. Chen J, Frey G, Peng H, Rits-Volloch S, Garrity J, Seaman M S, Chen B. 2014. Mechanism of HIV-1 neutralization by antibodies targeting a membrane-proximal region of gp41. Journal of virology 88:1249-1258.
6. Liu M, Yang G, Wiehe K, Nicely N I, Vandergrift N A, Rountree W, Bonsignori M, Alam S M, Gao J, Haynes B F, Kelsoe G. 2015. Polyreactivity and autoreactivity among HIV-1 antibodies. Journal of virology 89:784-798.
7. Haynes B F, Gilbert P B, McElrath M J, Zolla-Pazner S, Tomaras G D, Alam S M, Evans D T, Montefiori D C, Karnasuta C, Sutthent R, Liao H X, DeVico A L, Lewis G K, Williams C, Pinter A, Fong Y, Janes H, DeCamp A, Huang Y, Rao M, Billings E, Karasavvas N, Robb M L, Ngauy V, de Souza M S, Paris R, Ferrari G, Bailer R T, Soderberg K A, Andrews C, Berman P W, Frahm N, De Rosa S C, Alpert M D, Yates N L, Shen X, Koup R A, Pitisuttithum P, Kaewkungwal J, Nitayaphan S, Rerks-Ngarm S, Michael N L, Kim J H. 2012. Immune-correlates analysis of an HIV-1 vaccine efficacy trial. The New England journal of medicine 366:1275-1286.
8. Moir S, Ho J, Malaspina A, Wang W, DiPoto A C, O'Shea M A, Roby G, Kottilil S, Arthos J, Proschan M A, Chun T W, Fauci A S. 2008. Evidence for HIV-associated B cell exhaustion in a dysfunctional memory B cell compartment in HIV-infected viremic individuals. The Journal of experimental medicine 205:1797-1805.
9. Kardava L, Moir S, Shah N, Wang W, Wilson R, Buckner C M, Santich B H, Kim L J, Spurlin E E, Nelson A K, Wheatley A K, Harvey C J, McDermott A B, Wucherpfennig K W, Chun T W, Tsang J S, Li Y, Fauci A S. 2014. Abnormal B cell memory subsets dominate HIV-specific responses in infected individuals. The Journal of clinical investigation 124:3252-3262.
10. Boutz D R, Horton A P, Wine Y, Lavinder J J, Georgiou G, Marcotte E M. 2014. Proteomic identification of monoclonal antibodies from serum. Analytical chemistry 86:4758-4766.
11. Wrammert J, Koutsonanos D, Li G M, Edupuganti S, *Sui* J, Morrissey M, McCausland M, Skountzou I, Hornig M, Lipkin W I, Mehta A, Razavi B, Del Rio C, Zheng N Y, Lee J H, Huang M, Ali Z, Kaur K, Andrews S, *Amara* RR, Wang Y, Das S R, O'Donnell C D, Yewdell J W, Subbarao K, Marasco W A, Mulligan M J, Compans R, Ahmed R, Wilson P C. 2011. Broadly cross-reactive antibodies dominate the human B cell response against 2009 pandemic H1N1 influenza virus infection. The Journal of experimental medicine 208:181-193.
12. Purtha W E, Tedder T F, Johnson S, Bhattacharya D, Diamond M S. 2011. Memory B cells, but not long-lived plasma cells, possess antigen specificities for viral escape mutants. The Journal of experimental medicine 208:2599-2606.
13. Georgiev I S, Doria-Rose N A, Zhou T, Kwon Y D, Staupe R P, Moquin S, Chuang G Y, Louder M K, Schmidt S D, Altae-Tran H R, Bailer R T, McKee K, Nason M, O'Dell S, Ofek G, Pancera M, Srivatsan S, Shapiro L, Connors M, Migueles S A, Morris L, Nishimura Y, Martin M A, Mascola J R, Kwong P D. 2013. Delineating antibody recognition in polyclonal sera from patterns of HIV-1 isolate neutralization. Science 340:751-756.
14. Morris L, Chen X, Alam M, Tomaras G, Zhang R, Marshall D J, Chen B, Parks R, Foulger A, Jaeger F, Donathan M, Bilska M, Gray E S, Abdool Karim S S, Kepler T B, Whitesides J, Montefiori D, Moody M A, Liao H X, Haynes B F. 2011. Isolation of a human anti-HIV gp41 membrane proximal region neutralizing antibody by antigen-specific single B cell sorting. PloS one 6:e23532.
15. Lavinder J J, Wine Y, Giesecke C, Ippolito G C, Horton A P, Lungu O I, Hoi K H, DeKosky B J, Murrin E M, Wirth M M, Ellington A D, Dorner T, Marcotte E M, Boutz D R, Georgiou G. 2014. Identification and characterization of the constituent human serum antibodies elicited by vaccination. Proceedings of the National Academy of Sciences of the United States of America 111: 2259-2264.
16. Wine Y, Horton A P, Ippolito G C, Georgiou G. 2015. Serology in the 21st century: the molecular-level analysis of the serum antibody repertoire. Current opinion in immunology 35:89-97.
17. McDaniel J R, DeKosky B J, Tanno H, Ellington A D, Georgiou G. 2016. Ultra-high-throughput sequencing of the immune receptor repertoire from millions of lymphocytes. Nature protocols 11:429-442.
18. DeKosky B J, Ippolito G C, Deschner R P, Lavinder J J, Wine Y, Rawlings B M, Varadarajan N, Giesecke C, Dorner T, Andrews S F, Wilson P C, Hunicke-Smith S P, Willson C G, Ellington A D, Georgiou G. 2013. High-throughput sequencing of the paired human immunoglobulin heavy and light chain repertoire. Nature biotechnology 31:166-169.
19. DeKosky B J, Kojima T, Rodin A, Charab W, Ippolito G C, Ellington A D, Georgiou G. 2015. In-depth determination and analysis of the human paired heavy- and light-chain antibody repertoire. Nature medicine 21:86-91.
20. Gray E S, Madiga M C, Moore P L, Mlisana K, Abdool Karim S S, Binley J M, Shaw G M, Mascola J R, Morris L. 2009. Broad neutralization of human immunodeficiency virus type 1 mediated by plasma antibodies against the gp41 membrane proximal external region. Journal of virology 83:11265-11274.
21. Gray E S, Meyers T, Gray G, Montefiori D C, Morris L. 2006. Insensitivity of paediatric HIV-1 subtype C viruses to broadly neutralising monoclonal antibodies raised against subtype B. PLoS medicine 3:e255.
22. Alam S M, Morelli M, Dennison S M, Liao H X, Zhang R, Xia S M, Rits-Volloch S, Sun L, Harrison S C, Haynes B F, Chen B. 2009. Role of HIV membrane in neutralization by two broadly neutralizing antibodies. Proceedings of the National Academy of Sciences of the United States of America 106:20234-20239.
23. Alam S M, Liao H X, Dennison S M, Jaeger F, Parks R, Anasti K, Foulger A, Donathan M, Lucas J, Verkoczy L, Nicely N, Tomaras G D, Kelsoe G, Chen B, Kepler T B, Haynes B F. 2011. Differential reactivity of germ line allelic variants of a broadly neutralizing HIV-1 antibody to a gp41 fusion intermediate conformation. Journal of virology 85:11725-11731.
24. Shen X, Dennison S M, Liu P, Gao F, Jaeger F, Montefiori D C, Verkoczy L, Haynes B F, Alam S M, Tomaras G D. 2010. Prolonged exposure of the HIV-1 gp41 membrane proximal region with L669S substitution. Proceedings of the National Academy of Sciences of the United States of America 107:5972-5977.
25. Frey G, Chen J, Rits-Volloch S, Freeman M M, Zolla-Pazner S, Chen B. 2010. Distinct conformational states of HIV-1 gp41 are recognized by neutralizing and non-neutralizing antibodies. Nature structural & molecular biology 17:1486-1491.
26. Liao H X, Lynch R, Zhou T, Gao F, Alam S M, Boyd S D, Fire A Z, Roskin K M, Schramm C A, Zhang Z, Zhu J, Shapiro L, Program N C S, Mullikin J C, Gnanakaran S, Hraber P, Wiehe K, Kelsoe G, Yang G, Xia S M, Montefiori D C, Parks R, Lloyd K E, Scearce R M, Soderberg K A, Cohen M, Kamanga G, Louder M K, Tran L M, Chen Y, Cai F, Chen S, Moquin S, Du X, Joyce M G, Srivatsan S, Zhang B, Zheng A, Shaw G M, Hahn B H, Kepler T B, Korber B T, Kwong P D, Mascola J R, Haynes B F. 2013. Co-evolution of a broadly neutralizing HIV-1 antibody and founder virus. Nature 496:469-476.
27. Moody M A, Yates N L, Amos J D, Drinker M S, Eudailey J A, Gurley T C, Marshall D J, Whitesides J F, Chen X, Foulger A, Yu J S, Zhang R, Meyerhoff R R, Parks R, Scull J C, Wang L, Vandergrift N A, Pickeral J, Pollara J, Kelsoe G, Alam S M, Ferrari G, Montefiori D C, Voss G, Liao H X, Tomaras G D, Haynes B F. 2012. HIV-1 gp120 vaccine induces affinity maturation in both new and persistent antibody clonal lineages. Journal of virology 86:7496-7507.
28. Cheung W C, Beausoleil S A, Zhang X, Sato S, Schieferl S M, Wieler J S, Beaudet J G, Ramenani R K, Popova L, Comb M J, Rush J, Polakiewicz R D. 2012. A proteomics approach for the identification and cloning of monoclonal antibodies from serum. Nature biotechnology 30:447-452.
29. Wine Y, Boutz D R, Lavinder J J, Miklos A E, Hughes R A, Hoi K H, Jung S T, Horton A P, Murrin E M, Ellington A D, Marcotte E M, Georgiou G. 2013. Molecular deconvolution of the monoclonal antibodies that comprise the polyclonal serum response. Proceedings of the National Academy of Sciences of the United States of America 110:2993-2998.
30. Lavinder J J, Horton A P, Georgiou G, Ippolito G C. 2015. Next-generation sequencing and protein mass spectrometry for the comprehensive analysis of human cellular and serum antibody repertoires. Current opinion in chemical biology 24:112-120.
31. Levesque M C, Moody M A, Hwang K K, Marshall D J, Whitesides J F, Amos J D, Gurley T C, Allgood S, Haynes B B, Vandergrift N A, Plonk S, Parker D C, Cohen M S, Tomaras G D, Goepfert P A, Shaw G M, Schmitz J E, Eron J J, Shaheen N J, Hicks C B, Liao H X, Markowitz M, Kelsoe G, Margolis D M, Haynes B F. 2009. Polyclonal B cell differentiation and loss of gastrointestinal tract germinal centers in the earliest stages of HIV-1 infection. PLoS medicine 6:e1000107.
32. Scheid J F, Mouquet H, Feldhahn N, Seaman M S, Velinzon K, Pietzsch J, Ott R G, Anthony R M, Zebroski H, Hurley A, Phogat A, Chakrabarti B, Li Y, Connors M, Pereyra F, Walker B D, Wardemann H, Ho D, Wyatt R T, Mascola J R, Ravetch J V, Nussenzweig M C. 2009. Broad diversity of neutralizing antibodies isolated from memory B cells in HIV-infected individuals. Nature 458:636-640.
33. Tomaras G D, Binley J M, Gray E S, Crooks E T, Osawa K, Moore P L, Tumba N, Tong T, Shen X, Yates N L, Decker J, Wibmer C K, Gao F, Alam S M, Easterbrook P, Abdool Karim S, Kamanga G, Crump J A, Cohen M, Shaw G M, Mascola J R, Haynes B F, Montefiori D C, Morris L. 2011. Polyclonal B cell responses to conserved neutralization epitopes in a subset of HIV-1-infected individuals. Journal of virology 85:11502-11519.
34. Simek M D, Rida W, Priddy F H, Pung P, Carrow E, Laufer D S, Lehrman J K, Boaz M, Tarragona-Fiol T, Miiro G, Birungi J, Pozniak A, McPhee D A, Manigart O, Karita E, Inwoley A, Jaoko W, Dehovitz J, Bekker L G, Pitisuttithum P, Paris R, Walker L M, Poignard P, Wrin T, Fast P E, Burton D R, Koff W C. 2009. Human immunodeficiency virus type 1 elite neutralizers: individuals with broad and potent neutralizing activity identified by using a high-throughput neutralization assay together with an analytical selection algorithm. Journal of virology 83:7337-7348.
35. Walker L M, Phogat S K, Chan-Hui P Y, Wagner D, Phung P, Goss J L, Wrin T, Simek M D, Fling S, Mitcham J L, Lehrman J K, Priddy F H, Olsen O A, Frey S M, Hammond P W, Protocol GPI, Kaminsky S, Zamb T, Moyle M, Koff W C, Poignard P, Burton D R. 2009. Broad and potent neutralizing antibodies from an African donor reveal a new HIV-1 vaccine target. Science 326:285-289.
36. Walker L M, Huber M, Doores K J, Falkowska E, Pejchal R, Julien J P, Wang S K, Ramos A, Chan-Hui P Y, Moyle M, Mitcham J L, Hammond P W, Olsen O A, Phung P, Fling S, Wong C H, Phogat S, Wrin T, Simek M D, Protocol GPI, Koff W C, Wilson I A, Burton D R, Poignard P. 2011. Broad neutralization coverage of HIV by multiple highly potent antibodies. Nature 477:466-470.
37. Bonsignori M, Hwang K K, Chen X, Tsao C Y, Morris L, Gray E, Marshall D J, Crump J A, Kapiga S H, Sam N E, Sinangil F, Pancera M, Yongping Y, Zhang B, Zhu J, Kwong P D, O'Dell S, Mascola J R, Wu L, Nabel G J, Phogat S, Seaman M S, Whitesides J F, Moody M A, Kelsoe G, Yang X, Sodroski J, Shaw G M, Montefiori D C, Kepler T B, Tomaras G D, Alam S M, Liao H X, Haynes B F. 2011. Analysis of a clonal lineage of HIV-1 envelope V2/V3 conformational epitope-specific broadly neutralizing antibodies and their inferred unmutated common ancestors. Journal of virology 85:9998-10009.
38. Bonsignori M, Montefiori D C, Wu X, Chen X, Hwang K K, Tsao C Y, Kozink D M, Parks R J, Tomaras G D, Crump J A, Kapiga S H, Sam N E, Kwong P D, Kepler T B, Liao H X, Mascola J R, Haynes B F. 2012. Two distinct broadly neutralizing antibody specificities of different clonal lineages in a single HIV-1-infected donor: implications for vaccine design. Journal of virology 86:4688-4692.
39. Walker L M, Simek M D, Priddy F, Gach J S, Wagner D, Zwick M B, Phogat S K, Poignard P, Burton D R. 2010. A limited number of antibody specificities mediate broad and potent serum neutralization in selected HIV-1 infected individuals. PLoS pathogens 6:e1001028.

40. Gao F, Bonsignori M, Liao H X, Kumar A, Xia S M, Lu X, Cai F, Hwang K K, Song H, Zhou T, Lynch R M, Alam S M, Moody M A, Ferrari G, Berrong M, Kelsoe G, Shaw G M, Hahn B H, Montefiori D C, Kamanga G, Cohen M S, Hraber P, Kwong P D, Korber B T, Mascola J R, Kepler T B, Haynes B F. 2014. Cooperation of B cell lineages in induction of HIV-1-broadly neutralizing antibodies. Cell 158:481-491.

41. Amanna I J, Carlson N E, Slifka M K. 2007. Duration of humoral immunity to common viral and vaccine antigens. The New England journal of medicine 357:1903-1915.

42. Bonsignori M, Moody M A, Parks R J, Holl T M, Kelsoe G, Hicks C B, Vandergrift N, Tomaras G D, Haynes B F. 2009. HIV-1 envelope induces memory B cell responses that correlate with plasma antibody levels after envelope gp120 protein vaccination or HIV-1 infection. Journal of immunology 183:2708-2717.

Supplementary Materials and Methods

Donor Information

Plasma and peripheral blood mononuclear cells were collected from South African donor CH0210, chronically infected with a clade C virus for an unknown period at the time of enrollment in the Center for HIV/AIDS Vaccine Immunology (CHAVI) 001 chronic HIV-1 infection cohort (previously described in (33). Informed consent was obtained under clinical protocols approved by the Institutional Review Board of the Duke University Health System and clinical site in South Africa. The DH511 bnAb lineage was isolated from PBMC and plasma collected at 8 weeks post-study enrollment, where the viral load was 5,180 copies/ml and CD4 T cell count was unknown, at which time donor CH0210 had not initiated anti-retroviral therapy (ART).

Epitope Mapping and Neutralization-Based Epitope Prediction Analysis

Donor CH0210 plasma was screened for neutralization breadth utilizing standard experimental mapping and computational methods for epitope prediction (13, 43). Anti-MPER bnAb activity was detected using two different assays: plasma neutralization of the HIV-2/HIV-1 MPER chimeric pseudovirus C1C and plasma adsorption with MPER peptide coated magnetic beads, followed by testing of adsorbed plasmas for reduction of neutralization activity as described previously (44). An algorithm for Neutralization-based Epitope Prediction (NEP) (13, 43) was used to delineate the specificities mediating breadth against a panel of 21 diverse HIV-1 strains. The resulting linear coefficients on a scale of (0 to 1) from the computational procedure was used to predict the relative prevalence of each of the reference antibody specificities in donor CH0210 plasma.

Antigen-Specific Single Memory B Cell Sorting and Antibody Expression

As previously described (14), fluorescently-labeled MPER peptide tetramer probes were generated using biotinylated MPR. 03 peptide (KKKNEQELLELDKWASLWNWFDITNWLWYIRKKK-biotin (SEQ ID NO: 463)) (CPC Scientific Inc., San Jose, CA) conjugated to fluorophore-labeled streptavidins, yielding a tetramer with four MPER epitopes for surface Ig cross-linking. Eleven and a half million PBMC from donor CH0210 were stained with MPR.03-Alexa647 and MPR.03-Brilliant Violet 421 peptide tetramers and a cocktail of antibodies to identify MPER-specific memory B cells: surface IgM (FITC), surface IgD (phycoerythrin [PE]), CD3 (PE-Cy5), CD16 (Brilliant Violet 570), CD235a (PE-Cy5), and CD19 (allophycocyanin [APC]-Cy7) (BD Biosciences, San Jose, CA); CD14 (Brilliant Violet 605) (Invitrogen, Carlsbad, CA); CD27 (PE-Cy7), CD38 (APC-Alexa Fluor 700) (Beckman Coulter, Brea, CA), and CD10 (ECD) (Beckman Coulter, Brea, CA). Aqua blue vital dye (Invitrogen, Carlsbad, CA) was used to stain dead cells. Using a four laser FACS Aria cell sorter and FACSDiva software (BD Biosciences, San Jose, CA), MPR.03 double positive CD16-CD14-CD3-CD235-CD19+ IgD-CD38hi memory B cells were single cell sorted into individual wells of a 96-well plate containing reverse transcription (RT) reaction buffer (5 μL of 5' first-strand cDNA buffer, 0.5 μL of RNaseOUT [Invitrogen, Carlsbad, CA], 1.25 μL of dithiothreitol, 0.0625 μL Igepal CA-630 [Sigma, St. Louis, Mo.], 13.25 μL of distilled H2O [dH2O; Invitrogen, Carlsbad, CA]). Data were further analyzed using FlowJo software (TreeStar, Ashland, OR). Plates were stored at −80° C. until PCR could be performed.

PCR Amplification and Expression of Ig Genes

Immunoglobulin genes were amplified from RNA of isolated cells by reverse transcription-polymerase chain reaction (RT-PCR). For RT, 10 mM dNTPs (New England Biolabs, Ipswich, Mass.), 3 μl random hexamers at 150 ng/ml (GeneLink, Hawthorne, NY), and 1 μl SuperScript® III (Invitrogen, Carlsbad, CA) were added to each well and subjected to thermocycling under the following conditions: 42° C. for 10 minutes, 25° C. for 10 minutes, 50° C. for 60 minutes and 94° C. for 5 minutes. IgH, Igκ, and Igλ variable region genes were separately amplified from the cDNA by nested PCR, using AmpliTaq Gold® 360 Mastermix (Invitrogen, Carlsbad, Calif.), heavy-chain (45) and light-chain gene-specific primers as previously described (46). PCR amplicons were purified and sequenced, and $V_HDJ_H$ and VOL genes, mutation frequencies, and CDR3 lengths were determined using the Clonanalyst software (47). Clonal relatedness and inference of the unmutated common ancestor (UCA) and intermediate antibodies were determined by computational methods as described in (26, 40, 48). Maximum likelihood phylogenetic trees were constructed from V(D)J sequences using the Phylogeny Inference Package (PHYLIP) (version 3.69; (49). Transient small-scale expression of antibodies was achieved by overlapping PCR assembly of variable heavy and light-chain gene pairs into IgH, Igκ, and Igλ linear expression cassettes for production of full length IgG1 mAbs by transfection into 293T cells as described previously (46). Supernatants were screened for HIV-1 Env binding by ELISA and neutralization activity in TZM-bl cells. For large scale antibody production, antibody variable heavy-chain and light-chain genes were de novo synthesized (GenScript, Township, NJ), cloned into pcDNA3.1 expression vectors containing the constant regions of IgG1 (46), and co-transfected at equal ratios in Expi 293i cells using ExpiFectamine 293 transfection reagents (Thermo Fischer Scientific, Waltham, MA) according to the manufacturer's instructions. Culture supernatants were harvested and concentrated after 4-5 days incubation at 37° C. and 8% $CO_2$, followed by affinity purification by protein A column (Pierce, Thermo Fisher Scientific, Waltham, MA). Antibody purity was evaluated by SDS-Page and Coomassie Blue staining for heavy and light-chains of the appropriate size.

ELISA Assays

Binding of transiently transfected supernatants and mAbs to HIV-1 Env proteins and peptides was detected by enzyme-linked immunosorbent assay (ELISA). High-binding 384-well plates (Corning, Oneonta, NY) were coated overnight at 4° C. or for 2 hours at room temperature with 2 μg/ml HIV-1 protein or streptavidin (for detection of binding to biotinylated peptides) in 0.1 M sodium bicarbonate (Sigma Aldrich, St. Louis, MO). Plates were blocked for 1 hour at room temperature with assay diluent comprised of phosphate buffered saline (PBS), 4% (weight/volume) whey protein (BiPro USA, Prairie, MN), 15% normal goat serum (Invitrogen, Carlsbad, CA), 0.5% Tween 20, and 0.05% sodium azide (Sigma Aldrich, St. Louis, MO), followed by a 1 hour incubation with antibody at a starting concentration of 100 μg/ml, serially diluted 3-fold. Horseradish peroxidase-conjugated goat anti-human IgG Fc antibody (Jackson ImmunoResearch Laboratories, West Grove, PA) was added to each well and incubated for 1 hour, after which plates were washed with PBS/0.1% Tween 20 and developed with SureBlue Reserve TMB One Component Microwell Peroxidase Substrate for 15 minutes (KPL, Gaithersburg, MD). Development was stopped with 0.1 M HCl, and plates were read at 450 nm. Experiments were performed in duplicate, and results were reported as logarithm area under the curve (Log AUC). For epitope mapping, purified mAbs were screened as listed above against a panel of MPR.03 alanine scanned peptides. Epitope positions were defined by MPR.03 alanine scan mutations that reduced the Log AUC by >50% compared to the wild-type peptide.

Neutralization Assays

Neutralization assays were performed using HIV-1 Env pseudoviruses to infect TZM-bl cells as previously described (50, 51). A five-parameter hill slope equation was used to fit neutralization curves by non-linear regression and for determination of maximum percent inhibition (MPI) values. Titers were calculated as 50% or 80% inhibitory concentrations ($IC_{50}$ and $IC_{80}$) and reported as the concentration of antibody causing a 50% or 80% reduction in relative luminescence units compared to virus control wells. Mapping of the MPER residues critical for neutralization was performed using a panel of alanine scanned COT6.15 Env pseudoviruses as described previously (20, 21).

Poly/Autoreactivity Analysis

Antibody binding to a panel of nine autoantigens, including Sjogren's syndrome antigen (SSA), SSB, Smith antigen (Sm), ribonucleoprotein (RNP), scleroderma 70 (Scl-70), Jo-1, double-stranded DNA (dsDNA), centromere B (Cent B), and histone, was quantified by ELISA. Anti-cardiolipin reactivity was measured using the QUANTA Lite ACA IgG III ELISA kit (Nova Diagnostics, San Diego, CA) per the manufacturer's instructions as previously described (52). Antibodies were assayed for reactivity to the human epithelial cell line (HEp-2) by indirect immunofluorescence staining using the IFA ANA/Hep-2 Test System (Zeus Scientific, Somerville, N.J.) per the manufacturer's protocol. Antibodies were diluted to 50 μg/ml and 25 μg/ml and scored negative or positive (1+ to 4+) at each dilution. Antibodies were also screened for binding to a panel of >9,400 human proteins using a Protoarray microarray (Invitrogen, Carlsbad, Calif.) according to the manufacturer's instructions and as described in (6). Briefly, the array was blocked and incubated on ice with 2 μg/ml HIV-1 antibody or the isotype control antibody, human myeloma protein, 151K (Southern Biotech, Birmingham, AL) for 90 minutes. Antibody binding was detected with 1 μg/ml anti-human IgG-Alexa-647 secondary antibody (Invitrogen). Arrays were scanned using a GenePix 4000B scanner (Molecular Devices, Sunnyvale, CA) at a wavelength of 635 nm, 10 μm resolution, using 100% power and 650 gain. The fluorescence intensity of antibody binding was measured with the GenePix Pro 5.0 program (Molecular Devices, Sunnyvale, CA).

Surface Plasmon Resonance Affinity and Kinetics Measurements

Surface plasmon resonance analysis was performed on a Biacore 3000 instrument (GE Healthcare, Little Chalfont, UK) at 25° C. and data analyzed using the BIAevaluation 4.1 software (BIAcore) as described previously (Alam et al. JI 2007). To determine the affinity, association and dissociation rate constants of the DH511 clonal lineage to MPER, biotinylated MPR.03 peptide was coated on streptavidin sensors at a density of 58 response units (RUs). DH511 lineage Fabs were injected over flow cells at increasing concentrations at a flow and minute dissociation steps. Curves were blank surface and CH58 Fab analyte subtracted. Peptide-liposome conjugates were generated with MPER656.1-GTH1 peptides using an extrusion method (4) and analyzed for binding in a two-step encounter docking model as described previously (4).

Time Course of DH511.2 Neutralization

The time course of DH511.2 neutralization was determined using a post-attachment HIV-1 pseudotyped virus neutralization assay described previously (53). Inhibitory concentrations of DH511.2, 10E8, and 4E10 mAb were added to TZM-bl cells incubated with B.BG1168 virus at different time intervals after infection. Infectivity was measured in relative light units (RLUs).

High-Throughput Paired VH:VL Sequencing of Immunoglobulin Transcripts

Material & reagents. Protein G Plus agarose, NeutrAvidin agarose, immobilized pepsin resin and Hypersep SpinTip C18 columns (C18-SpinTips) were acquired from Pierce (Thermo Fisher Scientific, Rockford, IL). TRIS hydrocholoride (Tris-HCl), ammonium bicarbonate (NH4HCO3), 2,2,2-trifluoroethanol (TFE), dithiothrietol (DTT), and iodoacetamide (IAM) were obtained from Sigma-Aldrich (St. Louis, MO). LC-MS grade water, acetonitrile (ACN), and formic acid were purchased from EMD (Billerica, MA).

Isolation of memory B cells. Frozen PBMCs (10 million cells in 1 mL) were thawed at 37° C., resuspended in 50 mL of RPMI 1640 (Lonza) supplemented with 10% Fetal Bovine Serum, lx non-essential amino acids, lx sodium pyruvate, lx glutamine, lx penicillin/streptomycin, and 20 U/mL DNAse I, and recovered via centrifugation (300 g for 10 min at 20° C.). The cells were then resuspended in 4 mL of RPMI and allowed to recover at 37° C. for 30 min. The cells were diluted with 10 mL of cold MACS buffer (PBS supplemented with 0.5% BSA and 2 mM EDTA), collected by centrifugation (300 g for 10 min at 4° C.), and depleted of non-B cells using the Human Memory B Cell Isolation Kit with an LD column (Miltenyi Biotec) as per the manufacturer's instructions. This yielded 400,000-500,000 B cells per vial.

Amplification of the paired VH:VL repertoire. The paired VH and VL sequences were then determined using a custom designed axisymmetric flow focusing device (19) that is comprised of three concentric tubes. Total B cells were suspended in 6 mL of cold PBS and passed through the innermost tube at a rate of 0.5 mL/min. Oligo $d(T)_{25}$ magnetic beads (1 μm diameter at a concentration of 45 μL beads/mL solution; NEB) were washed, subjected to focused ultrasonication (Covaris) to dissociate any aggregates, resuspended in 6 mL of lysis buffer (100 mM Tris-HCl pH 7.5, 500 mM LiCl, 10 mM EDTA, 1% Lithium dodecyl sulfate (LiDS), 5 mM DTT), and passed through the middle tube at a rate of 0.5 mL/min. The outer tubing contained an oil phase (mineral oil containing 4.5% Span-80, 0.4% Tween-80, and 0.05% Triton X-100; Sigma-Aldrich) flowing at 3 mL/min. The cells, beads, and lysis buffer were emulsified as they passed through a custom designed 120 μm diameter orifice, and were subsequently collected in 2 mL microcentrifuge tubes. Each tube was inverted several times, incubated at 20° C. for 3 minutes, and then placed on ice.

Following the collection phase, emulsions were pooled into 50 mL conicals, and centrifuged (4,000 g for 5 min at 4° C.). The mineral oil (upper phase) was decanted, and the emulsions (bottom phase) were broken with water-saturated cold diethyl ether (Fischer). Magnetic beads were recovered following a second centrifugation step (4,000 g for 5 min at 4° C.) and resuspended in 1 mL of cold Buffer 1 (100 mM Tris pH 7.5, 500 mM LiCl, 10 mM EDTA, 1% LiDS, 5 mM DTT). The beads were then serially pelleted using a magnetic rack, and washed with the following buffers: 1 mL lysis buffer, 1 mL Buffer 1, and 0.5 mL Buffer 2 (20 mM Tris pH 7.5, 50 mM KCl, 3 mM MgCl). The beads were split into two aliquots, and each was then pelleted one final time and resuspended in an RT-PCR mixture (19) containing VH and VL Framework Region 1 (FR1) linkage primers or VH and VL leader peptide (LP) linkage primers (Supplementary Tables 28 and 29). The RT-PCR mixtures were then added dropwise to 9 mL of chilled oil phase in an IKA dispersing tube (DT-20, VWR) and emulsified using an emulsion dispersing apparatus (Ultra-Turrax® Tube Drive; IKA) for 5 min. The emulsions were aliquoted into 96-well PCR plates (100 uL/well), and subjected to RT-PCR under the following conditions: 30 min at 55° C. followed by 2 min at 94° C.; 4 cycles of 94° C. for 30 s, 50° C. for 30 s, 72° C. for 2 min; 4 cycles of 94° C. for 30 s, 55° C. for 30 s, 72° C. for 2 min; 32 cycles of 94° C. for 30 s, 60° C. for 30 s, 72° C. for 2 min; 72° C. for 7 min; held at 4° C.

Following RT-PCR, the emulsions were collected in 2 mL microcentrifuge tubes and centrifuged (16000 g for 10 min at 20° C.). The mineral oil (upper phase) was decanted, and water-saturated ether was used to break the emulsions. The aqueous phase (containing the DNA) was extracted three times by sequentially adding ether, centrifuging the samples (16000 g for 30 s at 20° C.), and removing the upper ether phase. Trace amounts of ether were removed using a SpeedVac for 30 min at 20° C. The DNA amplicons were purified using a silica spin column (Zymo-Spin™ I, Zymo Research) according to the manufacturer's instructions, and eluted in 40 μL $H_2O$. The two samples were then amplified through a nested PCR (see Supplementary Table 30 for primers) using Platinum Taq (Life Technologies) under the following conditions: (FR1 primer derived sample) 2 min at 94° C., 32 cycles of 94° C. for 30 s, 62° C. for 30 s, 72° C. for 20 s; 72° C. for 7 min; held at 4° C.; (LP primer derived sample) 2 min at 94° C., 27 cycles of 94° C. for 30 s, 62° C. for 30 s, 72° C. for 20 s; 72° C. for 7 min; held at 4° C. The amplicons, approximately 850 bp in length, were gel purified from 1% agarose using a gel extraction kit (Zymo Research) according to the manufacturer's instructions, and eluted in 20 μL $H_2O$.

To determine the full length VH and VL reads for antibody expression studies, the paired amplicon was subjected to an additional PCR using NEBNext high fidelity polymerase (NEB) to specifically amplify the full VH chain and the full VL chain separately in addition to the paired chains (Note: the paired reads sequence the entire J- and D-regions, and the fragment of the V regions spanning FR2 to CDR3). Each sample was split into 5 reactions and subjected to the following PCR conditions: 30 s at 98° C., X cycles of 98° C. for 10 s, 62° C. for 30 s, 72° C. for Y s; 72° C. for 7 min; held at 4° C. (See Supplementary Table 31 for the PCR conditions and Supplementary Table 32 for the primer sequences). Finally, these sequences were amplified one final time with TSBC compatible barcoding primers following the protocol shown in Supplementary Table 33, gel purified from 1% agarose using a gel purification kit according to manufacturer's instructions, and submitted for paired-end Illumina NGS.

Bioinformatic analysis of NGS data. Raw 2×300 MiSeq reads were quality filtered (minimum Phred score of 20 over half of the nucleotide sequence) and submitted to MiXCR (54) for CDR3 identification and gene annotation. Productive VH and VL reads were paired by Illumina MiSeq ID using a custom python script. Full length VH and VL reads were stitched together using FLAsH (55) and then quality filtered. Full length VH and VL constructs were designed by matching the paired CDRH3:CDRL3 nucleotide sequences to the respective CDR3 in the full length VH and VL libraries.

Sample preparation & LC-MS/MS analysis. Serum IgG from donor 0210 was purified by Protein G Plus agarose affinity chromatography, and $F(ab')_2$ fragments were generated by digestion with immobilized pepsin. Antigen-specific $F(ab')_2$ was isolated by affinity chromatography with the biotinylated MPER peptide coupled to NeutrAvidin agarose and eluted in 100 mM glycine pH 2.7. The collected fractions were neutralized and the protein containing fractions were pooled and prepared for LC-MS/MS as described previously (10). Briefly, protein samples were concentrated and resuspended in 50% (v/v) TFE, 50 mM $NH_4HCO_3$ and 2.5 mM DTT and incubated at 55° C. for 45 min. The reduced samples were then alkylated with IAM in the dark, at room temperature for 30 min. The reaction was quenched by addition of DTT and the samples were diluted to 5% TFE and digested with trypsin (trypsin/protein ration of 1:75 at 37° C. for 5 h). The digestion was stopped by addition of formic acid to 1% (v/v). The samples were then concentrated by SpeedVac, resuspended in 5% ACN, 0.1% formic acid and the peptides were washed on C18-SpinTips according to the manufacturer's protocol. Subsequently, the peptides were separated by reverse phase chromatography (Dionex UltiMate 3000 RSLCnano system with Dionex Acclaim PepMapRSLC C18 column, Thermo Scientific) and analyzed on-line by nano-ESI tandem MS on an Orbitrap Velos Pro (Thermo Scientific). MS1 scans were collected in the orbitrap at 60,000 resolution and ions with >+1 charge were fragmented by CID with up to 20 MS2 spectra collected per MS1.

Computational interpretation of peptide mass spectra. Full length VH and VL sequencing data (see above) was submitted to the IMGT/HighV-Quest Tool (56) for annotation and unique full length VH sequences were clustered into clonotypes according to their CDRH3 sequences with a cut-off of 85% identity as described previously (29). The sample-specific target protein sequence database was constructed from the full-length VH and VL sequences mentioned above (≥2 reads), Ensembl human protein-coding sequences and common contaminants (maxquant.org). The spectra were then searched against this database using the SEQUEST (Proteome Discoverer 1.4, Thermo Scientific) with previously described settings (15). The resulting PSMs were filtered with Percolator (Proteome Discoverer 1.4) to control false discovery rates (FDR) to <1% and the average mass deviation (AMD) was calculated for all high-confidence PSMs and peptides with an AMD of <1.5 ppm were kept for the final dataset. Informative peptides, as defined previously (15), were grouped by their CDRH1, 2 or 3 association and for each group the abundances of the corresponding clonotypes were determined by the sum of the extracted-ion chromatograms of the respective precursor ions.

Crystallization, Structure Determination, and Structural Analysis.

Purified DH511.1 and DH511.2 fragments of antigen binding (Fabs) were set up in crystallization trials in complex with a panel of gp41 MPER peptides. For each complex, 576 initial conditions from commercially available screens (Hampton Research, Rigaku) were set up as vapor diffusion sitting drops robotically (TTP Labtech). Crystals of DH511 Fab in complex with gp41 MPER peptide 656-683 were obtained in a condition composed of 30% PEG 1500, while those of DH511.2 Fab in complex with peptides MPR.03.DN4 and MPR.03.DN14, were obtained in 30% PEG 1500, 10% Isopropanol, 0.1 M $CaCl_2$, 0.1 M Imidazole pH 6.5 and in 20% PEG 8000, 10% PEG 400, 0.5 M NaCl, 0.1 M $C_2H_3NaO_2$ pH 5.5, respectively. Crystal hits were hand optimized and X-ray diffraction data extended to 2.8, 2.65, and 2.2 Å, respectively. Data was processed with HKL-2000 (57) and structures were solved by molecular replacement using the DH514 Fab unliganded structure as a search model in Phaser (58). The structures were refined to $R_{crystal}/R_{free}$ of 21.28/25.57, 25.61/28.99, and 19.03/22.63%, respectively, using Phenix (59) combined with iterative model building in Coot (60). Interactive surfaces were determined using Pisa (61) and structural alignments using LSQKAB (62). All graphical images were prepared with Pymol (PyMOL Molecular Graphics System). X-ray diffraction data was collected at SER CAT ID-22 or BM-22 beamlines of the Advanced Photon Source (Argonne, IL), under General User Proposal 44127 (G.O.).

SUPPLEMENTAL REFERENCES

1. Huang J, Ofek G, Laub L, Louder M K, Doria-Rose N A, Longo N S, Imamichi H, Bailer R T, Chakrabarti B, Sharma S K, Alam S M, Wang T, Yang Y, Zhang B, Migueles SA, Wyatt R, Haynes B F, Kwong P D, Mascola J R, Connors M. 2012. Broad and potent neutralization of HIV-1 by a gp41-specific human antibody. Nature 491: 406-412.
2. Zwick M B, Labrijn A F, Wang M, Spenlehauer C, Saphire E O, Binley J M, Moore J P, Stiegler G, Katinger H, Burton D R, Parren P W. 2001. Broadly neutralizing antibodies targeted to the membrane-proximal external region of human immunodeficiency virus type 1 glycoprotein gp41. Journal of virology 75:10892-10905.
3. Yang G, Holl T M, Liu Y, Li Y, Lu X, Nicely N I, Kepler T B, Alam S M, Liao H X, Cain D W, Spicer L, VandeBerg J L, Haynes B F, Kelsoe G. 2013. Identification of autoantigens recognized by the 2F5 and 4E10 broadly neutralizing HIV-1 antibodies. The Journal of experimental medicine 210:241-256.
4. Alam S M, McAdams M, Boren D, Rak M, Scearce R M, Gao F, Camacho Z T, Gewirth D, Kelsoe G, Chen P, Haynes B F. 2007. The role of antibody polyspecificity and lipid reactivity in binding of broadly neutralizing anti-HIV-1 envelope human monoclonal antibodies 2F5 and 4E10 to glycoprotein 41 membrane proximal envelope epitopes. Journal of immunology 178:4424-4435.
5. Chen J, Frey G, Peng H, Rits-Volloch S, Garrity J, Seaman M S, Chen B. 2014. Mechanism of HIV-1 neutralization by antibodies targeting a membrane-proximal region of gp41. Journal of virology 88:1249-1258.
6. Liu M, Yang G, Wiehe K, Nicely N I, Vandergrift N A, Rountree W, Bonsignori M, Alam S M, Gao J, Haynes B F, Kelsoe G. 2015. Polyreactivity and autoreactivity among HIV-1 antibodies. Journal of virology 89:784-798.
7. Haynes B F, Gilbert P B, McElrath M J, Zolla-Pazner S, Tomaras G D, Alam S M, Evans D T, Montefiori D C, Karnasuta C, Sutthent R, Liao H X, DeVico A L, Lewis G K, Williams C, Pinter A, Fong Y, Janes H, DeCamp A, Huang Y, Rao M, Billings E, Karasavvas N, Robb M L, Ngauy V, de Souza M S, Paris R, Ferrari G, Bailer R T, Soderberg K A, Andrews C, Berman P W, Frahm N, De Rosa S C, Alpert M D, Yates N L, Shen X, Koup R A, Pitisuttithum P, Kaewkungwal J, Nitayaphan S, Rerks-Ngarm S, Michael N L, Kim J H. 2012. Immune-correlates analysis of an HIV-1 vaccine efficacy trial. The New England journal of medicine 366:1275-1286.
8. Moir S, Ho J, Malaspina A, Wang W, DiPoto A C, O'Shea M A, Roby G, Kottilil S, Arthos J, Proschan M A, Chun T W, Fauci A S. 2008. Evidence for HIV-associated B cell exhaustion in a dysfunctional memory B cell compartment in HIV-infected viremic individuals. The Journal of experimental medicine 205:1797-1805.
9. Kardava L, Moir S, Shah N, Wang W, Wilson R, Buckner C M, Santich B H, Kim L J, Spurlin E E, Nelson A K, Wheatley A K, Harvey C J, McDermott A B, Wucherpfennig K W, Chun T W, Tsang J S, Li Y, Fauci A S. 2014. Abnormal B cell memory subsets dominate HIV-specific responses in infected individuals. The Journal of clinical investigation 124:3252-3262.
10. Boutz D R, Horton A P, Wine Y, Lavinder J J, Georgiou G, Marcotte E M. 2014. Proteomic identification of monoclonal antibodies from serum. Analytical chemistry 86:4758-4766.
11. Wrammert J, Koutsonanos D, Li G M, Edupuganti S, *Sui* J, Morrissey M, McCausland M, Skountzou I, Hornig M, Lipkin W I, Mehta A, Razavi B, Del Rio C, Zheng N Y, Lee J H, Huang M, Ali Z, Kaur K, Andrews S, *Amara* RR, Wang Y, Das S R, O'Donnell C D, Yewdell J W, Subbarao K, Marasco W A, Mulligan M J, Compans R, Ahmed R, Wilson P C. 2011. Broadly cross-reactive antibodies dominate the human B cell response against 2009 pandemic H1N1 influenza virus infection. The Journal of experimental medicine 208:181-193.
12. Purtha W E, Tedder T F, Johnson S, Bhattacharya D, Diamond M S. 2011. Memory B cells, but not long-lived plasma cells, possess antigen specificities for viral escape mutants. The Journal of experimental medicine 208:2599-2606.
13. Georgiev I S, Doria-Rose N A, Zhou T, Kwon Y D, Staupe R P, Moquin S, Chuang G Y, Louder M K, Schmidt S D, Altae-Tran H R, Bailer R T, McKee K, Nason M, O'Dell S, Ofek G, Pancera M, Srivatsan S, Shapiro L, Connors M, Migueles S A, Morris L, Nishimura Y, Martin M A, Mascola J R, Kwong P D. 2013. Delineating antibody recognition in polyclonal sera from patterns of HIV-1 isolate neutralization. Science 340:751-756.
14. Morris L, Chen X, Alam M, Tomaras G, Zhang R, Marshall D J, Chen B, Parks R, Foulger A, Jaeger F, Donathan M, Bilska M, Gray E S, Abdool Karim S S, Kepler T B, Whitesides J, Montefiori D, Moody M A, Liao H X, Haynes B F. 2011. Isolation of a human anti-HIV gp41 membrane proximal region neutralizing antibody by antigen-specific single B cell sorting. PloS one 6:e23532.
15. Lavinder J J, Wine Y, Giesecke C, Ippolito G C, Horton A P, Lungu O I, Hoi K H, DeKosky B J, Murrin E M, Wirth M M, Ellington A D, Dorner T, Marcotte E M, Boutz D R, Georgiou G. 2014. Identification and characterization of the constituent human serum antibodies elicited by vaccination. Proceedings of the National Academy of Sciences of the United States of America 111: 2259-2264.

16. Wine Y, Horton A P, Ippolito G C, Georgiou G. 2015. Serology in the 21st century: the molecular-level analysis of the serum antibody repertoire. Current opinion in immunology 35:89-97.
17. McDaniel J R, DeKosky B J, Tanno H, Ellington A D, Georgiou G. 2016. Ultra-high-throughput sequencing of the immune receptor repertoire from millions of lymphocytes. Nature protocols 11:429-442.
18. DeKosky B J, Ippolito G C, Deschner R P, Lavinder J J, Wine Y, Rawlings B M, Varadarajan N, Giesecke C, Dorner T, Andrews S F, Wilson P C, Hunicke-Smith S P, Willson C G, Ellington A D, Georgiou G. 2013. High-throughput sequencing of the paired human immunoglobulin heavy and light chain repertoire. Nature biotechnology 31:166-169.
19. DeKosky B J, Kojima T, Rodin A, Charab W, Ippolito G C, Ellington A D, Georgiou G. 2015. In-depth determination and analysis of the human paired heavy- and light-chain antibody repertoire. Nature medicine 21:86-91.
20. Gray E S, Madiga M C, Moore P L, Mlisana K, Abdool Karim S S, Binley J M, Shaw G M, Mascola J R, Morris L. 2009. Broad neutralization of human immunodeficiency virus type 1 mediated by plasma antibodies against the gp41 membrane proximal external region. Journal of virology 83:11265-11274.
21. Gray E S, Meyers T, Gray G, Montefiori D C, Morris L. 2006. Insensitivity of paediatric HIV-1 subtype C viruses to broadly neutralising monoclonal antibodies raised against subtype B. PLoS medicine 3:e255.
22. Alam S M, Morelli M, Dennison S M, Liao H X, Zhang R, Xia S M, Rits-Volloch S, Sun L, Harrison S C, Haynes B F, Chen B. 2009. Role of HIV membrane in neutralization by two broadly neutralizing antibodies. Proceedings of the National Academy of Sciences of the United States of America 106:20234-20239.
23. Alam S M, Liao H X, Dennison S M, Jaeger F, Parks R, Anasti K, Foulger A, Donathan M, Lucas J, Verkoczy L, Nicely N, Tomaras G D, Kelsoe G, Chen B, Kepler T B, Haynes B F. 2011. Differential reactivity of germ line allelic variants of a broadly neutralizing HIV-1 antibody to a gp41 fusion intermediate conformation. Journal of virology 85:11725-11731.
24. Shen X, Dennison S M, Liu P, Gao F, Jaeger F, Montefiori D C, Verkoczy L, Haynes B F, Alam S M, Tomaras G D. 2010. Prolonged exposure of the HIV-1 gp41 membrane proximal region with L669S substitution. Proceedings of the National Academy of Sciences of the United States of America 107:5972-5977.
25. Frey G, Chen J, Rits-Volloch S, Freeman M M, Zolla-Pazner S, Chen B. 2010. Distinct conformational states of HIV-1 gp41 are recognized by neutralizing and non-neutralizing antibodies. Nature structural & molecular biology 17:1486-1491.
26. Liao H X, Lynch R, Zhou T, Gao F, Alam S M, Boyd S D, Fire A Z, Roskin K M, Schramm C A, Zhang Z, Zhu J, Shapiro L, Program N C S, Mullikin J C, Gnanakaran S, Hraber P, Wiehe K, Kelsoe G, Yang G, Xia S M, Montefiori D C, Parks R, Lloyd K E, Scearce R M, Soderberg K A, Cohen M, Kamanga G, Louder M K, Tran L M, Chen Y, Cai F, Chen S, Moquin S, Du X, Joyce M G, Srivatsan S, Zhang B, Zheng A, Shaw G M, Hahn B H, Kepler T B, Korber B T, Kwong P D, Mascola J R, Haynes B F. 2013. Co-evolution of a broadly neutralizing HIV-1 antibody and founder virus. Nature 496:469-476.
27. Moody M A, Yates N L, Amos J D, Drinker M S, Eudailey J A, Gurley T C, Marshall D J, Whitesides J F, Chen X, Foulger A, Yu J S, Zhang R, Meyerhoff R R, Parks R, Scull J C, Wang L, Vandergrift N A, Pickeral J, Pollara J, Kelsoe G, Alam S M, Ferrari G, Montefiori D C, Voss G, Liao H X, Tomaras G D, Haynes B F. 2012. HIV-1 gp120 vaccine induces affinity maturation in both new and persistent antibody clonal lineages. Journal of virology 86:7496-7507.
28. Cheung W C, Beausoleil S A, Zhang X, Sato S, Schieferl S M, Wieler J S, Beaudet J G, Ramenani R K, Popova L, Comb M J, Rush J, Polakiewicz R D. 2012. A proteomics approach for the identification and cloning of monoclonal antibodies from serum. Nature biotechnology 30:447-452.
29. Wine Y, Boutz D R, Lavinder J J, Miklos A E, Hughes R A, Hoi K H, Jung S T, Horton A P, Murrin E M, Ellington A D, Marcotte E M, Georgiou G. 2013. Molecular deconvolution of the monoclonal antibodies that comprise the polyclonal serum response. Proceedings of the National Academy of Sciences of the United States of America 110:2993-2998.
30. Lavinder J J, Horton A P, Georgiou G, Ippolito G C. 2015. Next-generation sequencing and protein mass spectrometry for the comprehensive analysis of human cellular and serum antibody repertoires. Current opinion in chemical biology 24:112-120.
31. Levesque M C, Moody M A, Hwang K K, Marshall D J, Whitesides J F, Amos J D, Gurley T C, Allgood S, Haynes B B, Vandergrift N A, Plonk S, Parker D C, Cohen M S, Tomaras G D, Goepfert P A, Shaw G M, Schmitz J E, Eron J J, Shaheen N J, Hicks C B, Liao H X, Markowitz M, Kelsoe G, Margolis D M, Haynes B F. 2009. Polyclonal B cell differentiation and loss of gastrointestinal tract germinal centers in the earliest stages of HIV-1 infection. PLoS medicine 6:e1000107.
32. Scheid J F, Mouquet H, Feldhahn N, Seaman M S, Velinzon K, Pietzsch J, Ott R G, Anthony R M, Zebroski H, Hurley A, Phogat A, Chakrabarti B, Li Y, Connors M, Pereyra F, Walker B D, Wardemann H, Ho D, Wyatt R T, Mascola J R, Ravetch J V, Nussenzweig M C. 2009. Broad diversity of neutralizing antibodies isolated from memory B cells in HIV-infected individuals. Nature 458: 636-640.
33. Tomaras G D, Binley J M, Gray E S, Crooks E T, Osawa K, Moore P L, Tumba N, Tong T, Shen X, Yates N L, Decker J, Wibmer C K, Gao F, Alam S M, Easterbrook P, Abdool Karim S, Kamanga G, Crump J A, Cohen M, Shaw G M, Mascola J R, Haynes B F, Montefiori D C, Morris L. 2011. Polyclonal B cell responses to conserved neutralization epitopes in a subset of HIV-1-infected individuals. Journal of virology 85:11502-11519.
34. Simek M D, Rida W, Priddy F H, Pung P, Carrow E, Laufer D S, Lehrman J K, Boaz M, Tarragona-Fiol T, Miiro G, Birungi J, Pozniak A, McPhee D A, Manigart O, Karita E, Inwoley A, Jaoko W, Dehovitz J, Bekker L G, Pitisuttithum P, Paris R, Walker L M, Poignard P, Wrin T, Fast P E, Burton D R, Koff W C. 2009. Human immunodeficiency virus type 1 elite neutralizers: individuals with broad and potent neutralizing activity identified by using a high-throughput neutralization assay together with an analytical selection algorithm. Journal of virology 83:7337-7348.
35. Walker L M, Phogat S K, Chan-Hui P Y, Wagner D, Phung P, Goss J L, Wrin T, Simek M D, Fling S, Mitcham J L, Lehrman J K, Priddy F H, Olsen O A, Frey S M, Hammond P W, Protocol GPI, Kaminsky S, Zamb T, Moyle M, Koff W C, Poignard P, Burton D R. 2009. Broad and potent neutralizing antibodies from an African donor reveal a new HIV-1 vaccine target. Science 326: 285-289.

36. Walker L M, Huber M, Doores K J, Falkowska E, Pejchal R, Julien J P, Wang S K, Ramos A, Chan-Hui P Y, Moyle M, Mitcham J L, Hammond P W, Olsen O A, Phung P, Fling S, Wong C H, Phogat S, Wrin T, Simek M D, Protocol GPI, Koff W C, Wilson I A, Burton D R, Poignard P. 2011. Broad neutralization coverage of HIV by multiple highly potent antibodies. Nature 477:466-470.

37. Bonsignori M, Hwang K K, Chen X, Tsao C Y, Morris L, Gray E, Marshall D J, Crump J A, Kapiga S H, Sam N E, Sinangil F, Pancera M, Yongping Y, Zhang B, Zhu J, Kwong P D, O'Dell S, Mascola J R, Wu L, Nabel G J, Phogat S, Seaman M S, Whitesides J F, Moody M A, Kelsoe G, Yang X, Sodroski J, Shaw G M, Montefiori D C, Kepler T B, Tomaras GD, Alam S M, Liao H X, Haynes B F. 2011. Analysis of a clonal lineage of HIV-1 envelope V2/V3 conformational epitope-specific broadly neutralizing antibodies and their inferred unmutated common ancestors. Journal of virology 85:9998-10009.

38. Bonsignori M, Montefiori D C, Wu X, Chen X, Hwang K K, Tsao C Y, Kozink D M, Parks R J, Tomaras G D, Crump J A, Kapiga S H, Sam N E, Kwong P D, Kepler T B, Liao H X, Mascola J R, Haynes B F. 2012. Two distinct broadly neutralizing antibody specificities of different clonal lineages in a single HIV-1-infected donor: implications for vaccine design. Journal of virology 86:4688-4692.

39. Walker L M, Simek M D, Priddy F, Gach J S, Wagner D, Zwick M B, Phogat S K, Poignard P, Burton D R. 2010. A limited number of antibody specificities mediate broad and potent serum neutralization in selected HIV-1 infected individuals. PLoS pathogens 6:e1001028.

40. Gao F, Bonsignori M, Liao H X, Kumar A, Xia S M, Lu X, Cai F, Hwang K K, Song H, Zhou T, Lynch R M, Alam S M, Moody M A, Ferrari G, Berrong M, Kelsoe G, Shaw G M, Hahn B H, Montefiori D C, Kamanga G, Cohen M S, Hraber P, Kwong P D, Korber B T, Mascola J R, Kepler T B, Haynes B F. 2014. Cooperation of B cell lineages in induction of HIV-1-broadly neutralizing antibodies. Cell 158:481-491.

41. Amanna I J, Carlson N E, Slifka M K. 2007. Duration of humoral immunity to common viral and vaccine antigens. The New England journal of medicine 357:1903-1915.

42. Bonsignori M, Moody M A, Parks R J, Holl T M, Kelsoe G, Hicks C B, Vandergrift N, Tomaras G D, Haynes B F. 2009. HIV-1 envelope induces memory B cell responses that correlate with plasma antibody levels after envelope gp120 protein vaccination or HIV-1 infection. Journal of immunology 183:2708-2717.

43. Chuang G Y, Acharya P, Schmidt S D, Yang Y, Louder M K, Zhou T, Kwon Y D, Pancera M, Bailer R T, Doria-Rose N A, Nussenzweig M C, Mascola J R, Kwong P D, Georgiev I S. 2013. Residue-level prediction of HIV-1 antibody epitopes based on neutralization of diverse viral strains. Journal of virology 87:10047-10058.

44. Gray E S, Taylor N, Wycuff D, Moore P L, Tomaras G D, Wibmer C K, Puren A, DeCamp A, Gilbert P B, Wood B, Montefiori D C, Binley J M, Shaw G M, Haynes B F, Mascola J R, Morris L. 2009. Antibody specificities associated with neutralization breadth in plasma from human immunodeficiency virus type 1 subtype C-infected blood donors. Journal of virology 83:8925-8937.

45. Tiller T, Meffre E, Yurasov S, Tsuiji M, Nussenzweig M C, Wardemann H. 2008. Efficient generation of monoclonal antibodies from single human B cells by single cell RT-PCR and expression vector cloning. Journal of immunological methods 329:112-124.

46. Liao H X, Levesque M C, Nagel A, Dixon A, Zhang R, Walter E, Parks R, Whitesides J, Marshall D J, Hwang K K, Yang Y, Chen X, Gao F, Munshaw S, Kepler T B, Denny T, Moody M A, Haynes B F. 2009. High-throughput isolation of immunoglobulin genes from single human B cells and expression as monoclonal antibodies. Journal of virological methods 158:171-179.

47. Kepler T B. 2013. Reconstructing a B-cell clonal lineage. I. Statistical inference of unobserved ancestors. F1000Research 2:103.

48. Kepler T B, Munshaw S, Wiehe K, Zhang R, Yu J S, Woods C W, Denny T N, Tomaras G D, Alam S M, Moody M A, Kelsoe G, Liao H X, Haynes B F. 2014. Reconstructing a B-Cell Clonal Lineage. II. Mutation, Selection, and Affinity Maturation. Frontiers in immunology 5:170.

49. Felstein J. 2009. PHYLIP (Phylogeny Inference Package) version 3.69. Distributed by the author. Depai intent of Genome Sciences, University of Washington, Seattle.

50. Montefiori D C. 2005. Evaluating neutralizing antibodies against HIV, SIV, and SHIV in luciferase reporter gene assays. Current protocols in immunology/edited by John E. Coligan . . . [et al.] Chapter 12: Unit 12 11.

51. Seaman M S, Janes H, Hawkins N, Grandpre L E, Devoy C, Giri A, Coffey R T, Harris L, Wood B, Daniels M G, Bhattacharya T, Lapedes A, Polonis V R, McCutchan F E, Gilbert P B, Self S G, Korber B T, Montefiori D C, Mascola J R. 2010. Tiered categorization of a diverse panel of HIV-1 Env pseudoviruses for assessment of neutralizing antibodies. Journal of virology 84:1439-1452.

52. Haynes B F, Fleming J, St Clair E W, Katinger H, Stiegler G, Kunert R, Robinson J, Scearce R M, Plonk K, Staats H F, Ortel T L, Liao H X, Alam S M. 2005. Cardiolipin polyspecific autoreactivity in two broadly neutralizing HIV-1 antibodies. Science 308:1906-1908.

53. Sun Z Y, Oh K J, Kim M, Yu J, Brusic V, Song L, Qiao Z, Wang J H, Wagner G, Reinherz E L. 2008. HIV-1 broadly neutralizing antibody extracts its epitope from a kinked gp41 ectodomain region on the viral membrane. Immunity 28:52-63.

54. Bolotin D A, Poslaysky S, Mitrophanov I, Shugay M, Mamedov I Z, Putintseva E V, Chudakov D M. 2015. MiXCR: software for comprehensive adaptive immunity profiling. Nature methods 12:380-381.

55. Magoc T, Salzberg S L. 2011. FLASH: fast length adjustment of short reads to improve genome assemblies. Bioinformatics 27:2957-2963.

56. Alamyar E, Duroux P, Lefranc M P, Giudicelli V. 2012. IMGT® tools for the nucleotide analysis of immunoglobulin (IG) and T cell receptor (TR) V-(D)-J repertoires, polymorphisms, and IG mutations: IMGT/V-QUEST and IMGT/HighV-QUEST for NGS. Methods in molecular biology 882:569-604.

57. Otwinowski Z, Minor W. 1997. Processing of X-ray diffraction data collected in oscillation mode. Methods Enzymol. 276:307-326.

58. Adams P D, Afonine P V, Bunkoczi G, Chen V B, Davis I W, Echols N, Headd J J, Hung L W, Kapral G J, Grosse-Kunstleve R W, McCoy A J, Moriarty N W, Oeffner R, Read R J, Richardson D C, Richardson J S, Terwilliger T C, Zwart P H. 2010. PHENIX: a comprehensive Python-based system for macromolecular structure solution. Acta crystallographica. Section D, Biological crystallography 66:213-221.

59. Adams P D, Grosse-Kunstleve R W, Hung L W, loerger TR, McCoy A J, Moriarty N W, Read R J, Sacchettini J C, Sauter N K, Terwilliger T C. 2002. PHENIX: building new software for automated crystallographic structure determination. Acta Crystallogr. Sect. D-Biol. Crystallogr. 58:1948-1954.

60. Emsley P, Cowtan K. 2004. Coot: model-building tools for molecular graphics. Acta Crystallogr. Sect. D-Biol. Crystallogr. 60:2126-2132.

61. Krissinel E, Henrick K. 2007. Inference of macromolecular assemblies from crystalline state. Journal of molecular biology 372:774-797.

62. Winn M D, Ballard C C, Cowtan K D, Dodson E J, Emsley P, Evans P R, Keegan R M, Krissinel E B, Leslie A G, McCoy A, McNicholas S J, Murshudov G N, Pannu N S, Potterton E A, Powell H R, Read R J, Vagin A, Wilson K S. 2011. Overview of the CCP4 suite and current developments. Acta crystallographica. Section D, Biological crystallography 67:235-242.

What is claimed is:

1. A recombinant antibody or fragment thereof comprising: a heavy chain variable region comprising a heavy chain complementarity determining region (HCDR)1, a HCDR2, and a HCDR3 comprising amino acids at positions 26-33, 51-60 and 99-121 of SEQ ID NO: 230, SEQ ID NO: 240 or SEQ ID NO: 241, respectively and wherein the amino acid sequence of the heavy chain variable region outside of HCDR1, HCDR2, and HCDR3 has an overall sequence identity of at least 90% to SEQ ID NO: 230, SEQ ID NO:

240, or SEQ ID NO: 241; and a light chain variable region comprising a light chain complementarity determining region (LCDR)1, a LCDR2, and a LCDR3, comprising amino acids at positions 27-32, 50-52 and 89-99 of SEQ ID NO: 253, SEQ ID NO: 255 or SEQ ID NO: 261 respectively, and wherein the amino acid sequence of the light chain variable region outside of LCDR1, LCDR2, and LCDR3 has an overall sequence identity of at least 90% to SEQ ID NO: 253, SEQ ID NO: 255, or SEQ ID NO: 261, and wherein the antibody or fragment thereof binds gp41 MPER of HIV-1 envelope.

2. A recombinant antibody or fragment thereof comprising: a heavy chain variable region comprising heavy chain complementarity determining regions (HCDRs) that have an overall HCDR sequence identity of at least 90% to HCDR amino acids at positions 26-33, 51-60 and 99-121 of SEQ ID NO: 230, SEQ ID NO:240, or SEQ ID NO:241 and wherein the amino acid sequence of the heavy chain variable region outside of HCDR1, HCDR2, and HCDR3 has an overall sequence identity of at least 90% to SEQ ID NO: 230, SEQ ID NO: 240, or SEQ ID NO: 241; and a light chain variable region comprising light chain complementarity determining regions (LCDRs) that have an overall LCDR sequence identity of at least 90% to LCDR amino acids at positions 27-32, 50-52 and 89-99 of SEQ ID NO: 253, SEQ ID NO: 255 or SEQ ID NO: 261 and wherein the amino acid sequence of the light chain variable region outside of LCDR1, LCDR2, and LCDR3 has an overall sequence identity of at least 90% to SEQ ID NO: 253, SEQ ID NO: 255, or SEQ ID NO: 261, and wherein the antibody or fragment thereof binds gp41 MPER of HIV-1 envelope.

3. A recombinant antibody or fragment thereof comprising: a heavy chain variable region comprising a heavy chain complementarity determining region (HCDR)1, a HCDR2, and a HCDR3 comprising amino acids at positions 26-33, 51-60 and 99-121 of SEQ ID NO: 230, SEQ ID NO: 240 or SEQ ID NO: 241, respectively and wherein the V gene usage of the heavy chain variable region is IGHV3; and a light chain variable region comprising a light chain complementarity determining region (LCDR)1, a LCDR2, and a LCDR3, comprising amino acids at positions 27-32, 50-52 and 89-99 of SEQ ID NO: 253, SEQ ID NO: 255 or SEQ ID NO: 261 respectively, and wherein the V gene usage of the light chain variable region is a kappa light chain, and wherein the antibody or fragment thereof binds gp41 MPER of HIV-1 envelope.

4. A recombinant antibody or fragment thereof comprising: a heavy chain variable region comprising heavy chain complementarity determining regions (HCDRs) that have an overall HCDR sequence identity of at least 90% to HCDR amino acids at positions 26-33, 51-60 and 99-121 of SEQ ID NO: 230, SEQ ID NO:240, or SEQ ID NO:241 and wherein the V gene usage of the heavy chain variable region is IGHV3; and a light chain variable region comprising light chain complementarity determining regions (LCDRs) that have an overall LCDR sequence identity of at least 90% to LCDR amino acids at positions 27-32, 50-52 and 89-99 of SEQ ID NO: 253, SEQ ID NO: 255 or SEQ ID NO: 261, and wherein the V gene usage of the light chain variable region is a kappa light chain, and wherein the antibody or fragment thereof binds gp41 MPER of HIV-1 envelope.

5. The recombinant antibody or fragment thereof of claim 3 or 4, wherein the V gene usage of the heavy chain variable region is IGHV3-15.

6. The recombinant antibody or fragment thereof of claim 3 or 4, wherein the V gene usage of the light chain variable region is IGKV1-39.

7. The recombinant antibody or fragment thereof of claim 3 or 4, wherein the V gene usage of the heavy chain variable region is IGHV3-15 and the V gene usage of the light chain variable region is IGKV1-39.

8. The recombinant antibody or fragment thereof of claim 5, wherein the J gene usage of the heavy chain variable region is IGHJ6.

9. The recombinant antibody or fragment thereof of claim 5, wherein the J gene usage of the light chain variable region is IGKJ2.

10. The recombinant antibody or fragment thereof of claim 1 or 3, comprising: a heavy chain variable region comprising a HCDR1, a HCDR2, and a HCDR3 comprising amino acids at positions 26-33, 51-60 and 99-121 of SEQ ID NO: 230 and a LCDR1, a LCDR2, and a LCDR3, comprising amino acids at positions 27-32, 50-52 and 89-99 of SEQ ID NO: 253.

11. The recombinant antibody or fragment thereof of claim 1 or 3, comprising: a heavy chain variable region comprising a HCDR1, a HCDR2, and a HCDR3 comprising amino acids at positions 26-33, 51-60 and 99-121 of SEQ ID NO: 230 and a LCDR1, a LCDR2, and a LCDR3, comprising amino acids at positions 27-32, 50-52 and 89-99 of SEQ ID NO: 255.

12. The recombinant antibody or fragment thereof of claim 1 or 3, comprising: a heavy chain variable region comprising a HCDR1, a HCDR2, and a HCDR3 comprising amino acids at positions 26-33, 51-60 and 99-121 of SEQ ID NO: 240 and a LCDR1, a LCDR2, and a LCDR3, comprising amino acids at positions 27-32, 50-52 and 89-99 of SEQ ID NO: 261.

13. The recombinant antibody or fragment thereof of claim 1 or 3, comprising: a heavy chain variable region comprising a HCDR1, a HCDR2, and a HCDR3 comprising amino acids at positions 26-33, 51-60 and 99-121 of SEQ ID NO: 241 and a LCDR1, a LCDR2, and a LCDR3, comprising amino acids at positions 27-32, 50-52 and 89-99 of SEQ ID NO: 261.

14. The recombinant antibody or fragment thereof of claim 2 or 4, comprising: a heavy chain variable region comprising HCDRs that have an overall HCDR sequence identity of at least 90% to HCDR amino acids at positions 26-33, 51-60 and 99-121 of SEQ ID NO: 230; and a light chain variable region comprising LCDRs that have an overall LCDR sequence identity of at least 90% to LCDR amino acids at positions 27-32, 50-52 and 89-99 of SEQ ID NO: 253.

15. The recombinant antibody or fragment thereof of claim 2 or 4, comprising: a heavy chain variable region comprising HCDRs that have an overall HCDR sequence identity of at least 90% to HCDR amino acids at positions 26-33, 51-60 and 99-121 of SEQ ID NO: 230; and a light chain variable region comprising LCDRs that have an overall LCDR sequence identity of at least 90% to LCDR amino acids at positions 27-32, 50-52 and 89-99 of SEQ ID NO: 255.

16. The recombinant antibody or fragment thereof of claim 2 or 4, comprising: a heavy chain variable region comprising HCDRs that have an overall HCDR sequence identity of at least 90% to HCDR amino acids at positions 26-33, 51-60 and 99-121 of SEQ ID NO: 240; and a light chain variable region comprising LCDRs that have an overall LCDR sequence identity of at least 90% to LCDR amino acids at positions 27-32, 50-52 and 89-99 of SEQ ID NO: 261.

17. The recombinant antibody or fragment thereof of claim 2 or 4, comprising: a heavy chain variable region comprising HCDRs that have an overall HCDR sequence identity of at least 90% to HCDR amino acids at positions 26-33, 51-60 and 99-121 of SEQ ID NO: 241; and a light chain variable region comprising LCDRs that have an overall LCDR sequence identity of at least 90% to LCDR amino acids at positions 27-32, 50-52 and 89-99 of SEQ ID NO: 261.

18. A bispecific antibody comprising the recombinant antibody or fragment thereof of any one of claims 1-4.

19. The recombinant antibody or fragment thereof of any one of claims 1-4 wherein the antibody or fragment thereof comprises an Fc portion that is modified compared to a naturally occurring Fc domain.

20. A pharmaceutical composition comprising any one of the antibodies or fragments thereof of any one of claims 1-4, or any combination thereof.

21. The pharmaceutical composition of claim 20, further comprising another HIV-1 neutralizing antibody.

22. A pharmaceutical composition comprising a vector, the vector comprising a nucleic acid encoding an antibody or fragment thereof comprising a heavy chain variable region comprising a heavy chain variable region comprising a heavy chain complementarity determining region (HCDR)1, a HCDR2, and a HCDR3 comprising amino acids at positions 26-33, 51-60 and 99-121 of SEQ ID NO: 230, SEQ ID NO: 240 or SEQ ID NO: 241, respectively; and a light chain variable region comprising a light chain complementarity determining region (LCDR)1, a LCDR2, and a LCDR3, comprising amino acids at positions 27-32, 50-52 and 89-99 of SEQ ID NO: 253, SEQ ID NO: 255 or SEQ ID NO: 261 respectively, wherein the antibody or fragment thereof binds gp41 MPER of HIV-1 envelope.

23. The pharmaceutical composition of claim 22, wherein the vector is suitable for gene delivery and expression.

24. A pharmaceutical composition comprising a vector, the vector comprising a nucleic acid encoding an antibody or fragment thereof of any one of claims 1-4.

25. The pharmaceutical composition of claim 24, wherein the vector is suitable for gene delivery and expression.

26. A method to inhibit HIV-1 infection in a subject comprising administering to the subject the pharmaceutical composition of claim 20 in an effective amount.

27. The method of claim 26, wherein the pharmaceutical composition is administered in an effective regimen.

28. The method of claim 26 further comprising administering an additional HIV-1 neutralizing antibody.

* * * * *

SEQUENCE LISTING

```
<160> NUMBER OF SEQ ID NOS: 489

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Lys Lys Asn Glu Gln Glu Leu Leu Glu Leu Asp Lys Trp Ala Ser
1               5                   10                  15

Leu Trp Asn Trp Phe Asp Ile Thr Asn Trp Leu Trp Tyr Ile Arg
            20                  25                  30


<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Arg
            20                  25


<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Lys Lys Asn Glu Gln Glu Leu Leu Glu Leu Asp Lys Trp Ala Ser
1               5                   10                  15

Leu Trp Asn Trp Phe Asn Ile Thr Asn Trp Leu Trp Tyr Ile Lys
            20                  25                  30


<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 4

Lys Lys Lys Asn Glu Gln Asp Leu Leu Ala Leu Asp Lys Trp Ala Ser
1 5 10 15

Leu Trp Asn Trp Phe Asp Ile Ser Asn Trp Leu Trp Tyr Ile Lys Lys
20 25 30

Lys Lys

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Lys Lys Lys Asn Glu Lys Asp Leu Leu Ala Leu Asp Ser Trp Lys Asn
1 5 10 15

Leu Trp Asn Trp Phe Ser Ile Thr Lys Trp Leu Trp Tyr Ile Lys Lys
20 25 30

Lys Lys

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Lys Lys Lys Asn Glu Gln Glu Leu Leu Ala Leu Asp Lys Trp Asn Asn
1 5 10 15

Leu Trp Ser Trp Phe Asp Ile Thr Asn Trp Leu Trp Tyr Ile Arg Lys
20 25 30

Lys Lys

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Lys Lys Lys Asn Glu Lys Asp Leu Leu Ala Leu Asp Ser Trp Lys Asn
1 5 10 15

Leu Trp Asn Trp Phe Asp Ile Thr Lys Trp Leu Trp Tyr Ile Lys Lys
20 25 30

Lys Lys

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Lys Lys Lys Asn Glu Gln Glu Leu Leu Ala Leu Asp Lys Trp Asn Asn

```
1               5                   10                  15

Leu Trp Ser Trp Phe Asp Ile Thr Asn Trp Leu Trp Tyr Ile Arg Lys
            20                  25                  30

Lys Lys


<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Lys Lys Asn Glu Gln Glu Leu Leu Ala Leu Ala Lys Ala Asn Asn
1               5                   10                  15

Leu Trp Ser Trp Phe Asp Ile Thr Asn Trp Leu Trp Tyr Ile Arg Tyr
            20                  25                  30

Ile Lys Lys Lys Lys
        35


<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Lys Lys Lys Asn Glu Gln Glu Leu Leu Ala Leu Ala Lys Ala Asn Asn
1               5                   10                  15

Leu Trp Ser Trp Phe Asp Ile Thr Asn Trp Leu Trp Tyr Ile Arg Lys
            20                  25                  30

Lys Lys


<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Lys Lys Lys Asn Glu Lys Asp Leu Leu Ala Leu Asp Ser Trp Lys Asn
1               5                   10                  15

Leu Trp Asn Trp Phe Ser Ile Thr Lys Trp Leu Trp Tyr Ile Arg Lys
            20                  25                  30

Lys Lys


<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Lys Lys Asn Glu Gln Glu Leu Leu Ala Leu Ala Lys Trp Asn Asn
1               5                   10                  15
```

Leu Trp Ser Trp Phe Asp Ile Thr Asn Trp Leu Trp Tyr Ile Arg Tyr
20 25 30

Ile Lys Lys Lys Lys
35

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Lys Lys Lys Asn Glu Lys Asp Leu Leu Ala Leu Asp Ser Trp Lys Asn
1 5 10 15

Leu Trp Asn Trp Phe Asp Ile Thr Lys Trp Leu Trp Tyr Ile Arg Lys
20 25 30

Lys Lys

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Lys Lys Lys Asn Glu Gln Glu Leu Leu Glu Leu Asp Lys Trp Ala Ser
1 5 10 15

Leu Trp Asn Trp Phe Asp Ile Thr Asn Trp Leu Trp Tyr Ile Arg Lys
20 25 30

Lys Lys

<210> SEQ ID NO 15
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
gaggttcagc tggtggagtc tgggggaggc ttggtgaagc cggggggtc tcttagactc 60 cccggtgcag cctctggttt cactttcacc aacacgtgga tgagttgggt ccgtcaggcg 120
ccagggaagg gactggagtg ggtcggtcgg attagccgga acaaagatgg cgcgaaaaca 180
gagtacgccg cacccgtgag aggcagattc accatctcaa gagatgactc cagagacaca 240
ttgtatctgc agatgaccag cctgaaaata gaggattcag gccggtattt ttgcaccgca 300
gatcttgggg agcccgtggt gtcacgatcc atttttgagt gggggtctta ttattattat 360
atggacctct ggggcaaggg gaccacggtc accgtctctt ca 402

<210> SEQ ID NO 16
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
gacatccagt tgacccagtc tccatctccc ctgtctgcgt ctgtgggaga cacagtcact     60

atcacttgtc gggccagcca gaagattagc gactatttga actggtacca acagaagccg    120

gggagagccc ccaaaatact catttacgct gcgtccaagt tggggagtgg cgtcccatca    180

aggttcagtg gcagtggata tggcagagat ttcactctca ccatcaccgg tctgcagcct    240

gaagattttg caacctatta ttgtcaggag gcttacagtt ctactcccac gttaactttt    300

ggccagggga ccaggctgga tctcaaac                                       328


<210> SEQ ID NO 17
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

caggtgcagc tggtacagtc tgggggaggt ctggtgaagc cggggggtc cctcacactc      60

tcctgttcag cctctggatt ctttttcgat aattcatgga tggggtgggt ccgtcaggcg    120

ccagggaagg gactggagtg ggttggccgc attagaaggc tcaaagacgg tgcgacagga    180

gaatatggtg cagccgtgaa ggacagattc accatttcaa gagatgacag tagaaatatg    240

ctgtacctgc acatgaggac cctgaaaacc gaggactcag gcacttatta ttgtaccatg    300

gatgagggga ccccagtaac acgcttctta gaatggggct acttctatta ttatatggcc    360

gtttggggca gagggaccac ggtcatcgtc tcttca                              396


<210> SEQ ID NO 18
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

gacatcgtga tgacccagtc tccgtcctcc gtgtctgcat ctgtgggaga cagagtcacc     60

atcacttgcc gggcaagtca gaatattaga gactatttaa attggtatca acataaaccc    120

gggggatccc ctagactcct aatttatgct gcgtcaactt tgcaaactgg ggtcccgtcc    180

agattcagcg gcagtggatc tgggaacctt ttcactctca ccattaccaa tctgcaacct    240

gaagattttg caacttatta ttgtcaagag aattataata ctatcccctc gctcagcttt    300

ggtcagggga ccaaggtgga catcaggc                                       328


<210> SEQ ID NO 19
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

gaggttcagc tggtggagtc tgggggaggc ttggtgaagc cggggggtc tcttagactc      60

tcctgtgtag cctctggctt cactttcagc aacacgtgga tgagttgggt ccgtcaggcg    120

ccagggaagg gactggagtg ggtcggtcgg attagccgga acaaagatgg cgcgaaaaca    180

gagtacgccg cacccgtgag aggcagattc accatctcaa gagatgactc cagagacaca    240
```

ttgtatctgc agatgagcag cctgaaaata gaggattcag gccggtattt ttgcaccgca 300
gatcttgggg aggccgttgt gtcacgattt tttgagtggg ggtcctatta ttactacatg 360
gacttctggg gcaaggggac cacggtcacc gtctcttca 399

<210> SEQ ID NO 20
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
gacattcaga tgacccaatc tccatctccc ctgtctgcgt ctgtgggaga cacagtcact 60
atcacttgcc gggccagcca gaagattagc gactatttga actggtacca acagaggccg 120
gggagagccc ccaagatcct catttacgct gcgtccaagt tggcaagcga cgtcccatca 180
agatttagtg gcagtggata tggcagagat ttcactctca ccataaccgg tctgcagcct 240
gaagattttg caacctatta ttgtcaggag gcttacagtt ctacccccac gttaactttt 300
ggccagggga ccaggctgga tctcaaac 328

<210> SEQ ID NO 21
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
gaggtgcagc tggtggagtc tgggggcggc ttgataaagc cgggacagtc actcacacta 60
ttctgtgtgg gctttggatt caacttcgct aacgactgga tgggctgggt ccgccaggct 120
ccagggaagg gactggaatg ggttgggcgt ataaggagac tgaaagatgg tgcgaaagct 180
gaatatggat cttccgtgaa gggtagattc accatctcaa gggatgattc caaaaacacc 240
ctatacttgc acatgagcag cctcaaggtc gaagacacag ccgtctacta ttgcacccga 300
gacgaggggg ccccagttac ccggtttctg gagtggggct cctattacta ctacatggcc 360
gtctggggca aagggaccac ggtcaccgtc tcttca 396

<210> SEQ ID NO 22
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
gacatccagt tgacccagtc tccagcctct ctgtctgcat ctgtaggaga cacagtgact 60
atcacttgcc gggcaagtca gagtataaaa gattacataa attggtatca acacaaatcc 120
gggagcgccc ctagactcct gatttatgct gcgtcaacct tacaaagtgg aatctcgtca 180
aggttcactg gcagtgggtc tgggacacag ttcactctca ccattaacag tctgcaacct 240
gaagattttg cgacttatta ttgtcaagag gcttataaca ccaaccccac actctccttt 300
ggtcagggga ccagggtgga caagaagc 328

<210> SEQ ID NO 23
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
gaggttcagc tggtggagtc tgggggcggc ttggtgaagc cgggacagtc actcacactt 60
tcctgtgtgg gctttggatt caatttcgct aacgactgga tgggctgggt ccgccaggct 120
ccagggaagg gactggaatg ggttggtcga ataaggagac taaaagacgg tgcgacaaca 180
gaatattctt catccgtgaa ggggagattc agtgtctcaa gagatgattc aaggaacaca 240
gtatacttac acatgagtag cctcaaagtc caggacattg gcgtctatta ttgtactcga 300
gacgaggggg ccccggttac tcgatttctg gagtggggct cctattacta ctatatggcc 360
gtctggggca gagggaccac ggtcaccgtc tcttca 396

<210> SEQ ID NO 24
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
gacatccaga tgacccagtc tccaacctct ctgtctgcat ctgtaggaga cacagttgct 60
atcacttgcc gggcaagtca gagtgttaaa gattatgtga attggtatca acacaaatcc 120
gggagcgccc ctcgactcct gatttatgct gcctcagtct tacatactgg agtctcgtca 180
aggttcactg gcagtgggtc tgggacacag ttcactctca ccattagcag tctacaacct 240
gaagattttg ctacttatta ttgtcaagag gcttataaca cctatcccac actctccttt 300
ggtcagggga ccagggtgga caggaaac 328

<210> SEQ ID NO 25
<211> LENGTH: 399
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
gaggttcagc tggtggagtc tgggggaggc ttggtgaagc cggggggtc tcttagactc 60 tcctgtgtag cctctggctt cactttcagc aacacgtgga tgagttgggt ccgtcaggcg 120
ccagggaagg gactggagtg ggtcggtcgg attagccgga acaaagatgg cgcgaaaaca 180
gactacgccg cacccgtgag aggcagattc accatctcca gagatgactc cagagacaca 240
ttgtatctgc agatgagcag cctgaaaata gaggattcag gccggtattt ttgcaccgca 300
gatcttgggg aggccgtggt gtcacgattt tttgagtggg ggtcctatta ttactacatg 360
gacttctggg gcaaggggac cacggtcacc gtctcttca 399

<210> SEQ ID NO 26
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26
gatattgtga tgacccagtc tccacctccc ctgtctgcgt ctgtgggaga cacagtcact 60
atcacttgcc gggccagcca gaagattagc gactatttga actggtacca acagaggccg 120
gggagagccc ccaaaatact catttacgct gcgtccaagt tgggaagcga cgtcccatca 180
aggttcagtg gcagtggata tggcagagat ttcactctca ccatcaccgg tctgcagcct 240
gaagattttg caacctatta ttgtcaggag gcttacagtt ctactcccac gttaagtttt 300
ggccagggga ccaggctgga tctcaaac 328

<210> SEQ ID NO 27
<211> LENGTH: 399
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
gaaaggcagg tggtggaata tgggggaggc ttggtgaagc cggggggggtc tcttagactc 60 tcttgtttac cgtttgcctt tgggttcagg gccccctgga ggagttctgt ccgtcacgcg 120
cctgggggcg gagcggagtg ggtcggtcgg attagccgga acaaagatgg cgcgaaaaca 180
gagtacgccg cacccgtgag aggcagattc accatctcaa gagatgactc cagagacaca 240
ttgtatctgc agatgaccag cctgaaaata gaggattcag gccggtattt ttgcaccgca 300
gatcttgggg agcccgtggt gtcacgattt tttgagtggg ggtcttatta ttattatatg 360
gacctctggg gcaaggggac cacggtcacc gtctcttca 399

<210> SEQ ID NO 28
<211> LENGTH: 327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
tcttctgagc tgactcagga ccccactgtg tctgtggcct tgggccagac agtcaagatc 60
agatgccaag gagccagcct cagagactgt tatgcgacct ggtaccggca gaagccagga 120
caggccccaa cacttctcat ttatgatata aataagaggc cctcaggtat cccagaccga 180
ttctctgcct cctactcagg gagcacttct tccttgacca ttattggggc tcagccggaa 240
gatgaggctg actatttttg tgcttcgcgg gacaggagtg gtgaccgtct tggcgtcttc 300
ggcggtggga ccaaactgac cgtcctg 327

<210> SEQ ID NO 29
<211> LENGTH: 390
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
cagctgcagg agtcgggtcc cagactggtg aggccttcgg agaccctgtc cctcacctgc 60
actgtatctg gctctggtgt ctccgtcagt cgtgggagtt attattgggg ctggatacgc 120

-continued cagtccccag aaaagggact cgaatggatt ggaagtgtct attccactac tagtggaaaa 180
acctactaca acccgtccct caagagtcga gtcacctttt cgaaggacac gtcccagaac 240
gccttctccc tgactctgac gtctattacc gccgcggaca cggccgtcta ttactgtgca 300
agacaatttg gcttcatggg gggctttttg gagtggtatc cgcactattt tgacttctgg 360
ggcccgggaa tccaggtcgt cgtgtcttct 390

<210> SEQ ID NO 30
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
gacattgtga tgacccagtc tccatcctac ctgtctacat ctgtcggtga cagcatcacc 60
atcacttgcc gggcaagtca gagtattaaa acatatgtaa attggtatca acaaagacca 120
gggagagccc ctaaactcct catctattct tcatccactt tgcaacctgg ggtcccgtca 180
agattcagcg ccagtggatc tgggacagat ttcgttctct ccatcaccaa tttgcagtct 240
gaagattttg caacttacta ctgtcaacag acctactaca ccccctctac ttttggccag 300
gggaccacac tggacatcaa g 321

<210> SEQ ID NO 31
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
caggtgcagc tggtacagtc tggggctgag gtgaagaagc ctgggtcctc ggtcaaggtc 60
tcctgcaagg cctctggagg ctccttctac acctatacta tcaactgggt gcgacaggcc 120
cctggacaag ggcttgagtg gatgggcagg gtcaccacta tgtttggtgt aacactttac 180
gcacagaaat tccagggcag agtcacactt accgcggaca aatccacgag cacagcctac 240
atggaactga gcagtctaag atctgaggac acggccgtct attattgtgc gacagatggg 300
cctgacaatt tttggagtgg cttgtctcat gctttcgatc tctggggcca ggggacaatg 360
gtcaccgtct cttca 375

<210> SEQ ID NO 32
<211> LENGTH: 330
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
cagtctgccc tgactcagcc tgcctccgtg gctgggtctc ctggacagtc gatcaccatc 60
tcctgcactg gaaccagcag tgacattggt gattctaagt atgtctcctg gtaccaacag 120
ttcccaggca aagcccccaa agtcatgatt tatgaggtca gttatcggcc ctcaggagtc 180
tctagccgct tctctggctc caagtctggc aacacggcct ccctgaccat ctctggactc 240
cagactgagg acgaggctga ttattattgc atggcatata caggcacctt cactgctatt 300

-continued ttcggcggag ggaccaagct gaccgtcctg 330

<210> SEQ ID NO 33
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33
caggtgcagc tggtgcagtc tggggctgag gtgaggaagg ctgggtcgtc ggtgaaggtc 60
tcctgcaagg cttctggagg caccttcacc agctatggct tcagctggat acggcaggcc 120
cctggccaag ggcttgagtg gatgggaaac gtcatccctg tctttggttc aacaaactac 180
gcacagaaat ttcagggcag agtcagtatt accgcggacg aagccacggg cacagtccac 240
atggacctca ccagcctgac atctgacgac acggccgttt attactgtgt gaggtcgagt 300
agagaactgc caacgtcaat ggaacggtgg ttcgacccct ggggccaggg aacccaggtc 360
attgtctcct cg 372

<210> SEQ ID NO 34
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34
gacatccaga tgacccagtc tccatcctcc ctgtctgcat ctgtgggaga cagcgtcacc 60
attacttgcc gggcaagtca gagcattaac acctatttaa attggtatca gcagaaacca 120
gggaaggccc ctaaactcct gatctattct gcatccaatt tacacaatgg ggtcccatcg 180
aggttcagtg gcagtggatc tgggacatct ttcactctca ccatcaacaa tctacaacct 240
gaagattttg caacttacta ctgtcaacag agttacagtg ccccttacac ttttggccag 300
gggaccaagt cagacaccaa a 321

<210> SEQ ID NO 35
<211> LENGTH: 134
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Glu Val Gln Leu Val Glu Ser Gly Gly Gly Leu Val Lys Pro Gly Gly
1 5 10 15

Ser Leu Arg Leu Pro Gly Ala Ala Ser Gly Phe Thr Phe Thr Asn Thr
20 25 30

Trp Met Ser Trp Val Arg Gln Ala Pro Gly Lys Gly Leu Glu Trp Val
35 40 45

Gly Arg Ile Ser Arg Asn Lys Asp Gly Ala Lys Thr Glu Tyr Ala Ala
50 55 60

Pro Val Arg Gly Arg Phe Thr Ile Ser Arg Asp Asp Ser Arg Asp Thr
65 70 75 80

Leu Tyr Leu Gln Met Thr Ser Leu Lys Ile Glu Asp Ser Gly Arg Tyr
85 90 95

-continued

```
Phe Cys Thr Ala Asp Leu Gly Glu Pro Val Val Ser Arg Ser Ile Phe
            100                 105                 110

Glu Trp Gly Ser Tyr Tyr Tyr Tyr Met Asp Leu Trp Gly Lys Gly Thr
        115                 120                 125

Thr Val Thr Val Ser Ser
    130


<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Leu Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Lys Pro Gly Arg Ala Pro Lys Ile Leu Ile
        35                  40                  45

Tyr Ala Ala Ser Lys Leu Gly Ser Gly Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105


<210> SEQ ID NO 37
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 38
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Gly Ser Pro Arg Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105
```

<210> SEQ ID NO 39
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130
```

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Val Lys Asp Ile Gln Met Thr Gln Ser Pro Ser Pro Leu Ser Ala Ser
1               5                   10                  15

Val Gly Asp Thr Val Thr Ile Thr Cys Arg Ala Ser Gln Lys Ile Ser
            20                  25                  30

Asp Tyr Leu Asn Trp Tyr Gln Gln Arg Pro Gly Arg Ala Pro Lys Ile
        35                  40                  45

Leu Ile Tyr Ala Ala Ser Lys Leu Ala Ser Asp Val Pro Ser Arg Phe
    50                  55                  60

Ser Gly Ser Gly Tyr Gly Arg Asp Phe Thr Leu Thr Ile Thr Gly Leu
65                  70                  75                  80

Gln Pro Glu Asp Phe Ala Thr Tyr Tyr Cys Gln Glu Ala Tyr Ser Ser
                85                  90                  95

Thr Pro Thr Leu Thr Phe Gly Gln Gly Thr Arg Leu Asp Leu Lys
            100                 105                 110
```

<210> SEQ ID NO 41
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Glu Val Gln Leu Val Glu Ser Gly Gly Gly Leu Ile Lys Pro Gly Gln
1               5                   10                  15

Ser Leu Thr Leu Phe Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Lys Asn Thr
65                  70                  75                  80

Leu Tyr Leu His Met Ser Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Lys Gly Thr Thr Val
        115                 120                 125

Thr Val Ser Ser
    130
```

<210> SEQ ID NO 42
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Asp Ile Gln Leu Thr Gln Ser Pro Ala Ser Leu Ser Ala Ser Val Gly
1               5                   10                  15

Asp Thr Val Thr Ile Thr Cys Arg Ala Ser Gln Ser Ile Lys Asp Tyr
            20                  25                  30

Ile Asn Trp Tyr Gln His Lys Ser Gly Ser Ala Pro Arg Leu Leu Ile
```

```
        35                  40                  45

Tyr Ala Ala Ser Thr Leu Gln Ser Gly Ile Ser Ser Arg Phe Thr Gly
    50                  55                  60

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Lys Lys
            100                 105


<210> SEQ ID NO 43
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Lys Pro Gly Gln
1               5                   10                  15

Ser Leu Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Thr Glu Tyr Ser Ser
    50                  55                  60

Ser Val Lys Gly Arg Phe Ser Val Ser Arg Asp Asp Ser Arg Asn Thr
65                  70                  75                  80

Val Tyr Leu His Met Ser Ser Leu Lys Val Gln Asp Ile Gly Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Thr Val Ser Ser
    130


<210> SEQ ID NO 44
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Thr Ser Leu Ser Ala Ser Val Gly
1               5                   10                  15

Asp Thr Val Ala Ile Thr Cys Arg Ala Ser Gln Ser Val Lys Asp Tyr
            20                  25                  30

Val Asn Trp Tyr Gln His Lys Ser Gly Ser Ala Pro Arg Leu Leu Ile
        35                  40                  45

Tyr Ala Ala Ser Val Leu His Thr Gly Val Ser Ser Arg Phe Thr Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Glu Ala Tyr Asn Thr Tyr Pro
```

```
                85                  90                  95

Thr Leu Ser Phe Gly Gln Gly Thr Arg Val Asp Arg Lys
            100                 105


<210> SEQ ID NO 45
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Asp Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130


<210> SEQ ID NO 46
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Val Met Thr Gln Ser Pro Pro Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Gly Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Ser Phe Gly Gln Gly Thr Arg Leu Asp Leu Lys
            100                 105


<210> SEQ ID NO 47
<211> LENGTH: 133
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 47

Glu Arg Gln Val Val Glu Tyr Gly Gly Gly Leu Val Lys Pro Gly Gly
1               5                   10                  15

Ser Leu Arg Leu Ser Cys Leu Pro Phe Ala Phe Gly Phe Arg Ala Pro
            20                  25                  30

Trp Arg Ser Ser Val Arg His Ala Pro Gly Gly Gly Ala Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Phe Phe Glu
            100                 105                 110

Trp Gly Ser Tyr Tyr Tyr Tyr Met Asp Leu Trp Gly Lys Gly Thr Thr
        115                 120                 125

Val Thr Val Ser Ser
    130


<210> SEQ ID NO 48
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Ser Glu Leu Thr Gln Asp Pro Thr Val Ser Val Ala Leu Gly Gln
1               5                   10                  15

Thr Val Lys Ile Arg Cys Gln Gly Ala Ser Leu Arg Asp Cys Tyr Ala
            20                  25                  30

Thr Trp Tyr Arg Gln Lys Pro Gly Gln Ala Pro Thr Leu Leu Ile Tyr
        35                  40                  45

Asp Ile Asn Lys Arg Pro Ser Gly Ile Pro Asp Arg Phe Ser Ala Ser
    50                  55                  60

Tyr Ser Gly Ser Thr Ser Ser Leu Thr Ile Ile Gly Ala Gln Pro Glu
65                  70                  75                  80

Asp Glu Ala Asp Tyr Phe Cys Ala Ser Arg Asp Arg Ser Gly Asp Arg
                85                  90                  95

Leu Gly Val Phe Gly Gly Gly Thr Lys Leu Thr Val Leu
            100                 105


<210> SEQ ID NO 49
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Leu Gln Glu Ser Gly Pro Arg Leu Val Arg Pro Ser Glu Thr Leu
1               5                   10                  15
```

```
Ser Leu Thr Cys Thr Val Ser Gly Ser Gly Val Ser Val Ser Arg Gly
            20                  25                  30

Ser Tyr Tyr Trp Gly Trp Ile Arg Gln Ser Pro Glu Lys Gly Leu Glu
        35                  40                  45

Trp Ile Gly Ser Val Tyr Ser Thr Thr Ser Gly Lys Thr Tyr Tyr Asn
    50                  55                  60

Pro Ser Leu Lys Ser Arg Val Thr Phe Ser Lys Asp Thr Ser Gln Asn
65                  70                  75                  80

Ala Phe Ser Leu Thr Leu Thr Ser Ile Thr Ala Ala Asp Thr Ala Val
                85                  90                  95

Tyr Tyr Cys Ala Arg Gln Phe Gly Phe Met Gly Gly Phe Leu Glu Trp
            100                 105                 110

Tyr Pro His Tyr Phe Asp Phe Trp Gly Pro Gly Ile Gln Val Val Val
        115                 120                 125

Ser Ser
    130
```

<210> SEQ ID NO 50
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Val His Gln Val Gln Leu Val Gln Ser Gly Ala Glu Val Lys Lys Pro
1               5                   10                  15

Gly Ser Ser Val Lys Val Ser Cys Lys Ala Ser Gly Gly Ser Phe Tyr
            20                  25                  30

Thr Tyr Thr Ile Asn Trp Val Arg Gln Ala Pro Gly Gln Gly Leu Glu
        35                  40                  45

Trp Met Gly Arg Val Thr Thr Met Phe Gly Val Thr Leu Tyr Ala Gln
    50                  55                  60

Lys Phe Gln Gly Arg Val Thr Leu Thr Ala Asp Lys Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Thr Asp Gly Pro Asp Asn Phe Trp Ser Gly Leu Ser His
            100                 105                 110

Ala Phe Asp Leu Trp Gly Gln Gly Thr Met Val Thr Val Ser Ser
        115                 120                 125
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Asp Ile Val Met Thr Gln Ser Pro Ser Tyr Leu Ser Thr Ser Val Gly
1               5                   10                  15

Asp Ser Ile Thr Ile Thr Cys Arg Ala Ser Gln Ser Ile Lys Thr Tyr
            20                  25                  30

Val Asn Trp Tyr Gln Gln Arg Pro Gly Arg Ala Pro Lys Leu Leu Ile
        35                  40                  45
```

Tyr Ser Ser Ser Thr Leu Gln Pro Gly Val Pro Ser Arg Phe Ser Ala
    50                  55                  60

Ser Gly Ser Gly Thr Asp Phe Val Leu Ser Ile Thr Asn Leu Gln Ser
65                  70                  75                  80

Glu Asp Phe Ala Thr Tyr Tyr Cys Gln Gln Thr Tyr Tyr Thr Pro Ser
                85                  90                  95

Thr Phe Gly Gln Gly Thr Thr Leu Asp Ile Lys
            100                 105

<210> SEQ ID NO 52
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Tyr Thr Tyr
            20                  25                  30

Thr Ile Asn Trp Val Arg Gln Ala Pro Gly Gln Gly Leu Glu Trp Met
        35                  40                  45

Gly Arg Val Thr Thr Met Phe Gly Val Thr Leu Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Pro Asp Asn Phe Trp Ser Gly Leu Ser His Ala Phe
            100                 105                 110

Asp Leu Trp Gly Gln Gly Thr Met Val Thr Val Ser Ser
        115                 120                 125

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ser Ala Leu Thr Gln Pro Ala Ser Val Ala Gly Ser Pro Gly Gln
1               5                   10                  15

Ser Ile Thr Ile Ser Cys Thr Gly Thr Ser Ser Asp Ile Gly Asp Ser
            20                  25                  30

Lys Tyr Val Ser Trp Tyr Gln Gln Phe Pro Gly Lys Ala Pro Lys Val
        35                  40                  45

Met Ile Tyr Glu Val Ser Tyr Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Met Ala Tyr Thr Gly Thr
                85                  90                  95

Phe Thr Ala Ile Phe Gly Gly Gly Thr Lys Leu Thr Val Leu
            100                 105                 110

<210> SEQ ID NO 54
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Gln Leu Val Gln Ser Gly Ala Glu Val Arg Lys Ala Gly Ser
1               5                   10                  15

Ser Val Lys Val Ser Cys Lys Ala Ser Gly Gly Thr Phe Thr Ser Tyr
            20                  25                  30

Gly Phe Ser Trp Ile Arg Gln Ala Pro Gly Gln Gly Leu Glu Trp Met
        35                  40                  45

Gly Asn Val Ile Pro Val Phe Gly Ser Thr Asn Tyr Ala Gln Lys Phe
    50                  55                  60

Gln Gly Arg Val Ser Ile Thr Ala Asp Glu Ala Thr Gly Thr Val His
65                  70                  75                  80

Met Asp Leu Thr Ser Leu Thr Ser Asp Asp Thr Ala Val Tyr Tyr Cys
                85                  90                  95

Val Arg Ser Ser Arg Glu Leu Pro Thr Ser Met Glu Arg Trp Phe Asp
            100                 105                 110

Pro Trp Gly Gln Gly Thr Gln Val Ile Val Ser Ser
        115                 120
```

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Ser Ile Asn Thr Tyr
            20                  25                  30

Leu Asn Trp Tyr Gln Gln Lys Pro Gly Lys Ala Pro Lys Leu Leu Ile
        35                  40                  45

Tyr Ser Ala Ser Asn Leu His Asn Gly Val Pro Ser Arg Phe Ser Gly
    50                  55                  60

Ser Gly Ser Gly Thr Ser Phe Thr Leu Thr Ile Asn Asn Leu Gln Pro
65                  70                  75                  80

Glu Asp Phe Ala Thr Tyr Tyr Cys Gln Gln Ser Tyr Ser Ala Pro Tyr
                85                  90                  95

Thr Phe Gly Gln Gly Thr Lys Ser Asp Thr Lys
            100                 105
```

<210> SEQ ID NO 56
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

-continued

```
Glu Val Gln Leu Val Glu Ser Gly Gly Gly Leu Val Lys Pro Gly Gly
1               5                   10                  15

Ser Leu Arg Leu Pro Gly Ala Ala Ser Gly Phe Thr Phe Thr Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Ser Ile Phe
            100                 105                 110

Glu Trp Gly Ser Tyr Tyr Tyr Tyr Met Asp Leu Trp Gly Lys Gly Thr
        115                 120                 125

Thr Val Thr Val Ser Ser
    130
```

<210> SEQ ID NO 57
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 58
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Glu Val Gln Leu Val Glu Ser Gly Gly Gly Leu Val Lys Pro Gly Gly
1               5                   10                  15
```

```
Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130


<210> SEQ ID NO 59
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Ile Lys Pro Gly Gln
1               5                   10                  15

Ser Leu Thr Leu Phe Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Lys Asn Thr
65                  70                  75                  80

Leu Tyr Leu His Met Ser Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Lys Gly Thr Thr Val
        115                 120                 125

Thr Val Ser Ser
    130


<210> SEQ ID NO 60
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Lys Pro Gly Gln
1               5                   10                  15

Ser Leu Thr Leu Ser Cys Val Gly Phe Gly Phe Asn Phe Ala Asn Asp
            20                  25                  30
```

```
Trp Met Gly Trp Val Arg Gln Ala Pro Gly Lys Gly Leu Glu Trp Val
        35                  40                  45

Gly Arg Ile Arg Arg Leu Lys Asp Gly Ala Thr Thr Glu Tyr Ser Ser
    50                  55                  60

Ser Val Lys Gly Arg Phe Ser Val Ser Arg Asp Asp Ser Arg Asn Thr
65                  70                  75                  80

Val Tyr Leu His Met Ser Ser Leu Lys Val Gln Asp Ile Gly Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Thr Val Ser Ser
    130


<210> SEQ ID NO 61
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Asp Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130


<210> SEQ ID NO 62
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Leu Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Lys Pro Gly Arg Ala Pro Lys Ile Leu Ile
        35                  40                  45
```

```
Tyr Ala Ala Ser Lys Leu Gly Ser Gly Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105


<210> SEQ ID NO 63
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Gly Ser Pro Arg Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105


<210> SEQ ID NO 64
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Ala Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105


<210> SEQ ID NO 65
<211> LENGTH: 109
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Asp Ile Gln Leu Thr Gln Ser Pro Ala Ser Leu Ser Ala Ser Val Gly
1 5 10 15

Asp Thr Val Thr Ile Thr Cys Arg Ala Ser Gln Ser Ile Lys Asp Tyr
20 25 30

Ile Asn Trp Tyr Gln His Lys Ser Gly Ser Ala Pro Arg Leu Leu Ile
35 40 45

Tyr Ala Ala Ser Thr Leu Gln Ser Gly Ile Ser Ser Arg Phe Thr Gly
50 55 60

Ser Gly Ser Gly Thr Gln Phe Thr Leu Thr Ile Asn Ser Leu Gln Pro
65 70 75 80

Glu Asp Phe Ala Thr Tyr Tyr Cys Gln Glu Ala Tyr Asn Thr Asn Pro
85 90 95

Thr Leu Ser Phe Gly Gln Gly Thr Arg Val Asp Lys Lys
100 105

<210> SEQ ID NO 66
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Asp Ile Gln Met Thr Gln Ser Pro Thr Ser Leu Ser Ala Ser Val Gly
1 5 10 15

Asp Thr Val Ala Ile Thr Cys Arg Ala Ser Gln Ser Val Lys Asp Tyr
20 25 30

Val Asn Trp Tyr Gln His Lys Ser Gly Ser Ala Pro Arg Leu Leu Ile
35 40 45

Tyr Ala Ala Ser Val Leu His Thr Gly Val Ser Ser Arg Phe Thr Gly
50 55 60

Ser Gly Ser Gly Thr Gln Phe Thr Leu Thr Ile Ser Ser Leu Gln Pro
65 70 75 80

Glu Asp Phe Ala Thr Tyr Tyr Cys Gln Glu Ala Tyr Asn Thr Tyr Pro
85 90 95

Thr Leu Ser Phe Gly Gln Gly Thr Arg Val Asp Arg Lys
100 105

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Asp Ile Val Met Thr Gln Ser Pro Pro Pro Leu Ser Ala Ser Val Gly
1 5 10 15

Asp Thr Val Thr Ile Thr Cys Arg Ala Ser Gln Lys Ile Ser Asp Tyr
20 25 30

Leu Asn Trp Tyr Gln Gln Arg Pro Gly Arg Ala Pro Lys Ile Leu Ile

```
        35                  40                  45

Tyr Ala Ala Ser Lys Leu Gly Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Ser Phe Gly Gln Gly Thr Arg Leu Asp Leu Lys
            100                 105


<210> SEQ ID NO 68
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Glu Ser Gly Gly Gly Leu Val Lys Pro Gly Gly
1               5                   10                  15

Ser Leu Arg Leu Pro Gly Ala Ala Ser Gly Phe Thr Phe Thr Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Ser Ile Phe
            100                 105                 110

Glu Trp Gly Ser Tyr Tyr Tyr Tyr Met Asp Leu Trp Gly Lys Gly Thr
        115                 120                 125

Thr Val Thr Val Ser Ser
    130


<210> SEQ ID NO 69
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
```

```
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130


<210> SEQ ID NO 70
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130


<210> SEQ ID NO 71
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Ile Lys Pro Gly Gln
1               5                   10                  15

Ser Leu Thr Leu Phe Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Lys Asn Thr
65                  70                  75                  80

Leu Tyr Leu His Met Ser Ser Leu Lys Val Glu Asp Thr Ala Val Tyr
                85                  90                  95

Tyr Cys Thr Arg Asp Glu Gly Ala Pro Val Thr Arg Phe Leu Glu Trp
```

```
            100                 105                 110

Gly Ser Tyr Tyr Tyr Tyr Met Ala Val Trp Gly Lys Gly Thr Thr Val
        115                 120                 125

Thr Val Ser Ser
    130


<210> SEQ ID NO 72
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Lys Pro Gly Gln
1               5                   10                  15

Ser Leu Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Thr Glu Tyr Ser Ser
    50                  55                  60

Ser Val Lys Gly Arg Phe Ser Val Ser Arg Asp Asp Ser Arg Asn Thr
65                  70                  75                  80

Val Tyr Leu His Met Ser Ser Leu Lys Val Gln Asp Ile Gly Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Thr Val Ser Ser
    130


<210> SEQ ID NO 73
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Asp Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
```

115 120 125

Val Thr Val Ser Ser
130

<210> SEQ ID NO 74
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Glu Val Gln Leu Val Glu Ser Gly Gly Gly Leu Val Lys Pro Gly Gly
1 5 10 15

Ser Leu Arg Leu Ser Cys Ser Ala Ser Gly Phe Asp Phe Asp Asn Ala
20 25 30

Trp Met Thr Trp Val Arg Gln Pro Pro Gly Lys Gly Leu Glu Trp Val
35 40 45

Gly Arg Ile Thr Gly Pro Gly Glu Gly Trp Ser Val Asp Tyr Ala Ala
50 55 60

Pro Val Glu Gly Arg Phe Thr Ile Ser Arg Leu Asn Ser Ile Asn Phe
65 70 75 80

Leu Tyr Leu Glu Met Asn Asn Leu Arg Met Glu Asp Ser Gly Leu Tyr
85 90 95

Phe Cys Ala Arg Thr Gly Lys Tyr Tyr Asp Phe Trp Ser Gly Tyr Pro
100 105 110

Pro Gly Glu Glu Tyr Phe Gln Asp Trp Gly Arg Gly Thr Leu Val Thr
115 120 125

Val Ser Ser
130

<210> SEQ ID NO 75
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Gln Val Gln Leu Val Gln Ser Gly Ala Glu Val Lys Arg Pro Gly Ser
1 5 10 15

Ser Val Thr Val Ser Cys Lys Ala Ser Gly Gly Ser Phe Ser Thr Tyr
20 25 30

Ala Leu Ser Trp Val Arg Gln Ala Pro Gly Arg Gly Leu Glu Trp Met
35 40 45

Gly Gly Val Ile Pro Leu Leu Thr Ile Thr Asn Tyr Ala Pro Arg Phe
50 55 60

Gln Gly Arg Ile Thr Ile Thr Ala Asp Arg Ser Thr Ser Thr Ala Tyr
65 70 75 80

Leu Glu Leu Asn Ser Leu Arg Pro Glu Asp Thr Ala Val Tyr Tyr Cys
85 90 95

Ala Arg Glu Gly Thr Thr Gly Trp Gly Trp Leu Gly Lys Pro Ile Gly
100 105 110

Ala Phe Ala His Trp Gly Gln Gly Thr Leu Val Thr Val Ser Ser
115 120 125

<210> SEQ ID NO 76
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Arg Ile Thr Leu Lys Glu Ser Gly Pro Pro Leu Val Lys Pro Thr Gln
1               5                   10                  15

Thr Leu Thr Leu Thr Cys Ser Phe Ser Gly Phe Ser Leu Ser Asp Phe
            20                  25                  30

Gly Val Gly Val Gly Trp Ile Arg Gln Pro Pro Gly Lys Ala Leu Glu
        35                  40                  45

Trp Leu Ala Ile Ile Tyr Ser Asp Asp Asp Lys Arg Tyr Ser Pro Ser
    50                  55                  60

Leu Asn Thr Arg Leu Thr Ile Thr Lys Asp Thr Ser Lys Asn Gln Val
65                  70                  75                  80

Val Leu Val Met Thr Arg Val Ser Pro Val Asp Thr Ala Thr Tyr Phe
                85                  90                  95

Cys Ala His Arg Arg Gly Pro Thr Thr Leu Phe Gly Val Pro Ile Ala
            100                 105                 110

Arg Gly Pro Val Asn Ala Met Asp Val Trp Gly Gln Gly Ile Thr Val
        115                 120                 125

Thr Ile Ser Ser
    130
```

<210> SEQ ID NO 77
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Asp Ile Gln Leu Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Lys Pro Gly Arg Ala Pro Lys Ile Leu Ile
        35                  40                  45

Tyr Ala Ala Ser Lys Leu Gly Ser Gly Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105
```

<210> SEQ ID NO 78
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Gly Ser Pro Arg Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105


<210> SEQ ID NO 79
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Ala Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105


<210> SEQ ID NO 80
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Leu Thr Gln Ser Pro Ala Ser Leu Ser Ala Ser Val Gly
1               5                   10                  15

Asp Thr Val Thr Ile Thr Cys Arg Ala Ser Gln Ser Ile Lys Asp Tyr
            20                  25                  30

Ile Asn Trp Tyr Gln His Lys Ser Gly Ser Ala Pro Arg Leu Leu Ile
        35                  40                  45

Tyr Ala Ala Ser Thr Leu Gln Ser Gly Ile Ser Ser Arg Phe Thr Gly
    50                  55                  60

Ser Gly Ser Gly Thr Gln Phe Thr Leu Thr Ile Asn Ser Leu Gln Pro
65                  70                  75                  80
```

```
Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Lys Lys
            100                 105


<210> SEQ ID NO 81
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Thr Ser Leu Ser Ala Ser Val Gly
1               5                   10                  15

Asp Thr Val Ala Ile Thr Cys Arg Ala Ser Gln Ser Val Lys Asp Tyr
            20                  25                  30

Val Asn Trp Tyr Gln His Lys Ser Gly Ser Ala Pro Arg Leu Leu Ile
        35                  40                  45

Tyr Ala Ala Ser Val Leu His Thr Gly Val Ser Ser Arg Phe Thr Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Glu Ala Tyr Asn Thr Tyr Pro
                85                  90                  95

Thr Leu Ser Phe Gly Gln Gly Thr Arg Val Asp Arg Lys
            100                 105


<210> SEQ ID NO 82
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Val Met Thr Gln Ser Pro Pro Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Gly Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Ser Phe Gly Gln Gly Thr Arg Leu Asp Leu Lys
            100                 105


<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 83

```
Glu Ile Val Leu Thr Gln Ser Pro Gly Thr Gln Ser Leu Ser Pro Gly
1               5                   10                  15

Glu Arg Ala Thr Leu Ser Cys Arg Ala Ser Gln Ser Val Gly Asn Asn
            20                  25                  30

Lys Leu Ala Trp Tyr Gln Gln Arg Pro Gly Gln Ala Pro Arg Leu Leu
        35                  40                  45

Ile Tyr Gly Ala Ser Ser Arg Pro Ser Gly Val Ala Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gln Ser Leu
                85                  90                  95

Ser Thr Phe Gly Gln Gly Thr Lys Val Glu Val Lys
            100                 105
```

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Ala Leu Gln Leu Thr Gln Ser Pro Ser Ser Leu Ser Ala Ser Val Gly
1               5                   10                  15

Asp Arg Ile Thr Ile Thr Cys Arg Ala Ser Gln Gly Val Thr Ser Ala
            20                  25                  30

Leu Ala Trp Tyr Arg Gln Lys Pro Gly Ser Pro Pro Gln Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Thr Leu Arg Pro
65                  70                  75                  80

Glu Asp Phe Ala Thr Tyr Tyr Cys Gln Gln Leu His Phe Tyr Pro His
                85                  90                  95

Thr Phe Gly Gly Gly Thr Arg Val Asp Val Arg
            100                 105
```

<210> SEQ ID NO 85
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Val Pro Asp Arg Phe Ser Gly Ser
    50                  55                  60
```

Ala Ser Gly Asn Arg Ala Ser Leu Thr Ile Ser Gly Ala Gln Ala Glu
65 70 75 80

Asp Asp Ala Glu Tyr Tyr Cys Ser Ser Arg Asp Lys Ser Gly Ser Arg
85 90 95

Leu Ser Val Phe Gly Gly Gly Thr Lys Leu Thr Val Leu
100 105

<210> SEQ ID NO 86
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gly Gly Gly Gln Glu Leu Leu Glu Leu Asp Lys Trp Ala Ser Leu Trp
1 5 10 15

Asn Trp Phe Asn Ile Thr Asn Trp Leu Trp Tyr Ile Lys
20 25

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Gly Gly Gly Ala Glu Leu Leu Glu Leu Asp Lys Trp Ala Ser Leu Trp
1 5 10 15

Asn Trp Phe Asn Ile Thr Asn Trp Leu Trp Tyr Ile Lys
20 25

<210> SEQ ID NO 88
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gly Gly Gly Gln Ala Leu Leu Glu Leu Asp Lys Trp Ala Ser Leu Trp
1 5 10 15

Asn Trp Phe Asn Ile Thr Asn Trp Leu Trp Tyr Ile Lys
20 25

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Gly Gly Gly Gln Glu Ala Leu Glu Leu Asp Lys Trp Ala Ser Leu Trp
1 5 10 15

Asn Trp Phe Asn Ile Thr Asn Trp Leu Trp Tyr Ile Lys
20 25

<210> SEQ ID NO 90

-continued

<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Gly Gly Gly Gln Glu Leu Ala Glu Leu Asp Lys Trp Ala Ser Leu Trp
1 5 10 15

Asn Trp Phe Asn Ile Thr Asn Trp Leu Trp Tyr Ile Lys
20 25

<210> SEQ ID NO 91
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Gly Gly Gly Gln Glu Leu Leu Ala Leu Asp Lys Trp Ala Ser Leu Trp
1 5 10 15

Asn Trp Phe Asn Ile Thr Asn Trp Leu Trp Tyr Ile Lys
20 25

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gly Gly Gly Gln Glu Leu Leu Glu Ala Asp Lys Trp Ala Ser Leu Trp
1 5 10 15

Asn Trp Phe Asn Ile Thr Asn Trp Leu Trp Tyr Ile Lys
20 25

<210> SEQ ID NO 93
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Gly Gly Gly Gln Glu Leu Leu Glu Leu Ala Lys Trp Ala Ser Leu Trp
1 5 10 15

Asn Trp Phe Asn Ile Thr Asn Trp Leu Trp Tyr Ile Lys
20 25

<210> SEQ ID NO 94
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Gly Gly Gly Gln Glu Leu Leu Glu Leu Asp Ala Trp Ala Ser Leu Trp
1 5 10 15

Asn Trp Phe Asn Ile Thr Asn Trp Leu Trp Tyr Ile Lys
20 25

<210> SEQ ID NO 95
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Gly Gly Gly Gln Glu Leu Leu Glu Leu Asp Lys Ala Ala Ser Leu Trp
1 5 10 15

Asn Trp Phe Asn Ile Thr Asn Trp Leu Trp Tyr Ile Lys
20 25

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Gly Gly Gly Gln Glu Leu Leu Glu Leu Asp Lys Trp Asn Ser Leu Trp
1 5 10 15

Asn Trp Phe Asn Ile Thr Asn Trp Leu Trp Tyr Ile Lys
20 25

<210> SEQ ID NO 97
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Gly Gly Gly Gln Glu Leu Leu Glu Leu Asp Lys Trp Ala Ala Leu Trp
1 5 10 15

Asn Trp Phe Asn Ile Thr Asn Trp Leu Trp Tyr Ile Lys
20 25

<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Gly Gly Gly Gln Glu Leu Leu Glu Leu Asp Lys Trp Ala Ser Ala Trp
1 5 10 15

Asn Trp Phe Asn Ile Thr Asn Trp Leu Trp Tyr Ile Lys
20 25

<210> SEQ ID NO 99
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Gly Gly Gly Gln Glu Leu Leu Glu Leu Asp Lys Trp Ala Ser Leu Ala
1 5 10 15

Asn Trp Phe Asn Ile Thr Asn Trp Leu Trp Tyr Ile Lys
20 25

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Gly Gly Gly Gln Glu Leu Leu Glu Leu Asp Lys Trp Ala Ser Leu Trp
1 5 10 15

Ala Trp Phe Asn Ile Thr Asn Trp Leu Trp Tyr Ile Lys
20 25

<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Gly Gly Gly Gln Glu Leu Leu Glu Leu Asp Lys Trp Ala Ser Leu Trp
1 5 10 15

Asn Ala Phe Asn Ile Thr Asn Trp Leu Trp Tyr Ile Lys
20 25

<210> SEQ ID NO 102
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Gly Gly Gly Gln Glu Leu Leu Glu Leu Asp Lys Trp Ala Ser Leu Trp
1 5 10 15

Asn Trp Ala Asn Ile Thr Asn Trp Leu Trp Tyr Ile Lys
20 25

<210> SEQ ID NO 103
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Gly Gly Gly Gln Glu Leu Leu Glu Leu Asp Lys Trp Ala Ser Leu Trp
1 5 10 15

Asn Trp Phe Ala Ile Thr Asn Trp Leu Trp Tyr Ile Lys
20 25

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Gly Gly Gly Gln Glu Leu Leu Glu Leu Asp Lys Trp Ala Ser Leu Trp
1               5                   10                  15

Asn Trp Phe Asn Ala Thr Asn Trp Leu Trp Tyr Ile Lys
            20                  25
```

<210> SEQ ID NO 105
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Gly Gly Gly Gln Glu Leu Leu Glu Leu Asp Lys Trp Ala Ser Leu Trp
1               5                   10                  15

Asn Trp Phe Asn Ile Ala Asn Trp Leu Trp Tyr Ile Lys
            20                  25
```

<210> SEQ ID NO 106
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Gly Gly Gly Gln Glu Leu Leu Glu Leu Asp Lys Trp Ala Ser Leu Trp
1               5                   10                  15

Asn Trp Phe Asn Ile Thr Ala Trp Leu Trp Tyr Ile Lys
            20                  25
```

<210> SEQ ID NO 107
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Gly Gly Gly Gln Glu Leu Leu Glu Leu Asp Lys Trp Ala Ser Leu Trp
1               5                   10                  15

Asn Trp Phe Asn Ile Thr Asn Ala Leu Trp Tyr Ile Lys
            20                  25
```

<210> SEQ ID NO 108
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Gly Gly Gly Gln Glu Leu Leu Glu Leu Asp Lys Trp Ala Ser Leu Trp
```

1 5 10 15

Asn Trp Phe Asn Ile Thr Asn Trp Ala Trp Tyr Ile Lys
20 25

<210> SEQ ID NO 109
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Gly Gly Gly Gln Glu Leu Leu Glu Leu Asp Lys Trp Ala Ser Leu Trp
1 5 10 15

Asn Trp Phe Asn Ile Thr Asn Trp Leu Ala Tyr Ile Lys
20 25

<210> SEQ ID NO 110
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gly Gly Gly Gln Glu Leu Leu Glu Leu Asp Lys Trp Ala Ser Leu Trp
1 5 10 15

Asn Trp Phe Asn Ile Thr Asn Trp Leu Trp Ala Ile Lys
20 25

<210> SEQ ID NO 111
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Gly Gly Gly Gln Glu Leu Leu Glu Leu Asp Lys Trp Ala Ser Leu Trp
1 5 10 15

Asn Trp Phe Asn Ile Thr Asn Trp Leu Trp Tyr Ala Lys
20 25

<210> SEQ ID NO 112
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Gly Gly Gly Gln Glu Leu Leu Glu Leu Asp Lys Trp Ala Ser Leu Trp
1 5 10 15

Asn Trp Phe Asn Ile Thr Asn Trp Leu Trp Tyr Ile Ala
20 25

<210> SEQ ID NO 113
<211> LENGTH: 31
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 113

Lys Lys Lys Asn Glu Gln Glu Leu Leu Glu Leu Asp Lys Trp Ala Ser
1               5                   10                  15

Leu Trp Asn Trp Phe Asn Ile Thr Asn Trp Leu Trp Tyr Ile Lys
            20                  25                  30

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Lys Lys Lys Asn Glu Gln Asp Leu Leu Ala Leu Asp Lys Trp Ala Ser
1               5                   10                  15

Leu Trp Asn Trp Phe Asp Ile Ser Asn Trp Leu Trp Tyr Ile Lys Lys
            20                  25                  30

Lys Lys

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Lys Lys Lys Asn Glu Lys Asp Leu Leu Ala Leu Asp Ser Trp Lys Asn
1               5                   10                  15

Leu Trp Asn Trp Phe Ser Ile Thr Lys Trp Leu Trp Tyr Ile Lys Lys
            20                  25                  30

Lys Lys

<210> SEQ ID NO 116
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Lys Lys Lys Asn Glu Gln Glu Leu Leu Ala Leu Asp Lys Trp Asn Asn
1               5                   10                  15

Leu Trp Ser Trp Phe Asp Ile Thr Asn Trp Leu Trp Tyr Ile Arg Lys
            20                  25                  30

Lys Lys

<210> SEQ ID NO 117
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

-continued

```
Lys Lys Lys Asn Glu Lys Asp Leu Leu Ala Leu Asp Ser Trp Lys Asn
1               5                   10                  15

Leu Trp Asn Trp Phe Asp Ile Thr Lys Trp Leu Trp Tyr Ile Lys Lys
            20                  25                  30

Lys Lys


<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Lys Lys Lys Asn Glu Gln Glu Leu Leu Ala Leu Asp Lys Trp Asn Asn
1               5                   10                  15

Leu Trp Ser Trp Phe Asp Ile Thr Asn Trp Leu Trp Tyr Ile Arg Lys
            20                  25                  30

Lys Lys


<210> SEQ ID NO 119
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Lys Lys Lys Asn Glu Gln Glu Leu Leu Ala Leu Ala Lys Ala Asn Asn
1               5                   10                  15

Leu Trp Ser Trp Phe Asp Ile Thr Asn Trp Leu Trp Tyr Ile Arg Tyr
            20                  25                  30

Ile Lys Lys Lys Lys
        35


<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Lys Lys Lys Asn Glu Gln Glu Leu Leu Ala Leu Ala Lys Ala Asn Asn
1               5                   10                  15

Leu Trp Ser Trp Phe Asp Ile Thr Asn Trp Leu Trp Tyr Ile Arg Lys
            20                  25                  30

Lys Lys


<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Lys Lys Lys Asn Glu Lys Asp Leu Leu Ala Leu Asp Ser Trp Lys Asn
1               5                   10                  15
```

Leu Trp Asn Trp Phe Ser Ile Thr Lys Trp Leu Trp Tyr Ile Arg Lys
20 25 30

Lys Lys

<210> SEQ ID NO 122
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Lys Lys Lys Asn Glu Gln Glu Leu Leu Ala Leu Ala Lys Trp Asn Asn
1 5 10 15

Leu Trp Ser Trp Phe Asp Ile Thr Asn Trp Leu Trp Tyr Ile Arg Tyr
20 25 30

Ile Lys Lys Lys Lys
35

<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

Lys Lys Lys Asn Glu Lys Asp Leu Leu Ala Leu Asp Ser Trp Lys Asn
1 5 10 15

Leu Trp Asn Trp Phe Asp Ile Thr Lys Trp Leu Trp Tyr Ile Arg Lys
20 25 30

Lys Lys

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Lys Lys Lys Asn Glu Gln Glu Leu Leu Glu Leu Asp Lys Trp Ala Ser
1 5 10 15

Leu Trp Asn Trp Phe Asp Ile Thr Asn Trp Leu Trp Tyr Ile Arg Lys
20 25 30

Lys Lys

<210> SEQ ID NO 125
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125
caggtgcagc tggtgcagtc tggggctgag gtgaagaagc ctggggcctc agtgaaggtc 60
tcctgcaagg cttctggata caccttcacc ggctactata tgcactgggt gcgacaggcc 120

-continued

```
cctggacaag ggcttgagtg gatgggatgg atcaacccta acagtggtgg cacaaactat    180

gcacagaagt ttcagggcag ggtcaccatg accagggaca cgtccatcag cacagcctac    240

atggagctga gcaggctgag atctgacgac acggccgtgt attactgtgc gagagggggr    300

tggatcrgtc tttactatga tagtagtggt taccctaact ttgactactg ggccagggga    360

accctggtca ccgtctcctc ag                                             382
```

<210> SEQ ID NO 126
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
caggtgcagc tggtgcagtc tggggctgag rtgaagaagc ctggggcctc agtgaaggtc     60

tcctgcaagg cttctggata caccttcacc gactactata tacactgggt gcgacaggcc    120

cctggacaag ggcttgagtg gatgggatgg atcaacccta acastggtcg cacaaactmt    180

gcacagaagt ttcagggcag ggtcaccatg accagggaca cgtccatcag cacagcctac    240

atggagctga gcagvctgag atctgacgac acggccgtgt attactgtgc gagagggggr    300

tggatcrgtc tttactatga tagtagtggt taccctaact ttgactactg ggccagggga    360

accctggtca ccgtctcctc ag                                             382
```

<210> SEQ ID NO 127
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
caggtgcagc tggtgcagtc tggggctgag dtgaagaagc ctggggcctc agtgaaggtc     60

tcctgcaagg cttctggata caccttcacc gactactata tacactgggt gcgacaggcc    120

cctggacaag ggcttgagtg gatggcatgg atcaacccta ccastggtcg cacaarctmt    180

gcacggaagt ttcagggcag ggtcaccatg accagggaca cgtccatcag cacrgcctac    240

atggaactga gaagmctgag atctgacgac acggccgtct attactgtgc gagaggggga    300

tggatcrgtc tttacgttga ttatagtggt taccctaact ttgactcctg ggccagggga    360

accctggtca ccgtctcctc ag                                             382
```

<210> SEQ ID NO 128
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
gaggttcagc tggtggagtc tgggcctgag ttgaaggagc ctggggcctc agtgaaagtc     60

tcctgcaagg cttctggata caccttcacc gactactaca tacactgggt gcgacaggcc    120

cctggacaag gtcttgagtg gatggcatgg atcaacccta ccactggtcg ctctagcttt    180

gcccgggggt ttcagggcag ggtcaccatg accagggaaa cgtccgtcag cacggcctat    240
```

atggaactga gaagactgag atctgacgac acggccgtct attactgtgc gaaagcggga 300
tacatcgccc tttacgttga ctatagtggt taccctaact ttaattcctg gggccaggga 360
accctggtca ccgtctcctc ag 382

<210> SEQ ID NO 129
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129
caggtgcagc tggtgcagtc tggggctgaa ctgaagaagc ctggggcctc agtgaaggtc 60
tcctgcaagg cttctggata caccctcagc gactactatg tacactggct gcgacaggcc 120
cctggacagg ggcttgagtg ggtggcttgg atcaacccta ccagtggtcg cacaatctct 180
ccacggaagt ttcagggcag ggtcacgatg actacggaca cgtccatgaa tgttgcctac 240
atggaactga gaggcttgag atctgacgac acggccgtct atttctgtgc gagaggggga 300
tggatcagtc tctacgttga ttacagttat taccctaact ttgactcgtg gggccaggga 360
accctggtct ccgtctcttc ag 382

<210> SEQ ID NO 130
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130
caggtgcagc tggtgcagtc tggggctgag atgaagaagc ctggggcctc agtgaaggtc 60
tcctgcaagg cttctggata caccttcacc gactactata tacactgggt gcgacaggcc 120
cctggacaag ggcttgagtg gatgggatgg atcaacccta acactggtcg cacaaactmt 180
gcacagaagt ttcagggcag ggtcaccatg accagggaca cgtccatcag cacagcctac 240
atggagctga gcagvctgac atctgacgac acggccgtgt attactgtgc gacagggggr 300
tggatcrgtc tttactatga tagtagtggt taccctaact ttgactactg gggccaggga 360
accctggtca ccgtctcctc ag 382

<210> SEQ ID NO 131
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131
caggtgcagc tggtgcagtc tggggctgaa atgaagaacc ctggggcctc agtgaaggtc 60
tcctgcgcgs cttctggata taccttcacc gacttctaca tacactgggt gcgacaggcc 120
cctggacaag ggcttsagtg gatgggatgg atgaacccta agactggtcg cacaaacamt 180
gcacaaaact ttcagggcag ggtcaccatg accagggaca cgtccatcgg cacagcctac 240
atggagytga gvagcctgac atctgacgac acggccgtvt attactgtgc gacagggggr 300
tggatcagtc tttactatga tagtagttat taccctaact ttgaccactg gggtcaggga 360
accctggtca ccgtctcctc ag 382

<210> SEQ ID NO 132
<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 132
caggtgcagc tggtgcagtc tggggctcaa atgaagaacc ctggggcctc agtgaaggtc 60
tcctgcgcgc cttctggata taccttcacc gacttttaca tacattggtt gcgccaggcc 120
cctggccagg ggcttcagtg gatgggatgg atgaaccctc agactggtcg cacaaacact 180
gcacgaaact ttcaggggag ggtcaccatg accagggaca cgtccatcgg cacagcctac 240
atggagttga gaagcctgac atctgacgac acggccatat attactgtac gacaggggga 300
tggatcagtc tttactatga tagtagttat taccccaact ttgaccactg gggtcaggga 360
accctgctca ccgtctcctc ag 382

<210> SEQ ID NO 133
<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 133
caggtgcagc tggtgcagtc tggggctgaa atgaagaacc ctggggcctc agtgaaagtc 60
tcctgcgcgs cttctggata taccttcacc gacttctaca tacactgggt gcgactggcc 120
cctggacaag ggcttsagtg gatgggatgg atgaacccta agactggtcg cacaaataat 180
gcacaaaact ttcagggcag ggtcaccatg accagggaca cgtccatcgg cacagcctac 240
atggagytga ggagcctgac atctgacgac acggccgtct attactgtgt gacaggggggr 300 tggatcagtc httattatga tagtagttat taccctaact ttgaccactg gggtcaggga 360
accctggtca ccgtctcctc ag 382

<210> SEQ ID NO 134
<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 134
caggtgcagc tggtgcagtc tggggctgaa gtgaagaacc ctggggcctc agtgaaagtc 60
tcctgcgcgc cttctggata taccttcact gacttctaca tacactgggt gcgactggcc 120
cctggacaag ggcttgagtg gctggggtgg atgaacccta agactggtcg cacaaatcaa 180
ggacaaaact ttcagggcag ggtcaccatg accagggaca cgtccatcgg cacagcctac 240
atggagttga ggagcctcac atctgacgac acggccgtct attactgtgt gacaggggcc 300
tggatcagtg attattatga tagtagttat tatcctaact ttgaccactg gggtcaggga 360
accctggtca ccgtctcctc ag 382

<210> SEQ ID NO 135

<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 135
gaggtgcagc tggtgcagtc tggggctgaa atgaagaacc ctggggcctc agtgaaagtc 60
tcctgcgcgg cttctggata tggtttcacc gacttctaca tacactgggt gcgactggcc 120
cctggacacg ggctccagtg gatgggatgg atgaacccta agactggtcg cacaaataat 180
gcacaagatt ttcagggcag ggtcaccctg accagggaca cgtccatcgg cacagcctac 240
atggagctga ggaggctgac atctgacgac acggccgtct attactgtgt gacagggggg 300
tggatcagtc cttattatga tagtagttat taccctaatt ttgaccactg gggtcaggga 360
accctgatca ccgtctcctc ag 382

<210> SEQ ID NO 136
<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 136
caggtgcagc tggtgcagtc tggggctgag atgaagaagc ctggggcctc agtgagggtc 60
tcctgcaagg cttctggata caccttcacc gactactata tacactgggt gcgacaggcc 120
cctggacaag ggcctgagtg gatgggatgg atcaacccta gcactggtcg cacaaactct 180
ccacagaagt ttcagggcag ggtcaccatg accagggaca cgtccatcag cacagcctac 240
atggacctga acagactgac gtctgacgac acggccatgt attactgtac gaccgggggg 300
tggatcggtc tttactctga tactagtggt taccctaact ttgactactg gggccaggga 360
accctggtca ccgtctcctc ag 382

<210> SEQ ID NO 137
<211> LENGTH: 127
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 137

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125


<210> SEQ ID NO 138
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 138

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Xaa Gly Arg Thr Asn Xaa Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Xaa Leu Arg Ser Asp Asp Thr Ala Val Tyr Tyr Cys
                85                  90                  95

Ala Arg Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125


<210> SEQ ID NO 139
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 139

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Xaa Gly Arg Thr Xaa Xaa Ala Arg Lys Phe
    50                  55                  60

Gln Gly Arg Val Thr Met Thr Arg Asp Thr Ser Ile Ser Xaa Ala Tyr
65                  70                  75                  80

Met Glu Leu Arg Xaa Leu Arg Ser Asp Asp Thr Ala Val Tyr Tyr Cys
                85                  90                  95

Ala Arg Gly Gly Trp Ile Xaa Leu Tyr Val Asp Tyr Ser Gly Tyr Pro
            100                 105                 110

Asn Phe Asp Ser Trp Gly Gln Gly Thr Leu Val Thr Val Ser Ser
        115                 120                 125


<210> SEQ ID NO 140
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Thr Gly Arg Ser Ser Phe Ala Arg Gly Phe
    50                  55                  60

Gln Gly Arg Val Thr Met Thr Arg Glu Thr Ser Val Ser Thr Ala Tyr
65                  70                  75                  80

Met Glu Leu Arg Arg Leu Arg Ser Asp Asp Thr Ala Val Tyr Tyr Cys
                85                  90                  95
```

```
Ala Lys Ala Gly Tyr Ile Ala Leu Tyr Val Asp Tyr Ser Gly Tyr Pro
            100                 105                 110

Asn Phe Asn Ser Trp Gly Gln Gly Thr Leu Val Thr Val Ser Ser
        115                 120                 125


<210> SEQ ID NO 141
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
            20                  25                  30

Tyr Val His Trp Leu Arg Gln Ala Pro Gly Gln Gly Leu Glu Trp Val
        35                  40                  45

Ala Trp Ile Asn Pro Thr Ser Gly Arg Thr Ile Ser Pro Arg Lys Phe
    50                  55                  60

Gln Gly Arg Val Thr Met Thr Thr Asp Thr Ser Met Asn Val Ala Tyr
65                  70                  75                  80

Met Glu Leu Arg Gly Leu Arg Ser Asp Asp Thr Ala Val Tyr Phe Cys
                85                  90                  95

Ala Arg Gly Gly Trp Ile Ser Leu Tyr Val Asp Tyr Ser Tyr Tyr Pro
            100                 105                 110

Asn Phe Asp Ser Trp Gly Gln Gly Thr Leu Val Ser Val Ser Ser
        115                 120                 125


<210> SEQ ID NO 142
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 142

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Thr Gly Arg Thr Asn Xaa Ala Gln Lys Phe
```

```
    50                  55                  60

Gln Gly Arg Val Thr Met Thr Arg Asp Thr Ser Ile Ser Thr Ala Tyr
65                  70                  75                  80

Met Glu Leu Ser Xaa Leu Thr Ser Asp Asp Thr Ala Val Tyr Tyr Cys
                85                  90                  95

Ala Thr Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125


<210> SEQ ID NO 143
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (83)..(84)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 143

Gln Val Gln Leu Val Gln Ser Gly Ala Glu Met Lys Asn Pro Gly Ala
1               5                   10                  15

Ser Val Lys Val Ser Cys Ala Xaa Ser Gly Tyr Thr Phe Thr Asp Phe
            20                  25                  30

Tyr Ile His Trp Val Arg Gln Ala Pro Gly Gln Gly Leu Xaa Trp Met
        35                  40                  45

Gly Trp Met Asn Pro Lys Thr Gly Arg Thr Asn Xaa Ala Gln Asn Phe
    50                  55                  60

Gln Gly Arg Val Thr Met Thr Arg Asp Thr Ser Ile Gly Thr Ala Tyr
65                  70                  75                  80

Met Glu Xaa Xaa Ser Leu Thr Ser Asp Asp Thr Ala Xaa Tyr Tyr Cys
                85                  90                  95

Ala Thr Gly Xaa Trp Ile Ser Leu Tyr Tyr Asp Ser Ser Tyr Tyr Pro
            100                 105                 110

Asn Phe Asp His Trp Gly Gln Gly Thr Leu Val Thr Val Ser Ser
        115                 120                 125


<210> SEQ ID NO 144
<211> LENGTH: 127
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 144

Gln Val Gln Leu Val Gln Ser Gly Ala Gln Met Lys Asn Pro Gly Ala
1 5 10 15

Ser Val Lys Val Ser Cys Ala Pro Ser Gly Tyr Thr Phe Thr Asp Phe
20 25 30

Tyr Ile His Trp Leu Arg Gln Ala Pro Gly Gln Gly Leu Gln Trp Met
35 40 45

Gly Trp Met Asn Pro Gln Thr Gly Arg Thr Asn Thr Ala Arg Asn Phe
50 55 60

Gln Gly Arg Val Thr Met Thr Arg Asp Thr Ser Ile Gly Thr Ala Tyr
65 70 75 80

Met Glu Leu Arg Ser Leu Thr Ser Asp Asp Thr Ala Ile Tyr Tyr Cys
85 90 95

Thr Thr Gly Gly Trp Ile Ser Leu Tyr Tyr Asp Ser Ser Tyr Tyr Pro
100 105 110

Asn Phe Asp His Trp Gly Gln Gly Thr Leu Leu Thr Val Ser Ser
115 120 125

<210> SEQ ID NO 145
<211> LENGTH: 127
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 145

Gln Val Gln Leu Val Gln Ser Gly Ala Glu Met Lys Asn Pro Gly Ala
1 5 10 15

Ser Val Lys Val Ser Cys Ala Xaa Ser Gly Tyr Thr Phe Thr Asp Phe
20 25 30

Tyr Ile His Trp Val Arg Leu Ala Pro Gly Gln Gly Leu Xaa Trp Met
35 40 45

Gly Trp Met Asn Pro Lys Thr Gly Arg Thr Asn Asn Ala Gln Asn Phe
50 55 60

Gln Gly Arg Val Thr Met Thr Arg Asp Thr Ser Ile Gly Thr Ala Tyr
65 70 75 80

Met Glu Xaa Arg Ser Leu Thr Ser Asp Asp Thr Ala Val Tyr Tyr Cys
85 90 95

Val Thr Gly Xaa Trp Ile Ser Xaa Tyr Tyr Asp Ser Ser Tyr Tyr Pro

```
            100                 105                 110

Asn Phe Asp His Trp Gly Gln Gly Thr Leu Val Thr Val Ser Ser
        115                 120                 125


<210> SEQ ID NO 146
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Gln Ser Gly Ala Glu Val Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Val Arg Leu Ala Pro Gly Gln Gly Leu Glu Trp Leu
        35                  40                  45

Gly Trp Met Asn Pro Lys Thr Gly Arg Thr Asn Gln Gly Gln Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Val Tyr Tyr Cys
                85                  90                  95

Val Thr Gly Ala Trp Ile Ser Asp Tyr Tyr Asp Ser Ser Tyr Tyr Pro
            100                 105                 110

Asn Phe Asp His Trp Gly Gln Gly Thr Leu Val Thr Val Ser Ser
        115                 120                 125


<210> SEQ ID NO 147
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Ala Glu Met Lys Asn Pro Gly Ala
1               5                   10                  15

Ser Val Lys Val Ser Cys Ala Ala Ser Gly Tyr Gly Phe Thr Asp Phe
            20                  25                  30

Tyr Ile His Trp Val Arg Leu Ala Pro Gly His Gly Leu Gln Trp Met
        35                  40                  45

Gly Trp Met Asn Pro Lys Thr Gly Arg Thr Asn Asn Ala Gln Asp Phe
    50                  55                  60

Gln Gly Arg Val Thr Leu Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

Val Thr Gly Gly Trp Ile Ser Pro Tyr Tyr Asp Ser Ser Tyr Tyr Pro
            100                 105                 110

Asn Phe Asp His Trp Gly Gln Gly Thr Leu Ile Thr Val Ser Ser
        115                 120                 125


<210> SEQ ID NO 148
<211> LENGTH: 127
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 148

Gln Val Gln Leu Val Gln Ser Gly Ala Glu Met Lys Lys Pro Gly Ala
1 5 10 15

Ser Val Arg Val Ser Cys Lys Ala Ser Gly Tyr Thr Phe Thr Asp Tyr
20 25 30

Tyr Ile His Trp Val Arg Gln Ala Pro Gly Gln Gly Pro Glu Trp Met
35 40 45

Gly Trp Ile Asn Pro Ser Thr Gly Arg Thr Asn Ser Pro Gln Lys Phe
50 55 60

Gln Gly Arg Val Thr Met Thr Arg Asp Thr Ser Ile Ser Thr Ala Tyr
65 70 75 80

Met Asp Leu Asn Arg Leu Thr Ser Asp Asp Thr Ala Met Tyr Tyr Cys
85 90 95

Thr Thr Gly Gly Trp Ile Gly Leu Tyr Ser Asp Thr Ser Gly Tyr Pro
100 105 110

Asn Phe Asp Tyr Trp Gly Gln Gly Thr Leu Val Thr Val Ser Ser
115 120 125

<210> SEQ ID NO 149
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 149
cagtctgccc tgactcagcc tgcctccgtg tctgggtctc ctggacagtc gatcaccatc 60
tcctgcactg gaaccagcag tgatgttggg agttataacc ttgtctcctg gtaccaacag 120
cacccaggca aagcccccaa actcatgatt tatgaggtca gtaagcggcc ctcaggggtt 180
tctaatcgct tctctggctc caagtctggc aacacggcct ccctgacaat ctctgggctc 240
caggctgagg acgaggctga ttattactgc tgctcatatg caggtagtag cactgtawta 300
ttcggcggag ggaccaagct gaccgtccta g 331

<210> SEQ ID NO 150
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 150
cagtctgccc tgactcagcc tgcctccgtg tctgggtctc ctggacagtc gatcaccatc 60
tcctgcactg gaaccagcwr tgatgttggg agttataacc ttgtctcctg gtaccaacag 120
cacccaggca aagcccccaa actcatgatt tatgaggtca rtaagcggcc ctcaggggtt 180
tctaatcgct tctctggctc caagtctggc aacacggcct ccctgacaat ctctgggctc 240
caggctgagg acgaggctga ttattactgy tgctcatatg caggtagtag cactgtawta 300
ttcggcggag ggaccaagct gaccgtccta g 331

<210> SEQ ID NO 151

<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 151
cagtctgccc tgactcagcc tgcctccgtg tctgggtctc ctggacagtc gatcaccatc 60
tcctgcactg gaaccagcwr tgatgttggg agttataacc ttgtctcctg gtaccaacag 120
cacccaggca aagcccccaa actcatgatt tatgaggtca rtaagtggcc ctcaggggtt 180
tctaatcgct tctctggctc caagtctggc aacacggcct ccctgacaat ctctgggctc 240
caggctgagg acgaggctva ttattactgt tgctcatatg caggtagtag cactgtaata 300
ttcggcggag ggaccaagct gaccgtccta g 331

<210> SEQ ID NO 152
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 152
cagtctgccc tgactcagcc tgcctccgtg tctgggtctc ctggccagtc gatcaccatc 60
tcctgcactg gaaccagcta tgatgttggg agttataatc ttgtctcctg gtaccaacag 120
cacccaggca aagcccccaa actcattatt tatgaggtca gtcagtggcc ctcaggggtt 180
tctaagcgct tctctggctc caagtctggc aacacggcct ccctgacaat ctctgggctc 240
caggctgagg acgaggctca ttattactgt tgctcatatg caggcagtag cactgtaata 300
ttcggcggag ggacctcgct gaccgtccta g 331

<210> SEQ ID NO 153
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 153
cagcctgtgc tgactcagcc tgcctccgtg tctgggtctc ctggacagtc gatcaccatc 60
tcctgcactg gaagcagcag tgatgttggg agttataacc ttgtgtcctg gtaccagcag 120
cacccaggca aagcccccaa actgatgatt tatgaggtca ataagtgggc ctcaggggtt 180
tctgatcgct tcgctggctc caagtctggc aacacggcct ccctgacaat ctctagactc 240
caggctgagg acgaggctaa ttacttttgt tcctcatcta caaatagtgc cactgtcata 300
ttcggcggag ggaccaagct gaccgtccta g 331

<210> SEQ ID NO 154
<211> LENGTH: 331
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 154
cagtctgccc tgactcagcc tgcctccgtg tctgggtctc ctggacagtc gatcaccatc 60
tcctgcactg gaaccagtta tgatgttggg agttataacc ttgtctcctg gtaccaacag 120
cacccaggca aagcccccaa atacatgatt tatgaggtca ataagcggcc ctcaggggtt 180
tctaatcgct tctctggctc caagtctggc aacacggcct ccctgacaat ctctgggctc 240
caggctgagg acgaggctga ttattactgy tgctcatatg caggtagtag cactgtadtw 300
ttcggcggag ggaccaagct gaccgtccta g 331

<210> SEQ ID NO 155
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
cagtctgysc tgactcagcc tgcctccgtg tctgggtctc ctggacagtc gatcaccatc 60
tcctgcactg gaaccagtta tgatgttggg agttatgacc ttgtctcctg gtaccaacag 120
cacccaggca aagcccccaa atacatgatt tatgaagtca ataagcggcc ctcaggagtt 180
tctaatcgct tctctggctc caaatctggc aacacggcct ccctgacaat ctctgggctc 240
caggctgagg acgaggctga ctattattgc tgctcatttg gaggtagtgc cactgtrgtc 300
tgcggcggag ggaccaaggt gaccgtccta g 331

<210> SEQ ID NO 156
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156
accagtctgc tgactcagcc tgcctccgtg tctgggtctc ctggacagtc gatcaccatc 60
tcctgcactg gaaccaagta tgatgttggg agtcatgacc ttgtctcctg gtaccaacag 120
tacccaggca aagtccccaa atacatgatt tatgaagtca ataaacggcc ctcaggagtt 180
tctaatcgct tctctggctc caaatctggc aacacggcct ccctgacaat ctctgggctc 240
cgggctgagg acgaggctga ctattattgc tgttcatttg gagggagtgc caccgtggtc 300
tgcggcggcg ggaccaaggt gaccgtccta g 331

<210> SEQ ID NO 157
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157
cagtctgysc tgactcagcc tgcctccgtg tctgggtctc ctggacagtc gatcaccatc 60
tcctgcactg gaaccagtta tgatgttggg aagtttgacc ttgtctcctg gtaccaacag 120
cacccaggca aagcccccaa atacatgatt tatgaagtca ataagtggcc ctcaggagtt 180
tctcatcgct tctctggctc caaatctggc aacacggcct ccctgacaat ctctgggctc 240
caggctgagg acgaggctga ctattattgc tgctcattcg gaggtagtgc cactgtrgtc 300
tgcggcggag ggaccaaggt gaccgtccta g 331

<210> SEQ ID NO 158
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158

```
ctgcctgtgc tgactcagcc tgcctccgtg tctgggtctc ctgggcagtc gatcaccatc     60

tcctgcactg ggaccattta tgatgttggg aagtttgacc ttgtctcctg gtaccagcac    120

cacccaggca aagcccccaa atatttgatt tatgaagtca aaaagtggcc ctcaggagtt    180

tctcatcgct tctctggctc caaatctggc aacacggcct ccctgacaat ctctgggctc    240

caggttgagg acgaggctga ctattattgc tgctcattcg gaggtagtgc cgctgtggtc    300

tgcggcggag ggaccaaggt gaccgtccta g                                   331
```

<210> SEQ ID NO 159
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
cagtctgccc tgactcagcc tgcctccgtg tctgggtctc ctggacagtc gatcaccatc     60

tcctgcactg gaaccagtta tgatgttgcg aagtttgacc ttgtctcctg gttccaacag    120

cacccaggca aagcccccaa atacatgatt tatgaagtca ataagtggcc ctcaggagtt    180

tctcatcgct tctctggttc caaatctggc aacacggcct ccctgacaat ctctgggctc    240

caggctgagg acgaggctga ctattattgc tgctcattcg gaggtagtgc cactgtagtc    300

tgcggcggag ggaccaaggt gaccgtccta g                                   331
```

<210> SEQ ID NO 160
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160

```
cagtctgccc tgactcagcc tgcctccgtg tctgggtctc ctggacagtc gatcaccatc     60

tcctgcactg gaaccaatta tgatgttggg agttataacc ttgtctcctg gtatcaacag    120

cacccaggca aagtccccaa atacataatt tatgaggtca ataagcggcc ctcaggggtt    180

tctaatcgct tctctggctc caagtctggc aacacggcct ccctgacaat ctctgggctc    240

caggctgagg acgaggccac ttattactgt tgttcatatg caggtagtag cattatattt    300

ttcggcggtg ggaccaagct gaccgtcata g                                   331
```

<210> SEQ ID NO 161
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<221> NAME/KEY: MOD_RES
<222> LOCATION: (100)..(100)
<223> OTHER INFORMATION: Any amino acid

<400> SEQUENCE: 161

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Asn Leu Val Ser Trp Tyr Gln Gln His Pro Gly Lys Ala Pro Lys Leu
35 40 45

Met Ile Tyr Glu Val Ser Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Ser
85 90 95

Ser Thr Val Xaa
100

<210> SEQ ID NO 162
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 162

Gln Ser Ala Leu Thr Gln Pro Ala Ser Val Ser Gly Ser Pro Gly Gln
1 5 10 15

Ser Ile Thr Ile Ser Cys Thr Gly Thr Ser Xaa Asp Val Gly Ser Tyr
20 25 30

Asn Leu Val Ser Trp Tyr Gln Gln His Pro Gly Lys Ala Pro Lys Leu
35 40 45

Met Ile Tyr Glu Val Xaa Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Xaa Cys Ser Tyr Ala Gly Ser
85 90 95

Ser Thr Val Xaa
100

<210> SEQ ID NO 163
<211> LENGTH: 100
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (87)..(87)
<223> OTHER INFORMATION: Any amino acid

<400> SEQUENCE: 163

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Xaa Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Xaa Lys Trp Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Xaa Tyr Tyr Cys Cys Ser Tyr Ala Gly Ser
                85                  90                  95

Ser Thr Val Ile
            100
```

<210> SEQ ID NO 164
<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 164

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Leu
        35                  40                  45

Ile Ile Tyr Glu Val Ser Gln Trp Pro Ser Gly Val Ser Lys Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala His Tyr Tyr Cys Cys Ser Tyr Ala Gly Ser
                85                  90                  95

Ser Thr Val Ile
            100
```

<210> SEQ ID NO 165
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

Gln Pro Val Leu Thr Gln Pro Ala Ser Val Ser Gly Ser Pro Gly Gln
1 5 10 15

Ser Ile Thr Ile Ser Cys Thr Gly Ser Ser Ser Asp Val Gly Ser Tyr
20 25 30

Asn Leu Val Ser Trp Tyr Gln Gln His Pro Gly Lys Ala Pro Lys Leu
35 40 45

Met Ile Tyr Glu Val Asn Lys Trp Ala Ser Gly Val Ser Asp Arg Phe
50 55 60

Ala Gly Ser Lys Ser Gly Asn Thr Ala Ser Leu Thr Ile Ser Arg Leu
65 70 75 80

Gln Ala Glu Asp Glu Ala Asn Tyr Phe Cys Ser Ser Ser Thr Asn Ser
85 90 95

Ala Thr Val Ile
100

<210> SEQ ID NO 166
<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 166

Gln Ser Ala Leu Thr Gln Pro Ala Ser Val Ser Gly Ser Pro Gly Gln
1 5 10 15

Ser Ile Thr Ile Ser Cys Thr Gly Thr Ser Tyr Asp Val Gly Ser Tyr
20 25 30

Asn Leu Val Ser Trp Tyr Gln Gln His Pro Gly Lys Ala Pro Lys Tyr
35 40 45

Met Ile Tyr Glu Val Asn Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Xaa Cys Ser Tyr Ala Gly Ser
85 90 95

Ser Thr Val Xaa
100

<210> SEQ ID NO 167
<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (99)..(99)
<223> OTHER INFORMATION: Any amino acid

<400> SEQUENCE: 167

```
Gln Ser Xaa Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asp Leu Val Ser Trp Tyr Gln Gln His Pro Gly Lys Ala Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
                85                  90                  95

Ala Thr Xaa Val
            100
```

<210> SEQ ID NO 168
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

```
Thr Ser Leu Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val
            100
```

<210> SEQ ID NO 169
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (99)..(99)
<223> OTHER INFORMATION: Any amino acid

<400> SEQUENCE: 169

```
Gln Ser Xaa Leu Thr Gln Pro Ala Ser Val Ser Gly Ser Pro Gly Gln
1               5                   10                  15
```

Ser Ile Thr Ile Ser Cys Thr Gly Thr Ser Tyr Asp Val Gly Lys Phe
20 25 30

Asp Leu Val Ser Trp Tyr Gln Gln His Pro Gly Lys Ala Pro Lys Tyr
35 40 45

Met Ile Tyr Glu Val Asn Lys Trp Pro Ser Gly Val Ser His Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Phe Gly Gly Ser
85 90 95

Ala Thr Xaa Val
100

<210> SEQ ID NO 170
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Leu Pro Val Leu Thr Gln Pro Ala Ser Val Ser Gly Ser Pro Gly Gln
1 5 10 15

Ser Ile Thr Ile Ser Cys Thr Gly Thr Ile Tyr Asp Val Gly Lys Phe
20 25 30

Asp Leu Val Ser Trp Tyr Gln His His Pro Gly Lys Ala Pro Lys Tyr
35 40 45

Leu Ile Tyr Glu Val Lys Lys Trp Pro Ser Gly Val Ser His Arg Phe
50 55 60

Ser Gly Ser Lys Ser Gly Asn Thr Ala Ser Leu Thr Ile Ser Gly Leu
65 70 75 80

Gln Val Glu Asp Glu Ala Asp Tyr Tyr Cys Cys Ser Phe Gly Gly Ser
85 90 95

Ala Ala Val Val
100

<210> SEQ ID NO 171
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Gln Ser Ala Leu Thr Gln Pro Ala Ser Val Ser Gly Ser Pro Gly Gln
1 5 10 15

Ser Ile Thr Ile Ser Cys Thr Gly Thr Ser Tyr Asp Val Ala Lys Phe
20 25 30

Asp Leu Val Ser Trp Phe Gln Gln His Pro Gly Lys Ala Pro Lys Tyr
35 40 45

Met Ile Tyr Glu Val Asn Lys Trp Pro Ser Gly Val Ser His Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Phe Gly Gly Ser
85 90 95

Ala Thr Val Val
100

<210> SEQ ID NO 172
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Gln Ser Ala Leu Thr Gln Pro Ala Ser Val Ser Gly Ser Pro Gly Gln
1 5 10 15

Ser Ile Thr Ile Ser Cys Thr Gly Thr Asn Tyr Asp Val Gly Ser Tyr
20 25 30

Asn Leu Val Ser Trp Tyr Gln Gln His Pro Gly Lys Val Pro Lys Tyr
35 40 45

Ile Ile Tyr Glu Val Asn Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Thr Tyr Tyr Cys Cys Ser Tyr Ala Gly Ser
85 90 95

Ser Ile Ile Phe
100

<210> SEQ ID NO 173
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

Gln Val Arg Leu Ala Gln Tyr Gly Gly Gly Val Lys Arg Leu Gly Ala
1 5 10 15

Thr Met Thr Leu Ser Cys Val Ala Ser Gly Tyr Thr Phe Asn Asp Tyr
20 25 30

Tyr Ile His Trp Val Arg Gln Ala Pro Gly Gln Gly Phe Glu Leu Leu
35 40 45

Gly Tyr Ile Asp Pro Ala Asn Gly Arg Pro Asp Tyr Ala Gly Ala Leu
50 55 60

Arg Glu Arg Leu Ser Phe Tyr Arg Asp Lys Ser Met Glu Thr Leu Tyr
65 70 75 80

Met Asp Leu Arg Ser Leu Arg Tyr Asp Asp Thr Ala Met Tyr Tyr Cys
85 90 95

Val Arg Asn Val Gly Thr Ala Gly Ser Leu Leu His Tyr Asp His Trp
100 105 110

Gly Ser Gly Ser Pro Val Ile Val Ser Ser
115 120

<210> SEQ ID NO 174
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

```
Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Ser Val Arg Asn Asn
            20                  25                  30

Val Ala Trp Tyr Gln His Lys Gly Gly Gln Ser Pro Arg Leu Leu Ile
        35                  40                  45

Tyr Asp Ala Ser Thr Arg Ala Ala Gly Val Pro Ala Arg Phe Ser Gly
    50                  55                  60

Ser Ala Ser Gly Thr Glu Phe Thr Leu Ala Ile Ser Asn Leu Glu Ser
65                  70                  75                  80

Glu Asp Phe Thr Val Tyr Phe Cys Leu Gln Tyr Asn Asn Trp Trp Thr
                85                  90                  95

Phe Gly Gln Gly Thr Arg Val Asp Ile Lys
            100                 105
```

<210> SEQ ID NO 175
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175

```
caggtccgac tagcccaata tggtggtggg gtgaagaggc taggggccac aatgaccctt     60

tcctgcgtgg catctggata caccttcaac gactactaca tacattgggt gcggcaggcc    120

cctggacaag gctttgagtt gttgggatac atcgaccccg ctaatggtcg cccagactac    180

gcaggggcgt tgagggagag actctccttc tacagggaca agtccatgga gacgctgtac    240

atggacctga ggagcctaag atatgacgac acggccatgt attattgtgt tagaaatgtg    300

gggaccgctg gcagcttgct gcattatgac cactggggct cgggaagccc ggtcatcgtc    360

tcctcc                                                               366
```

<210> SEQ ID NO 176
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176

```
gaaattgtgt tgacgcagtc tccagccacc ctgtccgcgt ctccagggga aagagtcacc     60

ctaacttgca gggccagtcg gagtgtccga aacaacgtgg cctggtatca gcacaagggt    120

ggccagagtc ccaggctcct catttatgat gcgtccacga gggccgctgg tgtcccagcc    180

aggttcagcg gcagtgcatc tgggacagag ttcactctcg ccatcagcaa cttggagtct    240

gaagatttta cagtctactt ctgtctgcag tataataact ggtggacctt cggccaaggg    300

accagggtgg acatcaaa                                                  318
```

<210> SEQ ID NO 177
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Val Gly Thr Glu Gly Ser Leu Leu His Phe Asp Tyr Trp
100 105 110

Gly Gln Gly Thr Leu Val Thr Val Ser Ser
115 120

<210> SEQ ID NO 178
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 178

Gln Val Gln Leu Val Gln Ser Gly Thr Glu Val Arg Lys Pro Gly Ala
1 5 10 15

Ser Val Thr Ile Ser Cys Lys Ala Ser Gly Tyr Thr Phe Asn Asn Phe
20 25 30

Tyr Val His Trp Val Arg Gln Ala Pro Gly Gln Gly Leu Glu Cys Met
35 40 45

Gly Trp Ile Asp Pro Ser Val Gly Arg Ile Ser Tyr Gly Gln Lys Phe
50 55 60

Gln Gly Arg Val Thr Met Thr Arg Asp Arg Ser Thr Ser Thr Val Tyr
65 70 75 80

Met Gly Leu Ser Ser Leu Arg Ser Glu Asp Thr Ala Met Tyr Tyr Cys
85 90 95

Val Arg Asp Val Gly Thr Glu Gly Ser Leu Leu His Phe Asp His Trp
100 105 110

Gly Gln Gly Thr Leu Val Ile Val Ser Ala
115 120

<210> SEQ ID NO 179
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 179

Gln Val Gln Leu Val Gln Ser Gly Ala Glu Val Lys Lys Pro Gly Ala
1 5 10 15

Ser Val Thr Val Ser Cys Gln Ala Ser Gly Tyr Thr Phe Thr Asn Tyr
20 25 30

Tyr Val His Trp Val Arg Gln Ala Pro Gly Gln Gly Leu Gln Leu Met
35 40 45

Gly Trp Ile Asp Pro Ser Trp Gly Arg Thr Asn Tyr Ala Gln Asn Phe
50 55 60

Gln Gly Arg Ile Thr Met Thr Arg Asp Thr Ser Thr Ser Thr Val Tyr
65 70 75 80

Met Glu Met Arg Ser Leu Arg Ser Glu Asp Thr Ala Val Tyr Tyr Cys
85 90 95

Ala Arg Asn Val Ala Thr Glu Gly Ser Leu Leu His Tyr Asp Tyr Trp
100 105 110

Gly Gln Gly Thr Leu Val Thr Val Ser Ala
115 120

<210> SEQ ID NO 180
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Gln Val Gln Leu Val Gln Ser Gly Ala Glu Val Arg Lys Pro Gly Ala
1 5 10 15

Ser Val Thr Val Ser Cys Lys Ala Ser Gly Tyr Thr Phe Asn Asn Phe
20 25 30

Tyr Val His Trp Val Arg Gln Ala Pro Gly Gln Gly Leu Glu Cys Met
35 40 45

Gly Trp Ile Asp Pro Ser Val Gly Arg Ile Asn Tyr Ala Gln Lys Phe
50 55 60

Gln Gly Arg Val Thr Met Thr Arg Asp Arg Ser Thr Ser Thr Val Tyr
65 70 75 80

Met Gly Leu Ser Ser Leu Arg Ser Glu Asp Thr Ala Ile Tyr Tyr Cys
85 90 95

Val Arg Asp Val Gly Thr Glu Gly Ser Leu Leu His Phe Asp His Trp
100 105 110

Gly Gln Gly Thr Leu Val Ile Val Ser Ala
115 120

<210> SEQ ID NO 181
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

Gln Val Gln Leu Val Gln Ser Gly Ala Ala Val Lys Arg Pro Gly Ala
1 5 10 15

Ser Val Thr Ile Ser Cys Arg Ala Ser Gly Tyr Thr Phe Thr Thr Tyr
20 25 30

Tyr Ile His Trp Val Arg Gln Ala Pro Gly Gln Arg Leu Glu Leu Met
35 40 45

Gly Met Ile Asp Pro Ser Arg Gly Arg Thr Asp Tyr Ala Gln Lys Phe
50 55 60

Gln Gly Arg Val Thr Met Ser Arg Asp Thr Ser Thr Ser Thr Leu Tyr
65 70 75 80

Met Glu Leu Arg Ser Leu Arg Pro Asp Asp Thr Ala Leu Tyr Tyr Cys
85 90 95

Val Arg Asn Val Gly Thr Glu Gly Ser Leu Leu His Tyr Asp Tyr Trp
100 105 110

Gly Gln Gly Thr Leu Val Thr Val Ser Ser
115 120

<210> SEQ ID NO 182
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Gln Val Gln Leu Val Gln Ser Gly Ala Ala Val Lys Lys Pro Gly Ala
1 5 10 15

Ser Val Arg Val Ser Cys Lys Ala Ser Gly Tyr Thr Phe Thr Ser Ser
20 25 30

His Ile His Trp Val Arg Gln Ala Pro Gly Gln Gly Pro Glu Trp Met
35 40 45

Gly Met Ile Asp Pro Ser Val Gly Arg Pro Thr Thr Ala Gly Lys Phe
50 55 60

Gln Gly Arg Val Thr Met Thr Arg Asp Arg Tyr Thr Ser Thr Ala Tyr
65 70 75 80

Met Asp Leu Ser Ser Leu Arg Ser Glu Asp Thr Ala Val Tyr Tyr Cys
85 90 95

Ala Arg Ser Val Glu Thr Thr Gly Ser Leu Leu Tyr Phe Asp Tyr Trp
100 105 110

Gly Gln Gly Thr Leu Ile Thr Val Ser Ser
115 120

<210> SEQ ID NO 183
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Gln Val Gln Leu Val Gln Ser Gly Ala Ala Val Lys Arg Pro Gly Ala
1 5 10 15

Ser Val Thr Ile Ser Cys Arg Ala Ser Gly Tyr Thr Phe Thr Thr Tyr
20 25 30

Tyr Ile His Trp Val Arg Gln Ala Pro Gly Gln Gly Leu Glu Leu Met
35 40 45

Gly Trp Ile Asn Pro Arg Gly Gly Arg Thr Asp Tyr Ser Tyr Arg Phe
50 55 60

Glu Asp Arg Val Ser Met Tyr Arg Asp Thr Ser Met Ser Ile Val Tyr
65 70 75 80

Met Asp Leu Arg Asn Leu Lys Ser Ala Asp Thr Ala Val Tyr Tyr Cys
85 90 95

Val Arg Asn Val Gly Thr Ser Gly Ser Leu Leu His Tyr Asp Phe Trp
100 105 110

Gly Gln Gly Ser Leu Val Thr Val Ser Ser
115 120

<210> SEQ ID NO 184
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

```
Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
            20                  25                  30

Tyr Ile His Trp Val Arg Gln Ala Pro Gly Gln Gly Leu Glu Leu Met
        35                  40                  45

Gly Trp Ile Asp Pro Ser Gly Gly Arg Thr Asp Tyr Ala Gly Ala Phe
    50                  55                  60

Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                85                  90                  95

Val Arg Asn Val Gly Thr Ala Gly Ser Leu Leu His Tyr Asp His Trp
            100                 105                 110

Gly Leu Gly Val Met Val Thr Val Ser Ser
        115                 120
```

<210> SEQ ID NO 185
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Gln Val Gln Leu Val Gln Ser Gly Ala Thr Val Lys Lys Pro Arg Ala
1               5                   10                  15

Ser Val Thr Leu Ser Cys Arg Thr Ser Gly Tyr Asn Phe Ile Asp Tyr
            20                  25                  30

Phe Ile His Trp Val Arg Arg Ala Pro Gly Gln Arg Leu Glu Val Met
        35                  40                  45

Gly Tyr Ile Asp Pro Ser Arg Gly Arg Pro Asp Tyr Ala Pro Asn Phe
    50                  55                  60

Arg Asp Arg Val Ser Leu Tyr Arg Asp Thr Ser Met Ser Ile Val Tyr
65                  70                  75                  80

Leu Asp Leu Arg Asp Leu Thr Pro Asp Asp Thr Ala Ile Tyr Tyr Cys
                85                  90                  95

Val Arg Ser Glu Gly Thr Glu Gly Thr Val Leu His Tyr Asp His Trp
            100                 105                 110

Gly Pro Gly Thr Arg Val Thr Val Ser Pro
        115                 120
```

<210> SEQ ID NO 186
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

```
Gln Val Gln Leu Val Gln Ser Gly Gly Gly Val Lys Arg Pro Gly Ser
1               5                   10                  15

Thr Thr Thr Ile Ser Cys Val Ala Ser Gly Tyr Ser Phe Asn Asp Tyr
            20                  25                  30

Tyr Ile His Trp Val Arg Gln Ala Pro Gly Gln Gly Leu Glu Val Leu
        35                  40                  45

Gly Phe Ile Asp Pro Ser Asn Gly Arg Thr Asn Tyr Ala Gly Ala Phe
    50                  55                  60

Gly Asp Arg Phe Ser Met Tyr Arg Asp Lys Ser Met Glu Thr Leu Tyr
65                  70                  75                  80

Met Asp Leu Arg Asn Leu Arg Ser Asp Asp Thr Ala Met Tyr Tyr Cys
                85                  90                  95

Val Arg Asn Val Gly Thr Ala Gly Ser Leu Leu His Tyr Asp His Trp
            100                 105                 110

Gly Thr Gly Ser Lys Ile Ile Val Ser Ser
        115                 120
```

<210> SEQ ID NO 187
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

```
Gln Val Gln Leu Val Gln Ser Gly Gly Thr Val Lys Ser Pro Gly Thr
1               5                   10                  15

Ser Val Thr Leu Ser Cys Lys Thr Ser Gly Tyr Asn Phe Ile Asp Tyr
            20                  25                  30

Tyr Ile His Trp Val Arg Arg Ala Pro Gly Gln Arg Pro Glu Leu Met
        35                  40                  45

Gly Tyr Ile Asp Pro Ser His Gly Arg Pro Asp Tyr Glu Gly Lys Phe
    50                  55                  60

Arg Asp Arg Ile Ser Leu Tyr Arg Asp Thr Ser Thr Ser Val Val Tyr
65                  70                  75                  80

Met Asp Val Arg Gly Leu Arg Leu Asp Asp Thr Ala Leu Tyr Tyr Cys
                85                  90                  95

Val Arg Gly Gly Gly Val Glu Val Ser Ser Asn His Tyr Asp His Trp
            100                 105                 110

Gly Pro Gly Thr Met Val Phe Val Ser Pro
        115                 120
```

<210> SEQ ID NO 188
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

```
Gln Val Arg Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30
```

Tyr Ile His Trp Val Arg Gln Ala Pro Gly Gln Gly Phe Glu Leu Leu
35 40 45

Gly Tyr Ile Asp Pro Ala Asn Gly Arg Pro Asp Tyr Ala Gly Ala Leu
50 55 60

Arg Glu Arg Leu Ser Phe Tyr Arg Asp Lys Ser Met Glu Thr Leu Tyr
65 70 75 80

Met Asp Leu Arg Ser Leu Arg Tyr Asp Asp Thr Ala Met Tyr Tyr Cys
85 90 95

Val Arg Asn Val Gly Thr Ala Gly Ser Leu Leu His Tyr Asp His Trp
100 105 110

Gly Ser Gly Ser Pro Val Ile Val Ser Ser
115 120

<210> SEQ ID NO 189
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

Glu Ile Val Leu Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Trp Thr
85 90 95

Phe Gly Gln Gly Thr Lys Val Glu Ile Lys
100 105

<210> SEQ ID NO 190
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

Glu Ile Val Leu Thr Gln Ser Pro Ala Thr Leu Ser Val Ser Pro Gly
1 5 10 15

Glu Arg Val Thr Leu Ser Cys Arg Ala Ser Gln Ser Val Arg Asn Asn
20 25 30

Leu Ala Trp Tyr Arg Gln Lys Arg Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Met Gln Ser
65 70 75 80

Glu Asp Phe Ala Val Tyr Tyr Cys Gln Gln Tyr Asn Asn Trp Trp Thr
85 90 95

```
Phe Gly Gln Gly Thr Lys Val Glu Ile Lys
            100                 105


<210> SEQ ID NO 191
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Ser Asn
            20                  25                  30

Leu Ala Trp Tyr Gln Gln Lys Arg Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Val Gln Ser
65                  70                  75                  80

Glu Asp Phe Ala Val Tyr Tyr Cys Leu Gln Tyr Asn Asn Trp Trp Thr
                85                  90                  95

Phe Gly Gln Gly Thr Lys Val Glu Ile Lys
            100                 105


<210> SEQ ID NO 192
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Ile Ala Trp Tyr Gln Gln Lys Pro Gly Gln Ala Pro Arg Leu Leu Ile
        35                  40                  45

His Gly Ala Ser Thr Arg Ala Thr Gly Ile Pro Gly Arg Phe Ser Gly
    50                  55                  60

Ser Gly Ser Gly Pro Glu Phe Thr Leu Ala Ile Ser Ser Val Gln Ser
65                  70                  75                  80

Glu Asp Phe Ala Val Tyr Tyr Cys Gln Gln Tyr Asn Asp Trp Trp Thr
                85                  90                  95

Phe Gly Gln Gly Thr Lys Val Glu Ile Lys
            100                 105


<210> SEQ ID NO 193
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Ile Val Leu Thr Gln Ser Pro Ala Thr Leu Ser Val Ser Pro Gly
```

-continued

```
1               5                   10                  15

Glu Arg Ala Thr Leu Ser Cys Arg Ala Ser Gln Ser Val Arg Ser Asn
            20                  25                  30

Leu Ala Trp Tyr Gln Gln Arg Pro Gly Gln Ala Pro Arg Leu Leu Ile
        35                  40                  45

Tyr Gly Thr Ser Thr Arg Ala Thr Gly Val Pro Ala Arg Phe Ser Gly
    50                  55                  60

Arg Gly Ser Gly Thr Glu Phe Thr Leu Ala Ile Ser Ser Met Gln Ser
65                  70                  75                  80

Glu Asp Phe Ala Val Tyr Leu Cys Leu Gln Tyr Asn Asn Trp Trp Thr
                85                  90                  95

Phe Gly Gln Gly Thr Lys Val Glu Ile Lys
            100                 105


<210> SEQ ID NO 194
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Ser Asn
            20                  25                  30

Val Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ala Ser Met Gln Ser
65                  70                  75                  80

Glu Asp Phe Ala Val Tyr Tyr Cys Leu Gln Tyr Asp Asp Trp Trp Thr
                85                  90                  95

Phe Gly Gln Gly Thr Lys Val Glu Ile Lys
            100                 105


<210> SEQ ID NO 195
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Gly Val Arg Asn Asn
            20                  25                  30

Val Ala Trp Tyr Gln His Asn Val Gly Gln Ser Pro Arg Leu Leu Ile
        35                  40                  45

Tyr Asp Ala Ser Thr Arg Ala Pro Gly Ile Pro Ala Arg Phe Ser Gly
    50                  55                  60

Ser Ala Ser Gly Thr Glu Phe Thr Leu Ala Ile Ser Ser Ile Gln Ser
65                  70                  75                  80

Glu Asp Phe Thr Leu Tyr Tyr Cys His Gln Tyr Asn Asn Trp Trp Thr
```

```
                85                  90                  95

Phe Gly Gln Gly Thr Arg Val Asp Ile Asn
            100                 105


<210> SEQ ID NO 196
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Ser Val Arg Asn Asn
            20                  25                  30

Val Ala Trp Tyr Gln His Lys Gly Gly Gln Ser Pro Arg Leu Leu Ile
        35                  40                  45

Tyr Asp Ala Ser Thr Arg Ala Ala Gly Val Pro Ala Arg Phe Ser Gly
    50                  55                  60

Ser Ala Ser Gly Thr Glu Phe Thr Leu Ala Ile Ser Asn Leu Glu Ser
65                  70                  75                  80

Glu Asp Phe Thr Val Tyr Phe Cys Leu Gln Tyr Asn Asn Trp Trp Thr
                85                  90                  95

Phe Gly Gln Gly Thr Arg Val Asp Ile Lys
            100                 105


<210> SEQ ID NO 197
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Ile Val Leu Thr Gln Ser Pro Asp Thr Leu Ser Ala Ser Pro Gly
1               5                   10                  15

Glu Arg Val Thr Leu Ser Cys Arg Ala Ser Gln Ser Val Gly Thr Lys
            20                  25                  30

Val Ala Trp Tyr Arg His Val Arg Gly Gln Pro Pro Arg Leu Leu Ile
        35                  40                  45

Tyr Gly Ala Ser Thr Arg Ala Ala Gly Ile Pro Ala Arg Phe Ser Gly
    50                  55                  60

Gly Gly Ser Gly Thr Asn Phe Thr Leu Ile Ile Asn Asn Phe Gln Ser
65                  70                  75                  80

Glu Asp Phe Ala Glu Tyr Leu Cys Gln Gln Tyr Lys Ser Trp Trp Thr
                85                  90                  95

Phe Gly Gln Gly Thr Lys Val Asp Asn Lys
            100                 105


<210> SEQ ID NO 198
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198
```

Glu Thr Thr Leu Thr Gln Ser Pro Asp Thr Leu Ser Ala Ser Pro Gly
1 5 10 15

Glu Arg Val Thr Leu Ser Cys Arg Ala Ala Gln Ser Val Gly Ser Gln
20 25 30

Val Ala Trp Phe Arg His Ile Arg Gly Gln Pro Pro Arg Leu Leu Ile
35 40 45

Ser Gly Ala Ser Thr Arg Ala Ala Gly Val Pro Ala Arg Phe Ser Gly
50 55 60

Ser Gly Ser Gly Thr Asp Phe Thr Leu Thr Ile Ser Gly Met Gln Ser
65 70 75 80

Glu Asp Phe Ala Glu Tyr Phe Cys Gln Gln Tyr His Met Trp Trp Thr
85 90 95

Phe Gly Gln Gly Thr Arg Val Asp Lys Asn
100 105

<210> SEQ ID NO 199
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199
caggtgcagc tggtacagtc tgggggaggt ctggtgaagc cggggggggtc cctcacactc 60 tcctgttcag cctctggatt ctttttcgat aattcatgga tggggtgggt ccgtcaggcg 120
ccagggaagg gactggagtg ggttggccgc attagaaggc tcaaagacgg tgcgacagga 180
gaatatggtg cagccgtgaa ggacagattc accatttcaa gagatgacag tagaaatatg 240
ctgtacctgc acatgaggac cctgaaaacc gaggactcag gcacttatta ttgtaccatg 300
gatgagggga ccccagtaac acgcttctta gaatggggct acttctatta ttatatggcc 360
gtttggggca gagggaccac ggtcatcgtc tcttca 396

<210> SEQ ID NO 200
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Glu Gly Thr Pro Val Thr Arg Phe Leu Glu Trp
100 105 110

Gly Tyr Phe Tyr Tyr Tyr Met Ala Val Trp Gly Arg Gly Thr Thr Val
115 120 125

Ile Val Ser Ser
130

<210> SEQ ID NO 201
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 201

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Trp Gly Thr Pro Val Thr Arg Phe Leu Glu Trp
100 105 110

Gly Tyr Phe Tyr Tyr Tyr Met Ala Val Trp Gly Arg Gly Thr Thr Val
115 120 125

Ile Val Ser Ser
130

<210> SEQ ID NO 202
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Glu Trp Thr Pro Val Thr Arg Phe Leu Glu Trp
100 105 110

Gly Tyr Phe Tyr Tyr Tyr Met Ala Val Trp Gly Arg Gly Thr Thr Val
115 120 125

```
Ile Val Ser Ser
    130


<210> SEQ ID NO 203
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Trp Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130


<210> SEQ ID NO 204
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Trp Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 205
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Phe Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 206
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Ile Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 207
<211> LENGTH: 132

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Trp Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 208
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 208

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Trp Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 209
<211> LENGTH: 132
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 209

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Glu Gly Thr Pro Val Thr Arg Trp Leu Glu Trp
100 105 110

Gly Tyr Phe Tyr Tyr Tyr Met Ala Val Trp Gly Arg Gly Thr Thr Val
115 120 125

Ile Val Ser Ser
130

<210> SEQ ID NO 210
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Glu Gly Thr Pro Val Thr Arg Phe Trp Glu Trp
100 105 110

Gly Tyr Phe Tyr Tyr Tyr Met Ala Val Trp Gly Arg Gly Thr Thr Val
115 120 125

Ile Val Ser Ser
130

<210> SEQ ID NO 211
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Glu Gly Thr Pro Val Thr Arg Phe Phe Glu Trp
100 105 110

Gly Tyr Phe Tyr Tyr Tyr Met Ala Val Trp Gly Arg Gly Thr Thr Val
115 120 125

Ile Val Ser Ser
130

<210> SEQ ID NO 212
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

Ala Val Lys Asp Arg Phe Thr Ile Ser Arg Asp Asp Ser Arg Asn Met
65 70 75 80

Leu Tyr Leu His Met Arg Thr Leu Lys Thr Glu Asp Ser Gly Thr Tyr
85 90 95

Tyr Cys Thr Met Asp Glu Gly Thr Pro Val Thr Arg Phe Leu Trp Trp
100 105 110

Gly Tyr Phe Tyr Tyr Tyr Met Ala Val Trp Gly Arg Gly Thr Thr Val
115 120 125

Ile Val Ser Ser
130

<210> SEQ ID NO 213
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 213

Gln Val Gln Leu Val Gln Ser Gly Gly Gly Leu Val Lys Pro Gly Gly

```
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Trp Tyr Phe Tyr Tyr Tyr Met Ala Val Trp Gly Arg Gly Thr Thr Val
        115                 120                 125

Ile Val Ser Ser
    130
```

<210> SEQ ID NO 214
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Trp Phe Tyr Tyr Tyr Met Ala Val Trp Gly Arg Gly Thr Thr Val
        115                 120                 125

Ile Val Ser Ser
    130
```

<210> SEQ ID NO 215
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
```

```
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Trp Tyr Tyr Tyr Met Ala Val Trp Gly Arg Gly Thr Thr Val
        115                 120                 125

Ile Val Ser Ser
    130


<210> SEQ ID NO 216
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Trp Tyr Met Ala Val Trp Gly Arg Gly Thr Thr Val
        115                 120                 125

Ile Val Ser Ser
    130


<210> SEQ ID NO 217
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217

caggtgcagc tggtacagtc tgggggaggt ctggtgaagc cggggggtc cctcacactc      60

tcctgttcag cctctggatt ctttttcgat aattcatgga tggggtgggt ccgtcaggcg     120

ccagggaagg gactggagtg ggttggccgc attagaaggc tcaaagacgg tgcgacagga     180

gaatatggtg cagccgtgaa ggacagattc accatttcaa gagatgacag tagaaatatg     240
```

ctgtacctgc acatgaggac cctgaaaacc gaggactcag gcacttatta ttgtaccatg 300
gatgagggga ccccagtaac acgcttctta gaatggggct acttctatta ttatatggcc 360
gtttggggca gagggaccac ggtcatcgtc tcttca 396

<210> SEQ ID NO 218
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 218
caggtccagc tggtacagtc tgggggagcc ctggtaaagc ccggggggc ccttagactc 60 tcctgtgaag cctctggatt cactttcagc gatacgtgga tgagctgggt ccgccatctt 120
cccgggaagg gactggagtg gattggccgc attagaagga ccactgatgg tgggacaaca 180
gaatacgctt cacccgtgaa aggcagattc accatctcaa gagacgattc aagaaacacg 240
ctgtatctgg aaatgagtgg cctgagaatc gacgacacag cggtgtatta ttgtaccgct 300
gatcgggggg ccccagtctt acgtttttgg gagtggggct actatgacta ctacatggag 360
ttctggggca gagggacctc ggtcaccgtc tcctca 396

<210> SEQ ID NO 219
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 219
caggtgcagc tggtggaatc tgggggagcc ctggtaaagc ccggggggc ccttagactc 60 tcctgtgaag cctctggatt cactttcagc gatacgtgga tgagctgggt ccgccatctt 120
cccgggaagg gactggagtg gattggccgc attagaagga ccactgatgg tgggacaaca 180
gaatacgctt cacccgtgaa aggcagattc accatctcaa gagacgattc aagaaacacg 240
ctgtatctgg aaatgagtgg cctgagaatc gacgacacag cagtgtatta ttgtaccgct 300
gatcgggggg ccccagtctt acgtttttgg gagtggggct actatgacta ctacatggag 360
ttctggggca gagggacctc ggtcaccgtc tcctca 396

<210> SEQ ID NO 220
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 220
caggtgcagc tggtggagtc tgggggagcc ctggtaaagc ccggggggc ccttagactc 60 tcctgtgaag cctccggatt ccctttcagc gctacctgga tgagctgggt ccgccatctc 120
cccggaaagg gactggagtg gattggccgc attagagcga ccactaatgg tgggacaaca 180
gaatacgctt cacccgtgaa aggcagattc accatctcaa gggacgattc aagaaacaca 240
ctgtatctgg agatgagtgg cctgaaaatc gaggacactg ccgtgtatta ttgtaccgct 300
gatcgggggg ccccagtctt acgtttttgg gagtggggct attttgacta ctacatggag 360
ttctggggca aagggacctc ggtcaccgtc tcctca 396

<210> SEQ ID NO 221
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 221
caggtgcagc tggtgcaatc tgggggagcc ctggtaaagc ccgggggggc ccttagactc 60
tcctgtgaag cctccggatt ccctttcagc gctacctgga tgagctgggt ccgccatctc 120
cccggaaagg gactggagtg gattggccgc attagagcga ccactaatgg tgggacaaca 180
gaatacgctt cacccgtgaa aggcagattc accatctcaa gggacgattc aagaaacaca 240
ctgtatctgg agatgagtgg cctgaaaatc gaggacactg ccgtgtatta ttgtaccgct 300
gatcgggggg ccccagtctt acgtttttgg gagtggggct attttgacta ctacatggag 360
ttctggggca aagggacctc ggtcaccgtc tcctca 396

<210> SEQ ID NO 222
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 222
gaagtgcagc tggtggagtc tgggggagcc ctggtaaagc ccgggggggc ccttagaccc 60
tcctgtgaag cctccggatt ccctttcagc gctacctgga tgagctgggt ccgccatctc 120
cccggaaagg gactggagtg gattggccgc attagagcga ccactaatgg tgggacaaca 180
gaatacgctt cacccgtgaa aggcagattc acaatctcaa gggacgattc aagaaacaca 240
ctgtatctgg agatgagtgg cctgaaaatc gaggacactg ccgtgtatta ttgtaccgct 300
gatcgggggg ccccagtctt acgtttttgg gagtggggct attttgacta ctacatggag 360
ttctggggca aagggacctc ggtcaccgtc tcctca 396

<210> SEQ ID NO 223
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 223
gaggtgcagt tggtggagtc tgggggcggc ttggtgaagg cgggagagag agtcacagtc 60
tcctgtgaag gttatggatt cagattcgat gacgactgga tgggctgggt ccgccaggct 120
ccagggaggg gactggaatg ggttggtcgt ataagaagag taaaagacgg tgcgacgaca 180
gaatatggtg tacccgtgaa gggaagattc accatctcaa gggatgactc aaagaacaca 240
gtgtatctac acatgaataa cctgaaaatc gaagacacag gtgtatatta ttgtactaga 300
gatgaggggg ccccagttac acgacggttt ctggagtggg gctacttcta ctattacatg 360
gccgtctggg gcagagggac aacggtcacc gtctctcca 399

<210> SEQ ID NO 224
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 224
gaggtgcagc tggtgcagtc tgggggcggc ttggtaaagc cgggacagtc agtcacactt 60
tcctgtgtgg gctttggatt caatttcgct aatgactgga tgggctgggt ccgccaggct 120
ccagggaagg gactggaatg ggttggtcgt ataaggagac taaaagatgg tgcgaaagcg 180
gaatatggat catccgtgaa gggtagattc accatctcaa gagatgattc aagaaacacg 240
ctatatttgc acatgaatag cctcaaggtc gaagacacag ccgtctatta ttgtactcga 300
gacgaggggg ccccagttac ccgatttctg gagtggggct cctattacta ctacatggcc 360
gtctggggca gagggaccac ggtcatcgtc tcttca 396

<210> SEQ ID NO 225
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 225
caggtgcagc tggtgcaatc tgggggcggc ttggtaaagc cgggacagtc agtcacacct 60
tcctgtgtgg gctttggatt caatttcgct aatgactgga tgggctgggt ccgccaggct 120
ccagggaagg gactggaatg ggttggtcgt ataaggagac taaaagatgg tgcgaaagcg 180
gaatatggat catccgtgaa gggtagattc accatctcaa gagatgattc aagaaacacg 240
ctatatttgc acatgaatag cctcaaggtc gaagacacag ccgtctatta ttgtactcga 300
gacgaggggg ccccagttac ccgatttctg gagtggggct cctattacta ctacatggcc 360
gtctggggca gagggaccac ggtcatcgtc tcttca 396

<210> SEQ ID NO 226
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 226
caggtccagc ttgtacagtc tgggggcggc ttggtagagc cgggacagtc agtcacactt 60
tcctgtgtgg gctttggatt caatttcgct aatgactgga tgggctgggt ccgccaggct 120
ccagggaagg gactggaatg ggttggtcgt ataaggagac taaaagatgg tgcgaaagcg 180
gaatatggat catccgtgaa gggtagattc accatctcaa gagatgattc aagaaacacg 240
ctatatttgc acatgaatag cctcaaggtc gaagacacag ccgtctatta ttgtactcga 300
gacgaggggg ccccagttac ccgacttctg gagtggggct cctattacta ctacatggcc 360
gtctggggca gagggaccac ggtcatcgtc tcttca 396

<210> SEQ ID NO 227
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 227
caggtccagc tggtacagtc tgggggaggc ttggtaaagc ctgggggtc ccttacactc 60 tcctgtgtca cctctggatt tactttcagc aacacgtgga tgagttgggt ccgccagact 120
ccagggaagg gactggagtg ggttgcccgt attagtaggg tcggggatgg cccaataata 180
gactacgctg ctcccgtgaa aggcagattc ataatctcaa gagatgactc aagaaacaca 240
ctctttcttc acatgaacaa cctgaaaacc gaggacacag ccgtgtatta ttgtaccgct 300
gatgaggggg ccccaatttt aagatttttt gagtggggtt attacaacta ctacatggac 360
gtctggggca aggggaccac ggtcatcgtc tcctcg 396

<210> SEQ ID NO 228
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 228
caggtccagc ttgtacagtc tgggggaggc ttggtaaagc ctgggggtc ccttacaccc 60 tcctgtgtca cctctggatt tactttcagc aacacgtgga tgagttgggt ccgccagact 120
ccagggaagg gactggagtg ggttgcccgt attagtaggg tcggggatgg cccaataata 180
gactacgctg ctcccgtgaa aggcagattc ataatctcaa gagatgactc aagaaacaca 240
ctctttcttc acatgaacaa cctgaaaacc gaggacacag ccgtgtatta ttgtaccgct 300
gatgaggggg ccccaatttt aagatttttt gagtggggtt attacaacta ctacatggac 360
gtctggggca aggggaccac ggtcatcgtc tcctcg 396

<210> SEQ ID NO 229
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 229
gaggtgcagc tggtggagtc tgggggaggc ttggtgaagc ctggaggatc ccttagactc 60
tcatgttcag cctctggttt cgacttcgat aacgcctgga tgacttgggt ccgccagcct 120
ccagggaagg gcctcgaatg ggttggtcgt attacgggtc caggtgaagg ttggtcagtg 180
gactatgctg cacccgtgga aggcagattt accatctcga gactcaattc aataaatttc 240
ttatatttgg agatgaacaa tttaagaatg gaagactcag gcctttactt ctgtgcccgc 300
acgggaaaat attatgattt ttggagtggc tatccgccgg gagaagaata cttccaagac 360
tggggccggg gcaccctggt caccgtctcc tca 393

<210> SEQ ID NO 230
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 230

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 231
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Val Gln Ser Gly Gly Ala Leu Val Lys Pro Gly Gly
1               5                   10                  15

Ala Leu Arg Leu Ser Cys Glu Ala Ser Gly Phe Thr Phe Ser Asp Thr
            20                  25                  30

Trp Met Ser Trp Val Arg His Leu Pro Gly Lys Gly Leu Glu Trp Ile
        35                  40                  45

Gly Arg Ile Arg Arg Thr Thr Asp Gly Gly Thr Thr Glu Tyr Ala Ser
    50                  55                  60

Pro Val Lys Gly Arg Phe Thr Ile Ser Arg Asp Asp Ser Arg Asn Thr
65                  70                  75                  80

Leu Tyr Leu Glu Met Ser Gly Leu Arg Ile Asp Asp Thr Ala Val Tyr
                85                  90                  95

Tyr Cys Thr Ala Asp Arg Gly Ala Pro Val Leu Arg Phe Trp Glu Trp
            100                 105                 110

Gly Tyr Tyr Asp Tyr Tyr Met Glu Phe Trp Gly Arg Gly Thr Ser Val
        115                 120                 125

Thr Val Ser Ser
    130

<210> SEQ ID NO 232
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Val Glu Ser Gly Gly Ala Leu Val Lys Pro Gly Gly 1 5 10 15

Ala Leu Arg Leu Ser Cys Glu Ala Ser Gly Phe Thr Phe Ser Asp Thr
20 25 30

Trp Met Ser Trp Val Arg His Leu Pro Gly Lys Gly Leu Glu Trp Ile
35 40 45

Gly Arg Ile Arg Arg Thr Thr Asp Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Arg Ile Asp Asp Thr Ala Val Tyr
85 90 95

Tyr Cys Thr Ala Asp Arg Gly Ala Pro Val Leu Arg Phe Trp Glu Trp
100 105 110

Gly Tyr Tyr Asp Tyr Tyr Met Glu Phe Trp Gly Arg Gly Thr Ser Val
115 120 125

Thr Val Ser Ser
130

<210> SEQ ID NO 233
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

Gln Val Gln Leu Val Glu Ser Gly Gly Ala Leu Val Lys Pro Gly Gly
1 5 10 15

Ala Leu Arg Leu Ser Cys Glu Ala Ser Gly Phe Pro Phe Ser Ala Thr
20 25 30

Trp Met Ser Trp Val Arg His Leu Pro Gly Lys Gly Leu Glu Trp Ile
35 40 45

Gly Arg Ile Arg Ala Thr Thr Asn Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Lys Ile Glu Asp Thr Ala Val Tyr
85 90 95

Tyr Cys Thr Ala Asp Arg Gly Ala Pro Val Leu Arg Phe Trp Glu Trp
100 105 110

Gly Tyr Phe Asp Tyr Tyr Met Glu Phe Trp Gly Lys Gly Thr Ser Val
115 120 125

Thr Val Ser Ser
130

<210> SEQ ID NO 234
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 234

Gln Val Gln Leu Val Gln Ser Gly Gly Ala Leu Val Lys Pro Gly Gly
1 5 10 15

Ala Leu Arg Leu Ser Cys Glu Ala Ser Gly Phe Pro Phe Ser Ala Thr

```
            20                  25                  30

Trp Met Ser Trp Val Arg His Leu Pro Gly Lys Gly Leu Glu Trp Ile
        35                  40                  45

Gly Arg Ile Arg Ala Thr Thr Asn Gly Gly Thr Thr Glu Tyr Ala Ser
    50                  55                  60

Pro Val Lys Gly Arg Phe Thr Ile Ser Arg Asp Asp Ser Arg Asn Thr
65                  70                  75                  80

Leu Tyr Leu Glu Met Ser Gly Leu Lys Ile Glu Asp Thr Ala Val Tyr
                85                  90                  95

Tyr Cys Thr Ala Asp Arg Gly Ala Pro Val Leu Arg Phe Trp Glu Trp
            100                 105                 110

Gly Tyr Phe Asp Tyr Tyr Met Glu Phe Trp Gly Lys Gly Thr Ser Val
        115                 120                 125

Thr Val Ser Ser
    130


<210> SEQ ID NO 235
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Val Gln Leu Val Glu Ser Gly Gly Ala Leu Val Lys Pro Gly Gly
1               5                   10                  15

Ala Leu Arg Pro Ser Cys Glu Ala Ser Gly Phe Pro Phe Ser Ala Thr
            20                  25                  30

Trp Met Ser Trp Val Arg His Leu Pro Gly Lys Gly Leu Glu Trp Ile
        35                  40                  45

Gly Arg Ile Arg Ala Thr Thr Asn Gly Gly Thr Thr Glu Tyr Ala Ser
    50                  55                  60

Pro Val Lys Gly Arg Phe Thr Ile Ser Arg Asp Asp Ser Arg Asn Thr
65                  70                  75                  80

Leu Tyr Leu Glu Met Ser Gly Leu Lys Ile Glu Asp Thr Ala Val Tyr
                85                  90                  95

Tyr Cys Thr Ala Asp Arg Gly Ala Pro Val Leu Arg Phe Trp Glu Trp
            100                 105                 110

Gly Tyr Phe Asp Tyr Tyr Met Glu Phe Trp Gly Lys Gly Thr Ser Val
        115                 120                 125

Thr Val Ser Ser
    130


<210> SEQ ID NO 236
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Val Glu Ser Gly Gly Gly Leu Val Lys Ala Gly Glu
1               5                   10                  15

Arg Val Thr Val Ser Cys Glu Gly Tyr Gly Phe Arg Phe Asp Asp Asp
            20                  25                  30

Trp Met Gly Trp Val Arg Gln Ala Pro Gly Arg Gly Leu Glu Trp Val
```

```
        35                  40                  45

Gly Arg Ile Arg Arg Val Lys Asp Gly Ala Thr Thr Glu Tyr Gly Val
    50                  55                  60

Pro Val Lys Gly Arg Phe Thr Ile Ser Arg Asp Asp Ser Lys Asn Thr
65                  70                  75                  80

Val Tyr Leu His Met Asn Asn Leu Lys Ile Glu Asp Thr Gly Val Tyr
                85                  90                  95

Tyr Cys Thr Arg Asp Glu Gly Ala Pro Val Thr Arg Arg Phe Leu Glu
            100                 105                 110

Trp Gly Tyr Phe Tyr Tyr Tyr Met Ala Val Trp Gly Arg Gly Thr Thr
        115                 120                 125

Val Thr Val Ser Pro
    130
```

<210> SEQ ID NO 237
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 237

```
Glu Val Gln Leu Val Gln Ser Gly Gly Gly Leu Val Lys Pro Gly Gln
1               5                   10                  15

Ser Val Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Arg Asn Thr
65                  70                  75                  80

Leu Tyr Leu His Met Asn Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Ile Val Ser Ser
    130
```

<210> SEQ ID NO 238
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 238

```
Gln Val Gln Leu Val Gln Ser Gly Gly Gly Leu Val Lys Pro Gly Gln
1               5                   10                  15

Ser Val Thr Pro Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
```

```
    50                  55                  60

Ser Val Lys Gly Arg Phe Thr Ile Ser Arg Asp Asp Ser Arg Asn Thr
65                  70                  75                  80

Leu Tyr Leu His Met Asn Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Ile Val Ser Ser
    130


<210> SEQ ID NO 239
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Val Gln Ser Gly Gly Gly Leu Val Glu Pro Gly Gln
1               5                   10                  15

Ser Val Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Arg Asn Thr
65                  70                  75                  80

Leu Tyr Leu His Met Asn Ser Leu Lys Val Glu Asp Thr Ala Val Tyr
                85                  90                  95

Tyr Cys Thr Arg Asp Glu Gly Ala Pro Val Thr Arg Leu Leu Glu Trp
            100                 105                 110

Gly Ser Tyr Tyr Tyr Tyr Met Ala Val Trp Gly Arg Gly Thr Thr Val
        115                 120                 125

Ile Val Ser Ser
    130


<210> SEQ ID NO 240
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Gln Leu Val Gln Ser Gly Gly Gly Leu Val Lys Pro Gly Gly
1               5                   10                  15

Ser Leu Thr Leu Ser Cys Val Thr Ser Gly Phe Thr Phe Ser Asn Thr
            20                  25                  30

Trp Met Ser Trp Val Arg Gln Thr Pro Gly Lys Gly Leu Glu Trp Val
        35                  40                  45

Ala Arg Ile Ser Arg Val Gly Asp Gly Pro Ile Ile Asp Tyr Ala Ala
    50                  55                  60

Pro Val Lys Gly Arg Phe Ile Ile Ser Arg Asp Asp Ser Arg Asn Thr
```

```
65                  70                  75                  80

Leu Phe Leu His Met Asn Asn Leu Lys Thr Glu Asp Thr Ala Val Tyr
                85                  90                  95

Tyr Cys Thr Ala Asp Glu Gly Ala Pro Ile Leu Arg Phe Phe Glu Trp
            100                 105                 110

Gly Tyr Tyr Asn Tyr Tyr Met Asp Val Trp Gly Lys Gly Thr Thr Val
        115                 120                 125

Ile Val Ser Ser
    130


<210> SEQ ID NO 241
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Val Gln Leu Val Gln Ser Gly Gly Gly Leu Val Lys Pro Gly Gly
1               5                   10                  15

Ser Leu Thr Pro Ser Cys Val Thr Ser Gly Phe Thr Phe Ser Asn Thr
            20                  25                  30

Trp Met Ser Trp Val Arg Gln Thr Pro Gly Lys Gly Leu Glu Trp Val
        35                  40                  45

Ala Arg Ile Ser Arg Val Gly Asp Gly Pro Ile Ile Asp Tyr Ala Ala
    50                  55                  60

Pro Val Lys Gly Arg Phe Ile Ile Ser Arg Asp Asp Ser Arg Asn Thr
65                  70                  75                  80

Leu Phe Leu His Met Asn Asn Leu Lys Thr Glu Asp Thr Ala Val Tyr
                85                  90                  95

Tyr Cys Thr Ala Asp Glu Gly Ala Pro Ile Leu Arg Phe Phe Glu Trp
            100                 105                 110

Gly Tyr Tyr Asn Tyr Tyr Met Asp Val Trp Gly Lys Gly Thr Thr Val
        115                 120                 125

Ile Val Ser Ser
    130


<210> SEQ ID NO 242
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
```

-continued

```
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser
    130
```

```
<210> SEQ ID NO 243
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243

gacatcgtga tgacccagtc tccgtcctcc gtgtctgcat ctgtgggaga cagagtcacc     60

atcacttgcc gggcaagtca gaatattaga gactatttaa attggtatca acataaaccc    120

gggggatccc ctagactcct aatttatgct gcgtcaactt tgcaaactgg ggtcccgtcc    180

agattcagcg gcagtggatc tgggaacctt ttcactctca ccattaccaa tctgcaacct    240

gaagattttg caacttatta ttgtcaagag aattataata ctatcccctc gctcagcttt    300

ggtcagggga ccaaggtgga catcagg                                         327


<210> SEQ ID NO 244
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244

gacatccaga tcacgcagtc tccgtctttc ctgtacggct ctgtaggcga tagggtcacc     60

atcacttgcc gggcaagtca gaatattaag gactatttaa attggtatca gcagagacca    120

gggagagccc ctagactcct ggtctatgct gcatccaatt tgcaaagtgg ggtcccgtca    180

aggttcagtg gcagtggata tgggacagac ttcactctca tcatcagcag tctgcaacct    240

gaggactttg cgacttacta ctgtcaagag agttatagtt ccacgcccac acacaccttt    300

ggcctgggga ccaaattgga gatgaaac                                        328


<210> SEQ ID NO 245
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245

gacatccaga tgacccagtc tccgtctttc ctgtacggct ctgtaggcga tagagtcacc     60

atcacttgcc gggcaagtca gaatattaag gactatttaa attggtatca gcagagacca    120

gggagagccc ctagactcct gatctatgct gcatccaatt tgcaaagtgg ggtcccgtca    180

aggttcagtg gcagtggata tgggacagac tttactctca tcatcagcag tctgcaacct    240

gaggactttg cgacttattt ctgtcaagag agttatagtt ctacgcccac acacattttt    300

ggcctgggga ccaaattgga gaagaaac                                        328
```

<210> SEQ ID NO 246
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 246
gacatccaga tgacccagtt tccatcctcc ctgtctgcat ctgtgggaga cagagtcacc 60
atgacttgcc gggcaagtca gagcattaag gactatttaa attggtatca acacaccccg 120
gggaaggccc ctcgactcct gatttatggt gcgacgactt tacagagagg ggtcccatca 180
agattcagtg gcagtgggtc tgggaaccaa ttcactctca ccattaacag tctgcaacca 240
gaagattttg caacttatta ttgtcaagag agttaccaga ccgttcccac actcaccttt 300
ggtccgggga ccagggtgga caggaagc 328

<210> SEQ ID NO 247
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 247
gacatccaga tgactcagcc tccatcctcc ctgtctgcat ctgtgggaga cagagtcacc 60
atgacttgcc gggcaagtca gagcattaag gactatttaa attggtatca acacaccccg 120
gggaaggccc ctcgactcct gatttatggt gcgacgactt tacagagagg ggtcccatca 180
agattcagtg gcagtgggtc tgggaaccaa ttcactctca ccattaacag tctgcaacca 240
gaagattttg caacttatta ttgtcaagag agttaccaga ccgttcccac actcaccttt 300
ggtccgggga ccagggtgga caggaagc 328

<210> SEQ ID NO 248
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 248
gacatccgga tgacccagtc tccatcctcc ctgtctgcat ctgtgggaga cagagtcacc 60
atgacttgcc gggcaagtca gagcattaag gactatttaa attggtatca acacaccccg 120
gggaaggccc ctcgactcct gatttatggt gcgacgactt tacagagagg ggtcccatca 180
agattcagtg gcagtgggtc tgggaaccaa ttcactctca ccattaacag tctgcaacca 240
gaagattttg caacttatta ttgtcaagag agttaccaga ccgttcccac actcaccttt 300
ggtccgggga ccagggtgga caggaagc 328

<210> SEQ ID NO 249
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249
gacatccagg tgacccagtc tccaacctct ctgtctgcat ctgtaggaga cacagtcact 60
atcacttgcc gggcaagtca gagcattaaa aattatgtaa attggtatca acacaaatcc 120
gggagcgccc ctagactcct gatttatgct gcgtcagcct tacatagtgg gatcccgtca 180
aggttcactg gcagtgggtc tgggacacag ttcactctca ccattaacag tctgcaacct 240
gaagattttg caacttatta ttgtcaagag gcttataaca ccaaccccac actctccttt 300
ggtcagggga ccagggtgga caggaaac 328

<210> SEQ ID NO 250
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 250
gacatccaga tgacacagtt tccaacctct ctgtctgcat ctgtaggaga caccgtcact 60
atcacttgcc gggcaagtca gagcattaaa aattatgtaa attggtatca acacaaatcc 120
gggagcgccc ctagactcct gatttatgct gcgtcagcct tacatagtgg gatcccgtca 180
aggttcactg gcagtgggtc tgggacacag ttcactctca ccattaacag tctgcaacct 240
gaagattttg caacttatta ttgtcaagag gcttataaca ccaaccccac actctccttt 300
ggtcagggga ccagggtgga caggaaac 328

<210> SEQ ID NO 251
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 251
gacatccggt tgacccagtc tccatcctcc ctgtctgcat ctgttgggga cagaatcacc 60
atcacttgtc gggccagcca aagcattaaa gactatttaa attggtataa acaccggcca 120
ggggaagccc ccaaactcct catttattct gcatccaagt tgagaagtgg ggtctcatca 180
aggttcagtg gcagtggata tgggtcggcc ttcacactga ccatcagcag tctgcagcct 240
gaagattttg cgacttatta ttgtcaggag agttacagca gcgttcccat gtacattttc 300
ggccagggga ccaaggtgga cctcaaac 328

<210> SEQ ID NO 252
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 252
tcctatgagc tgactcagga gactggtgtc tctgtggccc tgggacggac agtcacaatc 60
acgtgccggg gagacagcct cagaagtcat tatgcaagtt ggtaccaaaa gaagccagga 120
caggccccta tacttctctt ctatggtaaa aataatcgtc cttcaggggt cccagaccga 180
ttctctggct ccgcctcagg aaacagagct tccttgacca tctctggggc tcaggcggaa 240
gacgacgcgg aatattattg tagttctcgg gacaagagtg gcagccgtct gtcggtcttc 300
ggcgggggga ccaaactgac cgtcctca 328

<210> SEQ ID NO 253
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

Asp Ile Val Met Thr Gln Ser Pro Ser Ser Val Ser Ala Ser Val Gly
1 5 10 15

Asp Arg Val Thr Ile Thr Cys Arg Ala Ser Gln Asn Ile Arg Asp Tyr
20 25 30

Leu Asn Trp Tyr Gln His Lys Pro Gly Gly Ser Pro Arg Leu Leu Ile
35 40 45

Tyr Ala Ala Ser Thr Leu Gln Thr Gly Val Pro Ser Arg Phe Ser Gly
50 55 60

Ser Gly Ser Gly Asn Leu Phe Thr Leu Thr Ile Thr Asn Leu Gln Pro
65 70 75 80

Glu Asp Phe Ala Thr Tyr Tyr Cys Gln Glu Asn Tyr Asn Thr Ile Pro
85 90 95

Ser Leu Ser Phe Gly Gln Gly Thr Lys Val Asp Ile Arg
100 105

<210> SEQ ID NO 254
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

Asp Ile Gln Ile Thr Gln Ser Pro Ser Phe Leu Tyr Gly Ser Val Gly
1 5 10 15

Asp Arg Val Thr Ile Thr Cys Arg Ala Ser Gln Asn Ile Lys Asp Tyr
20 25 30

Leu Asn Trp Tyr Gln Gln Arg Pro Gly Arg Ala Pro Arg Leu Leu Val
35 40 45

Tyr Ala Ala Ser Asn Leu Gln Ser Gly Val Pro Ser Arg Phe Ser Gly
50 55 60

Ser Gly Tyr Gly Thr Asp Phe Thr Leu Ile Ile Ser Ser Leu Gln Pro
65 70 75 80

Glu Asp Phe Ala Thr Tyr Tyr Cys Gln Glu Ser Tyr Ser Ser Thr Pro
85 90 95

Thr His Thr Phe Gly Leu Gly Thr Lys Leu Glu Met Lys
100 105

<210> SEQ ID NO 255
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Asp Ile Gln Met Thr Gln Ser Pro Ser Phe Leu Tyr Gly Ser Val Gly
1 5 10 15

Asp Arg Val Thr Ile Thr Cys Arg Ala Ser Gln Asn Ile Lys Asp Tyr
20 25 30

Leu Asn Trp Tyr Gln Gln Arg Pro Gly Arg Ala Pro Arg Leu Leu Ile
35 40 45

Tyr Ala Ala Ser Asn Leu Gln Ser Gly Val Pro Ser Arg Phe Ser Gly
50 55 60

Ser Gly Tyr Gly Thr Asp Phe Thr Leu Ile Ile Ser Ser Leu Gln Pro
65 70 75 80

Glu Asp Phe Ala Thr Tyr Phe Cys Gln Glu Ser Tyr Ser Ser Thr Pro
85 90 95

Thr His Ile Phe Gly Leu Gly Thr Lys Leu Glu Lys Lys
100 105

<210> SEQ ID NO 256
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

Asp Ile Gln Met Thr Gln Phe Pro Ser Ser Leu Ser Ala Ser Val Gly
1 5 10 15

Asp Arg Val Thr Met Thr Cys Arg Ala Ser Gln Ser Ile Lys Asp Tyr
20 25 30

Leu Asn Trp Tyr Gln His Thr Pro Gly Lys Ala Pro Arg Leu Leu Ile
35 40 45

Tyr Gly Ala Thr Thr Leu Gln Arg Gly Val Pro Ser Arg Phe Ser Gly
50 55 60

Ser Gly Ser Gly Asn Gln Phe Thr Leu Thr Ile Asn Ser Leu Gln Pro
65 70 75 80

Glu Asp Phe Ala Thr Tyr Tyr Cys Gln Glu Ser Tyr Gln Thr Val Pro
85 90 95

Thr Leu Thr Phe Gly Pro Gly Thr Arg Val Asp Arg Lys
100 105

<210> SEQ ID NO 257
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

Asp Ile Gln Met Thr Gln Pro Pro Ser Ser Leu Ser Ala Ser Val Gly
1 5 10 15

Asp Arg Val Thr Met Thr Cys Arg Ala Ser Gln Ser Ile Lys Asp Tyr
20 25 30

Leu Asn Trp Tyr Gln His Thr Pro Gly Lys Ala Pro Arg Leu Leu Ile
35 40 45

Tyr Gly Ala Thr Thr Leu Gln Arg Gly Val Pro Ser Arg Phe Ser Gly
50 55 60

Ser Gly Ser Gly Asn Gln Phe Thr Leu Thr Ile Asn Ser Leu Gln Pro
65 70 75 80

```
Glu Asp Phe Ala Thr Tyr Tyr Cys Gln Glu Ser Tyr Gln Thr Val Pro
                85                  90                  95

Thr Leu Thr Phe Gly Pro Gly Thr Arg Val Asp Arg Lys
            100                 105


<210> SEQ ID NO 258
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Asp Ile Arg Met Thr Gln Ser Pro Ser Ser Leu Ser Ala Ser Val Gly
1               5                   10                  15

Asp Arg Val Thr Met Thr Cys Arg Ala Ser Gln Ser Ile Lys Asp Tyr
            20                  25                  30

Leu Asn Trp Tyr Gln His Thr Pro Gly Lys Ala Pro Arg Leu Leu Ile
        35                  40                  45

Tyr Gly Ala Thr Thr Leu Gln Arg Gly Val Pro Ser Arg Phe Ser Gly
    50                  55                  60

Ser Gly Ser Gly Asn Gln Phe Thr Leu Thr Ile Asn Ser Leu Gln Pro
65                  70                  75                  80

Glu Asp Phe Ala Thr Tyr Tyr Cys Gln Glu Ser Tyr Gln Thr Val Pro
                85                  90                  95

Thr Leu Thr Phe Gly Pro Gly Thr Arg Val Asp Arg Lys
            100                 105


<210> SEQ ID NO 259
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Ile Gln Val Thr Gln Ser Pro Thr Ser Leu Ser Ala Ser Val Gly
1               5                   10                  15

Asp Thr Val Thr Ile Thr Cys Arg Ala Ser Gln Ser Ile Lys Asn Tyr
            20                  25                  30

Val Asn Trp Tyr Gln His Lys Ser Gly Ser Ala Pro Arg Leu Leu Ile
        35                  40                  45

Tyr Ala Ala Ser Ala Leu His Ser Gly Ile Pro Ser Arg Phe Thr Gly
    50                  55                  60

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Arg Lys
            100                 105


<210> SEQ ID NO 260
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 260

```
Asp Ile Gln Met Thr Gln Phe Pro Thr Ser Leu Ser Ala Ser Val Gly
1               5                   10                  15

Asp Thr Val Thr Ile Thr Cys Arg Ala Ser Gln Ser Ile Lys Asn Tyr
            20                  25                  30

Val Asn Trp Tyr Gln His Lys Ser Gly Ser Ala Pro Arg Leu Leu Ile
        35                  40                  45

Tyr Ala Ala Ser Ala Leu His Ser Gly Ile Pro Ser Arg Phe Thr Gly
    50                  55                  60

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Arg Lys
            100                 105
```

<210> SEQ ID NO 261
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 261

```
Asp Ile Arg Leu Thr Gln Ser Pro Ser Ser Leu Ser Ala Ser Val Gly
1               5                   10                  15

Asp Arg Ile Thr Ile Thr Cys Arg Ala Ser Gln Ser Ile Lys Asp Tyr
            20                  25                  30

Leu Asn Trp Tyr Lys His Arg Pro Gly Glu Ala Pro Lys Leu Leu Ile
        35                  40                  45

Tyr Ser Ala Ser Lys Leu Arg Ser Gly Val Ser Ser Arg Phe Ser Gly
    50                  55                  60

Ser Gly Tyr Gly Ser Ala Phe Thr Leu Thr Ile Ser Ser Leu Gln Pro
65                  70                  75                  80

Glu Asp Phe Ala Thr Tyr Tyr Cys Gln Glu Ser Tyr Ser Ser Val Pro
                85                  90                  95

Met Tyr Ile Phe Gly Gln Gly Thr Lys Val Asp Leu Lys
            100                 105
```

<210> SEQ ID NO 262
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (7)..(8)
<223> OTHER INFORMATION: Any amino acid

<400> SEQUENCE: 262

```
Ser Tyr Glu Leu Thr Gln Xaa Xaa Thr Gly Val Ser Val Ala Leu Gly
1               5                   10                  15

Arg Thr Val Thr Ile Thr Cys Arg Gly Asp Ser Leu Arg Ser His Tyr
            20                  25                  30

Ala Ser Trp Tyr Gln Lys Lys Pro Gly Gln Ala Pro Ile Leu Leu Phe
        35                  40                  45
```

```
Tyr Gly Lys Asn Asn Arg Pro Ser Gly Val Pro Asp Arg Phe Ser Gly
    50                  55                  60

Ser Ala Ser Gly Asn Arg Ala Ser Leu Thr Ile Ser Gly Ala Gln Ala
65                  70                  75                  80

Glu Asp Asp Ala Glu Tyr Tyr Cys Ser Ser Arg Asp Lys Ser Gly Ser
                85                  90                  95

Arg Leu Ser Val Phe Gly Gly Gly Thr Lys Leu Thr Val Leu
            100                 105                 110
```

<210> SEQ ID NO 263
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 263

```
caggtccagc tggtacagtc tgggggagcc ctggtaaagc ccgggggggc ccttagactc     60

tcctgtgaag cctctggatt cactttcagc gatacgtgga tgagctgggt ccgccatctt    120

cccgggaagg gactggagtg gattggccgc attagaagga ccactgatgg tgggacaaca    180

gaatacgctt cacccgtgaa aggcagattc accatctcaa gagacgattc aagaaacacg    240

ctgtatctgg aaatgagtgg cctgagaatc gacgacacag cggtgtatta ttgtaccgct    300

gatcgggggg ccccagtctt acgtttttgg gagtggggct actatgacta ctacatggag    360

ttctggggca gagggacctc ggtcaccgtc tcctca                              396
```

<210> SEQ ID NO 264
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 264

```
caggtgcagc tggtggaatc tgggggagcc ctggtaaagc ccgggggggc ccttagactc     60

tcctgtgaag cctctggatt cactttcagc gatacgtgga tgagctgggt ccgccatctt    120

cccgggaagg gactggagtg gattggccgc attagaagga ccactgatgg tgggacaaca    180

gaatacgctt cacccgtgaa aggcagattc accatctcaa gagacgattc aagaaacacg    240

ctgtatctgg aaatgagtgg cctgagaatc gacgacacag cagtgtatta ttgtaccgct    300

gatcgggggg ccccagtctt acgtttttgg gagtggggct actatgacta ctacatggag    360

ttctggggca gagggacctc ggtcaccgtc tcctca                              396
```

<210> SEQ ID NO 265
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 265

```
caggtgcagc tggtggagtc tgggggagcc ctggtaaagc ccgggggggc ccttagactc     60

tcctgtgaag cctccggatt ccctttcagc gctacctgga tgagctgggt ccgccatctc    120

cccggaaagg gactggagtg gattggccgc attagagcga ccactaatgg tgggacaaca    180
```

gaatacgctt cacccgtgaa aggcagattc accatctcaa gggacgattc aagaaacaca 240
ctgtatctgg agatgagtgg cctgaaaatc gaggacactg ccgtgtatta ttgtaccgct 300
gatcgggggg ccccagtctt acgtttttgg gagtggggct attttgacta ctacatggag 360
ttctggggca aagggacctc ggtcaccgtc tcctca 396

<210> SEQ ID NO 266
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 266
caggtgcagc tggtgcaatc tgggggagcc ctggtaaagc ccggggggc ccttagactc 60 tcctgtgaag cctccggatt ccctttcagc gctacctgga tgagctgggt ccgccatctc 120
cccggaaagg gactggagtg gattggccgc attagagcga ccactaatgg tgggacaaca 180
gaatacgctt cacccgtgaa aggcagattc accatctcaa gggacgattc aagaaacaca 240
ctgtatctgg agatgagtgg cctgaaaatc gaggacactg ccgtgtatta ttgtaccgct 300
gatcgggggg ccccagtctt acgtttttgg gagtggggct attttgacta ctacatggag 360
ttctggggca aagggacctc ggtcaccgtc tcctca 396

<210> SEQ ID NO 267
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267
gaagtgcagc tggtggagtc tgggggagcc ctggtaaagc ccggggggc ccttagaccc 60 tcctgtgaag cctccggatt ccctttcagc gctacctgga tgagctgggt ccgccatctc 120
cccggaaagg gactggagtg gattggccgc attagagcga ccactaatgg tgggacaaca 180
gaatacgctt cacccgtgaa aggcagattc acaatctcaa gggacgattc aagaaacaca 240
ctgtatctgg agatgagtgg cctgaaaatc gaggacactg ccgtgtatta ttgtaccgct 300
gatcgggggg ccccagtctt acgtttttgg gagtggggct attttgacta ctacatggag 360
ttctggggca aagggacctc ggtcaccgtc tcctca 396

<210> SEQ ID NO 268
<211> LENGTH: 399
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 268
gaggtgcagt tggtggagtc tgggggcggc ttggtgaagg cgggagagag agtcacagtc 60
tcctgtgaag gttatggatt cagattcgat gacgactgga tgggctgggt ccgccaggct 120
ccagggaggg gactggaatg ggttggtcgt ataagaagag taaaagacgg tgcgacgaca 180
gaatatggtg tacccgtgaa gggaagattc accatctcaa gggatgactc aaagaacaca 240
gtgtatctac acatgaataa cctgaaaatc gaagacacag gtgtatatta ttgtactaga 300
gatgaggggg ccccagttac acgacggttt ctggagtggg gctacttcta ctattacatg 360
gccgtctggg gcagagggac aacggtcacc gtctctcca 399

<210> SEQ ID NO 269
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 269
gaggtgcagc tggtgcagtc tgggggcggc ttggtaaagc cgggacagtc agtcacactt 60
tcctgtgtgg gctttggatt caatttcgct aatgactgga tgggctgggt ccgccaggct 120
ccagggaagg gactggaatg ggttggtcgt ataaggagac taaaagatgg tgcgaaagcg 180
gaatatggat catccgtgaa gggtagattc accatctcaa gagatgattc aagaaacacg 240
ctatatttgc acatgaatag cctcaaggtc gaagacacag ccgtctatta ttgtactcga 300
gacgaggggg ccccagttac ccgatttctg gagtggggct cctattacta ctacatggcc 360
gtctggggca gagggaccac ggtcatcgtc tcttca 396

<210> SEQ ID NO 270
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 270
caggtgcagc tggtgcaatc tgggggcggc ttggtaaagc cgggacagtc agtcacacct 60
tcctgtgtgg gctttggatt caatttcgct aatgactgga tgggctgggt ccgccaggct 120
ccagggaagg gactggaatg ggttggtcgt ataaggagac taaaagatgg tgcgaaagcg 180
gaatatggat catccgtgaa gggtagattc accatctcaa gagatgattc aagaaacacg 240
ctatatttgc acatgaatag cctcaaggtc gaagacacag ccgtctatta ttgtactcga 300
gacgaggggg ccccagttac ccgatttctg gagtggggct cctattacta ctacatggcc 360
gtctggggca gagggaccac ggtcatcgtc tcttca 396

<210> SEQ ID NO 271
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 271
caggtccagc ttgtacagtc tgggggcggc ttggtagagc cgggacagtc agtcacactt 60
tcctgtgtgg gctttggatt caatttcgct aatgactgga tgggctgggt ccgccaggct 120
ccagggaagg gactggaatg ggttggtcgt ataaggagac taaaagatgg tgcgaaagcg 180
gaatatggat catccgtgaa gggtagattc accatctcaa gagatgattc aagaaacacg 240
ctatatttgc acatgaatag cctcaaggtc gaagacacag ccgtctatta ttgtactcga 300
gacgaggggg ccccagttac ccgacttctg gagtggggct cctattacta ctacatggcc 360
gtctggggca gagggaccac ggtcatcgtc tcttca 396

<210> SEQ ID NO 272
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 272
caggtccagc tggtacagtc tgggggaggc ttggtaaagc ctgggggtc ccttacactc 60 tcctgtgtca cctctggatt tactttcagc aacacgtgga tgagttgggt ccgccagact 120
ccagggaagg gactggagtg ggttgcccgt attagtaggg tcggggatgg cccaataata 180
gactacgctg ctcccgtgaa aggcagattc ataatctcaa gagatgactc aagaaacaca 240
ctctttcttc acatgaacaa cctgaaaacc gaggacacag ccgtgtatta ttgtaccgct 300
gatgaggggg ccccaatttt aagatttttt gagtggggtt attacaacta ctacatggac 360
gtctggggca aggggaccac ggtcatcgtc tcctcg 396

<210> SEQ ID NO 273
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 273
caggtccagc ttgtacagtc tgggggaggc ttggtaaagc ctgggggtc ccttacaccc 60 tcctgtgtca cctctggatt tactttcagc aacacgtgga tgagttgggt ccgccagact 120
ccagggaagg gactggagtg ggttgcccgt attagtaggg tcggggatgg cccaataata 180
gactacgctg ctcccgtgaa aggcagattc ataatctcaa gagatgactc aagaaacaca 240
ctctttcttc acatgaacaa cctgaaaacc gaggacacag ccgtgtatta ttgtaccgct 300
gatgaggggg ccccaatttt aagatttttt gagtggggtt attacaacta ctacatggac 360
gtctggggca aggggaccac ggtcatcgtc tcctcg 396

<210> SEQ ID NO 274
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 274
gacatccaga tcacgcagtc tccgtctttc ctgtacggct ctgtaggcga tagggtcacc 60
atcacttgcc gggcaagtca gaatattaag gactatttaa attggtatca gcagagacca 120
gggagagccc ctagactcct ggtctatgct gcatccaatt tgcaaagtgg ggtcccgtca 180
aggttcagtg gcagtggata tgggacagac ttcactctca tcatcagcag tctgcaacct 240
gaggactttg cgacttacta ctgtcaagag agttatagtt ccacgcccac acacaccttt 300
ggcctgggga ccaaattgga gatgaaac 328

<210> SEQ ID NO 275
<211> LENGTH: 328
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 275
gacatccaga tgacccagtc tccgtctttc ctgtacggct ctgtaggcga tagagtcacc 60
atcacttgcc gggcaagtca gaatattaag gactatttaa attggtatca gcagagacca 120
gggagagccc ctagactcct gatctatgct gcatccaatt tgcaaagtgg ggtcccgtca 180
aggttcagtg gcagtggata tgggacagac tttactctca tcatcagcag tctgcaacct 240
gaggactttg cgacttattt ctgtcaagag agttatagtt ctacgcccac acacattttt 300
ggcctgggga ccaaattgga gaagaaac 328

<210> SEQ ID NO 276
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 276
gacatccaga tgacccagtt tccatcctcc ctgtctgcat ctgtgggaga cagagtcacc 60
atgacttgcc gggcaagtca gagcattaag gactatttaa attggtatca acacaccccg 120
gggaaggccc ctcgactcct gatttatggt gcgacgactt tacagagagg ggtcccatca 180
agattcagtg gcagtgggtc tgggaaccaa ttcactctca ccattaacag tctgcaacca 240
gaagattttg caacttatta ttgtcaagag agttaccaga ccgttcccac actcaccttt 300
ggtccgggga ccagggtgga caggaagc 328

<210> SEQ ID NO 277
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 277
gacatccaga tgactcagcc tccatcctcc ctgtctgcat ctgtgggaga cagagtcacc 60
atgacttgcc gggcaagtca gagcattaag gactatttaa attggtatca acacaccccg 120
gggaaggccc ctcgactcct gatttatggt gcgacgactt tacagagagg ggtcccatca 180
agattcagtg gcagtgggtc tgggaaccaa ttcactctca ccattaacag tctgcaacca 240
gaagattttg caacttatta ttgtcaagag agttaccaga ccgttcccac actcaccttt 300
ggtccgggga ccagggtgga caggaagc 328

<210> SEQ ID NO 278
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 278
gacatccgga tgacccagtc tccatcctcc ctgtctgcat ctgtgggaga cagagtcacc 60
atgacttgcc gggcaagtca gagcattaag gactatttaa attggtatca acacaccccg 120
gggaaggccc ctcgactcct gatttatggt gcgacgactt tacagagagg ggtcccatca 180
agattcagtg gcagtgggtc tgggaaccaa ttcactctca ccattaacag tctgcaacca 240
gaagattttg caacttatta ttgtcaagag agttaccaga ccgttcccac actcaccttt 300
ggtccgggga ccagggtgga caggaagc 328

<210> SEQ ID NO 279
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 279
gacatccagg tgacccagtc tccaacctct ctgtctgcat ctgtaggaga cacagtcact 60
atcacttgcc gggcaagtca gagcattaaa aattatgtaa attggtatca acacaaatcc 120
gggagcgccc ctagactcct gatttatgct gcgtcagcct tacatagtgg gatcccgtca 180
aggttcactg gcagtgggtc tgggacacag ttcactctca ccattaacag tctgcaacct 240
gaagattttg caacttatta ttgtcaagag gcttataaca ccaaccccac actctccttt 300
ggtcagggga ccagggtgga caggaaac 328

<210> SEQ ID NO 280
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280
gacatccaga tgacacagtt tccaacctct ctgtctgcat ctgtaggaga caccgtcact 60
atcacttgcc gggcaagtca gagcattaaa aattatgtaa attggtatca acacaaatcc 120
gggagcgccc ctagactcct gatttatgct gcgtcagcct tacatagtgg gatcccgtca 180
aggttcactg gcagtgggtc tgggacacag ttcactctca ccattaacag tctgcaacct 240
gaagattttg caacttatta ttgtcaagag gcttataaca ccaaccccac actctccttt 300
ggtcagggga ccagggtgga caggaaac 328

<210> SEQ ID NO 281
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
gacatccggt tgacccagtc tccatcctcc ctgtctgcat ctgttgggga cagaatcacc 60
atcacttgtc gggccagcca aagcattaaa gactatttaa attggtataa acaccggcca 120
ggggaagccc ccaaactcct catttattct gcatccaagt tgagaagtgg ggtctcatca 180
aggttcagtg gcagtggata tgggtcggcc ttcacactga ccatcagcag tctgcagcct 240
gaagattttg cgacttatta ttgtcaggag agttacagca gcgttcccat gtacattttc 300
ggccagggga ccaaggtgga cctcaaac 328

<210> SEQ ID NO 282
<211> LENGTH: 132

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

Gln Val Gln Leu Val Gln Ser Gly Gly Ala Leu Val Lys Pro Gly Gly
1 5 10 15

Ala Leu Arg Leu Ser Cys Glu Ala Ser Gly Phe Thr Phe Ser Asp Thr
20 25 30

Trp Met Ser Trp Val Arg His Leu Pro Gly Lys Gly Leu Glu Trp Ile
35 40 45

Gly Arg Ile Arg Arg Thr Thr Asp Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Arg Ile Asp Asp Thr Ala Val Tyr
85 90 95

Tyr Cys Thr Ala Asp Arg Gly Ala Pro Val Leu Arg Phe Trp Glu Trp
100 105 110

Gly Tyr Tyr Asp Tyr Tyr Met Glu Phe Trp Gly Arg Gly Thr Ser Val
115 120 125

Thr Val Ser Ser
130

<210> SEQ ID NO 283
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 283

Gln Val Gln Leu Val Glu Ser Gly Gly Ala Leu Val Lys Pro Gly Gly
1 5 10 15

Ala Leu Arg Leu Ser Cys Glu Ala Ser Gly Phe Thr Phe Ser Asp Thr
20 25 30

Trp Met Ser Trp Val Arg His Leu Pro Gly Lys Gly Leu Glu Trp Ile
35 40 45

Gly Arg Ile Arg Arg Thr Thr Asp Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Arg Ile Asp Asp Thr Ala Val Tyr
85 90 95

Tyr Cys Thr Ala Asp Arg Gly Ala Pro Val Leu Arg Phe Trp Glu Trp
100 105 110

Gly Tyr Tyr Asp Tyr Tyr Met Glu Phe Trp Gly Arg Gly Thr Ser Val
115 120 125

Thr Val Ser Ser
130

<210> SEQ ID NO 284
<211> LENGTH: 132
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 284

Gln Val Gln Leu Val Glu Ser Gly Gly Ala Leu Val Lys Pro Gly Gly
1 5 10 15

Ala Leu Arg Leu Ser Cys Glu Ala Ser Gly Phe Pro Phe Ser Ala Thr
20 25 30

Trp Met Ser Trp Val Arg His Leu Pro Gly Lys Gly Leu Glu Trp Ile
35 40 45

Gly Arg Ile Arg Ala Thr Thr Asn Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Lys Ile Glu Asp Thr Ala Val Tyr
85 90 95

Tyr Cys Thr Ala Asp Arg Gly Ala Pro Val Leu Arg Phe Trp Glu Trp
100 105 110

Gly Tyr Phe Asp Tyr Tyr Met Glu Phe Trp Gly Lys Gly Thr Ser Val
115 120 125

Thr Val Ser Ser
130

<210> SEQ ID NO 285
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 285

Gln Val Gln Leu Val Gln Ser Gly Gly Ala Leu Val Lys Pro Gly Gly
1 5 10 15

Ala Leu Arg Leu Ser Cys Glu Ala Ser Gly Phe Pro Phe Ser Ala Thr
20 25 30

Trp Met Ser Trp Val Arg His Leu Pro Gly Lys Gly Leu Glu Trp Ile
35 40 45

Gly Arg Ile Arg Ala Thr Thr Asn Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Lys Ile Glu Asp Thr Ala Val Tyr
85 90 95

Tyr Cys Thr Ala Asp Arg Gly Ala Pro Val Leu Arg Phe Trp Glu Trp
100 105 110

Gly Tyr Phe Asp Tyr Tyr Met Glu Phe Trp Gly Lys Gly Thr Ser Val
115 120 125

Thr Val Ser Ser
130

<210> SEQ ID NO 286
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 286

Glu Val Gln Leu Val Glu Ser Gly Gly Ala Leu Val Lys Pro Gly Gly
1 5 10 15

Ala Leu Arg Pro Ser Cys Glu Ala Ser Gly Phe Pro Phe Ser Ala Thr
20 25 30

Trp Met Ser Trp Val Arg His Leu Pro Gly Lys Gly Leu Glu Trp Ile
35 40 45

Gly Arg Ile Arg Ala Thr Thr Asn Gly Gly Thr Thr Glu Tyr Ala Ser
50 55 60

Pro Val Lys Gly Arg Phe Thr Ile Ser Arg Asp Asp Ser Arg Asn Thr
65 70 75 80

Leu Tyr Leu Glu Met Ser Gly Leu Lys Ile Glu Asp Thr Ala Val Tyr
85 90 95

Tyr Cys Thr Ala Asp Arg Gly Ala Pro Val Leu Arg Phe Trp Glu Trp
100 105 110

Gly Tyr Phe Asp Tyr Tyr Met Glu Phe Trp Gly Lys Gly Thr Ser Val
115 120 125

Thr Val Ser Ser
130

<210> SEQ ID NO 287
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 287

Glu Val Gln Leu Val Glu Ser Gly Gly Gly Leu Val Lys Ala Gly Glu
1 5 10 15

Arg Val Thr Val Ser Cys Glu Gly Tyr Gly Phe Arg Phe Asp Asp Asp
20 25 30

Trp Met Gly Trp Val Arg Gln Ala Pro Gly Arg Gly Leu Glu Trp Val
35 40 45

Gly Arg Ile Arg Arg Val Lys Asp Gly Ala Thr Thr Glu Tyr Gly Val
50 55 60

Pro Val Lys Gly Arg Phe Thr Ile Ser Arg Asp Asp Ser Lys Asn Thr
65 70 75 80

Val Tyr Leu His Met Asn Asn Leu Lys Ile Glu Asp Thr Gly Val Tyr
85 90 95

Tyr Cys Thr Arg Asp Glu Gly Ala Pro Val Thr Arg Arg Phe Leu Glu
100 105 110

Trp Gly Tyr Phe Tyr Tyr Tyr Met Ala Val Trp Gly Arg Gly Thr Thr
115 120 125

Val Thr Val Ser Pro
130

<210> SEQ ID NO 288
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

Glu Val Gln Leu Val Gln Ser Gly Gly Gly Leu Val Lys Pro Gly Gln

```
1               5                   10                  15

Ser Val Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Arg Asn Thr
65                  70                  75                  80

Leu Tyr Leu His Met Asn Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Ile Val Ser Ser
    130
```

<210> SEQ ID NO 289
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

```
Gln Val Gln Leu Val Gln Ser Gly Gly Gly Leu Val Lys Pro Gly Gln
1               5                   10                  15

Ser Val Thr Pro Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Arg Asn Thr
65                  70                  75                  80

Leu Tyr Leu His Met Asn Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Ile Val Ser Ser
    130
```

<210> SEQ ID NO 290
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

```
Gln Val Gln Leu Val Gln Ser Gly Gly Gly Leu Val Glu Pro Gly Gln
1               5                   10                  15

Ser Val Thr Leu Ser Cys Val Gly Phe Gly Phe Asn Phe Ala Asn Asp
```

```
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Arg Asn Thr
65                  70                  75                  80

Leu Tyr Leu His Met Asn Ser Leu Lys Val Glu Asp Thr Ala Val Tyr
                85                  90                  95

Tyr Cys Thr Arg Asp Glu Gly Ala Pro Val Thr Arg Leu Leu Glu Trp
            100                 105                 110

Gly Ser Tyr Tyr Tyr Tyr Met Ala Val Trp Gly Arg Gly Thr Thr Val
        115                 120                 125

Ile Val Ser Ser
    130


<210> SEQ ID NO 291
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Val Gln Leu Val Gln Ser Gly Gly Gly Leu Val Lys Pro Gly Gly
1               5                   10                  15

Ser Leu Thr Leu Ser Cys Val Thr Ser Gly Phe Thr Phe Ser Asn Thr
            20                  25                  30

Trp Met Ser Trp Val Arg Gln Thr Pro Gly Lys Gly Leu Glu Trp Val
        35                  40                  45

Ala Arg Ile Ser Arg Val Gly Asp Gly Pro Ile Ile Asp Tyr Ala Ala
    50                  55                  60

Pro Val Lys Gly Arg Phe Ile Ile Ser Arg Asp Asp Ser Arg Asn Thr
65                  70                  75                  80

Leu Phe Leu His Met Asn Asn Leu Lys Thr Glu Asp Thr Ala Val Tyr
                85                  90                  95

Tyr Cys Thr Ala Asp Glu Gly Ala Pro Ile Leu Arg Phe Phe Glu Trp
            100                 105                 110

Gly Tyr Tyr Asn Tyr Tyr Met Asp Val Trp Gly Lys Gly Thr Thr Val
        115                 120                 125

Ile Val Ser Ser
    130


<210> SEQ ID NO 292
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Gly Gly Leu Val Lys Pro Gly Gly
1               5                   10                  15

Ser Leu Thr Pro Ser Cys Val Thr Ser Gly Phe Thr Phe Ser Asn Thr
            20                  25                  30

Trp Met Ser Trp Val Arg Gln Thr Pro Gly Lys Gly Leu Glu Trp Val
```

```
        35                  40                  45

Ala Arg Ile Ser Arg Val Gly Asp Gly Pro Ile Ile Asp Tyr Ala Ala
    50                  55                  60

Pro Val Lys Gly Arg Phe Ile Ile Ser Arg Asp Asp Ser Arg Asn Thr
65                  70                  75                  80

Leu Phe Leu His Met Asn Asn Leu Lys Thr Glu Asp Thr Ala Val Tyr
                85                  90                  95

Tyr Cys Thr Ala Asp Glu Gly Ala Pro Ile Leu Arg Phe Phe Glu Trp
            100                 105                 110

Gly Tyr Tyr Asn Tyr Tyr Met Asp Val Trp Gly Lys Gly Thr Thr Val
        115                 120                 125

Ile Val Ser Ser
    130


<210> SEQ ID NO 293
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 293

Asp Ile Gln Ile Thr Gln Ser Pro Ser Phe Leu Tyr Gly Ser Val Gly
1               5                   10                  15

Asp Arg Val Thr Ile Thr Cys Arg Ala Ser Gln Asn Ile Lys Asp Tyr
            20                  25                  30

Leu Asn Trp Tyr Gln Gln Arg Pro Gly Arg Ala Pro Arg Leu Leu Val
        35                  40                  45

Tyr Ala Ala Ser Asn Leu Gln Ser Gly Val Pro Ser Arg Phe Ser Gly
    50                  55                  60

Ser Gly Tyr Gly Thr Asp Phe Thr Leu Ile Ile Ser Ser Leu Gln Pro
65                  70                  75                  80

Glu Asp Phe Ala Thr Tyr Tyr Cys Gln Glu Ser Tyr Ser Ser Thr Pro
                85                  90                  95

Thr His Thr Phe Gly Leu Gly Thr Lys Leu Glu Met Lys Xaa
            100                 105                 110


<210> SEQ ID NO 294
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 294

Asp Ile Gln Met Thr Gln Ser Pro Ser Phe Leu Tyr Gly Ser Val Gly
1               5                   10                  15

Asp Arg Val Thr Ile Thr Cys Arg Ala Ser Gln Asn Ile Lys Asp Tyr
            20                  25                  30

Leu Asn Trp Tyr Gln Gln Arg Pro Gly Arg Ala Pro Arg Leu Leu Ile
        35                  40                  45
```

```
Tyr Ala Ala Ser Asn Leu Gln Ser Gly Val Pro Ser Arg Phe Ser Gly
    50                  55                  60

Ser Gly Tyr Gly Thr Asp Phe Thr Leu Ile Ile Ser Ser Leu Gln Pro
65                  70                  75                  80

Glu Asp Phe Ala Thr Tyr Phe Cys Gln Glu Ser Tyr Ser Ser Thr Pro
                85                  90                  95

Thr His Ile Phe Gly Leu Gly Thr Lys Leu Glu Lys Lys Xaa
            100                 105                 110


<210> SEQ ID NO 295
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 295

Asp Ile Gln Met Thr Gln Phe Pro Ser Ser Leu Ser Ala Ser Val Gly
1               5                   10                  15

Asp Arg Val Thr Met Thr Cys Arg Ala Ser Gln Ser Ile Lys Asp Tyr
            20                  25                  30

Leu Asn Trp Tyr Gln His Thr Pro Gly Lys Ala Pro Arg Leu Leu Ile
        35                  40                  45

Tyr Gly Ala Thr Thr Leu Gln Arg Gly Val Pro Ser Arg Phe Ser Gly
    50                  55                  60

Ser Gly Ser Gly Asn Gln Phe Thr Leu Thr Ile Asn Ser Leu Gln Pro
65                  70                  75                  80

Glu Asp Phe Ala Thr Tyr Tyr Cys Gln Glu Ser Tyr Gln Thr Val Pro
                85                  90                  95

Thr Leu Thr Phe Gly Pro Gly Thr Arg Val Asp Arg Lys Xaa
            100                 105                 110


<210> SEQ ID NO 296
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 296

Asp Ile Gln Met Thr Gln Pro Pro Ser Ser Leu Ser Ala Ser Val Gly
1               5                   10                  15

Asp Arg Val Thr Met Thr Cys Arg Ala Ser Gln Ser Ile Lys Asp Tyr
            20                  25                  30

Leu Asn Trp Tyr Gln His Thr Pro Gly Lys Ala Pro Arg Leu Leu Ile
        35                  40                  45

Tyr Gly Ala Thr Thr Leu Gln Arg Gly Val Pro Ser Arg Phe Ser Gly
    50                  55                  60

Ser Gly Ser Gly Asn Gln Phe Thr Leu Thr Ile Asn Ser Leu Gln Pro
65                  70                  75                  80
```

```
Glu Asp Phe Ala Thr Tyr Tyr Cys Gln Glu Ser Tyr Gln Thr Val Pro
                85                  90                  95

Thr Leu Thr Phe Gly Pro Gly Thr Arg Val Asp Arg Lys Xaa
            100                 105                 110


<210> SEQ ID NO 297
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 297

Asp Ile Arg Met Thr Gln Ser Pro Ser Ser Leu Ser Ala Ser Val Gly
1               5                   10                  15

Asp Arg Val Thr Met Thr Cys Arg Ala Ser Gln Ser Ile Lys Asp Tyr
            20                  25                  30

Leu Asn Trp Tyr Gln His Thr Pro Gly Lys Ala Pro Arg Leu Leu Ile
        35                  40                  45

Tyr Gly Ala Thr Thr Leu Gln Arg Gly Val Pro Ser Arg Phe Ser Gly
    50                  55                  60

Ser Gly Ser Gly Asn Gln Phe Thr Leu Thr Ile Asn Ser Leu Gln Pro
65                  70                  75                  80

Glu Asp Phe Ala Thr Tyr Tyr Cys Gln Glu Ser Tyr Gln Thr Val Pro
                85                  90                  95

Thr Leu Thr Phe Gly Pro Gly Thr Arg Val Asp Arg Lys Xaa
            100                 105                 110


<210> SEQ ID NO 298
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 298

Asp Ile Gln Val Thr Gln Ser Pro Thr Ser Leu Ser Ala Ser Val Gly
1               5                   10                  15

Asp Thr Val Thr Ile Thr Cys Arg Ala Ser Gln Ser Ile Lys Asn Tyr
            20                  25                  30

Val Asn Trp Tyr Gln His Lys Ser Gly Ser Ala Pro Arg Leu Leu Ile
        35                  40                  45

Tyr Ala Ala Ser Ala Leu His Ser Gly Ile Pro Ser Arg Phe Thr Gly
    50                  55                  60

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Arg Lys Xaa
            100                 105                 110
```

<210> SEQ ID NO 299
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (110)..(110)
<223> OTHER INFORMATION: Any amino acid

<400> SEQUENCE: 299

Asp Ile Gln Met Thr Gln Phe Pro Thr Ser Leu Ser Ala Ser Val Gly
1               5                   10                  15

Asp Thr Val Thr Ile Thr Cys Arg Ala Ser Gln Ser Ile Lys Asn Tyr
            20                  25                  30

Val Asn Trp Tyr Gln His Lys Ser Gly Ser Ala Pro Arg Leu Leu Ile
        35                  40                  45

Tyr Ala Ala Ser Ala Leu His Ser Gly Ile Pro Ser Arg Phe Thr Gly
    50                  55                  60

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Arg Lys Xaa
            100                 105                 110

<210> SEQ ID NO 300
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (110)..(110)
<223> OTHER INFORMATION: Any amino acid

<400> SEQUENCE: 300

Asp Ile Arg Leu Thr Gln Ser Pro Ser Ser Leu Ser Ala Ser Val Gly
1               5                   10                  15

Asp Arg Ile Thr Ile Thr Cys Arg Ala Ser Gln Ser Ile Lys Asp Tyr
            20                  25                  30

Leu Asn Trp Tyr Lys His Arg Pro Gly Glu Ala Pro Lys Leu Leu Ile
        35                  40                  45

Tyr Ser Ala Ser Lys Leu Arg Ser Gly Val Ser Ser Arg Phe Ser Gly
    50                  55                  60

Ser Gly Tyr Gly Ser Ala Phe Thr Leu Thr Ile Ser Ser Leu Gln Pro
65                  70                  75                  80

Glu Asp Phe Ala Thr Tyr Tyr Cys Gln Glu Ser Tyr Ser Ser Val Pro
                85                  90                  95

Met Tyr Ile Phe Gly Gln Gly Thr Lys Val Asp Leu Lys Xaa
            100                 105                 110

<210> SEQ ID NO 301
<211> LENGTH: 476
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 301
gctagcacca tggagacaga cacactcctg ctatgggtac tgctgctctg ggttccaggt 60
tccactggtg accaggtcca gctggtacag tctgggggag gcttggtaaa gcctgggggg 120
tcccttacac tctcctgtgt cacctctgga tttactttca gcaacacgtg gatgagttgg 180
gtccgccaga ctccagggaa gggactggag tgggttgccc gtattagtag ggtcggggat 240
ggcccaataa tagactacgc tgctcccgtg aaaggcagat tcataatctc aagagatgac 300
tcaagaaaca cactctttct tcacatgaac aacctgaaaa ccgaggacac agccgtgtat 360
tattgtaccg ctgatgaggg ggccccaatt ttaagatttt ttgagtgggg ttattacaac 420
tactacatgg acgtctgggg caaggggacc acggtcatcg tctcctcggc gtcgac 476

<210> SEQ ID NO 302
<211> LENGTH: 792
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 302
gctagcacca tggagacaga cacactcctg ctatgggtac tgctgctctg ggttccaggt 60
tccactggtg accaggtcca gctggtacag tctgggggag gcttggtaaa gcctgggggg 120
tcccttacac tctcctgtgt cacctctgga tttactttca gcaacacgtg gatgagttgg 180
gtccgccaga ctccagggaa gggactggag tgggttgccc gtattagtag ggtcggggat 240
ggcccaataa tagactacgc tgctcccgtg aaaggcagat tcataatctc aagagatgac 300
tcaagaaaca cactctttct tcacatgaac aacctgaaaa ccgaggacac agccgtgtat 360
tattgtaccg ctgatgaggg ggccccaatt ttaagatttt ttgagtgggg ttattacaac 420
tactacatgg acgtctgggg caaggggacc acggtcatcg tctcctcggc gtcgaccaag 480
ggcccatcgg tcttccccct ggcaccctcc tccaagagca cctctggggg cacagcggcc 540
ctgggctgcc tggtcaagga ctacttcccc gaaccggtga cggtgtcgtg gaactcaggc 600
gccctgacca gcggcgtgca caccttcccg gctgtcctac agtcctcagg actctactcc 660
ctcagcagcg tggtgaccgt gccctccagc agcttgggta cccagaccta catctgcaac 720
gtgaatcaca agcccagcaa caccaaggtg gacaagagag ttgagcccaa atcttgtgac 780
aaatgatcta ga 792

<210> SEQ ID NO 303
<211> LENGTH: 476
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 303
gctagcacca tggagacaga cacactcctg ctatgggtac tgctgctctg ggttccaggt 60
tccactggtg accaggtcca gcttgtacag tctgggggag gcttggtaaa gcctgggggg 120
tcccttacac cctcctgtgt cacctctgga tttactttca gcaacacgtg gatgagttgg 180
gtccgccaga ctccagggaa gggactggag tgggttgccc gtattagtag ggtcggggat 240
ggcccaataa tagactacgc tgctcccgtg aaaggcagat tcataatctc aagagatgac 300

```
tcaagaaaca cactctttct tcacatgaac aacctgaaaa ccgaggacac agccgtgtat    360

tattgtaccg ctgatgaggg ggccccaatt ttaagatttt ttgagtgggg ttattacaac    420

tactacatgg acgtctgggg caaggggacc acggtcatcg tctcctcggc gtcgac        476
```

<210> SEQ ID NO 304
<211> LENGTH: 792
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 304

```
gctagcacca tggagacaga cacactcctg ctatgggtac tgctgctctg ggttccaggt     60

tccactggtg accaggtcca gcttgtacag tctgggggag gcttggtaaa gcctgggggg    120

tcccttacac cctcctgtgt cacctctgga tttactttca gcaacacgtg gatgagttgg    180

gtccgccaga ctccagggaa gggactggag tgggttgccc gtattagtag ggtcggggat    240

ggcccaataa tagactacgc tgctcccgtg aaaggcagat tcataatctc aagagatgac    300

tcaagaaaca cactctttct tcacatgaac aacctgaaaa ccgaggacac agccgtgtat    360

tattgtaccg ctgatgaggg ggccccaatt ttaagatttt ttgagtgggg ttattacaac    420

tactacatgg acgtctgggg caaggggacc acggtcatcg tctcctcggc gtcgaccaag    480

ggcccatcgg tcttccccct ggcaccctcc tccaagagca cctctggggg cacagcggcc    540

ctgggctgcc tggtcaagga ctacttcccc gaaccggtga cggtgtcgtg gaactcaggc    600

gccctgacca gcggcgtgca caccttcccg gctgtcctac agtcctcagg actctactcc    660

ctcagcagcg tggtgaccgt gccctccagc agcttgggta cccagaccta catctgcaac    720

gtgaatcaca agcccagcaa caccaaggtg gacaagagag ttgagcccaa atcttgtgac    780

aaatgatcta ga                                                        792
```

<210> SEQ ID NO 305
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 305

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100
```

<210> SEQ ID NO 306

<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 306

Glu Val Gln Leu Val Glu Ser Gly Gly Gly Leu Val Lys Pro Gly Gly
1 5 10 15

Ser Leu Arg Leu Ser Cys Ser Ala Ser Gly Phe Asp Phe Asp Asn Ala
20 25 30

Trp Met Thr Trp Val Arg Gln Pro Pro Gly Lys Gly Leu Glu Trp Val
35 40 45

Gly Arg Ile Thr Gly Pro Gly Glu Gly Trp Ser Val Asp Tyr Ala Ala
50 55 60

Pro Val Glu Gly Arg Phe Thr Ile Ser Arg Leu Asn Ser Ile Asn Phe
65 70 75 80

Leu Tyr Leu Glu Met Asn Asn Leu Arg Met Glu Asp Ser Gly Leu Tyr
85 90 95

Phe Cys Ala Arg
100

<210> SEQ ID NO 307
<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 307

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Thr
20 25 30

Trp Met Ser Trp Val Arg Gln Ala Pro Gly Lys Gly Leu Glu Trp Val
35 40 45

Gly Arg Ile Ser Arg Asn Lys Asp Gly Ala Lys Thr Glu Tyr Ala Ala
50 55 60

Pro Val Arg Gly Arg Phe Thr Ile Ser Arg Asp Asp Ser Arg Asp Thr
65 70 75 80

Leu Tyr Leu Gln Met Asn Ser Leu Lys Ile Glu Asp Ser Gly Arg Tyr
85 90 95

Phe Cys Thr Ala
100

<210> SEQ ID NO 308
<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 308

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

```
Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met
            100


<210> SEQ ID NO 309
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gln Val Gln Leu Val Gln Ser Gly Gly Gly Leu Val Lys Pro Gly Gly
1               5                   10                  15

Ser Leu Thr Leu Ser Cys Val Thr Ser Gly Phe Thr Phe Ser Asn Thr
            20                  25                  30

Trp Met Ser Trp Val Arg Gln Thr Pro Gly Lys Gly Leu Glu Trp Val
        35                  40                  45

Ala Arg Ile Ser Arg Val Gly Asp Gly Pro Ile Ile Asp Tyr Ala Ala
    50                  55                  60

Pro Val Lys Gly Arg Phe Ile Ile Ser Arg Asp Asp Ser Arg Asn Thr
65                  70                  75                  80

Leu Phe Leu His Met Asn Asn Leu Lys Thr Glu Asp Thr Ala Val Tyr
                85                  90                  95

Tyr Cys Thr Ala
            100


<210> SEQ ID NO 310
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Gln Val Gln Leu Val Gln Ser Gly Gly Gly Leu Val Lys Pro Gly Gly
1               5                   10                  15

Ser Leu Thr Pro Ser Cys Val Thr Ser Gly Phe Thr Phe Ser Asn Thr
            20                  25                  30

Trp Met Ser Trp Val Arg Gln Thr Pro Gly Lys Gly Leu Glu Trp Val
        35                  40                  45

Ala Arg Ile Ser Arg Val Gly Asp Gly Pro Ile Ile Asp Tyr Ala Ala
    50                  55                  60

Pro Val Lys Gly Arg Phe Ile Ile Ser Arg Asp Asp Ser Arg Asn Thr
65                  70                  75                  80

Leu Phe Leu His Met Asn Asn Leu Lys Thr Glu Asp Thr Ala Val Tyr
                85                  90                  95

Tyr Cys Thr Ala
            100
```

<210> SEQ ID NO 311
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 311

Thr Ala Asp Arg Gly Ala Pro Val Leu Arg Phe Trp Glu Trp Gly Tyr
1 5 10 15

Phe Asp Tyr Tyr Met Glu Phe
20

<210> SEQ ID NO 312
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 312

Thr Ala Asp Glu Gly Ala Pro Ile Leu Arg Phe Phe Glu Trp Gly Tyr
1 5 10 15

Tyr Asn Tyr Tyr Met Asp Val
20

<210> SEQ ID NO 313
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Val Lys Gly Ala Thr Pro Ser Ile Thr Ile Phe Gly Arg Val Ala Pro
1 5 10 15

Phe Asp His

<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

Ala Arg Val Glu Arg Pro Gly Asp Ser Asp Trp Tyr Phe Asp Leu
1 5 10 15

<210> SEQ ID NO 315
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 315

Ala Arg Thr Ala Val Ala Gly Thr Asn Tyr Phe Asp Tyr
1 5 10

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Thr Lys Asp Ile Val Trp Arg Tyr Ser Leu Ser Glu Gly Ala Phe Asp
1 5 10 15

Leu

<210> SEQ ID NO 317
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 317

Thr Arg Asp Glu Gly Ala Pro Val Thr Arg Phe Leu Glu Trp Gly Ser
1 5 10 15

Tyr Tyr Tyr Tyr Met Ala Val
20

<210> SEQ ID NO 318
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 318

Ala Arg Asp Gly Pro Ala Thr Phe Arg Leu Leu Glu Tyr Val Phe Met
1 5 10 15

Ser Ser Phe Asp Met
20

<210> SEQ ID NO 319
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 319

Ala Arg Gly Gly Ser Gly Ile Phe Arg Phe Pro Asn Tyr
1 5 10

<210> SEQ ID NO 320
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 320

Ala Lys Asp Thr Met Gly His Cys Ser Ser Ala Phe Cys Phe Ala Phe
1 5 10 15

Asp Phe

<210> SEQ ID NO 321
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

```
Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25
```

<210> SEQ ID NO 322
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

```
Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25
```

<210> SEQ ID NO 323
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

```
Asn Glu Lys Asp Leu Leu Ala Leu Asp Ser Trp Lys Asn Leu Trp Asn
1               5                   10                  15

Trp Phe Ser Ile Thr Lys Trp Leu Trp Tyr Ile Lys
            20                  25
```

<210> SEQ ID NO 324
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

```
Asn Glu Gln Glu Leu Leu Ala Leu Asp Lys Trp Asn Asn Leu Trp Ser
1               5                   10                  15

Trp Phe Asp Ile Thr Asn Trp Leu Trp Tyr Ile Arg
            20                  25
```

<210> SEQ ID NO 325
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Asn Glu Lys Asp Leu Leu Ala Leu Asp Ser Trp Lys Asn Leu Trp Asn
1 5 10 15

Trp Phe Asp Ile Thr Lys Trp Leu Trp Tyr Ile Lys
20 25

<210> SEQ ID NO 326
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Cys Ala Arg Thr Gly Lys Tyr Tyr Asp Phe Trp Ser Gly Tyr Pro Pro
1 5 10 15

Glu Glu Tyr Phe Gln Asp Trp Gly
20

<210> SEQ ID NO 327
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Cys Thr Ala Asp Leu Gly Glu Pro Val Val Ser Arg Phe Phe Glu Trp
1 5 10 15

Gly Ser Tyr Tyr Tyr Tyr Met Asp Leu Trp Gly
20 25

<210> SEQ ID NO 328
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Cys Thr Met Asp Glu Gly Thr Pro Val Thr Arg Phe Leu Glu Trp Gly
1 5 10 15

Tyr Phe Tyr Tyr Tyr Met Ala Val Trp Gly
20 25

<210> SEQ ID NO 329
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Cys Ala Arg Thr Gly Lys Tyr Tyr Asp Phe Trp Ser Gly Tyr Pro Pro
1 5 10 15

Glu Glu Tyr Phe Gln Asp Trp Gly
20

<210> SEQ ID NO 330
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Cys Thr Ala Asp Leu Gly Glu Pro Val Val Ser Arg Phe Phe Glu Trp
1 5 10 15

Gly Ser Tyr Tyr Tyr Tyr Met Asp Leu Trp Gly
20 25

<210> SEQ ID NO 331
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Cys Thr Met Asp Glu Gly Thr Pro Val Thr Arg Phe Leu Glu Trp Gly
1 5 10 15

Tyr Phe Tyr Tyr Tyr Met Ala Val Trp Gly
20 25

<210> SEQ ID NO 332
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Thr Ala Asp Leu Gly Glu Pro Val Val Ser Arg Phe Phe Glu Trp Gly
1 5 10 15

Ser Tyr Tyr Tyr Tyr Met Asp Leu
20

<210> SEQ ID NO 333
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Thr Met Asp Glu Gly Thr Pro Val Thr Arg Phe Leu Glu Trp Gly Tyr
1 5 10 15

Phe Tyr Tyr Tyr Met Ala Val
20

<210> SEQ ID NO 334
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Thr Ala Asp Leu Gly Glu Ala Val Val Ser Arg Phe Phe Glu Trp Gly
1 5 10 15

Ser Tyr Tyr Tyr Tyr Met Asp Phe
20

```
<210> SEQ ID NO 335
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Thr Arg Asp Glu Gly Ala Pro Val Thr Arg Phe Leu Glu Trp Gly Ser
1               5                   10                  15

Tyr Tyr Tyr Tyr Met Ala Val
            20


<210> SEQ ID NO 336
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Thr Arg Asp Glu Gly Ala Pro Val Thr Arg Phe Leu Glu Trp Gly Ser
1               5                   10                  15

Tyr Tyr Tyr Tyr Met Ala Val
            20


<210> SEQ ID NO 337
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Thr Ala Asp Leu Gly Glu Ala Val Val Ser Arg Phe Phe Glu Trp Gly
1               5                   10                  15

Ser Tyr Tyr Tyr Tyr Met Asp Phe
            20


<210> SEQ ID NO 338
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ala Arg Gly Thr Gly Val Val Val Gly Gly Ser Trp Thr Val Pro Pro
1               5                   10                  15

Gly Met Ala Tyr Tyr Leu Asp Val
            20


<210> SEQ ID NO 339
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339
```

Thr Thr Asp Leu Glu Gly Ala Pro Val Leu Arg Phe Leu Glu Trp Gly
1 5 10 15

Tyr Tyr Tyr Tyr Tyr Met Asp Val
20

<210> SEQ ID NO 340
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Thr Thr Asp Leu Glu Gly Ala Pro Val Ser Arg Phe Leu Glu Trp Gly
1 5 10 15

Tyr Tyr Tyr Tyr Tyr Met Asp Val
20

<210> SEQ ID NO 341
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Thr Ala Asp Leu Gly Glu Ala Val Val Ser Arg Phe Phe Glu Trp Gly
1 5 10 15

Ser Tyr Tyr Tyr Tyr Met Asp Phe
20

<210> SEQ ID NO 342
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Thr Ala Asp Leu Gly Glu Ala Val Val Ser Arg Phe Phe Glu Trp Gly
1 5 10 15

Ser Tyr Tyr Tyr Tyr Met Asp Phe
20

<210> SEQ ID NO 343
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Thr Ala Asp Leu Gly Glu Ala Val Val Ser Arg Phe Phe Glu Trp Gly
1 5 10 15

Ser Tyr Tyr Tyr Tyr Met Asp Phe
20

<210> SEQ ID NO 344
<211> LENGTH: 23
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 344

```
Thr Thr Asp Glu Gly Ala Pro Val Thr Arg Phe Leu Glu Trp Gly Tyr
1               5                   10                  15

Tyr Tyr Tyr Tyr Met Ala Val
            20
```

<210> SEQ ID NO 345
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

```
Thr Arg Asp Glu Gly Ala Pro Val Thr Arg Phe Leu Glu Trp Gly Ser
1               5                   10                  15

Tyr Tyr Tyr Tyr Met Ala Val
            20
```

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

```
Gln Glu Ala Tyr Ser Ser Thr Pro Thr Leu Thr
1               5                   10
```

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

```
Gln Glu Asn Tyr Asn Thr Ile Pro Ser Leu Ser
1               5                   10
```

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

```
Gln Glu Ala Tyr Ser Ser Thr Pro Thr Leu Thr
1               5                   10
```

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Gln Glu Ala Tyr Asn Thr Asn Pro Thr Leu Ser
1 5 10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Gln Glu Ala Tyr Asn Thr Tyr Pro Thr Leu Ser
1 5 10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Gln Glu Ala Tyr Ser Ser Thr Pro Thr Leu Ser
1 5 10

<210> SEQ ID NO 352
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Ala Ser Arg Asp Arg Ser Gly Asp Arg Leu Gly Val
1 5 10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Gln Gln Ser Tyr Ser Thr Pro Pro Thr Cys Thr
1 5 10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Gln Glu Thr Tyr Ser Thr Thr Pro Thr Phe Thr
1 5 10

<210> SEQ ID NO 355

<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 355

Gln Glu Ala Tyr Ser Ser Thr Pro Thr Leu Thr
1 5 10

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 356

Gln Glu Ala Tyr Ser Ser Thr Pro Thr Leu Thr
1 5 10

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Gln Glu Ala Tyr Ser Ser Thr Pro Thr Leu Thr
1 5 10

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 358

Gln Glu Thr Tyr Asn Thr Thr Pro Thr Leu Thr
1 5 10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 359

Gln Glu Ala Tyr Asn Thr Asn Pro Thr Leu Ser
1 5 10

<210> SEQ ID NO 360
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Thr Ala Asp Arg Gly Ala Pro Val Leu Arg Phe Trp Glu Trp Gly Tyr
1 5 10 15

Tyr Asp Tyr Tyr Met Glu Phe
20

<210> SEQ ID NO 361
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Thr Ala Asp Arg Gly Ala Pro Val Leu Arg Phe Trp Glu Trp Gly Tyr
1 5 10 15

Tyr Asp Tyr Tyr Met Glu Phe
20

<210> SEQ ID NO 362
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Thr Ala Asp Arg Gly Ala Pro Val Leu Arg Phe Trp Glu Trp Gly Tyr
1 5 10 15

Phe Asp Tyr Tyr Met Glu Phe
20

<210> SEQ ID NO 363
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 363

Thr Ala Asp Arg Gly Ala Pro Val Leu Arg Phe Trp Glu Trp Gly Tyr
1 5 10 15

Phe Asp Tyr Tyr Met Glu Phe
20

<210> SEQ ID NO 364
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Thr Ala Asp Arg Gly Ala Pro Val Leu Arg Phe Trp Glu Trp Gly Tyr
1 5 10 15

Phe Asp Tyr Tyr Met Glu Phe
20

<210> SEQ ID NO 365
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Thr Arg Asp Glu Gly Ala Pro Val Thr Arg Arg Phe Leu Glu Trp Gly
1               5                   10                  15

Tyr Phe Tyr Tyr Tyr Met Ala Val
            20

<210> SEQ ID NO 366
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 366

Thr Arg Asp Glu Gly Ala Pro Val Thr Arg Phe Leu Glu Trp Gly Ser
1               5                   10                  15

Tyr Tyr Tyr Tyr Met Ala Val
            20

<210> SEQ ID NO 367
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Thr Arg Asp Glu Gly Ala Pro Val Thr Arg Phe Leu Glu Trp Gly Ser
1               5                   10                  15

Tyr Tyr Tyr Tyr Met Ala Val
            20

<210> SEQ ID NO 368
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 368

Lys Lys Lys Asn Glu Gln Glu Leu Leu Glu Leu Asp Lys Trp Ala Ser
1               5                   10                  15

Leu Trp Asn Trp Phe Asp Ile Thr Asn Trp Leu Trp Tyr Ile Arg Lys
            20                  25                  30

Lys Lys

<210> SEQ ID NO 369
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 369

Lys Lys Lys Asn Glu Gln Glu Leu Leu Glu Leu Asp Lys Trp Ala Ser
1               5                   10                  15

Leu Trp Ala Trp Phe Asp Ile Thr Asn Trp Leu Trp Tyr Ile Arg Lys
20 25 30

Lys Lys

<210> SEQ ID NO 370
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 370

Lys Lys Lys Asn Glu Gln Glu Leu Leu Glu Leu Asp Lys Trp Ala Ser
1 5 10 15

Leu Trp Asn Ala Phe Asp Ile Thr Asn Trp Leu Trp Tyr Ile Arg Lys
20 25 30

Lys Lys

<210> SEQ ID NO 371
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 371

Lys Lys Lys Asn Glu Gln Glu Leu Leu Glu Leu Asp Lys Trp Ala Ser
1 5 10 15

Leu Trp Asn Trp Ala Asp Ile Thr Asn Trp Leu Trp Tyr Ile Arg Lys
20 25 30

Lys Lys

<210> SEQ ID NO 372
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 372

Lys Lys Lys Asn Glu Gln Glu Leu Leu Glu Leu Asp Lys Trp Ala Ser
1 5 10 15

Leu Trp Asn Trp Phe Ala Ile Thr Asn Trp Leu Trp Tyr Ile Arg Lys
20 25 30

Lys Lys

<210> SEQ ID NO 373
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 373

Lys Lys Lys Asn Glu Gln Glu Leu Leu Glu Leu Asp Lys Trp Ala Ser
1 5 10 15

Leu Trp Asn Trp Phe Asp Ala Thr Asn Trp Leu Trp Tyr Ile Arg Lys
20 25 30

Lys Lys

<210> SEQ ID NO 374
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 374

Lys Lys Lys Asn Glu Gln Glu Leu Leu Glu Leu Asp Lys Trp Ala Ser
1 5 10 15

Leu Trp Asn Trp Phe Asp Ile Ala Asn Trp Leu Trp Tyr Ile Arg Lys
20 25 30

Lys Lys

<210> SEQ ID NO 375
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 375

Lys Lys Lys Asn Glu Gln Glu Leu Leu Glu Leu Asp Lys Trp Ala Ser
1 5 10 15

Leu Trp Asn Trp Phe Asp Ile Thr Ala Trp Leu Trp Tyr Ile Arg Lys
20 25 30

Lys Lys

<210> SEQ ID NO 376
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 376

Lys Lys Lys Asn Glu Gln Glu Leu Leu Glu Leu Asp Lys Trp Ala Ser
1 5 10 15

Leu Trp Asn Trp Phe Asp Ile Thr Asn Ala Leu Trp Tyr Ile Arg Lys
20 25 30

Lys Lys

<210> SEQ ID NO 377
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 377

Lys Lys Lys Asn Glu Gln Glu Leu Leu Glu Leu Asp Lys Trp Ala Ser
1 5 10 15

Leu Trp Asn Trp Phe Asp Ile Thr Asn Trp Ala Trp Tyr Ile Arg Lys
20 25 30

Lys Lys

<210> SEQ ID NO 378
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Lys Lys Lys Asn Glu Gln Glu Leu Leu Glu Leu Asp Lys Trp Ala Ser
1               5                   10                  15

Leu Trp Asn Trp Phe Asp Ile Thr Asn Trp Leu Ala Tyr Ile Arg Lys
            20                  25                  30

Lys Lys

<210> SEQ ID NO 379
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Lys Lys Lys Asn Glu Gln Glu Leu Leu Glu Leu Asp Lys Trp Ala Ser
1               5                   10                  15

Leu Trp Asn Trp Phe Asp Ile Thr Asn Trp Leu Trp Ala Ile Arg Lys
            20                  25                  30

Lys Lys

<210> SEQ ID NO 380
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Lys Lys Lys Asn Glu Gln Glu Leu Leu Glu Leu Asp Lys Trp Ala Ser
1               5                   10                  15

Leu Trp Asn Trp Phe Asp Ile Thr Asn Trp Leu Trp Tyr Ala Arg Lys
            20                  25                  30

Lys Lys

<210> SEQ ID NO 381
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Lys Lys Lys Asn Glu Gln Glu Leu Leu Glu Leu Asp Lys Trp Ala Ser
1               5                   10                  15

Leu Trp Asn Trp Phe Asp Ile Thr Asn Trp Leu Trp Tyr Ile Ala Lys
            20                  25                  30

Lys Lys

<210> SEQ ID NO 382
<211> LENGTH: 29
<212> TYPE: PRT

<213> ORGANISM: Artificial Sequence
<220> FEATURE:
<223> OTHER INFORMATION: Description of Artificial Sequence: Synthetic peptide

<400> SEQUENCE: 382

Gln Glu Leu Leu Ala Leu Asp Ser Trp Lys Asn Leu Trp Ser Trp Phe
1 5 10 15

Asp Ile Thr Lys Trp Leu Trp Tyr Ile Lys Ile Phe Ile
20 25

<210> SEQ ID NO 383
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 383

Gln Glu Leu Leu Gly Leu Asp Ser Trp Lys Asn Leu Trp Ser Trp Phe
1 5 10 15

Asp Ile Thr Lys Trp Leu Trp Tyr Ile Lys Ile Phe Ile
20 25

<210> SEQ ID NO 384
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

Gln Glu Leu Leu Ala Ala Asp Ser Trp Lys Asn Leu Trp Ser Trp Phe
1 5 10 15

Asp Ile Thr Lys Trp Leu Trp Tyr Ile Lys Ile Phe Ile
20 25

<210> SEQ ID NO 385
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 385

Gln Glu Leu Leu Ala Leu Ala Ser Trp Lys Asn Leu Trp Ser Trp Phe
1 5 10 15

Asp Ile Thr Lys Trp Leu Trp Tyr Ile Lys Ile Phe Ile
20 25

<210> SEQ ID NO 386
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 386

Gln Glu Leu Leu Ala Leu Asp Ala Trp Lys Asn Leu Trp Ser Trp Phe
1 5 10 15

Asp Ile Thr Lys Trp Leu Trp Tyr Ile Lys Ile Phe Ile 20 25

<210> SEQ ID NO 387
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Gln Glu Leu Leu Ala Leu Asp Ser Ala Lys Asn Leu Trp Ser Trp Phe
1 5 10 15

Asp Ile Thr Lys Trp Leu Trp Tyr Ile Lys Ile Phe Ile
20 25

<210> SEQ ID NO 388
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

Gln Glu Leu Leu Ala Leu Asp Ser Trp Ala Asn Leu Trp Ser Trp Phe
1 5 10 15

Asp Ile Thr Lys Trp Leu Trp Tyr Ile Lys Ile Phe Ile
20 25

<210> SEQ ID NO 389
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 389

Gln Glu Leu Leu Ala Leu Asp Ser Trp Lys Ala Leu Trp Ser Trp Phe
1 5 10 15

Asp Ile Thr Lys Trp Leu Trp Tyr Ile Lys Ile Phe Ile
20 25

<210> SEQ ID NO 390
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

Gln Glu Leu Leu Ala Leu Asp Ser Trp Lys Asn Ala Trp Ser Trp Phe
1 5 10 15

Asp Ile Thr Lys Trp Leu Trp Tyr Ile Lys Ile Phe Ile
20 25

<210> SEQ ID NO 391
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Gln Glu Leu Leu Ala Leu Asp Ser Trp Lys Asn Leu Ala Ser Trp Phe
1 5 10 15

Asp Ile Thr Lys Trp Leu Trp Tyr Ile Lys Ile Phe Ile
20 25

<210> SEQ ID NO 392
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 392

Gln Glu Leu Leu Ala Leu Asp Ser Trp Lys Asn Leu Trp Ala Trp Phe
1 5 10 15

Asp Ile Thr Lys Trp Leu Trp Tyr Ile Lys Ile Phe Ile
20 25

<210> SEQ ID NO 393
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 393

Gln Glu Leu Leu Ala Leu Asp Ser Trp Lys Asn Leu Trp Ser Ala Phe
1 5 10 15

Asp Ile Thr Lys Trp Leu Trp Tyr Ile Lys Ile Phe Ile
20 25

<210> SEQ ID NO 394
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 394

Gln Glu Leu Leu Ala Leu Asp Ser Trp Lys Asn Leu Trp Ser Trp Ala
1 5 10 15

Asp Ile Thr Lys Trp Leu Trp Tyr Ile Lys Ile Phe Ile
20 25

<210> SEQ ID NO 395
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 395

Gln Glu Leu Leu Ala Leu Asp Ser Trp Lys Asn Leu Trp Ser Trp Phe
1 5 10 15

Ala Ile Thr Lys Trp Leu Trp Tyr Ile Lys Ile Phe Ile
20 25

<210> SEQ ID NO 396
<211> LENGTH: 29

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Gln Glu Leu Leu Ala Leu Asp Ser Trp Lys Asn Leu Trp Ser Trp Phe
1 5 10 15

Ser Ile Thr Lys Trp Leu Trp Tyr Ile Lys Ile Phe Ile
20 25

<210> SEQ ID NO 397
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 397

Gln Glu Leu Leu Ala Leu Asp Ser Trp Lys Asn Leu Trp Ser Trp Phe
1 5 10 15

Asn Ile Thr Lys Trp Leu Trp Tyr Ile Lys Ile Phe Ile
20 25

<210> SEQ ID NO 398
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

Gln Glu Leu Leu Ala Leu Asp Ser Trp Lys Asn Leu Trp Ser Trp Phe
1 5 10 15

Asp Ala Thr Lys Trp Leu Trp Tyr Ile Lys Ile Phe Ile
20 25

<210> SEQ ID NO 399
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Gln Glu Leu Leu Ala Leu Asp Ser Trp Lys Asn Leu Trp Ser Trp Phe
1 5 10 15

Asp Ile Ala Lys Trp Leu Trp Tyr Ile Lys Ile Phe Ile
20 25

<210> SEQ ID NO 400
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 400

Gln Glu Leu Leu Ala Leu Asp Ser Trp Lys Asn Leu Trp Ser Trp Phe
1 5 10 15

```
Asp Ile Thr Ala Trp Leu Trp Tyr Ile Lys Ile Phe Ile
            20                  25


<210> SEQ ID NO 401
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gln Glu Leu Leu Ala Leu Asp Ser Trp Lys Asn Leu Trp Ser Trp Phe
1               5                   10                  15

Asp Ile Thr Lys Ala Leu Trp Tyr Ile Lys Ile Phe Ile
            20                  25


<210> SEQ ID NO 402
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gln Glu Leu Leu Ala Leu Asp Ser Trp Lys Asn Leu Trp Ser Trp Phe
1               5                   10                  15

Asp Ile Thr Lys Trp Ala Trp Tyr Ile Lys Ile Phe Ile
            20                  25


<210> SEQ ID NO 403
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gln Glu Leu Leu Ala Leu Asp Ser Trp Lys Asn Leu Trp Ser Trp Phe
1               5                   10                  15

Asp Ile Thr Lys Trp Leu Ala Tyr Ile Lys Ile Phe Ile
            20                  25


<210> SEQ ID NO 404
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Arg Arg Arg Asn Glu Gln Glu Leu Leu Glu Leu Asp Lys Trp Ala Ser
1               5                   10                  15

Leu Trp Asn Trp Phe Asp Ile Thr Asn Trp Leu Trp Tyr Ile Arg Arg
            20                  25                  30

Arg Arg


<210> SEQ ID NO 405
<211> LENGTH: 28
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 405

```
Lys Lys Lys Glu Leu Asp Lys Trp Ala Ser Leu Trp Asn Trp Phe Asp
1               5                   10                  15

Ile Thr Asn Trp Leu Trp Tyr Ile Arg Lys Lys Lys
            20                  25
```

<210> SEQ ID NO 406
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

```
Lys Lys Lys Trp Asn Trp Phe Asp Ile Thr Asn Trp Leu Trp Tyr Ile
1               5                   10                  15

Arg Lys Lys Lys
            20
```

<210> SEQ ID NO 407
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 407
tattcccatc gcggcgccag gtccagctkg trcagtctgg 40

<210> SEQ ID NO 408
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 408
tattcccatc gcggcgccag gtgcagctgg tgsartctgg 40

<210> SEQ ID NO 409
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 409
tattcccatc gcggcgccag rtcaccttga aggagtctg 39

<210> SEQ ID NO 410
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410
tattcccatc gcggcgcgag gtgcagctgk tggagwcy 38

<210> SEQ ID NO 411
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 411
tattcccatc gcggcgccag gtgcagctgc aggagtcsg 39

<210> SEQ ID NO 412
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 412
tattcccatc gcggcgccag gtgcagctac agcagtggg 39

<210> SEQ ID NO 413
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 413
tattcccatc gcggcgccag gtacagctgc agcagtca 38

<210> SEQ ID NO 414
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 414
tattcccatc gcggcgctca acacaacggt tcccagtta 39

<210> SEQ ID NO 415
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 415
gcgccgcgat gggaatagct agccgacatc crgdtgaccc agtctcc 47

<210> SEQ ID NO 416
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 416
gcgccgcgat gggaatagct agccgatatt gtgmtgacbc agwctcc 47

<210> SEQ ID NO 417
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 417
gcgccgcgat gggaatagct agccgaaatt gtrwtgacrc agtctcc 47

<210> SEQ ID NO 418
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 418
gcgccgcgat gggaatagct agccgaaacg acactcacgc agtctc 46

<210> SEQ ID NO 419
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 419
gcgccgcgat gggaatagct agcccagtct gtsbtgacgc agccgcc 47

<210> SEQ ID NO 420
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 420
gcgccgcgat gggaatagct agcccagcct gtgctgactc aryc 44

<210> SEQ ID NO 421
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 421
gcgccgcgat gggaatagct agcccagccw gkgctgactc agccmcc 47

<210> SEQ ID NO 422
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 422
gcgccgcgat gggaatagct agcccagtct gyyctgaytc agcct 45

<210> SEQ ID NO 423
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 423
gcgccgcgat gggaatagct agcctcctat gwgctgacwc agccaa 46

<210> SEQ ID NO 424
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 424
gcgccgcgat gggaatagct agcctcctct gagctgastc aggascc 47

<210> SEQ ID NO 425
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 425
gcgccgcgat gggaatagct agcctcctat gagctgayrc agcyacc 47

<210> SEQ ID NO 426
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 426
gcgccgcgat gggaatagct agccaatttt atgctgactc agcccc 46

<210> SEQ ID NO 427
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 427
gcgccgcgat gggaatagct agcccagdct gtggtgacyc aggagcc 47

<210> SEQ ID NO 428
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 428
tattcccatc gcggcgcaca ggtgcccact cccaggtgca g 41

<210> SEQ ID NO 429

<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 429
tattcccatc gcggcgcaag gtgtccagtg tgargtgcag 40

<210> SEQ ID NO 430
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 430
tattcccatc gcggcgcccc agatgggtcc tgtcccaggt gcag 44

<210> SEQ ID NO 431
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 431
tattcccatc gcggcgccaa ggagtctgtt ccgaggtgca g 41

<210> SEQ ID NO 432
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 432
gcgccgcgat gggaatatct gctcgagttc ggtcaggtcc tgggcccagt ctgtgctg 58

<210> SEQ ID NO 433
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 433
gcgccgcgat gggaatatct gctcgagttc ggtcaggtcc tgggcccagt ctgccctg 58

<210> SEQ ID NO 434
<211> LENGTH: 62
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 434
gcgccgcgat gggaatatct gctcgagttc ggtcaywctg cacaggctct gtgacctcct 60
at 62

<210> SEQ ID NO 435
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 435
gcgccgcgat gggaatatct gctcgagttc ggtcaggtct ctctcscagc ytgtgctg 58

<210> SEQ ID NO 436
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 436
gcgccgcgat gggaatatct gctcgagttc ggtcagttct tgggccaatt ttatgctg 58

<210> SEQ ID NO 437
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 437
gcgccgcgat gggaatatct gctcgagttc ggtcaggtcc aattcycagg ctgtggtg 58

<210> SEQ ID NO 438
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 438
gcgccgcgat gggaatatct gctcgagttc ggtcagagtg gattctcaga ctgtggtg 58

<210> SEQ ID NO 439
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 439
gcgccgcgat gggaatatct gctcgagttc ggtcaatgag gstcccygct cagctgctgg 60

<210> SEQ ID NO 440
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 440
gcgccgcgat gggaatatct gctcgagttc ggtcactctt cctcctgcta ctctggctcc 60
cag 63

-continued

<210> SEQ ID NO 441
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 441
gcgccgcgat gggaatatct gctcgagttc ggtcaatttc tctgttgctc tggatctctg 60

<210> SEQ ID NO 442
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 442
nnnnatgggc cctgsgatgg gcccttggtg gargc 35

<210> SEQ ID NO 443
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 443
nnnnatgggc cctgggttgg ggcggatgca ctcc 34

<210> SEQ ID NO 444
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 444
nnnnatgggc cctgcttggg gctggtcggg gatg 34

<210> SEQ ID NO 445
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 445
nnnngtgcgg ccgcagatgg tgcagccaca gttc 34

<210> SEQ ID NO 446
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 446
nnnngtgcgg ccgcgagggy gggaacagag tgac 34

<210> SEQ ID NO 447
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 447

```
Cys Thr Ala Asp Leu Gly Glu Pro Val Val Ser Arg Phe Phe Glu Trp
1               5                   10                  15

Gly Ser Tyr Tyr Tyr Tyr Met Asp Leu Trp
            20                  25
```

<210> SEQ ID NO 448
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 448

```
Cys Thr Met Asp Glu Gly Thr Pro Val Thr Arg Phe Leu Glu Trp Gly
1               5                   10                  15

Tyr Phe Tyr Tyr Tyr Met Ala Val Trp
            20                  25
```

<210> SEQ ID NO 449
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 449

```
Cys Thr Ala Asp Leu Gly Glu Ala Val Val Ser Arg Phe Phe Glu Trp
1               5                   10                  15

Gly Ser Tyr Tyr Tyr Tyr Met Asp Phe Trp
            20                  25
```

<210> SEQ ID NO 450
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 450

Cys Thr Arg Asp Glu Gly Ala Pro Val Thr Arg Phe Leu Glu Trp Gly
1               5                   10                  15

Ser Tyr Tyr Tyr Tyr Met Ala Val Trp
            20                  25

<210> SEQ ID NO 451
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 451

Cys Thr Arg Asp Glu Gly Ala Pro Val Thr Arg Phe Leu Glu Trp Gly
1               5                   10                  15

Ser Tyr Tyr Tyr Tyr Met Ala Val Trp
            20                  25

<210> SEQ ID NO 452
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 452

Cys Thr Ala Asp Leu Gly Glu Ala Val Val Ser Arg Phe Phe Glu Trp
1               5                   10                  15

Gly Ser Tyr Tyr Tyr Tyr Met Asp Phe Trp
            20                  25

<210> SEQ ID NO 453
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 453

Cys Ala His Arg Arg Gly Pro Thr Thr Leu Phe Gly Val Pro Ile Ala
1               5                   10                  15

Arg Gly Pro Val Asn Ala Met Asp Val Trp
            20                  25

<210> SEQ ID NO 454
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 454

Cys Ala Arg Glu Gly Thr Thr Gly Trp Gly Trp Leu Gly Lys Pro Ile
1               5                   10                  15

Gly Ala Phe Ala His Trp
            20

<210> SEQ ID NO 455
<211> LENGTH: 24

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 455

Cys Ala Arg Thr Gly Lys Tyr Tyr Asp Phe Trp Ser Gly Tyr Pro Pro
1 5 10 15

Gly Glu Glu Tyr Phe Gln Asp Trp
20

<210> SEQ ID NO 456
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (35)..(38)
<223> OTHER INFORMATION: a, c, t, g, unknown or other

<400> SEQUENCE: 456
gtctcgtggg ctcggagatg tgtataagag acagnnnnat gggccctgsg atgggccctt 60 ggtggargc 69

<210> SEQ ID NO 457
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (35)..(38)
<223> OTHER INFORMATION: a, c, t, g, unknown or other

<400> SEQUENCE: 457
gtctcgtggg ctcggagatg tgtataagag acagnnnnat gggccctggg ttggggcgga 60
tgcactcc 68

<210> SEQ ID NO 458
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (35)..(38)
<223> OTHER INFORMATION: a, c, t, g, unknown or other

<400> SEQUENCE: 458
gtctcgtggg ctcggagatg tgtataagag acagnnnnat gggccctgct tggggctggt 60
cggggatg 68

<210> SEQ ID NO 459
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<221> NAME/KEY: modified_base
<222> LOCATION: (34)..(37)
<223> OTHER INFORMATION: a, c, t, g, unknown or other

<400> SEQUENCE: 459
tcgtcggcag cgtcagatgt gtataagaga cagnnnngtg cggccgcaga tggtgcagcc 60
acagttc 67

<210> SEQ ID NO 460
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (34)..(37)
<223> OTHER INFORMATION: a, c, t, g, unknown or other

<400> SEQUENCE: 460
tcgtcggcag cgtcagatgt gtataagaga cagnnnngtg cggccgcgag ggygggaaca 60
gagtgac 67

<210> SEQ ID NO 461
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (35)..(38)
<223> OTHER INFORMATION: a, c, t, g, unknown or other

<400> SEQUENCE: 461
gtctcgtggg ctcggagatg tgtataagag acagnnnngc gccgcgatgg gaat 54

<210> SEQ ID NO 462
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (34)..(37)
<223> OTHER INFORMATION: a, c, t, g, unknown or other

<400> SEQUENCE: 462
tcgtcggcag cgtcagatgt gtataagaga cagnnnnggc tagctattcc catcgcgg 58

<210> SEQ ID NO 463
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 463

Lys Lys Lys Asn Glu Gln Glu Leu Leu Glu Leu Asp Lys Trp Ala Ser
1 5 10 15

Leu Trp Asn Trp Phe Asp Ile Thr Asn Trp Leu Trp Tyr Ile Arg Lys 20 25 30

Lys Lys

<210> SEQ ID NO 464
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 464

Lys Trp Ala Ser Leu Trp Asn Trp Phe Asp Ile Thr Asn Trp Leu Trp
1 5 10 15

Tyr Ile Arg

<210> SEQ ID NO 465
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 465
caggtgcagc tggtgcagtc tggggctcaa atgaagaacc ctggggcctc agtgaaggtc 60
tcctgcgcgc cttctggata taccttcacc gacttttaca tacattggtt gcgccaggcc 120
cctggccagg ggcttcagtg gatgggatgg atgaaccctc agactggtcg cacaaacact 180
gcacgaaact ttcaggggag ggtcaccatg accagggaca cgtccatcgg cacagcctac 240
atggagttga gaagcctgac atctgacgac acggccatat attactgtac gacaggggga 300
tggatcagtc tttactatga tagtagttat taccccaact ttgaccactg gggtcaggga 360
accctgctca ccgtctcctc ag 382

<210> SEQ ID NO 466
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 466

Gln Val Gln Leu Val Gln Ser Gly Ala Gln Met Lys Asn Pro Gly Ala
1 5 10 15

Ser Val Lys Val Ser Cys Ala Pro Ser Gly Tyr Thr Phe Thr Asp Phe
20 25 30

Tyr Ile His Trp Leu Arg Gln Ala Pro Gly Gln Gly Leu Gln Trp Met
35 40 45

Gly Trp Met Asn Pro Gln Thr Gly Arg Thr Asn Thr Ala Arg Asn Phe
50 55 60

Gln Gly Arg Val Thr Met Thr Arg Asp Thr Ser Ile Gly Thr Ala Tyr
65 70 75 80

Met Glu Leu Arg Ser Leu Thr Ser Asp Asp Thr Ala Ile Tyr Tyr Cys
85 90 95

Thr Thr Gly Gly Trp Ile Ser Leu Tyr Tyr Asp Ser Ser Tyr Tyr Pro
100 105 110

Asn Phe Asp His Trp Gly Gln Gly Thr Leu Leu Thr Val Ser Ser
115 120 125

<210> SEQ ID NO 467
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 467
cagtctgccc tgactcagcc tgcctccgtg tctgggtctc ctggacagtc gatcaccatc 60
tcctgcactg gaaccaagta tgatgttggg agtcatgacc ttgtctcctg gtaccaacag 120
tacccaggca aagtccccaa atacatgatt tatgaagtca ataaacggcc ctcaggagtt 180
tctaatcgct tctctggctc caaatctggc aacacggcct ccctgacaat ctctgggctc 240
cgggctgagg acgaggctga ctattattgc tgttcatttg gagggagtgc caccgtggtc 300
tgcggcggcg ggaccaaggt gaccgtccta g 331

<210> SEQ ID NO 468
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 468

Gln Ser Ala Leu Thr Gln Pro Ala Ser Val Ser Gly Ser Pro Gly Gln
1 5 10 15

Ser Ile Thr Ile Ser Cys Thr Gly Thr Lys Tyr Asp Val Gly Ser His
20 25 30

Asp Leu Val Ser Trp Tyr Gln Gln Tyr Pro Gly Lys Val Pro Lys Tyr
35 40 45

Met Ile Tyr Glu Val Asn Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Arg Ala Glu Asp Glu Ala Asp Tyr Tyr Cys Cys Ser Phe Gly Gly Ser
85 90 95

Ala Thr Val Val Cys Gly Gly Gly Thr Lys Val Thr Val Leu
100 105 110

<210> SEQ ID NO 469
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 469

Gln Val Gln Leu Val Gln Ser Gly Gly Gly Leu Val Lys Pro Gly Gly
1 5 10 15

Ser Leu Thr Leu Ser Cys Ser Ala Ser Gly Phe Phe Phe Asp Asn Ser
20 25 30

Trp Met Gly Trp Val Arg Gln Ala Pro Gly Lys Gly Leu Glu Trp Val
35 40 45

Gly Arg Ile Arg Arg Leu Lys Asp Gly Ala Thr Gly Glu Tyr Gly Ala
50 55 60

```
Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130


<210> SEQ ID NO 470
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Gly Gly Gly Gly Ser Gly Gly Gly Gly Ser Gly Gly Gly Gly Ser
1               5                   10                  15


<210> SEQ ID NO 471
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Cys Thr Ala Asp Leu Gly Glu Pro Val Val Ser Arg Phe Phe Glu Trp
1               5                   10                  15

Gly Ser Tyr Tyr Tyr Tyr Met Asp Leu Trp Gly
            20                  25


<210> SEQ ID NO 472
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Cys Thr Met Asp Glu Gly Thr Pro Val Thr Arg Phe Leu Glu Trp Gly
1               5                   10                  15

Tyr Phe Tyr Tyr Tyr Met Ala Val Trp Gly
            20                  25


<210> SEQ ID NO 473
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Gly Phe Thr Phe Ser Asn Thr Trp
1               5


<210> SEQ ID NO 474
```

<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

Gly Phe Phe Phe Asp Asn Ser Trp
1               5

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

Ile Ser Arg Asn Lys Asp Gly Ala Lys Thr
1               5                   10

<210> SEQ ID NO 476
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

Ile Arg Arg Leu Lys Asp Gly Ala Thr Gly
1               5                   10

<210> SEQ ID NO 477
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 477

Asp Asp Ser Arg
1

<210> SEQ ID NO 478
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 478

Asp Asp Ser Arg
1

<210> SEQ ID NO 479
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

Thr Arg Asp Glu Gly Ala Pro Val Thr Arg Leu Leu Glu Trp Gly Ser
1 5 10 15

Tyr Tyr Tyr Tyr Met Ala Val
20

<210> SEQ ID NO 480
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 480

Thr Ala Asp Glu Gly Ala Pro Ile Leu Arg Phe Phe Glu Trp Gly Tyr
1 5 10 15

Tyr Asn Tyr Tyr Met Asp Val
20

<210> SEQ ID NO 481
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 481

Thr Ala Asp Glu Gly Ala Pro Ile Leu Arg Phe Phe Glu Trp Gly Tyr
1 5 10 15

Tyr Asn Tyr Tyr Met Asp Val
20

<210> SEQ ID NO 482
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 482

Gln Glu Ser Tyr Ser Ser Thr Pro Thr His Thr
1 5 10

<210> SEQ ID NO 483
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 483

Gln Glu Ser Tyr Ser Ser Thr Pro Thr His Ile
1 5 10

<210> SEQ ID NO 484
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 484

-continued

```
Gln Glu Ser Tyr Gln Thr Val Pro Thr Leu Thr
1               5                   10


<210> SEQ ID NO 485
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Gln Glu Ser Tyr Gln Thr Val Pro Thr Leu Thr
1               5                   10


<210> SEQ ID NO 486
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gln Glu Ser Tyr Gln Thr Val Pro Thr Leu Thr
1               5                   10


<210> SEQ ID NO 487
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Gln Glu Ala Tyr Asn Thr Asn Pro Thr Leu Ser
1               5                   10


<210> SEQ ID NO 488
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gln Glu Ala Tyr Asn Thr Asn Pro Thr Leu Ser
1               5                   10


<210> SEQ ID NO 489
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Gln Glu Ser Tyr Ser Ser Val Pro Met Tyr Ile
1               5                   10
```